US010968442B2

United States Patent
(12) United States Patent
Salas et al.

(10) Patent No.: US 10,968,442 B2
(45) Date of Patent: Apr. 6, 2021

(54) CHIMERIC CLOTTING FACTORS

(71) Applicant: Bioverativ Therapeutics Inc., Waltham, MA (US)

(72) Inventors: Joe Salas, Wayland, MA (US); Robert Peters, Needham, MA (US); Alan Bitonti, Acton, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 790 days.

(21) Appl. No.: 15/221,420

(22) Filed: Jul. 27, 2016

(65) Prior Publication Data

US 2017/0044512 A1 Feb. 16, 2017

Related U.S. Application Data

(63) Continuation of application No. 13/809,289, filed as application No. PCT/US2011/043597 on Jul. 11, 2011, now abandoned.

(60) Provisional application No. 61/363,183, filed on Jul. 9, 2010, provisional application No. 61/363,186, filed on Jul. 9, 2010, provisional application No. 61/442,055, filed on Feb. 11, 2011, provisional application No. 61/442,150, filed on Feb. 11, 2011, provisional application No. 61/442,029, filed on Feb. 11, 2011, provisional application No. 61/467,880, filed on Mar. 25, 2011, provisional application No. 61/491,762, filed on May 31, 2011.

(51) Int. Cl.

| | |
|---|---|
| *C12N 9/64* | (2006.01) |
| *A61K 38/00* | (2006.01) |
| *C07K 14/745* | (2006.01) |
| *C07K 16/28* | (2006.01) |
| *C07K 14/755* | (2006.01) |
| *C12N 9/96* | (2006.01) |
| *C07K 16/18* | (2006.01) |
| *A61K 39/00* | (2006.01) |

(52) U.S. Cl.

CPC ............ *C12N 9/644* (2013.01); *C07K 14/745* (2013.01); *C07K 14/755* (2013.01); *C07K 16/18* (2013.01); *C07K 16/28* (2013.01); *C07K 16/2848* (2013.01); *C12N 9/647* (2013.01); *C12N 9/6432* (2013.01); *C12N 9/6437* (2013.01); *C12N 9/96* (2013.01); *C12Y 304/21021* (2013.01); *C12Y 304/21022* (2013.01); *A61K 38/00* (2013.01); *A61K 2039/505* (2013.01); *C07K 2317/622* (2013.01); *C07K 2319/00* (2013.01); *C07K 2319/30* (2013.01); *C07K 2319/33* (2013.01)

(58) Field of Classification Search

CPC .... C12N 9/644; C12N 9/6432; C12N 9/6437; C12N 9/647; C07K 14/745; C07K 14/755; C07K 16/18; C07K 16/28; C07K 16/2848; C07K 2319/30; C07K 2319/33; C07K 2319/00; C12Y 304/21021; C12Y 304/21022

See application file for complete search history.

(56) References Cited

U.S. PATENT DOCUMENTS

| | | | |
|---|---|---|---|
| 4,444,878 | A | 4/1984 | Paulus |
| 4,683,195 | A | 7/1987 | Mullis et al. |
| 4,683,202 | A | 7/1987 | Mullis |
| 4,694,778 | A | 9/1987 | Learn et al. |
| 4,704,362 | A | 11/1987 | Itakura et al. |
| 4,745,055 | A | 5/1988 | Schenk et al. |
| 4,800,159 | A | 1/1989 | Mullis et al. |
| 4,845,075 | A | 7/1989 | Murray et al. |
| 4,868,112 | A | 9/1989 | Toole, Jr. |
| 4,889,919 | A | 12/1989 | Murray et al. |
| 4,925,793 | A | 5/1990 | Goeddel et al. |
| 4,929,554 | A | 5/1990 | Goeddel et al. |
| 4,965,188 | A | 10/1990 | Mullis et al. |
| 5,112,950 | A | 5/1992 | Meulien et al. |
| 5,157,021 | A | 10/1992 | Balschmidt et al. |
| 5,171,844 | A | 12/1992 | Van Ooyen et al. |
| 5,194,596 | A | 3/1993 | Tischer et al. |
| 5,227,158 | A | 7/1993 | Jardieu |
| 5,304,489 | A | 4/1994 | Rosen |
| 5,346,991 | A | 9/1994 | Roy et al. |
| 5,395,760 | A | 3/1995 | Smith et al. |
| 5,453,491 | A | 9/1995 | Takatsu et al. |

(Continued)

FOREIGN PATENT DOCUMENTS

| | | | |
|---|---|---|---|
| AU | 609829 | B2 | 5/1991 |
| EP | 0068763 | A2 | 1/1983 |

(Continued)

OTHER PUBLICATIONS

Phillips et al., Blood, vol. 71. No. 4 (Apr. 1988): pp. 831-843 (Year: 1988).*

(Continued)

*Primary Examiner* — Larry D Riggs, II
*Assistant Examiner* — Joseph Fischer
(74) *Attorney, Agent, or Firm* — Lathrop GPM LLP; James H. Velema, Esq.

(57) ABSTRACT

Chimeric clotting factors which localize the therapeutic to sites of coagulation (e.g., by being targeted to platelets or being activatable at sites of coagulation), have reduced clearance rates, have improved manufacturability, have reduced thrombogenicity, have enhanced activity, or have more than one of these characteristics are described as are methods for making chimeric clotting factors and methods for improving hemostasis using these clotting factors.

23 Claims, 68 Drawing Sheets

Specification includes a Sequence Listing.

(56) References Cited

U.S. PATENT DOCUMENTS

| | | | |
|---|---|---|---|
| 5,460,950 | A | 10/1995 | Barr et al. |
| 5,543,502 | A | 8/1996 | Nordfang et al. |
| 5,589,369 | A | 12/1996 | Seidman et al. |
| 5,591,669 | A | 1/1997 | Krimpenfort et al. |
| 5,595,886 | A | 1/1997 | Chapman et al. |
| 5,599,905 | A | 2/1997 | Mosley et al. |
| 5,610,278 | A | 3/1997 | Nordfang et al. |
| 5,639,605 | A | 6/1997 | Kitamura et al. |
| 5,648,260 | A | 7/1997 | Winter et al. |
| 5,648,273 | A | 7/1997 | Bottaro et al. |
| 5,658,570 | A | 8/1997 | Newman et al. |
| 5,686,292 | A | 11/1997 | Schwall et al. |
| 5,726,147 | A | 3/1998 | Ruf et al. |
| 5,736,137 | A | 4/1998 | Anderson et al. |
| 5,739,277 | A | 4/1998 | Presta et al. |
| 5,741,957 | A | 4/1998 | Deboer et al. |
| 5,789,203 | A | 8/1998 | Chapman et al. |
| 5,811,524 | A | 9/1998 | Brams et al. |
| 5,834,250 | A | 11/1998 | Wells et al. |
| 5,834,598 | A | 11/1998 | Lowman et al. |
| 5,840,529 | A | 11/1998 | Seidah et al. |
| 5,849,992 | A | 12/1998 | Meade et al. |
| 5,869,046 | A | 2/1999 | Presta et al. |
| 5,877,016 | A | 3/1999 | Presta et al. |
| 5,892,019 | A | 4/1999 | Schlom et al. |
| 5,910,574 | A | 6/1999 | Presta et al. |
| 5,935,815 | A | 8/1999 | Van De Ven et al. |
| 5,939,598 | A | 8/1999 | Kucherlapati et al. |
| 5,969,108 | A | 10/1999 | McCafferty et al. |
| 5,972,885 | A | 10/1999 | Spira et al. |
| 6,005,079 | A | 12/1999 | Casterman et al. |
| 6,017,729 | A | 1/2000 | Anderson et al. |
| 6,030,613 | A | 2/2000 | Blumberg et al. |
| 6,048,720 | A | 4/2000 | Dalborg et al. |
| 6,060,447 | A | 5/2000 | Chapman et al. |
| 6,075,181 | A | 6/2000 | Kucherlapati et al. |
| 6,086,875 | A | 7/2000 | Blumberg et al. |
| 6,096,871 | A | 8/2000 | Presta et al. |
| 6,099,841 | A | 8/2000 | Hillan et al. |
| 6,121,022 | A | 9/2000 | Presta et al. |
| 6,159,462 | A | 12/2000 | Matthews et al. |
| 6,159,730 | A | 12/2000 | Reff |
| 6,193,980 | B1 | 2/2001 | Efstathiou et al. |
| 6,194,551 | B1 | 2/2001 | Idusogie et al. |
| 6,228,620 | B1 | 5/2001 | Chapman et al. |
| 6,242,195 | B1 | 6/2001 | Idusogie et al. |
| 6,271,349 | B1 | 8/2001 | Dougall et al. |
| 6,277,375 | B1 | 8/2001 | Ward |
| 6,316,226 | B1 | 11/2001 | Van Ooyen et al. |
| 6,346,513 | B1 | 2/2002 | Van Ooyen et al. |
| 6,355,782 | B1 | 3/2002 | Zonana et al. |
| 6,380,171 | B1 | 4/2002 | Day et al. |
| 6,403,764 | B1 | 6/2002 | Dubaquie et al. |
| 6,413,777 | B1 | 7/2002 | Reff et al. |
| 6,458,563 | B1 | 10/2002 | Lollar |
| 6,479,635 | B1 | 11/2002 | Anderson et al. |
| 6,485,726 | B1 | 11/2002 | Blumberg et al. |
| 6,506,874 | B1 | 1/2003 | Dubaquie et al. |
| 6,528,482 | B1 | 3/2003 | Anderson et al. |
| 6,528,624 | B1 | 3/2003 | Idusogie et al. |
| 6,537,763 | B2 | 3/2003 | Dougall et al. |
| 6,538,124 | B1 | 3/2003 | Idusogie et al. |
| 6,562,948 | B2 | 5/2003 | Anderson |
| 6,576,608 | B1 | 6/2003 | Lee et al. |
| 6,596,847 | B2 | 7/2003 | Kelley et al. |
| 6,602,977 | B1 | 8/2003 | Ljungqvist et al. |
| 6,673,901 | B2 | 1/2004 | Koide |
| 6,686,179 | B2 | 2/2004 | Fleer et al. |
| 6,703,199 | B1 | 3/2004 | Koide |
| 6,737,056 | B1 | 5/2004 | Presta |
| 6,740,734 | B1 | 5/2004 | Nilsson et al. |
| 6,765,087 | B1 | 7/2004 | Casterman et al. |
| 6,821,505 | B2 | 11/2004 | Ward |
| 6,927,044 | B2 | 8/2005 | Stahl et al. |
| 6,998,253 | B1 | 2/2006 | Presta et al. |
| 7,041,635 | B2 | 5/2006 | Kim et al. |
| 7,078,490 | B2 | 7/2006 | Koide |
| 7,083,784 | B2 | 8/2006 | Dall'Acqua et al. |
| 7,119,171 | B2 | 10/2006 | Koide |
| 7,166,697 | B1 | 1/2007 | Galanis et al. |
| 7,317,091 | B2 | 1/2008 | Lazar et al. |
| 7,348,004 | B2 | 3/2008 | Peters et al. |
| 7,381,408 | B2 | 6/2008 | Mezo et al. |
| 7,404,956 | B2 | 7/2008 | Peters et al. |
| 7,417,130 | B2 | 8/2008 | Stumpp et al. |
| 7,566,565 | B2 | 7/2009 | Peters et al. |
| 7,566,595 | B2 | 7/2009 | Steinhoff |
| 7,592,010 | B2 | 9/2009 | Rosen et al. |
| 7,615,537 | B2 | 11/2009 | Scaria et al. |
| 7,795,400 | B2 | 9/2010 | Peters et al. |
| 7,812,136 | B2 | 10/2010 | Buettner et al. |
| 7,862,820 | B2 | 1/2011 | Peters et al. |
| 7,939,632 | B2 | 5/2011 | Metzner et al. |
| 7,951,918 | B2 | 5/2011 | Glaser et al. |
| 8,388,955 | B2 | 3/2013 | Lazar et al. |
| 8,765,915 | B2 | 7/2014 | Weimer et al. |
| 9,856,468 | B2 | 1/2018 | Salas et al. |
| 2002/0102208 | A1 | 8/2002 | Chinn et al. |
| 2003/0044908 | A1 | 3/2003 | Persson |
| 2003/0235536 | A1 | 12/2003 | Blumberg |
| 2004/0033225 | A1 | 2/2004 | Browning et al. |
| 2004/0102388 | A1 | 5/2004 | High et al. |
| 2004/0102440 | A1 | 5/2004 | Wong |
| 2004/0132028 | A1 | 7/2004 | Stumpp et al. |
| 2005/0147618 | A1 | 7/2005 | Rivera et al. |
| 2005/0202527 | A1 | 9/2005 | Le Bonniec et al. |
| 2006/0234299 | A1 | 10/2006 | Stemmer et al. |
| 2007/0087411 | A1 | 4/2007 | Sharma et al. |
| 2007/0218067 | A1 | 9/2007 | Buttner et al. |
| 2007/0231329 | A1 | 10/2007 | Lazar et al. |
| 2007/0237765 | A1 | 10/2007 | Lazar et al. |
| 2007/0237766 | A1 | 10/2007 | Lazar et al. |
| 2007/0237767 | A1 | 10/2007 | Lazar et al. |
| 2007/0243188 | A1 | 10/2007 | Lazar et al. |
| 2007/0248603 | A1 | 10/2007 | Lazar et al. |
| 2007/0286859 | A1 | 12/2007 | Lazar et al. |
| 2008/0057056 | A1 | 3/2008 | Lazar et al. |
| 2008/0193441 | A1 | 8/2008 | Trown et al. |
| 2008/0260738 | A1 | 10/2008 | Moore et al. |
| 2009/0175828 | A1 | 7/2009 | Schulte et al. |
| 2009/0291890 | A1 | 11/2009 | Madison et al. |
| 2010/0330059 | A1 | 12/2010 | Stafford et al. |
| 2012/0093840 | A1 | 4/2012 | Oestergaard et al. |
| 2012/0178908 | A1 | 7/2012 | Hilden et al. |
| 2013/0202596 | A1 | 8/2013 | Salas et al. |
| 2013/0216513 | A1 | 8/2013 | Salas et al. |
| 2018/0320159 | A1 | 11/2018 | Salas et al. |

FOREIGN PATENT DOCUMENTS

| | | | |
|---|---|---|---|
| EP | 0120694 | A2 | 10/1984 |
| EP | 0125023 | A1 | 11/1984 |
| EP | 0240975 | A2 | 10/1987 |
| EP | 0255694 | A1 | 2/1988 |
| EP | 0256654 | A2 | 2/1988 |
| EP | 0266663 | A1 | 5/1988 |
| EP | 0295597 | A2 | 12/1988 |
| EP | 0417014 | A2 | 3/1991 |
| EP | 0417563 | A2 | 3/1991 |
| EP | 0455460 | A2 | 11/1991 |
| EP | 0522530 | A2 | 1/1993 |
| EP | 0368684 | B1 | 3/1994 |
| EP | 0589877 | B1 | 11/1996 |
| JP | H10505327 | A | 5/1998 |
| WO | WO-8704187 | A1 | 7/1987 |
| WO | WO-8800831 | A1 | 2/1988 |
| WO | WO-8803559 | A1 | 5/1988 |
| WO | WO-8803565 | A1 | 5/1988 |
| WO | WO-8807089 | A1 | 9/1988 |
| WO | WO-9014359 | A1 | 11/1990 |
| WO | WO-9014425 | A1 | 11/1990 |
| WO | WO-9109122 | A1 | 6/1991 |
| WO | WO-9601653 | A1 | 1/1996 |
| WO | WO-9614339 | A1 | 5/1996 |

(56) References Cited

FOREIGN PATENT DOCUMENTS

| | | | | |
|---|---|---|---|---|
| WO | WO-9805787 A1 | | 2/1998 | |
| WO | WO-9823289 A1 | | 6/1998 | |
| WO | WO-9916873 A1 | | 4/1999 | |
| WO | WO-9937772 A1 | | 7/1999 | |
| WO | WO-9951642 A1 | | 10/1999 | |
| WO | WO-9958572 A1 | | 11/1999 | |
| WO | WO-0009560 A2 | | 2/2000 | |
| WO | WO-0032767 A1 | | 6/2000 | |
| WO | WO-0042072 A2 | | 7/2000 | |
| WO | WO-0063243 A1 | | 10/2000 | |
| WO | WO-0102439 A1 | | 1/2001 | |
| WO | WO-0102440 A1 | | 1/2001 | |
| WO | WO-0164942 A1 | | 9/2001 | |
| WO | WO-0170763 A1 | | 9/2001 | |
| WO | WO-0202781 A1 | | 1/2002 | |
| WO | WO-0220565 A2 | | 3/2002 | |
| WO | WO-0244215 A2 | | 6/2002 | |
| WO | WO-02060919 A2 | | 8/2002 | |
| WO | WO-02060955 A2 | | 8/2002 | |
| WO | WO-02088171 A2 | | 11/2002 | |
| WO | WO-02096948 A2 | | 12/2002 | |
| WO | WO-03074569 A2 | | 9/2003 | |
| WO | WO-03077834 A2 | | 9/2003 | |
| WO | WO-2004016750 A2 | | 2/2004 | |
| WO | WO-2004029207 A2 | | 4/2004 | |
| WO | WO-2004035752 A2 | | 4/2004 | |
| WO | WO-2004044011 A2 | | 5/2004 | |
| WO | WO-2004063351 A2 | | 7/2004 | |
| WO | WO-2004074455 A2 | | 9/2004 | |
| WO | WO-2004099249 A2 | | 11/2004 | |
| WO | WO-2004101740 A2 | | 11/2004 | |
| WO | WO-2004110472 A2 | | 12/2004 | |
| WO | WO-2005001025 A2 | * | 1/2005 | ................ A61P 7/00 |
| WO | WO-2005019254 A1 | | 3/2005 | |
| WO | WO-2005040217 A2 | | 5/2005 | |
| WO | WO-2005044859 A2 | | 5/2005 | |
| WO | WO-2005047327 A2 | | 5/2005 | |
| WO | WO-2005070963 A1 | | 8/2005 | |
| WO | WO-2005077981 A2 | | 8/2005 | |
| WO | WO-2005092925 A2 | | 10/2005 | |
| WO | WO-2005123780 A2 | | 12/2005 | |
| WO | WO-2006019447 A1 | | 2/2006 | |
| WO | WO-2006047350 A2 | | 5/2006 | |
| WO | WO-2006055689 A2 | | 5/2006 | |
| WO | WO-2006083275 A2 | | 8/2006 | |
| WO | WO-2006085967 A2 | | 8/2006 | |
| WO | WO-2006113665 A2 | | 10/2006 | |
| WO | WO-2007144173 A1 | | 12/2007 | |
| WO | WO-2008012543 A1 | | 1/2008 | |
| WO | WO-2008090215 A1 | | 7/2008 | |
| WO | WO-2008143954 A2 | | 11/2008 | |
| WO | WO-2009053368 A1 | | 4/2009 | |
| WO | WO-2009140598 A1 | * | 11/2009 | ................ A61P 7/00 |
| WO | WO-2010115866 A1 | * | 10/2010 | ............ C07K 16/18 |
| WO | WO-2010151736 A1 | | 12/2010 | |
| WO | WO-2011069164 A2 | | 6/2011 | |
| WO | WO-2012006624 A2 | | 1/2012 | |
| WO | WO-2012006633 A1 | | 1/2012 | |
| WO | WO-2012117091 A1 | | 9/2012 | |

OTHER PUBLICATIONS

Newman et al., Blood, vol. 65. No. 1 (Jan. 1985): pp. 227-232 (Year: 1985).*

Janeway, Immunobiology: The Immune System in Health and Disease. 5th edition, New York: Garland Science; 2001, 5 pages, Chapter 5 (Year: 2001).*

Benard et al., Identification of Peptide Antagonists to Glycoprotein Ibα That Selectively Inhibit von Willebrand Factor Dependent Platelet Aggregation, Biochem., 2008, 47, 4674-4682 (Year: 2008).*

Anderson & Anderson, Blood, vol. 76, No. 6 (Sep. 15. 1990): pp. 1165-1172 (Year: 1990).*

Adams, T.E. and Huntington, J.A., "Structural Transitions during Prothrombin Activation: On the Importance of Fragment 2," Biochimie 122:235-242, Scientifiques Elsevier, France (Mar. 2016).

Ager, S., et al., "Retroviral Display of Antibody Fragments; Interdomain Spacing Strongly Influences Vector Infectivity," Human Gene Therapy 7(17):2157-2164, Mary Ann Liebert Inc, United Kingdom (Nov. 1996).

Anderson, C.L., et al., "Perspective- FcRn Transports Albumin: Relevance to Immunology and Medicine," Trends in Immunology 27(7):343-348, Elsevier, United States (Jul. 2006).

Armour, K.L., et al., "Recombinant Human IgG Molecules Lacking Fcgamma Receptor I Binding and Monocyte Triggering Activities," European Journal of Immunology 29(8):2613-2624, Wiley-VCH, Germany (Aug. 1999).

Bajaj, S.P., et al., "Redetermination of the Rate-limiting Step in the Activation of Factor IX by Factor XIa and by Factor VIIa/tissue Factor. Explanation for Different Electrophoretic Radioactivity Profiles Obtained on Activation of 3H- and 125I-labeled Factor IX," Biochemistry 22(17):4047-4053, American Chemical Society, United States (Aug. 1983).

Baldassarre, H., et al., "Production of Transgenic Goats by Pronuclear Microinjection of In Vitro Produced Zygotes Derived From Oocytes Recovered by Laparoscopy," Theriogenology 59(3-4):831-839, Elsevier, United States (Feb. 2003).

Benard, S.A., et al., "Identification of Peptide Antagonists to Glycoprotein Ibα that Selectively Inhibit von Willebrand Factor Dependent Platelet Aggregation," Biochemistry 47(16):4674-4682, American Chemical Society, United States (Apr. 2008).

Benhar, I. and Pastan, I., "Cloning, Expression and Characterization of the Fv Fragments of the Anti-carbohydrate mAbs B1 and B5 as Single-chain Immunotoxins," Protein Engineering Design and Selection 7(11):1509-1515, Oxford University Press, England (Dec. 1994).

Beste, G., et al., "Small Antibody-like Proteins with Prescribed Ligand Specificities Derived from the Lipocalin Fold," Proceedings of the National Academy of Sciences 96(5):1898-1903, National Academy of Sciences, United States (Mar. 1999).

Better, M., et al., "*Escherichia coli* Secretion of an Active Chimeric Antibody Fragment," Science 240(4855):1041-1043, Association for the Advancement of Science, United States (May 1988).

Binz, H.K., et al., "High-affinity Binders Selected from Designed Ankyrin Repeat Protein Libraries," Nature Biotechnology 22(5):575-582, Nature America Publishing, United States (May 2004).

Bird, R.E., et al., "Single-chain Antigen-binding Proteins," Science 242(4877):423-426, Association for the Advancement of Science, United States (Oct. 1988).

Brandstetter, H., et al., "X-Ray Structure of Clotting Factor IXa: Active Site and Module Structure Related to Xase Activity and Hemophilia B," Proceedings of the National Academy of Sciences USA 92(21):9796-9800, The National Academy of Sciences, United States (Oct. 1995).

Brinster, R.L., et al., "Expression of a Microinjected Immunoglobulin Gene in the Spleen of Transgenic Mice," Nature 306(5941):332-336, Nature Publishing Group, England (Nov. 1983).

Brinster, R.L., et al., "Factors Affecting the Efficiency of Introducing Foreign DNA into Mice by Microinjecting Eggs," Proceedings of the National Academy of Sciences USA 82(13):4438-4442, National Academy of Sciences, United States (Jul. 1985).

Brunetti-Pierri, N., et al., "Bioengineered Factor IX Molecules with Increased Catalytic Activity Improve the Therapeutic Index of Gene Therapy Vectors for Hemophilia B," Human Gene Therapy 20(5):479-485, Mary Ann Liebert, Inc., United States (May 2009).

Burmeister, W.P., et al., "Crystal Structure of the Complex of Rat Neonatal Fc Receptor with Fc," Nature 372(6504):379-383, Nature Publishing Group, England (Nov. 1994).

Chang, J., et al., "Changing Residue 338 in Human Factor IX from Arginine to Alanine Causes an Increase in Catalytic Activity," The Journal of Biological Chemistry 273(20):12089-12094, American Society for Biochemistry and Molecular Biology,United States (May 1998).

Cripe, L.D., et al., "Structure of the Gene for Human Coagulation Factor V," Biochemistry 31(15):3777-3785, American Chemical Society, United States (Apr. 1992).

(56) References Cited

OTHER PUBLICATIONS

Culouscou, J.M., et al., "HER4 Receptor Activation and Phosphorylation of Shc Proteins by Recombinant Heregulin-Fc Fusion Proteins," Journal of Biological Chemistry 270(21):12857-12863, American Society for Biochemistry and Molecular Biology, United States (May 1995).
Dall Acqua, W.F., et al., "Increasing the Affinity of a Human IgG1 for the Neonatal Fc Receptor: Biological Consequences," The Journal of Immunology 169(9):5171-5180, American Association of Immunologists, United States (Nov. 2002).
Dumoulin, M., et al., "Single-Domain Antibody Fragments with High Conformational Stability," Protein Science 11(3):500-515, Cold Spring Harbor Laboratory Press, United States (Mar. 2002).
Eaton, D., et al., "Proteolytic Processing of Human Factor VIII. Correlation of Specific Cleavages by Thrombin, Factor Xa, and Activated Protein C with Activation and Inactivation of Factor VIII Coagulant Activity," Biochemistry 25(2):505-512, American Chemical Society, United States (Jan. 1986).
Eaton, D.L., et al., "Construction and Characterization of an Active Factor VIII Variant Lacking the Central One-third of the Molecule," Biochemistry 25(26):8343-8347, American Chemical Society, United States (Dec. 1986).
Eigenbrot, C., et al., "The Factor VII Zymogen Structure Reveals Reregistration of beta Strands during Activation," Structure 9(7):627-636, Cell Press, United States (Jul. 2001).
Ellman, J., et al., "Biosynthetic Method for Introducing Unnatural Amino Acids Site-Specifically into Proteins," Methods in Enzymology 202:301-336, Elsevier, United States (1991).
Falkner, F.G. and Zachau, H.G., "Expression of Mouse Immunoglobulin Genes in Monkey Cells," Nature 298(5871):286-288, Nature Publishing Group, England (Jul. 1982).
Fay, P.J., et al., "Human Factor VIIIa Subunit Structure. Reconstruction of Factor VIIIa from the Isolated A1/A3-C1-C2 Dimer and A2 Subunit," The Journal of Biological Chemistry 266(14):8957-8962, The American Society for Biochemistry and Molecular Biology, Inc., United States (May 1991).
Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (Dec. 1999).
Fuentes, R., et al., "Platelet-Targeted Pro-Urokinase as a Novel Thromboprophylaxis Fibrinolytic Strategy," American Society of Hematology Annual Meeting and Exposition Poster Presentation, 2 pages (Nov. 2010).
Ghetie, V., et al., "Increasing the Serum Persistence of an IgG Fragment by Random Mutagenesis," Nature Biotechnology 15(7):637-640, Nature America Publishing, United States (Jul. 1997).
Gitschier, J., et al., "Characterization of the Human Factor VIII Gene," Nature 312(5992):326-330, Nature Publishing Group, England (Nov. 1984).
Goding, J.W., "Production of Monoclonal Antibodies," in Monoclonal Antibodies: Principles and Practice, 2nd ed., pp. 59-103, Academic Press Inc., London (1986).
Gupta, S., et al., "Prioritization of Anticancer Drugs Against a Cancer Using Genomic Features of Cancer Cells: A Step Towards Personalized Medicine," Scientific Reports 6:23857, Nature Publishing Group, England (Mar. 2016).
Hamers-Casterman, C., et al., "Naturally Occurring Antibodies Devoid of Light Chains," Nature 363(6428):446-448, Nature Publishing Group, England (Jun. 1993).
Handl, H.L., et al., "Hitting Multiple Targets with Multimeric Ligands," Expert Opinion on Therapeutic Targets 8(6):565-586, Informa Healthcare, England (Dec. 2004).
Hanes, J. and Pluckthun, A., "In Vitro Selection Methods for Screening of Peptide and Protein Libraries," Current Topics in Microbiology and Immunology 243:107-122, Springer Verlag, Germany (1999).
Hanes, J., et al., "Picomolar Affinity Antibodies from a Fully Synthetic Naive Library Selected and Evolved by Ribosome Display," Nature Biotechnology 18(12):1287-1292, Nature America Publishing, United States (Dec. 2000).
Hanes, J., et al., "Ribosome Display Efficiently Selects and Evolves High-affinity Antibodies in Vitro from Immune Libraries," Proceedings of the National Academy of Sciences 95(24):14130-14135, National Academy of Sciences, United States (Nov. 1998).
Harrison, S., et al., "The Manufacturing Process for Recombinant Factor IX," Seminars in Hematology 35(2 Suppl 2):4-10, W.B. Saunders Company, United States (Apr. 1998).
He, M. and Taussig, M.J., "Antibody-ribosome-mRNA (ARM) Complexes as Efficient Selection Particles for in Vitro Display and Evolution of Antibody Combining Sites," Nucleic Acids Research 25(24):5132-5134, Oxford University Press, England (Dec. 1997).
Hedner, U., "NovoSeven® as a Universal Haemostatic Agent," Blood Coagulation & Fibrinolysis 11(Suppl 1):S107-S111, Lippincott Williams & Wilkins, England (Apr. 2000).
Ho, S.N., et al., "Site-directed Mutagenesis by Overlap Extension using the Polymerase Chain Reaction," Gene 77(1):51-59, Elsevier Science Publishers B.V., Netherlands (Apr. 1989).
Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (May 1990).
Honda, S., et al., "Topography of Ligand-induced Binding Sites, Including a Novel Cation-sensitive Epitope (AP5) at the Amino Terminus, of the Human Integrin beta 3 Subunit," Journal of Biological Chemistry 270(20):11947-11954, American Society for Biochemistry and Molecular Biology, Inc., United States (May 1995).
Hoogenboom, H.R. and Chames, P., "Natural and Designer Binding Sites made by Phage Display Technology," Immunology Today 21(8):371-378, Elsevier Science Publishers, United States (Aug. 2000).
Horton, R.M., et al., "Gene Splicing by Overlap Extension," Methods in Enzymology 217:270- 279, Academic Press, United States (1993).
Huie, M.A., et al., "Antibodies to Human Fetal Erythroid Cells from a Nonimmune Phage Antibody Library," Proceedings of the National Academy of Sciences 98(5):2682-2687, National Academy of Sciences, United States (Feb. 2001).
Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences USA 85(16):5879-5883, National Academy of Sciences, United States (Aug. 1988).
International Search Report and Written Opinion for International Application No. PCT/US2011/043599, European Patent Office, Netherlands, dated Jan. 12, 2011, 14 pages.
International Search Report and Written Opinion for International Application PCT/US2011/043597, European Patent Office, Netherlands, dated Nov. 11, 2011.
Irving, R.A., et al., "Ribosome Display and Affinity Maturation: From Antibodies to Single V-domains and Steps Towards Cancer Therapeutics," Journal of Immunological Methods 248(1-2):31-45, Elsevier Science Publishers, Netherlands (Feb. 2001).
Israel, E.J., et al., "Expression of the Neonatal Fc Receptor, FcRn, on Human Intestinal Epithelial Cells," Immunology 92(1):69-74, Blackwell Sciences, England (Sep. 1997).
Jendreyko, N., et al., "Protein Synthesis, Post-translation Modification, and Degradation: Intradiabodies, Bispecific, Tetravalent Antibodies for the Simultaneous Functional Knockout of Two Cell Surface Receptors," The Journal of Biological Chemistry 278(48):47812-47819, The American Society for Biochemistry and Molecular Biology, Inc., United States (Nov. 2003).
Jenny, R.J., et al., "Complete cDNA and Derived Amino acid Sequence of Human Factor V," Proceedings of the National Academy of Sciences USA 84(14):4846-4850, National Academy of Sciences, United States (Jul. 1987).
Jeong, K.J., et al., "Avimers Hold their Own," Nature Biotechnology 23(12):1493-1494, Nature America Publishing, United States (Dec. 2005).

(56) References Cited

OTHER PUBLICATIONS

Jones, E.W., et al., "Proteinase Mutants of *Saccharomyces cerevisiae*," Genetics 85:23-33, Genetics Society of America, United States (Jan. 1977).
Kane, W.H. and Davie, E.W., "Cloning of a cDNA Coding for Human Factor V, a Blood Coagulation Factor Homologous to Factor VIII and Ceruloplasmin," Proceedings of the National Academy of Sciences USA 83(18):6800-6804, National Academy of Sciences, United States (Sep. 1986).
Kang, A.S., et al., "Linkage of Recognition and Replication Functions by Assembling Combinatorial Antibody Fab Libraries along Phage Surfaces," Proceedings of National Academy of Science 88(10):4363-4366, National Academy of Science, United States (May 1991).
Kim, J.K., et al., "Identifying Amino Acid Residues that Influence Plasma Clearance of Murine IgG1 Fragments by Site-Directed Mutagenesis," European Journal of Immunology 24(3):542- 548, Wiley-VCH, Germany (Mar. 1994).
Kingsman, A.J., et al., "Replication in *Saccharomyces cerevisiae* of Plasmid pBR313 Carrying DNA from the Yeast Trpl Region," Gene 7(2):141-152, Elsevier/North-Holland Biomedical Press, Netherlands (Oct. 1979).
Kobayashi, N., et al., "FcRn-Mediated Transcytosis of Immunoglobulin G in Human Renal Proximal Tubular Epithelial Cells," American Journal of Physiology 282(2):F358-F365, American Physiological Society, United States (Feb. 2002).
Kohler, G. and Milstein, C., "Continuous Cultures of Fused Cells Secreting Antibody of Predefined Specificity," Nature 256(5517):495-497, Macmillan Journals Ltd., England (Aug. 1975).
Kohler, G., "Immunoglobulin Chain Loss in Hybridoma Lines," Proceedings of the National Academy of Sciences USA 77(4):2197-2199, National Academy of Sciences, United States (Apr. 1980).
Koide, A., et al., "The Fibronectin Type III Domain as a Scaffold for Novel Binding Proteins," Journal of Molecular Biology 284(4):1141-1151, Academic Press, United States (Dec. 1998).
Lai, E., et al., "Conserved Organization of the Human and Murine T-cell Receptor beta-gene Families," Nature 331(6156):543-546, Nature Publishing Group, England (Feb. 1988).
Langner, K-D., et al., "Synthesis of Biologically Active Deletion Mutants of Human Factor VIII:C," Behring Institute Mitteilungen 82:16-25, Behringwerke AG, Germany (Apr. 1988).
Larrick, J.W., et al., "Rapid Cloning of Rearranged Immunoglobulin Genes from Human Hybridoma Cells using Mixed Primers and the Polymerase Chain Reaction," Biochemical and Biophysical Research Communications 160(3):1250-1256, Academic Press, United States (May 1989).
Legendre, D., et al., "TEM-1 beta-lactamase as a Scaffold for Protein Recognition and Assay," Protein Science 11(6):1506-1518, Cold Spring Harbor Laboratory, United States (Jun. 2002).
Lin, C.N., et al., "Generation of a Novel Factor IX with Augmented Clotting Activities in Vitro and in Vivo," Journal of Thrombosis and Haemostasis 8(8):1773-1783, International Society on Thrombosis and Haemostasis, England (Aug. 2010).
Liu, B., et al., "Towards Proteome-wide Production of Monoclonal Antibody by Phage Display," Journal of Molecular Biology 315(5):1063-1073, Elsevier Science Publishers, England (Feb. 2002).
Lollar, P. and Parker, E.T., "Structural Basis for the Decreased Procoagulant Activity of Human Factor VIII Compared to the Porcine Homolog," Journal of Biological Chemistry 266(19):12481-12486, The American Society for Biochemistry and Molecular Biology, Inc., United States (Jul. 1991).
Louvain-Quintard, V.B., et al., "Thrombin-activable Factor X Re-establishes an Intrinsic Amplification in Tenase-deficient Plasmas," The Journal of Biological Chemistry 280(50):41352-41359, The American Society for Biochemistry and Molecular Biology, Inc., United States (Dec. 2005).
Lusson, J., et al., "cDNA Structure of the Mouse and Rat Subtilisin/kexin-like PC5: a Candidate Proprotein Convertase Expressed in Endocrine and Nonendocrine Cells," Proceedings of the National Academy of Sciences USA 90(14):6691-6695, National Academy of Sciences, United States (Jul. 1993).
Malassagne, B., et al., "Hypodermin A, A New Inhibitor of Human Complement for the Prevention of Xenogeneic Hyperacute Rejection," Xenotransplantation 10(3):267-277, John Wiley & Sons, United States (May 2003).
Margaritis, P., et al., "Novel Therapeutic Approach for Hemophilia using Gene Delivery of an Engineered Secreted Activated Factor VII," Journal of Clinical Investigation 113(7):1025-1031, American Society for Clinical Investigation, United States (Apr. 2004).
Marks, J.D., et al., "By-Passing Immunization: Building High Affinity Human Antibodies by Chain Shuffling," Biotechnology 10(7):779-783, Nature Publishing Company, United States (Jul. 1992).
McCafferty, J., et al., "Phage Antibodies: Filamentous Phage Displaying Antibody Variable Domains," Nature 348(6301):552-554, Nature Publishing Group, London (Dec. 1990).
McCue, J.T., et al., "Application of a Novel Affinity Adsorbent for the Capture and Purification of Recombinant Factor VIII Compounds," Journal of Chromatography A 1216(45):7824-7830, Elsevier, Netherlands (Nov. 2009).
McKnight, G.S., et al., "Expression of the Chicken Transferrin Gene in Transgenic Mice," Cell 34(2):335-341, Cell Press, United States (Sep. 1983).
Meulien, P., et al., "A New Recombinant Procoagulant Protein Derived from the cDNA Encoding Human Factor VIII," Protein Engineering 2(4):301-306, IRL Press Ltd., England (Oct. 1988).
Milenic, D.E., et al., "Construction, Binding Properties, Metabolism, and Tumor Targeting of a Single-chain Fv Derived from the Pancarcinoma Monoclonal Antibody CC49," Cancer Research 51:6363-6371, American Association of Cancer Research, United States (Dec. 1991).
Morrison, S.L., "Sequentially Derived Mutants of the Constant Region of the Heavy Chain of Murine Immunoglobulins," The Journal of Immunology 123(2):793-800, The Williams & Wilkins Co., United States (Aug. 1979).
Morrison, S.L., et al., "Chimeric Human Antibody Molecules: Mouse Antigen-binding Domains with Human Constant Region Domains," Proceedings of the National Academy of Sciences USA 81(21):6851-6855, National Academy of Sciences, United States (Nov. 1984).
Morrison, S.L., "Transfectomas Provide Novel Chimeric Antibodies," Science 229(4719):1202-1207, Association for the Advancement of Science, United States (Sep. 1985).
Morrison, S.L., "Transfer and Expression of Immunoglobulin Genes," Annual Review of Immunology 2:239-256, Annual Reviews, Inc., United States (1984).
Mount, J.D., et al., "Sustained Phenotypic Correction of Hemophilia B dogs with a Factor IX Null Mutation by Liver-directed Gene Therapy," Blood 99(8):2670-2676, The American Society of Hematology, United States (Apr. 2002).
Mullinax, R.L., et al., "Identification of Human Antibody Fragment Clones Specific for Tetanus Toxoid in a Bacteriophage λ Immunoexpression Library," Proceedings of the National Academy of Sciences USA 87(20):8095-8099, National Academy of Sciences, United States (Oct. 1990).
Nagy, Z.A., et al., "Fully Human, HLA-DR-Specific Monoclonal Antibodies Efficiently Induce Programmed Death of Malignant Lymphoid Cells," Nature Medicine 8(8):801-807, Nature Publishing Company, United States (Aug. 2002).
Nakagawa, T., et al., "Identification and Functional Expression of a New Member of the Mammalian Kex2-like Processing Endoprotease Family: Its Striking Structural Similarity to PACE4," The Journal of Biochemistry 113(2):132-135, Oxford University Press, England (Feb. 1993).
Nakayama, K., "Furin: A Mammalian Subtilisin/Kex2p-like Endoprotease Involved in Processing of a Wide Variety of Precursor Proteins," Biochemical Journal 327:625-635, Biochemical Society, England (Nov. 1997).
Neumann, E., et al., "Gene Transfer into Mouse Lyoma Cells by Electroporation in High Electric Fields," The EMBO Journal 1(7):841-845, IRL Press Limited, England (Feb. 1982).

(56) References Cited

OTHER PUBLICATIONS

Noel, M.J. and Ben Tahar, S., "Nucleotide Sequence of the Coat Protein Gene and Flanking Regions of Cucumber Virus (CMV) strain 117F," Nucleic Acids Research 18(5):1332, Oxford University Press, England (Mar. 1990).
Nord, K., et al., "Binding Proteins Selected from Combinatorial Libraries of an alpha-helical Bacterial Receptor Domain," Nature Biotechnology 15(8):772-777, Nature America Publishing, United States (Aug. 1997).
Noren, C.J., et al., "A General Method for Site-specific Incorporation of Unnatural Amino Acids into Proteins," Science 244(4901):182-188, Association for the Advancement of Science, United States (Apr. 1989).
Office Action dated Dec. 31, 2014 in U.S. Appl. No. 13/809,289, Salas, J., et al., filed Jul. 11, 2011.
Office Action dated Jul. 20, 2015 in U.S. Appl. No. 13/809,287, Salas, J., et al., filed Jul. 11, 2011.
Office Action dated Jun. 11, 2014 in U.S. Appl. No. 13/809,289, Salas, J., et al., filed Jul. 11, 2011.
Office Action dated Jun. 26, 2015 in U.S. Appl. No. 13/809,289, Salas, J., et al., filed Jul. 11, 2011.
Osterlund, M., et al., "Sequential Coagulation Factor VIIA Domain Binding to Tissue Factor," Biochemical and Biophysical Research Communications 337(4):1276-1282, Elsevier, United States (Dec. 2005).
Pancer, Z., et al., "Somatic Diversification of Variable Lymphocyte Receptors in the Agnathan Sea Lamprey," Nature 430(6996):174-180, Nature Publishing Group, England (Jul. 2004).
Panni, S., et al., "In Vitro Evolution of Recognition Specificity Mediated by SH3 Domains Reveals Target Recognition Rules," The Journal of Biological Chemistry 277(24):21666-21674, American Society for Biochemistry and Molecular Biology, United States (Jun. 2002).
Pantoliano, M.W., et al., "Conformational Stability, Folding, and Ligand-Binding Affinity of Single-Chain Fv Immunoglobulin Fragments Expressed in *Escherichia coli*," Biochemistry 30(42):10117-10125, American Chemical Society, United States (Oct. 1991).
Persson, E., et al., "Rational Design of Coagulation Factor VIIa Variants with Substantially Increased Intrinsic Activity," Proceedings of the National Academy of Sciences USA 98(24):13583-13588, National Academy of Sciences, United States (Nov. 2001).
Persson, E., et al., "Substitution of Valine for Leucine 305 in Factor VIIa Increases the Intrinsic Enzymatic Activity," Journal of Biological Chemistry 276(31):29195-29199, American Society for Biochemistry and Molecular Biology, United States (Aug. 2001).
Peterson, J.A., et al., "A Site Involving the "hybrid" and PSI Homology Domains of GPIIIa (beta 3-integrin subunit) is a Common Target for Antibodies Associated with Quinine-Induced Immune Thrombocytopenia," Blood 101(3):937-942, The American Society of Hematology, United States (Feb. 2003).
Petrovan, R.J. and Ruf, W., "Residue $Met^{156}$ Contributes to the Labile Enzyme Conformation of Coagulation Factor VIIa," The Journal of Biological Chemistry 276(9):6616-6620, The American Society for Biochemistry and Molecular Biology, Inc., United States (Mar. 2001).
Raso, V. and Griffin, T., "Hybrid Antibodies with Dual Specificity for the Delivery of Ricin to Immunoglobulin-bearing Target Cells," Cancer Research 41(6):2073-2078, American Association of Cancer Research, United States (Jun. 1981).
Registry of Standard Biological Parts, Part: BBa_K157018:Design, Oct. 26, 2008, accessed at http://partS.igem.Org/Part:BBa_K 157018 :Design, accessed on Dec. 18, 2014, 3 pages.
Rehemtulla, A., et al., "PACE4 is a Member of the Mammalian Propeptidase Family that has Overlapping but not Identical Substrate Specificity to PACE," Biochemistry 32(43):11586-11590, American Chemical Society, United States (Nov. 1993).
Ritchie, K.A., et al., "Allelic Exclusion and Control of Endogenous Immunoglobulin Gene Rearrangement in Kappa Transgenic Mice," Nature 312(5994):517-520, Nature Publishing Group, England (Dec. 1984).
Robl, J.M., et al., "Artificial Chromosome Vectors and Expression of Complex Proteins in Transgenic Animals," Theriogenology 59(1):107-113, Elsevier, United States (Jan. 2003).
Routledge, E.G., et al., "The Effect of Aglycosylation on the Immunogenicity of a Humanized Therapeutic CD3 Monoclonal Antibody," Transplantation 60(8):847-853, Lippincott Williams & Wilkins, United States (Oct. 1995).
Roux, K.H., et al., "Comparisons of the Ability of Human IgG3 Hinge Mutants, IgM, IgE, and IgA2, to form Small Immune Complexes: A Role for Flexibility and Geometry," The Journal of Immunology 161(8):4083-4090, American Association of Immunologists, United States (Oct. 1998).
Ruberti, F., et al., "The Use of the RACE Method to Clone Hybridoma cDNA when V Region Primers Fail," Journal of Immunological Methods 173(1):33-39, Elsevier, United States (Jul. 1994).
Ruther, U. and Muller-Hill, B., "Easy Identification of cDNA Clones," The EMBO Journal 2(10):1791-1794, IRL Press Ltd, England (1983).
Sarin, P.S., et al., "Inhibition of Acquired Immunodeficiency Syndrome Virus by Oligodeoxynucleoside Methylphosphonates," Proceedings of the National Academy of Sciences USA 85(20):7448-7451, National Academy of Science, United States (Oct. 1988).
Sarver, N., et al., "Stable Expression of Recombinant Factor VIII Molecules Using a Bovine Papillomavirus Vector," DNA 6(6):553-564, Mary Ann Liebert, Inc., United States (Dec. 1987).
Schellenberger, V., et al., "A Recombinant Polypeptide Extends the in Vivo Half-life of Peptides and Proteins in a Tunable Manner," Nature Biotechnology 27(12):1186-1190, Nature America, Inc., United States (Dec. 2009).
Schlehuber, S. and Skerra, A., "Lipocalins in Drug Discovery: From Natural Ligand-binding Proteins to "Anticalins"," Drug Discovery Today 10(1):23-33, Elsevier Science, England (Jan. 2005).
Schneider, S., et al., "Mutagenesis and Selection of PDZ Domains that Bind New Protein Targets," Nature Biotechnology 17(2):170-175, Nature America Publishing, United States (Feb. 1999).
Schulte, S., et al., "Prolonged in Vivo Half-life of FVIIa by Fusion to Albumin," CSL Behring GmbH, Preclinical R&D, Marburg, Germany, Jan. 20, 2008.
Schulte, S., "Half-life Extension through Albumin Fusion Technologies," Thrombosis Research 124(Suppl.2):S6-S8, Pergamon Press, United States (Dec. 2009).
Schulte, S., "Use of Albumin Fusion Technology to Prolong the Half-Life of Recombinant Factor VIIa," Thrombosis Research 122(Suppl 4):S14-S19, Pergamon Press, United States (2008).
Schwarz, M., et al., "Conformation-Specific Blockade of the Integrin GPIIb/IIIa: A Novel Antiplatelet Strategy that Selectively Targets Activated Platelets," Circulation Research 99(1):25-33, American Heart Association, Inc., United States (Jul. 2006).
Schwarz, M., et al., "Single-chain Antibodies for the Conformation-Specific Blockade of Activated Platelet Integrin alphaIIbbeta3 Designed by Subtractive Selection from Naive Human Phage Libraries," The FASEB Journal 18(14):1704-1706, Federation of American Societies for Experimental Biology, United States (Nov. 2004).
Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).
Sichler, K., et al., "Physiological fIXa Activation Involves a Cooperative Conformational Rearrangement of the 99-Loop," The Journal of Biological Chemistry 278(6):4121-4126, The American Society for Biochemistry and Molecular Biology, Inc., United States (Feb. 2003).
Simioni, P., et al., "X-Linked Thrombophilia with a Mutant Factor IX (Factor IX Padua)," The New England Journal of Medicine 361(17):1671-1675, Massachusetts Medical Society, United States (Oct. 2009).
Skerra, A. and Pluckthun, A., "Assembly of a Functional Immunoglobulin Fv Fragment in *Escherichia coli*," Science 240(4855):1038-1041, Association for the Advancement of Science, United States (May 1988).

(56) References Cited

OTHER PUBLICATIONS

Soejima, K., et al., "Factor VIIa Modified in the 170 Loop Shows Enhanced Catalytic Activity but does not Change the Zymogen-like Property," The Journal of Biological Chemistry 276(20):17229-17235, The American Society for Biochemistry and Molecular Biology, Inc., United States (May 2001).
Soejima, K., et al., "The 99 and 170 Loop-Modified Factor VIIa Mutants Show Enhanced Catalytic Activity Without Tissue Factor," The Journal of Biological Chemistry 277(50):49027-49035, The American Society for Biochemistry and Molecular Biology, Inc., United States (Dec. 2002).
Spitzer, S.G., et al., "Replacement of Isoleucine-397 by Threonine in the Clotting Proteinase Factor IXa (Los Angeles and Long Beach variants) Affects Macromolecular Catalysis but not L-Tosylarginine Methyl Ester Hydrolysis. Lack of Correlation between the ox Brain Prothrombin Time and the Mutation Site in the Variant Proteins," The Journal of Biological Chemistry 265(1):219-225, The American Society for Biochemistry and Molecular Biology, Inc., United States (Jan. 1990).
Stein, C.A., et al., "Physicochemical Properties of Phosphorothioate Oligodeoxynucleotides," Nucleic Acids Research 16(8):3209-3221, Oxford University Press, England (Apr. 1988).
Stinchcomb, D.T., et al., "Isolation and Characterisation of a Yeast Chromosomal Replicator," Nature 282(5734):39-43, Nature Publishing Group, England (Nov. 1979).
Stoop, A.A. and Craik, C.S., "Engineering of a Macromolecular Scaffold to Develop Specific Protease Inhibitors," Nature Biotechnology 21(9):1063-1068, Nature America Publishing, United States (Sep. 2003).
Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (Dec. 1994).
Stubbs, J.D., et al., "cDNA Cloning of a Mouse Mammary Epithelial Cell Surface Protein Reveals the Existence of Epidermal Growth Factor-like Domains Linked to Factor VIII-like Sequences," Proceedings of the National Academy of Sciences 87(21):8417-8421, The National Academy of Sciences of the United States (Nov. 1990).
Sturzebecher, J., et al., "Dramatic Enhancement of the Catalytic Activity of Coagulation Factor IXa by Alcohols," FEBS Letters 412(2):295-300, Federation of European Biochemical Societies, Netherlands (Jul. 1997).
Takahashi, N., et al., "Single-chain Structure of Human Ceruloplasmin: The Complete Amino Acid Sequence of the Whole Molecule," Proceedings of the National Academy of Sciences USA 81(2):390-394, National Academy of Sciences, United States (Jan. 1984).
Takkinen, K., et al., "An Active Single-chain Antibody Containing a Cellulase linker Domain is Secreted by *Escherichia coli*," Protein Engineering Design and Selection 4(7):837-841, Oxford University Press, England (Oct. 1991).
Toole, J.J., et al., "A Large Region (95 kDa) of Human Factor VIII is Dispensable for in Vitro Procoagulant Activity," Proceedings of the National Academy of Sciences USA 83(16):5939-5942, National Academy of Sciences, United States (Aug. 1986).
Toole, J.J., et al., "Molecular Cloning of a cDNA Encoding Human Antihaemophilic Factor," Nature 312(5992):342-347, Nature Publishing Group, England (Nov. 1984).
Tschumper, G. and Carbon, J., "Sequence of a Yeast DNA Fragment Containing a Chromosomal Replicator and the TRP1 Gene," Gene 10(2):157-166, Elsevier/North-Holland, Netherlands (Jul. 1980).
Tutt, A., et al., "Trispecific F(ab')3 Derivatives that use Cooperative Signaling via the TCR/CD3 Complex and CD2 to Activate and Redirect Resting Cytotoxic T Cells," The Journal of Immunology 147:60-69, The American Association of Immunologists, United States (Jul. 1991).
Unpublished U.S. Appl. No. 09/259,338 inventors Chinn, P., et al., filed Mar. 1, 1999.
Yang, X. and Walsh, P.N., "An Ordered Sequential Mechanism for Factor IX and Factor IXa Binding to Platelet Receptors in the Assembly of the Factor X-activating Complex," Biochemical Journal 390(1):157-167, Portland Press, England (Aug. 2005).
Zogg, T. and Brandstetter, H., "Structural Basis of the Cofactor- and Substrate-assisted Activation of Human Coagulation Factor IXa," Structure 17(12):1669-1678, Elsevier Ltd, England (Dec. 2009).
Van Den Ouweland, A.M., et al., "Structural Homology between the Human Fur Gene Product and the Subtilisin-like Protease Encoded by Yeast KEX2," Nucleic Acids Research 18(3):664, Oxford University Press, England (Feb. 1990).
Van Regenmortel, M.H.V., Structure of Antigens, vol. 3, 1995, Telford Press, pp. 49 and 50.
Vehar, G.A., et al., "Structure of Human Factor VIII," Nature 312(5992):337-342, Nature Publishing Group, England (Nov. 1984).
Venkateswarlu, D., "Structural Investigation of Zymogenic and Activated Forms of Human Blood Coagulation Factor VIII: A Computational Molecular Dynamics Study," BMC Structural Biology 10:7, BioMed Central, England (Feb. 2010).
Vita, C., et al., "Scorpion Toxins as Natural Scaffolds for Protein Engineering," Proceedings of the National Academy of Sciences USA 92(14):6404-6408, National Academy of Sciences, United States (Jul. 1995).
Vysotchin, A., et al., "Domain Structure and Domain-domain Interactions in Human Coagulation Factor IX," The Journal of Biological Chemistry 268(12):8436-8446, The American Society for Biochemistry and Molecular Biology, Inc., United States (Apr. 1993).
Wagner, T.E., et al., "Microinjection of a Rabbit beta-globin Gene into Zygotes and Its Subsequent Expression in Adult Mice and their Offspring," Proceedings of the National Academy of Sciences USA 78(10):6376-6380, National Academy of Sciences, United States (Oct. 1981).
Walsh, P.N., "Roles of Platelets and Factor XI in the Initiation of Blood Coagulation by Thrombin," Journal of Thrombosis and Haemostasis 86(1):75-82, International Society on Thrombosis and Haemostasis, England (Jul. 2001).
Ward, E.S. and Ghetie, V., "The Effector Functions of Immunoglobulins: Implications for Therapy," Therapeutic Immunology 2(2):77-94, Blackwell Science Ltd., England (Apr. 1995).
Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).
Wasley, L.C., et al., "PACE/Furin can Process the Vitamin K-dependent Pro-Factor IX Precursor within the Secretory Pathway," The Journal of Biological Chemistry 268(12):8458-8465, The American Society for Biochemistry and Molecular Biology, Inc., United States (Apr. 1993).
Weidler, B., et al., "Pharmakokinetische Merkmale als Kriterien fur den klinischen Einsatz von Hydroxyethylstarke," Arzneimittel-Forschung 41(5):494-498, Editio Cantor, Germany (May 1991).
Weisser, N.E. and Hall, J.C., "Applications of Single-chain Variable Fragment Antibodies in Therapeutics and Diagnostics," Biotechnology Advances 27(4):502-520, Elsevier, United States (Jul. 2009).
Wigler, M., et al., "Biochemical Transfer of Single-copy Eucaryotic Genes using Total Cellular DNA as Donor," Cell 14(3):725-731, Cell Press, United States (Jul. 1978).
Wilson, A. and Radtke, F., "Multiple Functions of Notch Signaling in Self-renewing Organs and Cancer," FEBS Letters 580(12):2860-2868, Elsevier Science, United States (May 2006).
Wilson, D.S., et al., "The Use of mRNA Display to Select High-affinity Protein-binding Peptides," Proceedings of the National Academy of Sciences USA 98(7):3750-3755, National Academy of Sciences, United States (Mar. 2001).

* cited by examiner

Activated FVII constructs, activatable FVII constructs with non-Fc fusions

| |
|---|
| 1. Seeblue2 |
| 2. Harvest |
| 3. FVIIFc-053 HIC Load |
| 4. FVIIFc-053 HIC F.T |
| 5. FVIIFc-053 HIC wash Fraction #A2 |
| 6. FVIIFc-053 HIC wash Fraction #A3 |
| 7. FVIIFc-053 HIC wash Fraction #A4 |
| 8. FVIIFc-053 HIC wash Fraction #A5 |
| 9. FVIIFc-053 HIC wash Fraction #A6 |
| 9. FVIIFc-053 HIC wash Fraction #A6 |
| 10. FVIIFc-053 HIC wash Fraction #B7 |
| 11. Empty |
| 12. FVIIFc-053 HIC Elution Fraction #B6 |
| 13. FVIIFc-053 HIC Elution Fraction #B5 |
| 14. FVIIFc-053 HIC Elution Fraction #B4 |
| 15. FVIIFc-053 HIC Elution Fraction #B3 |

Binding of FVII-011 and FVII-027 to activated platelets determined by FACs

Binding of FVII-011 and FVII-027 to activated platelets determined by FACs

Thrombin generation assay to measure activity of FVII-037 and Novoseven in the presence of activated platelets Thrombin generation assay to measure activity of FVII-037 and Novoseven in the presence of activated platelets Thrombin generation assay to measure activity of FVII-044, FVII-045, FVII-046, FVII-011 and Novoseven in the presence of activated platelets

| Peptide* | Affinity $K_D$, nM | FVIIFc |
|---|---|---|
| PS4 | 64 | -044 |
| OS1 | 0.74 | -045 |
| OS2 | 31 | -046 |

*Benard et al. Biochemistry 2008, 47: 4674-4682

Thrombin generation assay to measure activity of FVII-047, FVII-048, FVII-049, FVII-011 and Novoseven in the presence of activated platelets

| Peptide* | Affinity $K_D$, nM | FVIIFc |
|---|---|---|
| PS4 | 64 | -047 |
| OS1 | 0.74 | -048 |
| OS2 | 31 | -049 |

* Benard et al. Biochemistry 2008, 47: 4674-4682

Thrombin generation assay to measure activity of FVII-053 and FVII-011 in the presence of activated platelets

Western blot analysis of FVIIFc species following transient transfection of HEK 293 cells and protein A pulldown

FVII-011
Heavy chain and light chain expressed as single chain

FVII-010
Heavy chain-scFc and light chain expressed separately

FVII-013
Heavy chain and light chain-scFc expressed separately

FVII-018
Heavy chain-Fc and light chain-Fc expressed separately

FVII-003
Heavy chain and light chain expressed as single chain

▨ FVII light chain

▦ FVII heavy chain

▨ FC

∽ 4x(GGGGS) cscFc linker

▮ 6x(GGGGS) spacer linker

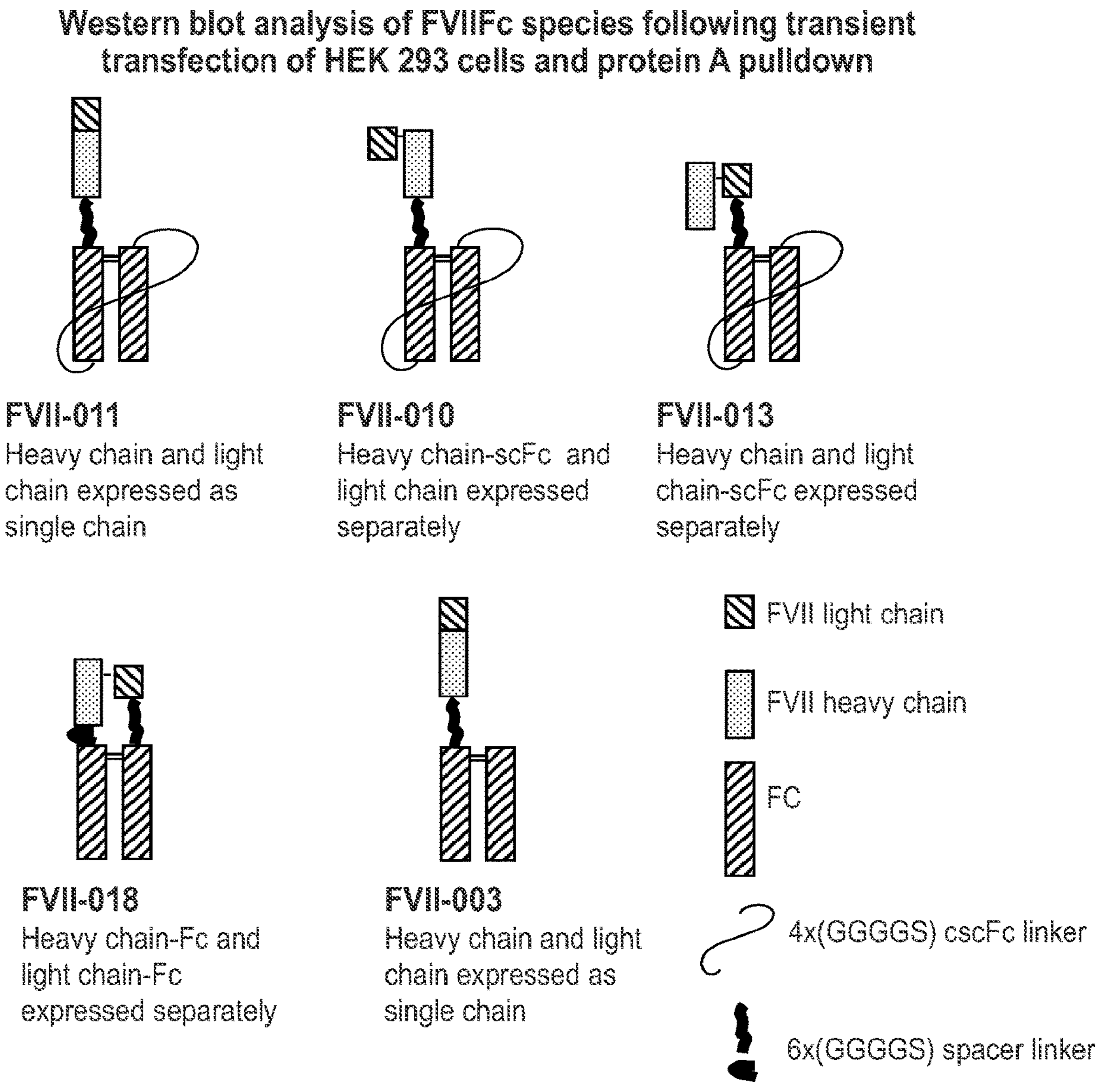

*Fig. 24*

Western blot analysis of FVIIFc species following transient transfection of HEK 293 cells and protein A pulldown
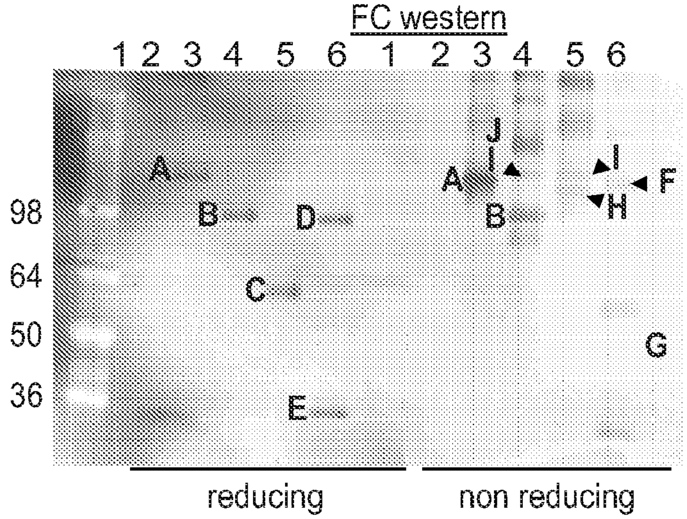
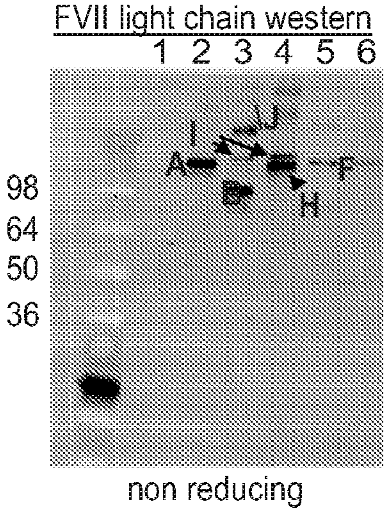
Interpretation of bands
A. FVII-scFc
B. Light chain-scFc
C. Light chain-Fc
D. FVII-Fc
E. Fc
F. FVII-Fc:Fc
G. Fc dimer
H. Light chain-Fc dimer
I. Light chain-Fc:HC-Fc
J. Light chain-scFc dimer
Proteins loaded in gel
1. FVII-010
2. FVII-011
3. FVII-013
4. FVII-018
5. FVII-003
6. No DNA in transfection
*Fig. 25*

Western blot of protein A immunoprecipitation following transient transfection of pSYN-FVII-024 with or without pSYN-PC5-003. Lane 1, Seeblue Plus2 marker; lane 2, pSYN-FVII-024, non reducing; lane 3, pSYN-FVII-024+pSYN-PC5-003, non reducing; lane 4, pSYN-FVII-024, reducing; lane 5, pSYN-FVII-024+pSYN-PC5-003, reducing.
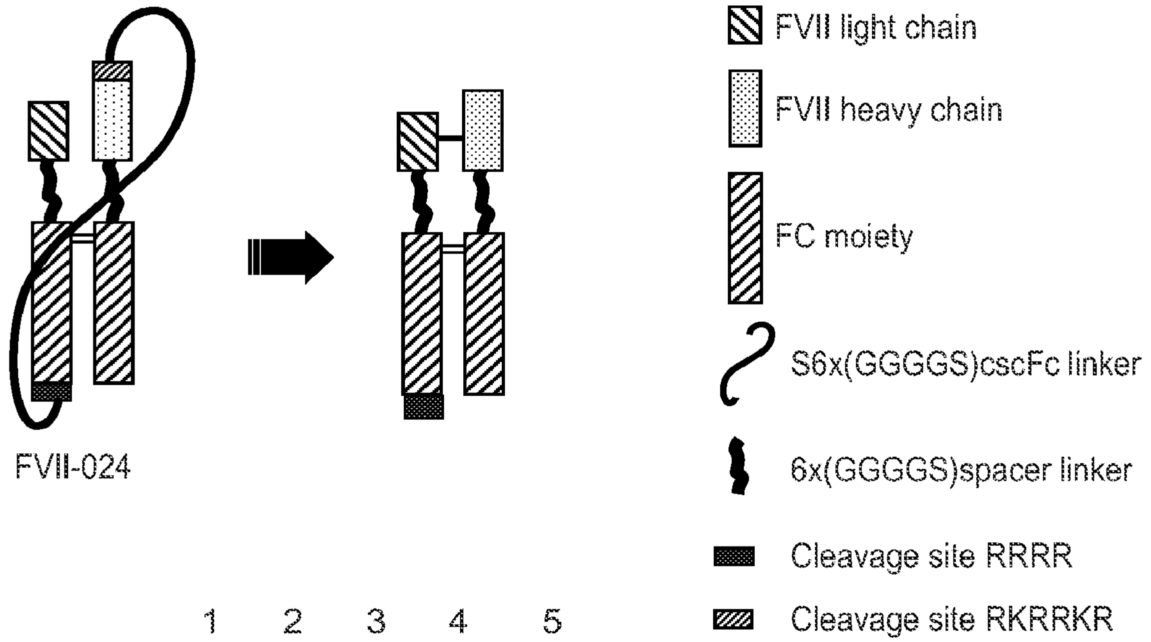
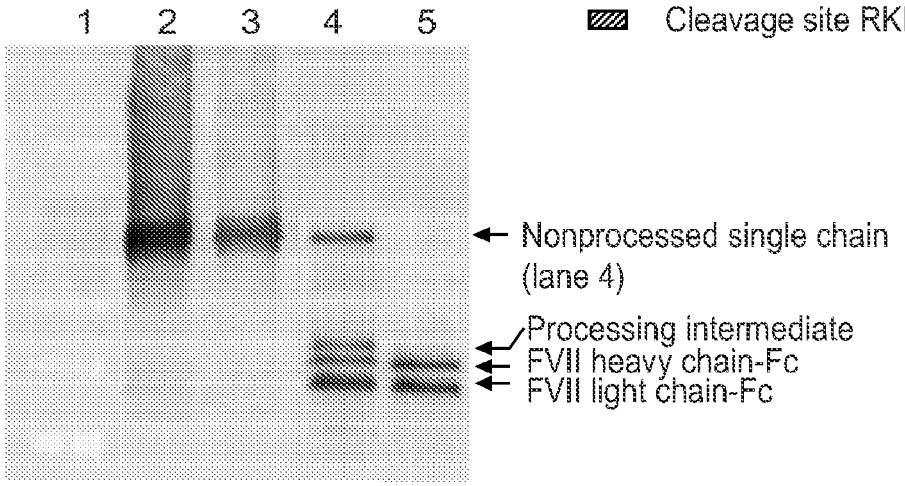
*Fig. 26*

Western blot analysis (Fc western) of FVIIFc species following transient transfection of HEK 293 cells and protein A pulldown
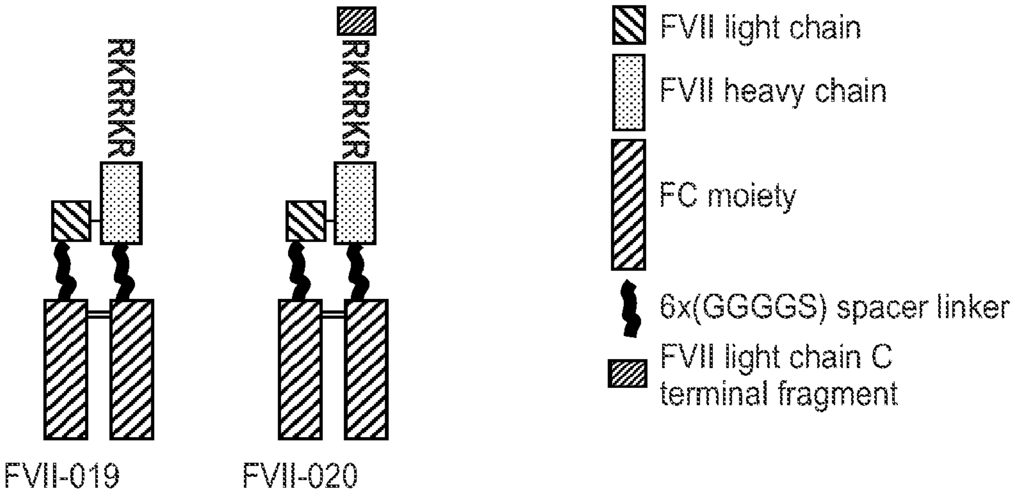
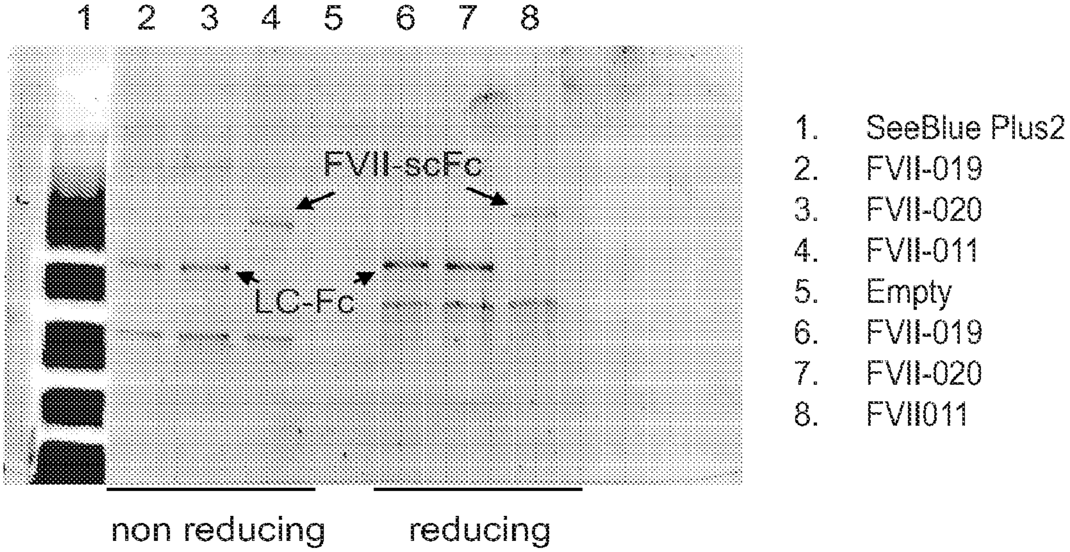
*Fig. 27*

1. Mark-12 (Invitrogen)
2. FVII-011
3. FVII-011+FXIa, 5' incubation
4. FVII-011+FXIa, 20' incubation
5. FVII-039
6. FVII-039+FXIa, 5' incubation
7. FVII-039+FXIa, 20' incubation
8. FXIa
9. FVII-011, activated
10. Mark-12 (Invitrogen)
11. FVII-040
12. FVII-040+FXIa, 5' incubation
13. FVII-040+FXIa, 20' incubation
14. FVII-011, activated
15. FXIa

SCE5

-scFv against active GPIIbIIIa

-Crossreacts with mouse and human receptors

Activatable Constructs

FXIa cleavage sites

LC-7x(GGGGS)-SVSQTSKLTR-IVGG: FVII-057

Thrombin cleavage sites

LC-7x(GGGGS)-DFLAEGGGVR-IVGG :FVII-058
LC-7x(GGGGS)-TTKIKPR-IVGG : FVII-059
LC-7x(GGGGS)-ALRPRVVGGA-VVGG : FVII-060
LC-7x(GGGGS)-ALRPRVVGGA-IVGG : FVII-061

Negative control

LC-8x(GGGGS)-IVGG: FVII-062

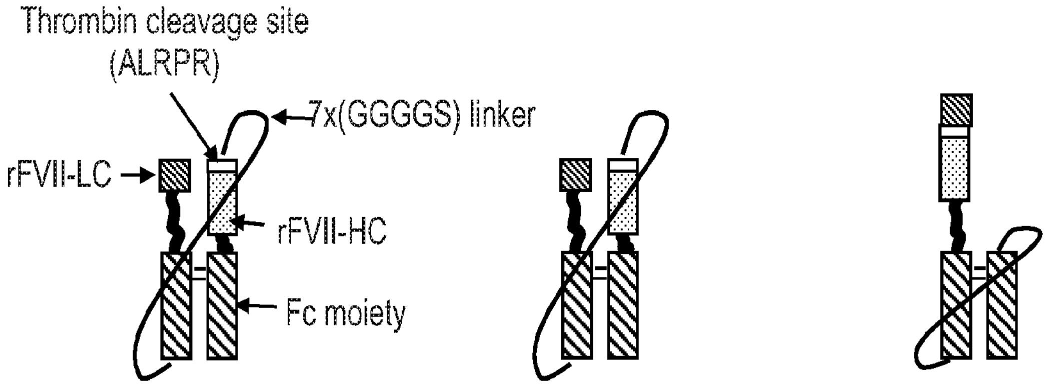

Activatable heterodimer structure

FVII-090

Activatable with high specific activity

FVII-100: 170 loop in the heavy chain replaced with 170 loop from trypsin. Same backbone as FVII-090

FVII-115: triple point mutation in heavy chain (V158D-E296V-M298Q). Same backbone as FVII-090

Activatable monomer structure

FVII-118 :R152 from light chain deleted, insert ALRPR between light chain and heavy chain

FVII-119 :R152 from light chain deleted, insert GGGGS-ALRPR between light chain and heavy chain

FVII-127: R152 from light chain deleted, insert ALRPR between light chain and heavy chain. Same high specific activity mutation found in FVII-100

*Fig. 41*

Thrombin generation assay to compare wild type activatable FVIIFc (FVII-118) to high specific activity variant (FVII-127)

Target FVIIa to active conformation of GIIbIIIa via scFv (SCE5)

FVII-066   FVII-067   FVII-094   FVII-011   Novoseven

- FVII light chain
- FVII heavy chain
- Linker
- Fc moiety linker

☐ -Targeting moiety
SCE5: scFv against active conformation of GPIIbIIIa

Thrombin generation assays in platelet-rich FVIII-deficient plasma

Targeting FVIIaFc to GPIb with peptides
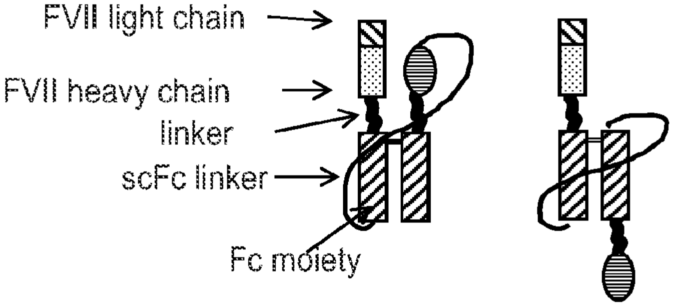
-Targeting moieties PS4, OS1 and OS2: peptides against GPIb-alpha
| N-terminus | C-terminus |
|---|---|
| -FVII-047 (PS4) | -FVII-044 (PS4) |
| -FVII-048 (OS1) | -FVII-045 (OS1) |
| -FVII-049 (OS2) | -FVII-046 (OS2) |
Fig. 46A Binding of FVII-045, FVII-048 and wild type FVIIaFc to platelets determined by FACS Affinity for the targeting peptides reported in Benard et al. Biochemistry 2008, 47: 4674-4682

| Peptide | Affinity $K_D$, nM |
|---|---|
| PS4 | 64 |
| OS1 | 0.74 |
| OS2 | 31 |

Target FIX to active conformation of GpIIbIIIa via scFv (SCE5)

SEQUENCE LISTING

```
<160> NUMBER OF SEQ ID NOS: 159

<210> SEQ ID NO 1
<211> LENGTH: 50
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(50)
<223> OTHER INFORMATION: Any grouping of "Gly Gly Gly Gly Ser" may be
      present or absent

<400> SEQUENCE: 1

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50


<210> SEQ ID NO 2
<211> LENGTH: 30
<212> TYPE: PRT
<213> ORGANISM: Artificial Sequence
<220> FEATURE:
<223> OTHER INFORMATION: Synthetic peptide
```

<400> SEQUENCE: 2

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser
20 25 30

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3

Gly Gly Gly Gly Ser Gly Gly Gly Gly Ser Gly Gly Gly Gly Ser Gly
1 5 10 15

Gly Gly Gly Ser
20

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Thr Gln Ser Phe Asn Asp Phe Thr Arg
1 5

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Ser Val Ser Gln Thr Ser Lys Leu Thr Arg
1 5 10

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Asp Phe Leu Ala Glu Gly Gly Gly Val Arg
1 5 10

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Thr Thr Lys Ile Lys Pro Arg
1 5

<210> SEQ ID NO 8

<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Ala Leu Arg Pro Arg Val Val Gly Gly Ala
1 5 10

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide

<400> SEQUENCE: 9

Glu Leu Leu Gly
1

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Pro Lys Asn Ser Ser Met Ile Ser Asn Thr Pro
1 5 10

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

His Gln Ser Leu Gly Thr Gln
1 5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

His Gln Asn Leu Ser Asp Gly Lys
1 5

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

His Gln Asn Ile Ser Asp Gly Lys
1 5

<210> SEQ ID NO 14
<211> LENGTH: 8

<212> TYPE: PRT
<213> ORGANISM: Artificial Sequence
<220> FEATURE:
<223> OTHER INFORMATION: Synthetic peptide

<400> SEQUENCE: 14

Val Ile Ser Ser His Leu Gly Gln
1 5

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24
<211> LENGTH: 15
<212> TYPE: PRT
<213> ORGANISM: Artificial Sequence
<220> FEATURE:

<223> OTHER INFORMATION: Synthetic peptide

<400> SEQUENCE: 24

```
Gly Gly Gly Gly Ser Gly Gly Gly Gly Ser Gly Gly Gly Gly Ser
1               5                   10                  15
```

<210> SEQ ID NO 25
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(31)
<223> OTHER INFORMATION: Any grouping of "Gly Gly Gly Gly Ser" may be present or absent

<400> SEQUENCE: 25

```
Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
            20                  25                  30
```

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34
<211> LENGTH: 25
<212> TYPE: PRT
<213> ORGANISM: Artificial Sequence
<220> FEATURE:
<223> OTHER INFORMATION: Synthetic peptide

<400> SEQUENCE: 34

Gly Gly Gly Gly Ser Gly Gly Gly Gly Ser Gly Gly Gly Gly Ser Gly
1 5 10 15

Gly Gly Gly Ser Gly Gly Gly Ala Ser
20 25

<210> SEQ ID NO 35

<400> SEQUENCE: 35

000

<210> SEQ ID NO 36
<211> LENGTH: 101
<212> TYPE: DNA
<213> ORGANISM: Artificial Sequence
<220> FEATURE:
<223> OTHER INFORMATION: Synthetic primer

<400> SEQUENCE: 36
catcggatcc cccgccaccg gaacctccac cgcctgatcc acccccacct gatccgccgc 60
caccgctccg gcggcgccgt ttacccggag acagggagag g 101

<210> SEQ ID NO 37
<211> LENGTH: 5
<212> TYPE: PRT
<213> ORGANISM: Artificial Sequence
<220> FEATURE:
<223> OTHER INFORMATION: Synthetic peptide

<400> SEQUENCE: 37

Arg Arg Arg Arg Ser
1 5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide

<400> SEQUENCE: 38

Arg Lys Arg Arg Lys Arg
1 5

<210> SEQ ID NO 39
<211> LENGTH: 37
<212> TYPE: DNA
<213> ORGANISM: Artificial Sequence
<220> FEATURE:
<223> OTHER INFORMATION: Synthetic primer

<400> SEQUENCE: 39
agtcaagctt gtcgactccg gaactcctgg gcggacc 37

<210> SEQ ID NO 40
<211> LENGTH: 86
<212> TYPE: DNA
<213> ORGANISM: Artificial Sequence
<220> FEATURE:
<223> OTHER INFORMATION: Synthetic primer

<400> SEQUENCE: 40
catcggatcc cccgccaccg gaacctccac cgcctgatcc acccccacct gatccgccgc 60
cacctttacc cggagacagg gagagg 86

<210> SEQ ID NO 41
<211> LENGTH: 35
<212> TYPE: DNA
<213> ORGANISM: Artificial Sequence
<220> FEATURE:
<223> OTHER INFORMATION: Synthetic primer

<400> SEQUENCE: 41
cagtcttgat cagacaaaac tcacacatgc ccacc 35

<210> SEQ ID NO 42
<211> LENGTH: 34
<212> TYPE: DNA
<213> ORGANISM: Artificial Sequence
<220> FEATURE:
<223> OTHER INFORMATION: Synthetic primer

<400> SEQUENCE: 42
actgacgaat tctcatttac ccggagacag ggag 34

<210> SEQ ID NO 43
<211> LENGTH: 40
<212> TYPE: DNA
<213> ORGANISM: Artificial Sequence
<220> FEATURE:
<223> OTHER INFORMATION: Synthetic primer

<400> SEQUENCE: 43
cgacaagctt gccgccacca tggtctccca ggccctcagg 40

<210> SEQ ID NO 44
<211> LENGTH: 156
<212> TYPE: DNA
<213> ORGANISM: Artificial Sequence
<220> FEATURE:
<223> OTHER INFORMATION: Synthetic primer

<400> SEQUENCE: 44
aggagttccg gagctgggca cggtgggcat gtgtgagttt tgtcggatcc cccgccaccg 60
gaacctccac cgcctgatcc acccccacct gatccgccgc caccggaccc acctccgccg 120
gagccaccgc caccgggaaa tggggctcgc aggagg 156

<210> SEQ ID NO 45
<211> LENGTH: 41
<212> TYPE: PRT
<213> ORGANISM: Artificial Sequence
<220> FEATURE:
<223> OTHER INFORMATION: Synthetic peptide

<400> SEQUENCE: 45

Arg Arg Arg Arg Ser Gly Gly Gly Gly Ser Gly Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser Arg Lys Arg Arg Lys Arg
        35                  40

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
gggaatgtca acaggcaggg                                               20

<210> SEQ ID NO 47
<211> LENGTH: 21
<212> TYPE: DNA
<213> ORGANISM: Artificial Sequence
<220> FEATURE:
<223> OTHER INFORMATION: Synthetic primer

<400> SEQUENCE: 47
cttggctttc tctccacagg c                                             21

<210> SEQ ID NO 48
<211> LENGTH: 62
<212> TYPE: DNA
<213> ORGANISM: Artificial Sequence
<220> FEATURE:
<223> OTHER INFORMATION: Synthetic primer

<400> SEQUENCE: 48
cgactccgga gctgggcacg gtgggcatgt gtgagttttg tcgggaaatg gggctcgcag   60
gg                                                                  62

<210> SEQ ID NO 49
<211> LENGTH: 20
<212> TYPE: DNA
<213> ORGANISM: Artificial Sequence
<220> FEATURE:
<223> OTHER INFORMATION: Synthetic primer

<400> SEQUENCE: 49
catccccagc acgtacgtcc                                               20

<210> SEQ ID NO 50
<211> LENGTH: 132
<212> TYPE: DNA
<213> ORGANISM: Artificial Sequence
<220> FEATURE:
<223> OTHER INFORMATION: Synthetic primer

<400> SEQUENCE: 50
gggcatgtgt gagttttgtc tgatcccccg ccaccggaac ctccaccgcc tgatccaccc   60
ccacctgatc cgccgccacc ggacccacct ccgccggagc caccgccacc gggaaatggg  120
gctcgcagga gg                                                      132

<210> SEQ ID NO 51
<211> LENGTH: 23
<212> TYPE: DNA
<213> ORGANISM: Artificial Sequence
<220> FEATURE:

<223> OTHER INFORMATION: Synthetic primer

<400> SEQUENCE: 51
gacaaaactc acacatgccc acc 23

<210> SEQ ID NO 52
<211> LENGTH: 23
<212> TYPE: DNA
<213> ORGANISM: Artificial Sequence
<220> FEATURE:
<223> OTHER INFORMATION: Synthetic primer

<400> SEQUENCE: 52
gcagaattct catttacccg gag 23

<210> SEQ ID NO 53
<211> LENGTH: 152
<212> TYPE: DNA
<213> ORGANISM: Artificial Sequence
<220> FEATURE:
<223> OTHER INFORMATION: Synthetic primer

<400> SEQUENCE: 53
gagttccgga gctgggcacg gtgggcatgt gtgagttttg tctgatcccc cgccaccgga 60
acctccaccg cctgatccac ccccacctga tccgccgcca ccggacccac ctccgccgga 120
gccaccgcca cctcggcctt ggggtttgct gg 152

<210> SEQ ID NO 54
<211> LENGTH: 82
<212> TYPE: DNA
<213> ORGANISM: Artificial Sequence
<220> FEATURE:
<223> OTHER INFORMATION: Synthetic primer

<400> SEQUENCE: 54
cagtctggat ccggcggtgg aggttccggt gggggtggat caaggaagag gaggaagagg 60
attgtggggg gcaaggtgtg cc 82

<210> SEQ ID NO 55
<211> LENGTH: 37
<212> TYPE: DNA
<213> ORGANISM: Artificial Sequence
<220> FEATURE:
<223> OTHER INFORMATION: Synthetic primer

<400> SEQUENCE: 55
atgtctgaat tctcatttac ccggagacag ggagagg 37

<210> SEQ ID NO 56
<211> LENGTH: 10
<212> TYPE: PRT
<213> ORGANISM: Artificial Sequence
<220> FEATURE:
<223> OTHER INFORMATION: Synthetic peptide

<400> SEQUENCE: 56

Gly Gly Gly Gly Ser Gly Gly Gly Gly Ser
1 5 10

<210> SEQ ID NO 57
<211> LENGTH: 5
<212> TYPE: PRT
<213> ORGANISM: Artificial Sequence
<220> FEATURE:

<223> OTHER INFORMATION: Synthetic peptide

<400> SEQUENCE: 57

Gly Gly Gly Gly Ser
1               5

<210> SEQ ID NO 58
<211> LENGTH: 102
<212> TYPE: DNA
<213> ORGANISM: Artificial Sequence
<220> FEATURE:
<223> OTHER INFORMATION: Synthetic primer

<400> SEQUENCE: 58
actgacaagc ttgccgccac catggagaca gacacactcc tgctatgggt actgctgctc 60
tgggttccag gttccactgg tattgtgggg ggcaaggtgt gc 102

<210> SEQ ID NO 59
<211> LENGTH: 36
<212> TYPE: DNA
<213> ORGANISM: Artificial Sequence
<220> FEATURE:
<223> OTHER INFORMATION: Synthetic primer

<400> SEQUENCE: 59
actgacgcgg ccgcgccgcc accatggtct cccagg 36

<210> SEQ ID NO 60
<211> LENGTH: 35
<212> TYPE: DNA
<213> ORGANISM: Artificial Sequence
<220> FEATURE:
<223> OTHER INFORMATION: Synthetic primer

<400> SEQUENCE: 60
actgacctcg agttatcggc cttggggttt gctgg 35

<210> SEQ ID NO 61
<211> LENGTH: 118
<212> TYPE: DNA
<213> ORGANISM: Artificial Sequence
<220> FEATURE:
<223> OTHER INFORMATION: Synthetic primer

<400> SEQUENCE: 61
ractgacgga tcccccgcca ccggaacctc caccgcctga tccaccccca cctgatccgc 60
cgccaccgga cccacctccg ccggagccac cgccacctcg gccttggggt ttgctggc 118

<210> SEQ ID NO 62
<211> LENGTH: 35
<212> TYPE: DNA
<213> ORGANISM: Artificial Sequence
<220> FEATURE:
<223> OTHER INFORMATION: Synthetic primer

<400> SEQUENCE: 62
actgacgcgg ccgcgccgcc accatggaga cagac 35

<210> SEQ ID NO 63
<211> LENGTH: 36
<212> TYPE: DNA
<213> ORGANISM: Artificial Sequence
<220> FEATURE:
<223> OTHER INFORMATION: Synthetic primer

<400> SEQUENCE: 63
actgacctcg agttagggaa atggggctcg caggag 36

<210> SEQ ID NO 64
<211> LENGTH: 30
<212> TYPE: DNA
<213> ORGANISM: Artificial Sequence
<220> FEATURE:
<223> OTHER INFORMATION: Synthetic primer

<400> SEQUENCE: 64
agctctcgag tcatttaccc ggagacaggg 30

<210> SEQ ID NO 65
<211> LENGTH: 10
<212> TYPE: PRT
<213> ORGANISM: Artificial Sequence
<220> FEATURE:
<223> OTHER INFORMATION: Synthetic peptide

<400> SEQUENCE: 65

Gly Gly Gly Gly Ser Ala Leu Arg Pro Arg
1 5 10

<210> SEQ ID NO 66
<211> LENGTH: 1272
<212> TYPE: PRT
<213> ORGANISM: Artificial Sequence
<220> FEATURE:
<223> OTHER INFORMATION: Synthetic construct: FVII-027 amino acid sequence

<400> SEQUENCE: 66

Met Val Ser Gln Ala Leu Arg Leu Leu Cys Leu Leu Leu Gly Leu Gln
1 5 10 15

Gly Cys Leu Ala Ala Val Phe Val Thr Gln Glu Glu Ala His Gly Val
20 25 30

Leu His Arg Arg Arg Arg Ala Asn Ala Phe Leu Glu Glu Leu Arg Pro
35 40 45

Gly Ser Leu Glu Arg Glu Cys Lys Glu Glu Gln Cys Ser Phe Glu Glu
50 55 60

Ala Arg Glu Ile Phe Lys Asp Ala Glu Arg Thr Lys Leu Phe Trp Ile
65 70 75 80

Ser Tyr Ser Asp Gly Asp Gln Cys Ala Ser Ser Pro Cys Gln Asn Gly
85 90 95

Gly Ser Cys Lys Asp Gln Leu Gln Ser Tyr Ile Cys Phe Cys Leu Pro
100 105 110

Ala Phe Glu Gly Arg Asn Cys Glu Thr His Lys Asp Asp Gln Leu Ile
115 120 125

Cys Val Asn Glu Asn Gly Gly Cys Glu Gln Tyr Cys Ser Asp His Thr
130 135 140

Gly Thr Lys Arg Ser Cys Arg Cys His Glu Gly Tyr Ser Leu Leu Ala
145 150 155 160

Asp Gly Val Ser Cys Thr Pro Thr Val Glu Tyr Pro Cys Gly Lys Ile
165 170 175

Pro Ile Leu Glu Lys Arg Asn Ala Ser Lys Pro Gln Gly Arg Ile Val
180 185 190

Gly Gly Lys Val Cys Pro Lys Gly Glu Cys Pro Trp Gln Val Leu Leu
195 200 205

```
Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
```

-continued

```
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Arg Arg Arg
    690                 695                 700

Arg Ser Gly Gly Gly Gly Ser Gly Gly Gly Gly Ser Gly Gly Gly Gly
705                 710                 715                 720

Ser Gly Gly Gly Gly Ser Gly Gly Gly Gly Ser Gly Gly Gly Gly Ser
                725                 730                 735

Arg Lys Arg Arg Lys Arg Ala Glu Val Gln Leu Val Gln Ser Gly Ala
            740                 745                 750

Glu Val Asn Lys Pro Gly Ala Ser Val Lys Val Ser Cys Lys Ala Ser
        755                 760                 765

Gly Tyr Thr Phe Thr Gly Tyr Tyr Met His Trp Val Arg Gln Ala Pro
    770                 775                 780

Gly Gln Gly Leu Glu Trp Met Gly Trp Ile Asn Pro Asn Ser Gly Gly
785                 790                 795                 800

Thr Asn Tyr Ala Gln Lys Phe Gln Gly Trp Val Thr Met Thr Arg Asp
                805                 810                 815

Thr Ser Ile Ser Thr Ala Tyr Met Glu Leu Ser Arg Leu Arg Ser Asp
            820                 825                 830

Asp Thr Ala Val Tyr Tyr Cys Ala Arg Gly Arg Ala Leu Tyr Asn Arg
        835                 840                 845

Asn Asp Arg Ser Pro Asn Trp Phe Asp Pro Trp Gly Gln Gly Thr Leu
    850                 855                 860

Val Thr Val Ser Ser Gly Ser Ala Ser Ala Pro Thr Leu Lys Leu Glu
865                 870                 875                 880

Glu Gly Glu Phe Ser Glu Ala Arg Val Gln Ala Val Leu Thr Gln Pro
                885                 890                 895

Pro Ser Val Ser Val Ala Pro Gly Gln Thr Ala Arg Ile Thr Cys Gly
            900                 905                 910

Gly Asn Asn Ile Gly Ser Lys Ser Val Gln Trp Tyr Gln Gln Lys Pro
        915                 920                 925

Gly Gln Ala Pro Val Leu Val Val Tyr Asp Asp Ser Asp Arg Pro Ser
    930                 935                 940

Gly Ile Pro Glu Arg Phe Ser Gly Ser Asn Ser Gly Asn Met Ala Thr
945                 950                 955                 960

Leu Thr Ile Ser Arg Val Glu Ala Gly Asp Glu Ala Asp Tyr Tyr Cys
                965                 970                 975

Gln Val Trp Asp Ser Ser Ser Asp His Val Val Phe Gly Gly Gly Thr
            980                 985                 990

Lys Leu Thr Val Leu Gly Gln Pro  Lys Ala Ala Pro Ser  Val Thr Leu
        995                 1000                1005

Phe Pro  Pro Ser Ala Ala Ala  Gly Gly Gly Gly Ser  Gly Gly Gly
    1010                1015                1020

Gly Ser  Gly Gly Gly Gly Ser  Gly Gly Gly Gly Ser  Gly Gly Gly
    1025                1030                1035

Gly Ser  Gly Gly Gly Gly Ser  Asp Lys Thr His Thr  Cys Pro Pro
    1040                1045                1050
```

```
Cys Pro  Ala Pro Glu Leu Leu  Gly Gly Pro Ser Val  Phe Leu Phe
    1055                 1060                 1065

Pro Pro  Lys Pro Lys Asp Thr  Leu Met Ile Ser Arg  Thr Pro Glu
    1070                 1075                 1080

Val Thr  Cys Val Val Val Asp  Val Ser His Glu Asp  Pro Glu Val
    1085                 1090                 1095

Lys Phe  Asn Trp Tyr Val Asp  Gly Val Glu Val His  Asn Ala Lys
    1100                 1105                 1110

Thr Lys  Pro Arg Glu Glu Gln  Tyr Asn Ser Thr Tyr  Arg Val Val
    1115                 1120                 1125

Ser Val  Leu Thr Val Leu His  Gln Asp Trp Leu Asn  Gly Lys Glu
    1130                 1135                 1140

Tyr Lys  Cys Lys Val Ser Asn  Lys Ala Leu Pro Ala  Pro Ile Glu
    1145                 1150                 1155

Lys Thr  Ile Ser Lys Ala Lys  Gly Gln Pro Arg Glu  Pro Gln Val
    1160                 1165                 1170

Tyr Thr  Leu Pro Pro Ser Arg  Asp Glu Leu Thr Lys  Asn Gln Val
    1175                 1180                 1185

Ser Leu  Thr Cys Leu Val Lys  Gly Phe Tyr Pro Ser  Asp Ile Ala
    1190                 1195                 1200

Val Glu  Trp Glu Ser Asn Gly  Gln Pro Glu Asn Asn  Tyr Lys Thr
    1205                 1210                 1215

Thr Pro  Pro Val Leu Asp Ser  Asp Gly Ser Phe Phe  Leu Tyr Ser
    1220                 1225                 1230

Lys Leu  Thr Val Asp Lys Ser  Arg Trp Gln Gln Gly  Asn Val Phe
    1235                 1240                 1245

Ser Cys  Ser Val Met His Glu  Ala Leu His Asn His  Tyr Thr Gln
    1250                 1255                 1260

Lys Ser  Leu Ser Leu Ser Pro  Gly Lys
    1265                 1270
```

<210> SEQ ID NO 67
<211> LENGTH: 3819
<212> TYPE: DNA
<213> ORGANISM: Artificial Sequence
<220> FEATURE:
<223> OTHER INFORMATION: Synthetic construct: DNA sequence of FVII-027

<400> SEQUENCE: 67

```
atggtctccc aggccctcag gctcctctgc cttctgcttg ggcttcaggg ctgcctggct     60

gcagtcttcg taacccagga ggaagcccac ggcgtcctgc accggcgccg gcgcgccaac    120

gcgttcctgg aggagctgcg gccgggctcc ctggagaggg agtgcaagga ggagcagtgc    180

tccttcgagg aggcccggga gatcttcaag gacgcggaga ggacgaagct gttctggatt    240

tcttacagtg atggggacca gtgtgcctca agtccatgcc agaatggggg ctcctgcaag    300

gaccagctcc agtcctatat ctgcttctgc ctccctgcct tcgagggccg gaactgtgag    360

acgcacaagg atgaccagct gatctgtgtg aacgagaacg gcggctgtga gcagtactgc    420

agtgaccaca cgggcaccaa gcgctcctgt cggtgccacg aggggtactc tctgctggca    480

gacggggtgt cctgcacacc cacagttgaa tatccatgtg gaaaaatacc tattctagaa    540

aaaagaaatg ccagcaaacc ccaaggccga attgtggggg gcaaggtgtg ccccaaaggg    600

gagtgtccat ggcaggtcct gttgttggtg aatggagctc agttgtgtgg ggggaccctg    660

atcaacacca tctgggtggt ctccgcggcc cactgtttcg acaaaatcaa gaactggagg    720
```

aacctgatcg cggtgctggg cgagcacgac ctcagcgagc acgacgggga tgagcagagc 780
cggcgggtgg cgcaggtcat catccccagc acgtacgtcc cgggcaccac caaccacgac 840
atcgcgctgc tccgcctgca ccagcccgtg gtcctcactg accatgtggt gcccctctgc 900
ctgcccgaac ggacgttctc tgagaggacg ctggccttcg tgcgcttctc attggtcagc 960
ggctggggcc agctgctgga ccgtggcgcc acggccctgg agctcatggt cctcaacgtg 1020
ccccggctga tgacccagga ctgcctgcag cagtcacgga aggtgggaga ctccccaaat 1080
atcacggagt acatgttctg tgccggctac tcggatggca gcaaggactc ctgcaagggg 1140
gacagtggag gcccacatgc cacccactac cggggcacgt ggtacctgac gggcatcgtc 1200
agctggggcc agggctgcgc aaccgtgggc cactttgggg tgtacaccag ggtctcccag 1260
tacatcgagt ggctgcaaaa gctcatgcgc tcagagccac gcccaggagt cctcctgcga 1320
gccccatttc ccggtggcgg tggctccggc ggaggtgggt ccggtggcgg cggatcaggt 1380
gggggtggat caggcggtgg aggttccggt ggcgggggat ccgacaaaac tcacacatgc 1440
ccaccgtgcc cagctccgga actcctgggc ggaccgtcag tcttcctctt ccccccaaaa 1500
cccaaggaca ccctcatgat ctcccggacc cctgaggtca catgcgtggt ggtggacgtg 1560
agccacgaag accctgaggt caagttcaac tggtacgtgg acggcgtgga ggtgcataat 1620
gccaagacaa agccgcggga ggagcagtac aacagcacgt accgtgtggt cagcgtcctc 1680
accgtcctgc accaggactg gctgaatggc aaggagtaca agtgcaaggt ctccaacaaa 1740
gccctcccag cccccatcga gaaaaccatc tccaaagcca aagggcagcc ccgagaacca 1800
caggtgtaca ccctgccccc atcccgggat gagctgacca agaaccaggt cagcctgacc 1860
tgcctggtca aaggcttcta tcccagcgac atcgccgtgg agtgggagag caatgggcag 1920
ccggagaaca actacaagac cacgcctccc gtgttggact ccgacggctc cttcttcctc 1980
tacagcaagc tcaccgtgga caagagcagg tggcagcagg ggaacgtctt ctcatgctcc 2040
gtgatgcatg aggctctgca caaccactac acgcagaaga gcctctccct gtctccgggt 2100
aaacggcgcc gccggagcgg tggcggcgga tcaggtgggg gtggatcagg cggtggaggt 2160
tccggtggcg gggggatccgg cggtggaggt tccggtgggg gtggatcaag gaagaggagg 2220
aagagggcgg aagtgcagct ggtgcagtct ggagctgagg tgaataagcc tggggcctca 2280
gtgaaggtct cctgcaaggc ttctggatac accttcaccg gctactatat gcactgggtg 2340
cgacaggccc ctggacaagg gcttgagtgg atgggatgga tcaaccctaa cagtggtggc 2400
acaaactatg cacagaagtt tcagggctgg gtcaccatga ccagggacac gtccatcagc 2460
accgcctaca tggagctgag caggctgaga tctgacgaca cggccgtgta ttactgtgcg 2520
agaggccgtg ctttgtataa ccggaacgac cggtccccca actggttcga cccctggggc 2580
cagggaaccc tggtcaccgt ctcctcaggg agtgcatccg ccccaaccct taagcttgaa 2640
gaaggtgaat tctcagaagc acgcgtacag gctgtgctga ctcagccgcc ctcggtgtca 2700
gtggccccag gacagacggc caggattacc tgtgggggaa acaacattgg aagtaaaagt 2760
gtgcagtggt accagcagaa gccaggccag gcccctgtgc tggtcgtcta tgatgatagc 2820
gaccggccct cagggatccc tgagcgattc tctggctcca actctgggaa catggccacc 2880
ctgaccatca gcagggtcga agccggggat gaggccgact attactgtca ggtgtgggat 2940
agtagtagtg atcatgtggt attcggcgga gggaccaagc tgaccgtcct aggtcagccc 3000
aaggctgccc cctcggtcac tctgttcccg ccgtccgcgg ccgctggtgg cggtggctcc 3060
ggcggaggtg ggtccggtgg cggcggatca ggtgggggtg gatcaggcgg tggaggttcc 3120
ggtggcgggg gatcagacaa aactcacaca tgcccaccgt gcccagcacc tgaactcctg 3180
ggaggaccgt cagtcttcct cttcccccca aaacccaagg acaccctcat gatctcccgg 3240
acccctgagg tcacatgcgt ggtggtggac gtgagccacg aagaccctga ggtcaagttc 3300
aactggtacg tggacggcgt ggaggtgcat aatgccaaga caaagccgcg ggaggagcag 3360
tacaacagca cgtaccgtgt ggtcagcgtc ctcaccgtcc tgcaccagga ctggctgaat 3420
ggcaaggagt acaagtgcaa ggtctccaac aaagccctcc cagcccccat cgagaaaacc 3480
atctccaaag ccaaagggca gccccgagaa ccacaggtgt acaccctgcc cccatcccgc 3540
gatgagctga ccaagaacca ggtcagcctg acctgcctgg tcaaaggctt ctatcccagc 3600
gacatcgccg tggagtggga gagcaatggg cagccggaga acaactacaa gaccacgcct 3660
cccgtgttgg actccgacgg ctccttcttc ctctacagca agctcaccgt ggacaagagc 3720
aggtggcagc aggggaacgt cttctcatgc tccgtgatgc atgaggctct gcacaaccac 3780
tacacgcaga agagcctctc cctgtctccg ggtaaatga 3819

<210> SEQ ID NO 68
<211> LENGTH: 577
<212> TYPE: DNA
<213> ORGANISM: Artificial Sequence
<220> FEATURE:
<223> OTHER INFORMATION: Synthetic construct: Genscript-FVII-027-1 DNA sequence

<400> SEQUENCE: 68
gaagagcctc tccctgtctc cgggtaaacg gcgccgccgg agcggtggcg gcggatcagg 60
tgggggtgga tcaggcggtg gaggttccgg tggcggggga tccggcggtg gaggttccgg 120
tgggggtgga tcaaggaaga ggaggaagag ggcggaagtg cagctggtgc agtctggagc 180
tgaggtgaat aagcctgggg cctcagtgaa ggtctcctgc aaggcttctg gatacacctt 240
caccggctac tatatgcact gggtgcgaca ggcccctgga caagggcttg agtggatggg 300
atggatcaac cctaacagtg gtggcacaaa ctatgcacag aagtttcagg gctgggtcac 360
catgaccagg gacacgtcca tcagcaccgc ctacatggag ctgagcaggc tgagatctga 420
cgacacggcc gtgtattact gtgcgagagg ccgtgctttg tataaccgga acgaccggtc 480 cccaactgg ttcgacccct ggggccaggg aaccctggtc accgtctcct cagggagtgc 540
atccgcccca acccttaagc ttgaagaagg tgaattc 577

<210> SEQ ID NO 69
<211> LENGTH: 1179
<212> TYPE: DNA
<213> ORGANISM: Artificial Sequence
<220> FEATURE:
<223> OTHER INFORMATION: Synthetic construct: Genscript-FVII-026-2 DNA sequence

<400> SEQUENCE: 69
gaattctcag aagcacgcgt acaggctgtg ctgactcagc cgccctcggt gtcagtggcc 60
ccaggacaga cggccaggat tacctgtggg ggaaacaaca ttggaagtaa aagtgtgcag 120
tggtaccagc agaagccagg ccaggcccct gtgctggtcg tctatgatga tagcgaccgg 180
ccctcaggga tccctgagcg attctctggc tccaactctg ggaacatggc caccctgacc 240
atcagcaggg tcgaagccgg ggatgaggcc gactattact gtcaggtgtg ggatagtagt 300
agtgatcatg tggtattcgg cggagggacc aagctgaccg tcctaggtca gcccaaggct 360

-continued

```
gccccctcgg tcactctgtt cccgccgtcc gcggccgctg gtggcggtgg ctccggcgga    420
ggtgggtccg gtggcggcgg atcaggtggg ggtggatcag gcggtggagg ttccggtggc    480
gggggatcag acaaaactca cacatgccca ccgtgcccag cacctgaact cctgggagga    540
ccgtcagtct tcctcttccc cccaaaaccc aaggacaccc tcatgatctc ccggacccct    600
gaggtcacat gcgtggtggt ggacgtgagc cacgaagacc ctgaggtcaa gttcaactgg    660
tacgtggacg gcgtggaggt gcataatgcc aagacaaagc cgcgggagga gcagtacaac    720
agcacgtacc gtgtggtcag cgtcctcacc gtcctgcacc aggactggct gaatggcaag    780
gagtacaagt gcaaggtctc caacaaagcc ctcccagccc ccatcgagaa aaccatctcc    840
aaagccaaag ggcagccccg agaaccacag gtgtacaccc tgcccccatc ccgcgatgag    900
ctgaccaaga accaggtcag cctgacctgc ctggtcaaag gcttctatcc cagcgacatc    960
gccgtggagt gggagagcaa tgggcagccg gagaacaact acaagaccac gcctcccgtg   1020
ttggactccg acggctcctt cttcctctac agcaagctca ccgtggacaa gagcaggtgg   1080
cagcagggga acgtcttctc atgctccgtg atgcatgagg ctctgcacaa ccactacacg   1140
cagaagagcc tctccctgtc tccgggtaaa tgagaattc                          1179
```

<210> SEQ ID NO 70
<211> LENGTH: 1250
<212> TYPE: PRT
<213> ORGANISM: Artificial Sequence
<220> FEATURE:
<223> OTHER INFORMATION: Synthetic construct: FVII-037 amino acid sequence.

<400> SEQUENCE: 70

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu His Lys Asp Asp Gln Leu Ile Cys
        115                 120                 125

Val Asn Glu Asn Gly Gly Cys Glu Gln Tyr Cys Ser Asp His Thr Gly
    130                 135                 140

Thr Lys Arg Ser Cys Arg Cys His Glu Gly Tyr Ser Leu Leu Ala Asp
145                 150                 155                 160

Gly Val Ser Cys Thr Pro Thr Val Glu Tyr Pro Cys Gly Lys Ile Pro
                165                 170                 175

Ile Leu Glu Lys Arg Asn Ala Ser Lys Pro Gln Gly Arg Ile Val Gly
            180                 185                 190

Gly Lys Val Cys Pro Lys Gly Glu Cys Pro Trp Gln Val Leu Leu Leu
        195                 200                 205
```

-continued

```
Val Asn Gly Ala Gln Leu Cys Gly Gly Thr Leu Ile Asn Thr Ile Trp
    210                 215                 220

Val Val Ser Ala Ala His Cys Phe Asp Lys Ile Lys Asn Trp Arg Asn
225                 230                 235                 240

Leu Ile Ala Val Leu Gly Glu His Asp Leu Ser Glu His Asp Gly Asp
                245                 250                 255

Glu Gln Ser Arg Arg Val Ala Gln Val Ile Ile Pro Ser Thr Tyr Val
            260                 265                 270

Pro Gly Thr Thr Asn His Asp Ile Ala Leu Leu Arg Leu His Gln Pro
        275                 280                 285

Val Val Leu Thr Asp His Val Val Pro Leu Cys Leu Pro Glu Arg Thr
    290                 295                 300

Phe Ser Glu Arg Thr Leu Ala Phe Val Arg Phe Ser Leu Val Ser Gly
305                 310                 315                 320

Trp Gly Gln Leu Leu Asp Arg Gly Ala Thr Ala Leu Glu Leu Met Val
                325                 330                 335

Leu Asn Val Pro Arg Leu Met Thr Gln Asp Cys Leu Gln Gln Ser Arg
            340                 345                 350

Lys Val Gly Asp Ser Pro Asn Ile Thr Glu Tyr Met Phe Cys Ala Gly
        355                 360                 365

Tyr Ser Asp Gly Ser Lys Asp Ser Cys Lys Gly Asp Ser Gly Gly Pro
    370                 375                 380

His Ala Thr His Tyr Arg Gly Thr Trp Tyr Leu Thr Gly Ile Val Ser
385                 390                 395                 400

Trp Gly Gln Gly Cys Ala Thr Val Gly His Phe Gly Val Tyr Thr Arg
                405                 410                 415

Val Ser Gln Tyr Ile Glu Trp Leu Gln Lys Leu Met Arg Ser Glu Pro
            420                 425                 430

Arg Pro Gly Val Leu Leu Arg Ala Pro Phe Pro Gly Gly Gly Gly Ser
        435                 440                 445

Gly Gly Gly Gly Ser Gly Gly Gly Gly Ser Gly Gly Gly Gly Ser Gly
    450                 455                 460

Gly Gly Gly Ser Gly Gly Gly Gly Ser Asp Lys Thr His Thr Cys Pro
465                 470                 475                 480

Pro Cys Pro Ala Pro Glu Leu Leu Gly Gly Pro Ser Val Phe Leu Phe
                485                 490                 495

Pro Pro Lys Pro Lys Asp Thr Leu Met Ile Ser Arg Thr Pro Glu Val
            500                 505                 510

Thr Cys Val Val Val Asp Val Ser His Glu Asp Pro Glu Val Lys Phe
        515                 520                 525

Asn Trp Tyr Val Asp Gly Val Glu Val His Asn Ala Lys Thr Lys Pro
    530                 535                 540

Arg Glu Glu Gln Tyr Asn Ser Thr Tyr Arg Val Val Ser Val Leu Thr
545                 550                 555                 560

Val Leu His Gln Asp Trp Leu Asn Gly Lys Glu Tyr Lys Cys Lys Val
                565                 570                 575

Ser Asn Lys Ala Leu Pro Ala Pro Ile Glu Lys Thr Ile Ser Lys Ala
            580                 585                 590

Lys Gly Gln Pro Arg Glu Pro Gln Val Tyr Thr Leu Pro Pro Ser Arg
        595                 600                 605

Asp Glu Leu Thr Lys Asn Gln Val Ser Leu Thr Cys Leu Val Lys Gly
    610                 615                 620

Phe Tyr Pro Ser Asp Ile Ala Val Glu Trp Glu Ser Asn Gly Gln Pro
```

```
625                 630                 635                 640

Glu Asn Asn Tyr Lys Thr Thr Pro Pro Val Leu Asp Ser Asp Gly Ser
                645                 650                 655

Phe Phe Leu Tyr Ser Lys Leu Thr Val Asp Lys Ser Arg Trp Gln Gln
            660                 665                 670

Gly Asn Val Phe Ser Cys Ser Val Met His Glu Ala Leu His Asn His
        675                 680                 685

Tyr Thr Gln Lys Ser Leu Ser Leu Ser Pro Gly Lys Gly Gly Gly Gly
    690                 695                 700

Ser Gly Gly Gly Gly Ser Gly Gly Gly Gly Ser Gly Gly Gly Gly Ser
705                 710                 715                 720

Asp Lys Thr His Thr Cys Pro Pro Cys Pro Ala Pro Glu Leu Leu Gly
                725                 730                 735

Gly Pro Ser Val Phe Leu Phe Pro Pro Lys Pro Lys Asp Thr Leu Met
            740                 745                 750

Ile Ser Arg Thr Pro Glu Val Thr Cys Val Val Val Asp Val Ser His
        755                 760                 765

Glu Asp Pro Glu Val Lys Phe Asn Trp Tyr Val Asp Gly Val Glu Val
    770                 775                 780

His Asn Ala Lys Thr Lys Pro Arg Glu Glu Gln Tyr Asn Ser Thr Tyr
785                 790                 795                 800

Arg Val Val Ser Val Leu Thr Val Leu His Gln Asp Trp Leu Asn Gly
                805                 810                 815

Lys Glu Tyr Lys Cys Lys Val Ser Asn Lys Ala Leu Pro Ala Pro Ile
            820                 825                 830

Glu Lys Thr Ile Ser Lys Ala Lys Gly Gln Pro Arg Glu Pro Gln Val
        835                 840                 845

Tyr Thr Leu Pro Pro Ser Arg Asp Glu Leu Thr Lys Asn Gln Val Ser
    850                 855                 860

Leu Thr Cys Leu Val Lys Gly Phe Tyr Pro Ser Asp Ile Ala Val Glu
865                 870                 875                 880

Trp Glu Ser Asn Gly Gln Pro Glu Asn Asn Tyr Lys Thr Thr Pro Pro
                885                 890                 895

Val Leu Asp Ser Asp Gly Ser Phe Phe Leu Tyr Ser Lys Leu Thr Val
            900                 905                 910

Asp Lys Ser Arg Trp Gln Gln Gly Asn Val Phe Ser Cys Ser Val Met
        915                 920                 925

His Glu Ala Leu His Asn His Tyr Thr Gln Lys Ser Leu Ser Leu Ser
    930                 935                 940

Pro Gly Lys Gly Gly Gly Gly Ser Gly Gly Gly Gly Ser Gly Gly Gly
945                 950                 955                 960

Gly Ser Gly Gly Gly Gly Ser Gly Gly Gly Gly Ser Gly Gly Gly Gly
                965                 970                 975

Ser Ala Glu Val Gln Leu Val Gln Ser Gly Ala Glu Val Asn Lys Pro
            980                 985                 990

Gly Ala Ser Val Lys Val Ser Cys  Lys Ala Ser Gly Tyr  Thr Phe Thr
        995                 1000                1005

Gly Tyr  Tyr Met His Trp Val  Arg Gln Ala Pro Gly  Gln Gly Leu
    1010                1015                1020

Glu Trp  Met Gly Trp Ile Asn  Pro Asn Ser Gly Gly  Thr Asn Tyr
    1025                1030                1035

Ala Gln  Lys Phe Gln Gly Trp  Val Thr Met Thr Arg  Asp Thr Ser
    1040                1045                1050
```

```
Ile Ser  Thr Ala Tyr Met Glu  Leu Ser Arg Leu Arg  Ser Asp Asp
    1055                 1060                 1065

Thr Ala  Val Tyr Tyr Cys Ala  Arg Gly Arg Ala Leu  Tyr Asn Arg
    1070                 1075                 1080

Asn Asp  Arg Ser Pro Asn Trp  Phe Asp Pro Trp Gly  Gln Gly Thr
    1085                 1090                 1095

Leu Val  Thr Val Ser Ser Gly  Ser Ala Ser Ala Pro  Thr Leu Lys
    1100                 1105                 1110

Leu Glu  Glu Gly Glu Phe Ser  Glu Ala Arg Val Gln  Ala Val Leu
    1115                 1120                 1125

Thr Gln  Pro Pro Ser Val Ser  Val Ala Pro Gly Gln  Thr Ala Arg
    1130                 1135                 1140

Ile Thr  Cys Gly Gly Asn Asn  Ile Gly Ser Lys Ser  Val Gln Trp
    1145                 1150                 1155

Tyr Gln  Gln Lys Pro Gly Gln  Ala Pro Val Leu Val  Val Tyr Asp
    1160                 1165                 1170

Asp Ser  Asp Arg Pro Ser Gly  Ile Pro Glu Arg Phe  Ser Gly Ser
    1175                 1180                 1185

Asn Ser  Gly Asn Met Ala Thr  Leu Thr Ile Ser Arg  Val Glu Ala
    1190                 1195                 1200

Gly Asp  Glu Ala Asp Tyr Tyr  Cys Gln Val Trp Asp  Ser Ser Ser
    1205                 1210                 1215

Asp His  Val Val Phe Gly Gly  Gly Thr Lys Leu Thr  Val Leu Gly
    1220                 1225                 1230

Gln Pro  Lys Ala Ala Pro Ser  Val Thr Leu Phe Pro  Pro Ser Ala
    1235                 1240                 1245

Ala Ala
    1250


<210> SEQ ID NO 71
<211> LENGTH: 3756
<212> TYPE: DNA
<213> ORGANISM: Artificial Sequence
<220> FEATURE:
<223> OTHER INFORMATION: Synthetic construct: FIX-037 DNA sequence

<400> SEQUENCE: 71

atggtctccc aggccctcag gctcctctgc cttctgcttg ggcttcaggg ctgcctggct     60

gcagtcttcg taacccagga ggaagcccac ggcgtcctgc accggcgccg gcgcgccaac    120

gcgttcctgg aggagctgcg gccgggctcc ctggagaggg agtgcaagga ggagcagtgc    180

tccttcgagg aggcccggga gatcttcaag gacgcggaga ggacgaagct gttctggatt    240

tcttacagtg atggggacca gtgtgcctca agtccatgcc agaatggggg ctcctgcaag    300

gaccagctcc agtcctatat ctgcttctgc ctccctgcct tcgagggccg gaactgtgag    360

acgcacaagg atgaccagct gatctgtgtg aacgagaacg gcggctgtga gcagtactgc    420

agtgaccaca cgggcaccaa gcgctcctgt cggtgccacg aggggtactc tctgctggca    480

gacggggtgt cctgcacacc cacagttgaa tatccatgtg gaaaaatacc tattctagaa    540

aaaagaaatg ccagcaaacc ccaaggccga attgtggggg gcaaggtgtg ccccaaaggg    600

gagtgtccat ggcaggtcct gttgttggtg aatggagctc agttgtgtgg ggggaccctg    660

atcaacacca tctgggtggt ctccgcggcc cactgtttcg acaaaatcaa gaactggagg    720

aacctgatcg cggtgctggg cgagcacgac ctcagcgagc acgacgggga tgagcagagc    780
```

-continued

```
cggcgggtgg cgcaggtcat catccccagc acgtacgtcc cgggcaccac caaccacgac    840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg   1020
ccccggctga tgacccagga ctgcctgcag cagtcacgga aggtgggaga ctccccaaat   1080
atcacggagt acatgttctg tgccggctac tcggatggca gcaaggactc ctgcaagggg   1140
gacagtggag gcccacatgc cacccactac cggggcacgt ggtacctgac gggcatcgtc   1200
agctggggcc agggctgcgc aaccgtgggc cactttgggg tgtacaccag ggtctcccag   1260
tacatcgagt ggctgcaaaa gctcatgcgc tcagagccac gcccaggagt cctcctgcga   1320
gccccatttc ccggtggcgg tggctccggc ggaggtgggt ccggtggcgg cggatcaggt   1380
gggggtggat caggcggtgg aggttccggt ggcgggggat ccgacaaaac tcacacatgc   1440
ccaccgtgcc cagctccgga actcctgggc ggaccgtcag tcttcctctt ccccccaaaa   1500
cccaaggaca ccctcatgat ctcccggacc cctgaggtca catgcgtggt ggtggacgtg   1560
agccacgaag accctgaggt caagttcaac tggtacgtgg acggcgtgga ggtgcataat   1620
gccaagacaa agccgcggga ggagcagtac aacagcacgt accgtgtggt cagcgtcctc   1680
accgtcctgc accaggactg gctgaatggc aaggagtaca agtgcaaggt ctccaacaaa   1740
gccctcccag cccccatcga gaaaaccatc tccaaagcca aagggcagcc ccgagaacca   1800
caggtgtaca ccctgccccc atcccgggat gagctgacca agaaccaggt cagcctgacc   1860
tgcctggtca aaggcttcta tcccagcgac atcgccgtgg agtgggagag caatgggcag   1920
ccggagaaca actacaagac cacgcctccc gtgttggact ccgacggctc cttcttcctc   1980
tacagcaagc tcaccgtgga caagagcagg tggcagcagg ggaacgtctt ctcatgctcc   2040
gtgatgcatg aggctctgca caaccactac acgcagaaga gcctctccct gtctccgggt   2100
aaaggtggcg gcggatcagg tgggggtgga tcaggcggtg gaggttccgg tggcggggga   2160
tcagacaaaa ctcacacatg cccaccgtgc ccagcacctg aactcctggg aggaccgtca   2220
gtcttcctct tccccccaaa acccaaggac accctcatga tctcccggac ccctgaggtc   2280
acatgcgtgg tggtggacgt gagccacgaa gaccctgagg tcaagttcaa ctggtacgtg   2340
gacggcgtgg aggtgcataa tgccaagaca aagccgcggg aggagcagta caacagcacg   2400
taccgtgtgg tcagcgtcct caccgtcctg caccaggact ggctgaatgg caaggagtac   2460
aagtgcaagg tctccaacaa agccctccca gcccccatcg agaaaaccat ctccaaagcc   2520
aaagggcagc cccgagaacc acaggtgtac accctgcccc catcccgcga tgagctgacc   2580
aagaaccagg tcagcctgac ctgcctggtc aaaggcttct atcccagcga catcgccgtg   2640
gagtgggaga gcaatgggca gccggagaac aactacaaga ccacgcctcc cgtgttggac   2700
tccgacggct ccttcttcct ctacagcaag ctcaccgtcg acaagagcag gtggcagcag   2760
gggaacgtct tctcatgctc cgtgatgcat gaggctctgc acaaccacta cacgcagaag   2820
agcctctccc tgtctccggg taaaggtggc ggtggctccg gcggaggtgg gtccggtggc   2880
ggcggatcag gtgggggtgg atcaggcggt ggaggttccg gtggcggggg atcagcggaa   2940
gtgcagctgg tgcagtctgg agctgaggtg aataagcctg ggcctcagt gaaggtctcc   3000
tgcaaggctt ctggatacac cttcaccggc tactatatgc actgggtgcg acaggcccct   3060
ggacaagggc ttgagtggat gggatggatc aaccctaaca gtggtggcac aaactatgca   3120
cagaagtttc agggctgggt caccatgacc agggacacgt ccatcagcac cgcctacatg   3180
```

gagctgagca ggctgagatc tgacgacacg gccgtgtatt actgtgcgag aggccgtgct 3240
ttgtataacc ggaacgaccg gtcccccaac tggttcgacc cctggggcca gggaaccctg 3300
gtcaccgtct cctcagggag tgcatccgcc ccaaccctta agcttgaaga aggtgaattt 3360
tcagaagcac gcgtacaggc tgtgctgact cagccgccct cggtgtcagt ggccccagga 3420
cagacggcca ggattacctg tgggggaaac aacattggaa gtaaaagtgt gcagtggtac 3480
cagcagaagc caggccaggc ccctgtgctg gtcgtctatg atgatagcga ccggccctca 3540
gggatccctg agcgattctc tggctccaac tctgggaaca tggccaccct gaccatcagc 3600
agggtcgaag ccggggatga ggccgactat tactgtcagg tgtgggatag tagtagtgat 3660
catgtggtat tcggcggagg gaccaagctg accgtcctag gtcagcccaa ggctgccccc 3720
tcggtcactc tgttcccgcc gtccgcggcc gcttga 3756

<210> SEQ ID NO 72
<211> LENGTH: 1174
<212> TYPE: PRT
<213> ORGANISM: Artificial Sequence
<220> FEATURE:
<223> OTHER INFORMATION: Synthetic construct: FVII-053 amino acid sequence

<400> SEQUENCE: 72

Met Val Ser Gln Ala Leu Arg Leu Leu Cys Leu Leu Leu Gly Leu Gln
1 5 10 15

Gly Cys Leu Ala Ala Glu Val Gln Leu Val Gln Ser Gly Ala Glu Val
20 25 30

Asn Lys Pro Gly Ala Ser Val Lys Val Ser Cys Lys Ala Ser Gly Tyr
35 40 45

Thr Phe Thr Gly Tyr Tyr Met His Trp Val Arg Gln Ala Pro Gly Gln
50 55 60

Gly Leu Glu Trp Met Gly Trp Ile Asn Pro Asn Ser Gly Gly Thr Asn
65 70 75 80

Tyr Ala Gln Lys Phe Gln Gly Trp Val Thr Met Thr Arg Asp Thr Ser
85 90 95

Ile Ser Thr Ala Tyr Met Glu Leu Ser Arg Leu Arg Ser Asp Asp Thr
100 105 110

Ala Val Tyr Tyr Cys Ala Arg Gly Arg Ala Leu Tyr Asn Arg Asn Asp
115 120 125

Arg Ser Pro Asn Trp Phe Asp Pro Trp Gly Gln Gly Thr Leu Val Thr
130 135 140

Val Ser Ser Gly Ser Ala Ser Ala Pro Thr Leu Lys Leu Glu Glu Gly
145 150 155 160

Glu Phe Ser Glu Ala Arg Val Gln Ala Val Leu Thr Gln Pro Pro Ser
165 170 175

Val Ser Val Ala Pro Gly Gln Thr Ala Arg Ile Thr Cys Gly Gly Asn
180 185 190

Asn Ile Gly Ser Lys Ser Val Gln Trp Tyr Gln Gln Lys Pro Gly Gln
195 200 205

Ala Pro Val Leu Val Val Tyr Asp Asp Ser Asp Arg Pro Ser Gly Ile
210 215 220

Pro Glu Arg Phe Ser Gly Ser Asn Ser Gly Asn Met Ala Thr Leu Thr
225 230 235 240

Ile Ser Arg Val Glu Ala Gly Asp Glu Ala Asp Tyr Tyr Cys Gln Val
245 250 255

-continued

```
Trp Asp Ser Ser Ser Asp His Val Val Phe Gly Gly Gly Thr Lys Leu
            260                 265                 270

Thr Val Leu Gly Gln Pro Lys Ala Ala Pro Ser Val Thr Leu Phe Pro
        275                 280                 285

Pro Ser Ala Ala Ala Arg Thr Lys Leu Phe Trp Ile Ser Tyr Ser Asp
    290                 295                 300

Gly Asp Gln Cys Ala Ser Ser Pro Cys Gln Asn Gly Gly Ser Cys Lys
305                 310                 315                 320

Asp Gln Leu Gln Ser Tyr Ile Cys Phe Cys Leu Pro Ala Phe Glu Gly
                325                 330                 335

Arg Asn Cys Glu Thr His Lys Asp Asp Gln Leu Ile Cys Val Asn Glu
            340                 345                 350

Asn Gly Gly Cys Glu Gln Tyr Cys Ser Asp His Thr Gly Thr Lys Arg
        355                 360                 365

Ser Cys Arg Cys His Glu Gly Tyr Ser Leu Leu Ala Asp Gly Val Ser
    370                 375                 380

Cys Thr Pro Thr Val Glu Tyr Pro Cys Gly Lys Ile Pro Ile Leu Glu
385                 390                 395                 400

Lys Arg Asn Ala Ser Lys Pro Gln Gly Arg Arg Lys Arg Arg Lys Arg
                405                 410                 415

Ile Val Gly Gly Lys Val Cys Pro Lys Gly Glu Cys Pro Trp Gln Val
            420                 425                 430

Leu Leu Leu Val Asn Gly Ala Gln Leu Cys Gly Gly Thr Leu Ile Asn
        435                 440                 445

Thr Ile Trp Val Val Ser Ala Ala His Cys Phe Asp Lys Ile Lys Asn
    450                 455                 460

Trp Arg Asn Leu Ile Ala Val Leu Gly Glu His Asp Leu Ser Glu His
465                 470                 475                 480

Asp Gly Asp Glu Gln Ser Arg Arg Val Ala Gln Val Ile Ile Pro Ser
                485                 490                 495

Thr Tyr Val Pro Gly Thr Thr Asn His Asp Ile Ala Leu Leu Arg Leu
            500                 505                 510

His Gln Pro Val Val Leu Thr Asp His Val Val Pro Leu Cys Leu Pro
        515                 520                 525

Glu Arg Thr Phe Ser Glu Arg Thr Leu Ala Phe Val Arg Phe Ser Leu
    530                 535                 540

Val Ser Gly Trp Gly Gln Leu Leu Asp Arg Gly Ala Thr Ala Leu Glu
545                 550                 555                 560

Leu Met Val Leu Asn Val Pro Arg Leu Met Thr Gln Asp Cys Leu Gln
                565                 570                 575

Gln Ser Arg Lys Val Gly Asp Ser Pro Asn Ile Thr Glu Tyr Met Phe
            580                 585                 590

Cys Ala Gly Tyr Ser Asp Gly Ser Lys Asp Ser Cys Lys Gly Asp Ser
        595                 600                 605

Gly Gly Pro His Ala Thr His Tyr Arg Gly Thr Trp Tyr Leu Thr Gly
    610                 615                 620

Ile Val Ser Trp Gly Gln Gly Cys Ala Thr Val Gly His Phe Gly Val
625                 630                 635                 640

Tyr Thr Arg Val Ser Gln Tyr Ile Glu Trp Leu Gln Lys Leu Met Arg
                645                 650                 655

Ser Glu Pro Arg Pro Gly Val Leu Leu Arg Ala Pro Phe Pro Gly Gly
            660                 665                 670
```

```
Gly Gly Ser Gly Gly Gly Gly Ser Gly Gly Gly Gly Ser Gly Gly Gly
        675                 680                 685

Gly Ser Gly Gly Gly Gly Ser Gly Gly Gly Gly Ser Asp Lys Thr His
    690                 695                 700

Thr Cys Pro Pro Cys Pro Ala Pro Glu Leu Leu Gly Gly Pro Ser Val
705                 710                 715                 720

Phe Leu Phe Pro Pro Lys Pro Lys Asp Thr Leu Met Ile Ser Arg Thr
                725                 730                 735

Pro Glu Val Thr Cys Val Val Val Asp Val Ser His Glu Asp Pro Glu
            740                 745                 750

Val Lys Phe Asn Trp Tyr Val Asp Gly Val Glu Val His Asn Ala Lys
        755                 760                 765

Thr Lys Pro Arg Glu Glu Gln Tyr Asn Ser Thr Tyr Arg Val Val Ser
    770                 775                 780

Val Leu Thr Val Leu His Gln Asp Trp Leu Asn Gly Lys Glu Tyr Lys
785                 790                 795                 800

Cys Lys Val Ser Asn Lys Ala Leu Pro Ala Pro Ile Glu Lys Thr Ile
                805                 810                 815

Ser Lys Ala Lys Gly Gln Pro Arg Glu Pro Gln Val Tyr Thr Leu Pro
            820                 825                 830

Pro Ser Arg Asp Glu Leu Thr Lys Asn Gln Val Ser Leu Thr Cys Leu
        835                 840                 845

Val Lys Gly Phe Tyr Pro Ser Asp Ile Ala Val Glu Trp Glu Ser Asn
    850                 855                 860

Gly Gln Pro Glu Asn Asn Tyr Lys Thr Thr Pro Pro Val Leu Asp Ser
865                 870                 875                 880

Asp Gly Ser Phe Phe Leu Tyr Ser Lys Leu Thr Val Asp Lys Ser Arg
                885                 890                 895

Trp Gln Gln Gly Asn Val Phe Ser Cys Ser Val Met His Glu Ala Leu
            900                 905                 910

His Asn His Tyr Thr Gln Lys Ser Leu Ser Leu Ser Pro Gly Lys Gly
        915                 920                 925

Gly Gly Gly Ser Gly Gly Gly Gly Ser Gly Gly Gly Gly Ser Gly Gly
    930                 935                 940

Gly Gly Ser Asp Lys Thr His Thr Cys Pro Pro Cys Pro Ala Pro Glu
945                 950                 955                 960

Leu Leu Gly Gly Pro Ser Val Phe Leu Phe Pro Pro Lys Pro Lys Asp
                965                 970                 975

Thr Leu Met Ile Ser Arg Thr Pro Glu Val Thr Cys Val Val Val Asp
            980                 985                 990

Val Ser His Glu Asp Pro Glu Val  Lys Phe Asn Trp Tyr  Val Asp Gly
        995                 1000                1005

Val Glu  Val His Asn Ala Lys  Thr Lys Pro Arg Glu  Glu Gln Tyr
    1010                1015                1020

Asn Ser  Thr Tyr Arg Val Val  Ser Val Leu Thr Val  Leu His Gln
    1025                1030                1035

Asp Trp  Leu Asn Gly Lys Glu  Tyr Lys Cys Lys Val  Ser Asn Lys
    1040                1045                1050

Ala Leu  Pro Ala Pro Ile Glu  Lys Thr Ile Ser Lys  Ala Lys Gly
    1055                1060                1065

Gln Pro  Arg Glu Pro Gln Val  Tyr Thr Leu Pro Pro  Ser Arg Asp
    1070                1075                1080

Glu Leu  Thr Lys Asn Gln Val  Ser Leu Thr Cys Leu  Val Lys Gly
```

1085 1090 1095

Phe Tyr Pro Ser Asp Ile Ala Val Glu Trp Glu Ser Asn Gly Gln
1100 1105 1110

Pro Glu Asn Asn Tyr Lys Thr Thr Pro Pro Val Leu Asp Ser Asp
1115 1120 1125

Gly Ser Phe Phe Leu Tyr Ser Lys Leu Thr Val Asp Lys Ser Arg
1130 1135 1140

Trp Gln Gln Gly Asn Val Phe Ser Cys Ser Val Met His Glu Ala
1145 1150 1155

Leu His Asn His Tyr Thr Gln Lys Ser Leu Ser Leu Ser Pro Gly
1160 1165 1170

Lys

<210> SEQ ID NO 73
<211> LENGTH: 3525
<212> TYPE: DNA
<213> ORGANISM: Artificial Sequence
<220> FEATURE:
<223> OTHER INFORMATION: Synthetic construct: FVII-053 DNA sequence

<400> SEQUENCE: 73
atggtctccc aggccctcag gctcctctgc cttctgcttg ggcttcaggg ctgcctggct 60
gcggaagtgc agctggtgca gtctggagct gaggtgaata agcctggggc ctcagtgaag 120
gtctcctgca aggcttctgg atacaccttc accggctact atatgcactg ggtgcgacag 180
gcccctggac aagggcttga gtggatggga tggatcaacc ctaacagtgg tggcacaaac 240
tatgcacaga agtttcaggg ctgggtcacc atgaccaggg acacgtccat cagcaccgcc 300
tacatggagc tgagcaggct gagatctgac gacacggccg tgtattactg tgcgagaggc 360
cgtgctttgt ataaccggaa cgaccggtcc cccaactggt tcgacccctg gggccaggga 420
accctggtca ccgtctcctc agggagtgca tccgccccaa cccttaaact tgaagaaggt 480
gaattttcag aagcacgcgt acaggctgtg ctgactcagc cgccctcggt gtcagtggcc 540
ccaggacaga cggccaggat tacctgtggg ggaaacaaca ttggaagtaa aagtgtgcag 600
tggtaccagc agaagccagg ccaggcccct gtgctggtcg tctatgatga tagcgaccgg 660
ccctcaggga tccctgagcg attctctggc tccaactctg ggaacatggc caccctgacc 720
atcagcaggg tcgaagccgg ggatgaggcc gactattact gtcaggtgtg ggatagtagt 780
agtgatcatg tggtattcgg cggagggacc aagctgaccg tcctaggtca gcccaaggct 840
gccccctcgg tcactctgtt cccgccgtcc gcggccgcta ggacgaagct gttctggatt 900
tcttacagtg atggggacca gtgtgcctca agtccatgcc agaatggggg ctcctgcaag 960
gaccagctcc agtcctatat ctgcttctgc ctccctgcct tcgagggccg gaactgtgag 1020
acgcacaagg atgaccagct gatctgtgtg aacgagaacg gcggctgtga gcagtactgc 1080
agtgaccaca cgggcaccaa gcgctcctgt cggtgccacg aggggtactc tctgctggca 1140
gacggggtgt cctgcacacc cacagttgaa tatccatgtg gaaaaatacc tattctagaa 1200
aaaagaaatg ccagcaaacc ccaaggccga aggaagagga ggaagaggat tgtgggggc 1260 aaggtgtgcc ccaaagggga gtgtccatgg caggtcctgt tgttggtgaa tggagctcag 1320
ttgtgtgggg ggaccctgat caacaccatc tgggtggtct ccgcggccca ctgtttcgac 1380
aaaatcaaga actggaggaa cctgatcgcg gtgctgggcg agcacgacct cagcgagcac 1440
gacggggatg agcagagccg gcgggtggcg caggtcatca tccccagcac gtacgtcccg 1500

-continued

```
ggcaccacca accacgacat cgcgctgctc cgcctgcacc agcccgtggt cctcactgac   1560

catgtggtgc ccctctgcct gcccgaacgg acgttctctg agaggacgct ggccttcgtg   1620

cgcttctcat tggtcagcgg ctggggccag ctgctggacc gtggcgccac ggccctggag   1680

ctcatggtcc tcaacgtgcc ccggctgatg acccaggact gcctgcagca gtcacggaag   1740

gtgggagact ccccaaatat cacggagtac atgttctgtg ccggctactc ggatggcagc   1800

aaggactcct gcaaggggga cagtggaggc ccacatgcca cccactaccg gggcacgtgg   1860

tacctgacgg gcatcgtcag ctggggccag ggctgcgcaa ccgtgggcca ctttggggtg   1920

tacaccaggg tctcccagta catcgagtgg ctgcaaaagc tcatgcgctc agagccacgc   1980

ccaggagtcc tcctgcgagc cccatttccc ggtggcggtg gctccggcgg aggtgggtcc   2040

ggtggcggcg gatcaggtgg gggtggatca ggcggtggag gttccggtgg cgggggatcc   2100

gacaaaactc acacatgccc accgtgccca gctccggaac tcctgggcgg accgtcagtc   2160

ttcctcttcc ccccaaaacc caaggacacc ctcatgatct cccggacccc tgaggtcaca   2220

tgcgtggtgg tggacgtgag ccacgaagac cctgaggtca agttcaactg gtacgtggac   2280

ggcgtggagg tgcataatgc caagacaaag ccgcgggagg agcagtacaa cagcacgtac   2340

cgtgtggtca gcgtcctcac cgtcctgcac caggactggc tgaatggcaa ggagtacaag   2400

tgcaaggtct ccaacaaagc cctcccagcc cccatcgaga aaaccatctc caaagccaaa   2460

gggcagcccc gagaaccaca ggtgtacacc ctgcccccat cccgggatga gctgaccaag   2520

aaccaggtca gcctgacctg cctggtcaaa ggcttctatc ccagcgacat cgccgtggag   2580

tgggagagca atgggcagcc ggagaacaac tacaagacca cgcctcccgt gttggactcc   2640

gacggctcct tcttcctcta cagcaagctc accgtggaca agagcaggtg gcagcagggg   2700

aacgtcttct catgctccgt gatgcatgag gctctgcaca accactacac gcagaagagc   2760

ctctccctgt ctccgggtaa aggtggcggc ggatcaggtg ggggtggatc aggcggtgga   2820

ggttccggtg gcgggggatc cgacaaaact cacacatgcc caccgtgccc agcacctgaa   2880

ctcctgggag gaccgtcagt cttcctcttc cccccaaaac ccaaggacac cctcatgatc   2940

tcccggaccc ctgaggtcac atgcgtggtg gtggacgtga gccacgaaga ccctgaggtc   3000

aagttcaact ggtacgtgga cggcgtggag gtgcataatg ccaagacaaa gccgcgggag   3060

gagcagtaca acagcacgta ccgtgtggtc agcgtcctca ccgtcctgca ccaggactgg   3120

ctgaatggca aggagtacaa gtgcaaggtc tccaacaaag ccctcccagc ccccatcgag   3180

aaaaccatct ccaaagccaa agggcagccc cgagaaccac aggtgtacac cctgccccca   3240

tcccgcgatg agctgaccaa gaaccaggtc agcctgacct gcctggtcaa aggcttctat   3300

cccagcgaca tcgccgtgga gtgggagagc aatgggcagc cggagaacaa ctacaagacc   3360

acgcctcccg tgttggactc cgacggctcc ttcttcctct acagcaagct caccgtggac   3420

aagagcaggt ggcagcaggg gaacgtcttc tcatgctccg tgatgcatga ggctctgcac   3480

aaccactaca cgcagaagag cctctccctg tctccgggta aatga                   3525
```

<210> SEQ ID NO 74
<211> LENGTH: 982
<212> TYPE: PRT
<213> ORGANISM: Artificial Sequence
<220> FEATURE:
<223> OTHER INFORMATION: Synthetic construct: FVII-044 amino acid sequence

<400> SEQUENCE: 74

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
```

```
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Gly Gly Gly
    690                 695                 700

Gly Ser Gly Gly Gly Gly Ser Gly Gly Gly Gly Ser Gly Gly Gly Gly
705                 710                 715                 720

Ser Asp Lys Thr His Thr Cys Pro Pro Cys Pro Ala Pro Glu Leu Leu
                725                 730                 735

Gly Gly Pro Ser Val Phe Leu Phe Pro Pro Lys Pro Lys Asp Thr Leu
            740                 745                 750

Met Ile Ser Arg Thr Pro Glu Val Thr Cys Val Val Val Asp Val Ser
        755                 760                 765

His Glu Asp Pro Glu Val Lys Phe Asn Trp Tyr Val Asp Gly Val Glu
    770                 775                 780

Val His Asn Ala Lys Thr Lys Pro Arg Glu Glu Gln Tyr Asn Ser Thr
785                 790                 795                 800

Tyr Arg Val Val Ser Val Leu Thr Val Leu His Gln Asp Trp Leu Asn
                805                 810                 815

Gly Lys Glu Tyr Lys Cys Lys Val Ser Asn Lys Ala Leu Pro Ala Pro
            820                 825                 830

Ile Glu Lys Thr Ile Ser Lys Ala Lys Gly Gln Pro Arg Glu Pro Gln
        835                 840                 845
```

```
Val Tyr Thr Leu Pro Pro Ser Arg Asp Glu Leu Thr Lys Asn Gln Val
    850                 855                 860

Ser Leu Thr Cys Leu Val Lys Gly Phe Tyr Pro Ser Asp Ile Ala Val
865                 870                 875                 880

Glu Trp Glu Ser Asn Gly Gln Pro Glu Asn Asn Tyr Lys Thr Thr Pro
                885                 890                 895

Pro Val Leu Asp Ser Asp Gly Ser Phe Phe Leu Tyr Ser Lys Leu Thr
            900                 905                 910

Val Asp Lys Ser Arg Trp Gln Gln Gly Asn Val Phe Ser Cys Ser Val
        915                 920                 925

Met His Glu Ala Leu His Asn His Tyr Thr Gln Lys Ser Leu Ser Leu
    930                 935                 940

Ser Pro Gly Lys Gly Gly Gly Gly Ser Gly Gly Gly Gly Ser Gly Gly
945                 950                 955                 960

Gly Gly Ser Gly Gly Gly Gly Ser Ala Cys Thr Glu Arg Trp Ala Leu
                965                 970                 975

His Asn Leu Cys Gly Gly
            980
```

<210> SEQ ID NO 75
<211> LENGTH: 2949
<212> TYPE: DNA
<213> ORGANISM: Artificial Sequence
<220> FEATURE:
<223> OTHER INFORMATION: Synthetic construct: FVII-044 DNA sequence

<400> SEQUENCE: 75

```
atggtctccc aggccctcag gctcctctgc cttctgcttg ggcttcaggg ctgcctggct     60

gcagtcttcg taacccagga ggaagcccac ggcgtcctgc accggcgccg gcgcgccaac    120

gcgttcctgg aggagctgcg gccgggctcc ctggagaggg agtgcaagga ggagcagtgc    180

tccttcgagg aggcccggga gatcttcaag gacgcggaga ggacgaagct gttctggatt    240

tcttacagtg atggggacca gtgtgcctca agtccatgcc agaatggggg ctcctgcaag    300

gaccagctcc agtcctatat ctgcttctgc ctccctgcct tcgagggccg gaactgtgag    360

acgcacaagg atgaccagct gatctgtgtg aacgagaacg gcggctgtga gcagtactgc    420

agtgaccaca cgggcaccaa gcgctcctgt cggtgccacg aggggtactc tctgctggca    480

gacggggtgt cctgcacacc cacagttgaa tatccatgtg gaaaaatacc tattctagaa    540

aaaagaaatg ccagcaaacc ccaaggccga attgtggggg gcaaggtgtg ccccaaaggg    600

gagtgtccat ggcaggtcct gttgttggtg aatggagctc agttgtgtgg ggggaccctg    660

atcaacacca tctgggtggt ctccgcggcc cactgtttcg acaaaatcaa gaactggagg    720

aacctgatcg cggtgctggg cgagcacgac ctcagcgagc acgacgggga tgagcagagc    780

cggcgggtgg cgcaggtcat catccccagc acgtacgtcc cgggcaccac caaccacgac    840

atcgcgctgc tccgcctgca ccagcccgtg gtcctcactg accatgtggt gcccctctgc    900

ctgcccgaac ggacgttctc tgagaggacg ctggccttcg tgcgcttctc attggtcagc    960

ggctggggcc agctgctgga ccgtggcgcc acggccctgg agctcatggt cctcaacgtg   1020

ccccggctga tgacccagga ctgcctgcag cagtcacgga aggtgggaga ctccccaaat   1080

atcacggagt acatgttctg tgccggctac tcggatggca gcaaggactc ctgcaagggg   1140

gacagtggag gcccacatgc cacccactac cggggcacgt ggtacctgac gggcatcgtc   1200

agctggggcc agggctgcgc aaccgtgggc cactttgggg tgtacaccag ggtctcccag   1260
```

tacatcgagt ggctgcaaaa gctcatgcgc tcagagccac gcccaggagt cctcctgcga 1320
gccccatttc ccggtggcgg tggctccggc ggaggtgggt ccggtggcgg cggatcaggt 1380
gggggtggat caggcggtgg aggttccggt ggcgggggat ccgacaaaac tcacacatgc 1440
ccaccgtgcc cagctccgga actcctgggc ggaccgtcag tcttcctctt ccccccaaaa 1500
cccaaggaca ccctcatgat ctcccggacc cctgaggtca catgcgtggt ggtggacgtg 1560
agccacgaag accctgaggt caagttcaac tggtacgtgg acggcgtgga ggtgcataat 1620
gccaagacaa agccgcggga ggagcagtac aacagcacgt accgtgtggt cagcgtcctc 1680
accgtcctgc accaggactg gctgaatggc aaggagtaca agtgcaaggt ctccaacaaa 1740
gccctcccag cccccatcga gaaaaccatc tccaaagcca aagggcagcc ccgagaacca 1800
caggtgtaca ccctgccccc atcccgggat gagctgacca agaaccaggt cagcctgacc 1860
tgcctggtca aaggcttcta tcccagcgac atcgccgtgg agtgggagag caatgggcag 1920
ccggagaaca actacaagac cacgcctccc gtgttggact ccgacggctc cttcttcctc 1980
tacagcaagc tcaccgtgga caagagcagg tggcagcagg ggaacgtctt ctcatgctcc 2040
gtgatgcatg aggctctgca caaccactac acgcagaaga gcctctccct gtctccgggt 2100
aaaggtggcg gcggatcagg tgggggtgga tcaggcggtg gaggttccgg tggcggggga 2160
tcagacaaaa ctcacacatg cccaccgtgc ccagcacctg aactcctggg aggaccgtca 2220
gtcttcctct tccccccaaa acccaaggac accctcatga tctcccggac ccctgaggtc 2280
acatgcgtgg tggtggacgt gagccacgaa gaccctgagg tcaagttcaa ctggtacgtg 2340
gacggcgtgg aggtgcataa tgccaagaca aagccgcggg aggagcagta caacagcacg 2400
taccgtgtgg tcagcgtcct caccgtcctg caccaggact ggctgaatgg caaggagtac 2460
aagtgcaagg tctccaacaa agccctccca gcccccatcg agaaaaccat ctccaaagcc 2520
aaagggcagc cccgagaacc acaggtgtac accctgcccc catcccgcga tgagctgacc 2580
aagaaccagg tcagcctgac ctgcctggtc aaaggcttct atcccagcga catcgccgtg 2640
gagtgggaga gcaatgggca gccggagaac aactacaaga ccacgcctcc cgtgttggac 2700
tccgacggct ccttcttcct ctacagcaag ctcaccgtcg acaagagcag gtggcagcag 2760
gggaacgtct tctcatgctc cgtgatgcat gaggctctgc acaaccacta cacgcagaag 2820
agcctctccc tgtctccggg taaaggtggc ggcggatcag gtgggggtgg atcaggcggt 2880
ggaggttccg gtggcggggg atcagcctgc accgagcggt gggccctgca caacctgtgc 2940
ggcgggtga 2949

<210> SEQ ID NO 76
<211> LENGTH: 982
<212> TYPE: PRT
<213> ORGANISM: Artificial Sequence
<220> FEATURE:
<223> OTHER INFORMATION: Synthetic construct: FVII-045 amino acid sequence

<400> SEQUENCE: 76

Met Val Ser Gln Ala Leu Arg Leu Leu Cys Leu Leu Leu Gly Leu Gln
1 5 10 15

Gly Cys Leu Ala Ala Val Phe Val Thr Gln Glu Glu Ala His Gly Val
20 25 30

Leu His Arg Arg Arg Arg Ala Asn Ala Phe Leu Glu Glu Leu Arg Pro
35 40 45

-continued

```
Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Lys Thr His Thr Cys
```

-continued

```
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Gly Gly Gly
    690                 695                 700

Gly Ser Gly Gly Gly Gly Ser Gly Gly Gly Gly Ser Gly Gly Gly Gly
705                 710                 715                 720

Ser Asp Lys Thr His Thr Cys Pro Pro Cys Pro Ala Pro Glu Leu Leu
                725                 730                 735

Gly Gly Pro Ser Val Phe Leu Phe Pro Pro Lys Pro Lys Asp Thr Leu
            740                 745                 750

Met Ile Ser Arg Thr Pro Glu Val Thr Cys Val Val Val Asp Val Ser
        755                 760                 765

His Glu Asp Pro Glu Val Lys Phe Asn Trp Tyr Val Asp Gly Val Glu
    770                 775                 780

Val His Asn Ala Lys Thr Lys Pro Arg Glu Glu Gln Tyr Asn Ser Thr
785                 790                 795                 800

Tyr Arg Val Val Ser Val Leu Thr Val Leu His Gln Asp Trp Leu Asn
                805                 810                 815

Gly Lys Glu Tyr Lys Cys Lys Val Ser Asn Lys Ala Leu Pro Ala Pro
            820                 825                 830

Ile Glu Lys Thr Ile Ser Lys Ala Lys Gly Gln Pro Arg Glu Pro Gln
        835                 840                 845

Val Tyr Thr Leu Pro Pro Ser Arg Asp Glu Leu Thr Lys Asn Gln Val
    850                 855                 860

Ser Leu Thr Cys Leu Val Lys Gly Phe Tyr Pro Ser Asp Ile Ala Val
865                 870                 875                 880

Glu Trp Glu Ser Asn Gly Gln Pro Glu Asn Asn Tyr Lys Thr Thr Pro
                885                 890                 895
```

```
Pro Val Leu Asp Ser Asp Gly Ser Phe Phe Leu Tyr Ser Lys Leu Thr
            900                 905                 910

Val Asp Lys Ser Arg Trp Gln Gln Gly Asn Val Phe Ser Cys Ser Val
        915                 920                 925

Met His Glu Ala Leu His Asn His Tyr Thr Gln Lys Ser Leu Ser Leu
    930                 935                 940

Ser Pro Gly Lys Gly Gly Gly Gly Ser Gly Gly Gly Gly Ser Gly Gly
945                 950                 955                 960

Gly Gly Ser Gly Gly Gly Gly Ser Ala Cys Thr Glu Arg Met Ala Leu
                965                 970                 975

His Asn Leu Cys Gly Gly
            980
```

<210> SEQ ID NO 77
<211> LENGTH: 2949
<212> TYPE: DNA
<213> ORGANISM: Artificial Sequence
<220> FEATURE:
<223> OTHER INFORMATION: Synthetic construct: FVII-045 DNA sequence

<400> SEQUENCE: 77

```
atggtctccc aggccctcag gctcctctgc cttctgcttg ggcttcaggg ctgcctggct      60

gcagtcttcg taacccagga ggaagcccac ggcgtcctgc accggcgccg gcgcgccaac     120

gcgttcctgg aggagctgcg gccgggctcc ctggagaggg agtgcaagga ggagcagtgc     180

tccttcgagg aggcccggga gatcttcaag gacgcggaga ggacgaagct gttctggatt     240

tcttacagtg atggggacca gtgtgcctca agtccatgcc agaatggggg ctcctgcaag     300

gaccagctcc agtcctatat ctgcttctgc ctccctgcct tcgagggccg gaactgtgag     360

acgcacaagg atgaccagct gatctgtgtg aacgagaacg gcggctgtga gcagtactgc     420

agtgaccaca cgggcaccaa gcgctcctgt cggtgccacg aggggtactc tctgctggca     480

gacggggtgt cctgcacacc cacagttgaa tatccatgtg gaaaaatacc tattctagaa     540

aaaagaaatg ccagcaaacc ccaaggccga attgtggggg gcaaggtgtg ccccaaaggg     600

gagtgtccat ggcaggtcct gttgttggtg aatggagctc agttgtgtgg ggggaccctg     660

atcaacacca tctgggtggt ctccgcggcc cactgtttcg acaaaatcaa gaactggagg     720

aacctgatcg cggtgctggg cgagcacgac ctcagcgagc acgacgggga tgagcagagc     780

cggcgggtgg cgcaggtcat catccccagc acgtacgtcc cgggcaccac caaccacgac     840

atcgcgctgc tccgcctgca ccagcccgtg gtcctcactg accatgtggt gcccctctgc     900

ctgcccgaac ggacgttctc tgagaggacg ctggccttcg tgcgcttctc attggtcagc     960

ggctggggcc agctgctgga ccgtggcgcc acggccctgg agctcatggt cctcaacgtg    1020

ccccggctga tgacccagga ctgcctgcag cagtcacgga aggtgggaga ctccccaaat    1080

atcacggagt acatgttctg tgccggctac tcggatggca gcaaggactc ctgcaagggg    1140

gacagtggag gcccacatgc cacccactac cggggcacgt ggtacctgac gggcatcgtc    1200

agctggggcc agggctgcgc aaccgtgggc cactttgggg tgtacaccag ggtctcccag    1260

tacatcgagt ggctgcaaaa gctcatgcgc tcagagccac gcccaggagt cctcctgcga    1320

gccccatttc ccggtggcgg tggctccggc ggaggtgggt ccggtggcgg cggatcaggt    1380

gggggtggat caggcggtgg aggttccggt ggcgggggat ccgacaaaac tcacacatgc    1440

ccaccgtgcc cagctccgga actcctgggc ggaccgtcag tcttcctctt ccccccaaaa    1500
```

cccaaggaca ccctcatgat ctcccggacc cctgaggtca catgcgtggt ggtggacgtg 1560
agccacgaag accctgaggt caagttcaac tggtacgtgg acggcgtgga ggtgcataat 1620
gccaagacaa agccgcggga ggagcagtac aacagcacgt accgtgtggt cagcgtcctc 1680
accgtcctgc accaggactg gctgaatggc aaggagtaca agtgcaaggt ctccaacaaa 1740
gccctcccag cccccatcga gaaaaccatc tccaaagcca aagggcagcc ccgagaacca 1800
caggtgtaca ccctgccccc atcccgggat gagctgacca agaaccaggt cagcctgacc 1860
tgcctggtca aaggcttcta tcccagcgac atcgccgtgg agtgggagag caatgggcag 1920
ccggagaaca actacaagac cacgcctccc gtgttggact ccgacggctc cttcttcctc 1980
tacagcaagc tcaccgtgga caagagcagg tggcagcagg ggaacgtctt ctcatgctcc 2040
gtgatgcatg aggctctgca caaccactac acgcagaaga gcctctccct gtctccgggt 2100
aaaggtggcg gcggatcagg tgggggtgga tcaggcggtg gaggttccgg tggcggggga 2160
tcagacaaaa ctcacacatg cccaccgtgc ccagcacctg aactcctggg aggaccgtca 2220
gtcttcctct tccccccaaa acccaaggac accctcatga tctcccggac ccctgaggtc 2280
acatgcgtgg tggtggacgt gagccacgaa gaccctgagg tcaagttcaa ctggtacgtg 2340
gacggcgtgg aggtgcataa tgccaagaca aagccgcggg aggagcagta caacagcacg 2400
taccgtgtgg tcagcgtcct caccgtcctg caccaggact ggctgaatgg caaggagtac 2460
aagtgcaagg tctccaacaa agccctccca gcccccatcg agaaaaccat ctccaaagcc 2520
aaagggcagc cccgagaacc acaggtgtac accctgcccc catcccgcga tgagctgacc 2580
aagaaccagg tcagcctgac ctgcctggtc aaaggcttct atcccagcga catcgccgtg 2640
gagtgggaga gcaatgggca gccggagaac aactacaaga ccacgcctcc cgtgttggac 2700
tccgacggct ccttcttcct ctacagcaag ctcaccgtcg acaagagcag gtggcagcag 2760
gggaacgtct tctcatgctc cgtgatgcat gaggctctgc acaaccacta cacgcagaag 2820
agcctctccc tgtctccggg taaaggtggc ggcggatcag gtgggggtgg atcaggcggt 2880
ggaggttccg gtggcggggg atcagcctgc accgagcgga tggccctgca caacctgtgc 2940
ggcgggtga 2949

<210> SEQ ID NO 78
<211> LENGTH: 982
<212> TYPE: PRT
<213> ORGANISM: Artificial Sequence
<220> FEATURE:
<223> OTHER INFORMATION: Synthetic construct: FVII-046 amino acid sequence

<400> SEQUENCE: 78

Met Val Ser Gln Ala Leu Arg Leu Leu Cys Leu Leu Leu Gly Leu Gln
1 5 10 15

Gly Cys Leu Ala Ala Val Phe Val Thr Gln Glu Glu Ala His Gly Val
20 25 30

Leu His Arg Arg Arg Arg Ala Asn Ala Phe Leu Glu Glu Leu Arg Pro
35 40 45

Gly Ser Leu Glu Arg Glu Cys Lys Glu Glu Gln Cys Ser Phe Glu Glu
50 55 60

Ala Arg Glu Ile Phe Lys Asp Ala Glu Arg Thr Lys Leu Phe Trp Ile
65 70 75 80

Ser Tyr Ser Asp Gly Asp Gln Cys Ala Ser Ser Pro Cys Gln Asn Gly
85 90 95

```
Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
```

-continued

```
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Gly Gly Gly
    690                 695                 700

Gly Ser Gly Gly Gly Gly Ser Gly Gly Gly Gly Ser Gly Gly Gly Gly
705                 710                 715                 720

Ser Asp Lys Thr His Thr Cys Pro Pro Cys Pro Ala Pro Glu Leu Leu
                725                 730                 735

Gly Gly Pro Ser Val Phe Leu Phe Pro Pro Lys Pro Lys Asp Thr Leu
            740                 745                 750

Met Ile Ser Arg Thr Pro Glu Val Thr Cys Val Val Val Asp Val Ser
        755                 760                 765

His Glu Asp Pro Glu Val Lys Phe Asn Trp Tyr Val Asp Gly Val Glu
    770                 775                 780

Val His Asn Ala Lys Thr Lys Pro Arg Glu Glu Gln Tyr Asn Ser Thr
785                 790                 795                 800

Tyr Arg Val Val Ser Val Leu Thr Val Leu His Gln Asp Trp Leu Asn
                805                 810                 815

Gly Lys Glu Tyr Lys Cys Lys Val Ser Asn Lys Ala Leu Pro Ala Pro
            820                 825                 830

Ile Glu Lys Thr Ile Ser Lys Ala Lys Gly Gln Pro Arg Glu Pro Gln
        835                 840                 845

Val Tyr Thr Leu Pro Pro Ser Arg Asp Glu Leu Thr Lys Asn Gln Val
    850                 855                 860

Ser Leu Thr Cys Leu Val Lys Gly Phe Tyr Pro Ser Asp Ile Ala Val
865                 870                 875                 880

Glu Trp Glu Ser Asn Gly Gln Pro Glu Asn Asn Tyr Lys Thr Thr Pro
                885                 890                 895

Pro Val Leu Asp Ser Asp Gly Ser Phe Phe Leu Tyr Ser Lys Leu Thr
            900                 905                 910

Val Asp Lys Ser Arg Trp Gln Gln Gly Asn Val Phe Ser Cys Ser Val
        915                 920                 925

Met His Glu Ala Leu His Asn His Tyr Thr Gln Lys Ser Leu Ser Leu
    930                 935                 940
```

Ser Pro Gly Lys Gly Gly Gly Gly Ser Gly Gly Gly Gly Ser Gly Gly
945 950 955 960

Gly Gly Ser Gly Gly Gly Gly Ser Ala Cys Thr Glu Arg Asp Ala Leu
965 970 975

His Asn Leu Cys Gly Gly
980

<210> SEQ ID NO 79
<211> LENGTH: 2949
<212> TYPE: DNA
<213> ORGANISM: Artificial Sequence
<220> FEATURE:
<223> OTHER INFORMATION: Synthetic construct: FVII-046 DNA sequence

<400> SEQUENCE: 79
atggtctccc aggccctcag gctcctctgc cttctgcttg ggcttcaggg ctgcctggct 60
gcagtcttcg taacccagga ggaagcccac ggcgtcctgc accggcgccg gcgcgccaac 120
gcgttcctgg aggagctgcg gccgggctcc ctggagaggg agtgcaagga ggagcagtgc 180
tccttcgagg aggcccggga gatcttcaag gacgcggaga ggacgaagct gttctggatt 240
tcttacagtg atggggacca gtgtgcctca agtccatgcc agaatggggg ctcctgcaag 300
gaccagctcc agtcctatat ctgcttctgc ctccctgcct tcgagggccg gaactgtgag 360
acgcacaagg atgaccagct gatctgtgtg aacgagaacg gcggctgtga gcagtactgc 420
agtgaccaca cgggcaccaa gcgctcctgt cggtgccacg aggggtactc tctgctggca 480
gacggggtgt cctgcacacc cacagttgaa tatccatgtg gaaaaatacc tattctagaa 540
aaaagaaatg ccagcaaacc ccaaggccga attgtggggg gcaaggtgtg ccccaaaggg 600
gagtgtccat ggcaggtcct gttgttggtg aatggagctc agttgtgtgg ggggaccctg 660
atcaacacca tctgggtggt ctccgcggcc cactgtttcg acaaaatcaa gaactggagg 720
aacctgatcg cggtgctggg cgagcacgac ctcagcgagc acgacgggga tgagcagagc 780
cggcgggtgg cgcaggtcat catccccagc acgtacgtcc cgggcaccac caaccacgac 840
atcgcgctgc tccgcctgca ccagcccgtg gtcctcactg accatgtggt gcccctctgc 900
ctgcccgaac ggacgttctc tgagaggacg ctggccttcg tgcgcttctc attggtcagc 960
ggctggggcc agctgctgga ccgtggcgcc acggccctgg agctcatggt cctcaacgtg 1020
ccccggctga tgacccagga ctgcctgcag cagtcacgga aggtgggaga ctccccaaat 1080
atcacggagt acatgttctg tgccggctac tcggatggca gcaaggactc ctgcaagggg 1140
gacagtggag gcccacatgc cacccactac cggggcacgt ggtacctgac gggcatcgtc 1200
agctggggcc agggctgcgc aaccgtgggc cactttgggg tgtacaccag ggtctcccag 1260
tacatcgagt ggctgcaaaa gctcatgcgc tcagagccac gcccaggagt cctcctgcga 1320
gccccatttc ccggtggcgg tggctccggc ggaggtgggt ccggtggcgg cggatcaggt 1380
gggggtggat caggcggtgg aggttccggt ggcgggggat ccgacaaaac tcacacatgc 1440
ccaccgtgcc cagctccgga actcctgggc ggaccgtcag tcttcctctt ccccccaaaa 1500
cccaaggaca ccctcatgat ctcccggacc cctgaggtca catgcgtggt ggtggacgtg 1560
agccacgaag accctgaggt caagttcaac tggtacgtgg acggcgtgga ggtgcataat 1620
gccaagacaa agccgcggga ggagcagtac aacagcacgt accgtgtggt cagcgtcctc 1680
accgtcctgc accaggactg gctgaatggc aaggagtaca agtgcaaggt ctccaacaaa 1740
gccctcccag cccccatcga gaaaaccatc tccaaagcca aagggcagcc ccgagaacca 1800
caggtgtaca ccctgccccc atcccgggat gagctgacca agaaccaggt cagcctgacc 1860
tgcctggtca aaggcttcta tcccagcgac atcgccgtgg agtgggagag caatgggcag 1920
ccggagaaca actacaagac cacgcctccc gtgttggact ccgacggctc cttcttcctc 1980
tacagcaagc tcaccgtgga caagagcagg tggcagcagg ggaacgtctt ctcatgctcc 2040
gtgatgcatg aggctctgca caaccactac acgcagaaga gcctctccct gtctccgggt 2100
aaaggtggcg gcggatcagg tgggggtgga tcaggcggtg gaggttccgg tggcggggga 2160
tcagacaaaa ctcacacatg cccaccgtgc ccagcacctg aactcctggg aggaccgtca 2220
gtcttcctct tccccccaaa acccaaggac accctcatga tctcccggac ccctgaggtc 2280
acatgcgtgg tggtggacgt gagccacgaa gaccctgagg tcaagttcaa ctggtacgtg 2340
gacggcgtgg aggtgcataa tgccaagaca aagccgcggg aggagcagta caacagcacg 2400
taccgtgtgg tcagcgtcct caccgtcctg caccaggact ggctgaatgg caaggagtac 2460
aagtgcaagg tctccaacaa agccctccca gcccccatcg agaaaaccat ctccaaagcc 2520
aaagggcagc cccgagaacc acaggtgtac accctgcccc catcccgcga tgagctgacc 2580
aagaaccagg tcagcctgac ctgcctggtc aaaggcttct atcccagcga catcgccgtg 2640
gagtgggaga gcaatgggca gccggagaac aactacaaga ccacgcctcc cgtgttggac 2700
tccgacggct ccttcttcct ctacagcaag ctcaccgtcg acaagagcag gtggcagcag 2760
gggaacgtct tctcatgctc cgtgatgcat gaggctctgc acaaccacta cacgcagaag 2820
agcctctccc tgtctccggg taaaggtggc ggcggatcag gtgggggtgg atcaggcggt 2880
ggaggttccg gtggcggggg atcagcctgc accgagcggg acgccctgca caacctgtgc 2940
ggcgggtga 2949

<210> SEQ ID NO 80
<211> LENGTH: 1000
<212> TYPE: PRT
<213> ORGANISM: Artificial Sequence
<220> FEATURE:
<223> OTHER INFORMATION: Synthetic construct: FVII-047 amino acid sequence

<400> SEQUENCE: 80

Met Val Ser Gln Ala Leu Arg Leu Leu Cys Leu Leu Leu Gly Leu Gln
1 5 10 15

Gly Cys Leu Ala Ala Val Phe Val Thr Gln Glu Glu Ala His Gly Val
20 25 30

Leu His Arg Arg Arg Arg Ala Asn Ala Phe Leu Glu Glu Leu Arg Pro
35 40 45

Gly Ser Leu Glu Arg Glu Cys Lys Glu Glu Gln Cys Ser Phe Glu Glu
50 55 60

Ala Arg Glu Ile Phe Lys Asp Ala Glu Arg Thr Lys Leu Phe Trp Ile
65 70 75 80

Ser Tyr Ser Asp Gly Asp Gln Cys Ala Ser Ser Pro Cys Gln Asn Gly
85 90 95

Gly Ser Cys Lys Asp Gln Leu Gln Ser Tyr Ile Cys Phe Cys Leu Pro
100 105 110

Ala Phe Glu Gly Arg Asn Cys Glu Thr His Lys Asp Asp Gln Leu Ile
115 120 125

Cys Val Asn Glu Asn Gly Gly Cys Glu Gln Tyr Cys Ser Asp His Thr
130 135 140

-continued

```
Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
```

-continued

```
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Gly Gly Gly
    690                 695                 700

Gly Ser Gly Gly Gly Gly Ser Gly Gly Gly Gly Ser Gly Gly Gly Gly
705                 710                 715                 720

Ser Gly Gly Gly Gly Ser Gly Gly Gly Gly Ser Ala Cys Thr Glu Arg
                725                 730                 735

Trp Ala Leu His Asn Leu Cys Gly Gly Gly Gly Ser Gly Gly Gly Gly
            740                 745                 750

Ser Gly Gly Gly Gly Ser Gly Gly Gly Gly Ser Gly Gly Gly Gly Ser
        755                 760                 765

Gly Gly Gly Gly Ser Asp Lys Thr His Thr Cys Pro Pro Cys Pro Ala
    770                 775                 780

Pro Glu Leu Leu Gly Gly Pro Ser Val Phe Leu Phe Pro Pro Lys Pro
785                 790                 795                 800

Lys Asp Thr Leu Met Ile Ser Arg Thr Pro Glu Val Thr Cys Val Val
                805                 810                 815

Val Asp Val Ser His Glu Asp Pro Glu Val Lys Phe Asn Trp Tyr Val
            820                 825                 830

Asp Gly Val Glu Val His Asn Ala Lys Thr Lys Pro Arg Glu Glu Gln
        835                 840                 845

Tyr Asn Ser Thr Tyr Arg Val Val Ser Val Leu Thr Val Leu His Gln
    850                 855                 860

Asp Trp Leu Asn Gly Lys Glu Tyr Lys Cys Lys Val Ser Asn Lys Ala
865                 870                 875                 880

Leu Pro Ala Pro Ile Glu Lys Thr Ile Ser Lys Ala Lys Gly Gln Pro
                885                 890                 895

Arg Glu Pro Gln Val Tyr Thr Leu Pro Pro Ser Arg Asp Glu Leu Thr
            900                 905                 910

Lys Asn Gln Val Ser Leu Thr Cys Leu Val Lys Gly Phe Tyr Pro Ser
        915                 920                 925

Asp Ile Ala Val Glu Trp Glu Ser Asn Gly Gln Pro Glu Asn Asn Tyr
    930                 935                 940

Lys Thr Thr Pro Pro Val Leu Asp Ser Asp Gly Ser Phe Phe Leu Tyr
945                 950                 955                 960

Ser Lys Leu Thr Val Asp Lys Ser Arg Trp Gln Gln Gly Asn Val Phe
                965                 970                 975

Ser Cys Ser Val Met His Glu Ala Leu His Asn His Tyr Thr Gln Lys
            980                 985                 990
```

```
Ser Leu Ser Leu Ser Pro Gly Lys
        995                 1000


<210> SEQ ID NO 81
<211> LENGTH: 3003
<212> TYPE: DNA
<213> ORGANISM: Artificial Sequence
<220> FEATURE:
<223> OTHER INFORMATION: Synthetic construct: FVII-047 DNA sequence

<400> SEQUENCE: 81

atggtctccc aggccctcag gctcctctgc cttctgcttg ggcttcaggg ctgcctggct     60

gcagtcttcg taacccagga ggaagcccac ggcgtcctgc accggcgccg gcgcgccaac    120

gcgttcctgg aggagctgcg gccgggctcc ctggagaggg agtgcaagga ggagcagtgc    180

tccttcgagg aggcccggga gatcttcaag gacgcggaga ggacgaagct gttctggatt    240

tcttacagtg atggggacca gtgtgcctca agtccatgcc agaatggggg ctcctgcaag    300

gaccagctcc agtcctatat ctgcttctgc ctccctgcct tcgagggccg gaactgtgag    360

acgcacaagg atgaccagct gatctgtgtg aacgagaacg gcggctgtga gcagtactgc    420

agtgaccaca cgggcaccaa gcgctcctgt cggtgccacg aggggtactc tctgctggca    480

gacggggtgt cctgcacacc cacagttgaa tatccatgtg gaaaaatacc tattctagaa    540

aaaagaaatg ccagcaaacc ccaaggccga attgtggggg gcaaggtgtg ccccaaaggg    600

gagtgtccat ggcaggtcct gttgttggtg aatggagctc agttgtgtgg ggggaccctg    660

atcaacacca tctgggtggt ctccgcggcc cactgtttcg acaaaatcaa gaactggagg    720

aacctgatcg cggtgctggg cgagcacgac ctcagcgagc acgacgggga tgagcagagc    780

cggcgggtgg cgcaggtcat catccccagc acgtacgtcc cgggcaccac caaccacgac    840

atcgcgctgc tccgcctgca ccagcccgtg gtcctcactg accatgtggt gcccctctgc    900

ctgcccgaac ggacgttctc tgagaggacg ctggccttcg tgcgcttctc attggtcagc    960

ggctggggcc agctgctgga ccgtggcgcc acggccctgg agctcatggt cctcaacgtg   1020

ccccggctga tgacccagga ctgcctgcag cagtcacgga aggtgggaga ctccccaaat   1080

atcacggagt acatgttctg tgccggctac tcggatggca gcaaggactc ctgcaagggg   1140

gacagtggag gcccacatgc cacccactac cggggcacgt ggtacctgac gggcatcgtc   1200

agctggggcc agggctgcgc aaccgtgggc cactttgggg tgtacaccag ggtctcccag   1260

tacatcgagt ggctgcaaaa gctcatgcgc tcagagccac gcccaggagt cctcctgcga   1320

gccccatttc ccggtggcgg tggctccggc ggaggtgggt ccggtggcgg cggatcaggt   1380

gggggtggat caggcggtgg aggttccggt ggcgggggat ccgacaaaac tcacacatgc   1440

ccaccgtgcc cagctccgga actcctggga ggaccgtcag tcttcctctt ccccccaaaa   1500

cccaaggaca ccctcatgat ctcccggacc cctgaggtca catgcgtggt ggtggacgtg   1560

agccacgaag accctgaggt caagttcaac tggtacgtgg acggcgtgga ggtgcataat   1620

gccaagacaa agccgcggga ggagcagtac aacagcacgt accgtgtggt cagcgtcctc   1680

accgtcctgc accaggactg gctgaatggc aaggagtaca agtgcaaggt ctccaacaaa   1740

gccctcccag cccccatcga gaaaaccatc tccaaagcca aagggcagcc ccgagaacca   1800

caggtgtaca ccctgccccc atcccgggat gagctgacca agaaccaggt cagcctgacc   1860

tgcctggtca aaggcttcta tcccagcgac atcgccgtgg agtgggagag caatgggcag   1920

ccggagaaca actacaagac cacgcctccc gtgttggact ccgacggctc cttcttcctc   1980
```

```
tacagcaagc tcaccgtcga caagagcagg tggcagcagg ggaacgtctt ctcatgctcc   2040

gtgatgcatg aggctctgca caaccactac acgcagaaga gcctctccct gtctccgggt   2100

aaaggcggtg gcggttcagg tggaggaggg tcaggcggtg gtggatccgg cgggggcgga   2160

tccggtggcg gagggtcagg cggtggcgga tcagcctgca ccgagcggtg ggccctgcac   2220

aacctgtgcg gtggcggtgg ctccggcgga ggtgggtccg gtggcggcgg atcaggtggg   2280

ggtggatcag gcggtggagg ttccggtggc gggggatccg acaaaactca cacatgccca   2340

ccgtgcccag caccggaact cctgggcgga ccgtcagtct tcctcttccc cccaaaaccc   2400

aaggacaccc tcatgatctc ccggacccct gaggtcacat gcgtggtggt ggacgtgagc   2460

cacgaagacc ctgaggtcaa gttcaactgg tacgtggacg gcgtggaggt gcataatgcc   2520

aagacaaagc cgcgggagga gcagtacaac agcacgtacc gtgtggtcag cgtcctcacc   2580

gtcctgcacc aggactggct gaatggcaag gagtacaagt gcaaggtctc caacaaagcc   2640

ctcccagccc ccatcgagaa aaccatctcc aaagccaaag ggcagccccg agaaccacag   2700

gtgtacaccc tgcccccatc ccgggatgag ctgaccaaga accaggtcag cctgacctgc   2760

ctggtcaaag gcttctatcc cagcgacatc gccgtggagt gggagagcaa tgggcagccg   2820

gagaacaact acaagaccac gcctcccgtg ttggactccg acggctcctt cttcctctac   2880

agcaagctca ccgtggacaa gagcaggtgg cagcagggga acgtcttctc atgctccgtg   2940

atgcatgagg ctctgcacaa ccactacacg cagaagagcc tctccctgtc tccgggtaaa   3000

tga                                                                 3003
```

<210> SEQ ID NO 82

<400> SEQUENCE: 82

000

<210> SEQ ID NO 83

<400> SEQUENCE: 83

000

<210> SEQ ID NO 84
<211> LENGTH: 1000
<212> TYPE: PRT
<213> ORGANISM: Artificial Sequence
<220> FEATURE:
<223> OTHER INFORMATION: Synthetic construct: FVII-048 amino acid sequence.

<400> SEQUENCE: 84

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95
```

```
Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510
```

```
Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Gly Gly Gly
    690                 695                 700

Gly Ser Gly Gly Gly Gly Ser Gly Gly Gly Gly Ser Gly Gly Gly Gly
705                 710                 715                 720

Ser Gly Gly Gly Gly Ser Gly Gly Gly Gly Ser Ala Cys Thr Glu Arg
                725                 730                 735

Met Ala Leu His Asn Leu Cys Gly Gly Gly Gly Ser Gly Gly Gly Gly
            740                 745                 750

Ser Gly Gly Gly Gly Ser Gly Gly Gly Gly Ser Gly Gly Gly Gly Ser
        755                 760                 765

Gly Gly Gly Gly Ser Asp Lys Thr His Thr Cys Pro Pro Cys Pro Ala
    770                 775                 780

Pro Glu Leu Leu Gly Gly Pro Ser Val Phe Leu Phe Pro Pro Lys Pro
785                 790                 795                 800

Lys Asp Thr Leu Met Ile Ser Arg Thr Pro Glu Val Thr Cys Val Val
                805                 810                 815

Val Asp Val Ser His Glu Asp Pro Glu Val Lys Phe Asn Trp Tyr Val
            820                 825                 830

Asp Gly Val Glu Val His Asn Ala Lys Thr Lys Pro Arg Glu Glu Gln
        835                 840                 845

Tyr Asn Ser Thr Tyr Arg Val Val Ser Val Leu Thr Val Leu His Gln
    850                 855                 860

Asp Trp Leu Asn Gly Lys Glu Tyr Lys Cys Lys Val Ser Asn Lys Ala
865                 870                 875                 880

Leu Pro Ala Pro Ile Glu Lys Thr Ile Ser Lys Ala Lys Gly Gln Pro
                885                 890                 895

Arg Glu Pro Gln Val Tyr Thr Leu Pro Pro Ser Arg Asp Glu Leu Thr
            900                 905                 910

Lys Asn Gln Val Ser Leu Thr Cys Leu Val Lys Gly Phe Tyr Pro Ser
        915                 920                 925

Asp Ile Ala Val Glu Trp Glu Ser Asn Gly Gln Pro Glu Asn Asn Tyr
```

```
    930                 935                 940

Lys Thr Thr Pro Pro Val Leu Asp Ser Asp Gly Ser Phe Phe Leu Tyr
945                 950                 955                 960

Ser Lys Leu Thr Val Asp Lys Ser Arg Trp Gln Gln Gly Asn Val Phe
                965                 970                 975

Ser Cys Ser Val Met His Glu Ala Leu His Asn His Tyr Thr Gln Lys
            980                 985                 990

Ser Leu Ser Leu Ser Pro Gly Lys
        995                 1000


<210> SEQ ID NO 85
<211> LENGTH: 3003
<212> TYPE: DNA
<213> ORGANISM: Artificial Sequence
<220> FEATURE:
<223> OTHER INFORMATION: Synthetic construct: DNA sequence of FVII-048

<400> SEQUENCE: 85

atggtctccc aggccctcag gctcctctgc cttctgcttg ggcttcaggg ctgcctggct     60

gcagtcttcg taacccagga ggaagcccac ggcgtcctgc accggcgccg gcgcgccaac    120

gcgttcctgg aggagctgcg gccgggctcc ctggagaggg agtgcaagga ggagcagtgc    180

tccttcgagg aggcccggga gatcttcaag gacgcggaga ggacgaagct gttctggatt    240

tcttacagtg atggggacca gtgtgcctca agtccatgcc agaatggggg ctcctgcaag    300

gaccagctcc agtcctatat ctgcttctgc ctccctgcct tcgagggccg gaactgtgag    360

acgcacaagg atgaccagct gatctgtgtg aacgagaacg gcggctgtga gcagtactgc    420

agtgaccaca cgggcaccaa gcgctcctgt cggtgccacg aggggtactc tctgctggca    480

gacggggtgt cctgcacacc cacagttgaa tatccatgtg gaaaaatacc tattctagaa    540

aaaagaaatg ccagcaaacc ccaaggccga attgtggggg gcaaggtgtg ccccaaaggg    600

gagtgtccat ggcaggtcct gttgttggtg aatggagctc agttgtgtgg ggggaccctg    660

atcaacacca tctgggtggt ctccgcggcc cactgtttcg acaaaatcaa gaactggagg    720

aacctgatcg cggtgctggg cgagcacgac ctcagcgagc acgacgggga tgagcagagc    780

cggcgggtgg cgcaggtcat catccccagc acgtacgtcc cgggcaccac caaccacgac    840

atcgcgctgc tccgcctgca ccagcccgtg gtcctcactg accatgtggt gcccctctgc    900

ctgcccgaac ggacgttctc tgagaggacg ctggccttcg tgcgcttctc attggtcagc    960

ggctggggcc agctgctgga ccgtggcgcc acggccctgg agctcatggt cctcaacgtg   1020

ccccggctga tgacccagga ctgcctgcag cagtcacgga aggtgggaga ctccccaaat   1080

atcacggagt acatgttctg tgccggctac tcggatggca gcaaggactc ctgcaagggg   1140

gacagtggag gcccacatgc cacccactac cggggcacgt ggtacctgac gggcatcgtc   1200

agctggggcc agggctgcgc aaccgtgggc cactttgggg tgtacaccag ggtctcccag   1260

tacatcgagt ggctgcaaaa gctcatgcgc tcagagccac gcccaggagt cctcctgcga   1320

gccccatttc ccggtggcgg tggctccggc ggaggtgggt ccggtggcgg cggatcaggt   1380

gggggtggat caggcggtgg aggttccggt ggcgggggat ccgacaaaac tcacacatgc   1440

ccaccgtgcc cagctccgga actcctggga ggaccgtcag tcttcctctt ccccccaaaa   1500

cccaaggaca ccctcatgat ctcccggacc cctgaggtca catgcgtggt ggtggacgtg   1560

agccacgaag accctgaggt caagttcaac tggtacgtgg acggcgtgga ggtgcataat   1620

gccaagacaa agccgcggga ggagcagtac aacagcacgt accgtgtggt cagcgtcctc   1680
```

```
accgtcctgc accaggactg gctgaatggc aaggagtaca agtgcaaggt ctccaacaaa   1740

gccctcccag cccccatcga gaaaaccatc tccaaagcca aagggcagcc ccgagaacca   1800

caggtgtaca ccctgccccc atcccgggat gagctgacca agaaccaggt cagcctgacc   1860

tgcctggtca aaggcttcta tcccagcgac atcgccgtgg agtgggagag caatgggcag   1920

ccggagaaca actacaagac cacgcctccc gtgttggact ccgacggctc cttcttcctc   1980

tacagcaagc tcaccgtcga caagagcagg tggcagcagg ggaacgtctt ctcatgctcc   2040

gtgatgcatg aggctctgca caaccactac acgcagaaga gcctctccct gtctccgggt   2100

aaaggcggtg gcggttcagg tggaggaggg tcaggcggtg gtggatccgg cgggggcgga   2160

tccggtggcg gagggtcagg cggtggcgga tcagcctgca ccgagcggat ggccctgcac   2220

aacctgtgcg gtggcggtgg ctccggcgga ggtgggtccg gtggcggcgg atcaggtggg   2280

ggtggatcag gcggtggagg ttccggtggc gggggatccg acaaaactca cacatgccca   2340

ccgtgcccag caccggaact cctgggcgga ccgtcagtct tcctcttccc cccaaaaccc   2400

aaggacaccc tcatgatctc ccggacccct gaggtcacat gcgtggtggt ggacgtgagc   2460

cacgaagacc ctgaggtcaa gttcaactgg tacgtggacg gcgtggaggt gcataatgcc   2520

aagacaaagc cgcgggagga gcagtacaac agcacgtacc gtgtggtcag cgtcctcacc   2580

gtcctgcacc aggactggct gaatggcaag gagtacaagt gcaaggtctc caacaaagcc   2640

ctcccagccc ccatcgagaa aaccatctcc aaagccaaag ggcagccccg agaaccacag   2700

gtgtacaccc tgcccccatc ccgggatgag ctgaccaaga accaggtcag cctgacctgc   2760

ctggtcaaag gcttctatcc cagcgacatc gccgtggagt gggagagcaa tgggcagccg   2820

gagaacaact acaagaccac gcctcccgtg ttggactccg acggctcctt cttcctctac   2880

agcaagctca ccgtggacaa gagcaggtgg cagcagggga acgtcttctc atgctccgtg   2940

atgcatgagg ctctgcacaa ccactacacg cagaagagcc tctccctgtc tccgggtaaa   3000

tga                                                                 3003
```

<210> SEQ ID NO 86
<211> LENGTH: 1000
<212> TYPE: PRT
<213> ORGANISM: Artificial Sequence
<220> FEATURE:
<223> OTHER INFORMATION: Synthetic construct: FVII-049 amino acid sequence

<400> SEQUENCE: 86

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110
```

```
Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
```

```
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Gly Gly Gly
    690                 695                 700

Gly Ser Gly Gly Gly Gly Ser Gly Gly Gly Gly Ser Gly Gly Gly Gly
705                 710                 715                 720

Ser Gly Gly Gly Gly Ser Gly Gly Gly Gly Ser Ala Cys Thr Glu Arg
                725                 730                 735

Asp Ala Leu His Asn Leu Cys Gly Gly Gly Gly Ser Gly Gly Gly Gly
            740                 745                 750

Ser Gly Gly Gly Gly Ser Gly Gly Gly Gly Ser Gly Gly Gly Gly Ser
        755                 760                 765

Gly Gly Gly Gly Ser Asp Lys Thr His Thr Cys Pro Pro Cys Pro Ala
    770                 775                 780

Pro Glu Leu Leu Gly Gly Pro Ser Val Phe Leu Phe Pro Pro Lys Pro
785                 790                 795                 800

Lys Asp Thr Leu Met Ile Ser Arg Thr Pro Glu Val Thr Cys Val Val
                805                 810                 815

Val Asp Val Ser His Glu Asp Pro Glu Val Lys Phe Asn Trp Tyr Val
            820                 825                 830

Asp Gly Val Glu Val His Asn Ala Lys Thr Lys Pro Arg Glu Glu Gln
        835                 840                 845

Tyr Asn Ser Thr Tyr Arg Val Val Ser Val Leu Thr Val Leu His Gln
    850                 855                 860

Asp Trp Leu Asn Gly Lys Glu Tyr Lys Cys Lys Val Ser Asn Lys Ala
865                 870                 875                 880

Leu Pro Ala Pro Ile Glu Lys Thr Ile Ser Lys Ala Lys Gly Gln Pro
                885                 890                 895

Arg Glu Pro Gln Val Tyr Thr Leu Pro Pro Ser Arg Asp Glu Leu Thr
            900                 905                 910

Lys Asn Gln Val Ser Leu Thr Cys Leu Val Lys Gly Phe Tyr Pro Ser
        915                 920                 925

Asp Ile Ala Val Glu Trp Glu Ser Asn Gly Gln Pro Glu Asn Asn Tyr
    930                 935                 940

Lys Thr Thr Pro Pro Val Leu Asp Ser Asp Gly Ser Phe Phe Leu Tyr
945                 950                 955                 960
```

```
Ser Lys Leu Thr Val Asp Lys Ser Arg Trp Gln Gln Gly Asn Val Phe
                965                 970                 975

Ser Cys Ser Val Met His Glu Ala Leu His Asn His Tyr Thr Gln Lys
            980                 985                 990

Ser Leu Ser Leu Ser Pro Gly Lys
        995                 1000
```

<210> SEQ ID NO 87
<211> LENGTH: 3003
<212> TYPE: DNA
<213> ORGANISM: Artificial Sequence
<220> FEATURE:
<223> OTHER INFORMATION: Synthetic construct: DNA sequence of FVII-049

<400> SEQUENCE: 87

```
atggtctccc aggccctcag gctcctctgc cttctgcttg ggcttcaggg ctgcctggct     60
gcagtcttcg taacccagga ggaagcccac ggcgtcctgc accggcgccg gcgcgccaac    120
gcgttcctgg aggagctgcg gccgggctcc ctggagaggg agtgcaagga ggagcagtgc    180
tccttcgagg aggcccggga gatcttcaag gacgcggaga ggacgaagct gttctggatt    240
tcttacagtg atggggacca gtgtgcctca agtccatgcc agaatggggg ctcctgcaag    300
gaccagctcc agtcctatat ctgcttctgc ctccctgcct tcgagggccg gaactgtgag    360
acgcacaagg atgaccagct gatctgtgtg aacgagaacg gcggctgtga gcagtactgc    420
agtgaccaca cgggcaccaa gcgctcctgt cggtgccacg aggggtactc tctgctggca    480
gacggggtgt cctgcacacc cacagttgaa tatccatgtg gaaaaatacc tattctagaa    540
aaaagaaatg ccagcaaacc ccaaggccga attgtggggg gcaaggtgtg ccccaaaggg    600
gagtgtccat ggcaggtcct gttgttggtg aatggagctc agttgtgtgg ggggaccctg    660
atcaacacca tctgggtggt ctccgcggcc cactgtttcg acaaaatcaa gaactggagg    720
aacctgatcg cggtgctggg cgagcacgac ctcagcgagc acgacgggga tgagcagagc    780
cggcgggtgg cgcaggtcat catccccagc acgtacgtcc cgggcaccac caaccacgac    840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg   1020
ccccggctga tgacccagga ctgcctgcag cagtcacgga aggtgggaga ctccccaaat   1080
atcacggagt acatgttctg tgccggctac tcggatggca gcaaggactc ctgcaagggg   1140
gacagtggag gcccacatgc cacccactac cggggcacgt ggtacctgac gggcatcgtc   1200
agctggggcc agggctgcgc aaccgtgggc cactttgggg tgtacaccag ggtctcccag   1260
tacatcgagt ggctgcaaaa gctcatgcgc tcagagccac gcccaggagt cctcctgcga   1320
gccccatttc ccggtggcgg tggctccggc ggaggtgggt ccggtggcgg cggatcaggt   1380
gggggtggat caggcggtgg aggttccggt ggcgggggat ccgacaaaac tcacacatgc   1440
ccaccgtgcc cagctccgga actcctggga ggaccgtcag tcttcctctt ccccccaaaa   1500
cccaaggaca ccctcatgat ctcccggacc cctgaggtca catgcgtggt ggtggacgtg   1560
agccacgaag accctgaggt caagttcaac tggtacgtgg acggcgtgga ggtgcataat   1620
gccaagacaa agccgcggga ggagcagtac aacagcacgt accgtgtggt cagcgtcctc   1680
accgtcctgc accaggactg gctgaatggc aaggagtaca agtgcaaggt ctccaacaaa   1740
gccctcccag cccccatcga gaaaaccatc tccaaagcca aagggcagcc ccgagaacca   1800
```

```
caggtgtaca ccctgccccc atcccgggat gagctgacca agaaccaggt cagcctgacc   1860

tgcctggtca aaggcttcta tcccagcgac atcgccgtgg agtgggagag caatgggcag   1920

ccggagaaca actacaagac cacgcctccc gtgttggact ccgacggctc cttcttcctc   1980

tacagcaagc tcaccgtcga caagagcagg tggcagcagg ggaacgtctt ctcatgctcc   2040

gtgatgcatg aggctctgca caaccactac acgcagaaga gcctctccct gtctccgggt   2100

aaaggcggtg gcggttcagg tggaggaggg tcaggcggtg gtggatccgg cgggggcgga   2160

tccggtggcg gagggtcagg cggtggcgga tcagcctgca ccgagcggga cgccctgcac   2220

aacctgtgcg gtggcggtgg ctccggcgga ggtgggtccg gtggcggcgg atcaggtggg   2280

ggtggatcag gcggtggagg ttccggtggc gggggatccg acaaaactca cacatgccca   2340

ccgtgcccag caccggaact cctgggcgga ccgtcagtct tcctcttccc cccaaaaccc   2400

aaggacaccc tcatgatctc ccggacccct gaggtcacat gcgtggtggt ggacgtgagc   2460

cacgaagacc ctgaggtcaa gttcaactgg tacgtggacg gcgtggaggt gcataatgcc   2520

aagacaaagc cgcgggagga gcagtacaac agcacgtacc gtgtggtcag cgtcctcacc   2580

gtcctgcacc aggactggct gaatggcaag gagtacaagt gcaaggtctc caacaaagcc   2640

ctcccagccc ccatcgagaa aaccatctcc aaagccaaag ggcagccccg agaaccacag   2700

gtgtacaccc tgcccccatc ccgggatgag ctgaccaaga accaggtcag cctgacctgc   2760

ctggtcaaag gcttctatcc cagcgacatc gccgtggagt gggagagcaa tgggcagccg   2820

gagaacaact acaagaccac gcctcccgtg ttggactccg acggctcctt cttcctctac   2880

agcaagctca ccgtggacaa gagcaggtgg cagcagggga acgtcttctc atgctccgtg   2940

atgcatgagg ctctgcacaa ccactacacg cagaagagcc tctccctgtc tccgggtaaa   3000

tga                                                                 3003
```

```
<210> SEQ ID NO 88
<211> LENGTH: 948
<212> TYPE: PRT
<213> ORGANISM: Artificial Sequence
<220> FEATURE:
<223> OTHER INFORMATION: Synthetic construct: FVII-011 amino acid
      sequence

<400> SEQUENCE: 88

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
```

-continued

```
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560
```

```
Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Gly Gly Gly
    690                 695                 700

Gly Ser Gly Gly Gly Gly Ser Gly Gly Gly Gly Ser Gly Gly Gly Gly
705                 710                 715                 720

Ser Asp Lys Thr His Thr Cys Pro Pro Cys Pro Ala Pro Glu Leu Leu
                725                 730                 735

Gly Gly Pro Ser Val Phe Leu Phe Pro Pro Lys Pro Lys Asp Thr Leu
            740                 745                 750

Met Ile Ser Arg Thr Pro Glu Val Thr Cys Val Val Val Asp Val Ser
        755                 760                 765

His Glu Asp Pro Glu Val Lys Phe Asn Trp Tyr Val Asp Gly Val Glu
    770                 775                 780

Val His Asn Ala Lys Thr Lys Pro Arg Glu Glu Gln Tyr Asn Ser Thr
785                 790                 795                 800

Tyr Arg Val Val Ser Val Leu Thr Val Leu His Gln Asp Trp Leu Asn
                805                 810                 815

Gly Lys Glu Tyr Lys Cys Lys Val Ser Asn Lys Ala Leu Pro Ala Pro
            820                 825                 830

Ile Glu Lys Thr Ile Ser Lys Ala Lys Gly Gln Pro Arg Glu Pro Gln
        835                 840                 845

Val Tyr Thr Leu Pro Pro Ser Arg Asp Glu Leu Thr Lys Asn Gln Val
    850                 855                 860

Ser Leu Thr Cys Leu Val Lys Gly Phe Tyr Pro Ser Asp Ile Ala Val
865                 870                 875                 880

Glu Trp Glu Ser Asn Gly Gln Pro Glu Asn Asn Tyr Lys Thr Thr Pro
                885                 890                 895

Pro Val Leu Asp Ser Asp Gly Ser Phe Phe Leu Tyr Ser Lys Leu Thr
            900                 905                 910

Val Asp Lys Ser Arg Trp Gln Gln Gly Asn Val Phe Ser Cys Ser Val
        915                 920                 925

Met His Glu Ala Leu His Asn His Tyr Thr Gln Lys Ser Leu Ser Leu
    930                 935                 940

Ser Pro Gly Lys
945
```

<210> SEQ ID NO 89
<211> LENGTH: 2847

<212> TYPE: DNA
<213> ORGANISM: Artificial Sequence
<220> FEATURE:
<223> OTHER INFORMATION: Synthetic construct: FVII-011 DNA sequence

<400> SEQUENCE: 89

```
atggtctccc aggccctcag gctcctctgc cttctgcttg ggcttcaggg ctgcctggct     60
gcagtcttcg taacccagga ggaagcccac ggcgtcctgc accggcgccg gcgcgccaac    120
gcgttcctgg aggagctgcg gccgggctcc ctggagaggg agtgcaagga ggagcagtgc    180
tccttcgagg aggcccggga gatcttcaag gacgcggaga ggacgaagct gttctggatt    240
tcttacagtg atggggacca gtgtgcctca agtccatgcc agaatggggg ctcctgcaag    300
gaccagctcc agtcctatat ctgcttctgc ctccctgcct tcgagggccg gaactgtgag    360
acgcacaagg atgaccagct gatctgtgtg aacgagaacg gcggctgtga gcagtactgc    420
agtgaccaca cgggcaccaa gcgctcctgt cggtgccacg aggggtactc tctgctggca    480
gacggggtgt cctgcacacc cacagttgaa tatccatgtg gaaaaatacc tattctagaa    540
aaaagaaatg ccagcaaacc ccaaggccga attgtggggg gcaaggtgtg ccccaaaggg    600
gagtgtccat ggcaggtcct gttgttggtg aatggagctc agttgtgtgg ggggaccctg    660
atcaacacca tctgggtggt ctccgcggcc cactgtttcg acaaaatcaa gaactggagg    720
aacctgatcg cggtgctggg cgagcacgac ctcagcgagc acgacgggga tgagcagagc    780
cggcgggtgg cgcaggtcat catccccagc acgtacgtcc cgggcaccac caaccacgac    840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg   1020
ccccggctga tgacccagga ctgcctgcag cagtcacgga aggtgggaga ctccccaaat   1080
atcacggagt acatgttctg tgccggctac tcggatggca gcaaggactc ctgcaagggg   1140
gacagtggag gcccacatgc cacccactac cggggcacgt ggtacctgac gggcatcgtc   1200
agctggggcc agggctgcgc aaccgtgggc cactttgggg tgtacaccag ggtctcccag   1260
tacatcgagt ggctgcaaaa gctcatgcgc tcagagccac gcccaggagt cctcctgcga   1320
gccccatttc ccggtggcgg tggctccggc ggaggtgggt ccggtggcgg cggatcaggt   1380
gggggtggat caggcggtgg aggttccggt ggcgggggat ccgacaaaac tcacacatgc   1440
ccaccgtgcc cagctccgga actcctgggc ggaccgtcag tcttcctctt ccccccaaaa   1500
cccaaggaca ccctcatgat ctcccggacc cctgaggtca catgcgtggt ggtggacgtg   1560
agccacgaag accctgaggt caagttcaac tggtacgtgg acggcgtgga ggtgcataat   1620
gccaagacaa agccgcggga ggagcagtac aacagcacgt accgtgtggt cagcgtcctc   1680
accgtcctgc accaggactg gctgaatggc aaggagtaca agtgcaaggt ctccaacaaa   1740
gccctcccag cccccatcga gaaaaccatc tccaaagcca aagggcagcc ccgagaacca   1800
caggtgtaca ccctgccccc atcccgggat gagctgacca agaaccaggt cagcctgacc   1860
tgcctggtca aaggcttcta tcccagcgac atcgccgtgg agtgggagag caatgggcag   1920
ccggagaaca actacaagac cacgcctccc gtgttggact ccgacggctc cttcttcctc   1980
tacagcaagc tcaccgtgga caagagcagg tggcagcagg ggaacgtctt ctcatgctcc   2040
gtgatgcatg aggctctgca caaccactac acgcagaaga gcctctccct gtctccgggt   2100
aaaggtggcg gcggatcagg tgggggtgga tcaggcggtg gaggttccgg tggcggggga   2160
```

```
tcagacaaaa ctcacacatg cccaccgtgc ccagcacctg aactcctggg aggaccgtca    2220

gtcttcctct tccccccaaa acccaaggac accctcatga tctcccggac ccctgaggtc    2280

acatgcgtgg tggtggacgt gagccacgaa gaccctgagg tcaagttcaa ctggtacgtg    2340

gacggcgtgg aggtgcataa tgccaagaca aagccgcggg aggagcagta caacagcacg    2400

taccgtgtgg tcagcgtcct caccgtcctg caccaggact ggctgaatgg caaggagtac    2460

aagtgcaagg tctccaacaa agccctccca gcccccatcg agaaaaccat ctccaaagcc    2520

aaagggcagc cccgagaacc acaggtgtac accctgcccc catcccgcga tgagctgacc    2580

aagaaccagg tcagcctgac ctgcctggtc aaaggcttct atcccagcga catcgccgtg    2640

gagtgggaga gcaatgggca gccggagaac aactacaaga ccacgcctcc cgtgttggac    2700

tccgacggct ccttcttcct ctacagcaag ctcaccgtgg acaagagcag gtggcagcag    2760

gggaacgtct tctcatgctc cgtgatgcat gaggctctgc acaaccacta cacgcagaag    2820

agcctctccc tgtctccggg taaatga                                        2847
```

<210> SEQ ID NO 90
<211> LENGTH: 1457
<212> TYPE: PRT
<213> ORGANISM: Artificial Sequence
<220> FEATURE:
<223> OTHER INFORMATION: Synthetic construct: B domain deleted FVIII
      amino acid sequence

<400> SEQUENCE: 90

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240
```

```
Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655
```

```
Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
```

```
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230

Gly Lys  Lys Trp Gln Thr Tyr  Arg Gly Asn Ser Thr  Gly Thr Leu
    1235                1240                1245

Met Val  Phe Phe Gly Asn Val  Asp Ser Ser Gly Ile  Lys His Asn
    1250                1255                1260

Ile Phe  Asn Pro Pro Ile Ile  Ala Arg Tyr Ile Arg  Leu His Pro
    1265                1270                1275

Thr His  Tyr Ser Ile Arg Ser  Thr Leu Arg Met Glu  Leu Met Gly
    1280                1285                1290

Cys Asp  Leu Asn Ser Cys Ser  Met Pro Leu Gly Met  Glu Ser Lys
    1295                1300                1305

Ala Ile  Ser Asp Ala Gln Ile  Thr Ala Ser Ser Tyr  Phe Thr Asn
    1310                1315                1320

Met Phe  Ala Thr Trp Ser Pro  Ser Lys Ala Arg Leu  His Leu Gln
    1325                1330                1335

Gly Arg  Ser Asn Ala Trp Arg  Pro Gln Val Asn Asn  Pro Lys Glu
    1340                1345                1350

Trp Leu  Gln Val Asp Phe Gln  Lys Thr Met Lys Val  Thr Gly Val
    1355                1360                1365

Thr Thr  Gln Gly Val Lys Ser  Leu Leu Thr Ser Met  Tyr Val Lys
    1370                1375                1380

Glu Phe  Leu Ile Ser Ser Ser  Gln Asp Gly His Gln  Trp Thr Leu
    1385                1390                1395

Phe Phe  Gln Asn Gly Lys Val  Lys Val Phe Gln Gly  Asn Gln Asp
    1400                1405                1410

Ser Phe  Thr Pro Val Val Asn  Ser Leu Asp Pro Pro  Leu Leu Thr
    1415                1420                1425

Arg Tyr  Leu Arg Ile His Pro  Gln Ser Trp Val His  Gln Ile Ala
    1430                1435                1440

Leu Arg  Met Glu Val Leu Gly  Cys Glu Ala Gln Asp  Leu Tyr
    1445                1450                1455
```

<210> SEQ ID NO 91

<211> LENGTH: 2351
<212> TYPE: PRT
<213> ORGANISM: Artificial Sequence
<220> FEATURE:
<223> OTHER INFORMATION: Synthetic construct: Full length FVIII amino acid sequence

<400> SEQUENCE: 91

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
```

-continued

```
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800
```

```
Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro  Ala Leu Leu Thr Lys  Asp Asn Ala
        995                 1000                1005

Leu Phe  Lys Val Ser Ile Ser  Leu Leu Lys Thr Asn  Lys Thr Ser
    1010                1015                1020

Asn Asn  Ser Ala Thr Asn Arg  Lys Thr His Ile Asp  Gly Pro Ser
    1025                1030                1035

Leu Leu  Ile Glu Asn Ser Pro  Ser Val Trp Gln Asn  Ile Leu Glu
    1040                1045                1050

Ser Asp  Thr Glu Phe Lys Lys  Val Thr Pro Leu Ile  His Asp Arg
    1055                1060                1065

Met Leu  Met Asp Lys Asn Ala  Thr Ala Leu Arg Leu  Asn His Met
    1070                1075                1080

Ser Asn  Lys Thr Thr Ser Ser  Lys Asn Met Glu Met  Val Gln Gln
    1085                1090                1095

Lys Lys  Glu Gly Pro Ile Pro  Pro Asp Ala Gln Asn  Pro Asp Met
    1100                1105                1110

Ser Phe  Phe Lys Met Leu Phe  Leu Pro Glu Ser Ala  Arg Trp Ile
    1115                1120                1125

Gln Arg  Thr His Gly Lys Asn  Ser Leu Asn Ser Gly  Gln Gly Pro
    1130                1135                1140

Ser Pro  Lys Gln Leu Val Ser  Leu Gly Pro Glu Lys  Ser Val Glu
    1145                1150                1155

Gly Gln  Asn Phe Leu Ser Glu  Lys Asn Lys Val Val  Val Gly Lys
    1160                1165                1170

Gly Glu  Phe Thr Lys Asp Val  Gly Leu Lys Glu Met  Val Phe Pro
    1175                1180                1185

Ser Ser  Arg Asn Leu Phe Leu  Thr Asn Leu Asp Asn  Leu His Glu
    1190                1195                1200
```

-continued

Asn Asn Thr His Asn Gln Glu Lys Lys Ile Gln Glu Glu Ile Glu
1205 1210 1215

Lys Lys Glu Thr Leu Ile Gln Glu Asn Val Val Leu Pro Gln Ile
1220 1225 1230

His Thr Val Thr Gly Thr Lys Asn Phe Met Lys Asn Leu Phe Leu
1235 1240 1245

Leu Ser Thr Arg Gln Asn Val Glu Gly Ser Tyr Asp Gly Ala Tyr
1250 1255 1260

Ala Pro Val Leu Gln Asp Phe Arg Ser Leu Asn Asp Ser Thr Asn
1265 1270 1275

Arg Thr Lys Lys His Thr Ala His Phe Ser Lys Lys Gly Glu Glu
1280 1285 1290

Glu Asn Leu Glu Gly Leu Gly Asn Gln Thr Lys Gln Ile Val Glu
1295 1300 1305

Lys Tyr Ala Cys Thr Thr Arg Ile Ser Pro Asn Thr Ser Gln Gln
1310 1315 1320

Asn Phe Val Thr Gln Arg Ser Lys Arg Ala Leu Lys Gln Phe Arg
1325 1330 1335

Leu Pro Leu Glu Glu Thr Glu Leu Glu Lys Arg Ile Ile Val Asp
1340 1345 1350

Asp Thr Ser Thr Gln Trp Ser Lys Asn Met Lys His Leu Thr Pro
1355 1360 1365

Ser Thr Leu Thr Gln Ile Asp Tyr Asn Glu Lys Glu Lys Gly Ala
1370 1375 1380

Ile Thr Gln Ser Pro Leu Ser Asp Cys Leu Thr Arg Ser His Ser
1385 1390 1395

Ile Pro Gln Ala Asn Arg Ser Pro Leu Pro Ile Ala Lys Val Ser
1400 1405 1410

Ser Phe Pro Ser Ile Arg Pro Ile Tyr Leu Thr Arg Val Leu Phe
1415 1420 1425

Gln Asp Asn Ser Ser His Leu Pro Ala Ala Ser Tyr Arg Lys Lys
1430 1435 1440

Asp Ser Gly Val Gln Glu Ser Ser His Phe Leu Gln Gly Ala Lys
1445 1450 1455

Lys Asn Asn Leu Ser Leu Ala Ile Leu Thr Leu Glu Met Thr Gly
1460 1465 1470

Asp Gln Arg Glu Val Gly Ser Leu Gly Thr Ser Ala Thr Asn Ser
1475 1480 1485

Val Thr Tyr Lys Lys Val Glu Asn Thr Val Leu Pro Lys Pro Asp
1490 1495 1500

Leu Pro Lys Thr Ser Gly Lys Val Glu Leu Leu Pro Lys Val His
1505 1510 1515

Ile Tyr Gln Lys Asp Leu Phe Pro Thr Glu Thr Ser Asn Gly Ser
1520 1525 1530

Pro Gly His Leu Asp Leu Val Glu Gly Ser Leu Leu Gln Gly Thr
1535 1540 1545

Glu Gly Ala Ile Lys Trp Asn Glu Ala Asn Arg Pro Gly Lys Val
1550 1555 1560

Pro Phe Leu Arg Val Ala Thr Glu Ser Ser Ala Lys Thr Pro Ser
1565 1570 1575

Lys Leu Leu Asp Pro Leu Ala Trp Asp Asn His Tyr Gly Thr Gln
1580 1585 1590

Ile Pro Lys Glu Glu Trp Lys Ser Gln Glu Lys Ser Pro Glu Lys

```
    1595                1600                1605

Thr Ala  Phe Lys Lys Lys Asp  Thr Ile Leu Ser Leu  Asn Ala Cys
    1610                1615                1620

Glu Ser  Asn His Ala Ile Ala  Ala Ile Asn Glu Gly  Gln Asn Lys
    1625                1630                1635

Pro Glu  Ile Glu Val Thr Trp  Ala Lys Gln Gly Arg  Thr Glu Arg
    1640                1645                1650

Leu Cys  Ser Gln Asn Pro Pro  Val Leu Lys Arg His  Gln Arg Glu
    1655                1660                1665

Ile Thr  Arg Thr Thr Leu Gln  Ser Asp Gln Glu Glu  Ile Asp Tyr
    1670                1675                1680

Asp Asp  Thr Ile Ser Val Glu  Met Lys Lys Glu Asp  Phe Asp Ile
    1685                1690                1695

Tyr Asp  Glu Asp Glu Asn Gln  Ser Pro Arg Ser Phe  Gln Lys Lys
    1700                1705                1710

Thr Arg  His Tyr Phe Ile Ala  Ala Val Glu Arg Leu  Trp Asp Tyr
    1715                1720                1725

Gly Met  Ser Ser Ser Pro His  Val Leu Arg Asn Arg  Ala Gln Ser
    1730                1735                1740

Gly Ser  Val Pro Gln Phe Lys  Lys Val Val Phe Gln  Glu Phe Thr
    1745                1750                1755

Asp Gly  Ser Phe Thr Gln Pro  Leu Tyr Arg Gly Glu  Leu Asn Glu
    1760                1765                1770

His Leu  Gly Leu Leu Gly Pro  Tyr Ile Arg Ala Glu  Val Glu Asp
    1775                1780                1785

Asn Ile  Met Val Thr Phe Arg  Asn Gln Ala Ser Arg  Pro Tyr Ser
    1790                1795                1800

Phe Tyr  Ser Ser Leu Ile Ser  Tyr Glu Glu Asp Gln  Arg Gln Gly
    1805                1810                1815

Ala Glu  Pro Arg Lys Asn Phe  Val Lys Pro Asn Glu  Thr Lys Thr
    1820                1825                1830

Tyr Phe  Trp Lys Val Gln His  His Met Ala Pro Thr  Lys Asp Glu
    1835                1840                1845

Phe Asp  Cys Lys Ala Trp Ala  Tyr Phe Ser Asp Val  Asp Leu Glu
    1850                1855                1860

Lys Asp  Val His Ser Gly Leu  Ile Gly Pro Leu Leu  Val Cys His
    1865                1870                1875

Thr Asn  Thr Leu Asn Pro Ala  His Gly Arg Gln Val  Thr Val Gln
    1880                1885                1890

Glu Phe  Ala Leu Phe Phe Thr  Ile Phe Asp Glu Thr  Lys Ser Trp
    1895                1900                1905

Tyr Phe  Thr Glu Asn Met Glu  Arg Asn Cys Arg Ala  Pro Cys Asn
    1910                1915                1920

Ile Gln  Met Glu Asp Pro Thr  Phe Lys Glu Asn Tyr  Arg Phe His
    1925                1930                1935

Ala Ile  Asn Gly Tyr Ile Met  Asp Thr Leu Pro Gly  Leu Val Met
    1940                1945                1950

Ala Gln  Asp Gln Arg Ile Arg  Trp Tyr Leu Leu Ser  Met Gly Ser
    1955                1960                1965

Asn Glu  Asn Ile His Ser Ile  His Phe Ser Gly His  Val Phe Thr
    1970                1975                1980

Val Arg  Lys Lys Glu Glu Tyr  Lys Met Ala Leu Tyr  Asn Leu Tyr
    1985                1990                1995
```

```
Pro Gly  Val Phe Glu Thr Val  Glu Met Leu Pro Ser  Lys Ala Gly
    2000                 2005                 2010

Ile Trp  Arg Val Glu Cys Leu  Ile Gly Glu His Leu  His Ala Gly
    2015                 2020                 2025

Met Ser  Thr Leu Phe Leu Val  Tyr Ser Asn Lys Cys  Gln Thr Pro
    2030                 2035                 2040

Leu Gly  Met Ala Ser Gly His  Ile Arg Asp Phe Gln  Ile Thr Ala
    2045                 2050                 2055

Ser Gly  Gln Tyr Gly Gln Trp  Ala Pro Lys Leu Ala  Arg Leu His
    2060                 2065                 2070

Tyr Ser  Gly Ser Ile Asn Ala  Trp Ser Thr Lys Glu  Pro Phe Ser
    2075                 2080                 2085

Trp Ile  Lys Val Asp Leu Leu  Ala Pro Met Ile Ile  His Gly Ile
    2090                 2095                 2100

Lys Thr  Gln Gly Ala Arg Gln  Lys Phe Ser Ser Leu  Tyr Ile Ser
    2105                 2110                 2115

Gln Phe  Ile Ile Met Tyr Ser  Leu Asp Gly Lys Lys  Trp Gln Thr
    2120                 2125                 2130

Tyr Arg  Gly Asn Ser Thr Gly  Thr Leu Met Val Phe  Phe Gly Asn
    2135                 2140                 2145

Val Asp  Ser Ser Gly Ile Lys  His Asn Ile Phe Asn  Pro Pro Ile
    2150                 2155                 2160

Ile Ala  Arg Tyr Ile Arg Leu  His Pro Thr His Tyr  Ser Ile Arg
    2165                 2170                 2175

Ser Thr  Leu Arg Met Glu Leu  Met Gly Cys Asp Leu  Asn Ser Cys
    2180                 2185                 2190

Ser Met  Pro Leu Gly Met Glu  Ser Lys Ala Ile Ser  Asp Ala Gln
    2195                 2200                 2205

Ile Thr  Ala Ser Ser Tyr Phe  Thr Asn Met Phe Ala  Thr Trp Ser
    2210                 2215                 2220

Pro Ser  Lys Ala Arg Leu His  Leu Gln Gly Arg Ser  Asn Ala Trp
    2225                 2230                 2235

Arg Pro  Gln Val Asn Asn Pro  Lys Glu Trp Leu Gln  Val Asp Phe
    2240                 2245                 2250

Gln Lys  Thr Met Lys Val Thr  Gly Val Thr Thr Gln  Gly Val Lys
    2255                 2260                 2265

Ser Leu  Leu Thr Ser Met Tyr  Val Lys Glu Phe Leu  Ile Ser Ser
    2270                 2275                 2280

Ser Gln  Asp Gly His Gln Trp  Thr Leu Phe Phe Gln  Asn Gly Lys
    2285                 2290                 2295

Val Lys  Val Phe Gln Gly Asn  Gln Asp Ser Phe Thr  Pro Val Val
    2300                 2305                 2310

Asn Ser  Leu Asp Pro Pro Leu  Leu Thr Arg Tyr Leu  Arg Ile His
    2315                 2320                 2325

Pro Gln  Ser Trp Val His Gln  Ile Ala Leu Arg Met  Glu Val Leu
    2330                 2335                 2340

Gly Cys  Glu Ala Gln Asp Leu  Tyr
    2345                 2350
```

<210> SEQ ID NO 92
<211> LENGTH: 461
<212> TYPE: PRT
<213> ORGANISM: Artificial Sequence
<220> FEATURE:

<223> OTHER INFORMATION: Synthetic construct: FIX amino acid sequence

<400> SEQUENCE: 92

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400
```

```
Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460
```

<210> SEQ ID NO 93
<211> LENGTH: 1384
<212> TYPE: DNA
<213> ORGANISM: Artificial Sequence
<220> FEATURE:
<223> OTHER INFORMATION: Synthetic construct: FIX DNA sequence

<400> SEQUENCE: 93

```
atgcagcgcg tgaacatgat catggcagaa tcaccaggcc tcatcaccat ctgcctttta     60

ggatatctac tcagtgctga atgtacagtt tttcttgatc atgaaaacgc acaaaattct    120

gaatcggcca aagaggtata attcaggtaa attggaagag tttgttcaag ggaatctaga    180

gagagaatgt atggaagaaa agtgtagttt tgaagaagca cgagaagttt ttgaaaacac    240

tgaaagaaca actgaatttt ggaagcagta tgttgatgga gatcagtgtg agtccaatcc    300

atgtttaaat ggcggcagtt gcaaggatga cattaattcc tatgaatgtt ggtgtccctt    360

tggatttgaa ggaaagaact gtgaattaga tgtaacatgt aacattaaga atggcagatg    420

cgagcagttt tgtaaaaata gtgctgataa caaggtggtt tgctcctgta ctgagggata    480

tcgacttgca gaaaaccaga agtcctgtga accagcagtg ccatttccat gtggaagagt    540

ttctgtttca caaacttcta agctcacccg tgctgagact gtttttcctg atgtggacta    600

tgtaaattct actgaagctg aaaccatttt ggataacatc actcaaagca cccaatcatt    660

taatgacttc actcgggttg ttggtggaga agatgccaaa ccaggtcaat tcccttggca    720

ggttgttttg aatggtaaag ttgatgcatt ctgtggaggc tctatcgtta atgaaaaatg    780

gattgtaact gctgcccact gtgttgaaac tggtgttaaa attacagttg tcgcaggtga    840

acataatatt gaggagacag aacatacaga gcaaaagcga aatgtgattc gaattattcc    900

tcaccacaac tacaatgcag ctattaataa gtacaaccat gacattgccc ttctggaact    960

ggacgaaccc ttagtgctaa acagctacgt tacacctatt tgcattgctg acaaggaata   1020

cacgaacatc ttcctcaaat ttggatctgg ctatgtaagt ggctggggaa gagtcttcca   1080

caaagggaga tcagctttag ttcttcagta ccttagagtt ccacttgttg accgagccac   1140

atgtcttcga tctacaaagt tcaccatcta taacaacatg ttctgtgctg gcttccatga   1200

aggaggtaga gattcatgtc aaggagatag tgggggaccc catgttactg aagtggaagg   1260

gaccagtttc ttaactggaa ttattagctg ggtgaagag tgtgcaatga aaggcaaata   1320

tggaatatat accaaggtat cccggtatgt caactggatt aaggaaaaaa caaagctcac   1380

ttga                                                                1384
```

<210> SEQ ID NO 94
<211> LENGTH: 488
<212> TYPE: PRT
<213> ORGANISM: Artificial Sequence
<220> FEATURE:
<223> OTHER INFORMATION: Synthetic construct: FX amino acid sequence

<400> SEQUENCE: 94

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415
```

```
Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485
```

<210> SEQ ID NO 95
<211> LENGTH: 1467
<212> TYPE: DNA
<213> ORGANISM: Artificial Sequence
<220> FEATURE:
<223> OTHER INFORMATION: Synthetic construct: FX DNA sequence

<400> SEQUENCE: 95

```
atggggcgcc cactgcacct cgtcctgctc agtgcctccc tggctggcct cctgctgctc     60

ggggaaagtc tgttcatccg cagggagcag gccaacaaca tcctggcgag ggtcacgagg    120

gccaattcct ttcttgaaga gatgaagaaa ggacacctcg aaagagagtg catggaagag    180

acctgctcat acgaagaggc ccgcgaggtc tttgaggaca gcgacaagac gaatgaattc    240

tggaataaat acaaagatgg cgaccagtgt gagaccagtc cttgccagaa ccagggcaaa    300

tgtaaagacg gcctcgggga atacacctgc acctgtttag aaggattcga aggcaaaaac    360

tgtgaattat tcacacggaa gctctgcagc ctggacaacg gggactgtga ccagttctgc    420

cacgaggaac agaactctgt ggtgtgctcc tgcgcccgcg ggtacaccct ggctgacaac    480

ggcaaggcct gcattcccac agggccctac ccctgtggga aacagaccct ggaacgcagg    540

aagaggtcag tggcccaggc caccagcagc agcggggagg cccctgacag catcacatgg    600

aagccatatg atgcagccga cctggacccc accgagaacc ccttcgacct gcttgacttc    660

aaccagacgc agcctgagag gggcgacaac aacctcacca ggatcgtggg aggccaggaa    720

tgcaaggacg gggagtgtcc ctggcaggcc ctgctcatca atgaggaaaa cgagggtttc    780

tgtggtggaa ccattctgag cgagttctac atcctaacgg cagcccactg tctctaccaa    840

gccaagagat tcaaggtgag ggtaggggac cggaacacgg agcaggagga gggcggtgag    900

gcggtgcacg aggtggaggt ggtcatcaag cacaaccggt tcacaaagga gacctatgac    960

ttcgacatcg ccgtgctccg gctcaagacc cccatcacct tccgcatgaa cgtggcgcct   1020

gcctgcctcc ccgagcgtga ctgggccgag tccacgctga tgacgcagaa gacggggatt   1080

gtgagcggct tcgggcgcac ccacgagaag ggccggcagt ccaccaggct caagatgctg   1140

gaggtgccct acgtggaccg caacagctgc aagctgtcca gcagcttcat catcacccag   1200

aacatgttct gtgccggcta cgacaccaag caggaggatg cctgccaggg ggacagcggg   1260

ggcccgcacg tcacccgctt caaggacacc tacttcgtga caggcatcgt cagctgggga   1320

gagggctgtg cccgtaaggg gaagtacggg atctacacca aggtcaccgc cttcctcaag   1380

tggatcgaca ggtccatgaa aaccaggggc ttgcccaagg ccaagagcca tgccccggag   1440

gtcataacgt cctctccatt aaagtga                                       1467
```

<210> SEQ ID NO 96
<211> LENGTH: 3813
<212> TYPE: DNA

<213> ORGANISM: Artificial Sequence
<220> FEATURE:
<223> OTHER INFORMATION: Synthetic construct: DNA sequence of FVII-066

<400> SEQUENCE: 96
atggtctccc aggccctcag gctcctctgc cttctgcttg ggcttcaggg ctgcctggct 60
gcagtcttcg taacccagga ggaagcccac ggcgtcctgc accggcgccg gcgcgccaac 120
gcgttcctgg aggagctgcg gccgggctcc ctggagaggg agtgcaagga ggagcagtgc 180
tccttcgagg aggcccggga gatcttcaag gacgcggaga ggacgaagct gttctggatt 240
tcttacagtg atggggacca gtgtgcctca agtccatgcc agaatggggg ctcctgcaag 300
gaccagctcc agtcctatat ctgcttctgc ctccctgcct tcgagggccg gaactgtgag 360
acgcacaagg atgaccagct gatctgtgtg aacgagaacg gcggctgtga gcagtactgc 420
agtgaccaca cgggcaccaa gcgctcctgt cggtgccacg aggggtactc tctgctggca 480
gacggggtgt cctgcacacc cacagttgaa tatccatgtg gaaaaatacc tattctagaa 540
aaaagaaatg ccagcaaacc ccaaggccga attgtggggg gcaaggtgtg ccccaaaggg 600
gagtgtccat ggcaggtcct gttgttggtg aatggagctc agttgtgtgg ggggaccctg 660
atcaacacca tctgggtggt ctccgcggcc cactgtttcg acaaaatcaa gaactggagg 720
aacctgatcg cggtgctggg cgagcacgac ctcagcgagc acgacgggga tgagcagagc 780
cggcgggtgg cgcaggtcat catccccagc acgtacgtcc cgggcaccac caaccacgac 840
atcgcgctgc tccgcctgca ccagcccgtg gtcctcactg accatgtggt gcccctctgc 900
ctgcccgaac ggacgttctc tgagaggacg ctggccttcg tgcgcttctc attggtcagc 960
ggctggggcc agctgctgga ccgtggcgcc acggccctgg agctcatggt cctcaacgtg 1020
ccccggctga tgacccagga ctgcctgcag cagtcacgga aggtgggaga ctccccaaat 1080
atcacggagt acatgttctg tgccggctac tcggatggca gcaaggactc ctgcaagggg 1140
gacagtggag gcccacatgc cacccactac cggggcacgt ggtacctgac gggcatcgtc 1200
agctggggcc agggctgcgc aaccgtgggc cactttgggg tgtacaccag ggtctcccag 1260
tacatcgagt ggctgcaaaa gctcatgcgc tcagagccac gcccaggagt cctcctgcga 1320
gccccatttc ccggtggcgg tggctccggc ggaggtgggt ccggtggcgg cggatcaggt 1380
gggggtggat caggcggtgg aggttccggt ggcgggggat ccgacaaaac tcacacatgc 1440
ccaccgtgcc cagctccgga actcctggga ggaccgtcag tcttcctctt ccccccaaaa 1500
cccaaggaca ccctcatgat ctcccggacc cctgaggtca catgcgtggt ggtggacgtg 1560
agccacgaag accctgaggt caagttcaac tggtacgtgg acggcgtgga ggtgcataat 1620
gccaagacaa agccgcggga ggagcagtac aacagcacgt accgtgtggt cagcgtcctc 1680
accgtcctgc accaggactg gctgaatggc aaggagtaca agtgcaaggt ctccaacaaa 1740
gccctcccag cccccatcga gaaaaccatc tccaaagcca aagggcagcc ccgagaacca 1800
caggtgtaca ccctgccccc atcccgggat gagctgacca agaaccaggt cagcctgacc 1860
tgcctggtca aaggcttcta tcccagcgac atcgccgtgg agtgggagag caatgggcag 1920
ccggagaaca actacaagac cacgcctccc gtgttggact ccgacggctc cttcttcctc 1980
tacagcaagc tcaccgtcga caagagcagg tggcagcagg ggaacgtctt ctcatgctcc 2040
gtgatgcatg aggctctgca caaccactac acgcagaaga gcctctccct gtctccgggt 2100
aaacggcgcc gccggagcgg tggcggcgga tcaggtgggg gtggatcagg cggtggaggt 2160
tccggtggcg gggggatccgg cggtggaggt tccggtgggg gtggatcaag gaagaggagg 2220

```
aagagggcgc aggtgcagct gcaggagtct gggggaggct tggtacagcc tggggggtcc   2280

ctgagactct cctgtgcagc ctctggattc atgtttagca ggtatgccat gagctgggtc   2340

cgccaggctc cagggaaggg gccagagtgg gtctcaggta ttagtggtag tggtggtagt   2400

acatactacg cagactccgt gaagggccgg ttcaccgtct ccagagacaa ttccaagaac   2460

acgctgtatc tgcaaatgaa cagcctgaga gccgaggaca cggctgtata ttactgcgcc   2520

cggggcgcca cctacaccag ccggagcgac gtgcccgacc agaccagctt cgactactgg   2580

ggccagggaa ccctggtcac cgtctcctca gggagtgcat ccgccccaaa gcttgaagaa   2640

ggtgaatttt cagaagcacg cgtatctgaa ctgactcagg accctgctgt gtctgtggcc   2700

ttgggacaga cagtcaggat cacatgccaa ggagacagcc tcagaaactt ttatgcaagc   2760

tggtaccagc agaagccagg acaggcccct actcttgtca tctatggttt aagtaaaagg   2820

ccctcaggga tcccagaccg attctctgcc tccagctcag gaaacacagc ttccttgacc   2880

atcactgggg ctcaggcgga agatgaggct gactattact gcctgctgta ctacggcggc   2940

ggccagcagg gcgtgttcgg cggcggcacc aagctgaccg tcctacgtca gcccaaggct   3000

gccccctcgg tcactctgtt cccgccctct tctgcggccg gtggcggtgg ctccggcgga   3060

ggtgggtccg gtggcggcgg atcaggtggg ggtggatcag gcggtggagg ttccggtggc   3120

gggggatcag acaaaactca cacatgccca ccgtgcccag caccggaact cctgggcgga   3180

ccgtcagtct tcctcttccc cccaaaaccc aaggacaccc tcatgatctc ccggacccct   3240

gaggtcacat gcgtggtggt ggacgtgagc cacgaagacc ctgaggtcaa gttcaactgg   3300

tacgtggacg gcgtggaggt gcataatgcc aagacaaagc cgcgggagga gcagtacaac   3360

agcacgtacc gtgtggtcag cgtcctcacc gtcctgcacc aggactggct gaatggcaag   3420

gagtacaagt gcaaggtctc caacaaagcc ctcccagccc ccatcgagaa aaccatctcc   3480

aaagccaaag ggcagccccg agaaccacag gtgtacaccc tgcccccatc ccgggatgag   3540

ctgaccaaga accaggtcag cctgacctgc ctggtcaaag gcttctatcc cagcgacatc   3600

gccgtggagt gggagagcaa tgggcagccg gagaacaact acaagaccac gcctcccgtg   3660

ttggactccg acggctcctt cttcctctac agcaagctca ccgtggacaa gagcaggtgg   3720

cagcagggga acgtcttctc atgctccgtg atgcatgagg ctctgcacaa ccactacacg   3780

cagaagagcc tctccctgtc tccgggtaaa tga                                3813


<210> SEQ ID NO 97
<211> LENGTH: 1270
<212> TYPE: PRT
<213> ORGANISM: Artificial Sequence
<220> FEATURE:
<223> OTHER INFORMATION: Synthetic construct: FVII-066 amino acid
      sequence

<400> SEQUENCE: 97

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
```

```
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Lys Thr His Thr Cys
465                 470                 475                 480

Pro Pro Cys Pro Ala Pro Glu Leu Leu Gly Gly Pro Ser Val Phe Leu
                485                 490                 495
```

```
Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Arg Arg Arg
    690                 695                 700

Arg Ser Gly Gly Gly Gly Ser Gly Gly Gly Gly Ser Gly Gly Gly Gly
705                 710                 715                 720

Ser Gly Gly Gly Gly Ser Gly Gly Gly Gly Ser Gly Gly Gly Gly Ser
                725                 730                 735

Arg Lys Arg Arg Lys Arg Ala Gln Val Gln Leu Gln Glu Ser Gly Gly
            740                 745                 750

Gly Leu Val Gln Pro Gly Gly Ser Leu Arg Leu Ser Cys Ala Ala Ser
        755                 760                 765

Gly Phe Met Phe Ser Arg Tyr Ala Met Ser Trp Val Arg Gln Ala Pro
    770                 775                 780

Gly Lys Gly Pro Glu Trp Val Ser Gly Ile Ser Gly Ser Gly Gly Ser
785                 790                 795                 800

Thr Tyr Tyr Ala Asp Ser Val Lys Gly Arg Phe Thr Val Ser Arg Asp
                805                 810                 815

Asn Ser Lys Asn Thr Leu Tyr Leu Gln Met Asn Ser Leu Arg Ala Glu
            820                 825                 830

Asp Thr Ala Val Tyr Tyr Cys Ala Arg Gly Ala Thr Tyr Thr Ser Arg
        835                 840                 845

Ser Asp Val Pro Asp Gln Thr Ser Phe Asp Tyr Trp Gly Gln Gly Thr
    850                 855                 860

Leu Val Thr Val Ser Ser Gly Ser Ala Ser Ala Pro Lys Leu Glu Glu
865                 870                 875                 880

Gly Glu Phe Ser Glu Ala Arg Val Ser Glu Leu Thr Gln Asp Pro Ala
                885                 890                 895

Val Ser Val Ala Leu Gly Gln Thr Val Arg Ile Thr Cys Gln Gly Asp
            900                 905                 910
```

-continued

```
Ser Leu Arg Asn Phe Tyr Ala Ser Trp Tyr Gln Gln Lys Pro Gly Gln
        915                 920                 925

Ala Pro Thr Leu Val Ile Tyr Gly Leu Ser Lys Arg Pro Ser Gly Ile
    930                 935                 940

Pro Asp Arg Phe Ser Ala Ser Ser Ser Gly Asn Thr Ala Ser Leu Thr
945                 950                 955                 960

Ile Thr Gly Ala Gln Ala Glu Asp Glu Ala Asp Tyr Tyr Cys Leu Leu
                965                 970                 975

Tyr Tyr Gly Gly Gly Gln Gln Gly Val Phe Gly Gly Gly Thr Lys Leu
            980                 985                 990

Thr Val Leu Arg Gln Pro Lys Ala  Ala Pro Ser Val Thr  Leu Phe Pro
        995                 1000                1005

Pro Ser  Ser Ala Ala Gly Gly  Gly Gly Ser Gly Gly  Gly Gly Ser
    1010                1015                1020

Gly Gly  Gly Gly Ser Gly Gly  Gly Gly Ser Gly Gly  Gly Gly Ser
    1025                1030                1035

Gly Gly  Gly Gly Ser Asp Lys  Thr His Thr Cys Pro  Pro Cys Pro
    1040                1045                1050

Ala Pro  Glu Leu Leu Gly Gly  Pro Ser Val Phe Leu  Phe Pro Pro
    1055                1060                1065

Lys Pro  Lys Asp Thr Leu Met  Ile Ser Arg Thr Pro  Glu Val Thr
    1070                1075                1080

Cys Val  Val Val Asp Val Ser  His Glu Asp Pro Glu  Val Lys Phe
    1085                1090                1095

Asn Trp  Tyr Val Asp Gly Val  Glu Val His Asn Ala  Lys Thr Lys
    1100                1105                1110

Pro Arg  Glu Glu Gln Tyr Asn  Ser Thr Tyr Arg Val  Val Ser Val
    1115                1120                1125

Leu Thr  Val Leu His Gln Asp  Trp Leu Asn Gly Lys  Glu Tyr Lys
    1130                1135                1140

Cys Lys  Val Ser Asn Lys Ala  Leu Pro Ala Pro Ile  Glu Lys Thr
    1145                1150                1155

Ile Ser  Lys Ala Lys Gly Gln  Pro Arg Glu Pro Gln  Val Tyr Thr
    1160                1165                1170

Leu Pro  Pro Ser Arg Asp Glu  Leu Thr Lys Asn Gln  Val Ser Leu
    1175                1180                1185

Thr Cys  Leu Val Lys Gly Phe  Tyr Pro Ser Asp Ile  Ala Val Glu
    1190                1195                1200

Trp Glu  Ser Asn Gly Gln Pro  Glu Asn Asn Tyr Lys  Thr Thr Pro
    1205                1210                1215

Pro Val  Leu Asp Ser Asp Gly  Ser Phe Phe Leu Tyr  Ser Lys Leu
    1220                1225                1230

Thr Val  Asp Lys Ser Arg Trp  Gln Gln Gly Asn Val  Phe Ser Cys
    1235                1240                1245

Ser Val  Met His Glu Ala Leu  His Asn His Tyr Thr  Gln Lys Ser
    1250                1255                1260

Leu Ser  Leu Ser Pro Gly Lys
    1265                1270
```

<210> SEQ ID NO 98
<211> LENGTH: 3012
<212> TYPE: DNA
<213> ORGANISM: Artificial Sequence
<220> FEATURE:
<223> OTHER INFORMATION: Synthetic construct: DNA sequence for FVII-057

<400> SEQUENCE: 98
atggtctccc aggccctcag gctcctctgc cttctgcttg ggcttcaggg ctgcctggct 60
gcagtcttcg taacccagga ggaagcccac ggcgtcctgc accggcgccg gcgcgccaac 120
gcgttcctgg aggagctgcg gccgggctcc ctggagaggg agtgcaagga ggagcagtgc 180
tccttcgagg aggcccggga gatcttcaag gacgcggaga ggacgaagct gttctggatt 240
tcttacagtg atggggacca gtgtgcctca agtccatgcc agaatggggg ctcctgcaag 300
gaccagctcc agtcctatat ctgcttctgc ctccctgcct tcgagggccg gaactgtgag 360
acgcacaagg atgaccagct gatctgtgtg aacgagaacg gcggctgtga gcagtactgc 420
agtgaccaca cgggcaccaa gcgctcctgt cggtgccacg aggggtactc tctgctggca 480
gacggggtgt cctgcacacc cacagttgaa tatccatgtg gaaaaatacc tattctagaa 540
aaaagaaatg ccagcaaacc ccaaggccga ggtggcggtg gctccggcgg aggtgggtcc 600
ggtggcggcg gatcaggtgg gggtggatca ggcggtggag gttccggtgg cgggggatcc 660
gacaaaactc acacatgccc accgtgccca gctccggaac tcctgggagg accgtcagtc 720
ttcctcttcc ccccaaaacc caaggacacc ctcatgatct cccggacccc tgaggtcaca 780
tgcgtggtgg tggacgtgag ccacgaagac cctgaggtca agttcaactg gtacgtggac 840
ggcgtggagg tgcataatgc caagacaaag ccgcgggagg agcagtacaa cagcacgtac 900
cgtgtggtca gcgtcctcac cgtcctgcac caggactggc tgaatggcaa ggagtacaag 960
tgcaaggtct ccaacaaagc cctcccagcc cccatcgaga aaaccatctc caaagccaaa 1020
gggcagcccc gagaaccaca ggtgtacacc ctgcccccat cccgggatga gctgaccaag 1080
aaccaggtca gcctgacctg cctggtcaaa ggcttctatc ccagcgacat cgccgtggag 1140
tgggagagca atgggcagcc ggagaacaac tacaagacca cgcctcccgt gttggactcc 1200
gacggctcct tcttcctcta cagcaagctc accgtcgaca agagcaggtg gcagcagggg 1260
aacgtcttct catgctccgt gatgcatgag gctctgcaca accactacac gcagaagagc 1320
ctctccctgt ctccgggtaa aggtggcggc ggatcaggtg ggggtggatc aggcggtgga 1380
ggttccggtg gcgggggatc cggcggtgga ggttccggtg ggggtggatc aggaggaggt 1440
ggttcaagcg tgagccagac cagcaagctg acccggattg tgggggggcaa ggtgtgcccc 1500 aaaggggagt gtccatggca ggtcctgttg ttggtgaatg gagctcagtt gtgtgggggg 1560
accctgatca acaccatctg ggtggtctcc gcggcccact gtttcgacaa aatcaagaac 1620
tggaggaacc tgatcgcggt gctgggcgag cacgacctca gcgagcacga cggggatgag 1680
cagagccggc gggtggcgca ggtcatcatc cccagcacgt acgtcccggg caccaccaac 1740
cacgacatcg cgctgctccg cctgcaccag cccgtggtcc tcactgacca tgtggtgccc 1800
ctctgcctgc ccgaacggac gttctctgag aggacgctgg ccttcgtgcg cttctcattg 1860
gtcagcggct ggggccagct gctggaccgt ggcgccacgg ccctggagct catggtcctc 1920
aacgtgcccc ggctgatgac ccaggactgc ctgcagcagt cacggaaggt gggagactcc 1980
ccaaatatca cggagtacat gttctgtgcc ggctactcgg atggcagcaa ggactcctgc 2040
aagggggaca gtggaggccc acatgccacc cactaccggg gcacgtggta cctgacgggc 2100
atcgtcagct ggggccaggg ctgcgcaacc gtgggccact ttggggtgta caccagggtc 2160
tcccagtaca tcgagtggct gcaaaagctc atgcgctcag agccacgccc aggagtcctc 2220
ctgcgagccc catttcccgg tggcggtggc tccggcggag gtgggtccgg tggcggcgga 2280

```
tcaggtgggg gtggatcagg cggtggaggt tccggtggcg gggggatcaga caaaactcac   2340

acatgcccac cgtgcccagc acctgaactc ctgggaggac cgtcagtctt cctcttcccc   2400

ccaaaaccca aggacaccct catgatctcc cggacccctg aggtcacatg cgtggtggtg   2460

gacgtgagcc acgaagaccc tgaggtcaag ttcaactggt acgtggacgg cgtggaggtg   2520

cataatgcca agacaaagcc gcgggaggag cagtacaaca gcacgtaccg tgtggtcagc   2580

gtcctcaccg tcctgcacca ggactggctg aatggcaagg agtacaagtg caaggtctcc   2640

aacaaagccc tcccagcccc catcgagaaa accatctcca aagccaaagg gcagccccga   2700

gaaccacagg tgtacaccct gcccccatcc cgggatgagc tgaccaagaa ccaggtcagc   2760

ctgacctgcc tggtcaaagg cttctatccc agcgacatcg ccgtggagtg ggagagcaat   2820

gggcagccgg agaacaacta caagaccacg cctcccgtgt tggactccga cggctccttc   2880

ttcctctaca gcaagctcac cgtggacaag agcaggtggc agcaggggaa cgtcttctca   2940

tgctccgtga tgcatgaggc tctgcacaac cactacacgc agaagagcct ctccctgtct   3000

ccgggtaaat ga                                                        3012


<210> SEQ ID NO 99
<211> LENGTH: 1003
<212> TYPE: PRT
<213> ORGANISM: Artificial Sequence
<220> FEATURE:
<223> OTHER INFORMATION: Synthetic construct: FVII-057 amino acid
      sequence

<400> SEQUENCE: 99

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Asp Lys Thr His
    210                 215                 220
```

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys Gly
435 440 445

Gly Gly Gly Ser Gly Gly Gly Gly Ser Gly Gly Gly Gly Ser Gly Gly
450 455 460

Gly Gly Ser Gly Gly Gly Gly Ser Gly Gly Gly Gly Ser Gly Gly Gly
465 470 475 480

Gly Ser Ser Val Ser Gln Thr Ser Lys Leu Thr Arg Ile Val Gly Gly
485 490 495

Lys Val Cys Pro Lys Gly Glu Cys Pro Trp Gln Val Leu Leu Leu Val
500 505 510

Asn Gly Ala Gln Leu Cys Gly Gly Thr Leu Ile Asn Thr Ile Trp Val
515 520 525

Val Ser Ala Ala His Cys Phe Asp Lys Ile Lys Asn Trp Arg Asn Leu
530 535 540

Ile Ala Val Leu Gly Glu His Asp Leu Ser Glu His Asp Gly Asp Glu
545 550 555 560

Gln Ser Arg Arg Val Ala Gln Val Ile Ile Pro Ser Thr Tyr Val Pro
565 570 575

Gly Thr Thr Asn His Asp Ile Ala Leu Leu Arg Leu His Gln Pro Val
580 585 590

Val Leu Thr Asp His Val Val Pro Leu Cys Leu Pro Glu Arg Thr Phe
595 600 605

Ser Glu Arg Thr Leu Ala Phe Val Arg Phe Ser Leu Val Ser Gly Trp
610 615 620

Gly Gln Leu Leu Asp Arg Gly Ala Thr Ala Leu Glu Leu Met Val Leu
625 630 635 640

Asn Val Pro Arg Leu Met Thr Gln Asp Cys Leu Gln Gln Ser Arg Lys

-continued

```
                645                 650                 655

Val Gly Asp Ser Pro Asn Ile Thr Glu Tyr Met Phe Cys Ala Gly Tyr
            660                 665                 670

Ser Asp Gly Ser Lys Asp Ser Cys Lys Gly Asp Ser Gly Gly Pro His
        675                 680                 685

Ala Thr His Tyr Arg Gly Thr Trp Tyr Leu Thr Gly Ile Val Ser Trp
    690                 695                 700

Gly Gln Gly Cys Ala Thr Val Gly His Phe Gly Val Tyr Thr Arg Val
705                 710                 715                 720

Ser Gln Tyr Ile Glu Trp Leu Gln Lys Leu Met Arg Ser Glu Pro Arg
                725                 730                 735

Pro Gly Val Leu Leu Arg Ala Pro Phe Pro Gly Gly Gly Gly Ser Gly
            740                 745                 750

Gly Gly Gly Ser Gly Gly Gly Gly Ser Gly Gly Gly Gly Ser Gly Gly
        755                 760                 765

Gly Gly Ser Gly Gly Gly Gly Ser Asp Lys Thr His Thr Cys Pro Pro
    770                 775                 780

Cys Pro Ala Pro Glu Leu Leu Gly Gly Pro Ser Val Phe Leu Phe Pro
785                 790                 795                 800

Pro Lys Pro Lys Asp Thr Leu Met Ile Ser Arg Thr Pro Glu Val Thr
                805                 810                 815

Cys Val Val Val Asp Val Ser His Glu Asp Pro Glu Val Lys Phe Asn
            820                 825                 830

Trp Tyr Val Asp Gly Val Glu Val His Asn Ala Lys Thr Lys Pro Arg
        835                 840                 845

Glu Glu Gln Tyr Asn Ser Thr Tyr Arg Val Val Ser Val Leu Thr Val
    850                 855                 860

Leu His Gln Asp Trp Leu Asn Gly Lys Glu Tyr Lys Cys Lys Val Ser
865                 870                 875                 880

Asn Lys Ala Leu Pro Ala Pro Ile Glu Lys Thr Ile Ser Lys Ala Lys
                885                 890                 895

Gly Gln Pro Arg Glu Pro Gln Val Tyr Thr Leu Pro Pro Ser Arg Asp
            900                 905                 910

Glu Leu Thr Lys Asn Gln Val Ser Leu Thr Cys Leu Val Lys Gly Phe
        915                 920                 925

Tyr Pro Ser Asp Ile Ala Val Glu Trp Glu Ser Asn Gly Gln Pro Glu
    930                 935                 940

Asn Asn Tyr Lys Thr Thr Pro Pro Val Leu Asp Ser Asp Gly Ser Phe
945                 950                 955                 960

Phe Leu Tyr Ser Lys Leu Thr Val Asp Lys Ser Arg Trp Gln Gln Gly
                965                 970                 975

Asn Val Phe Ser Cys Ser Val Met His Glu Ala Leu His Asn His Tyr
            980                 985                 990

Thr Gln Lys Ser Leu Ser Leu Ser  Pro Gly Lys
        995                 1000
```

<210> SEQ ID NO 100
<211> LENGTH: 3012
<212> TYPE: DNA
<213> ORGANISM: Artificial Sequence
<220> FEATURE:
<223> OTHER INFORMATION: Synthetic construct: DNA sequence for FVII-058

<400> SEQUENCE: 100

```
atggtctccc aggccctcag gctcctctgc cttctgcttg ggcttcaggg ctgcctggct     60
```

gcagtcttcg taacccagga ggaagcccac ggcgtcctgc accggcgccg gcgcgccaac 120
gcgttcctgg aggagctgcg gccgggctcc ctggagaggg agtgcaagga ggagcagtgc 180
tccttcgagg aggcccggga gatcttcaag gacgcggaga ggacgaagct gttctggatt 240
tcttacagtg atggggacca gtgtgcctca agtccatgcc agaatggggg ctcctgcaag 300
gaccagctcc agtcctatat ctgcttctgc ctccctgcct tcgagggccg gaactgtgag 360
acgcacaagg atgaccagct gatctgtgtg aacgagaacg gcggctgtga gcagtactgc 420
agtgaccaca cgggcaccaa gcgctcctgt cggtgccacg aggggtactc tctgctggca 480
gacggggtgt cctgcacacc cacagttgaa tatccatgtg gaaaaatacc tattctagaa 540
aaaagaaatg ccagcaaacc ccaaggccga ggtggcggtg gctccggcgg aggtgggtcc 600
ggtggcggcg gatcaggtgg gggtggatca ggcggtggag gttccggtgg cgggggatcc 660
gacaaaactc acacatgccc accgtgccca gctccggaac tcctgggagg accgtcagtc 720
ttcctcttcc ccccaaaacc caaggacacc ctcatgatct cccggacccc tgaggtcaca 780
tgcgtggtgg tggacgtgag ccacgaagac cctgaggtca agttcaactg gtacgtggac 840
ggcgtggagg tgcataatgc caagacaaag ccgcgggagg agcagtacaa cagcacgtac 900
cgtgtggtca gcgtcctcac cgtcctgcac caggactggc tgaatggcaa ggagtacaag 960
tgcaaggtct ccaacaaagc cctcccagcc cccatcgaga aaaccatctc caaagccaaa 1020
gggcagcccc gagaaccaca ggtgtacacc ctgcccccat cccgggatga gctgaccaag 1080
aaccaggtca gcctgacctg cctggtcaaa ggcttctatc ccagcgacat cgccgtggag 1140
tgggagagca atgggcagcc ggagaacaac tacaagacca cgcctcccgt gttggactcc 1200
gacggctcct tcttcctcta cagcaagctc accgtcgaca agagcaggtg gcagcagggg 1260
aacgtcttct catgctccgt gatgcatgag gctctgcaca accactacac gcagaagagc 1320
ctctccctgt ctccgggtaa aggtggcggc ggatcaggtg gggggtggatc aggcggtgga 1380
ggttccggtg gcgggggatc cggcggtgga ggttccggtg gggggtggatc aggaggaggt 1440
ggttcagact tcctggccga gggcggcggc gtgcggattg tgggggggcaa ggtgtgcccc 1500
aaaggggagt gtccatggca ggtcctgttg ttggtgaatg gagctcagtt gtgtgggggg 1560
accctgatca acaccatctg ggtggtctcc gcggcccact gtttcgacaa aatcaagaac 1620
tggaggaacc tgatcgcggt gctgggcgag cacgacctca gcgagcacga cggggatgag 1680
cagagccggc gggtggcgca ggtcatcatc cccagcacgt acgtcccggg caccaccaac 1740
cacgacatcg cgctgctccg cctgcaccag cccgtggtcc tcactgacca tgtggtgccc 1800
ctctgcctgc ccgaacggac gttctctgag aggacgctgg ccttcgtgcg cttctcattg 1860
gtcagcggct ggggccagct gctggaccgt ggcgccacgg ccctggagct catggtcctc 1920
aacgtgcccc ggctgatgac ccaggactgc ctgcagcagt cacggaaggt gggagactcc 1980
ccaaatatca cggagtacat gttctgtgcc ggctactcgg atggcagcaa ggactcctgc 2040
aagggggaca gtggaggccc acatgccacc cactaccggg gcacgtggta cctgacgggc 2100
atcgtcagct ggggccaggg ctgcgcaacc gtgggccact ttggggtgta caccagggtc 2160
tcccagtaca tcgagtggct gcaaaagctc atgcgctcag agccacgccc aggagtcctc 2220
ctgcgagccc catttcccgg tggcggtggc tccggcggag gtgggtccgg tggcggcgga 2280
tcaggtgggg gtggatcagg cggtggaggt tccggtggcg gggggatcaga caaaactcac 2340
acatgcccac cgtgcccagc acctgaactc ctgggaggac cgtcagtctt cctcttcccc 2400

```
ccaaaaccca aggacaccct catgatctcc cggacccctg aggtcacatg cgtggtggtg   2460

gacgtgagcc acgaagaccc tgaggtcaag ttcaactggt acgtggacgg cgtggaggtg   2520

cataatgcca agacaaagcc gcgggaggag cagtacaaca gcacgtaccg tgtggtcagc   2580

gtcctcaccg tcctgcacca ggactggctg aatggcaagg agtacaagtg caaggtctcc   2640

aacaaagccc tcccagcccc catcgagaaa accatctcca aagccaaagg gcagccccga   2700

gaaccacagg tgtacaccct gcccccatcc cgggatgagc tgaccaagaa ccaggtcagc   2760

ctgacctgcc tggtcaaagg cttctatccc agcgacatcg ccgtggagtg ggagagcaat   2820

gggcagccgg agaacaacta caagaccacg cctcccgtgt tggactccga cggctccttc   2880

ttcctctaca gcaagctcac cgtggacaag agcaggtggc agcaggggaa cgtcttctca   2940

tgctccgtga tgcatgaggc tctgcacaac cactacacgc agaagagcct ctccctgtct   3000

ccgggtaaat ga                                                       3012


<210> SEQ ID NO 101
<211> LENGTH: 1003
<212> TYPE: PRT
<213> ORGANISM: Artificial Sequence
<220> FEATURE:
<223> OTHER INFORMATION: Synthetic construct: FVII-058 amino acid
      sequence

<400> SEQUENCE: 101

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

-continued

```
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Gly Gly
    450                 455                 460

Gly Gly Ser Gly Gly Gly Gly Ser Gly Gly Gly Gly Ser Gly Gly Gly
465                 470                 475                 480

Gly Ser Asp Phe Leu Ala Glu Gly Gly Gly Val Arg Ile Val Gly Gly
                485                 490                 495

Lys Val Cys Pro Lys Gly Glu Cys Pro Trp Gln Val Leu Leu Leu Val
            500                 505                 510

Asn Gly Ala Gln Leu Cys Gly Gly Thr Leu Ile Asn Thr Ile Trp Val
        515                 520                 525

Val Ser Ala Ala His Cys Phe Asp Lys Ile Lys Asn Trp Arg Asn Leu
    530                 535                 540

Ile Ala Val Leu Gly Glu His Asp Leu Ser Glu His Asp Gly Asp Glu
545                 550                 555                 560

Gln Ser Arg Arg Val Ala Gln Val Ile Ile Pro Ser Thr Tyr Val Pro
                565                 570                 575

Gly Thr Thr Asn His Asp Ile Ala Leu Leu Arg Leu His Gln Pro Val
            580                 585                 590

Val Leu Thr Asp His Val Val Pro Leu Cys Leu Pro Glu Arg Thr Phe
        595                 600                 605

Ser Glu Arg Thr Leu Ala Phe Val Arg Phe Ser Leu Val Ser Gly Trp
    610                 615                 620

Gly Gln Leu Leu Asp Arg Gly Ala Thr Ala Leu Glu Leu Met Val Leu
625                 630                 635                 640

Asn Val Pro Arg Leu Met Thr Gln Asp Cys Leu Gln Gln Ser Arg Lys
                645                 650                 655

Val Gly Asp Ser Pro Asn Ile Thr Glu Tyr Met Phe Cys Ala Gly Tyr
            660                 665                 670
```

```
Ser Asp Gly Ser Lys Asp Ser Cys Lys Gly Asp Ser Gly Gly Pro His
        675                 680                 685

Ala Thr His Tyr Arg Gly Thr Trp Tyr Leu Thr Gly Ile Val Ser Trp
    690                 695                 700

Gly Gln Gly Cys Ala Thr Val Gly His Phe Gly Val Tyr Thr Arg Val
705                 710                 715                 720

Ser Gln Tyr Ile Glu Trp Leu Gln Lys Leu Met Arg Ser Glu Pro Arg
                725                 730                 735

Pro Gly Val Leu Leu Arg Ala Pro Phe Pro Gly Gly Gly Gly Ser Gly
            740                 745                 750

Gly Gly Gly Ser Gly Gly Gly Gly Ser Gly Gly Gly Gly Ser Gly Gly
        755                 760                 765

Gly Gly Ser Gly Gly Gly Gly Ser Asp Lys Thr His Thr Cys Pro Pro
    770                 775                 780

Cys Pro Ala Pro Glu Leu Leu Gly Gly Pro Ser Val Phe Leu Phe Pro
785                 790                 795                 800

Pro Lys Pro Lys Asp Thr Leu Met Ile Ser Arg Thr Pro Glu Val Thr
                805                 810                 815

Cys Val Val Val Asp Val Ser His Glu Asp Pro Glu Val Lys Phe Asn
            820                 825                 830

Trp Tyr Val Asp Gly Val Glu Val His Asn Ala Lys Thr Lys Pro Arg
        835                 840                 845

Glu Glu Gln Tyr Asn Ser Thr Tyr Arg Val Val Ser Val Leu Thr Val
    850                 855                 860

Leu His Gln Asp Trp Leu Asn Gly Lys Glu Tyr Lys Cys Lys Val Ser
865                 870                 875                 880

Asn Lys Ala Leu Pro Ala Pro Ile Glu Lys Thr Ile Ser Lys Ala Lys
                885                 890                 895

Gly Gln Pro Arg Glu Pro Gln Val Tyr Thr Leu Pro Pro Ser Arg Asp
            900                 905                 910

Glu Leu Thr Lys Asn Gln Val Ser Leu Thr Cys Leu Val Lys Gly Phe
        915                 920                 925

Tyr Pro Ser Asp Ile Ala Val Glu Trp Glu Ser Asn Gly Gln Pro Glu
    930                 935                 940

Asn Asn Tyr Lys Thr Thr Pro Pro Val Leu Asp Ser Asp Gly Ser Phe
945                 950                 955                 960

Phe Leu Tyr Ser Lys Leu Thr Val Asp Lys Ser Arg Trp Gln Gln Gly
                965                 970                 975

Asn Val Phe Ser Cys Ser Val Met His Glu Ala Leu His Asn His Tyr
            980                 985                 990

Thr Gln Lys Ser Leu Ser Leu Ser  Pro Gly Lys
        995                 1000
```

<210> SEQ ID NO 102
<211> LENGTH: 3003
<212> TYPE: DNA
<213> ORGANISM: Artificial Sequence
<220> FEATURE:
<223> OTHER INFORMATION: Synthetic construct: DNA sequence for FVII-059

<400> SEQUENCE: 102

```
atggtctccc aggccctcag gctcctctgc cttctgcttg ggcttcaggg ctgcctggct      60

gcagtcttcg taacccagga ggaagcccac ggcgtcctgc accggcgccg gcgcgccaac     120

gcgttcctgg aggagctgcg gccgggctcc ctggagaggg agtgcaagga ggagcagtgc     180
```

tccttcgagg aggcccggga gatcttcaag gacgcggaga ggacgaagct gttctggatt 240
tcttacagtg atggggacca gtgtgcctca agtccatgcc agaatggggg ctcctgcaag 300
gaccagctcc agtcctatat ctgcttctgc ctccctgcct tcgagggccg gaactgtgag 360
acgcacaagg atgaccagct gatctgtgtg aacgagaacg gcggctgtga gcagtactgc 420
agtgaccaca cgggcaccaa gcgctcctgt cggtgccacg aggggtactc tctgctggca 480
gacggggtgt cctgcacacc cacagttgaa tatccatgtg gaaaaatacc tattctagaa 540
aaaagaaatg ccagcaaacc ccaaggccga ggtggcggtg gctccggcgg aggtgggtcc 600
ggtggcggcg gatcaggtgg gggtggatca ggcggtggag gttccggtgg cgggggatcc 660
gacaaaactc acacatgccc accgtgccca gctccggaac tcctgggagg accgtcagtc 720
ttcctcttcc ccccaaaacc caaggacacc ctcatgatct cccggacccc tgaggtcaca 780
tgcgtggtgg tggacgtgag ccacgaagac cctgaggtca agttcaactg gtacgtggac 840
ggcgtggagg tgcataatgc caagacaaag ccgcgggagg agcagtacaa cagcacgtac 900
cgtgtggtca gcgtcctcac cgtcctgcac caggactggc tgaatggcaa ggagtacaag 960
tgcaaggtct ccaacaaagc cctcccagcc cccatcgaga aaaccatctc caaagccaaa 1020
gggcagcccc gagaaccaca ggtgtacacc ctgcccccat cccgggatga gctgaccaag 1080
aaccaggtca gcctgacctg cctggtcaaa ggcttctatc ccagcgacat cgccgtggag 1140
tgggagagca atgggcagcc ggagaacaac tacaagacca cgcctcccgt gttggactcc 1200
gacggctcct tcttcctcta cagcaagctc accgtcgaca agagcaggtg gcagcagggg 1260
aacgtcttct catgctccgt gatgcatgag gctctgcaca accactacac gcagaagagc 1320
ctctccctgt ctccgggtaa aggtggcggc ggatcaggtg gggtggatc aggcggtgga 1380
ggttccggtg gcgggggatc cggcggtgga ggttccggtg gggtggatc aggaggaggt 1440
ggttcaacca ccaagatcaa gccccggatt gtgggggca aggtgtgccc caaaggggag 1500
tgtccatggc aggtcctgtt gttggtgaat ggagctcagt tgtgtgggggg gaccctgatc 1560
aacaccatct gggtggtctc cgcggcccac tgtttcgaca aaatcaagaa ctggaggaac 1620
ctgatcgcgg tgctgggcga gcacgacctc agcgagcacg acggggatga gcagagccgg 1680
cgggtggcgc aggtcatcat ccccagcacg tacgtcccgg gcaccaccaa ccacgacatc 1740
gcgctgctcc gcctgcacca gcccgtggtc ctcactgacc atgtggtgcc cctctgcctg 1800
cccgaacgga cgttctctga gaggacgctg gccttcgtgc gcttctcatt ggtcagcggc 1860
tggggccagc tgctggaccg tggcgccacg gccctggagc tcatggtcct caacgtgccc 1920
cggctgatga cccaggactg cctgcagcag tcacggaagg tgggagactc cccaaatatc 1980
acggagtaca tgttctgtgc cggctactcg gatggcagca aggactcctg caagggggac 2040
agtggaggcc cacatgccac ccactaccgg ggcacgtggt acctgacggg catcgtcagc 2100
tggggccagg gctgcgcaac cgtgggccac tttggggtgt acaccagggt ctcccagtac 2160
atcgagtggc tgcaaaagct catgcgctca gagccacgcc caggagtcct cctgcgagcc 2220
ccatttcccg gtggcggtgg ctccggcgga ggtgggtccg gtggcggcgg atcaggtggg 2280
ggtggatcag gcggtggagg ttccggtggc gggggatcag acaaaactca cacatgccca 2340
ccgtgcccag cacctgaact cctgggagga ccgtcagtct tcctcttccc cccaaaaccc 2400
aaggacaccc tcatgatctc ccggacccct gaggtcacat gcgtggtggt ggacgtgagc 2460
cacgaagacc ctgaggtcaa gttcaactgg tacgtggacg gcgtggaggt gcataatgcc 2520

```
aagacaaagc cgcgggagga gcagtacaac agcacgtacc gtgtggtcag cgtcctcacc   2580

gtcctgcacc aggactggct gaatggcaag gagtacaagt gcaaggtctc caacaaagcc   2640

ctcccagccc ccatcgagaa aaccatctcc aaagccaaag ggcagccccg agaaccacag   2700

gtgtacaccc tgcccccatc ccgggatgag ctgaccaaga accaggtcag cctgacctgc   2760

ctggtcaaag gcttctatcc cagcgacatc gccgtggagt gggagagcaa tgggcagccg   2820

gagaacaact acaagaccac gcctcccgtg ttggactccg acggctcctt cttcctctac   2880

agcaagctca ccgtggacaa gagcaggtgg cagcagggga acgtcttctc atgctccgtg   2940

atgcatgagg ctctgcacaa ccactacacg cagaagagcc tctccctgtc tccgggtaaa   3000

tga                                                                 3003


<210> SEQ ID NO 103
<211> LENGTH: 1000
<212> TYPE: PRT
<213> ORGANISM: Artificial Sequence
<220> FEATURE:
<223> OTHER INFORMATION: Synthetic construct: FVII-059 amino acid
      sequence

<400> SEQUENCE: 103

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Gly Gly
    450                 455                 460

Gly Gly Ser Gly Gly Gly Gly Ser Gly Gly Gly Gly Ser Gly Gly Gly
465                 470                 475                 480

Gly Ser Thr Thr Lys Ile Lys Pro Arg Ile Val Gly Gly Lys Val Cys
                485                 490                 495

Pro Lys Gly Glu Cys Pro Trp Gln Val Leu Leu Leu Val Asn Gly Ala
            500                 505                 510

Gln Leu Cys Gly Gly Thr Leu Ile Asn Thr Ile Trp Val Val Ser Ala
        515                 520                 525

Ala His Cys Phe Asp Lys Ile Lys Asn Trp Arg Asn Leu Ile Ala Val
    530                 535                 540

Leu Gly Glu His Asp Leu Ser Glu His Asp Gly Asp Glu Gln Ser Arg
545                 550                 555                 560

Arg Val Ala Gln Val Ile Ile Pro Ser Thr Tyr Val Pro Gly Thr Thr
                565                 570                 575

Asn His Asp Ile Ala Leu Leu Arg Leu His Gln Pro Val Val Leu Thr
            580                 585                 590

Asp His Val Val Pro Leu Cys Leu Pro Glu Arg Thr Phe Ser Glu Arg
        595                 600                 605

Thr Leu Ala Phe Val Arg Phe Ser Leu Val Ser Gly Trp Gly Gln Leu
    610                 615                 620

Leu Asp Arg Gly Ala Thr Ala Leu Glu Leu Met Val Leu Asn Val Pro
625                 630                 635                 640

Arg Leu Met Thr Gln Asp Cys Leu Gln Gln Ser Arg Lys Val Gly Asp
                645                 650                 655

Ser Pro Asn Ile Thr Glu Tyr Met Phe Cys Ala Gly Tyr Ser Asp Gly
            660                 665                 670

Ser Lys Asp Ser Cys Lys Gly Asp Ser Gly Gly Pro His Ala Thr His
        675                 680                 685
```

```
Tyr Arg Gly Thr Trp Tyr Leu Thr Gly Ile Val Ser Trp Gly Gln Gly
    690                 695                 700

Cys Ala Thr Val Gly His Phe Gly Val Tyr Thr Arg Val Ser Gln Tyr
705                 710                 715                 720

Ile Glu Trp Leu Gln Lys Leu Met Arg Ser Glu Pro Arg Pro Gly Val
                725                 730                 735

Leu Leu Arg Ala Pro Phe Pro Gly Gly Gly Gly Ser Gly Gly Gly Gly
            740                 745                 750

Ser Gly Gly Gly Gly Ser Gly Gly Gly Gly Ser Gly Gly Gly Gly Ser
        755                 760                 765

Gly Gly Gly Gly Ser Asp Lys Thr His Thr Cys Pro Pro Cys Pro Ala
    770                 775                 780

Pro Glu Leu Leu Gly Gly Pro Ser Val Phe Leu Phe Pro Pro Lys Pro
785                 790                 795                 800

Lys Asp Thr Leu Met Ile Ser Arg Thr Pro Glu Val Thr Cys Val Val
                805                 810                 815

Val Asp Val Ser His Glu Asp Pro Glu Val Lys Phe Asn Trp Tyr Val
            820                 825                 830

Asp Gly Val Glu Val His Asn Ala Lys Thr Lys Pro Arg Glu Glu Gln
        835                 840                 845

Tyr Asn Ser Thr Tyr Arg Val Val Ser Val Leu Thr Val Leu His Gln
    850                 855                 860

Asp Trp Leu Asn Gly Lys Glu Tyr Lys Cys Lys Val Ser Asn Lys Ala
865                 870                 875                 880

Leu Pro Ala Pro Ile Glu Lys Thr Ile Ser Lys Ala Lys Gly Gln Pro
                885                 890                 895

Arg Glu Pro Gln Val Tyr Thr Leu Pro Pro Ser Arg Asp Glu Leu Thr
            900                 905                 910

Lys Asn Gln Val Ser Leu Thr Cys Leu Val Lys Gly Phe Tyr Pro Ser
        915                 920                 925

Asp Ile Ala Val Glu Trp Glu Ser Asn Gly Gln Pro Glu Asn Asn Tyr
    930                 935                 940

Lys Thr Thr Pro Pro Val Leu Asp Ser Asp Gly Ser Phe Phe Leu Tyr
945                 950                 955                 960

Ser Lys Leu Thr Val Asp Lys Ser Arg Trp Gln Gln Gly Asn Val Phe
                965                 970                 975

Ser Cys Ser Val Met His Glu Ala Leu His Asn His Tyr Thr Gln Lys
            980                 985                 990

Ser Leu Ser Leu Ser Pro Gly Lys
        995                 1000


<210> SEQ ID NO 104
<211> LENGTH: 3012
<212> TYPE: DNA
<213> ORGANISM: Artificial Sequence
<220> FEATURE:
<223> OTHER INFORMATION: Synthetic construct: DNA sequence for FVII-060

<400> SEQUENCE: 104

atggtctccc aggccctcag gctcctctgc cttctgcttg ggcttcaggg ctgcctggct      60

gcagtcttcg taacccagga ggaagcccac ggcgtcctgc accggcgccg gcgcgccaac     120

gcgttcctgg aggagctgcg gccgggctcc ctggagaggg agtgcaagga ggagcagtgc     180

tccttcgagg aggcccggga gatcttcaag gacgcggaga ggacgaagct gttctggatt     240

tcttacagtg atggggacca gtgtgcctca agtccatgcc agaatggggg ctcctgcaag     300
```

gaccagctcc agtcctatat ctgcttctgc ctccctgcct tcgagggccg gaactgtgag 360
acgcacaagg atgaccagct gatctgtgtg aacgagaacg gcggctgtga gcagtactgc 420
agtgaccaca cgggcaccaa gcgctcctgt cggtgccacg aggggtactc tctgctggca 480
gacggggtgt cctgcacacc cacagttgaa tatccatgtg gaaaaatacc tattctagaa 540
aaaagaaatg ccagcaaacc ccaaggccga ggtggcggtg gctccggcgg aggtgggtcc 600
ggtggcggcg gatcaggtgg gggtggatca ggcggtggag gttccggtgg cgggggatcc 660
gacaaaactc acacatgccc accgtgccca gctccggaac tcctgggagg accgtcagtc 720
ttcctcttcc ccccaaaacc caaggacacc ctcatgatct cccggacccc tgaggtcaca 780
tgcgtggtgg tggacgtgag ccacgaagac cctgaggtca agttcaactg gtacgtggac 840
ggcgtggagg tgcataatgc caagacaaag ccgcgggagg agcagtacaa cagcacgtac 900
cgtgtggtca gcgtcctcac cgtcctgcac caggactggc tgaatggcaa ggagtacaag 960
tgcaaggtct ccaacaaagc cctcccagcc cccatcgaga aaaccatctc caaagccaaa 1020
gggcagcccc gagaaccaca ggtgtacacc ctgcccccat cccgggatga gctgaccaag 1080
aaccaggtca gcctgacctg cctggtcaaa ggcttctatc ccagcgacat cgccgtggag 1140
tgggagagca atgggcagcc ggagaacaac tacaagacca cgcctcccgt gttggactcc 1200
gacggctcct tcttcctcta cagcaagctc accgtcgaca agagcaggtg gcagcagggg 1260
aacgtcttct catgctccgt gatgcatgag gctctgcaca accactacac gcagaagagc 1320
ctctccctgt ctccgggtaa aggtggcggc ggatcaggtg gggtggatc aggcggtgga 1380
ggttccggtg gcgggggatc cggcggtgga ggttccggtg gggtggatc aggaggaggt 1440
ggttcagccc tgcggccccg ggtggtgggc ggcgccgtgg tgggggcaa ggtgtgcccc 1500
aaaggggagt gtccatggca ggtcctgttg ttggtgaatg gagctcagtt gtgtgggggg 1560
accctgatca acaccatctg ggtggtctcc gcggcccact gtttcgacaa aatcaagaac 1620
tggaggaacc tgatcgcggt gctgggcgag cacgacctca gcgagcacga cggggatgag 1680
cagagccggc gggtggcgca ggtcatcatc cccagcacgt acgtcccggg caccaccaac 1740
cacgacatcg cgctgctccg cctgcaccag cccgtggtcc tcactgacca tgtggtgccc 1800
ctctgcctgc ccgaacggac gttctctgag aggacgctgg ccttcgtgcg cttctcattg 1860
gtcagcggct ggggccagct gctggaccgt ggcgccacgg ccctggagct catggtcctc 1920
aacgtgcccc ggctgatgac ccaggactgc ctgcagcagt cacggaaggt gggagactcc 1980
ccaaatatca cggagtacat gttctgtgcc ggctactcgg atggcagcaa ggactcctgc 2040
aagggggaca gtggaggccc acatgccacc cactaccggg gcacgtggta cctgacgggc 2100
atcgtcagct ggggccaggg ctgcgcaacc gtgggccact ttggggtgta caccagggtc 2160
tcccagtaca tcgagtggct gcaaaagctc atgcgctcag agccacgccc aggagtcctc 2220
ctgcgagccc catttcccgg tggcggtggc tccggcggag gtgggtccgg tggcggcgga 2280
tcaggtgggg gtggatcagg cggtggaggt tccggtggcg gggatcaga caaaactcac 2340
acatgcccac cgtgcccagc acctgaactc ctgggaggac cgtcagtctt cctcttcccc 2400
ccaaaaccca aggacaccct catgatctcc cggacccctg aggtcacatg cgtggtggtg 2460
gacgtgagcc acgaagaccc tgaggtcaag ttcaactggt acgtggacgg cgtggaggtg 2520
cataatgcca agacaaagcc gcgggaggag cagtacaaca gcacgtaccg tgtggtcagc 2580
gtcctcaccg tcctgcacca ggactggctg aatggcaagg agtacaagtg caaggtctcc 2640

```
aacaaagccc tcccagcccc catcgagaaa accatctcca aagccaaagg gcagccccga   2700

gaaccacagg tgtacaccct gcccccatcc cgggatgagc tgaccaagaa ccaggtcagc   2760

ctgacctgcc tggtcaaagg cttctatccc agcgacatcg ccgtggagtg ggagagcaat   2820

gggcagccgg agaacaacta caagaccacg cctcccgtgt tggactccga cggctccttc   2880

ttcctctaca gcaagctcac cgtggacaag agcaggtggc agcaggggaa cgtcttctca   2940

tgctccgtga tgcatgaggc tctgcacaac cactacacgc agaagagcct ctccctgtct   3000

ccgggtaaat ga                                                       3012


<210> SEQ ID NO 105
<211> LENGTH: 1003
<212> TYPE: PRT
<213> ORGANISM: Artificial Sequence
<220> FEATURE:
<223> OTHER INFORMATION: Synthetic construct: FVII-060 amino acid
      sequence

<400> SEQUENCE: 105

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

-continued

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Gly Gly
    450                 455                 460

Gly Gly Ser Gly Gly Gly Gly Ser Gly Gly Gly Gly Ser Gly Gly Gly
465                 470                 475                 480

Gly Ser Ala Leu Arg Pro Arg Val Val Gly Gly Ala Val Val Gly Gly
                485                 490                 495

Lys Val Cys Pro Lys Gly Glu Cys Pro Trp Gln Val Leu Leu Leu Val
            500                 505                 510

Asn Gly Ala Gln Leu Cys Gly Gly Thr Leu Ile Asn Thr Ile Trp Val
        515                 520                 525

Val Ser Ala Ala His Cys Phe Asp Lys Ile Lys Asn Trp Arg Asn Leu
    530                 535                 540

Ile Ala Val Leu Gly Glu His Asp Leu Ser Glu His Asp Gly Asp Glu
545                 550                 555                 560

Gln Ser Arg Arg Val Ala Gln Val Ile Ile Pro Ser Thr Tyr Val Pro
                565                 570                 575

Gly Thr Thr Asn His Asp Ile Ala Leu Leu Arg Leu His Gln Pro Val
            580                 585                 590

Val Leu Thr Asp His Val Val Pro Leu Cys Leu Pro Glu Arg Thr Phe
        595                 600                 605

Ser Glu Arg Thr Leu Ala Phe Val Arg Phe Ser Leu Val Ser Gly Trp
    610                 615                 620

Gly Gln Leu Leu Asp Arg Gly Ala Thr Ala Leu Glu Leu Met Val Leu
625                 630                 635                 640

Asn Val Pro Arg Leu Met Thr Gln Asp Cys Leu Gln Gln Ser Arg Lys
                645                 650                 655

Val Gly Asp Ser Pro Asn Ile Thr Glu Tyr Met Phe Cys Ala Gly Tyr
            660                 665                 670

Ser Asp Gly Ser Lys Asp Ser Cys Lys Gly Asp Ser Gly Gly Pro His
        675                 680                 685

Ala Thr His Tyr Arg Gly Thr Trp Tyr Leu Thr Gly Ile Val Ser Trp
    690                 695                 700

Gly Gln Gly Cys Ala Thr Val Gly His Phe Gly Val Tyr Thr Arg Val
```

705 710 715 720

Ser Gln Tyr Ile Glu Trp Leu Gln Lys Leu Met Arg Ser Glu Pro Arg
725 730 735

Pro Gly Val Leu Leu Arg Ala Pro Phe Pro Gly Gly Gly Gly Ser Gly
740 745 750

Gly Gly Gly Ser Gly Gly Gly Gly Ser Gly Gly Gly Gly Ser Gly Gly
755 760 765

Gly Gly Ser Gly Gly Gly Gly Ser Asp Lys Thr His Thr Cys Pro Pro
770 775 780

Cys Pro Ala Pro Glu Leu Leu Gly Gly Pro Ser Val Phe Leu Phe Pro
785 790 795 800

Pro Lys Pro Lys Asp Thr Leu Met Ile Ser Arg Thr Pro Glu Val Thr
805 810 815

Cys Val Val Val Asp Val Ser His Glu Asp Pro Glu Val Lys Phe Asn
820 825 830

Trp Tyr Val Asp Gly Val Glu Val His Asn Ala Lys Thr Lys Pro Arg
835 840 845

Glu Glu Gln Tyr Asn Ser Thr Tyr Arg Val Val Ser Val Leu Thr Val
850 855 860

Leu His Gln Asp Trp Leu Asn Gly Lys Glu Tyr Lys Cys Lys Val Ser
865 870 875 880

Asn Lys Ala Leu Pro Ala Pro Ile Glu Lys Thr Ile Ser Lys Ala Lys
885 890 895

Gly Gln Pro Arg Glu Pro Gln Val Tyr Thr Leu Pro Pro Ser Arg Asp
900 905 910

Glu Leu Thr Lys Asn Gln Val Ser Leu Thr Cys Leu Val Lys Gly Phe
915 920 925

Tyr Pro Ser Asp Ile Ala Val Glu Trp Glu Ser Asn Gly Gln Pro Glu
930 935 940

Asn Asn Tyr Lys Thr Thr Pro Pro Val Leu Asp Ser Asp Gly Ser Phe
945 950 955 960

Phe Leu Tyr Ser Lys Leu Thr Val Asp Lys Ser Arg Trp Gln Gln Gly
965 970 975

Asn Val Phe Ser Cys Ser Val Met His Glu Ala Leu His Asn His Tyr
980 985 990

Thr Gln Lys Ser Leu Ser Leu Ser Pro Gly Lys
995 1000

<210> SEQ ID NO 106
<211> LENGTH: 3012
<212> TYPE: DNA
<213> ORGANISM: Artificial Sequence
<220> FEATURE:
<223> OTHER INFORMATION: Synthetic construct: DNA sequence for FVII-061

<400> SEQUENCE: 106
atggtctccc aggccctcag gctcctctgc cttctgcttg ggcttcaggg ctgcctggct 60
gcagtcttcg taacccagga ggaagcccac ggcgtcctgc accggcgccg gcgcgccaac 120
gcgttcctgg aggagctgcg gccgggctcc ctggagaggg agtgcaagga ggagcagtgc 180
tccttcgagg aggcccggga gatcttcaag gacgcggaga ggacgaagct gttctggatt 240
tcttacagtg atggggacca gtgtgcctca agtccatgcc agaatggggg ctcctgcaag 300
gaccagctcc agtcctatat ctgcttctgc ctccctgcct tcgagggccg gaactgtgag 360
acgcacaagg atgaccagct gatctgtgtg aacgagaacg gcggctgtga gcagtactgc 420

```
agtgaccaca cgggcaccaa gcgctcctgt cggtgccacg aggggtactc tctgctggca    480
gacggggtgt cctgcacacc cacagttgaa tatccatgtg gaaaaatacc tattctagaa    540
aaaagaaatg ccagcaaacc ccaaggccga ggtggcggtg gctccggcgg aggtgggtcc    600
ggtggcggcg gatcaggtgg gggtggatca ggcggtggag gttccggtgg cgggggatcc    660
gacaaaactc acacatgccc accgtgccca gctccggaac tcctgggagg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggatga gctgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gttggactcc   1200
gacggctcct tcttcctcta cagcaagctc accgtcgaca agagcaggtg gcagcagggg   1260
aacgtcttct catgctccgt gatgcatgag gctctgcaca accactacac gcagaagagc   1320
ctctccctgt ctccgggtaa aggtggcggc ggatcaggtg gggtggatc aggcggtgga    1380
ggttccggtg gcgggggatc cggcggtgga ggttccggtg gggtggatc aggaggaggt    1440
ggttcagccc tgcggccccg ggtggtgggc ggcgccattg tgggggcaa ggtgtgcccc    1500
aaaggggagt gtccatggca ggtcctgttg ttggtgaatg gagctcagtt gtgtgggggg   1560
accctgatca acaccatctg ggtggtctcc gcggcccact gtttcgacaa aatcaagaac   1620
tggaggaacc tgatcgcggt gctgggcgag cacgacctca gcgagcacga cggggatgag   1680
cagagccggc gggtggcgca ggtcatcatc cccagcacgt acgtcccggg caccaccaac   1740
cacgacatcg cgctgctccg cctgcaccag cccgtggtcc tcactgacca tgtggtgccc   1800
ctctgcctgc ccgaacggac gttctctgag aggacgctgg ccttcgtgcg cttctcattg   1860
gtcagcggct ggggccagct gctggaccgt ggcgccacgg ccctggagct catggtcctc   1920
aacgtgcccc ggctgatgac ccaggactgc ctgcagcagt cacggaaggt gggagactcc   1980
ccaaatatca cggagtacat gttctgtgcc ggctactcgg atggcagcaa ggactcctgc   2040
aagggggaca gtggaggccc acatgccacc cactaccggg gcacgtggta cctgacgggc   2100
atcgtcagct ggggccaggg ctgcgcaacc gtgggccact ttggggtgta caccagggtc   2160
tcccagtaca tcgagtggct gcaaaagctc atgcgctcag agccacgccc aggagtcctc   2220
ctgcgagccc catttcccgg tggcggtggc tccggcggag gtgggtccgg tggcggcgga   2280
tcaggtgggg gtggatcagg cggtggaggt tccggtggcg ggggatcaga caaaactcac   2340
acatgcccac cgtgcccagc acctgaactc ctgggaggac cgtcagtctt cctcttcccc   2400
ccaaaaccca aggacaccct catgatctcc cggacccctg aggtcacatg cgtggtggtg   2460
gacgtgagcc acgaagaccc tgaggtcaag ttcaactggt acgtggacgg cgtggaggtg   2520
cataatgcca agacaaagcc gcgggaggag cagtacaaca gcacgtaccg tgtggtcagc   2580
gtcctcaccg tcctgcacca ggactggctg aatggcaagg agtacaagtg caaggtctcc   2640
aacaaagccc tcccagcccc catcgagaaa accatctcca aagccaaagg gcagccccga   2700
gaaccacagg tgtacaccct gcccccatcc cgggatgagc tgaccaagaa ccaggtcagc   2760
```

```
ctgacctgcc tggtcaaagg cttctatccc agcgacatcg ccgtggagtg ggagagcaat   2820

gggcagccgg agaacaacta caagaccacg cctcccgtgt tggactccga cggctccttc   2880

ttcctctaca gcaagctcac cgtggacaag agcaggtggc agcaggggaa cgtcttctca   2940

tgctccgtga tgcatgaggc tctgcacaac cactacacgc agaagagcct ctccctgtct   3000

ccgggtaaat ga                                                       3012


<210> SEQ ID NO 107
<211> LENGTH: 1003
<212> TYPE: PRT
<213> ORGANISM: Artificial Sequence
<220> FEATURE:
<223> OTHER INFORMATION: Synthetic construct: FVII-061 amino acid
      sequence

<400> SEQUENCE: 107

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
```

-continued

```
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Gly Gly
    450                 455                 460

Gly Gly Ser Gly Gly Gly Gly Ser Gly Gly Gly Gly Ser Gly Gly Gly
465                 470                 475                 480

Gly Ser Ala Leu Arg Pro Arg Val Val Gly Gly Ala Ile Val Gly Gly
                485                 490                 495

Lys Val Cys Pro Lys Gly Glu Cys Pro Trp Gln Val Leu Leu Leu Val
            500                 505                 510

Asn Gly Ala Gln Leu Cys Gly Gly Thr Leu Ile Asn Thr Ile Trp Val
        515                 520                 525

Val Ser Ala Ala His Cys Phe Asp Lys Ile Lys Asn Trp Arg Asn Leu
    530                 535                 540

Ile Ala Val Leu Gly Glu His Asp Leu Ser Glu His Asp Gly Asp Glu
545                 550                 555                 560

Gln Ser Arg Arg Val Ala Gln Val Ile Ile Pro Ser Thr Tyr Val Pro
                565                 570                 575

Gly Thr Thr Asn His Asp Ile Ala Leu Leu Arg Leu His Gln Pro Val
            580                 585                 590

Val Leu Thr Asp His Val Val Pro Leu Cys Leu Pro Glu Arg Thr Phe
        595                 600                 605

Ser Glu Arg Thr Leu Ala Phe Val Arg Phe Ser Leu Val Ser Gly Trp
    610                 615                 620

Gly Gln Leu Leu Asp Arg Gly Ala Thr Ala Leu Glu Leu Met Val Leu
625                 630                 635                 640

Asn Val Pro Arg Leu Met Thr Gln Asp Cys Leu Gln Gln Ser Arg Lys
                645                 650                 655

Val Gly Asp Ser Pro Asn Ile Thr Glu Tyr Met Phe Cys Ala Gly Tyr
            660                 665                 670

Ser Asp Gly Ser Lys Asp Ser Cys Lys Gly Asp Ser Gly Gly Pro His
        675                 680                 685

Ala Thr His Tyr Arg Gly Thr Trp Tyr Leu Thr Gly Ile Val Ser Trp
    690                 695                 700

Gly Gln Gly Cys Ala Thr Val Gly His Phe Gly Val Tyr Thr Arg Val
705                 710                 715                 720

Ser Gln Tyr Ile Glu Trp Leu Gln Lys Leu Met Arg Ser Glu Pro Arg
                725                 730                 735
```

```
Pro Gly Val Leu Leu Arg Ala Pro Phe Pro Gly Gly Gly Gly Ser Gly
            740                 745                 750

Gly Gly Gly Ser Gly Gly Gly Gly Ser Gly Gly Gly Gly Ser Gly Gly
        755                 760                 765

Gly Gly Ser Gly Gly Gly Gly Ser Asp Lys Thr His Thr Cys Pro Pro
    770                 775                 780

Cys Pro Ala Pro Glu Leu Leu Gly Gly Pro Ser Val Phe Leu Phe Pro
785                 790                 795                 800

Pro Lys Pro Lys Asp Thr Leu Met Ile Ser Arg Thr Pro Glu Val Thr
                805                 810                 815

Cys Val Val Val Asp Val Ser His Glu Asp Pro Glu Val Lys Phe Asn
            820                 825                 830

Trp Tyr Val Asp Gly Val Glu Val His Asn Ala Lys Thr Lys Pro Arg
        835                 840                 845

Glu Glu Gln Tyr Asn Ser Thr Tyr Arg Val Val Ser Val Leu Thr Val
    850                 855                 860

Leu His Gln Asp Trp Leu Asn Gly Lys Glu Tyr Lys Cys Lys Val Ser
865                 870                 875                 880

Asn Lys Ala Leu Pro Ala Pro Ile Glu Lys Thr Ile Ser Lys Ala Lys
                885                 890                 895

Gly Gln Pro Arg Glu Pro Gln Val Tyr Thr Leu Pro Pro Ser Arg Asp
            900                 905                 910

Glu Leu Thr Lys Asn Gln Val Ser Leu Thr Cys Leu Val Lys Gly Phe
        915                 920                 925

Tyr Pro Ser Asp Ile Ala Val Glu Trp Glu Ser Asn Gly Gln Pro Glu
    930                 935                 940

Asn Asn Tyr Lys Thr Thr Pro Pro Val Leu Asp Ser Asp Gly Ser Phe
945                 950                 955                 960

Phe Leu Tyr Ser Lys Leu Thr Val Asp Lys Ser Arg Trp Gln Gln Gly
                965                 970                 975

Asn Val Phe Ser Cys Ser Val Met His Glu Ala Leu His Asn His Tyr
            980                 985                 990

Thr Gln Lys Ser Leu Ser Leu Ser  Pro Gly Lys
        995                 1000
```

<210> SEQ ID NO 108
<211> LENGTH: 2997
<212> TYPE: DNA
<213> ORGANISM: Artificial Sequence
<220> FEATURE:
<223> OTHER INFORMATION: Synthetic construct: DNA sequence for FVII-062

<400> SEQUENCE: 108

```
atggtctccc aggccctcag gctcctctgc cttctgcttg ggcttcaggg ctgcctggct      60

gcagtcttcg taacccagga ggaagcccac ggcgtcctgc accggcgccg gcgcgccaac     120

gcgttcctgg aggagctgcg gccgggctcc ctggagaggg agtgcaagga ggagcagtgc     180

tccttcgagg aggcccggga gatcttcaag gacgcggaga ggacgaagct gttctggatt     240

tcttacagtg atggggacca gtgtgcctca agtccatgcc agaatggggg ctcctgcaag     300

gaccagctcc agtcctatat ctgcttctgc ctccctgcct tcgagggccg gaactgtgag     360

acgcacaagg atgaccagct gatctgtgtg aacgagaacg gcggctgtga gcagtactgc     420

agtgaccaca cgggcaccaa gcgctcctgt cggtgccacg aggggtactc tctgctggca     480

gacggggtgt cctgcacacc cacagttgaa tatccatgtg gaaaaatacc tattctagaa     540
```

```
aaaagaaatg ccagcaaacc ccaaggccga ggtggcggtg gctccggcgg aggtgggtcc    600
ggtggcggcg gatcaggtgg gggtggatca ggcggtggag gttccggtgg cgggggatca    660
gacaaaactc acacatgccc accgtgccca gctccggaac tcctgggcgg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggatga gctgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gttggactcc   1200
gacggctcct tcttcctcta cagcaagctc accgtcgaca agagcaggtg gcagcagggg   1260
aacgtcttct catgctccgt gatgcatgag gctctgcaca accactacac gcagaagagc   1320
ctctccctgt ctccgggtaa aggtggcggc ggatcaggtg ggggtggatc aggcggtgga   1380
ggttccggtg gcgggggatc cggcggtgga ggttccggtg gggggtggatc aggaggaggt   1440
ggttcaggtg gtggaggatc cattgtgggg ggcaaggtgt gccccaaagg ggagtgtcca   1500
tggcaggtcc tgttgttggt gaatggagct cagttgtgtg gggggaccct gatcaacacc   1560
atctgggtgg tctccgcggc ccactgtttc gacaaaatca agaactggag gaacctgatc   1620
gcggtgctgg gcgagcacga cctcagcgag cacgacgggg atgagcagag ccggcgggtg   1680
gcgcaggtca tcatccccag cacgtacgtc ccgggcacca ccaaccacga catcgcgctg   1740
ctccgcctgc accagcccgt ggtcctcact gaccatgtgg tgcccctctg cctgcccgaa   1800
cggacgttct ctgagaggac gctggccttc gtgcgcttct cattggtcag cggctggggc   1860
cagctgctgg accgtggcgc cacggccctg gagctcatgg tcctcaacgt gccccggctg   1920
atgacccagg actgcctgca gcagtcacgg aaggtgggag actccccaaa tatcacggag   1980
tacatgttct gtgccggcta ctcggatggc agcaaggact cctgcaaggg ggacagtgga   2040
ggcccacatg ccacccacta ccggggcacg tggtacctga cgggcatcgt cagctggggc   2100
cagggctgcg caaccgtggg ccactttggg gtgtacacca gggtctccca gtacatcgag   2160
tggctgcaaa agctcatgcg ctcagagcca cgcccaggag tcctcctgcg agccccattt   2220
cccggtggcg gtggctccgg cggaggtggg tccggtggcg gcggatcagg tgggggtgga   2280
tcaggcggtg gaggttccgg tggcggggga tcagacaaaa ctcacacatg cccaccgtgc   2340
ccagcacctg aactcctggg aggaccgtca gtcttcctct tccccccaaa acccaaggac   2400
accctcatga tctcccggac ccctgaggtc acatgcgtgg tggtggacgt gagccacgaa   2460
gaccctgagg tcaagttcaa ctggtacgtg gacggcgtgg aggtgcataa tgccaagaca   2520
aagccgcggg aggagcagta caacagcacg taccgtgtgg tcagcgtcct caccgtcctg   2580
caccaggact ggctgaatgg caaggagtac aagtgcaagg tctccaacaa agccctccca   2640
gcccccatcg agaaaaccat ctccaaagcc aaagggcagc cccgagaacc acaggtgtac   2700
accctgcccc catcccggga tgagctgacc aagaaccagg tcagcctgac ctgcctggtc   2760
aaaggcttct atcccagcga catcgccgtg gagtgggaga gcaatgggca gccggagaac   2820
aactacaaga ccacgcctcc cgtgttggac tccgacggct ccttcttcct ctacagcaag   2880
```

ctcaccgtgg acaagagcag gtggcagcag gggaacgtct tctcatgctc cgtgatgcat 2940
gaggctctgc acaaccacta cacgcagaag agcctctccc tgtctccggg taaatga 2997

<210> SEQ ID NO 109
<211> LENGTH: 998
<212> TYPE: PRT
<213> ORGANISM: Artificial Sequence
<220> FEATURE:
<223> OTHER INFORMATION: Synthetic construct: FVII-062 amino acid sequence

<400> SEQUENCE: 109

Met Val Ser Gln Ala Leu Arg Leu Leu Cys Leu Leu Leu Gly Leu Gln
1 5 10 15

Gly Cys Leu Ala Ala Val Phe Val Thr Gln Glu Glu Ala His Gly Val
20 25 30

Leu His Arg Arg Arg Arg Ala Asn Ala Phe Leu Glu Glu Leu Arg Pro
35 40 45

Gly Ser Leu Glu Arg Glu Cys Lys Glu Glu Gln Cys Ser Phe Glu Glu
50 55 60

Ala Arg Glu Ile Phe Lys Asp Ala Glu Arg Thr Lys Leu Phe Trp Ile
65 70 75 80

Ser Tyr Ser Asp Gly Asp Gln Cys Ala Ser Ser Pro Cys Gln Asn Gly
85 90 95

Gly Ser Cys Lys Asp Gln Leu Gln Ser Tyr Ile Cys Phe Cys Leu Pro
100 105 110

Ala Phe Glu Gly Arg Asn Cys Glu Thr His Lys Asp Asp Gln Leu Ile
115 120 125

Cys Val Asn Glu Asn Gly Gly Cys Glu Gln Tyr Cys Ser Asp His Thr
130 135 140

Gly Thr Lys Arg Ser Cys Arg Cys His Glu Gly Tyr Ser Leu Leu Ala
145 150 155 160

Asp Gly Val Ser Cys Thr Pro Thr Val Glu Tyr Pro Cys Gly Lys Ile
165 170 175

Pro Ile Leu Glu Lys Arg Asn Ala Ser Lys Pro Gln Gly Arg Gly Gly
180 185 190

Gly Gly Ser Gly Gly Gly Gly Ser Gly Gly Gly Gly Ser Gly Gly Gly
195 200 205

Gly Ser Gly Gly Gly Gly Ser Gly Gly Gly Gly Ser Asp Lys Thr His
210 215 220

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro

-continued

```
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Gly Gly
    450                 455                 460

Gly Gly Ser Gly Gly Gly Gly Ser Gly Gly Gly Gly Ser Gly Gly Gly
465                 470                 475                 480

Gly Ser Gly Gly Gly Gly Ser Ile Val Gly Gly Lys Val Cys Pro Lys
                485                 490                 495

Gly Glu Cys Pro Trp Gln Val Leu Leu Leu Val Asn Gly Ala Gln Leu
            500                 505                 510

Cys Gly Gly Thr Leu Ile Asn Thr Ile Trp Val Val Ser Ala Ala His
        515                 520                 525

Cys Phe Asp Lys Ile Lys Asn Trp Arg Asn Leu Ile Ala Val Leu Gly
    530                 535                 540

Glu His Asp Leu Ser Glu His Asp Gly Asp Glu Gln Ser Arg Arg Val
545                 550                 555                 560

Ala Gln Val Ile Ile Pro Ser Thr Tyr Val Pro Gly Thr Thr Asn His
                565                 570                 575

Asp Ile Ala Leu Leu Arg Leu His Gln Pro Val Val Leu Thr Asp His
            580                 585                 590

Val Val Pro Leu Cys Leu Pro Glu Arg Thr Phe Ser Glu Arg Thr Leu
        595                 600                 605

Ala Phe Val Arg Phe Ser Leu Val Ser Gly Trp Gly Gln Leu Leu Asp
    610                 615                 620

Arg Gly Ala Thr Ala Leu Glu Leu Met Val Leu Asn Val Pro Arg Leu
625                 630                 635                 640

Met Thr Gln Asp Cys Leu Gln Gln Ser Arg Lys Val Gly Asp Ser Pro
                645                 650                 655

Asn Ile Thr Glu Tyr Met Phe Cys Ala Gly Tyr Ser Asp Gly Ser Lys
            660                 665                 670

Asp Ser Cys Lys Gly Asp Ser Gly Gly Pro His Ala Thr His Tyr Arg
        675                 680                 685

Gly Thr Trp Tyr Leu Thr Gly Ile Val Ser Trp Gly Gln Gly Cys Ala
    690                 695                 700

Thr Val Gly His Phe Gly Val Tyr Thr Arg Val Ser Gln Tyr Ile Glu
705                 710                 715                 720

Trp Leu Gln Lys Leu Met Arg Ser Glu Pro Arg Pro Gly Val Leu Leu
                725                 730                 735

Arg Ala Pro Phe Pro Gly Gly Gly Gly Ser Gly Gly Gly Gly Ser Gly
            740                 745                 750

Gly Gly Gly Ser Gly Gly Gly Gly Ser Gly Gly Gly Gly Ser Gly Gly
        755                 760                 765
```

```
Gly Gly Ser Asp Lys Thr His Thr Cys Pro Pro Cys Pro Ala Pro Glu
    770                 775                 780

Leu Leu Gly Gly Pro Ser Val Phe Leu Phe Pro Pro Lys Pro Lys Asp
785                 790                 795                 800

Thr Leu Met Ile Ser Arg Thr Pro Glu Val Thr Cys Val Val Val Asp
                805                 810                 815

Val Ser His Glu Asp Pro Glu Val Lys Phe Asn Trp Tyr Val Asp Gly
            820                 825                 830

Val Glu Val His Asn Ala Lys Thr Lys Pro Arg Glu Glu Gln Tyr Asn
        835                 840                 845

Ser Thr Tyr Arg Val Val Ser Val Leu Thr Val Leu His Gln Asp Trp
    850                 855                 860

Leu Asn Gly Lys Glu Tyr Lys Cys Lys Val Ser Asn Lys Ala Leu Pro
865                 870                 875                 880

Ala Pro Ile Glu Lys Thr Ile Ser Lys Ala Lys Gly Gln Pro Arg Glu
                885                 890                 895

Pro Gln Val Tyr Thr Leu Pro Pro Ser Arg Asp Glu Leu Thr Lys Asn
            900                 905                 910

Gln Val Ser Leu Thr Cys Leu Val Lys Gly Phe Tyr Pro Ser Asp Ile
        915                 920                 925

Ala Val Glu Trp Glu Ser Asn Gly Gln Pro Glu Asn Asn Tyr Lys Thr
    930                 935                 940

Thr Pro Pro Val Leu Asp Ser Asp Gly Ser Phe Phe Leu Tyr Ser Lys
945                 950                 955                 960

Leu Thr Val Asp Lys Ser Arg Trp Gln Gln Gly Asn Val Phe Ser Cys
                965                 970                 975

Ser Val Met His Glu Ala Leu His Asn His Tyr Thr Gln Lys Ser Leu
            980                 985                 990

Ser Leu Ser Pro Gly Lys
        995


<210> SEQ ID NO 110
<211> LENGTH: 2997
<212> TYPE: DNA
<213> ORGANISM: Artificial Sequence
<220> FEATURE:
<223> OTHER INFORMATION: Synthetic construct: DNA sequence for FVII-090

<400> SEQUENCE: 110

atggtctccc aggccctcag gctcctctgc cttctgcttg ggcttcaggg ctgcctggct     60

gcagtcttcg taacccagga ggaagcccac ggcgtcctgc accggcgccg gcgcgccaac    120

gcgttcctgg aggagctgcg gccgggctcc ctggagaggg agtgcaagga ggagcagtgc    180

tccttcgagg aggcccggga gatcttcaag gacgcggaga ggacgaagct gttctggatt    240

tcttacagtg atggggacca gtgtgcctca agtccatgcc agaatggggg ctcctgcaag    300

gaccagctcc agtcctatat ctgcttctgc ctccctgcct tcgagggccg gaactgtgag    360

acgcacaagg atgaccagct gatctgtgtg aacgagaacg gcggctgtga gcagtactgc    420

agtgaccaca cgggcaccaa gcgctcctgt cggtgccacg aggggtactc tctgctggca    480

gacggggtgt cctgcacacc cacagttgaa tatccatgtg gaaaaatacc tattctagaa    540

aaaagaaatg ccagcaaacc ccaaggccga ggtggcggtg gctccggcgg aggtgggtcc    600

ggtggcggcg gatcaggtgg gggtggatca ggcggtggag gttccggtgg cgggggatca    660

gacaaaactc acacatgccc accgtgccca gctccggaac tcctgggcgg accgtcagtc    720
```

```
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggatga gctgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gttggactcc   1200
gacggctcct tcttcctcta cagcaagctc accgtcgaca agagcaggtg gcagcagggg   1260
aacgtcttct catgctccgt gatgcatgag gctctgcaca accactacac gcagaagagc   1320
ctctccctgt ctccgggtaa aggtggcggc ggatcaggtg gggggtggatc aggcggtgga  1380
ggttccggtg gcgggggatc cggcggtgga ggttccggtg gggggtggatc aggaggaggt  1440
ggttcagccc tgcggccccg gattgtgggg ggcaaggtgt gccccaaagg ggagtgtcca   1500
tggcaggtcc tgttgttggt gaatggagct cagttgtgtg gggggaccct gatcaacacc   1560
atctgggtgg tctccgcggc ccactgtttc gacaaaatca agaactggag gaacctgatc   1620
gcggtgctgg gcgagcacga cctcagcgag cacgacgggg atgagcagag ccggcgggtg   1680
gcgcaggtca tcatccccag cacgtacgtc ccgggcacca ccaaccacga catcgcgctg   1740
ctccgcctgc accagcccgt ggtcctcact gaccatgtgg tgcccctctg cctgcccgaa   1800
cggacgttct ctgagaggac gctggccttc gtgcgcttct cattggtcag cggctggggc   1860
cagctgctgg accgtggcgc cacggccctg gagctcatgg tcctcaacgt gccccggctg   1920
atgacccagg actgcctgca gcagtcacgg aaggtgggag actccccaaa tatcacggag   1980
tacatgttct gtgccggcta ctcggatggc agcaaggact cctgcaaggg ggacagtgga   2040
ggcccacatg ccacccacta ccggggcacg tggtacctga cgggcatcgt cagctggggc   2100
cagggctgcg caaccgtggg ccactttggg gtgtacacca gggtctccca gtacatcgag   2160
tggctgcaaa agctcatgcg ctcagagcca cgcccaggag tcctcctgcg agccccattt   2220
cccggtggcg gtggctccgg cggaggtggg tccggtggcg gcggatcagg tgggggtgga   2280
tcaggcggtg gaggttccgg tggcggggga tcagacaaaa ctcacacatg cccaccgtgc   2340
ccagcacctg aactcctggg aggaccgtca gtcttcctct tcccccccaaa acccaaggac  2400
accctcatga tctcccggac ccctgaggtc acatgcgtgg tggtggacgt gagccacgaa   2460
gaccctgagg tcaagttcaa ctggtacgtg gacggcgtgg aggtgcataa tgccaagaca   2520
aagccgcggg aggagcagta caacagcacg taccgtgtgg tcagcgtcct caccgtcctg   2580
caccaggact ggctgaatgg caaggagtac aagtgcaagg tctccaacaa agccctccca   2640
gcccccatcg agaaaaccat ctccaaagcc aaagggcagc cccgagaacc acaggtgtac   2700
accctgcccc catcccggga tgagctgacc aagaaccagg tcagcctgac ctgcctggtc   2760
aaaggcttct atcccagcga catcgccgtg gagtgggaga gcaatgggca gccggagaac   2820
aactacaaga ccacgcctcc cgtgttggac tccgacggct ccttcttcct ctacagcaag   2880
ctcaccgtgg acaagagcag gtggcagcag gggaacgtct tctcatgctc cgtgatgcat   2940
gaggctctgc acaaccacta cacgcagaag agcctctccc tgtctccggg taaatga      2997
```

<210> SEQ ID NO 111

<211> LENGTH: 998
<212> TYPE: PRT
<213> ORGANISM: Artificial Sequence
<220> FEATURE:
<223> OTHER INFORMATION: Synthetic construct: FVII-090 amino acid sequence

<400> SEQUENCE: 111

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
```

```
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Gly Gly
    450                 455                 460

Gly Gly Ser Gly Gly Gly Gly Ser Gly Gly Gly Gly Ser Gly Gly Gly
465                 470                 475                 480

Gly Ser Ala Leu Arg Pro Arg Ile Val Gly Gly Lys Val Cys Pro Lys
                485                 490                 495

Gly Glu Cys Pro Trp Gln Val Leu Leu Leu Val Asn Gly Ala Gln Leu
            500                 505                 510

Cys Gly Gly Thr Leu Ile Asn Thr Ile Trp Val Val Ser Ala Ala His
        515                 520                 525

Cys Phe Asp Lys Ile Lys Asn Trp Arg Asn Leu Ile Ala Val Leu Gly
    530                 535                 540

Glu His Asp Leu Ser Glu His Asp Gly Asp Glu Gln Ser Arg Arg Val
545                 550                 555                 560

Ala Gln Val Ile Ile Pro Ser Thr Tyr Val Pro Gly Thr Thr Asn His
                565                 570                 575

Asp Ile Ala Leu Leu Arg Leu His Gln Pro Val Val Leu Thr Asp His
            580                 585                 590

Val Val Pro Leu Cys Leu Pro Glu Arg Thr Phe Ser Glu Arg Thr Leu
        595                 600                 605

Ala Phe Val Arg Phe Ser Leu Val Ser Gly Trp Gly Gln Leu Leu Asp
    610                 615                 620

Arg Gly Ala Thr Ala Leu Glu Leu Met Val Leu Asn Val Pro Arg Leu
625                 630                 635                 640

Met Thr Gln Asp Cys Leu Gln Gln Ser Arg Lys Val Gly Asp Ser Pro
                645                 650                 655

Asn Ile Thr Glu Tyr Met Phe Cys Ala Gly Tyr Ser Asp Gly Ser Lys
            660                 665                 670

Asp Ser Cys Lys Gly Asp Ser Gly Gly Pro His Ala Thr His Tyr Arg
        675                 680                 685

Gly Thr Trp Tyr Leu Thr Gly Ile Val Ser Trp Gly Gln Gly Cys Ala
    690                 695                 700

Thr Val Gly His Phe Gly Val Tyr Thr Arg Val Ser Gln Tyr Ile Glu
705                 710                 715                 720

Trp Leu Gln Lys Leu Met Arg Ser Glu Pro Arg Pro Gly Val Leu Leu
                725                 730                 735

Arg Ala Pro Phe Pro Gly Gly Gly Gly Ser Gly Gly Gly Gly Ser Gly
            740                 745                 750

Gly Gly Gly Ser Gly Gly Gly Gly Ser Gly Gly Gly Gly Ser Gly Gly
        755                 760                 765

Gly Gly Ser Asp Lys Thr His Thr Cys Pro Pro Cys Pro Ala Pro Glu
    770                 775                 780

Leu Leu Gly Gly Pro Ser Val Phe Leu Phe Pro Pro Lys Pro Lys Asp
785                 790                 795                 800
```

```
Thr Leu Met Ile Ser Arg Thr Pro Glu Val Thr Cys Val Val Val Asp
                805                 810                 815

Val Ser His Glu Asp Pro Glu Val Lys Phe Asn Trp Tyr Val Asp Gly
            820                 825                 830

Val Glu Val His Asn Ala Lys Thr Lys Pro Arg Glu Glu Gln Tyr Asn
        835                 840                 845

Ser Thr Tyr Arg Val Val Ser Val Leu Thr Val Leu His Gln Asp Trp
    850                 855                 860

Leu Asn Gly Lys Glu Tyr Lys Cys Lys Val Ser Asn Lys Ala Leu Pro
865                 870                 875                 880

Ala Pro Ile Glu Lys Thr Ile Ser Lys Ala Lys Gly Gln Pro Arg Glu
                885                 890                 895

Pro Gln Val Tyr Thr Leu Pro Pro Ser Arg Asp Glu Leu Thr Lys Asn
            900                 905                 910

Gln Val Ser Leu Thr Cys Leu Val Lys Gly Phe Tyr Pro Ser Asp Ile
        915                 920                 925

Ala Val Glu Trp Glu Ser Asn Gly Gln Pro Glu Asn Asn Tyr Lys Thr
    930                 935                 940

Thr Pro Pro Val Leu Asp Ser Asp Gly Ser Phe Phe Leu Tyr Ser Lys
945                 950                 955                 960

Leu Thr Val Asp Lys Ser Arg Trp Gln Gln Gly Asn Val Phe Ser Cys
                965                 970                 975

Ser Val Met His Glu Ala Leu His Asn His Tyr Thr Gln Lys Ser Leu
            980                 985                 990

Ser Leu Ser Pro Gly Lys
        995
```

<210> SEQ ID NO 112
<211> LENGTH: 2982
<212> TYPE: DNA
<213> ORGANISM: Artificial Sequence
<220> FEATURE:
<223> OTHER INFORMATION: Synthetic construct: DNA sequence for FVII-100

<400> SEQUENCE: 112

```
atggtctccc aggccctcag gctcctctgc cttctgcttg ggcttcaggg ctgcctggct      60

gcagtcttcg taacccagga ggaagcccac ggcgtcctgc accggcgccg gcgcgccaac     120

gcgttcctgg aggagctgcg gccgggctcc ctggagaggg agtgcaagga ggagcagtgc     180

tccttcgagg aggcccggga gatcttcaag gacgcggaga ggacgaagct gttctggatt     240

tcttacagtg atggggacca gtgtgcctca agtccatgcc agaatggggg ctcctgcaag     300

gaccagctcc agtcctatat ctgcttctgc ctccctgcct tcgagggccg gaactgtgag     360

acgcacaagg atgaccagct gatctgtgtg aacgagaacg gcggctgtga gcagtactgc     420

agtgaccaca cgggcaccaa gcgctcctgt cggtgccacg aggggtactc tctgctggca     480

gacggggtgt cctgcacacc cacagttgaa tatccatgtg gaaaaatacc tattctagaa     540

aaaagaaatg ccagcaaacc ccaaggccga ggtggcggtg gctccggcgg aggtgggtcc     600

ggtggcggcg gatcaggtgg gggtggatca ggcggtggag gttccggtgg cgggggatcc     660

gacaaaactc acacatgccc accgtgccca gctccggaac tcctgggagg accgtcagtc     720

ttcctcttcc ccccaaaacc caaggacacc ctcatgatct cccggacccc tgaggtcaca     780

tgcgtggtgg tggacgtgag ccacgaagac cctgaggtca agttcaactg gtacgtggac     840

ggcgtggagg tgcataatgc caagacaaag ccgcgggagg agcagtacaa cagcacgtac     900
```

```
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggatga gctgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gttggactcc   1200
gacggctcct tcttcctcta cagcaagctc accgtcgaca agagcaggtg gcagcagggg   1260
aacgtcttct catgctccgt gatgcatgag gctctgcaca accactacac gcagaagagc   1320
ctctccctgt ctccgggtaa aggtggcggc ggatcaggtg gggtggatc aggcggtgga   1380
ggttccggtg gcgggggatc cggcggtgga ggttccggtg gggtggatc aggaggaggt   1440
ggttcagccc tgcggccccg gattgtgggg ggcaaggtgt gccccaaagg ggagtgtcca   1500
tggcaggtcc tgttgttggt gaatggagct cagttgtgtg gggggaccct gatcaacacc   1560
atctgggtgg tctccgcggc ccactgtttc gacaaaatca agaactggag gaacctgatc   1620
gcggtgctgg gcgagcacga cctcagcgag cacgacgggg atgagcagag ccggcgggtg   1680
gcgcaggtca tcatccccag cacgtacgtc ccgggcacca ccaaccacga catcgcgctg   1740
ctccgcctgc accagcccgt ggtcctcact gaccatgtgg tgcccctctg cctgcccgaa   1800
cggacgttct ctgagaggac gctggccttc gtgcgcttct cattggtcag cggctggggc   1860
cagctgctgg accgtggcgc cacggccctg gagctcatgg tcctcaacgt gccccggctg   1920
atgacccagg actgcgaggc cagctacccc ggcaagatca cggagtacat gttctgtgcc   1980
ggctactcgg atggcagcaa ggactcctgc aagggggaca gtggaggccc acatgccacc   2040
cactaccggg gcacgtggta cctgacgggc atcgtcagct ggggccaggg ctgcgcaacc   2100
gtgggccact tggggtgta caccagggtc tcccagtaca tcgagtggct gcaaaagctc   2160
atgcgctcag agccacgccc aggagtcctc ctgcgagccc catttcccgg tggcggtggc   2220
tccggcggag gtgggtccgg tggcggcgga tcaggtgggg gtggatcagg cggtggaggt   2280
tccggtggcg gggatcaga caaaactcac acatgcccac cgtgcccagc acctgaactc   2340
ctgggaggac cgtcagtctt cctcttcccc ccaaaaccca aggacaccct catgatctcc   2400
cggacccctg aggtcacatg cgtggtggtg gacgtgagcc acgaagaccc tgaggtcaag   2460
ttcaactggt acgtggacgg cgtggaggtg cataatgcca agacaaagcc gcgggaggag   2520
cagtacaaca gcacgtaccg tgtggtcagc gtcctcaccg tcctgcacca ggactggctg   2580
aatggcaagg agtacaagtg caaggtctcc aacaaagccc tcccagcccc catcgagaaa   2640
accatctcca aagccaaagg gcagccccga gaaccacagg tgtacaccct gcccccatcc   2700
cgggatgagc tgaccaagaa ccaggtcagc ctgacctgcc tggtcaaagg cttctatccc   2760
agcgacatcg ccgtggagtg ggagagcaat gggcagccgg agaacaacta caagaccacg   2820
cctcccgtgt tggactccga cggctccttc ttcctctaca gcaagctcac cgtggacaag   2880
agcaggtggc agcaggggaa cgtcttctca tgctccgtga tgcatgaggc tctgcacaac   2940
cactacacgc agaagagcct ctccctgtct ccgggtaaat ga                      2982
```

<210> SEQ ID NO 113
<211> LENGTH: 993
<212> TYPE: PRT
<213> ORGANISM: Artificial Sequence
<220> FEATURE:
<223> OTHER INFORMATION: Synthetic construct: FVII-100 amino acid sequence

<400> SEQUENCE: 113

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
```

```
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Gly Gly
    450                 455                 460

Gly Gly Ser Gly Gly Gly Gly Ser Gly Gly Gly Gly Ser Gly Gly Gly
465                 470                 475                 480

Gly Ser Ala Leu Arg Pro Arg Ile Val Gly Gly Lys Val Cys Pro Lys
                485                 490                 495

Gly Glu Cys Pro Trp Gln Val Leu Leu Leu Val Asn Gly Ala Gln Leu
            500                 505                 510

Cys Gly Gly Thr Leu Ile Asn Thr Ile Trp Val Val Ser Ala Ala His
        515                 520                 525

Cys Phe Asp Lys Ile Lys Asn Trp Arg Asn Leu Ile Ala Val Leu Gly
    530                 535                 540

Glu His Asp Leu Ser Glu His Asp Gly Asp Glu Gln Ser Arg Arg Val
545                 550                 555                 560

Ala Gln Val Ile Ile Pro Ser Thr Tyr Val Pro Gly Thr Thr Asn His
                565                 570                 575

Asp Ile Ala Leu Leu Arg Leu His Gln Pro Val Val Leu Thr Asp His
            580                 585                 590

Val Val Pro Leu Cys Leu Pro Glu Arg Thr Phe Ser Glu Arg Thr Leu
        595                 600                 605

Ala Phe Val Arg Phe Ser Leu Val Ser Gly Trp Gly Gln Leu Leu Asp
    610                 615                 620

Arg Gly Ala Thr Ala Leu Glu Leu Met Val Leu Asn Val Pro Arg Leu
625                 630                 635                 640

Met Thr Gln Asp Cys Glu Ala Ser Tyr Pro Gly Lys Ile Thr Glu Tyr
                645                 650                 655

Met Phe Cys Ala Gly Tyr Ser Asp Gly Ser Lys Asp Ser Cys Lys Gly
            660                 665                 670

Asp Ser Gly Gly Pro His Ala Thr His Tyr Arg Gly Thr Trp Tyr Leu
        675                 680                 685

Thr Gly Ile Val Ser Trp Gly Gln Gly Cys Ala Thr Val Gly His Phe
    690                 695                 700

Gly Val Tyr Thr Arg Val Ser Gln Tyr Ile Glu Trp Leu Gln Lys Leu
705                 710                 715                 720

Met Arg Ser Glu Pro Arg Pro Gly Val Leu Leu Arg Ala Pro Phe Pro
                725                 730                 735

Gly Gly Gly Gly Ser Gly Gly Gly Gly Ser Gly Gly Gly Gly Ser Gly
            740                 745                 750

Gly Gly Gly Ser Gly Gly Gly Gly Ser Gly Gly Gly Gly Ser Asp Lys
        755                 760                 765

Thr His Thr Cys Pro Pro Cys Pro Ala Pro Glu Leu Leu Gly Gly Pro
    770                 775                 780

Ser Val Phe Leu Phe Pro Pro Lys Pro Lys Asp Thr Leu Met Ile Ser
785                 790                 795                 800

Arg Thr Pro Glu Val Thr Cys Val Val Val Asp Val Ser His Glu Asp
                805                 810                 815

Pro Glu Val Lys Phe Asn Trp Tyr Val Asp Gly Val Glu Val His Asn
            820                 825                 830
```

```
Ala Lys Thr Lys Pro Arg Glu Glu Gln Tyr Asn Ser Thr Tyr Arg Val
        835                 840                 845

Val Ser Val Leu Thr Val Leu His Gln Asp Trp Leu Asn Gly Lys Glu
    850                 855                 860

Tyr Lys Cys Lys Val Ser Asn Lys Ala Leu Pro Ala Pro Ile Glu Lys
865                 870                 875                 880

Thr Ile Ser Lys Ala Lys Gly Gln Pro Arg Glu Pro Gln Val Tyr Thr
                885                 890                 895

Leu Pro Pro Ser Arg Asp Glu Leu Thr Lys Asn Gln Val Ser Leu Thr
            900                 905                 910

Cys Leu Val Lys Gly Phe Tyr Pro Ser Asp Ile Ala Val Glu Trp Glu
        915                 920                 925

Ser Asn Gly Gln Pro Glu Asn Asn Tyr Lys Thr Thr Pro Pro Val Leu
    930                 935                 940

Asp Ser Asp Gly Ser Phe Phe Leu Tyr Ser Lys Leu Thr Val Asp Lys
945                 950                 955                 960

Ser Arg Trp Gln Gln Gly Asn Val Phe Ser Cys Ser Val Met His Glu
                965                 970                 975

Ala Leu His Asn His Tyr Thr Gln Lys Ser Leu Ser Leu Ser Pro Gly
            980                 985                 990

Lys
```

<210> SEQ ID NO 114
<211> LENGTH: 2997
<212> TYPE: DNA
<213> ORGANISM: Artificial Sequence
<220> FEATURE:
<223> OTHER INFORMATION: Synthetic construct: DNA sequence for FVII-115

<400> SEQUENCE: 114

```
atggtctccc aggccctcag gctcctctgc cttctgcttg ggcttcaggg ctgcctggct      60

gcagtcttcg taacccagga ggaagcccac ggcgtcctgc accggcgccg gcgcgccaac     120

gcgttcctgg aggagctgcg gccgggctcc ctggagaggg agtgcaagga ggagcagtgc     180

tccttcgagg aggcccggga gatcttcaag gacgcggaga ggacgaagct gttctggatt     240

tcttacagtg atggggacca gtgtgcctca agtccatgcc agaatggggg ctcctgcaag     300

gaccagctcc agtcctatat ctgcttctgc ctccctgcct tcgagggccg gaactgtgag     360

acgcacaagg atgaccagct gatctgtgtg aacgagaacg gcggctgtga gcagtactgc     420

agtgaccaca cgggcaccaa gcgctcctgt cggtgccacg aggggtactc tctgctggca     480

gacggggtgt cctgcacacc cacagttgaa tatccatgtg gaaaaatacc tattctagaa     540

aaaagaaatg ccagcaaacc ccaaggccga ggtggcggtg gctccggcgg aggtgggtcc     600

ggtggcggcg gatcaggtgg gggtggatca ggcggtggag gttccggtgg cgggggatca     660

gacaaaactc acacatgccc accgtgccca gctccggaac tcctgggcgg accgtcagtc     720

ttcctcttcc ccccaaaacc caaggacacc ctcatgatct cccggacccc tgaggtcaca     780

tgcgtggtgg tggacgtgag ccacgaagac cctgaggtca agttcaactg gtacgtggac     840

ggcgtggagg tgcataatgc caagacaaag ccgcgggagg agcagtacaa cagcacgtac     900

cgtgtggtca gcgtcctcac cgtcctgcac caggactggc tgaatggcaa ggagtacaag     960

tgcaaggtct ccaacaaagc cctcccagcc cccatcgaga aaaccatctc caaagccaaa    1020

gggcagcccc gagaaccaca ggtgtacacc ctgcccccat cccgggatga gctgaccaag    1080
```

aaccaggtca gcctgacctg cctggtcaaa ggcttctatc ccagcgacat cgccgtggag 1140
tgggagagca atgggcagcc ggagaacaac tacaagacca cgcctcccgt gttggactcc 1200
gacggctcct tcttcctcta cagcaagctc accgtcgaca agagcaggtg gcagcagggg 1260
aacgtcttct catgctccgt gatgcatgag gctctgcaca accactacac gcagaagagc 1320
ctctccctgt ctccgggtaa aggtggcggc ggatcaggtg gggtggatc aggcggtgga 1380 ggttccggtg gcgggggatc cggcggtgga ggttccggtg gggtggatc aggaggaggt 1440 ggttcagccc tgcggccccg gattgtgggg ggcaaggact gccccaaagg ggagtgtcca 1500
tggcaggtcc tgttgttggt gaatggagct cagttgtgtg gggggaccct gatcaacacc 1560
atctgggtgg tctccgcggc ccactgtttc gacaaaatca agaactggag gaacctgatc 1620
gcggtgctgg gcgagcacga cctcagcgag cacgacgggg atgagcagag ccggcgggtg 1680
gcgcaggtca tcatccccag cacgtacgtc ccgggcacca ccaaccacga catcgcgctg 1740
ctccgcctgc accagcccgt ggtcctcact gaccatgtgg tgcccctctg cctgcccgaa 1800
cggacgttct ctgagaggac gctggccttc gtgcgcttct cattggtcag cggctggggc 1860
cagctgctgg accgtggcgc cacggccctg gtactccaag tcctcaacgt gccccggctg 1920
atgacccagg actgcctgca gcagtcacgg aaggtgggag actccccaaa tatcacggag 1980
tacatgttct gtgccggcta ctcggatggc agcaaggact cctgcaaggg ggacagtgga 2040
ggcccacatg ccacccacta ccggggcacg tggtacctga cgggcatcgt cagctggggc 2100
cagggctgcg caaccgtggg ccactttggg gtgtacacca gggtctccca gtacatcgag 2160
tggctgcaaa agctcatgcg ctcagagcca cgcccaggag tcctcctgcg agccccattt 2220
cccggtggcg gtggctccgg cggaggtggg tccggtggcg gcggatcagg tgggggtgga 2280
tcaggcggtg gaggttccgg tggcggggga tcagacaaaa ctcacacatg cccaccgtgc 2340
ccagcacctg aactcctggg aggaccgtca gtcttcctct tcccccaaa acccaaggac 2400 accctcatga tctcccggac ccctgaggtc acatgcgtgg tggtggacgt gagccacgaa 2460
gaccctgagg tcaagttcaa ctggtacgtg gacggcgtgg aggtgcataa tgccaagaca 2520
aagccgcggg aggagcagta caacagcacg taccgtgtgg tcagcgtcct caccgtcctg 2580
caccaggact ggctgaatgg caaggagtac aagtgcaagg tctccaacaa agccctccca 2640
gcccccatcg agaaaaccat ctccaaagcc aaagggcagc cccgagaacc acaggtgtac 2700
accctgcccc catcccggga tgagctgacc aagaaccagg tcagcctgac ctgcctggtc 2760
aaaggcttct atcccagcga catcgccgtg gagtgggaga gcaatgggca gccggagaac 2820
aactacaaga ccacgcctcc cgtgttggac tccgacggct ccttcttcct ctacagcaag 2880
ctcaccgtgg acaagagcag gtggcagcag gggaacgtct tctcatgctc cgtgatgcat 2940
gaggctctgc acaaccacta cacgcagaag agcctctccc tgtctccggg taaatga 2997

<210> SEQ ID NO 115
<211> LENGTH: 998
<212> TYPE: PRT
<213> ORGANISM: Artificial Sequence
<220> FEATURE:
<223> OTHER INFORMATION: Synthetic construct: FVII-115 amino acid sequence

<400> SEQUENCE: 115

Met Val Ser Gln Ala Leu Arg Leu Leu Cys Leu Leu Leu Gly Leu Gln
1 5 10 15

Gly Cys Leu Ala Ala Val Phe Val Thr Gln Glu Glu Ala His Gly Val

-continued

```
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445
```

```
Gly Gly Gly Ser Gly Gly Gly Gly Ser Gly Gly Gly Gly Ser Gly Gly
    450                 455                 460

Gly Gly Ser Gly Gly Gly Gly Ser Gly Gly Gly Gly Ser Gly Gly Gly
465                 470                 475                 480

Gly Ser Ala Leu Arg Pro Arg Ile Val Gly Gly Lys Asp Cys Pro Lys
                485                 490                 495

Gly Glu Cys Pro Trp Gln Val Leu Leu Leu Val Asn Gly Ala Gln Leu
            500                 505                 510

Cys Gly Gly Thr Leu Ile Asn Thr Ile Trp Val Val Ser Ala Ala His
        515                 520                 525

Cys Phe Asp Lys Ile Lys Asn Trp Arg Asn Leu Ile Ala Val Leu Gly
    530                 535                 540

Glu His Asp Leu Ser Glu His Asp Gly Asp Glu Gln Ser Arg Arg Val
545                 550                 555                 560

Ala Gln Val Ile Ile Pro Ser Thr Tyr Val Pro Gly Thr Thr Asn His
                565                 570                 575

Asp Ile Ala Leu Leu Arg Leu His Gln Pro Val Val Leu Thr Asp His
            580                 585                 590

Val Val Pro Leu Cys Leu Pro Glu Arg Thr Phe Ser Glu Arg Thr Leu
        595                 600                 605

Ala Phe Val Arg Phe Ser Leu Val Ser Gly Trp Gly Gln Leu Leu Asp
    610                 615                 620

Arg Gly Ala Thr Ala Leu Val Leu Gln Val Leu Asn Val Pro Arg Leu
625                 630                 635                 640

Met Thr Gln Asp Cys Leu Gln Gln Ser Arg Lys Val Gly Asp Ser Pro
                645                 650                 655

Asn Ile Thr Glu Tyr Met Phe Cys Ala Gly Tyr Ser Asp Gly Ser Lys
            660                 665                 670

Asp Ser Cys Lys Gly Asp Ser Gly Gly Pro His Ala Thr His Tyr Arg
        675                 680                 685

Gly Thr Trp Tyr Leu Thr Gly Ile Val Ser Trp Gly Gln Gly Cys Ala
    690                 695                 700

Thr Val Gly His Phe Gly Val Tyr Thr Arg Val Ser Gln Tyr Ile Glu
705                 710                 715                 720

Trp Leu Gln Lys Leu Met Arg Ser Glu Pro Arg Pro Gly Val Leu Leu
                725                 730                 735

Arg Ala Pro Phe Pro Gly Gly Gly Gly Ser Gly Gly Gly Gly Ser Gly
            740                 745                 750

Gly Gly Gly Ser Gly Gly Gly Gly Ser Gly Gly Gly Gly Ser Gly Gly
        755                 760                 765

Gly Gly Ser Asp Lys Thr His Thr Cys Pro Pro Cys Pro Ala Pro Glu
    770                 775                 780

Leu Leu Gly Gly Pro Ser Val Phe Leu Phe Pro Pro Lys Pro Lys Asp
785                 790                 795                 800

Thr Leu Met Ile Ser Arg Thr Pro Glu Val Thr Cys Val Val Val Asp
                805                 810                 815

Val Ser His Glu Asp Pro Glu Val Lys Phe Asn Trp Tyr Val Asp Gly
            820                 825                 830

Val Glu Val His Asn Ala Lys Thr Lys Pro Arg Glu Glu Gln Tyr Asn
        835                 840                 845

Ser Thr Tyr Arg Val Val Ser Val Leu Thr Val Leu His Gln Asp Trp
    850                 855                 860
```

```
Leu Asn Gly Lys Glu Tyr Lys Cys Lys Val Ser Asn Lys Ala Leu Pro
865                 870                 875                 880

Ala Pro Ile Glu Lys Thr Ile Ser Lys Ala Lys Gly Gln Pro Arg Glu
                885                 890                 895

Pro Gln Val Tyr Thr Leu Pro Pro Ser Arg Asp Glu Leu Thr Lys Asn
            900                 905                 910

Gln Val Ser Leu Thr Cys Leu Val Lys Gly Phe Tyr Pro Ser Asp Ile
        915                 920                 925

Ala Val Glu Trp Glu Ser Asn Gly Gln Pro Glu Asn Asn Tyr Lys Thr
    930                 935                 940

Thr Pro Pro Val Leu Asp Ser Asp Gly Ser Phe Phe Leu Tyr Ser Lys
945                 950                 955                 960

Leu Thr Val Asp Lys Ser Arg Trp Gln Gln Gly Asn Val Phe Ser Cys
                965                 970                 975

Ser Val Met His Glu Ala Leu His Asn His Tyr Thr Gln Lys Ser Leu
            980                 985                 990

Ser Leu Ser Pro Gly Lys
        995


<210> SEQ ID NO 116
<211> LENGTH: 2859
<212> TYPE: DNA
<213> ORGANISM: Artificial Sequence
<220> FEATURE:
<223> OTHER INFORMATION: Synthetic construct: DNA sequence for FVII-118

<400> SEQUENCE: 116

atggtctccc aggccctcag gctcctctgc cttctgcttg ggcttcaggg ctgcctggct     60

gcagtcttcg taacccagga ggaagcccac ggcgtcctgc accggcgccg gcgcgccaac    120

gcgttcctgg aggagctgcg gccgggctcc ctggagaggg agtgcaagga ggagcagtgc    180

tccttcgagg aggcccggga gatcttcaag gacgcggaga ggacgaagct gttctggatt    240

tcttacagtg atggggacca gtgtgcctca agtccatgcc agaatggggg ctcctgcaag    300

gaccagctcc agtcctatat ctgcttctgc ctccctgcct tcgagggccg gaactgtgag    360

acgcacaagg atgaccagct gatctgtgtg aacgagaacg gcggctgtga gcagtactgc    420

agtgaccaca cgggcaccaa gcgctcctgt cggtgccacg aggggtactc tctgctggca    480

gacggggtgt cctgcacacc cacagttgaa tatccatgtg gaaaaatacc tattctagaa    540

aaaagaaatg ccagcaaacc ccaaggcgcc ctgcggcccc ggattgtggg gggcaaggtg    600

tgccccaaag gggagtgtcc atggcaggtc ctgttgttgg tgaatggagc tcagttgtgt    660

ggggggaccc tgatcaacac catctgggtg gtctccgcgg cccactgttt cgacaaaatc    720

aagaactgga ggaacctgat cgcggtgctg ggcgagcacg acctcagcga gcacgacggg    780

gatgagcaga gccggcgggt ggcgcaggtc atcatcccca gcacgtacgt cccgggcacc    840

accaaccacg acatcgcgct gctccgcctg caccagcccg tggtcctcac tgaccatgtg    900

gtgcccctct gcctgcccga acggacgttc tctgagagga cgctggcctt cgtgcgcttc    960

tcattggtca gcggctgggg ccagctgctg gaccgtggcg ccacggccct ggagctcatg   1020

gtcctcaacg tgccccggct gatgacccag gactgcctgc agcagtcacg gaaggtggga   1080

gactccccaa atatcacgga gtacatgttc tgtgccggct actcggatgg cagcaaggac   1140

tcctgcaagg gggacagtgg aggcccacat gccacccact accggggcac gtggtacctg   1200

acgggcatcg tcagctgggg ccagggctgc gcaaccgtgg gccactttgg ggtgtacacc   1260
```

```
agggtctccc agtacatcga gtggctgcaa aagctcatgc gctcagagcc acgcccagga   1320

gtcctcctgc gagccccatt tcccggtggc ggtggctccg gcggaggtgg gtccggtggc   1380

ggcggatcag gtgggggtgg atcaggcggt ggaggttccg gtggcggggg atccgacaaa   1440

actcacacat gcccaccgtg cccagctccg gaactcctgg gcggaccgtc agtcttcctc   1500

ttccccccaa aacccaagga caccctcatg atctcccgga cccctgaggt cacatgcgtg   1560

gtggtggacg tgagccacga agaccctgag gtcaagttca actggtacgt ggacggcgtg   1620

gaggtgcata atgccaagac aaagccgcgg gaggagcagt acaacagcac gtaccgtgtg   1680

gtcagcgtcc tcaccgtcct gcaccaggac tggctgaatg gcaaggagta caagtgcaag   1740

gtctccaaca aagccctccc agcccccatc gagaaaacca tctccaaagc caaagggcag   1800

ccccgagaac cacaggtgta caccctgccc ccatcccggg atgagctgac caagaaccag   1860

gtcagcctga cctgcctggt caaaggcttc tatcccagcg acatcgccgt ggagtgggag   1920

agcaatgggc agccggagaa caactacaag accacgcctc ccgtgttgga ctccgacggc   1980

tccttcttcc tctacagcaa gctcaccgtg gacaagagca ggtggcagca ggggaacgtc   2040

ttctcatgct ccgtgatgca tgaggctctg cacaaccact acacgcagaa gagcctctcc   2100

ctgtctccgg gtaaaggtgg cggcggatca ggtgggggtg gatcaggcgg tggaggttcc   2160

ggtggcgggg gatcagacaa aactcacaca tgcccaccgt gcccagcacc tgaactcctg   2220

ggaggaccgt cagtcttcct cttcccccca aaacccaagg acaccctcat gatctcccgg   2280

acccctgagg tcacatgcgt ggtggtggac gtgagccacg aagaccctga ggtcaagttc   2340

aactggtacg tggacggcgt ggaggtgcat aatgccaaga caaagccgcg ggaggagcag   2400

tacaacagca cgtaccgtgt ggtcagcgtc ctcaccgtcc tgcaccagga ctggctgaat   2460

ggcaaggagt acaagtgcaa ggtctccaac aaagccctcc cagcccccat cgagaaaacc   2520

atctccaaag ccaaagggca gccccgagaa ccacaggtgt acaccctgcc cccatcccgc   2580

gatgagctga ccaagaacca ggtcagcctg acctgcctgg tcaaaggctt ctatcccagc   2640

gacatcgccg tggagtggga gagcaatggg cagccggaga acaactacaa gaccacgcct   2700

cccgtgttgg actccgacgg ctccttcttc ctctacagca agctcaccgt ggacaagagc   2760

aggtggcagc aggggaacgt cttctcatgc tccgtgatgc atgaggctct gcacaaccac   2820

tacacgcaga agagcctctc cctgtctccg ggtaaatga                          2859
```

```
<210> SEQ ID NO 117
<211> LENGTH: 952
<212> TYPE: PRT
<213> ORGANISM: Artificial Sequence
<220> FEATURE:
<223> OTHER INFORMATION: Synthetic construct: FVII-118 amino acid
      sequence

<400> SEQUENCE: 117

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80
```

```
Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Ala Leu Arg
            180                 185                 190

Pro Arg Ile Val Gly Gly Lys Val Cys Pro Lys Gly Glu Cys Pro Trp
        195                 200                 205

Gln Val Leu Leu Leu Val Asn Gly Ala Gln Leu Cys Gly Gly Thr Leu
    210                 215                 220

Ile Asn Thr Ile Trp Val Val Ser Ala Ala His Cys Phe Asp Lys Ile
225                 230                 235                 240

Lys Asn Trp Arg Asn Leu Ile Ala Val Leu Gly Glu His Asp Leu Ser
                245                 250                 255

Glu His Asp Gly Asp Glu Gln Ser Arg Arg Val Ala Gln Val Ile Ile
            260                 265                 270

Pro Ser Thr Tyr Val Pro Gly Thr Thr Asn His Asp Ile Ala Leu Leu
        275                 280                 285

Arg Leu His Gln Pro Val Val Leu Thr Asp His Val Val Pro Leu Cys
    290                 295                 300

Leu Pro Glu Arg Thr Phe Ser Glu Arg Thr Leu Ala Phe Val Arg Phe
305                 310                 315                 320

Ser Leu Val Ser Gly Trp Gly Gln Leu Leu Asp Arg Gly Ala Thr Ala
                325                 330                 335

Leu Glu Leu Met Val Leu Asn Val Pro Arg Leu Met Thr Gln Asp Cys
            340                 345                 350

Leu Gln Gln Ser Arg Lys Val Gly Asp Ser Pro Asn Ile Thr Glu Tyr
        355                 360                 365

Met Phe Cys Ala Gly Tyr Ser Asp Gly Ser Lys Asp Ser Cys Lys Gly
    370                 375                 380

Asp Ser Gly Gly Pro His Ala Thr His Tyr Arg Gly Thr Trp Tyr Leu
385                 390                 395                 400

Thr Gly Ile Val Ser Trp Gly Gln Gly Cys Ala Thr Val Gly His Phe
                405                 410                 415

Gly Val Tyr Thr Arg Val Ser Gln Tyr Ile Glu Trp Leu Gln Lys Leu
            420                 425                 430

Met Arg Ser Glu Pro Arg Pro Gly Val Leu Leu Arg Ala Pro Phe Pro
        435                 440                 445

Gly Gly Gly Gly Ser Gly Gly Gly Gly Ser Gly Gly Gly Gly Ser Gly
    450                 455                 460

Gly Gly Gly Ser Gly Gly Gly Gly Ser Gly Gly Gly Gly Ser Asp Lys
465                 470                 475                 480

Thr His Thr Cys Pro Pro Cys Pro Ala Pro Glu Leu Leu Gly Gly Pro
                485                 490                 495
```

```
Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser His Glu Asp
        515                 520                 525

Pro Glu Val Lys Phe Asn Trp Tyr Val Asp Gly Val Glu Val His Asn
    530                 535                 540

Ala Lys Thr Lys Pro Arg Glu Glu Gln Tyr Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
        595                 600                 605

Leu Pro Pro Ser Arg Asp Glu Leu Thr Lys Asn Gln Val Ser Leu Thr
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Lys Leu Thr Val Asp Lys
            660                 665                 670

Ser Arg Trp Gln Gln Gly Asn Val Phe Ser Cys Ser Val Met His Glu
        675                 680                 685

Ala Leu His Asn His Tyr Thr Gln Lys Ser Leu Ser Leu Ser Pro Gly
    690                 695                 700

Lys Gly Gly Gly Gly Ser Gly Gly Gly Gly Ser Gly Gly Gly Gly Ser
705                 710                 715                 720

Gly Gly Gly Gly Ser Asp Lys Thr His Thr Cys Pro Pro Cys Pro Ala
                725                 730                 735

Pro Glu Leu Leu Gly Gly Pro Ser Val Phe Leu Phe Pro Pro Lys Pro
            740                 745                 750

Lys Asp Thr Leu Met Ile Ser Arg Thr Pro Glu Val Thr Cys Val Val
        755                 760                 765

Val Asp Val Ser His Glu Asp Pro Glu Val Lys Phe Asn Trp Tyr Val
    770                 775                 780

Asp Gly Val Glu Val His Asn Ala Lys Thr Lys Pro Arg Glu Glu Gln
785                 790                 795                 800

Tyr Asn Ser Thr Tyr Arg Val Val Ser Val Leu Thr Val Leu His Gln
                805                 810                 815

Asp Trp Leu Asn Gly Lys Glu Tyr Lys Cys Lys Val Ser Asn Lys Ala
            820                 825                 830

Leu Pro Ala Pro Ile Glu Lys Thr Ile Ser Lys Ala Lys Gly Gln Pro
        835                 840                 845

Arg Glu Pro Gln Val Tyr Thr Leu Pro Pro Ser Arg Asp Glu Leu Thr
    850                 855                 860

Lys Asn Gln Val Ser Leu Thr Cys Leu Val Lys Gly Phe Tyr Pro Ser
865                 870                 875                 880

Asp Ile Ala Val Glu Trp Glu Ser Asn Gly Gln Pro Glu Asn Asn Tyr
                885                 890                 895

Lys Thr Thr Pro Pro Val Leu Asp Ser Asp Gly Ser Phe Phe Leu Tyr
            900                 905                 910

Ser Lys Leu Thr Val Asp Lys Ser Arg Trp Gln Gln Gly Asn Val Phe
```

```
        915                 920                 925

Ser Cys Ser Val Met His Glu Ala Leu His Asn His Tyr Thr Gln Lys
    930                 935                 940

Ser Leu Ser Leu Ser Pro Gly Lys
945                 950
```

<210> SEQ ID NO 118
<211> LENGTH: 2874
<212> TYPE: DNA
<213> ORGANISM: Artificial Sequence
<220> FEATURE:
<223> OTHER INFORMATION: Synthetic construct: DNA sequence for FVII-119

<400> SEQUENCE: 118

```
atggtctccc aggccctcag gctcctctgc cttctgcttg ggcttcaggg ctgcctggct     60

gcagtcttcg taacccagga ggaagcccac ggcgtcctgc accggcgccg gcgcgccaac    120

gcgttcctgg aggagctgcg gccgggctcc ctggagaggg agtgcaagga ggagcagtgc    180

tccttcgagg aggcccggga gatcttcaag gacgcggaga ggacgaagct gttctggatt    240

tcttacagtg atggggacca gtgtgcctca agtccatgcc agaatggggg ctcctgcaag    300

gaccagctcc agtcctatat ctgcttctgc ctccctgcct tcgagggccg gaactgtgag    360

acgcacaagg atgaccagct gatctgtgtg aacgagaacg gcggctgtga gcagtactgc    420

agtgaccaca cgggcaccaa gcgctcctgt cggtgccacg aggggtactc tctgctggca    480

gacggggtgt cctgcacacc cacagttgaa tatccatgtg gaaaaatacc tattctagaa    540

aaaagaaatg ccagcaaacc ccaaggcgga ggaggtggtt cagccctgcg gccccggatt    600

gtgggggggca aggtgtgccc caaaggggag tgtccatggc aggtcctgtt gttggtgaat    660

ggagctcagt tgtgtggggg gaccctgatc aacaccatct gggtggtctc cgcggcccac    720

tgtttcgaca aaatcaagaa ctggaggaac ctgatcgcgg tgctgggcga gcacgacctc    780

agcgagcacg acggggatga gcagagccgg cgggtggcgc aggtcatcat ccccagcacg    840

tacgtcccgg gcaccaccaa ccacgacatc gcgctgctcc gcctgcacca gcccgtggtc    900

ctcactgacc atgtggtgcc cctctgcctg cccgaacgga cgttctctga gaggacgctg    960

gccttcgtgc gcttctcatt ggtcagcggc tggggccagc tgctggaccg tggcgccacg   1020

gccctggagc tcatggtcct caacgtgccc cggctgatga cccaggactg cctgcagcag   1080

tcacggaagg tgggagactc cccaaatatc acggagtaca tgttctgtgc cggctactcg   1140

gatggcagca aggactcctg caagggggac agtggaggcc cacatgccac ccactaccgg   1200

ggcacgtggt acctgacggg catcgtcagc tggggccagg gctgcgcaac cgtgggccac   1260

tttggggtgt acaccagggt ctcccagtac atcgagtggc tgcaaaagct catgcgctca   1320

gagccacgcc caggagtcct cctgcgagcc ccatttcccg gtggcggtgg ctccggcgga   1380

ggtgggtccg gtggcggcgg atcaggtggg ggtggatcag gcggtggagg ttccggtggc   1440

gggggatccg acaaaactca cacatgccca ccgtgcccag ctccggaact cctgggcgga   1500

ccgtcagtct tcctcttccc cccaaaaccc aaggacaccc tcatgatctc ccggacccct   1560

gaggtcacat gcgtggtggt ggacgtgagc cacgaagacc ctgaggtcaa gttcaactgg   1620

tacgtggacg gcgtggaggt gcataatgcc aagacaaagc cgcgggagga gcagtacaac   1680

agcacgtacc gtgtggtcag cgtcctcacc gtcctgcacc aggactggct gaatggcaag   1740

gagtacaagt gcaaggtctc caacaaagcc ctcccagccc ccatcgagaa aaccatctcc   1800

aaagccaaag ggcagccccg agaaccacag gtgtacaccc tgcccccatc ccgggatgag   1860
```

-continued

```
ctgaccaaga accaggtcag cctgacctgc ctggtcaaag gcttctatcc cagcgacatc   1920

gccgtggagt gggagagcaa tgggcagccg gagaacaact acaagaccac gcctcccgtg   1980

ttggactccg acggctcctt cttcctctac agcaagctca ccgtggacaa gagcaggtgg   2040

cagcagggga acgtcttctc atgctccgtg atgcatgagg ctctgcacaa ccactacacg   2100

cagaagagcc tctccctgtc tccgggtaaa ggtggcggcg gatcaggtgg gggtggatca   2160

ggcggtggag gttccggtgg cgggggatca gacaaaactc acacatgccc accgtgccca   2220

gcacctgaac tcctgggagg accgtcagtc ttcctcttcc ccccaaaacc caaggacacc   2280

ctcatgatct cccggacccc tgaggtcaca tgcgtggtgg tggacgtgag ccacgaagac   2340

cctgaggtca agttcaactg gtacgtggac ggcgtggagg tgcataatgc caagacaaag   2400

ccgcgggagg agcagtacaa cagcacgtac cgtgtggtca gcgtcctcac cgtcctgcac   2460

caggactggc tgaatggcaa ggagtacaag tgcaaggtct ccaacaaagc cctcccagcc   2520

cccatcgaga aaaccatctc caaagccaaa gggcagcccc gagaaccaca ggtgtacacc   2580

ctgcccccat cccgcgatga gctgaccaag aaccaggtca gcctgacctg cctggtcaaa   2640

ggcttctatc ccagcgacat cgccgtggag tgggagagca atgggcagcc ggagaacaac   2700

tacaagacca cgcctcccgt gttggactcc gacggctcct tcttcctcta cagcaagctc   2760

accgtggaca agagcaggtg gcagcagggg aacgtcttct catgctccgt gatgcatgag   2820

gctctgcaca accactacac gcagaagagc ctctccctgt ctccgggtaa atga         2874
```

```
<210> SEQ ID NO 119
<211> LENGTH: 957
<212> TYPE: PRT
<213> ORGANISM: Artificial Sequence
<220> FEATURE:
<223> OTHER INFORMATION: Synthetic construct: FVII-119 amino acid
      sequence

<400> SEQUENCE: 119

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175
```

```
Pro Ile Leu Glu Lys Arg Asn Ala Ser Lys Pro Gln Gly Gly Gly Gly
            180                 185                 190

Gly Ser Ala Leu Arg Pro Arg Ile Val Gly Gly Lys Val Cys Pro Lys
        195                 200                 205

Gly Glu Cys Pro Trp Gln Val Leu Leu Leu Val Asn Gly Ala Gln Leu
    210                 215                 220

Cys Gly Gly Thr Leu Ile Asn Thr Ile Trp Val Val Ser Ala Ala His
225                 230                 235                 240

Cys Phe Asp Lys Ile Lys Asn Trp Arg Asn Leu Ile Ala Val Leu Gly
                245                 250                 255

Glu His Asp Leu Ser Glu His Asp Gly Asp Glu Gln Ser Arg Arg Val
            260                 265                 270

Ala Gln Val Ile Ile Pro Ser Thr Tyr Val Pro Gly Thr Thr Asn His
        275                 280                 285

Asp Ile Ala Leu Leu Arg Leu His Gln Pro Val Val Leu Thr Asp His
    290                 295                 300

Val Val Pro Leu Cys Leu Pro Glu Arg Thr Phe Ser Glu Arg Thr Leu
305                 310                 315                 320

Ala Phe Val Arg Phe Ser Leu Val Ser Gly Trp Gly Gln Leu Leu Asp
                325                 330                 335

Arg Gly Ala Thr Ala Leu Glu Leu Met Val Leu Asn Val Pro Arg Leu
            340                 345                 350

Met Thr Gln Asp Cys Leu Gln Gln Ser Arg Lys Val Gly Asp Ser Pro
        355                 360                 365

Asn Ile Thr Glu Tyr Met Phe Cys Ala Gly Tyr Ser Asp Gly Ser Lys
    370                 375                 380

Asp Ser Cys Lys Gly Asp Ser Gly Gly Pro His Ala Thr His Tyr Arg
385                 390                 395                 400

Gly Thr Trp Tyr Leu Thr Gly Ile Val Ser Trp Gly Gln Gly Cys Ala
                405                 410                 415

Thr Val Gly His Phe Gly Val Tyr Thr Arg Val Ser Gln Tyr Ile Glu
            420                 425                 430

Trp Leu Gln Lys Leu Met Arg Ser Glu Pro Arg Pro Gly Val Leu Leu
        435                 440                 445

Arg Ala Pro Phe Pro Gly Gly Gly Gly Ser Gly Gly Gly Gly Ser Gly
    450                 455                 460

Gly Gly Gly Ser Gly Gly Gly Gly Ser Gly Gly Gly Gly Ser Gly Gly
465                 470                 475                 480

Gly Gly Ser Asp Lys Thr His Thr Cys Pro Pro Cys Pro Ala Pro Glu
                485                 490                 495

Leu Leu Gly Gly Pro Ser Val Phe Leu Phe Pro Pro Lys Pro Lys Asp
            500                 505                 510

Thr Leu Met Ile Ser Arg Thr Pro Glu Val Thr Cys Val Val Val Asp
        515                 520                 525

Val Ser His Glu Asp Pro Glu Val Lys Phe Asn Trp Tyr Val Asp Gly
    530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Pro
            580                 585                 590

Ala Pro Ile Glu Lys Thr Ile Ser Lys Ala Lys Gly Gln Pro Arg Glu
```

```
        595                 600                 605

Pro Gln Val Tyr Thr Leu Pro Pro Ser Arg Asp Glu Leu Thr Lys Asn
    610                 615                 620

Gln Val Ser Leu Thr Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
        675                 680                 685

Ser Val Met His Glu Ala Leu His Asn His Tyr Thr Gln Lys Ser Leu
    690                 695                 700

Ser Leu Ser Pro Gly Lys Gly Gly Gly Gly Ser Gly Gly Gly Gly Ser
705                 710                 715                 720

Gly Gly Gly Gly Ser Gly Gly Gly Gly Ser Asp Lys Thr His Thr Cys
                725                 730                 735

Pro Pro Cys Pro Ala Pro Glu Leu Leu Gly Gly Pro Ser Val Phe Leu
            740                 745                 750

Phe Pro Pro Lys Pro Lys Asp Thr Leu Met Ile Ser Arg Thr Pro Glu
        755                 760                 765

Val Thr Cys Val Val Val Asp Val Ser His Glu Asp Pro Glu Val Lys
    770                 775                 780

Phe Asn Trp Tyr Val Asp Gly Val Glu Val His Asn Ala Lys Thr Lys
785                 790                 795                 800

Pro Arg Glu Glu Gln Tyr Asn Ser Thr Tyr Arg Val Val Ser Val Leu
                805                 810                 815

Thr Val Leu His Gln Asp Trp Leu Asn Gly Lys Glu Tyr Lys Cys Lys
            820                 825                 830

Val Ser Asn Lys Ala Leu Pro Ala Pro Ile Glu Lys Thr Ile Ser Lys
        835                 840                 845

Ala Lys Gly Gln Pro Arg Glu Pro Gln Val Tyr Thr Leu Pro Pro Ser
    850                 855                 860

Arg Asp Glu Leu Thr Lys Asn Gln Val Ser Leu Thr Cys Leu Val Lys
865                 870                 875                 880

Gly Phe Tyr Pro Ser Asp Ile Ala Val Glu Trp Glu Ser Asn Gly Gln
                885                 890                 895

Pro Glu Asn Asn Tyr Lys Thr Thr Pro Pro Val Leu Asp Ser Asp Gly
            900                 905                 910

Ser Phe Phe Leu Tyr Ser Lys Leu Thr Val Asp Lys Ser Arg Trp Gln
        915                 920                 925

Gln Gly Asn Val Phe Ser Cys Ser Val Met His Glu Ala Leu His Asn
    930                 935                 940

His Tyr Thr Gln Lys Ser Leu Ser Leu Ser Pro Gly Lys
945                 950                 955
```

<210> SEQ ID NO 120
<211> LENGTH: 2844
<212> TYPE: DNA
<213> ORGANISM: Artificial Sequence
<220> FEATURE:
<223> OTHER INFORMATION: Synthetic construct: DNA sequence for FVII-127

<400> SEQUENCE: 120

```
atggtctccc aggccctcag gctcctctgc cttctgcttg ggcttcaggg ctgcctggct     60
```

```
gcagtcttcg taacccagga ggaagcccac ggcgtcctgc accggcgccg gcgcgccaac    120
gcgttcctgg aggagctgcg gccgggctcc ctggagaggg agtgcaagga ggagcagtgc    180
tccttcgagg aggcccggga gatcttcaag gacgcggaga ggacgaagct gttctggatt    240
tcttacagtg atggggacca gtgtgcctca agtccatgcc agaatggggg ctcctgcaag    300
gaccagctcc agtcctatat ctgcttctgc ctccctgcct tcgagggccg gaactgtgag    360
acgcacaagg atgaccagct gatctgtgtg aacgagaacg gcggctgtga gcagtactgc    420
agtgaccaca cgggcaccaa gcgctcctgt cggtgccacg aggggtactc tctgctggca    480
gacggggtgt cctgcacacc cacagttgaa tatccatgtg gaaaaatacc tattctagaa    540
aaaagaaatg ccagcaaacc ccaaggcgcc ctgcggcccc ggattgtggg gggcaaggtg    600
tgccccaaag gggagtgtcc atggcaggtc ctgttgttgg tgaatggagc tcagttgtgt    660
ggggggaccc tgatcaacac catctgggtg gtctccgcgg cccactgttt cgacaaaatc    720
aagaactgga ggaacctgat cgcggtgctg ggcgagcacg acctcagcga gcacgacggg    780
gatgagcaga gccggcgggt ggcgcaggtc atcatcccca gcacgtacgt cccgggcacc    840
accaaccacg acatcgcgct gctccgcctg caccagcccg tggtcctcac tgaccatgtg    900
gtgcccctct gcctgcccga acggacgttc tctgagagga cgctggcctt cgtgcgcttc    960
tcattggtca gcggctgggg ccagctgctg gaccgtggcg ccacggccct ggagctcatg   1020
gtcctcaacg tgccccggct gatgacccag gactgcgagg ccagctaccc cggcaagatc   1080
acggagtaca tgttctgtgc cggctactcg gatggcagca aggactcctg caagggggac   1140
agtggaggcc cacatgccac ccactaccgg ggcacgtggt acctgacggg catcgtcagc   1200
tggggccagg gctgcgcaac cgtgggccac tttggggtgt acaccagggt ctcccagtac   1260
atcgagtggc tgcaaaagct catgcgctca gagccacgcc caggagtcct cctgcgagcc   1320
ccatttcccg gtggcggtgg ctccggcgga ggtgggtccg gtggcggcgg atcaggtggg   1380
ggtggatcag gcggtggagg ttccggtggc gggggatcag acaaaactca cacatgccca   1440
ccgtgcccag ctccggaact cctgggcgga ccgtcagtct tcctcttccc cccaaaaccc   1500
aaggacaccc tcatgatctc ccggacccct gaggtcacat gcgtggtggt ggacgtgagc   1560
cacgaagacc ctgaggtcaa gttcaactgg tacgtggacg gcgtggaggt gcataatgcc   1620
aagacaaagc cgcgggagga gcagtacaac agcacgtacc gtgtggtcag cgtcctcacc   1680
gtcctgcacc aggactggct gaatggcaag gagtacaagt gcaaggtctc caacaaagcc   1740
ctcccagccc ccatcgagaa aaccatctcc aaagccaaag ggcagccccg agaaccacag   1800
gtgtacaccc tgcccccatc ccgggatgag ctgaccaaga accaggtcag cctgacctgc   1860
ctggtcaaag gcttctatcc cagcgacatc gccgtggagt gggagagcaa tgggcagccg   1920
gagaacaact acaagaccac gcctcccgtg ttggactccg acggctcctt cttcctctac   1980
agcaagctca ccgtggacaa gagcaggtgg cagcagggga acgtcttctc atgctccgtg   2040
atgcatgagg ctctgcacaa ccactacacg cagaagagcc tctccctgtc tccgggtaaa   2100
ggtggcggcg gatcaggtgg gggtggatca ggcggtggag gttccggtgg cgggggatca   2160
gacaaaactc acacatgccc accgtgccca gcacctgaac tcctgggagg accgtcagtc   2220
ttcctcttcc ccccaaaacc caaggacacc ctcatgatct cccggacccc tgaggtcaca   2280
tgcgtggtgg tggacgtgag ccacgaagac cctgaggtca agttcaactg gtacgtggac   2340
ggcgtggagg tgcataatgc caagacaaag ccgcgggagg agcagtacaa cagcacgtac   2400
```

```
cgtgtggtca gcgtcctcac cgtcctgcac caggactggc tgaatggcaa ggagtacaag   2460

tgcaaggtct ccaacaaagc cctcccagcc cccatcgaga aaaccatctc caaagccaaa   2520

gggcagcccc gagaaccaca ggtgtacacc ctgcccccat cccgcgatga gctgaccaag   2580

aaccaggtca gcctgacctg cctggtcaaa ggcttctatc ccagcgacat cgccgtggag   2640

tgggagagca atgggcagcc ggagaacaac tacaagacca cgcctcccgt gttggactcc   2700

gacggctcct tcttcctcta cagcaagctc accgtggaca agagcaggtg gcagcagggg   2760

aacgtcttct catgctccgt gatgcatgag gctctgcaca accactacac gcagaagagc   2820

ctctccctgt ctccgggtaa atga                                          2844


<210> SEQ ID NO 121
<211> LENGTH: 947
<212> TYPE: PRT
<213> ORGANISM: Artificial Sequence
<220> FEATURE:
<223> OTHER INFORMATION: Synthetic construct: FVII-127 amino acid
      sequence

<400> SEQUENCE: 121

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Ala Leu Arg
            180                 185                 190

Pro Arg Ile Val Gly Gly Lys Val Cys Pro Lys Gly Glu Cys Pro Trp
        195                 200                 205

Gln Val Leu Leu Leu Val Asn Gly Ala Gln Leu Cys Gly Gly Thr Leu
    210                 215                 220

Ile Asn Thr Ile Trp Val Val Ser Ala Ala His Cys Phe Asp Lys Ile
225                 230                 235                 240

Lys Asn Trp Arg Asn Leu Ile Ala Val Leu Gly Glu His Asp Leu Ser
                245                 250                 255

Glu His Asp Gly Asp Glu Gln Ser Arg Arg Val Ala Gln Val Ile Ile
            260                 265                 270

Pro Ser Thr Tyr Val Pro Gly Thr Thr Asn His Asp Ile Ala Leu Leu
```

```
        275                 280                 285

Arg Leu His Gln Pro Val Val Leu Thr Asp His Val Val Pro Leu Cys
    290                 295                 300

Leu Pro Glu Arg Thr Phe Ser Glu Arg Thr Leu Ala Phe Val Arg Phe
305                 310                 315                 320

Ser Leu Val Ser Gly Trp Gly Gln Leu Leu Asp Arg Gly Ala Thr Ala
                325                 330                 335

Leu Glu Leu Met Val Leu Asn Val Pro Arg Leu Met Thr Gln Asp Cys
            340                 345                 350

Glu Ala Ser Tyr Pro Gly Lys Ile Thr Glu Tyr Met Phe Cys Ala Gly
        355                 360                 365

Tyr Ser Asp Gly Ser Lys Asp Ser Cys Lys Gly Asp Ser Gly Gly Pro
    370                 375                 380

His Ala Thr His Tyr Arg Gly Thr Trp Tyr Leu Thr Gly Ile Val Ser
385                 390                 395                 400

Trp Gly Gln Gly Cys Ala Thr Val Gly His Phe Gly Val Tyr Thr Arg
                405                 410                 415

Val Ser Gln Tyr Ile Glu Trp Leu Gln Lys Leu Met Arg Ser Glu Pro
            420                 425                 430

Arg Pro Gly Val Leu Leu Arg Ala Pro Phe Pro Gly Gly Gly Gly Ser
        435                 440                 445

Gly Gly Gly Gly Ser Gly Gly Gly Gly Ser Gly Gly Gly Gly Ser Gly
    450                 455                 460

Gly Gly Gly Ser Gly Gly Gly Gly Ser Asp Lys Thr His Thr Cys Pro
465                 470                 475                 480

Pro Cys Pro Ala Pro Glu Leu Leu Gly Gly Pro Ser Val Phe Leu Phe
                485                 490                 495

Pro Pro Lys Pro Lys Asp Thr Leu Met Ile Ser Arg Thr Pro Glu Val
            500                 505                 510

Thr Cys Val Val Val Asp Val Ser His Glu Asp Pro Glu Val Lys Phe
        515                 520                 525

Asn Trp Tyr Val Asp Gly Val Glu Val His Asn Ala Lys Thr Lys Pro
    530                 535                 540

Arg Glu Glu Gln Tyr Asn Ser Thr Tyr Arg Val Val Ser Val Leu Thr
545                 550                 555                 560

Val Leu His Gln Asp Trp Leu Asn Gly Lys Glu Tyr Lys Cys Lys Val
                565                 570                 575

Ser Asn Lys Ala Leu Pro Ala Pro Ile Glu Lys Thr Ile Ser Lys Ala
            580                 585                 590

Lys Gly Gln Pro Arg Glu Pro Gln Val Tyr Thr Leu Pro Pro Ser Arg
        595                 600                 605

Asp Glu Leu Thr Lys Asn Gln Val Ser Leu Thr Cys Leu Val Lys Gly
    610                 615                 620

Phe Tyr Pro Ser Asp Ile Ala Val Glu Trp Glu Ser Asn Gly Gln Pro
625                 630                 635                 640

Glu Asn Asn Tyr Lys Thr Thr Pro Pro Val Leu Asp Ser Asp Gly Ser
                645                 650                 655

Phe Phe Leu Tyr Ser Lys Leu Thr Val Asp Lys Ser Arg Trp Gln Gln
            660                 665                 670

Gly Asn Val Phe Ser Cys Ser Val Met His Glu Ala Leu His Asn His
        675                 680                 685

Tyr Thr Gln Lys Ser Leu Ser Leu Ser Pro Gly Lys Gly Gly Gly Gly
    690                 695                 700
```

```
Ser Gly Gly Gly Gly Ser Gly Gly Gly Gly Ser Gly Gly Gly Gly Ser
705                 710                 715                 720

Asp Lys Thr His Thr Cys Pro Pro Cys Pro Ala Pro Glu Leu Leu Gly
                725                 730                 735

Gly Pro Ser Val Phe Leu Phe Pro Pro Lys Pro Lys Asp Thr Leu Met
            740                 745                 750

Ile Ser Arg Thr Pro Glu Val Thr Cys Val Val Val Asp Val Ser His
        755                 760                 765

Glu Asp Pro Glu Val Lys Phe Asn Trp Tyr Val Asp Gly Val Glu Val
    770                 775                 780

His Asn Ala Lys Thr Lys Pro Arg Glu Glu Gln Tyr Asn Ser Thr Tyr
785                 790                 795                 800

Arg Val Val Ser Val Leu Thr Val Leu His Gln Asp Trp Leu Asn Gly
                805                 810                 815

Lys Glu Tyr Lys Cys Lys Val Ser Asn Lys Ala Leu Pro Ala Pro Ile
            820                 825                 830

Glu Lys Thr Ile Ser Lys Ala Lys Gly Gln Pro Arg Glu Pro Gln Val
        835                 840                 845

Tyr Thr Leu Pro Pro Ser Arg Asp Glu Leu Thr Lys Asn Gln Val Ser
    850                 855                 860

Leu Thr Cys Leu Val Lys Gly Phe Tyr Pro Ser Asp Ile Ala Val Glu
865                 870                 875                 880

Trp Glu Ser Asn Gly Gln Pro Glu Asn Asn Tyr Lys Thr Thr Pro Pro
                885                 890                 895

Val Leu Asp Ser Asp Gly Ser Phe Phe Leu Tyr Ser Lys Leu Thr Val
            900                 905                 910

Asp Lys Ser Arg Trp Gln Gln Gly Asn Val Phe Ser Cys Ser Val Met
        915                 920                 925

His Glu Ala Leu His Asn His Tyr Thr Gln Lys Ser Leu Ser Leu Ser
    930                 935                 940

Pro Gly Lys
945
```

<210> SEQ ID NO 122
<211> LENGTH: 2169
<212> TYPE: DNA
<213> ORGANISM: Artificial Sequence
<220> FEATURE:
<223> OTHER INFORMATION: Synthetic construct: DNA sequence for FVII-125

<400> SEQUENCE: 122

```
atggtctccc aggccctcag gctcctctgc cttctgcttg ggcttcaggg ctgcctggct     60

gcagtcttcg taacccagga ggaagcccac ggcgtcctgc accggcgccg gcgcgccaac    120

gcgttcctgg aggagctgcg gccgggctcc ctggagaggg agtgcaagga ggagcagtgc    180

tccttcgagg aggcccggga gatcttcaag gacgcggaga ggacgaagct gttctggatt    240

tcttacagtg atggggacca gtgtgcctca agtccatgcc agaatggggg ctcctgcaag    300

gaccagctcc agtcctatat ctgcttctgc ctccctgcct tcgagggccg gaactgtgag    360

acgcacaagg atgaccagct gatctgtgtg aacgagaacg gcggctgtga gcagtactgc    420

agtgaccaca cgggcaccaa gcgctcctgt cggtgccacg aggggtactc tctgctggca    480

gacggggtgt cctgcacacc cacagttgaa tatccatgtg gaaaaatacc tattctagaa    540

aaaagaaatg ccagcaaacc ccaaggccga attgtggggg gcaaggtgtg ccccaaaggg    600
```

```
gagtgtccat ggcaggtcct gttgttggtg aatggagctc agttgtgtgg ggggaccctg    660

atcaacacca tctgggtggt ctccgcggcc cactgtttcg acaaaatcaa gaactggagg    720

aacctgatcg cggtgctggg cgagcacgac ctcagcgagc acgacgggga tgagcagagc    780

cggcgggtgg cgcaggtcat catccccagc acgtacgtcc cgggcaccac caaccacgac    840

atcgcgctgc tccgcctgca ccagcccgtg gtcctcactg accatgtggt gcccctctgc    900

ctgcccgaac ggacgttctc tgagaggacg ctggccttcg tgcgcttctc attggtcagc    960

ggctggggcc agctgctgga ccgtggcgcc acggccctgg agctcatggt cctcaacgtg   1020

ccccggctga tgacccagga ctgcctgcag cagtcacgga aggtgggaga ctccccaaat   1080

atcacggagt acatgttctg tgccggctac tcggatggca gcaaggactc ctgcaagggg   1140

gacagtggag gcccacatgc cacccactac cggggcacgt ggtacctgac gggcatcgtc   1200

agctggggcc agggctgcgc aaccgtgggc cactttgggg tgtacaccag ggtctcccag   1260

tacatcgagt ggctgcaaaa gctcatgcgc tcagagccac gcccaggagt cctcctgcga   1320

gccccatttc ccggtggcgg tggctccggc ggaggtgggt ccggtggcgg cggatcaggt   1380

gggggtggat caggcggtgg aggttccggt ggcgggggat ccgacatcgt gatgacccag   1440

gccgccccca gcgtgcccgt gacccccggc gagagcgtga gcatcagctg ccggagcagc   1500

cggagcctgc tgcacagcaa cggcaacacc tacctgtgct ggttcctgca gcggcccggc   1560

cagagccccc agctgctgat ctaccggatg agcaacctgg ccagcggcgt gcccgaccgg   1620

ttcagcggca gcggcagcgg caccgccttc accctgcgga tcagccgggt ggaggccgag   1680

gacgtgggcg tgtactactg catgcagcac ctggagtacc ccttcacctt cggcagcggc   1740

accaagctgg agatcaagcg gggcggcggc ggcagcggcg gcggcggcag cggcggcggc   1800

ggcagccagg tgcagctgca gcagagcggc gccgagctgg tgcggcccgg caccagcgtg   1860

aagatcagct gcaaggccag cggctacacc ttcaccaact actggctggg ctgggtgaag   1920

cagcggcccg gccacggcct ggagtggatc ggcgacatct accccggcgg cggctacaac   1980

aagtacaacg agaacttcaa gggcaaggcc accctgaccg ccgacaccag cagcagcacc   2040

gcctacatgc agctgagcag cctgaccagc gaggacagcg ccgtgtactt ctgcgcccgg   2100

gagtacggca actacgacta cgccatggac agctggggcc agggcaccag cgtgaccgtg   2160

agcagctga                                                            2169
```

```
<210> SEQ ID NO 123
<211> LENGTH: 722
<212> TYPE: PRT
<213> ORGANISM: Artificial Sequence
<220> FEATURE:
<223> OTHER INFORMATION: Synthetic construct: FVII-125 amino acid
      sequence

<400> SEQUENCE: 123

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80
```

```
Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Ile Val Met Thr Gln
465                 470                 475                 480

Ala Ala Pro Ser Val Pro Val Thr Pro Gly Glu Ser Val Ser Ile Ser
                485                 490                 495
```

```
Cys Arg Ser Ser Arg Ser Leu Leu His Ser Asn Gly Asn Thr Tyr Leu
            500                 505                 510

Cys Trp Phe Leu Gln Arg Pro Gly Gln Ser Pro Gln Leu Leu Ile Tyr
        515                 520                 525

Arg Met Ser Asn Leu Ala Ser Gly Val Pro Asp Arg Phe Ser Gly Ser
    530                 535                 540

Gly Ser Gly Thr Ala Phe Thr Leu Arg Ile Ser Arg Val Glu Ala Glu
545                 550                 555                 560

Asp Val Gly Val Tyr Tyr Cys Met Gln His Leu Glu Tyr Pro Phe Thr
                565                 570                 575

Phe Gly Ser Gly Thr Lys Leu Glu Ile Lys Arg Gly Gly Gly Gly Ser
            580                 585                 590

Gly Gly Gly Gly Ser Gly Gly Gly Gly Ser Gln Val Gln Leu Gln Gln
        595                 600                 605

Ser Gly Ala Glu Leu Val Arg Pro Gly Thr Ser Val Lys Ile Ser Cys
    610                 615                 620

Lys Ala Ser Gly Tyr Thr Phe Thr Asn Tyr Trp Leu Gly Trp Val Lys
625                 630                 635                 640

Gln Arg Pro Gly His Gly Leu Glu Trp Ile Gly Asp Ile Tyr Pro Gly
                645                 650                 655

Gly Gly Tyr Asn Lys Tyr Asn Glu Asn Phe Lys Gly Lys Ala Thr Leu
            660                 665                 670

Thr Ala Asp Thr Ser Ser Ser Thr Ala Tyr Met Gln Leu Ser Ser Leu
        675                 680                 685

Thr Ser Glu Asp Ser Ala Val Tyr Phe Cys Ala Arg Glu Tyr Gly Asn
    690                 695                 700

Tyr Asp Tyr Ala Met Asp Ser Trp Gly Gln Gly Thr Ser Val Thr Val
705                 710                 715                 720

Ser Ser
```

<210> SEQ ID NO 124
<211> LENGTH: 3750
<212> TYPE: DNA
<213> ORGANISM: Artificial Sequence
<220> FEATURE:
<223> OTHER INFORMATION: Synthetic construct: DNA sequence for FVII-067

<400> SEQUENCE: 124

```
atggtctccc aggccctcag gctcctctgc cttctgcttg ggcttcaggg ctgcctggct      60

gcagtcttcg taacccagga ggaagcccac ggcgtcctgc accggcgccg gcgcgccaac     120

gcgttcctgg aggagctgcg gccgggctcc ctggagaggg agtgcaagga ggagcagtgc     180

tccttcgagg aggcccggga gatcttcaag gacgcggaga ggacgaagct gttctggatt     240

tcttacagtg atggggacca gtgtgcctca agtccatgcc agaatggggg ctcctgcaag     300

gaccagctcc agtcctatat ctgcttctgc ctccctgcct tcgagggccg gaactgtgag     360

acgcacaagg atgaccagct gatctgtgtg aacgagaacg gcggctgtga gcagtactgc     420

agtgaccaca cgggcaccaa gcgctcctgt cggtgccacg aggggtactc tctgctggca     480

gacggggtgt cctgcacacc cacagttgaa tatccatgtg gaaaaatacc tattctagaa     540

aaaagaaatg ccagcaaacc ccaaggccga attgtggggg gcaaggtgtg ccccaaaggg     600

gagtgtccat ggcaggtcct gttgttggtg aatggagctc agttgtgtgg ggggaccctg     660

atcaacacca tctgggtggt ctccgcggcc cactgtttcg acaaaatcaa gaactggagg     720

aacctgatcg cggtgctggg cgagcacgac ctcagcgagc acgacgggga tgagcagagc     780
```

```
cggcgggtgg cgcaggtcat catccccagc acgtacgtcc cgggcaccac caaccacgac    840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg   1020
ccccggctga tgacccagga ctgcctgcag cagtcacgga aggtgggaga ctccccaaat   1080
atcacggagt acatgttctg tgccggctac tcggatggca gcaaggactc ctgcaagggg   1140
gacagtggag gcccacatgc cacccactac cggggcacgt ggtacctgac gggcatcgtc   1200
agctggggcc agggctgcgc aaccgtgggc cactttgggg tgtacaccag ggtctcccag   1260
tacatcgagt ggctgcaaaa gctcatgcgc tcagagccac gcccaggagt cctcctgcga   1320
gccccatttc ccggtggcgg tggctccggc ggaggtgggt ccggtggcgg cggatcaggt   1380
gggggtggat caggcggtgg aggttccggt ggcgggggat ccgacaaaac tcacacatgc   1440
ccaccgtgcc cagctccgga actcctgggc ggaccgtcag tcttcctctt ccccccaaaa   1500
cccaaggaca ccctcatgat ctcccggacc cctgaggtca catgcgtggt ggtggacgtg   1560
agccacgaag accctgaggt caagttcaac tggtacgtgg acggcgtgga ggtgcataat   1620
gccaagacaa agccgcggga ggagcagtac aacagcacgt accgtgtggt cagcgtcctc   1680
accgtcctgc accaggactg gctgaatggc aaggagtaca agtgcaaggt ctccaacaaa   1740
gccctcccag cccccatcga gaaaaccatc tccaaagcca aagggcagcc ccgagaacca   1800
caggtgtaca ccctgccccc atcccgggat gagctgacca agaaccaggt cagcctgacc   1860
tgcctggtca aaggcttcta tcccagcgac atcgccgtgg agtgggagag caatgggcag   1920
ccggagaaca actacaagac cacgcctccc gtgttggact ccgacggctc cttcttcctc   1980
tacagcaagc tcaccgtgga caagagcagg tggcagcagg ggaacgtctt ctcatgctcc   2040
gtgatgcatg aggctctgca caaccactac acgcagaaga gcctctccct gtctccgggt   2100
aaaggtggcg gcggatcagg tgggggtgga tcaggcggtg gaggttccgg tggcggggga   2160
tcagacaaaa ctcacacatg cccaccgtgc ccagcacctg aactcctggg aggaccgtca   2220
gtcttcctct tccccccaaa acccaaggac accctcatga tctcccggac ccctgaggtc   2280
acatgcgtgg tggtggacgt gagccacgaa gaccctgagg tcaagttcaa ctggtacgtg   2340
gacggcgtgg aggtgcataa tgccaagaca aagccgcggg aggagcagta caacagcacg   2400
taccgtgtgg tcagcgtcct caccgtcctg caccaggact ggctgaatgg caaggagtac   2460
aagtgcaagg tctccaacaa agccctccca gcccccatcg agaaaaccat ctccaaagcc   2520
aaagggcagc cccgagaacc acaggtgtac accctgcccc catcccgcga tgagctgacc   2580
aagaaccagg tcagcctgac ctgcctggtc aaaggcttct atcccagcga catcgccgtg   2640
gagtgggaga gcaatgggca gccggagaac aactacaaga ccacgcctcc cgtgttggac   2700
tccgacggct ccttcttcct ctacagcaag ctcaccgtcg acaagagcag gtggcagcag   2760
gggaacgtct tctcatgctc cgtgatgcat gaggctctgc acaaccacta cacgcagaag   2820
agcctctccc tgtctccggg taaaggtggc ggtggctccg gcggaggtgg gtccggtggc   2880
ggcggatcag gtgggggtgg atcaggcggt ggaggttccg gtggcggggg atcagcgcag   2940
gtgcagctgc aggagtctgg gggaggcttg gtacagcctg gggggtccct gagactctcc   3000
tgtgcagcct ctggattcat gtttagcagg tatgccatga gctgggtccg ccaggctcca   3060
gggaaggggc cagagtgggt ctcaggtatt agtggtagtg gtggtagtac atactacgca   3120
```

```
gactccgtga agggccggtt caccgtctcc agagacaatt ccaagaacac gctgtatctg   3180

caaatgaaca gcctgagagc cgaggacacg gctgtatatt actgcgcccg gggcgccacc   3240

tacaccagcc ggagcgacgt gcccgaccag accagcttcg actactgggg ccagggaacc   3300

ctggtcaccg tctcctcagg gagtgcatcc gccccaaagc ttgaagaagg tgaattttca   3360

gaagcacgcg tatctgaact gactcaggac cctgctgtgt ctgtggcctt gggacagaca   3420

gtcaggatca catgccaagg agacagcctc agaaactttt atgcaagctg gtaccagcag   3480

aagccaggac aggcccctac tcttgtcatc tatggtttaa gtaaaaggcc ctcagggatc   3540

ccagaccgat tctctgcctc cagctcagga aacacagctt ccttgaccat cactggggct   3600

caggcggaag atgaggctga ctattactgc ctgctgtact acggcggcgg ccagcagggc   3660

gtgttcggcg gcggcaccaa gctgaccgtc ctacgtcagc ccaaggctgc cccctcggtc   3720

actctgttcc cgccctcttc tgcggcctga                                    3750
```

```
<210> SEQ ID NO 125
<211> LENGTH: 1249
<212> TYPE: PRT
<213> ORGANISM: Artificial Sequence
<220> FEATURE:
<223> OTHER INFORMATION: Synthetic construct: FVII-067 amino acid
      sequence

<400> SEQUENCE: 125

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
```

```
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670
```

```
Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Gly Gly Gly
    690                 695                 700

Gly Ser Gly Gly Gly Gly Ser Gly Gly Gly Gly Ser Gly Gly Gly Gly
705                 710                 715                 720

Ser Asp Lys Thr His Thr Cys Pro Pro Cys Pro Ala Pro Glu Leu Leu
                725                 730                 735

Gly Gly Pro Ser Val Phe Leu Phe Pro Pro Lys Pro Lys Asp Thr Leu
            740                 745                 750

Met Ile Ser Arg Thr Pro Glu Val Thr Cys Val Val Val Asp Val Ser
        755                 760                 765

His Glu Asp Pro Glu Val Lys Phe Asn Trp Tyr Val Asp Gly Val Glu
    770                 775                 780

Val His Asn Ala Lys Thr Lys Pro Arg Glu Glu Gln Tyr Asn Ser Thr
785                 790                 795                 800

Tyr Arg Val Val Ser Val Leu Thr Val Leu His Gln Asp Trp Leu Asn
                805                 810                 815

Gly Lys Glu Tyr Lys Cys Lys Val Ser Asn Lys Ala Leu Pro Ala Pro
            820                 825                 830

Ile Glu Lys Thr Ile Ser Lys Ala Lys Gly Gln Pro Arg Glu Pro Gln
        835                 840                 845

Val Tyr Thr Leu Pro Pro Ser Arg Asp Glu Leu Thr Lys Asn Gln Val
    850                 855                 860

Ser Leu Thr Cys Leu Val Lys Gly Phe Tyr Pro Ser Asp Ile Ala Val
865                 870                 875                 880

Glu Trp Glu Ser Asn Gly Gln Pro Glu Asn Asn Tyr Lys Thr Thr Pro
                885                 890                 895

Pro Val Leu Asp Ser Asp Gly Ser Phe Phe Leu Tyr Ser Lys Leu Thr
            900                 905                 910

Val Asp Lys Ser Arg Trp Gln Gln Gly Asn Val Phe Ser Cys Ser Val
        915                 920                 925

Met His Glu Ala Leu His Asn His Tyr Thr Gln Lys Ser Leu Ser Leu
    930                 935                 940

Ser Pro Gly Lys Gly Gly Gly Gly Ser Gly Gly Gly Gly Ser Gly Gly
945                 950                 955                 960

Gly Gly Ser Gly Gly Gly Gly Ser Gly Gly Gly Gly Ser Gly Gly Gly
                965                 970                 975

Gly Ser Ala Gln Val Gln Leu Gln Glu Ser Gly Gly Gly Leu Val Gln
            980                 985                 990

Pro Gly Gly Ser Leu Arg Leu Ser  Cys Ala Ala Ser Gly  Phe Met Phe
        995                 1000                1005

Ser Arg  Tyr Ala Met Ser Trp  Val Arg Gln Ala Pro  Gly Lys Gly
    1010                1015                1020

Pro Glu  Trp Val Ser Gly Ile  Ser Gly Ser Gly Gly  Ser Thr Tyr
    1025                1030                1035

Tyr Ala  Asp Ser Val Lys Gly  Arg Phe Thr Val Ser  Arg Asp Asn
    1040                1045                1050

Ser Lys  Asn Thr Leu Tyr Leu  Gln Met Asn Ser Leu  Arg Ala Glu
    1055                1060                1065

Asp Thr  Ala Val Tyr Tyr Cys  Ala Arg Gly Ala Thr  Tyr Thr Ser
    1070                1075                1080
```

```
Arg Ser  Asp Val Pro Asp Gln  Thr Ser Phe Asp Tyr  Trp Gly Gln
    1085                 1090                 1095

Gly Thr  Leu Val Thr Val Ser  Ser Gly Ser Ala Ser  Ala Pro Lys
    1100                 1105                 1110

Leu Glu  Glu Gly Glu Phe Ser  Glu Ala Arg Val Ser  Glu Leu Thr
    1115                 1120                 1125

Gln Asp  Pro Ala Val Ser Val  Ala Leu Gly Gln Thr  Val Arg Ile
    1130                 1135                 1140

Thr Cys  Gln Gly Asp Ser Leu  Arg Asn Phe Tyr Ala  Ser Trp Tyr
    1145                 1150                 1155

Gln Gln  Lys Pro Gly Gln Ala  Pro Thr Leu Val Ile  Tyr Gly Leu
    1160                 1165                 1170

Ser Lys  Arg Pro Ser Gly Ile  Pro Asp Arg Phe Ser  Ala Ser Ser
    1175                 1180                 1185

Ser Gly  Asn Thr Ala Ser Leu  Thr Ile Thr Gly Ala  Gln Ala Glu
    1190                 1195                 1200

Asp Glu  Ala Asp Tyr Tyr Cys  Leu Leu Tyr Tyr Gly  Gly Gly Gln
    1205                 1210                 1215

Gln Gly  Val Phe Gly Gly Gly  Thr Lys Leu Thr Val  Leu Arg Gln
    1220                 1225                 1230

Pro Lys  Ala Ala Pro Ser Val  Thr Leu Phe Pro Pro  Ser Ser Ala
    1235                 1240                 1245

Ala
```

<210> SEQ ID NO 126
<211> LENGTH: 2244
<212> TYPE: DNA
<213> ORGANISM: Artificial Sequence
<220> FEATURE:
<223> OTHER INFORMATION: Synthetic construct: DNA sequence for FVII-094

<400> SEQUENCE: 126

```
atggtctccc aggccctcag gctcctctgc cttctgcttg ggcttcaggg ctgcctggct     60

gcagtcttcg taacccagga ggaagcccac ggcgtcctgc accggcgccg gcgcgccaac    120

gcgttcctgg aggagctgcg gccgggctcc ctggagaggg agtgcaagga ggagcagtgc    180

tccttcgagg aggcccggga gatcttcaag gacgcggaga ggacgaagct gttctggatt    240

tcttacagtg atggggacca gtgtgcctca agtccatgcc agaatggggg ctcctgcaag    300

gaccagctcc agtcctatat ctgcttctgc ctccctgcct tcgagggccg gaactgtgag    360

acgcacaagg atgaccagct gatctgtgtg aacgagaacg gcggctgtga gcagtactgc    420

agtgaccaca cgggcaccaa gcgctcctgt cggtgccacg aggggtactc tctgctggca    480

gacggggtgt cctgcacacc cacagttgaa tatccatgtg gaaaaatacc tattctagaa    540

aaaagaaatg ccagcaaacc ccaaggccga attgtggggg gcaaggtgtg ccccaaaggg    600

gagtgtccat ggcaggtcct gttgttggtg aatggagctc agttgtgtgg ggggaccctg    660

atcaacacca tctgggtggt ctccgcggcc cactgtttcg acaaaatcaa gaactggagg    720

aacctgatcg cggtgctggg cgagcacgac ctcagcgagc acgacgggga tgagcagagc    780

cggcgggtgg cgcaggtcat catccccagc acgtacgtcc cgggcaccac caaccacgac    840

atcgcgctgc tccgcctgca ccagcccgtg gtcctcactg accatgtggt gcccctctgc    900

ctgcccgaac ggacgttctc tgagaggacg ctggccttcg tgcgcttctc attggtcagc    960

ggctggggcc agctgctgga ccgtggcgcc acggccctgg agctcatggt cctcaacgtg   1020
```

-continued

```
ccccggctga tgacccagga ctgcctgcag cagtcacgga aggtgggaga ctccccaaat   1080

atcacggagt acatgttctg tgccggctac tcggatggca gcaaggactc ctgcaagggg   1140

gacagtggag gcccacatgc cacccactac cggggcacgt ggtacctgac gggcatcgtc   1200

agctggggcc agggctgcgc aaccgtgggc cactttgggg tgtacaccag ggtctcccag   1260

tacatcgagt ggctgcaaaa gctcatgcgc tcagagccac gcccaggagt cctcctgcga   1320

gccccatttc ccgatatcgg tggcggtggc tccggcggag gtgggtccgg tggcggcgga   1380

tcaggtgggg gtggatcagg cggtggaggt tccggtggcg gggatcagc gcaggtgcag    1440

ctgcaggagt ctggggagg cttggtacag cctggggggt ccctgagact ctcctgtgca    1500

gcctctggat tcatgtttag caggtatgcc atgagctggg tccgccaggc tccagggaag   1560

gggccagagt gggtctcagg tattagtggt agtggtggta gtacatacta cgcagactcc   1620

gtgaagggcc ggttcaccgt ctccagagac aattccaaga acacgctgta tctgcaaatg   1680

aacagcctga gagccgagga cacggctgta tattactgcg cccggggcgc cacctacacc   1740

agccggagcg acgtgcccga ccagaccagc ttcgactact ggggccaggg aaccctggtc   1800

accgtctcct cagggagtgc atccgcccca aagcttgaag aaggtgaatt ttcagaagca   1860

cgcgtatctg aactgactca ggaccctgct gtgtctgtgg ccttgggaca gacagtcagg   1920

atcacatgcc aaggagacag cctcagaaac ttttatgcaa gctggtacca gcagaagcca   1980

ggacaggccc ctactcttgt catctatggt ttaagtaaaa ggccctcagg gatcccagac   2040

cgattctctg cctccagctc aggaaacaca gcttccttga ccatcactgg ggctcaggcg   2100

gaagatgagg ctgactatta ctgcctgctg tactacggcg gcggccagca gggcgtgttc   2160

ggcggcggca ccaagctgac cgtcctacgt cagcccaagg ctgccccctc ggtcactctg   2220

ttcccgccct cttctgcggc ctga                                          2244
```

<210> SEQ ID NO 127
<211> LENGTH: 747
<212> TYPE: PRT
<213> ORGANISM: Artificial Sequence
<220> FEATURE:
<223> OTHER INFORMATION: Synthetic construct: FVII-094 amino acid sequence

<400> SEQUENCE: 127

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140
```

```
Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Asp Ile Gly Gly
        435                 440                 445

Gly Gly Ser Gly Gly Gly Gly Ser Gly Gly Gly Gly Ser Gly Gly Gly
    450                 455                 460

Gly Ser Gly Gly Gly Gly Ser Gly Gly Gly Gly Ser Ala Gln Val Gln
465                 470                 475                 480

Leu Gln Glu Ser Gly Gly Gly Leu Val Gln Pro Gly Gly Ser Leu Arg
                485                 490                 495

Leu Ser Cys Ala Ala Ser Gly Phe Met Phe Ser Arg Tyr Ala Met Ser
            500                 505                 510

Trp Val Arg Gln Ala Pro Gly Lys Gly Pro Glu Trp Val Ser Gly Ile
        515                 520                 525

Ser Gly Ser Gly Gly Ser Thr Tyr Tyr Ala Asp Ser Val Lys Gly Arg
    530                 535                 540

Phe Thr Val Ser Arg Asp Asn Ser Lys Asn Thr Leu Tyr Leu Gln Met
545                 550                 555                 560
```

-continued

```
Asn Ser Leu Arg Ala Glu Asp Thr Ala Val Tyr Tyr Cys Ala Arg Gly
                565                 570                 575

Ala Thr Tyr Thr Ser Arg Ser Asp Val Pro Asp Gln Thr Ser Phe Asp
            580                 585                 590

Tyr Trp Gly Gln Gly Thr Leu Val Thr Val Ser Ser Gly Ser Ala Ser
        595                 600                 605

Ala Pro Lys Leu Glu Glu Gly Glu Phe Ser Glu Ala Arg Val Ser Glu
    610                 615                 620

Leu Thr Gln Asp Pro Ala Val Ser Val Ala Leu Gly Gln Thr Val Arg
625                 630                 635                 640

Ile Thr Cys Gln Gly Asp Ser Leu Arg Asn Phe Tyr Ala Ser Trp Tyr
                645                 650                 655

Gln Gln Lys Pro Gly Gln Ala Pro Thr Leu Val Ile Tyr Gly Leu Ser
            660                 665                 670

Lys Arg Pro Ser Gly Ile Pro Asp Arg Phe Ser Ala Ser Ser Ser Gly
        675                 680                 685

Asn Thr Ala Ser Leu Thr Ile Thr Gly Ala Gln Ala Glu Asp Glu Ala
    690                 695                 700

Asp Tyr Tyr Cys Leu Leu Tyr Tyr Gly Gly Gly Gln Gln Gly Val Phe
705                 710                 715                 720

Gly Gly Gly Thr Lys Leu Thr Val Leu Arg Gln Pro Lys Ala Ala Pro
                725                 730                 735

Ser Val Thr Leu Phe Pro Pro Ser Ser Ala Ala
            740                 745
```

<210> SEQ ID NO 128
<211> LENGTH: 3507
<212> TYPE: DNA
<213> ORGANISM: Artificial Sequence
<220> FEATURE:
<223> OTHER INFORMATION: Synthetic construct: DNA sequence for FVII-028

<400> SEQUENCE: 128

```
atggtctccc aggccctcag gctcctctgc cttctgcttg ggcttcaggg ctgcctggct      60

gcggaagtgc agctggtgca gtctggagct gaggtgaata agcctggggc ctcagtgaag     120

gtctcctgca aggcttctgg atacaccttc accggctact atatgcactg ggtgcgacag     180

gcccctggac aagggcttga gtggatggga tggatcaacc ctaacagtgg tggcacaaac     240

tatgcacaga agtttcaggg ctgggtcacc atgaccaggg acacgtccat cagcaccgcc     300

tacatggagc tgagcaggct gagatctgac gacacggccg tgtattactg tgcgagaggc     360

cgtgctttgt ataaccggaa cgaccggtcc cccaactggt tcgacccctg gggccaggga     420

accctggtca ccgtctcctc agggagtgca tccgccccaa cccttaaact tgaagaaggt     480

gaattttcag aagcacgcgt acaggctgtg ctgactcagc cgccctcggt gtcagtggcc     540

ccaggacaga cggccaggat tacctgtggg ggaaacaaca ttggaagtaa aagtgtgcag     600

tggtaccagc agaagccagg ccaggcccct gtgctggtcg tctatgatga tagcgaccgg     660

ccctcaggga tccctgagcg attctctggc tccaactctg ggaacatggc caccctgacc     720

atcagcaggg tcgaagccgg ggatgaggcc gactattact gtcaggtgtg ggatagtagt     780

agtgatcatg tggtattcgg cggagggacc aagctgaccg tcctaggtca gcccaaggct     840

gccccctcgg tcactctgtt cccgccgtcc gcggccgcta ggacgaagct gttctggatt     900

tcttacagtg atggggacca gtgtgcctca agtccatgcc agaatggggg ctcctgcaag     960

gaccagctcc agtcctatat ctgcttctgc ctccctgcct tcgagggccg gaactgtgag    1020
```

acgcacaagg atgaccagct gatctgtgtg aacgagaacg gcggctgtga gcagtactgc 1080
agtgaccaca cgggcaccaa gcgctcctgt cggtgccacg aggggtactc tctgctggca 1140
gacggggtgt cctgcacacc cacagttgaa tatccatgtg gaaaaatacc tattctagaa 1200
aaaagaaatg ccagcaaacc ccaaggccga attgtggggg gcaaggtgtg ccccaaaggg 1260
gagtgtccat ggcaggtcct gttgttggtg aatggagctc agttgtgtgg ggggaccctg 1320
atcaacacca tctgggtggt ctccgcggcc cactgtttcg acaaaatcaa gaactggagg 1380
aacctgatcg cggtgctggg cgagcacgac ctcagcgagc acgacgggga tgagcagagc 1440
cggcgggtgg cgcaggtcat catccccagc acgtacgtcc cgggcaccac caaccacgac 1500
atcgcgctgc tccgcctgca ccagcccgtg gtcctcactg accatgtggt gcccctctgc 1560
ctgcccgaac ggacgttctc tgagaggacg ctggccttcg tgcgcttctc attggtcagc 1620
ggctggggcc agctgctgga ccgtggcgcc acggccctgg agctcatggt cctcaacgtg 1680
ccccggctga tgacccagga ctgcctgcag cagtcacgga aggtgggaga ctccccaaat 1740
atcacggagt acatgttctg tgccggctac tcggatggca gcaaggactc ctgcaagggg 1800
gacagtggag gcccacatgc cacccactac cggggcacgt ggtacctgac gggcatcgtc 1860
agctggggcc agggctgcgc aaccgtgggc cactttgggg tgtacaccag ggtctcccag 1920
tacatcgagt ggctgcaaaa gctcatgcgc tcagagccac gcccaggagt cctcctgcga 1980
gccccatttc ccggtggcgg tggctccggc ggaggtgggt ccggtggcgg cggatcaggt 2040
gggggtggat caggcggtgg aggttccggt ggcgggggat ccgacaaaac tcacacatgc 2100
ccaccgtgcc cagctccgga actcctgggc ggaccgtcag tcttcctctt ccccccaaaa 2160
cccaaggaca ccctcatgat ctcccggacc cctgaggtca catgcgtggt ggtggacgtg 2220
agccacgaag accctgaggt caagttcaac tggtacgtgg acggcgtgga ggtgcataat 2280
gccaagacaa agccgcggga ggagcagtac aacagcacgt accgtgtggt cagcgtcctc 2340
accgtcctgc accaggactg gctgaatggc aaggagtaca agtgcaaggt ctccaacaaa 2400
gccctcccag cccccatcga gaaaaccatc tccaaagcca aagggcagcc ccgagaacca 2460
caggtgtaca ccctgccccc atcccgggat gagctgacca agaaccaggt cagcctgacc 2520
tgcctggtca aaggcttcta tcccagcgac atcgccgtgg agtgggagag caatgggcag 2580
ccggagaaca actacaagac cacgcctccc gtgttggact ccgacggctc cttcttcctc 2640
tacagcaagc tcaccgtgga caagagcagg tggcagcagg ggaacgtctt ctcatgctcc 2700
gtgatgcatg aggctctgca caaccactac acgcagaaga gcctctccct gtctccgggt 2760
aaaggtggcg gcggatcagg tgggggtgga tcaggcggtg gaggttccgg tggcggggga 2820
tccgacaaaa ctcacacatg cccaccgtgc ccagcacctg aactcctggg aggaccgtca 2880
gtcttcctct tccccccaaa acccaaggac accctcatga tctcccggac ccctgaggtc 2940
acatgcgtgg tggtggacgt gagccacgaa gaccctgagg tcaagttcaa ctggtacgtg 3000
gacggcgtgg aggtgcataa tgccaagaca aagccgcggg aggagcagta caacagcacg 3060
taccgtgtgg tcagcgtcct caccgtcctg caccaggact ggctgaatgg caaggagtac 3120
aagtgcaagg tctccaacaa agccctccca gcccccatcg agaaaaccat ctccaaagcc 3180
aaagggcagc cccgagaacc acaggtgtac accctgcccc catcccgcga tgagctgacc 3240
aagaaccagg tcagcctgac ctgcctggtc aaaggcttct atcccagcga catcgccgtg 3300
gagtgggaga gcaatgggca gccggagaac aactacaaga ccacgcctcc cgtgttggac 3360
tccgacggct ccttcttcct ctacagcaag ctcaccgtgg acaagagcag gtggcagcag 3420
gggaacgtct tctcatgctc cgtgatgcat gaggctctgc acaaccacta cacgcagaag 3480
agcctctccc tgtctccggg taaatga 3507

<210> SEQ ID NO 129
<211> LENGTH: 1168
<212> TYPE: PRT
<213> ORGANISM: Artificial Sequence
<220> FEATURE:
<223> OTHER INFORMATION: Synthetic construct: FVII-028 amino acid sequence

<400> SEQUENCE: 129

Met Val Ser Gln Ala Leu Arg Leu Leu Cys Leu Leu Leu Gly Leu Gln
1 5 10 15

Gly Cys Leu Ala Ala Glu Val Gln Leu Val Gln Ser Gly Ala Glu Val
20 25 30

Asn Lys Pro Gly Ala Ser Val Lys Val Ser Cys Lys Ala Ser Gly Tyr
35 40 45

Thr Phe Thr Gly Tyr Tyr Met His Trp Val Arg Gln Ala Pro Gly Gln
50 55 60

Gly Leu Glu Trp Met Gly Trp Ile Asn Pro Asn Ser Gly Gly Thr Asn
65 70 75 80

Tyr Ala Gln Lys Phe Gln Gly Trp Val Thr Met Thr Arg Asp Thr Ser
85 90 95

Ile Ser Thr Ala Tyr Met Glu Leu Ser Arg Leu Arg Ser Asp Asp Thr
100 105 110

Ala Val Tyr Tyr Cys Ala Arg Gly Arg Ala Leu Tyr Asn Arg Asn Asp
115 120 125

Arg Ser Pro Asn Trp Phe Asp Pro Trp Gly Gln Gly Thr Leu Val Thr
130 135 140

Val Ser Ser Gly Ser Ala Ser Ala Pro Thr Leu Lys Leu Glu Glu Gly
145 150 155 160

Glu Phe Ser Glu Ala Arg Val Gln Ala Val Leu Thr Gln Pro Pro Ser
165 170 175

Val Ser Val Ala Pro Gly Gln Thr Ala Arg Ile Thr Cys Gly Gly Asn
180 185 190

Asn Ile Gly Ser Lys Ser Val Gln Trp Tyr Gln Gln Lys Pro Gly Gln
195 200 205

Ala Pro Val Leu Val Val Tyr Asp Asp Ser Asp Arg Pro Ser Gly Ile
210 215 220

Pro Glu Arg Phe Ser Gly Ser Asn Ser Gly Asn Met Ala Thr Leu Thr
225 230 235 240

Ile Ser Arg Val Glu Ala Gly Asp Glu Ala Asp Tyr Tyr Cys Gln Val
245 250 255

Trp Asp Ser Ser Ser Asp His Val Val Phe Gly Gly Gly Thr Lys Leu
260 265 270

Thr Val Leu Gly Gln Pro Lys Ala Ala Pro Ser Val Thr Leu Phe Pro
275 280 285

Pro Ser Ala Ala Ala Arg Thr Lys Leu Phe Trp Ile Ser Tyr Ser Asp
290 295 300

Gly Asp Gln Cys Ala Ser Ser Pro Cys Gln Asn Gly Gly Ser Cys Lys
305 310 315 320

Asp Gln Leu Gln Ser Tyr Ile Cys Phe Cys Leu Pro Ala Phe Glu Gly
325 330 335

```
Arg Asn Cys Glu Thr His Lys Asp Asp Gln Leu Ile Cys Val Asn Glu
            340                 345                 350

Asn Gly Gly Cys Glu Gln Tyr Cys Ser Asp His Thr Gly Thr Lys Arg
        355                 360                 365

Ser Cys Arg Cys His Glu Gly Tyr Ser Leu Leu Ala Asp Gly Val Ser
    370                 375                 380

Cys Thr Pro Thr Val Glu Tyr Pro Cys Gly Lys Ile Pro Ile Leu Glu
385                 390                 395                 400

Lys Arg Asn Ala Ser Lys Pro Gln Gly Arg Ile Val Gly Gly Lys Val
                405                 410                 415

Cys Pro Lys Gly Glu Cys Pro Trp Gln Val Leu Leu Leu Val Asn Gly
            420                 425                 430

Ala Gln Leu Cys Gly Gly Thr Leu Ile Asn Thr Ile Trp Val Val Ser
        435                 440                 445

Ala Ala His Cys Phe Asp Lys Ile Lys Asn Trp Arg Asn Leu Ile Ala
    450                 455                 460

Val Leu Gly Glu His Asp Leu Ser Glu His Asp Gly Asp Glu Gln Ser
465                 470                 475                 480

Arg Arg Val Ala Gln Val Ile Ile Pro Ser Thr Tyr Val Pro Gly Thr
                485                 490                 495

Thr Asn His Asp Ile Ala Leu Leu Arg Leu His Gln Pro Val Val Leu
            500                 505                 510

Thr Asp His Val Val Pro Leu Cys Leu Pro Glu Arg Thr Phe Ser Glu
        515                 520                 525

Arg Thr Leu Ala Phe Val Arg Phe Ser Leu Val Ser Gly Trp Gly Gln
    530                 535                 540

Leu Leu Asp Arg Gly Ala Thr Ala Leu Glu Leu Met Val Leu Asn Val
545                 550                 555                 560

Pro Arg Leu Met Thr Gln Asp Cys Leu Gln Gln Ser Arg Lys Val Gly
                565                 570                 575

Asp Ser Pro Asn Ile Thr Glu Tyr Met Phe Cys Ala Gly Tyr Ser Asp
            580                 585                 590

Gly Ser Lys Asp Ser Cys Lys Gly Asp Ser Gly Gly Pro His Ala Thr
        595                 600                 605

His Tyr Arg Gly Thr Trp Tyr Leu Thr Gly Ile Val Ser Trp Gly Gln
    610                 615                 620

Gly Cys Ala Thr Val Gly His Phe Gly Val Tyr Thr Arg Val Ser Gln
625                 630                 635                 640

Tyr Ile Glu Trp Leu Gln Lys Leu Met Arg Ser Glu Pro Arg Pro Gly
                645                 650                 655

Val Leu Leu Arg Ala Pro Phe Pro Gly Gly Gly Gly Ser Gly Gly Gly
            660                 665                 670

Gly Ser Gly Gly Gly Gly Ser Gly Gly Gly Gly Ser Gly Gly Gly Gly
        675                 680                 685

Ser Gly Gly Gly Gly Ser Asp Lys Thr His Thr Cys Pro Pro Cys Pro
    690                 695                 700

Ala Pro Glu Leu Leu Gly Gly Pro Ser Val Phe Leu Phe Pro Pro Lys
705                 710                 715                 720

Pro Lys Asp Thr Leu Met Ile Ser Arg Thr Pro Glu Val Thr Cys Val
                725                 730                 735

Val Val Asp Val Ser His Glu Asp Pro Glu Val Lys Phe Asn Trp Tyr
            740                 745                 750
```

```
Val Asp Gly Val Glu Val His Asn Ala Lys Thr Lys Pro Arg Glu Glu
        755                 760                 765

Gln Tyr Asn Ser Thr Tyr Arg Val Val Ser Val Leu Thr Val Leu His
    770                 775                 780

Gln Asp Trp Leu Asn Gly Lys Glu Tyr Lys Cys Lys Val Ser Asn Lys
785                 790                 795                 800

Ala Leu Pro Ala Pro Ile Glu Lys Thr Ile Ser Lys Ala Lys Gly Gln
                805                 810                 815

Pro Arg Glu Pro Gln Val Tyr Thr Leu Pro Pro Ser Arg Asp Glu Leu
            820                 825                 830

Thr Lys Asn Gln Val Ser Leu Thr Cys Leu Val Lys Gly Phe Tyr Pro
        835                 840                 845

Ser Asp Ile Ala Val Glu Trp Glu Ser Asn Gly Gln Pro Glu Asn Asn
    850                 855                 860

Tyr Lys Thr Thr Pro Pro Val Leu Asp Ser Asp Gly Ser Phe Phe Leu
865                 870                 875                 880

Tyr Ser Lys Leu Thr Val Asp Lys Ser Arg Trp Gln Gln Gly Asn Val
                885                 890                 895

Phe Ser Cys Ser Val Met His Glu Ala Leu His Asn His Tyr Thr Gln
            900                 905                 910

Lys Ser Leu Ser Leu Ser Pro Gly Lys Gly Gly Gly Gly Ser Gly Gly
        915                 920                 925

Gly Gly Ser Gly Gly Gly Gly Ser Gly Gly Gly Gly Ser Asp Lys Thr
    930                 935                 940

His Thr Cys Pro Pro Cys Pro Ala Pro Glu Leu Leu Gly Gly Pro Ser
945                 950                 955                 960

Val Phe Leu Phe Pro Pro Lys Pro Lys Asp Thr Leu Met Ile Ser Arg
                965                 970                 975

Thr Pro Glu Val Thr Cys Val Val Val Asp Val Ser His Glu Asp Pro
            980                 985                 990

Glu Val Lys Phe Asn Trp Tyr Val  Asp Gly Val Glu Val  His Asn Ala
        995                 1000                1005

Lys Thr  Lys Pro Arg Glu Glu  Gln Tyr Asn Ser Thr  Tyr Arg Val
    1010                1015                1020

Val Ser  Val Leu Thr Val Leu  His Gln Asp Trp Leu  Asn Gly Lys
    1025                1030                1035

Glu Tyr  Lys Cys Lys Val Ser  Asn Lys Ala Leu Pro  Ala Pro Ile
    1040                1045                1050

Glu Lys  Thr Ile Ser Lys Ala  Lys Gly Gln Pro Arg  Glu Pro Gln
    1055                1060                1065

Val Tyr  Thr Leu Pro Pro Ser  Arg Asp Glu Leu Thr  Lys Asn Gln
    1070                1075                1080

Val Ser  Leu Thr Cys Leu Val  Lys Gly Phe Tyr Pro  Ser Asp Ile
    1085                1090                1095

Ala Val  Glu Trp Glu Ser Asn  Gly Gln Pro Glu Asn  Asn Tyr Lys
    1100                1105                1110

Thr Thr  Pro Pro Val Leu Asp  Ser Asp Gly Ser Phe  Phe Leu Tyr
    1115                1120                1125

Ser Lys  Leu Thr Val Asp Lys  Ser Arg Trp Gln Gln  Gly Asn Val
    1130                1135                1140

Phe Ser  Cys Ser Val Met His  Glu Ala Leu His Asn  His Tyr Thr
    1145                1150                1155

Gln Lys  Ser Leu Ser Leu Ser  Pro Gly Lys
```

1160 1165

<210> SEQ ID NO 130
<211> LENGTH: 2868
<212> TYPE: DNA
<213> ORGANISM: Artificial Sequence
<220> FEATURE:
<223> OTHER INFORMATION: Synthetic construct: DNA sequence FVII-039

<400> SEQUENCE: 130
atggtctccc aggccctcag gctcctctgc cttctgcttg ggcttcaggg ctgcctggct 60
gcagtcttcg taacccagga ggaagcccac ggcgtcctgc accggcgccg gcgcgccaac 120
gcgttcctgg aggagctgcg gccgggctcc ctggagaggg agtgcaagga ggagcagtgc 180
tccttcgagg aggcccggga gatcttcaag gacgcggaga ggacgaagct gttctggatt 240
tcttacagtg atggggacca gtgtgcctca agtccatgcc agaatggggg ctcctgcaag 300
gaccagctcc agtcctatat ctgcttctgc ctccctgcct tcgagggccg gaactgtgag 360
acgcacaagg atgaccagct gatctgtgtg aacgagaacg gcggctgtga gcagtactgc 420
agtgaccaca cgggcaccaa gcgctcctgt cggtgccacg aggggtactc tctgctggca 480
gacggggtgt cctgcacacc cacagttgaa tatccatgtg gaaaaatacc tattctagaa 540
aaaagaaatg ccagcaaacc ccaaggccga ggcggaggag acttcactcg ggttgtgggg 600
ggcaaggtgt gccccaaagg ggagtgtcca tggcaggtcc tgttgttggt gaatggagct 660
cagttgtgtg gggggaccct gatcaacacc atctgggtgg tctccgcggc ccactgtttc 720
gacaaaatca agaactggag gaacctgatc gcggtgctgg gcgagcacga cctcagcgag 780
cacgacgggg atgagcagag ccggcgggtg gcgcaggtca tcatccccag cacgtacgtc 840
ccgggcacca ccaaccacga catcgcgctg ctccgcctgc accagcccgt ggtcctcact 900
gaccatgtgg tgcccctctg cctgcccgaa cggacgttct ctgagaggac gctggccttc 960
gtgcgcttct cattggtcag cggctggggc cagctgctgg accgtggcgc cacggccctg 1020
gagctcatgg tcctcaacgt gccccggctg atgacccagg actgcctgca gcagtcacgg 1080
aaggtgggag actccccaaa tatcacggag tacatgttct gtgccggcta ctcggatggc 1140
agcaaggact cctgcaaggg ggacagtgga ggcccacatg ccacccacta ccggggcacg 1200
tggtacctga cgggcatcgt cagctggggc cagggctgcg caaccgtggg ccactttggg 1260
gtgtacacca gggtctccca gtacatcgag tggctgcaaa agctcatgcg ctcagagcca 1320
cgcccaggag tcctcctgcg agccccattt cccggtggcg gtggctccgg cggaggtggg 1380
tccggtggcg gcggatcagg tgggggtgga tcaggcggtg gaggttccgg tggcggggga 1440
tccgacaaaa ctcacacatg cccaccgtgc ccagctccgg aactcctggg cggaccgtca 1500
gtcttcctct tccccccaaa acccaaggac accctcatga tctcccggac ccctgaggtc 1560
acatgcgtgg tggtggacgt gagccacgaa gaccctgagg tcaagttcaa ctggtacgtg 1620
gacggcgtgg aggtgcataa tgccaagaca aagccgcggg aggagcagta caacagcacg 1680
taccgtgtgg tcagcgtcct caccgtcctg caccaggact ggctgaatgg caaggagtac 1740
aagtgcaagg tctccaacaa agccctccca gcccccatcg agaaaaccat ctccaaagcc 1800
aaagggcagc cccgagaacc acaggtgtac accctgcccc catcccggga tgagctgacc 1860
aagaaccagg tcagcctgac ctgcctggtc aaaggcttct atcccagcga catcgccgtg 1920
gagtgggaga gcaatgggca gccggagaac aactacaaga ccacgcctcc cgtgttggac 1980
tccgacggct ccttcttcct ctacagcaag ctcaccgtgg acaagagcag gtggcagcag 2040

```
gggaacgtct tctcatgctc cgtgatgcat gaggctctgc acaaccacta cacgcagaag   2100

agcctctccc tgtctccggg taaaggtggc ggcggatcag gtgggggtgg atcaggcggt   2160

ggaggttccg gtggcggggg atcagacaaa actcacacat gcccaccgtg cccagcacct   2220

gaactcctgg gaggaccgtc agtcttcctc ttccccccaa aacccaagga caccctcatg   2280

atctcccgga cccctgaggt cacatgcgtg gtggtggacg tgagccacga agaccctgag   2340

gtcaagttca actggtacgt ggacggcgtg gaggtgcata atgccaagac aaagccgcgg   2400

gaggagcagt acaacagcac gtaccgtgtg gtcagcgtcc tcaccgtcct gcaccaggac   2460

tggctgaatg gcaaggagta caagtgcaag gtctccaaca aagccctccc agcccccatc   2520

gagaaaacca tctccaaagc caaagggcag ccccgagaac cacaggtgta caccctgccc   2580

ccatcccgcg atgagctgac caagaaccag gtcagcctga cctgcctggt caaaggcttc   2640

tatcccagcg acatcgccgt ggagtgggag agcaatgggc agccggagaa caactacaag   2700

accacgcctc ccgtgttgga ctccgacggc tccttcttcc tctacagcaa gctcaccgtg   2760

gacaagagca ggtggcagca ggggaacgtc ttctcatgct ccgtgatgca tgaggctctg   2820

cacaaccact acacgcagaa gagcctctcc ctgtctccgg gtaaatga               2868
```

<210> SEQ ID NO 131
<211> LENGTH: 955
<212> TYPE: PRT
<213> ORGANISM: Artificial Sequence
<220> FEATURE:
<223> OTHER INFORMATION: Synthetic construct: FVII-039 amino acid sequence

<400> SEQUENCE: 131

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Gly
            180                 185                 190

Gly Asp Phe Thr Arg Val Val Gly Gly Lys Val Cys Pro Lys Gly Glu
        195                 200                 205
```

-continued

```
Cys Pro Trp Gln Val Leu Leu Leu Val Asn Gly Ala Gln Leu Cys Gly
    210                 215                 220

Gly Thr Leu Ile Asn Thr Ile Trp Val Val Ser Ala Ala His Cys Phe
225                 230                 235                 240

Asp Lys Ile Lys Asn Trp Arg Asn Leu Ile Ala Val Leu Gly Glu His
                245                 250                 255

Asp Leu Ser Glu His Asp Gly Asp Glu Gln Ser Arg Arg Val Ala Gln
            260                 265                 270

Val Ile Ile Pro Ser Thr Tyr Val Pro Gly Thr Thr Asn His Asp Ile
        275                 280                 285

Ala Leu Leu Arg Leu His Gln Pro Val Val Leu Thr Asp His Val Val
    290                 295                 300

Pro Leu Cys Leu Pro Glu Arg Thr Phe Ser Glu Arg Thr Leu Ala Phe
305                 310                 315                 320

Val Arg Phe Ser Leu Val Ser Gly Trp Gly Gln Leu Leu Asp Arg Gly
                325                 330                 335

Ala Thr Ala Leu Glu Leu Met Val Leu Asn Val Pro Arg Leu Met Thr
            340                 345                 350

Gln Asp Cys Leu Gln Gln Ser Arg Lys Val Gly Asp Ser Pro Asn Ile
        355                 360                 365

Thr Glu Tyr Met Phe Cys Ala Gly Tyr Ser Asp Gly Ser Lys Asp Ser
    370                 375                 380

Cys Lys Gly Asp Ser Gly Gly Pro His Ala Thr His Tyr Arg Gly Thr
385                 390                 395                 400

Trp Tyr Leu Thr Gly Ile Val Ser Trp Gly Gln Gly Cys Ala Thr Val
                405                 410                 415

Gly His Phe Gly Val Tyr Thr Arg Val Ser Gln Tyr Ile Glu Trp Leu
            420                 425                 430

Gln Lys Leu Met Arg Ser Glu Pro Arg Pro Gly Val Leu Leu Arg Ala
        435                 440                 445

Pro Phe Pro Gly Gly Gly Gly Ser Gly Gly Gly Gly Ser Gly Gly Gly
    450                 455                 460

Gly Ser Gly Gly Gly Gly Ser Gly Gly Gly Gly Ser Gly Gly Gly Gly
465                 470                 475                 480

Ser Asp Lys Thr His Thr Cys Pro Pro Cys Pro Ala Pro Glu Leu Leu
                485                 490                 495

Gly Gly Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
        515                 520                 525

His Glu Asp Pro Glu Val Lys Phe Asn Trp Tyr Val Asp Gly Val Glu
    530                 535                 540

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
                565                 570                 575

Gly Lys Glu Tyr Lys Cys Lys Val Ser Asn Lys Ala Leu Pro Ala Pro
            580                 585                 590

Ile Glu Lys Thr Ile Ser Lys Ala Lys Gly Gln Pro Arg Glu Pro Gln
        595                 600                 605

Val Tyr Thr Leu Pro Pro Ser Arg Asp Glu Leu Thr Lys Asn Gln Val
    610                 615                 620

Ser Leu Thr Cys Leu Val Lys Gly Phe Tyr Pro Ser Asp Ile Ala Val
```

```
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
        675                 680                 685

Met His Glu Ala Leu His Asn His Tyr Thr Gln Lys Ser Leu Ser Leu
    690                 695                 700

Ser Pro Gly Lys Gly Gly Gly Gly Ser Gly Gly Gly Gly Ser Gly Gly
705                 710                 715                 720

Gly Gly Ser Gly Gly Gly Gly Ser Asp Lys Thr His Thr Cys Pro Pro
                725                 730                 735

Cys Pro Ala Pro Glu Leu Leu Gly Gly Pro Ser Val Phe Leu Phe Pro
            740                 745                 750

Pro Lys Pro Lys Asp Thr Leu Met Ile Ser Arg Thr Pro Glu Val Thr
        755                 760                 765

Cys Val Val Val Asp Val Ser His Glu Asp Pro Glu Val Lys Phe Asn
    770                 775                 780

Trp Tyr Val Asp Gly Val Glu Val His Asn Ala Lys Thr Lys Pro Arg
785                 790                 795                 800

Glu Glu Gln Tyr Asn Ser Thr Tyr Arg Val Val Ser Val Leu Thr Val
                805                 810                 815

Leu His Gln Asp Trp Leu Asn Gly Lys Glu Tyr Lys Cys Lys Val Ser
            820                 825                 830

Asn Lys Ala Leu Pro Ala Pro Ile Glu Lys Thr Ile Ser Lys Ala Lys
        835                 840                 845

Gly Gln Pro Arg Glu Pro Gln Val Tyr Thr Leu Pro Pro Ser Arg Asp
    850                 855                 860

Glu Leu Thr Lys Asn Gln Val Ser Leu Thr Cys Leu Val Lys Gly Phe
865                 870                 875                 880

Tyr Pro Ser Asp Ile Ala Val Glu Trp Glu Ser Asn Gly Gln Pro Glu
                885                 890                 895

Asn Asn Tyr Lys Thr Thr Pro Pro Val Leu Asp Ser Asp Gly Ser Phe
            900                 905                 910

Phe Leu Tyr Ser Lys Leu Thr Val Asp Lys Ser Arg Trp Gln Gln Gly
        915                 920                 925

Asn Val Phe Ser Cys Ser Val Met His Glu Ala Leu His Asn His Tyr
    930                 935                 940

Thr Gln Lys Ser Leu Ser Leu Ser Pro Gly Lys
945                 950                 955


<210> SEQ ID NO 132
<211> LENGTH: 2865
<212> TYPE: DNA
<213> ORGANISM: Artificial Sequence
<220> FEATURE:
<223> OTHER INFORMATION: Synthetic construct: DNA sequence for FVII-040

<400> SEQUENCE: 132

atggtctccc aggccctcag gctcctctgc cttctgcttg ggcttcaggg ctgcctggct      60

gcagtcttcg taacccagga ggaagcccac ggcgtcctgc accggcgccg gcgcgccaac     120

gcgttcctgg aggagctgcg gccgggctcc ctggagaggg agtgcaagga ggagcagtgc     180

tccttcgagg aggcccggga gatcttcaag gacgcggaga ggacgaagct gttctggatt     240
```

```
tcttacagtg atggggacca gtgtgcctca agtccatgcc agaatggggg ctcctgcaag    300
gaccagctcc agtcctatat ctgcttctgc ctccctgcct tcgagggccg gaactgtgag    360
acgcacaagg atgaccagct gatctgtgtg aacgagaacg gcggctgtga gcagtactgc    420
agtgaccaca cgggcaccaa gcgctcctgt cggtgccacg aggggtactc tctgctggca    480
gacggggtgt cctgcacacc cacagttgaa tatccatgtg gaaaaatacc tattctagaa    540
aaaagaaatg ccagcaaacc ccaaggcggc ggaggagact tcactcgggt tgtgggggc     600
aaggtgtgcc ccaaagggga gtgtccatgg caggtcctgt tgttggtgaa tggagctcag    660
ttgtgtgggg ggaccctgat caacaccatc tgggtggtct ccgcggccca ctgtttcgac    720
aaaatcaaga actggaggaa cctgatcgcg gtgctgggcg agcacgacct cagcgagcac    780
gacggggatg agcagagccg gcgggtggcg caggtcatca tccccagcac gtacgtcccg    840
ggcaccacca accacgacat cgcgctgctc cgcctgcacc agcccgtggt cctcactgac    900
catgtggtgc ccctctgcct gcccgaacgg acgttctctg agaggacgct ggccttcgtg    960
cgcttctcat tggtcagcgg ctggggccag ctgctggacc gtggcgccac ggccctggag   1020
ctcatggtcc tcaacgtgcc ccggctgatg acccaggact gcctgcagca gtcacggaag   1080
gtgggagact ccccaaatat cacggagtac atgttctgtg ccggctactc ggatggcagc   1140
aaggactcct gcaaggggga cagtggaggc ccacatgcca cccactaccg gggcacgtgg   1200
tacctgacgg gcatcgtcag ctggggccag ggctgcgcaa ccgtgggcca ctttggggtg   1260
tacaccaggg tctcccagta catcgagtgg ctgcaaaagc tcatgcgctc agagccacgc   1320
ccaggagtcc tcctgcgagc cccatttccc ggtggcggtg gctccggcgg aggtgggtcc   1380
ggtggcggcg gatcaggtgg gggtggatca ggcggtggag gttccggtgg cgggggatcc   1440
gacaaaactc acacatgccc accgtgccca gctccggaac tcctgggcgg accgtcagtc   1500
ttcctcttcc ccccaaaacc caaggacacc ctcatgatct cccggacccc tgaggtcaca   1560
tgcgtggtgg tggacgtgag ccacgaagac cctgaggtca agttcaactg gtacgtggac   1620
ggcgtggagg tgcataatgc caagacaaag ccgcgggagg agcagtacaa cagcacgtac   1680
cgtgtggtca gcgtcctcac cgtcctgcac caggactggc tgaatggcaa ggagtacaag   1740
tgcaaggtct ccaacaaagc cctcccagcc cccatcgaga aaaccatctc caaagccaaa   1800
gggcagcccc gagaaccaca ggtgtacacc ctgcccccat cccgggatga gctgaccaag   1860
aaccaggtca gcctgacctg cctggtcaaa ggcttctatc ccagcgacat cgccgtggag   1920
tgggagagca atgggcagcc ggagaacaac tacaagacca cgcctcccgt gttggactcc   1980
gacggctcct tcttcctcta cagcaagctc accgtggaca agagcaggtg gcagcagggg   2040
aacgtcttct catgctccgt gatgcatgag gctctgcaca accactacac gcagaagagc   2100
ctctccctgt ctccgggtaa aggtggcggc ggatcaggtg gggtggatc aggcggtgga    2160
ggttccggtg gcgggggatc agacaaaact cacacatgcc caccgtgccc agcacctgaa   2220
ctcctgggag gaccgtcagt cttcctcttc cccccaaaac ccaaggacac cctcatgatc   2280
tcccggaccc ctgaggtcac atgcgtggtg gtggacgtga gccacgaaga ccctgaggtc   2340
aagttcaact ggtacgtgga cggcgtggag gtgcataatg ccaagacaaa gccgcgggag   2400
gagcagtaca acagcacgta ccgtgtggtc agcgtcctca ccgtcctgca ccaggactgg   2460
ctgaatggca aggagtacaa gtgcaaggtc tccaacaaag ccctcccagc ccccatcgag   2520
aaaaccatct ccaaagccaa agggcagccc cgagaaccac aggtgtacac cctgccccca   2580
```

```
tcccgcgatg agctgaccaa gaaccaggtc agcctgacct gcctggtcaa aggcttctat   2640

cccagcgaca tcgccgtgga gtgggagagc aatgggcagc cggagaacaa ctacaagacc   2700

acgcctcccg tgttggactc cgacggctcc ttcttcctct acagcaagct caccgtggac   2760

aagagcaggt ggcagcaggg gaacgtcttc tcatgctccg tgatgcatga ggctctgcac   2820

aaccactaca cgcagaagag cctctccctg tctccgggta aatga                    2865


<210> SEQ ID NO 133
<211> LENGTH: 954
<212> TYPE: PRT
<213> ORGANISM: Artificial Sequence
<220> FEATURE:
<223> OTHER INFORMATION: Synthetic construct: FVII-040 amino acid
      sequence

<400> SEQUENCE: 133

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Gly Gly Gly
            180                 185                 190

Asp Phe Thr Arg Val Val Gly Gly Lys Val Cys Pro Lys Gly Glu Cys
        195                 200                 205

Pro Trp Gln Val Leu Leu Leu Val Asn Gly Ala Gln Leu Cys Gly Gly
    210                 215                 220

Thr Leu Ile Asn Thr Ile Trp Val Val Ser Ala Ala His Cys Phe Asp
225                 230                 235                 240

Lys Ile Lys Asn Trp Arg Asn Leu Ile Ala Val Leu Gly Glu His Asp
                245                 250                 255

Leu Ser Glu His Asp Gly Asp Glu Gln Ser Arg Arg Val Ala Gln Val
            260                 265                 270

Ile Ile Pro Ser Thr Tyr Val Pro Gly Thr Thr Asn His Asp Ile Ala
        275                 280                 285

Leu Leu Arg Leu His Gln Pro Val Val Leu Thr Asp His Val Val Pro
    290                 295                 300

Leu Cys Leu Pro Glu Arg Thr Phe Ser Glu Arg Thr Leu Ala Phe Val
```

```
305                 310                 315                 320

Arg Phe Ser Leu Val Ser Gly Trp Gly Gln Leu Leu Asp Arg Gly Ala
                325                 330                 335

Thr Ala Leu Glu Leu Met Val Leu Asn Val Pro Arg Leu Met Thr Gln
            340                 345                 350

Asp Cys Leu Gln Gln Ser Arg Lys Val Gly Asp Ser Pro Asn Ile Thr
        355                 360                 365

Glu Tyr Met Phe Cys Ala Gly Tyr Ser Asp Gly Ser Lys Asp Ser Cys
    370                 375                 380

Lys Gly Asp Ser Gly Gly Pro His Ala Thr His Tyr Arg Gly Thr Trp
385                 390                 395                 400

Tyr Leu Thr Gly Ile Val Ser Trp Gly Gln Gly Cys Ala Thr Val Gly
                405                 410                 415

His Phe Gly Val Tyr Thr Arg Val Ser Gln Tyr Ile Glu Trp Leu Gln
            420                 425                 430

Lys Leu Met Arg Ser Glu Pro Arg Pro Gly Val Leu Leu Arg Ala Pro
        435                 440                 445

Phe Pro Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Asp Lys Thr His Thr Cys Pro Pro Cys Pro Ala Pro Glu Leu Leu Gly
                485                 490                 495

Gly Pro Ser Val Phe Leu Phe Pro Pro Lys Pro Lys Asp Thr Leu Met
            500                 505                 510

Ile Ser Arg Thr Pro Glu Val Thr Cys Val Val Val Asp Val Ser His
        515                 520                 525

Glu Asp Pro Glu Val Lys Phe Asn Trp Tyr Val Asp Gly Val Glu Val
    530                 535                 540

His Asn Ala Lys Thr Lys Pro Arg Glu Glu Gln Tyr Asn Ser Thr Tyr
545                 550                 555                 560

Arg Val Val Ser Val Leu Thr Val Leu His Gln Asp Trp Leu Asn Gly
                565                 570                 575

Lys Glu Tyr Lys Cys Lys Val Ser Asn Lys Ala Leu Pro Ala Pro Ile
            580                 585                 590

Glu Lys Thr Ile Ser Lys Ala Lys Gly Gln Pro Arg Glu Pro Gln Val
        595                 600                 605

Tyr Thr Leu Pro Pro Ser Arg Asp Glu Leu Thr Lys Asn Gln Val Ser
    610                 615                 620

Leu Thr Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Lys Leu Thr Val
            660                 665                 670

Asp Lys Ser Arg Trp Gln Gln Gly Asn Val Phe Ser Cys Ser Val Met
        675                 680                 685

His Glu Ala Leu His Asn His Tyr Thr Gln Lys Ser Leu Ser Leu Ser
    690                 695                 700

Pro Gly Lys Gly Gly Gly Gly Ser Gly Gly Gly Gly Ser Gly Gly Gly
705                 710                 715                 720

Gly Ser Gly Gly Gly Gly Ser Asp Lys Thr His Thr Cys Pro Pro Cys
                725                 730                 735
```

Pro Ala Pro Glu Leu Leu Gly Gly Pro Ser Val Phe Leu Phe Pro Pro
740 745 750

Lys Pro Lys Asp Thr Leu Met Ile Ser Arg Thr Pro Glu Val Thr Cys
755 760 765

Val Val Val Asp Val Ser His Glu Asp Pro Glu Val Lys Phe Asn Trp
770 775 780

Tyr Val Asp Gly Val Glu Val His Asn Ala Lys Thr Lys Pro Arg Glu
785 790 795 800

Glu Gln Tyr Asn Ser Thr Tyr Arg Val Val Ser Val Leu Thr Val Leu
805 810 815

His Gln Asp Trp Leu Asn Gly Lys Glu Tyr Lys Cys Lys Val Ser Asn
820 825 830

Lys Ala Leu Pro Ala Pro Ile Glu Lys Thr Ile Ser Lys Ala Lys Gly
835 840 845

Gln Pro Arg Glu Pro Gln Val Tyr Thr Leu Pro Pro Ser Arg Asp Glu
850 855 860

Leu Thr Lys Asn Gln Val Ser Leu Thr Cys Leu Val Lys Gly Phe Tyr
865 870 875 880

Pro Ser Asp Ile Ala Val Glu Trp Glu Ser Asn Gly Gln Pro Glu Asn
885 890 895

Asn Tyr Lys Thr Thr Pro Pro Val Leu Asp Ser Asp Gly Ser Phe Phe
900 905 910

Leu Tyr Ser Lys Leu Thr Val Asp Lys Ser Arg Trp Gln Gln Gly Asn
915 920 925

Val Phe Ser Cys Ser Val Met His Glu Ala Leu His Asn His Tyr Thr
930 935 940

Gln Lys Ser Leu Ser Leu Ser Pro Gly Lys
945 950

<210> SEQ ID NO 134
<211> LENGTH: 3107
<212> TYPE: DNA
<213> ORGANISM: Artificial Sequence
<220> FEATURE:
<223> OTHER INFORMATION: Synthetic construct: DNA sequence for FIX-042

<400> SEQUENCE: 134
atgcagcgcg tgaacatgat catggcagaa tcaccaggcc tcatcaccat ctgcctttta 60
ggatatctac tcagtgctga atgtacaggt ttgtttcctt ttttaaaata cattgagtat 120
gcttgccttt tagatataga aatatctgat gctgtcttct tcactaaatt ttgattacat 180
gatttgacag caatattgaa gagtctaaca gccagcacgc aggttggtaa gtactgtggg 240
aacatcacag attttggctc catgccctaa agagaaattg gctttcagat tatttggatt 300
aaaaacaaag actttcttaa gagatgtaaa attttcatga tgttttcttt tttgctaaaa 360
ctaaagaatt attcttttac atttcagttt ttcttgatca tgaaaacgcc aacaaaattc 420
tgaatcggcc aaagaggtat aattcaggta aattggaaga gtttgttcaa gggaatctag 480
agagagaatg tatggaagaa aagtgtagtt ttgaagaagc acgagaagtt tttgaaaaca 540
ctgaaagaac aactgaattt tggaagcagt atgttgatgg agatcagtgt gagtccaatc 600
catgtttaaa tggcggcagt tgcaaggatg acattaattc ctatgaatgt tggtgtccct 660
ttggatttga aggaaagaac tgtgaattag atgtaacatg taacattaag aatggcagat 720
gcgagcagtt ttgtaaaaat agtgctgata acaaggtggt ttgctcctgt actgagggat 780

```
atcgacttgc agaaaaccag aagtcctgtg aaccagcagt gccatttcca tgtggaagag    840
tttctgtttc acaaacttct aagctcaccc gtgctgagac tgtttttcct gatgtggact    900
atgtaaattc tactgaagct gaaaccattt tggataacat cactcaaagc acccaatcat    960
ttaatgactt cactcgggtt gttggtggag aagatgccaa accaggtcaa ttcccttggc   1020
aggttgtttt gaatggtaaa gttgatgcat tctgtggagg ctctatcgtt aatgaaaaat   1080
ggattgtaac tgctgcccac tgtgttgaaa ctggtgttaa aattacagtt gtcgcaggtg   1140
aacataatat tgaggagaca gaacatacag agcaaaagcg aaatgtgatt cgaattattc   1200
ctcaccacaa ctacaatgca gctattaata agtacaacca tgacattgcc cttctggaac   1260
tggacgaacc cttagtgcta aacagctacg ttacacctat ttgcattgct gacaaggaat   1320
acacgaacat cttcctcaaa tttggatctg gctatgtaag tggctgggga agagtcttcc   1380
acaaagggag atcagcttta gttcttcagt accttagagt tccacttgtt gaccgagcca   1440
catgtcttcg atctacaaag ttcaccatct ataacaacat gttctgtgct ggcttccatg   1500
aaggaggtag agattcatgt caaggagata gtgggggacc ccatgttact gaagtggaag   1560
ggaccagttt cttaactgga attattagct ggggtgaaga gtgtgcaatg aaaggcaaat   1620
atggaatata taccaaggtg tcccggtatg tcaactggat taaggaaaaa acaaagctca   1680
ctgacaaaac tcacacatgc ccaccgtgcc cagctccgga actcctgggc ggaccgtcag   1740
tcttcctctt ccccccaaaa cccaaggaca ccctcatgat ctcccggacc cctgaggtca   1800
catgcgtggt ggtggacgtg agccacgaag accctgaggt caagttcaac tggtacgtgg   1860
acggcgtgga ggtgcataat gccaagacaa agccgcggga ggagcagtac aacagcacgt   1920
accgtgtggt cagcgtcctc accgtcctgc accaggactg gctgaatggc aaggagtaca   1980
agtgcaaggt ctccaacaaa gccctcccag cccccatcga gaaaaccatc tccaaagcca   2040
aagggcagcc ccgagaacca caggtgtaca ccctgccccc atcccgggat gagctgacca   2100
agaaccaggt cagcctgacc tgcctggtca aaggcttcta tcccagcgac atcgccgtgg   2160
agtgggagag caatgggcag ccggagaaca actacaagac cacgcctccc gtgttggact   2220
ccgacggctc cttcttcctc tacagcaagc tcaccgtgga caagagcagg tggcagcagg   2280
ggaacgtctt ctcatgctcc gtgatgcatg aggctctgca caaccactac acgcagaaga   2340
gcctctccct gtctccgggt aaaggtggcg gcggatcagg tgggggtgga tcaggcggtg   2400
gaggttccgg tggcggggga tcagacaaaa ctcacacatg cccaccgtgc ccagcacctg   2460
aactcctggg aggaccgtca gtcttcctct tccccccaaa acccaaggac accctcatga   2520
tctcccggac ccctgaggtc acatgcgtgg tggtggacgt gagccacgaa gaccctgagg   2580
tcaagttcaa ctggtacgtg gacggcgtgg aggtgcataa tgccaagaca aagccgcggg   2640
aggagcagta caacagcacg taccgtgtgg tcagcgtcct caccgtcctg caccaggact   2700
ggctgaatgg caaggagtac aagtgcaagg tctccaacaa agccctccca gcccccatcg   2760
agaaaaccat ctccaaagcc aaagggcagc cccgagaacc acaggtgtac accctgcccc   2820
catcccgcga tgagctgacc aagaaccagg tcagcctgac ctgcctggtc aaaggcttct   2880
atcccagcga catcgccgtg gagtgggaga gcaatgggca gccggagaac aactacaaga   2940
ccacgcctcc cgtgttggac tccgacggct ccttcttcct ctacagcaag ctcaccgtgg   3000
acaagagcag gtggcagcag gggaacgtct tctcatgctc cgtgatgcat gaggctctgc   3060
acaaccacta cacgcagaag agcctctccc tgtctccggg taaatga                 3107
```

<210> SEQ ID NO 135
<211> LENGTH: 935
<212> TYPE: PRT
<213> ORGANISM: Artificial Sequence
<220> FEATURE:
<223> OTHER INFORMATION: Synthetic construct: FIX-042 amino acid
sequence

<400> SEQUENCE: 135

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365
```

-continued

```
Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Asp Lys Thr
    450                 455                 460

His Thr Cys Pro Pro Cys Pro Ala Pro Glu Leu Leu Gly Gly Pro Ser
465                 470                 475                 480

Val Phe Leu Phe Pro Pro Lys Pro Lys Asp Thr Leu Met Ile Ser Arg
                485                 490                 495

Thr Pro Glu Val Thr Cys Val Val Val Asp Val Ser His Glu Asp Pro
            500                 505                 510

Glu Val Lys Phe Asn Trp Tyr Val Asp Gly Val Glu Val His Asn Ala
        515                 520                 525

Lys Thr Lys Pro Arg Glu Glu Gln Tyr Asn Ser Thr Tyr Arg Val Val
    530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Pro Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Ser Arg Asp Glu Leu Thr Lys Asn Gln Val Ser Leu Thr Cys
        595                 600                 605

Leu Val Lys Gly Phe Tyr Pro Ser Asp Ile Ala Val Glu Trp Glu Ser
    610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

Gly Gly Gly Gly Ser Gly Gly Gly Gly Ser Gly Gly Gly Gly Ser Gly
    690                 695                 700

Gly Gly Gly Ser Asp Lys Thr His Thr Cys Pro Pro Cys Pro Ala Pro
705                 710                 715                 720

Glu Leu Leu Gly Gly Pro Ser Val Phe Leu Phe Pro Pro Lys Pro Lys
                725                 730                 735

Asp Thr Leu Met Ile Ser Arg Thr Pro Glu Val Thr Cys Val Val Val
            740                 745                 750

Asp Val Ser His Glu Asp Pro Glu Val Lys Phe Asn Trp Tyr Val Asp
        755                 760                 765

Gly Val Glu Val His Asn Ala Lys Thr Lys Pro Arg Glu Glu Gln Tyr
    770                 775                 780

Asn Ser Thr Tyr Arg Val Val Ser Val Leu Thr Val Leu His Gln Asp
```

785 790 795 800

Trp Leu Asn Gly Lys Glu Tyr Lys Cys Lys Val Ser Asn Lys Ala Leu
805 810 815

Pro Ala Pro Ile Glu Lys Thr Ile Ser Lys Ala Lys Gly Gln Pro Arg
820 825 830

Glu Pro Gln Val Tyr Thr Leu Pro Pro Ser Arg Asp Glu Leu Thr Lys
835 840 845

Asn Gln Val Ser Leu Thr Cys Leu Val Lys Gly Phe Tyr Pro Ser Asp
850 855 860

Ile Ala Val Glu Trp Glu Ser Asn Gly Gln Pro Glu Asn Asn Tyr Lys
865 870 875 880

Thr Thr Pro Pro Val Leu Asp Ser Asp Gly Ser Phe Phe Leu Tyr Ser
885 890 895

Lys Leu Thr Val Asp Lys Ser Arg Trp Gln Gln Gly Asn Val Phe Ser
900 905 910

Cys Ser Val Met His Glu Ala Leu His Asn His Tyr Thr Gln Lys Ser
915 920 925

Leu Ser Leu Ser Pro Gly Lys
930 935

<210> SEQ ID NO 136
<211> LENGTH: 4073
<212> TYPE: DNA
<213> ORGANISM: Artificial Sequence
<220> FEATURE:
<223> OTHER INFORMATION: Synthetic construct: DNA sequence for FIX-068

<400> SEQUENCE: 136
atgcagcgcg tgaacatgat catggcagaa tcaccaggcc tcatcaccat ctgcctttta 60
ggatatctac tcagtgctga atgtacaggt ttgtttcctt ttttaaaata cattgagtat 120
gcttgccttt tagatataga aatatctgat gctgtcttct tcactaaatt ttgattacat 180
gatttgacag caatattgaa gagtctaaca gccagcacgc aggttggtaa gtactgtggg 240
aacatcacag attttggctc catgccctaa agagaaattg gctttcagat tatttggatt 300
aaaaacaaag actttcttaa gagatgtaaa attttcatga tgttttcttt tttgctaaaa 360
ctaaagaatt attcttttac atttcagttt ttcttgatca tgaaaacgcc aacaaaattc 420
tgaatcggcc aaagaggtat aattcaggta aattggaaga gtttgttcaa gggaatctag 480
agagagaatg tatggaagaa aagtgtagtt ttgaagaagc acgagaagtt tttgaaaaca 540
ctgaaagaac aactgaattt tggaagcagt atgttgatgg agatcagtgt gagtccaatc 600
catgtttaaa tggcggcagt tgcaaggatg acattaattc ctatgaatgt tggtgtccct 660
ttggatttga aggaaagaac tgtgaattag atgtaacatg taacattaag aatggcagat 720
gcgagcagtt ttgtaaaaat agtgctgata acaaggtggt ttgctcctgt actgagggat 780
atcgacttgc agaaaaccag aagtcctgtg aaccagcagt gccatttcca tgtggaagag 840
tttctgtttc acaaacttct aagctcaccc gtgctgagac tgtttttcct gatgtggact 900
atgtaaattc tactgaagct gaaaccattt tggataacat cactcaaagc acccaatcat 960
ttaatgactt cactcgggtt gttggtggag aagatgccaa accaggtcaa ttcccttggc 1020
aggttgtttt gaatggtaaa gttgatgcat tctgtggagg ctctatcgtt aatgaaaaat 1080
ggattgtaac tgctgcccac tgtgttgaaa ctggtgttaa aattacagtt gtcgcaggtg 1140
aacataatat tgaggagaca gaacatacag agcaaaagcg aaatgtgatt cgaattattc 1200
ctcaccacaa ctacaatgca gctattaata agtacaacca tgacattgcc cttctggaac 1260
tggacgaacc cttagtgcta aacagctacg ttacacctat ttgcattgct gacaaggaat 1320
acacgaacat cttcctcaaa tttggatctg gctatgtaag tggctgggga agagtcttcc 1380
acaaagggag atcagcttta gttcttcagt accttagagt tccacttgtt gaccgagcca 1440
catgtcttcg atctacaaag ttcaccatct ataacaacat gttctgtgct ggcttccatg 1500
aaggaggtag agattcatgt caaggagata gtgggggacc ccatgttact gaagtggaag 1560
ggaccagttt cttaactgga attattagct ggggtgaaga gtgtgcaatg aaaggcaaat 1620
atggaatata taccaaggtg tcccggtatg tcaactggat taaggaaaaa acaaagctca 1680
ctgacaaaac tcacacatgc ccaccgtgcc cagctccgga actcctgggc ggaccgtcag 1740
tcttcctctt ccccccaaaa cccaaggaca ccctcatgat ctcccggacc cctgaggtca 1800
catgcgtggt ggtggacgtg agccacgaag accctgaggt caagttcaac tggtacgtgg 1860
acggcgtgga ggtgcataat gccaagacaa agccgcggga ggagcagtac aacagcacgt 1920
accgtgtggt cagcgtcctc accgtcctgc accaggactg gctgaatggc aaggagtaca 1980
agtgcaaggt ctccaacaaa gccctcccag cccccatcga gaaaaccatc tccaaagcca 2040
aagggcagcc ccgagaacca caggtgtaca ccctgccccc atcccgggat gagctgacca 2100
agaaccaggt cagcctgacc tgcctggtca aaggcttcta tcccagcgac atcgccgtgg 2160
agtgggagag caatgggcag ccggagaaca actacaagac cacgcctccc gtgttggact 2220
ccgacggctc cttcttcctc tacagcaagc tcaccgtcga caagagcagg tggcagcagg 2280
ggaacgtctt ctcatgctcc gtgatgcatg aggctctgca caaccactac acgcagaaga 2340
gcctctccct gtctccgggt aaacggcgcc gccggagcgg tggcggcgga tcaggtgggg 2400
gtggatcagg cggtggaggt tccggtggcg gggggatccgg cggtggaggt tccggtgggg 2460
gtggatcaag gaagaggagg aagagggcgc aggtgcagct gcaggagtct gggggaggct 2520
tggtacagcc tggggggtcc ctgagactct cctgtgcagc ctctggattc atgtttagca 2580
ggtatgccat gagctgggtc cgccaggctc cagggaaggg gccagagtgg gtctcaggta 2640
ttagtggtag tggtggtagt acatactacg cagactccgt gaagggccgg ttcaccgtct 2700
ccagagacaa ttccaagaac acgctgtatc tgcaaatgaa cagcctgaga gccgaggaca 2760
cggctgtata ttactgcgcc cggggcgcca cctacaccag ccggagcgac gtgcccgacc 2820
agaccagctt cgactactgg ggccagggaa ccctggtcac cgtctcctca gggagtgcat 2880
ccgccccaaa gcttgaagaa ggtgaatttt cagaagcacg cgtatctgaa ctgactcagg 2940
accctgctgt gtctgtggcc ttgggacaga cagtcaggat cacatgccaa ggagacagcc 3000
tcagaaactt ttatgcaagc tggtaccagc agaagccagg acaggcccct actcttgtca 3060
tctatggttt aagtaaaagg ccctcaggga tcccagaccg attctctgcc tccagctcag 3120
gaaacacagc ttccttgacc atcactgggg ctcaggcgga agatgaggct gactattact 3180
gcctgctgta ctacggcggc ggccagcagg gcgtgttcgg cggcggcacc aagctgaccg 3240
tcctacgtca gcccaaggct gccccctcgg tcactctgtt cccgccctct tctgcggccg 3300
gtggcggtgg ctccggcgga ggtgggtccg gtggcggcgg atcaggtggg ggtggatcag 3360
gcggtggagg ttccggtggc gggggatcag acaaaactca cacatgccca ccgtgcccag 3420
caccggaact cctgggcgga ccgtcagtct tcctcttccc cccaaaaccc aaggacaccc 3480
tcatgatctc ccggacccct gaggtcacat gcgtggtggt ggacgtgagc cacgaagacc 3540
ctgaggtcaa gttcaactgg tacgtggacg gcgtggaggt gcataatgcc aagacaaagc 3600

```
cgcgggagga gcagtacaac agcacgtacc gtgtggtcag cgtcctcacc gtcctgcacc   3660

aggactggct gaatggcaag gagtacaagt gcaaggtctc caacaaagcc ctcccagccc   3720

ccatcgagaa aaccatctcc aaagccaaag ggcagccccg agaaccacag gtgtacaccc   3780

tgcccccatc ccgcgatgag ctgaccaaga accaggtcag cctgacctgc ctggtcaaag   3840

gcttctatcc cagcgacatc gccgtggagt gggagagcaa tgggcagccg gagaacaact   3900

acaagaccac gcctcccgtg ttggactccg acggctcctt cttcctctac agcaagctca   3960

ccgtggacaa gagcaggtgg cagcagggga acgtcttctc atgctccgtg atgcatgagg   4020

ctctgcacaa ccactacacg cagaagagcc tctccctgtc tccgggtaaa tga          4073
```

```
<210> SEQ ID NO 137
<211> LENGTH: 1257
<212> TYPE: PRT
<213> ORGANISM: Artificial Sequence
<220> FEATURE:
<223> OTHER INFORMATION: Synthetic construct: FIX-068 amino acid
      sequence

<400> SEQUENCE: 137

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270
```

Val Lys Ile Thr Val Val Ala Gly Glu His Asn Ile Glu Glu Thr Glu
275 280 285

His Thr Glu Gln Lys Arg Asn Val Ile Arg Ile Ile Pro His His Asn
290 295 300

Tyr Asn Ala Ala Ile Asn Lys Tyr Asn His Asp Ile Ala Leu Leu Glu
305 310 315 320

Leu Asp Glu Pro Leu Val Leu Asn Ser Tyr Val Thr Pro Ile Cys Ile
325 330 335

Ala Asp Lys Glu Tyr Thr Asn Ile Phe Leu Lys Phe Gly Ser Gly Tyr
340 345 350

Val Ser Gly Trp Gly Arg Val Phe His Lys Gly Arg Ser Ala Leu Val
355 360 365

Leu Gln Tyr Leu Arg Val Pro Leu Val Asp Arg Ala Thr Cys Leu Arg
370 375 380

Ser Thr Lys Phe Thr Ile Tyr Asn Asn Met Phe Cys Ala Gly Phe His
385 390 395 400

Glu Gly Gly Arg Asp Ser Cys Gln Gly Asp Ser Gly Gly Pro His Val
405 410 415

Thr Glu Val Glu Gly Thr Ser Phe Leu Thr Gly Ile Ile Ser Trp Gly
420 425 430

Glu Glu Cys Ala Met Lys Gly Lys Tyr Gly Ile Tyr Thr Lys Val Ser
435 440 445

Arg Tyr Val Asn Trp Ile Lys Glu Lys Thr Lys Leu Thr Asp Lys Thr
450 455 460

His Thr Cys Pro Pro Cys Pro Ala Pro Glu Leu Leu Gly Gly Pro Ser
465 470 475 480

Val Phe Leu Phe Pro Pro Lys Pro Lys Asp Thr Leu Met Ile Ser Arg
485 490 495

Thr Pro Glu Val Thr Cys Val Val Val Asp Val Ser His Glu Asp Pro
500 505 510

Glu Val Lys Phe Asn Trp Tyr Val Asp Gly Val Glu Val His Asn Ala
515 520 525

Lys Thr Lys Pro Arg Glu Glu Gln Tyr Asn Ser Thr Tyr Arg Val Val
530 535 540

Ser Val Leu Thr Val Leu His Gln Asp Trp Leu Asn Gly Lys Glu Tyr
545 550 555 560

Lys Cys Lys Val Ser Asn Lys Ala Leu Pro Ala Pro Ile Glu Lys Thr
565 570 575

Ile Ser Lys Ala Lys Gly Gln Pro Arg Glu Pro Gln Val Tyr Thr Leu
580 585 590

Pro Pro Ser Arg Asp Glu Leu Thr Lys Asn Gln Val Ser Leu Thr Cys
595 600 605

Leu Val Lys Gly Phe Tyr Pro Ser Asp Ile Ala Val Glu Trp Glu Ser
610 615 620

Asn Gly Gln Pro Glu Asn Asn Tyr Lys Thr Thr Pro Pro Val Leu Asp
625 630 635 640

Ser Asp Gly Ser Phe Phe Leu Tyr Ser Lys Leu Thr Val Asp Lys Ser
645 650 655

Arg Trp Gln Gln Gly Asn Val Phe Ser Cys Ser Val Met His Glu Ala
660 665 670

Leu His Asn His Tyr Thr Gln Lys Ser Leu Ser Leu Ser Pro Gly Lys
675 680 685

Arg Arg Arg Arg Ser Gly Gly Gly Gly Ser Gly Gly Gly Gly Ser Gly

```
    690                 695                 700

Gly Gly Gly Ser Gly Gly Gly Gly Ser Gly Gly Gly Gly Ser Gly Gly
705                 710                 715                 720

Gly Gly Ser Arg Lys Arg Arg Lys Arg Ala Gln Val Gln Leu Gln Glu
                725                 730                 735

Ser Gly Gly Gly Leu Val Gln Pro Gly Gly Ser Leu Arg Leu Ser Cys
            740                 745                 750

Ala Ala Ser Gly Phe Met Phe Ser Arg Tyr Ala Met Ser Trp Val Arg
        755                 760                 765

Gln Ala Pro Gly Lys Gly Pro Glu Trp Val Ser Gly Ile Ser Gly Ser
    770                 775                 780

Gly Gly Ser Thr Tyr Tyr Ala Asp Ser Val Lys Gly Arg Phe Thr Val
785                 790                 795                 800

Ser Arg Asp Asn Ser Lys Asn Thr Leu Tyr Leu Gln Met Asn Ser Leu
                805                 810                 815

Arg Ala Glu Asp Thr Ala Val Tyr Tyr Cys Ala Arg Gly Ala Thr Tyr
            820                 825                 830

Thr Ser Arg Ser Asp Val Pro Asp Gln Thr Ser Phe Asp Tyr Trp Gly
        835                 840                 845

Gln Gly Thr Leu Val Thr Val Ser Ser Gly Ser Ala Ser Ala Pro Lys
    850                 855                 860

Leu Glu Glu Gly Glu Phe Ser Glu Ala Arg Val Ser Glu Leu Thr Gln
865                 870                 875                 880

Asp Pro Ala Val Ser Val Ala Leu Gly Gln Thr Val Arg Ile Thr Cys
                885                 890                 895

Gln Gly Asp Ser Leu Arg Asn Phe Tyr Ala Ser Trp Tyr Gln Gln Lys
            900                 905                 910

Pro Gly Gln Ala Pro Thr Leu Val Ile Tyr Gly Leu Ser Lys Arg Pro
        915                 920                 925

Ser Gly Ile Pro Asp Arg Phe Ser Ala Ser Ser Ser Gly Asn Thr Ala
    930                 935                 940

Ser Leu Thr Ile Thr Gly Ala Gln Ala Glu Asp Glu Ala Asp Tyr Tyr
945                 950                 955                 960

Cys Leu Leu Tyr Tyr Gly Gly Gly Gln Gln Gly Val Phe Gly Gly Gly
                965                 970                 975

Thr Lys Leu Thr Val Leu Arg Gln Pro Lys Ala Ala Pro Ser Val Thr
            980                 985                 990

Leu Phe Pro Pro Ser Ser Ala Ala  Gly Gly Gly Gly Ser  Gly Gly Gly
        995                 1000                1005

Gly Ser  Gly Gly Gly Gly Ser  Gly Gly Gly Gly Ser  Gly Gly Gly
    1010                1015                1020

Gly Ser  Gly Gly Gly Gly Ser  Asp Lys Thr His Thr  Cys Pro Pro
    1025                1030                1035

Cys Pro  Ala Pro Glu Leu Leu  Gly Gly Pro Ser Val  Phe Leu Phe
    1040                1045                1050

Pro Pro  Lys Pro Lys Asp Thr  Leu Met Ile Ser Arg  Thr Pro Glu
    1055                1060                1065

Val Thr  Cys Val Val Val Asp  Val Ser His Glu Asp  Pro Glu Val
    1070                1075                1080

Lys Phe  Asn Trp Tyr Val Asp  Gly Val Glu Val His  Asn Ala Lys
    1085                1090                1095

Thr Lys  Pro Arg Glu Glu Gln  Tyr Asn Ser Thr Tyr  Arg Val Val
    1100                1105                1110
```

```
Ser Val  Leu Thr Val Leu His  Gln Asp Trp Leu Asn  Gly Lys Glu
    1115                 1120                 1125

Tyr Lys  Cys Lys Val Ser Asn  Lys Ala Leu Pro Ala  Pro Ile Glu
    1130                 1135                 1140

Lys Thr  Ile Ser Lys Ala Lys  Gly Gln Pro Arg Glu  Pro Gln Val
    1145                 1150                 1155

Tyr Thr  Leu Pro Pro Ser Arg  Asp Glu Leu Thr Lys  Asn Gln Val
    1160                 1165                 1170

Ser Leu  Thr Cys Leu Val Lys  Gly Phe Tyr Pro Ser  Asp Ile Ala
    1175                 1180                 1185

Val Glu  Trp Glu Ser Asn Gly  Gln Pro Glu Asn Asn  Tyr Lys Thr
    1190                 1195                 1200

Thr Pro  Pro Val Leu Asp Ser  Asp Gly Ser Phe Phe  Leu Tyr Ser
    1205                 1210                 1215

Lys Leu  Thr Val Asp Lys Ser  Arg Trp Gln Gln Gly  Asn Val Phe
    1220                 1225                 1230

Ser Cys  Ser Val Met His Glu  Ala Leu His Asn His  Tyr Thr Gln
    1235                 1240                 1245

Lys Ser  Leu Ser Leu Ser Pro  Gly Lys
    1250                 1255
```

<210> SEQ ID NO 138
<211> LENGTH: 4010
<212> TYPE: DNA
<213> ORGANISM: Artificial Sequence
<220> FEATURE:
<223> OTHER INFORMATION: Synthetic construct: DNA sequence for FIX-088

<400> SEQUENCE: 138

```
atgcagcgcg tgaacatgat catggcagaa tcaccaggcc tcatcaccat ctgcctttta     60

ggatatctac tcagtgctga atgtacaggt ttgtttcctt ttttaaaata cattgagtat    120

gcttgccttt tagatataga aatatctgat gctgtcttct tcactaaatt ttgattacat    180

gatttgacag caatattgaa gagtctaaca gccagcacgc aggttggtaa gtactgtggg    240

aacatcacag attttggctc catgccctaa agagaaattg gctttcagat tatttggatt    300

aaaaacaaag actttcttaa gagatgtaaa attttcatga tgttttcttt tttgctaaaa    360

ctaaagaatt attcttttac atttcagttt ttcttgatca tgaaaacgcc aacaaaattc    420

tgaatcggcc aaagaggtat aattcaggta aattggaaga gtttgttcaa gggaatctag    480

agagagaatg tatggaagaa aagtgtagtt ttgaagaagc acgagaagtt tttgaaaaca    540

ctgaaagaac aactgaattt tggaagcagt atgttgatgg agatcagtgt gagtccaatc    600

catgtttaaa tggcggcagt tgcaaggatg acattaattc ctatgaatgt tggtgtccct    660

ttggatttga aggaaagaac tgtgaattag atgtaacatg taacattaag aatggcagat    720

gcgagcagtt ttgtaaaaat agtgctgata acaaggtggt ttgctcctgt actgagggat    780

atcgacttgc agaaaaccag aagtcctgtg aaccagcagt gccatttcca tgtggaagag    840

tttctgtttc acaaacttct aagctcaccc gtgctgagac tgtttttcct gatgtggact    900

atgtaaattc tactgaagct gaaaccattt tggataacat cactcaaagc acccaatcat    960

ttaatgactt cactcgggtt gttggtggag aagatgccaa accaggtcaa ttcccttggc   1020

aggttgtttt gaatggtaaa gttgatgcat tctgtggagg ctctatcgtt aatgaaaaat   1080

ggattgtaac tgctgcccac tgtgttgaaa ctggtgttaa aattacagtt gtcgcaggtg   1140
```

-continued

```
aacataatat tgaggagaca gaacatacag agcaaaagcg aaatgtgatt cgaattattc   1200
ctcaccacaa ctacaatgca gctattaata agtacaacca tgacattgcc cttctggaac   1260
tggacgaacc cttagtgcta aacagctacg ttacacctat ttgcattgct gacaaggaat   1320
acacgaacat cttcctcaaa tttggatctg gctatgtaag tggctgggga agagtcttcc   1380
acaaagggag atcagcttta gttcttcagt accttagagt tccacttgtt gaccgagcca   1440
catgtcttcg atctacaaag ttcaccatct ataacaacat gttctgtgct ggcttccatg   1500
aaggaggtag agattcatgt caaggagata gtgggggacc ccatgttact gaagtggaag   1560
ggaccagttt cttaactgga attattagct ggggtgaaga gtgtgcaatg aaaggcaaat   1620
atggaatata taccaaggtg tcccggtatg tcaactggat taaggaaaaa acaaagctca   1680
ctgacaaaac tcacacatgc ccaccgtgcc cagctccgga actcctgggc ggaccgtcag   1740
tcttcctctt ccccccaaaa cccaaggaca ccctcatgat ctcccggacc cctgaggtca   1800
catgcgtggt ggtggacgtg agccacgaag accctgaggt caagttcaac tggtacgtgg   1860
acggcgtgga ggtgcataat gccaagacaa agccgcggga ggagcagtac aacagcacgt   1920
accgtgtggt cagcgtcctc accgtcctgc accaggactg gctgaatggc aaggagtaca   1980
agtgcaaggt ctccaacaaa gccctcccag cccccatcga gaaaaccatc tccaaagcca   2040
aagggcagcc ccgagaacca caggtgtaca ccctgccccc atcccgggat gagctgacca   2100
agaaccaggt cagcctgacc tgcctggtca aaggcttcta tcccagcgac atcgccgtgg   2160
agtgggagag caatgggcag ccggagaaca actacaagac cacgcctccc gtgttggact   2220
ccgacggctc cttcttcctc tacagcaagc tcaccgtgga caagagcagg tggcagcagg   2280
ggaacgtctt ctcatgctcc gtgatgcatg aggctctgca caaccactac acgcagaaga   2340
gcctctccct gtctccgggt aaaggtggcg gcggatcagg tgggggtgga tcaggcggtg   2400
gaggttccgg tggcggggga tcagacaaaa ctcacacatg cccaccgtgc ccagcacctg   2460
aactcctggg aggaccgtca gtcttcctct tccccccaaa acccaaggac accctcatga   2520
tctcccggac ccctgaggtc acatgcgtgg tggtggacgt gagccacgaa gaccctgagg   2580
tcaagttcaa ctggtacgtg gacggcgtgg aggtgcataa tgccaagaca aagccgcggg   2640
aggagcagta caacagcacg taccgtgtgg tcagcgtcct caccgtcctg caccaggact   2700
ggctgaatgg caaggagtac aagtgcaagg tctccaacaa agccctccca gcccccatcg   2760
agaaaaccat ctccaaagcc aaagggcagc cccgagaacc acaggtgtac accctgcccc   2820
catcccgcga tgagctgacc aagaaccagg tcagcctgac ctgcctggtc aaaggcttct   2880
atcccagcga catcgccgtg gagtgggaga gcaatgggca gccggagaac aactacaaga   2940
ccacgcctcc cgtgttggac tccgacggct ccttcttcct ctacagcaag ctcaccgtcg   3000
acaagagcag gtggcagcag gggaacgtct tctcatgctc cgtgatgcat gaggctctgc   3060
acaaccacta cacgcagaag agcctctccc tgtctccggg taaaggtggc ggtggctccg   3120
gcggaggtgg gtccggtggc ggcggatcag gtgggggtgg atcaggcggt ggaggttccg   3180
gtggcggggg atcagcgcag gtgcagctgc aggagtctgg gggaggcttg gtacagcctg   3240
gggggtccct gagactctcc tgtgcagcct ctggattcat gtttagcagg tatgccatga   3300
gctgggtccg ccaggctcca gggaaggggc cagagtgggt ctcaggtatt agtggtagtg   3360
gtggtagtac atactacgca gactccgtga agggccggtt caccgtctcc agagacaatt   3420
ccaagaacac gctgtatctg caaatgaaca gcctgagagc cgaggacacg gctgtatatt   3480
actgcgcccg gggcgccacc tacaccagcc ggagcgacgt gcccgaccag accagcttcg   3540
```

```
actactgggg ccagggaacc ctggtcaccg tctcctcagg gagtgcatcc gccccaaagc   3600

ttgaagaagg tgaattttca gaagcacgcg tatctgaact gactcaggac cctgctgtgt   3660

ctgtggcctt gggacagaca gtcaggatca catgccaagg agacagcctc agaaactttt   3720

atgcaagctg gtaccagcag aagccaggac aggcccctac tcttgtcatc tatggtttaa   3780

gtaaaaggcc ctcagggatc ccagaccgat tctctgcctc cagctcagga aacacagctt   3840

ccttgaccat cactggggct caggcggaag atgaggctga ctattactgc ctgctgtact   3900

acggcggcgg ccagcagggc gtgttcggcg gcggcaccaa gctgaccgtc ctacgtcagc   3960

ccaaggctgc cccctcggtc actctgttcc cgccctcttc tgcggcctga               4010


<210> SEQ ID NO 139
<211> LENGTH: 1236
<212> TYPE: PRT
<213> ORGANISM: Artificial Sequence
<220> FEATURE:
<223> OTHER INFORMATION: Synthetic construct: FIX-088 amino acid
      sequence

<400> SEQUENCE: 139

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270
```

-continued

```
Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Asp Lys Thr
    450                 455                 460

His Thr Cys Pro Pro Cys Pro Ala Pro Glu Leu Leu Gly Gly Pro Ser
465                 470                 475                 480

Val Phe Leu Phe Pro Pro Lys Pro Lys Asp Thr Leu Met Ile Ser Arg
                485                 490                 495

Thr Pro Glu Val Thr Cys Val Val Val Asp Val Ser His Glu Asp Pro
            500                 505                 510

Glu Val Lys Phe Asn Trp Tyr Val Asp Gly Val Glu Val His Asn Ala
        515                 520                 525

Lys Thr Lys Pro Arg Glu Glu Gln Tyr Asn Ser Thr Tyr Arg Val Val
    530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Pro Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Ser Arg Asp Glu Leu Thr Lys Asn Gln Val Ser Leu Thr Cys
        595                 600                 605

Leu Val Lys Gly Phe Tyr Pro Ser Asp Ile Ala Val Glu Trp Glu Ser
    610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

Gly Gly Gly Gly Ser Gly Gly Gly Gly Ser Gly Gly Gly Gly Ser Gly
```

```
    690                 695                 700

Gly Gly Gly Ser Asp Lys Thr His Thr Cys Pro Pro Cys Pro Ala Pro
705                 710                 715                 720

Glu Leu Leu Gly Gly Pro Ser Val Phe Leu Phe Pro Pro Lys Pro Lys
                725                 730                 735

Asp Thr Leu Met Ile Ser Arg Thr Pro Glu Val Thr Cys Val Val Val
            740                 745                 750

Asp Val Ser His Glu Asp Pro Glu Val Lys Phe Asn Trp Tyr Val Asp
        755                 760                 765

Gly Val Glu Val His Asn Ala Lys Thr Lys Pro Arg Glu Glu Gln Tyr
    770                 775                 780

Asn Ser Thr Tyr Arg Val Val Ser Val Leu Thr Val Leu His Gln Asp
785                 790                 795                 800

Trp Leu Asn Gly Lys Glu Tyr Lys Cys Lys Val Ser Asn Lys Ala Leu
                805                 810                 815

Pro Ala Pro Ile Glu Lys Thr Ile Ser Lys Ala Lys Gly Gln Pro Arg
            820                 825                 830

Glu Pro Gln Val Tyr Thr Leu Pro Pro Ser Arg Asp Glu Leu Thr Lys
        835                 840                 845

Asn Gln Val Ser Leu Thr Cys Leu Val Lys Gly Phe Tyr Pro Ser Asp
    850                 855                 860

Ile Ala Val Glu Trp Glu Ser Asn Gly Gln Pro Glu Asn Asn Tyr Lys
865                 870                 875                 880

Thr Thr Pro Pro Val Leu Asp Ser Asp Gly Ser Phe Phe Leu Tyr Ser
                885                 890                 895

Lys Leu Thr Val Asp Lys Ser Arg Trp Gln Gln Gly Asn Val Phe Ser
            900                 905                 910

Cys Ser Val Met His Glu Ala Leu His Asn His Tyr Thr Gln Lys Ser
        915                 920                 925

Leu Ser Leu Ser Pro Gly Lys Gly Gly Gly Gly Ser Gly Gly Gly Gly
    930                 935                 940

Ser Gly Gly Gly Gly Ser Gly Gly Gly Gly Ser Gly Gly Gly Gly Ser
945                 950                 955                 960

Gly Gly Gly Gly Ser Ala Gln Val Gln Leu Gln Glu Ser Gly Gly Gly
                965                 970                 975

Leu Val Gln Pro Gly Gly Ser Leu Arg Leu Ser Cys Ala Ala Ser Gly
            980                 985                 990

Phe Met Phe Ser Arg Tyr Ala Met  Ser Trp Val Arg Gln  Ala Pro Gly
        995                 1000                1005

Lys Gly  Pro Glu Trp Val Ser  Gly Ile Ser Gly Ser  Gly Gly Ser
    1010                1015                1020

Thr Tyr  Tyr Ala Asp Ser Val  Lys Gly Arg Phe Thr  Val Ser Arg
    1025                1030                1035

Asp Asn  Ser Lys Asn Thr Leu  Tyr Leu Gln Met Asn  Ser Leu Arg
    1040                1045                1050

Ala Glu  Asp Thr Ala Val Tyr  Tyr Cys Ala Arg Gly  Ala Thr Tyr
    1055                1060                1065

Thr Ser  Arg Ser Asp Val Pro  Asp Gln Thr Ser Phe  Asp Tyr Trp
    1070                1075                1080

Gly Gln  Gly Thr Leu Val Thr  Val Ser Ser Gly Ser  Ala Ser Ala
    1085                1090                1095

Pro Lys  Leu Glu Glu Gly Glu  Phe Ser Glu Ala Arg  Val Ser Glu
    1100                1105                1110
```

```
Leu Thr  Gln Asp Pro Ala Val  Ser Val Ala Leu Gly  Gln Thr Val
    1115                 1120                 1125

Arg Ile  Thr Cys Gln Gly Asp  Ser Leu Arg Asn Phe  Tyr Ala Ser
    1130                 1135                 1140

Trp Tyr  Gln Gln Lys Pro Gly  Gln Ala Pro Thr Leu  Val Ile Tyr
    1145                 1150                 1155

Gly Leu  Ser Lys Arg Pro Ser  Gly Ile Pro Asp Arg  Phe Ser Ala
    1160                 1165                 1170

Ser Ser  Ser Gly Asn Thr Ala  Ser Leu Thr Ile Thr  Gly Ala Gln
    1175                 1180                 1185

Ala Glu  Asp Glu Ala Asp Tyr  Tyr Cys Leu Leu Tyr  Tyr Gly Gly
    1190                 1195                 1200

Gly Gln  Gln Gly Val Phe Gly  Gly Gly Thr Lys Leu  Thr Val Leu
    1205                 1210                 1215

Arg Gln  Pro Lys Ala Ala Pro  Ser Val Thr Leu Phe  Pro Pro Ser
    1220                 1225                 1230

Ser Ala  Ala
    1235
```

<210> SEQ ID NO 140
<211> LENGTH: 3263
<212> TYPE: DNA
<213> ORGANISM: Artificial Sequence
<220> FEATURE:
<223> OTHER INFORMATION: Synthetic construct: DNA sequence for FIX-089

<400> SEQUENCE: 140

```
atgcagcgcg tgaacatgat catggcagaa tcaccaggcc tcatcaccat ctgcctttta     60

ggatatctac tcagtgctga atgtacaggt ttgtttcctt ttttaaaata cattgagtat    120

gcttgccttt tagatataga aatatctgat gctgtcttct tcactaaatt ttgattacat    180

gatttgacag caatattgaa gagtctaaca gccagcacgc aggttggtaa gtactgtggg    240

aacatcacag attttggctc catgccctaa agagaaattg gctttcagat tatttggatt    300

aaaaacaaag actttcttaa gagatgtaaa attttcatga tgttttcttt tttgctaaaa    360

ctaaagaatt attcttttac atttcagttt ttcttgatca tgaaaacgcc aacaaaattc    420

tgaatcggcc aaagaggtat aattcaggta aattggaaga gtttgttcaa gggaatctag    480

agagagaatg tatggaagaa aagtgtagtt ttgaagaagc acgagaagtt tttgaaaaca    540

ctgaaagaac aactgaattt tggaagcagt atgttgatgg agatcagtgt gagtccaatc    600

catgtttaaa tggcggcagt tgcaaggatg acattaattc ctatgaatgt tggtgtccct    660

ttggatttga aggaaagaac tgtgaattag atgtaacatg taacattaag aatggcagat    720

gcgagcagtt ttgtaaaaat agtgctgata acaaggtggt ttgctcctgt actgagggat    780

atcgacttgc agaaaaccag aagtcctgtg aaccagcagt gccatttcca tgtggaagag    840

tttctgtttc acaaacttct aagctcaccc gtgctgagac tgtttttcct gatgtggact    900

atgtaaattc tactgaagct gaaaccattt tggataacat cactcaaagc acccaatcat    960

ttaatgactt cactcgggtt gttggtggag aagatgccaa accaggtcaa ttcccttggc   1020

aggttgtttt gaatggtaaa gttgatgcat tctgtggagg ctctatcgtt aatgaaaaat   1080

ggattgtaac tgctgcccac tgtgttgaaa ctggtgttaa aattacagtt gtcgcaggtg   1140

aacataatat tgaggagaca gaacatacag agcaaaagcg aaatgtgatt cgaattattc   1200

ctcaccacaa ctacaatgca gctattaata agtacaacca tgacattgcc cttctggaac   1260
```

```
tggacgaacc cttagtgcta aacagctacg ttacacctat ttgcattgct gacaaggaat   1320

acacgaacat cttcctcaaa tttggatctg gctatgtaag tggctgggga agagtcttcc   1380

acaaagggag atcagcttta gttcttcagt accttagagt tccacttgtt gaccgagcca   1440

catgtcttcg atctacaaag ttcaccatct ataacaacat gttctgtgct ggcttccatg   1500

aaggaggtag agattcatgt caaggagata gtgggggacc ccatgttact gaagtggaag   1560

ggaccagttt cttaactgga attattagct ggggtgaaga gtgtgcaatg aaaggcaaat   1620

atggaatata taccaaggtg tcccggtatg tcaactggat taaggaaaaa acaaagctca   1680

ctgacaaaac tcacacatgc ccaccgtgcc cagctccgga actcctggga ggaccgtcag   1740

tcttcctctt ccccccaaaa cccaaggaca ccctcatgat ctcccggacc cctgaggtca   1800

catgcgtggt ggtggacgtg agccacgaag accctgaggt caagttcaac tggtacgtgg   1860

acggcgtgga ggtgcataat gccaagacaa agccgcggga ggagcagtac aacagcacgt   1920

accgtgtggt cagcgtcctc accgtcctgc accaggactg gctgaatggc aaggagtaca   1980

agtgcaaggt ctccaacaaa gccctcccag cccccatcga gaaaaccatc tccaaagcca   2040

aagggcagcc ccgagaacca caggtgtaca ccctgccccc atcccgggat gagctgacca   2100

agaaccaggt cagcctgacc tgcctggtca aaggcttcta tcccagcgac atcgccgtgg   2160

agtgggagag caatgggcag ccggagaaca actacaagac cacgcctccc gtgttggact   2220

ccgacggctc cttcttcctc tacagcaagc tcaccgtcga caagagcagg tggcagcagg   2280

ggaacgtctt ctcatgctcc gtgatgcatg aggctctgca caaccactac acgcagaaga   2340

gcctctccct gtctccgggt aaaggcggtg gcggttcagg tggaggaggg tcaggcggtg   2400

gtggatccgg cgggggcgga tccggtggcg gagggtcagg cggtggcgga tcagcctgca   2460

ccgagcggat ggccctgcac aacctgtgcg gtggcggtgg ctccggcgga ggtgggtccg   2520

gtggcggcgg atcaggtggg ggtggatcag gcggtggagg ttccggtggc gggggatccg   2580

acaaaactca cacatgccca ccgtgcccag caccggaact cctgggcgga ccgtcagtct   2640

tcctcttccc cccaaaaccc aaggacaccc tcatgatctc ccggacccct gaggtcacat   2700

gcgtggtggt ggacgtgagc cacgaagacc ctgaggtcaa gttcaactgg tacgtggacg   2760

gcgtggaggt gcataatgcc aagacaaagc cgcgggagga gcagtacaac agcacgtacc   2820

gtgtggtcag cgtcctcacc gtcctgcacc aggactggct gaatggcaag gagtacaagt   2880

gcaaggtctc caacaaagcc ctcccagccc ccatcgagaa aaccatctcc aaagccaaag   2940

ggcagccccg agaaccacag gtgtacaccc tgcccccatc ccgggatgag ctgaccaaga   3000

accaggtcag cctgacctgc ctggtcaaag gcttctatcc cagcgacatc gccgtggagt   3060

gggagagcaa tgggcagccg gagaacaact acaagaccac gcctcccgtg ttggactccg   3120

acggctcctt cttcctctac agcaagctca ccgtggacaa gagcaggtgg cagcagggga   3180

acgtcttctc atgctccgtg atgcatgagg ctctgcacaa ccactacacg cagaagagcc   3240

tctccctgtc tccgggtaaa tga                                           3263
```

<210> SEQ ID NO 141
<211> LENGTH: 987
<212> TYPE: PRT
<213> ORGANISM: Artificial Sequence
<220> FEATURE:
<223> OTHER INFORMATION: Synthetic construct: FIX-089 amino acid
      sequence

<400> SEQUENCE: 141

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415
```

Thr Glu Val Glu Gly Thr Ser Phe Leu Thr Gly Ile Ile Ser Trp Gly
420 425 430

Glu Glu Cys Ala Met Lys Gly Lys Tyr Gly Ile Tyr Thr Lys Val Ser
435 440 445

Arg Tyr Val Asn Trp Ile Lys Glu Lys Thr Lys Leu Thr Asp Lys Thr
450 455 460

His Thr Cys Pro Pro Cys Pro Ala Pro Glu Leu Leu Gly Gly Pro Ser
465 470 475 480

Val Phe Leu Phe Pro Pro Lys Pro Lys Asp Thr Leu Met Ile Ser Arg
485 490 495

Thr Pro Glu Val Thr Cys Val Val Val Asp Val Ser His Glu Asp Pro
500 505 510

Glu Val Lys Phe Asn Trp Tyr Val Asp Gly Val Glu Val His Asn Ala
515 520 525

Lys Thr Lys Pro Arg Glu Glu Gln Tyr Asn Ser Thr Tyr Arg Val Val
530 535 540

Ser Val Leu Thr Val Leu His Gln Asp Trp Leu Asn Gly Lys Glu Tyr
545 550 555 560

Lys Cys Lys Val Ser Asn Lys Ala Leu Pro Ala Pro Ile Glu Lys Thr
565 570 575

Ile Ser Lys Ala Lys Gly Gln Pro Arg Glu Pro Gln Val Tyr Thr Leu
580 585 590

Pro Pro Ser Arg Asp Glu Leu Thr Lys Asn Gln Val Ser Leu Thr Cys
595 600 605

Leu Val Lys Gly Phe Tyr Pro Ser Asp Ile Ala Val Glu Trp Glu Ser
610 615 620

Asn Gly Gln Pro Glu Asn Asn Tyr Lys Thr Thr Pro Pro Val Leu Asp
625 630 635 640

Ser Asp Gly Ser Phe Phe Leu Tyr Ser Lys Leu Thr Val Asp Lys Ser
645 650 655

Arg Trp Gln Gln Gly Asn Val Phe Ser Cys Ser Val Met His Glu Ala
660 665 670

Leu His Asn His Tyr Thr Gln Lys Ser Leu Ser Leu Ser Pro Gly Lys
675 680 685

Gly Gly Gly Gly Ser Gly Gly Gly Gly Ser Gly Gly Gly Gly Ser Gly
690 695 700

Gly Gly Gly Ser Gly Gly Gly Gly Ser Gly Gly Gly Gly Ser Ala Cys
705 710 715 720

Thr Glu Arg Met Ala Leu His Asn Leu Cys Gly Gly Gly Gly Ser Gly
725 730 735

Gly Gly Gly Ser Gly Gly Gly Gly Ser Gly Gly Gly Gly Ser Gly Gly
740 745 750

Gly Gly Ser Gly Gly Gly Gly Ser Asp Lys Thr His Thr Cys Pro Pro
755 760 765

Cys Pro Ala Pro Glu Leu Leu Gly Gly Pro Ser Val Phe Leu Phe Pro
770 775 780

Pro Lys Pro Lys Asp Thr Leu Met Ile Ser Arg Thr Pro Glu Val Thr
785 790 795 800

Cys Val Val Val Asp Val Ser His Glu Asp Pro Glu Val Lys Phe Asn
805 810 815

Trp Tyr Val Asp Gly Val Glu Val His Asn Ala Lys Thr Lys Pro Arg
820 825 830

Glu Glu Gln Tyr Asn Ser Thr Tyr Arg Val Val Ser Val Leu Thr Val

```
        835                 840                 845

Leu His Gln Asp Trp Leu Asn Gly Lys Glu Tyr Lys Cys Lys Val Ser
    850                 855                 860

Asn Lys Ala Leu Pro Ala Pro Ile Glu Lys Thr Ile Ser Lys Ala Lys
865                 870                 875                 880

Gly Gln Pro Arg Glu Pro Gln Val Tyr Thr Leu Pro Pro Ser Arg Asp
                885                 890                 895

Glu Leu Thr Lys Asn Gln Val Ser Leu Thr Cys Leu Val Lys Gly Phe
            900                 905                 910

Tyr Pro Ser Asp Ile Ala Val Glu Trp Glu Ser Asn Gly Gln Pro Glu
        915                 920                 925

Asn Asn Tyr Lys Thr Thr Pro Pro Val Leu Asp Ser Asp Gly Ser Phe
    930                 935                 940

Phe Leu Tyr Ser Lys Leu Thr Val Asp Lys Ser Arg Trp Gln Gln Gly
945                 950                 955                 960

Asn Val Phe Ser Cys Ser Val Met His Glu Ala Leu His Asn His Tyr
                965                 970                 975

Thr Gln Lys Ser Leu Ser Leu Ser Pro Gly Lys
            980                 985
```

<210> SEQ ID NO 142
<211> LENGTH: 2588
<212> TYPE: DNA
<213> ORGANISM: Artificial Sequence
<220> FEATURE:
<223> OTHER INFORMATION: Synthetic construct: DNA sequence for FIX-090

<400> SEQUENCE: 142

```
atgcagcgcg tgaacatgat catggcagaa tcaccaggcc tcatcaccat ctgcctttta     60

ggatatctac tcagtgctga atgtacaggt ttgtttcctt ttttaaaata cattgagtat    120

gcttgccttt tagatataga aatatctgat gctgtcttct tcactaaatt ttgattacat    180

gatttgacag caatattgaa gagtctaaca gccagcacgc aggttggtaa gtactgtggg    240

aacatcacag attttggctc catgccctaa agagaaattg gctttcagat tatttggatt    300

aaaaacaaag actttcttaa gagatgtaaa attttcatga tgttttcttt tttgctaaaa    360

ctaaagaatt attcttttac atttcagttt ttcttgatca tgaaaacgcc aacaaaattc    420

tgaatcggcc aaagaggtat aattcaggta aattggaaga gtttgttcaa gggaatctag    480

agagagaatg tatggaagaa aagtgtagtt ttgaagaagc acgagaagtt tttgaaaaca    540

ctgaaagaac aactgaattt tggaagcagt atgttgatgg agatcagtgt gagtccaatc    600

catgtttaaa tggcggcagt tgcaaggatg acattaattc ctatgaatgt tggtgtccct    660

ttggatttga aggaaagaac tgtgaattag atgtaacatg taacattaag aatggcagat    720

gcgagcagtt ttgtaaaaat agtgctgata acaaggtggt ttgctcctgt actgagggat    780

atcgacttgc agaaaaccag aagtcctgtg aaccagcagt gccatttcca tgtggaagag    840

tttctgtttc acaaacttct aagctcaccc gtgctgagac tgtttttcct gatgtggact    900

atgtaaattc tactgaagct gaaaccattt tggataacat cactcaaagc acccaatcat    960

ttaatgactt cactcgggtt gttggtggag aagatgccaa accaggtcaa ttcccttggc   1020

aggttgtttt gaatggtaaa gttgatgcat tctgtggagg ctctatcgtt aatgaaaaat   1080

ggattgtaac tgctgcccac tgtgttgaaa ctggtgttaa aattacagtt gtcgcaggtg   1140

aacataatat tgaggagaca gaacatacag agcaaaagcg aaatgtgatt cgaattattc   1200
```

```
ctcaccacaa ctacaatgca gctattaata agtacaacca tgacattgcc cttctggaac   1260

tggacgaacc cttagtgcta aacagctacg ttacacctat ttgcattgct gacaaggaat   1320

acacgaacat cttcctcaaa tttggatctg gctatgtaag tggctgggga agagtcttcc   1380

acaaagggag atcagcttta gttcttcagt accttagagt tccacttgtt gaccgagcca   1440

catgtcttcg atctacaaag ttcaccatct ataacaacat gttctgtgct ggcttccatg   1500

aaggaggtag agattcatgt caaggagata gtgggggacc ccatgttact gaagtggaag   1560

ggaccagttt cttaactgga attattagct ggggtgaaga gtgtgcaatg aaaggcaaat   1620

atggaatata taccaaggtg tcccggtatg tcaactggat taaggaaaaa acaaagctca   1680

ctggtggcgg tggctccggc ggaggtgggt ccggtggcgg cggatcaggt gggggtggat   1740

caggcggtgg aggttccggt ggcgggggat cagcgcaggt gcagctgcag gagtctgggg   1800

gaggcttggt acagcctggg gggtccctga gactctcctg tgcagcctct ggattcatgt   1860

ttagcaggta tgccatgagc tgggtccgcc aggctccagg gaaggggcca gagtgggtct   1920

caggtattag tggtagtggt ggtagtacat actacgcaga ctccgtgaag ggccggttca   1980

ccgtctccag agacaattcc aagaacacgc tgtatctgca aatgaacagc ctgagagccg   2040

aggacacggc tgtatattac tgcgcccggg gcgccaccta caccagccgg agcgacgtgc   2100

ccgaccagac cagcttcgac tactggggcc agggaaccct ggtcaccgtc tcctcaggga   2160

gtgcatccgc cccaaagctt gaagaaggtg aattttcaga agcacgcgta tctgaactga   2220

ctcaggaccc tgctgtgtct gtggccttgg gacagacagt caggatcaca tgccaaggag   2280

acagcctcag aaacttttat gcaagctggt accagcagaa gccaggacag gcccctactc   2340

ttgtcatcta tggtttaagt aaaaggccct cagggatccc agaccgattc tctgcctcca   2400

gctcaggaaa cacagcttcc ttgaccatca ctggggctca ggcggaagat gaggctgact   2460

attactgcct gctgtactac ggcggcggcc agcagggcgt gttcggcggc ggcaccaagc   2520

tgaccgtcct acgtcagccc aaggctgccc cctcggtcac tctgttcccg ccctcttctg   2580

cggcctga                                                            2588
```

```
<210> SEQ ID NO 143
<211> LENGTH: 762
<212> TYPE: PRT
<213> ORGANISM: Artificial Sequence
<220> FEATURE:
<223> OTHER INFORMATION: Synthetic construct: FIX-90 amino acid sequence

<400> SEQUENCE: 143

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110
```

```
Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Gly Gly Gly
    450                 455                 460

Gly Ser Gly Gly Gly Gly Ser Gly Gly Gly Gly Ser Gly Gly Gly Gly
465                 470                 475                 480

Ser Gly Gly Gly Gly Ser Gly Gly Gly Gly Ser Ala Gln Val Gln Leu
                485                 490                 495

Gln Glu Ser Gly Gly Gly Leu Val Gln Pro Gly Gly Ser Leu Arg Leu
            500                 505                 510

Ser Cys Ala Ala Ser Gly Phe Met Phe Ser Arg Tyr Ala Met Ser Trp
        515                 520                 525

Val Arg Gln Ala Pro Gly Lys Gly Pro Glu Trp Val Ser Gly Ile Ser
```

```
    530                 535                 540

Gly Ser Gly Gly Ser Thr Tyr Tyr Ala Asp Ser Val Lys Gly Arg Phe
545                 550                 555                 560

Thr Val Ser Arg Asp Asn Ser Lys Asn Thr Leu Tyr Leu Gln Met Asn
                565                 570                 575

Ser Leu Arg Ala Glu Asp Thr Ala Val Tyr Tyr Cys Ala Arg Gly Ala
            580                 585                 590

Thr Tyr Thr Ser Arg Ser Asp Val Pro Asp Gln Thr Ser Phe Asp Tyr
        595                 600                 605

Trp Gly Gln Gly Thr Leu Val Thr Val Ser Ser Gly Ser Ala Ser Ala
    610                 615                 620

Pro Lys Leu Glu Glu Gly Glu Phe Ser Glu Ala Arg Val Ser Glu Leu
625                 630                 635                 640

Thr Gln Asp Pro Ala Val Ser Val Ala Leu Gly Gln Thr Val Arg Ile
                645                 650                 655

Thr Cys Gln Gly Asp Ser Leu Arg Asn Phe Tyr Ala Ser Trp Tyr Gln
            660                 665                 670

Gln Lys Pro Gly Gln Ala Pro Thr Leu Val Ile Tyr Gly Leu Ser Lys
        675                 680                 685

Arg Pro Ser Gly Ile Pro Asp Arg Phe Ser Ala Ser Ser Ser Gly Asn
    690                 695                 700

Thr Ala Ser Leu Thr Ile Thr Gly Ala Gln Ala Glu Asp Glu Ala Asp
705                 710                 715                 720

Tyr Tyr Cys Leu Leu Tyr Tyr Gly Gly Gly Gln Gln Gly Val Phe Gly
                725                 730                 735

Gly Gly Thr Lys Leu Thr Val Leu Arg Gln Pro Lys Ala Ala Pro Ser
            740                 745                 750

Val Thr Leu Phe Pro Pro Ser Ser Ala Ala
        755                 760
```

<210> SEQ ID NO 144
<211> LENGTH: 3744
<212> TYPE: DNA
<213> ORGANISM: Artificial Sequence
<220> FEATURE:
<223> OTHER INFORMATION: Synthetic construct: DNA sequence for FVII-088

<400> SEQUENCE: 144

```
atggtctccc aggccctcag gctcctctgc cttctgcttg ggcttcaggg ctgcctggct     60

gcagtcttcg taacccagga ggaagcccac ggcgtcctgc accggcgccg gcgcgccaac    120

gcgttcctgg aggagctgcg gccgggctcc ctggagaggg agtgcaagga ggagcagtgc    180

tccttcgagg aggcccggga gatcttcaag gacgcggaga ggacgaagct gttctggatt    240

tcttacagtg atggggacca gtgtgcctca agtccatgcc agaatggggg ctcctgcaag    300

gaccagctcc agtcctatat ctgcttctgc ctccctgcct tcgagggccg gaactgtgag    360

acgcacaagg atgaccagct gatctgtgtg aacgagaacg gcggctgtga gcagtactgc    420

agtgaccaca cgggcaccaa gcgctcctgt cggtgccacg aggggtactc tctgctggca    480

gacggggtgt cctgcacacc cacagttgaa tatccatgtg gaaaaatacc tattctagaa    540

aaaagaaatg ccagcaaacc ccaaggccga attgtggggg gcaaggtgtg ccccaaaggg    600

gagtgtccat ggcaggtcct gttgttggtg aatggagctc agttgtgtgg ggggaccctg    660

atcaacacca tctgggtggt ctccgcggcc cactgtttcg acaaaatcaa gaactggagg    720

aacctgatcg cggtgctggg cgagcacgac ctcagcgagc acgacgggga tgagcagagc    780
```

cggcgggtgg cgcaggtcat catccccagc acgtacgtcc cgggcaccac caaccacgac 840
atcgcgctgc tccgcctgca ccagcccgtg gtcctcactg accatgtggt gcccctctgc 900
ctgcccgaac ggacgttctc tgagaggacg ctggccttcg tgcgcttctc attggtcagc 960
ggctggggcc agctgctgga ccgtggcgcc acggccctgg agctcatggt cctcaacgtg 1020
ccccggctga tgacccagga ctgcctgcag cagtcacgga aggtgggaga ctccccaaat 1080
atcacggagt acatgttctg tgccggctac tcggatggca gcaaggactc ctgcaagggg 1140
gacagtggag gcccacatgc cacccactac cggggcacgt ggtacctgac gggcatcgtc 1200
agctggggcc agggctgcgc aaccgtgggc cactttgggg tgtacaccag ggtctcccag 1260
tacatcgagt ggctgcaaaa gctcatgcgc tcagagccac gcccaggagt cctcctgcga 1320
gccccatttc ccggtggcgg tggctccggc ggaggtgggt ccggtggcgg cggatcaggt 1380
gggggtggat caggcggtgg aggttccggt ggcgggggat ccgacaaaac tcacacatgc 1440
ccaccgtgcc cagctccgga actcctggga ggaccgtcag tcttcctctt ccccccaaaa 1500
cccaaggaca ccctcatgat ctcccggacc cctgaggtca catgcgtggt ggtggacgtg 1560
agccacgaag accctgaggt caagttcaac tggtacgtgg acggcgtgga ggtgcataat 1620
gccaagacaa agccgcggga ggagcagtac aacagcacgt accgtgtggt cagcgtcctc 1680
accgtcctgc accaggactg gctgaatggc aaggagtaca agtgcaaggt ctccaacaaa 1740
gccctcccag cccccatcga gaaaaccatc tccaaagcca aagggcagcc ccgagaacca 1800
caggtgtaca ccctgccccc atcccgggat gagctgacca agaaccaggt cagcctgacc 1860
tgcctggtca aaggcttcta tcccagcgac atcgccgtgg agtgggagag caatgggcag 1920
ccggagaaca actacaagac cacgcctccc gtgttggact ccgacggctc cttcttcctc 1980
tacagcaagc tcaccgtcga caagagcagg tggcagcagg ggaacgtctt ctcatgctcc 2040
gtgatgcatg aggctctgca caaccactac acgcagaaga gcctctccct gtctccgggt 2100
aaacggcgcc gccggagcgg tggcggcgga tcaggtgggg gtggatcagg cggtggaggt 2160
tccggtggcg gggggatccgg cggtggaggt tccggtgggg gtggatcaag gaagaggagg 2220
aagagggaca tcgtgatgac ccaggccgcc cccagcgtgc ccgtgacccc cggcgagagc 2280
gtgagcatca gctgccggag cagccggagc ctgctgcaca gcaacggcaa cacctacctg 2340
tgctggttcc tgcagcggcc cggccagagc ccccagctgc tgatctaccg gatgagcaac 2400
ctggccagcg gcgtgcccga ccggttcagc ggcagcggca gcggcaccgc cttcaccctg 2460
cggatcagcc gggtggaggc cgaggacgtg ggcgtgtact actgcatgca gcacctggag 2520
taccccttca ccttcggcag cggcaccaag ctggagatca agcggggcgg cggcggcagc 2580
ggcggcggcg gcagcggcgg cggcggcagc caggtgcagc tgcagcagag cggcgccgag 2640
ctggtgcggc ccggcaccag cgtgaagatc agctgcaagg ccagcggcta caccttcacc 2700
aactactggc tgggctgggt gaagcagcgg cccggccacg gcctggagtg gatcggcgac 2760
atctaccccg gcggcggcta caacaagtac aacgagaact tcaagggcaa ggccaccctg 2820
accgccgaca ccagcagcag caccgcctac atgcagctga gcagcctgac cagcgaggac 2880
agcgccgtgt acttctgcgc ccgggagtac ggcaactacg actacgccat ggacagctgg 2940
ggccagggca ccagcgtgac cgtgagcagc ggtggcggtg gctccggcgg aggtgggtcc 3000
ggtggcggcg gatcaggtgg gggtggatca ggcggtggag gttccggtgg cgggggatca 3060
gacaaaactc acacatgccc accgtgccca gcaccggaac tcctgggcgg accgtcagtc 3120

```
ttcctcttcc ccccaaaacc caaggacacc ctcatgatct cccggacccc tgaggtcaca   3180

tgcgtggtgg tggacgtgag ccacgaagac cctgaggtca agttcaactg gtacgtggac   3240

ggcgtggagg tgcataatgc caagacaaag ccgcgggagg agcagtacaa cagcacgtac   3300

cgtgtggtca gcgtcctcac cgtcctgcac caggactggc tgaatggcaa ggagtacaag   3360

tgcaaggtct ccaacaaagc cctcccagcc cccatcgaga aaaccatctc caaagccaaa   3420

gggcagcccc gagaaccaca ggtgtacacc ctgcccccat cccgggatga gctgaccaag   3480

aaccaggtca gcctgacctg cctggtcaaa ggcttctatc ccagcgacat cgccgtggag   3540

tgggagagca atgggcagcc ggagaacaac tacaagacca cgcctcccgt gttggactcc   3600

gacggctcct tcttcctcta cagcaagctc accgtggaca agagcaggtg gcagcagggg   3660

aacgtcttct catgctccgt gatgcatgag gctctgcaca accactacac gcagaagagc   3720

ctctccctgt ctccgggtaa atga                                          3744
```

<210> SEQ ID NO 145
<211> LENGTH: 1247
<212> TYPE: PRT
<213> ORGANISM: Artificial Sequence
<220> FEATURE:
<223> OTHER INFORMATION: Synthetic construct: FVII-088 amino acid sequence

<400> SEQUENCE: 145

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
```

-continued

```
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Gly Gly Gly
        435                 440                 445

Ser Gly Gly Gly Gly Ser Gly Gly Gly Gly Ser Gly Gly Gly Gly Ser
    450                 455                 460

Gly Gly Gly Gly Ser Gly Gly Gly Gly Ser Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670
```

```
Gln Gly Asn Val Phe Ser Cys Ser Val Met His Glu Ala Leu His Asn
        675                 680                 685

His Tyr Thr Gln Lys Ser Leu Ser Leu Ser Pro Gly Lys Arg Arg Arg
    690                 695                 700

Arg Ser Gly Gly Gly Gly Ser Gly Gly Gly Gly Ser Gly Gly Gly Gly
705                 710                 715                 720

Ser Gly Gly Gly Gly Ser Gly Gly Gly Gly Ser Gly Gly Gly Gly Ser
                725                 730                 735

Arg Lys Arg Arg Lys Arg Asp Ile Val Met Thr Gln Ala Ala Pro Ser
            740                 745                 750

Val Pro Val Thr Pro Gly Glu Ser Val Ser Ile Ser Cys Arg Ser Ser
        755                 760                 765

Arg Ser Leu Leu His Ser Asn Gly Asn Thr Tyr Leu Cys Trp Phe Leu
    770                 775                 780

Gln Arg Pro Gly Gln Ser Pro Gln Leu Leu Ile Tyr Arg Met Ser Asn
785                 790                 795                 800

Leu Ala Ser Gly Val Pro Asp Arg Phe Ser Gly Ser Gly Ser Gly Thr
                805                 810                 815

Ala Phe Thr Leu Arg Ile Ser Arg Val Glu Ala Glu Asp Val Gly Val
            820                 825                 830

Tyr Tyr Cys Met Gln His Leu Glu Tyr Pro Phe Thr Phe Gly Ser Gly
        835                 840                 845

Thr Lys Leu Glu Ile Lys Arg Gly Gly Gly Gly Ser Gly Gly Gly Gly
    850                 855                 860

Ser Gly Gly Gly Gly Ser Gln Val Gln Leu Gln Gln Ser Gly Ala Glu
865                 870                 875                 880

Leu Val Arg Pro Gly Thr Ser Val Lys Ile Ser Cys Lys Ala Ser Gly
                885                 890                 895

Tyr Thr Phe Thr Asn Tyr Trp Leu Gly Trp Val Lys Gln Arg Pro Gly
            900                 905                 910

His Gly Leu Glu Trp Ile Gly Asp Ile Tyr Pro Gly Gly Gly Tyr Asn
        915                 920                 925

Lys Tyr Asn Glu Asn Phe Lys Gly Lys Ala Thr Leu Thr Ala Asp Thr
    930                 935                 940

Ser Ser Ser Thr Ala Tyr Met Gln Leu Ser Ser Leu Thr Ser Glu Asp
945                 950                 955                 960

Ser Ala Val Tyr Phe Cys Ala Arg Glu Tyr Gly Asn Tyr Asp Tyr Ala
                965                 970                 975

Met Asp Ser Trp Gly Gln Gly Thr Ser Val Thr Val Ser Ser Gly Gly
            980                 985                 990

Gly Gly Ser Gly Gly Gly Gly Ser  Gly Gly Gly Gly Ser  Gly Gly Gly
        995                 1000                1005

Gly Ser  Gly Gly Gly Gly Ser  Gly Gly Gly Gly Ser  Asp Lys Thr
    1010                1015                1020

His Thr  Cys Pro Pro Cys Pro  Ala Pro Glu Leu Leu  Gly Gly Pro
    1025                1030                1035

Ser Val  Phe Leu Phe Pro Pro  Lys Pro Lys Asp Thr  Leu Met Ile
    1040                1045                1050

Ser Arg  Thr Pro Glu Val Thr  Cys Val Val Val Asp  Val Ser His
    1055                1060                1065

Glu Asp  Pro Glu Val Lys Phe  Asn Trp Tyr Val Asp  Gly Val Glu
    1070                1075                1080
```

```
Val His  Asn Ala Lys Thr Lys  Pro Arg Glu Glu Gln  Tyr Asn Ser
    1085                 1090                 1095

Thr Tyr  Arg Val Val Ser Val  Leu Thr Val Leu His  Gln Asp Trp
    1100                 1105                 1110

Leu Asn  Gly Lys Glu Tyr Lys  Cys Lys Val Ser Asn  Lys Ala Leu
    1115                 1120                 1125

Pro Ala  Pro Ile Glu Lys Thr  Ile Ser Lys Ala Lys  Gly Gln Pro
    1130                 1135                 1140

Arg Glu  Pro Gln Val Tyr Thr  Leu Pro Pro Ser Arg  Asp Glu Leu
    1145                 1150                 1155

Thr Lys  Asn Gln Val Ser Leu  Thr Cys Leu Val Lys  Gly Phe Tyr
    1160                 1165                 1170

Pro Ser  Asp Ile Ala Val Glu  Trp Glu Ser Asn Gly  Gln Pro Glu
    1175                 1180                 1185

Asn Asn  Tyr Lys Thr Thr Pro  Pro Val Leu Asp Ser  Asp Gly Ser
    1190                 1195                 1200

Phe Phe  Leu Tyr Ser Lys Leu  Thr Val Asp Lys Ser  Arg Trp Gln
    1205                 1210                 1215

Gln Gly  Asn Val Phe Ser Cys  Ser Val Met His Glu  Ala Leu His
    1220                 1225                 1230

Asn His  Tyr Thr Gln Lys Ser  Leu Ser Leu Ser Pro  Gly Lys
    1235                 1240                 1245


<210> SEQ ID NO 146
<211> LENGTH: 5796
<212> TYPE: DNA
<213> ORGANISM: Artificial Sequence
<220> FEATURE:
<223> OTHER INFORMATION: Synthetic construct: DNA sequence for FVIII-041

<400> SEQUENCE: 146

atgcaaatag agctctccac ctgcttcttt ctgtgccttt tgcgattctg ctttagtgcc     60

accagaagat actacctggg tgcagtggaa ctgtcatggg actatatgca aagtgatctc    120

ggtgagctgc ctgtggacgc aagatttcct cctagagtgc caaaatcttt tccattcaac    180

acctcagtcg tgtacaaaaa gactctgttt gtagaattca cggatcacct tttcaacatc    240

gctaagccaa ggccaccctg gatgggtctg ctaggtccta ccatccaggc tgaggtttat    300

gatacagtgg tcattacact taagaacatg gcttcccatc ctgtcagtct tcatgctgtt    360

ggtgtatcct actggaaagc ttctgaggga gctgaatatg atgatcagac cagtcaaagg    420

gagaaagaag atgataaagt cttccctggt ggaagccata catatgtctg gcaggtcctg    480

aaagagaatg gtccaatggc ctctgaccca ctgtgcctta cctactcata tctttctcat    540

gtggacctgg taaaagactt gaattcaggc ctcattggag ccctactagt atgtagagaa    600

gggagtctgg ccaaggaaaa gacacagacc ttgcacaaat ttatactact ttttgctgta    660

tttgatgaag ggaaaagttg gcactcagaa acaaagaact ccttgatgca ggatagggat    720

gctgcatctg ctcgggcctg gcctaaaatg cacacagtca atggttatgt aaacaggtct    780

ctgccaggtc tgattggatg ccacaggaaa tcagtctatt ggcatgtgat tggaatgggc    840

accactcctg aagtgcactc aatattcctc gaaggtcaca catttcttgt gaggaaccat    900

cgccaggcgt ccttggaaat ctcgccaata actttcctta ctgctcaaac actcttgatg    960

gaccttggac agtttctact gttttgtcat atctcttccc accaacatga tggcatggaa   1020

gcttatgtca aagtagacag ctgtccagag gaaccccaac tacgaatgaa aaataatgaa   1080
```

-continued

```
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt tttcaccat ctttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac actttttctg   3420
gtgtacagca ataagtgtca gactcccctg ggaatggctt ctggacacat tagagatttt   3480
```

```
cagattacag cttcaggaca atatggacag tgggccccaa agctggccag acttcattat   3540
tccggatcaa tcaatgcctg gagcaccaag gagccctttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata tttttaaccc tccaattatt gctcgataca tccgtttgca cccaactcat   3840
tatagcattc gcagcactct tcgcatggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga aagtcacagg agtaactact cagggagtaa aatctctgct taccagcatg   4140
tatgtgaagg agttcctcat ctccagcagt caagatggcc atcagtggac tctctttttt   4200
cagaatggca aagtaaaggt ttttcaggga aatcaagact ccttcacacc tgtggtgaac   4260
tctctagacc caccgttact gactcgctac cttcgaattc acccccagag ttgggtgcac   4320
cagattgccc tgaggatgga ggttctgggc tgcgaggcac aggacctcta cgacaaaact   4380
cacacatgcc caccgtgccc agctccagaa ctcctgggcg gaccgtcagt cttcctcttc   4440
cccccaaaac ccaaggacac cctcatgatc tcccggaccc ctgaggtcac atgcgtggtg   4500
gtggacgtga gccacgaaga ccctgaggtc aagttcaact ggtacgtgga cggcgtggag   4560
gtgcataatg ccaagacaaa gccgcgggag gagcagtaca acagcacgta ccgtgtggtc   4620
agcgtcctca ccgtcctgca ccaggactgg ctgaatggca aggagtacaa gtgcaaggtc   4680
tccaacaaag ccctcccagc ccccatcgag aaaaccatct ccaaagccaa agggcagccc   4740
cgagaaccac aggtgtacac cctgccccca tcccgggatg agctgaccaa gaaccaggtc   4800
agcctgacct gcctggtcaa aggcttctat cccagcgaca tcgccgtgga gtgggagagc   4860
aatgggcagc cggagaacaa ctacaagacc acgcctcccg tgttggactc cgacggctcc   4920
ttcttcctct acagcaagct caccgtggac aagagcaggt ggcagcaggg gaacgtcttc   4980
tcatgctccg tgatgcatga ggctctgcac aaccactaca cgcagaagag cctctccctg   5040
tctccgggta aaggtggcgg cggatcaggt gggggtggat caggcggtgg aggttccggt   5100
ggcgggggat cagacaaaac tcacacatgc ccaccgtgcc cagcacctga actcctggga   5160
ggaccgtcag tcttcctctt ccccccaaaa cccaaggaca ccctcatgat ctcccggacc   5220
cctgaggtca catgcgtggt ggtggacgtg agccacgaag accctgaggt caagttcaac   5280
tggtacgtgg acggcgtgga ggtgcataat gccaagacaa agccgcggga ggagcagtac   5340
aacagcacgt accgtgtggt cagcgtcctc accgtcctgc accaggactg gctgaatggc   5400
aaggagtaca agtgcaaggt ctccaacaaa gccctcccag cccccatcga gaaaaccatc   5460
tccaaagcca aagggcagcc ccgagaacca caggtgtaca ccctgccccc atcccgcgat   5520
gagctgacca agaaccaggt cagcctgacc tgcctggtca aaggcttcta tcccagcgac   5580
atcgccgtgg agtgggagag caatgggcag ccggagaaca actacaagac cacgcctccc   5640
gtgttggact ccgacggctc cttcttcctc tacagcaagc tcaccgtgga caagagcagg   5700
tggcagcagg ggaacgtctt ctcatgctcc gtgatgcatg aggctctgca caaccactac   5760
acgcagaaga gcctctccct gtctccgggt aaatga                             5796
```

<210> SEQ ID NO 147
<211> LENGTH: 1931
<212> TYPE: PRT
<213> ORGANISM: Artificial Sequence
<220> FEATURE:
<223> OTHER INFORMATION: Synthetic construct: FVIII-041 amino acid sequence

<400> SEQUENCE: 147

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Ile Thr Leu Lys Asn Met Ala Ser
100 105 110

His Pro Val Ser Leu His Ala Val Gly Val Ser Tyr Trp Lys Ala Ser
115 120 125

Glu Gly Ala Glu Tyr Asp Asp Gln Thr Ser Gln Arg Glu Lys Glu Asp
130 135 140

Asp Lys Val Phe Pro Gly Gly Ser His Thr Tyr Val Trp Gln Val Leu
145 150 155 160

Lys Glu Asn Gly Pro Met Ala Ser Asp Pro Leu Cys Leu Thr Tyr Ser
165 170 175

Tyr Leu Ser His Val Asp Leu Val Lys Asp Leu Asn Ser Gly Leu Ile
180 185 190

Gly Ala Leu Leu Val Cys Arg Glu Gly Ser Leu Ala Lys Glu Lys Thr
195 200 205

Gln Thr Leu His Lys Phe Ile Leu Leu Phe Ala Val Phe Asp Glu Gly
210 215 220

Lys Ser Trp His Ser Glu Thr Lys Asn Ser Leu Met Gln Asp Arg Asp
225 230 235 240

Ala Ala Ser Ala Arg Ala Trp Pro Lys Met His Thr Val Asn Gly Tyr
245 250 255

Val Asn Arg Ser Leu Pro Gly Leu Ile Gly Cys His Arg Lys Ser Val
260 265 270

Tyr Trp His Val Ile Gly Met Gly Thr Thr Pro Glu Val His Ser Ile
275 280 285

Phe Leu Glu Gly His Thr Phe Leu Val Arg Asn His Arg Gln Ala Ser
290 295 300

Leu Glu Ile Ser Pro Ile Thr Phe Leu Thr Ala Gln Thr Leu Leu Met
305 310 315 320

Asp Leu Gly Gln Phe Leu Leu Phe Cys His Ile Ser Ser His Gln His
325 330 335

Asp Gly Met Glu Ala Tyr Val Lys Val Asp Ser Cys Pro Glu Glu Pro
340 345 350

Gln Leu Arg Met Lys Asn Asn Glu Glu Ala Glu Asp Tyr Asp Asp Asp
355 360 365

```
Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780
```

```
Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
```

```
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230

Gly Lys  Lys Trp Gln Thr Tyr  Arg Gly Asn Ser Thr  Gly Thr Leu
    1235                1240                1245

Met Val  Phe Phe Gly Asn Val  Asp Ser Ser Gly Ile  Lys His Asn
    1250                1255                1260

Ile Phe  Asn Pro Pro Ile Ile  Ala Arg Tyr Ile Arg  Leu His Pro
    1265                1270                1275

Thr His  Tyr Ser Ile Arg Ser  Thr Leu Arg Met Glu  Leu Met Gly
    1280                1285                1290

Cys Asp  Leu Asn Ser Cys Ser  Met Pro Leu Gly Met  Glu Ser Lys
    1295                1300                1305

Ala Ile  Ser Asp Ala Gln Ile  Thr Ala Ser Ser Tyr  Phe Thr Asn
    1310                1315                1320

Met Phe  Ala Thr Trp Ser Pro  Ser Lys Ala Arg Leu  His Leu Gln
    1325                1330                1335

Gly Arg  Ser Asn Ala Trp Arg  Pro Gln Val Asn Asn  Pro Lys Glu
    1340                1345                1350

Trp Leu  Gln Val Asp Phe Gln  Lys Thr Met Lys Val  Thr Gly Val
    1355                1360                1365

Thr Thr  Gln Gly Val Lys Ser  Leu Leu Thr Ser Met  Tyr Val Lys
    1370                1375                1380

Glu Phe  Leu Ile Ser Ser Ser  Gln Asp Gly His Gln  Trp Thr Leu
    1385                1390                1395

Phe Phe  Gln Asn Gly Lys Val  Lys Val Phe Gln Gly  Asn Gln Asp
    1400                1405                1410

Ser Phe  Thr Pro Val Val Asn  Ser Leu Asp Pro Pro  Leu Leu Thr
    1415                1420                1425

Arg Tyr  Leu Arg Ile His Pro  Gln Ser Trp Val His  Gln Ile Ala
    1430                1435                1440

Leu Arg  Met Glu Val Leu Gly  Cys Glu Ala Gln Asp  Leu Tyr Asp
    1445                1450                1455

Lys Thr  His Thr Cys Pro Pro  Cys Pro Ala Pro Glu  Leu Leu Gly
    1460                1465                1470

Gly Pro  Ser Val Phe Leu Phe  Pro Pro Lys Pro Lys  Asp Thr Leu
    1475                1480                1485

Met Ile  Ser Arg Thr Pro Glu  Val Thr Cys Val Val  Val Asp Val
    1490                1495                1500

Ser His  Glu Asp Pro Glu Val  Lys Phe Asn Trp Tyr  Val Asp Gly
    1505                1510                1515

Val Glu  Val His Asn Ala Lys  Thr Lys Pro Arg Glu  Glu Gln Tyr
    1520                1525                1530

Asn Ser  Thr Tyr Arg Val Val  Ser Val Leu Thr Val  Leu His Gln
    1535                1540                1545

Asp Trp  Leu Asn Gly Lys Glu  Tyr Lys Cys Lys Val  Ser Asn Lys
    1550                1555                1560

Ala Leu  Pro Ala Pro Ile Glu  Lys Thr Ile Ser Lys  Ala Lys Gly
    1565                1570                1575

Gln Pro  Arg Glu Pro Gln Val  Tyr Thr Leu Pro Pro  Ser Arg Asp
    1580                1585                1590
```

```
Glu Leu Thr Lys Asn Gln Val Ser Leu Thr Cys Leu Val Lys Gly
    1595                1600                1605

Phe Tyr Pro Ser Asp Ile Ala Val Glu Trp Glu Ser Asn Gly Gln
    1610                1615                1620

Pro Glu Asn Asn Tyr Lys Thr Thr Pro Pro Val Leu Asp Ser Asp
    1625                1630                1635

Gly Ser Phe Phe Leu Tyr Ser Lys Leu Thr Val Asp Lys Ser Arg
    1640                1645                1650

Trp Gln Gln Gly Asn Val Phe Ser Cys Ser Val Met His Glu Ala
    1655                1660                1665

Leu His Asn His Tyr Thr Gln Lys Ser Leu Ser Leu Ser Pro Gly
    1670                1675                1680

Lys Gly Gly Gly Gly Ser Gly Gly Gly Gly Ser Gly Gly Gly Gly
    1685                1690                1695

Ser Gly Gly Gly Gly Ser Asp Lys Thr His Thr Cys Pro Pro Cys
    1700                1705                1710

Pro Ala Pro Glu Leu Leu Gly Gly Pro Ser Val Phe Leu Phe Pro
    1715                1720                1725

Pro Lys Pro Lys Asp Thr Leu Met Ile Ser Arg Thr Pro Glu Val
    1730                1735                1740

Thr Cys Val Val Val Asp Val Ser His Glu Asp Pro Glu Val Lys
    1745                1750                1755

Phe Asn Trp Tyr Val Asp Gly Val Glu Val His Asn Ala Lys Thr
    1760                1765                1770

Lys Pro Arg Glu Glu Gln Tyr Asn Ser Thr Tyr Arg Val Val Ser
    1775                1780                1785

Val Leu Thr Val Leu His Gln Asp Trp Leu Asn Gly Lys Glu Tyr
    1790                1795                1800

Lys Cys Lys Val Ser Asn Lys Ala Leu Pro Ala Pro Ile Glu Lys
    1805                1810                1815

Thr Ile Ser Lys Ala Lys Gly Gln Pro Arg Glu Pro Gln Val Tyr
    1820                1825                1830

Thr Leu Pro Pro Ser Arg Asp Glu Leu Thr Lys Asn Gln Val Ser
    1835                1840                1845

Leu Thr Cys Leu Val Lys Gly Phe Tyr Pro Ser Asp Ile Ala Val
    1850                1855                1860

Glu Trp Glu Ser Asn Gly Gln Pro Glu Asn Asn Tyr Lys Thr Thr
    1865                1870                1875

Pro Pro Val Leu Asp Ser Asp Gly Ser Phe Phe Leu Tyr Ser Lys
    1880                1885                1890

Leu Thr Val Asp Lys Ser Arg Trp Gln Gln Gly Asn Val Phe Ser
    1895                1900                1905

Cys Ser Val Met His Glu Ala Leu His Asn His Tyr Thr Gln Lys
    1910                1915                1920

Ser Leu Ser Leu Ser Pro Gly Lys
    1925                1930
```

<210> SEQ ID NO 148
<211> LENGTH: 6762
<212> TYPE: DNA
<213> ORGANISM: Artificial Sequence
<220> FEATURE:
<223> OTHER INFORMATION: Synthetic construct: DNA sequence for FVIII-108

<400> SEQUENCE: 148

```
atgcaaatag agctctccac ctgcttcttt ctgtgccttt tgcgattctg ctttagtgcc     60
accagaagat actacctggg tgcagtggaa ctgtcatggg actatatgca aagtgatctc    120
ggtgagctgc ctgtggacgc aagatttcct cctagagtgc caaaatcttt tccattcaac    180
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc catcaacggg aaataactcg tactactctt   2340
```

```
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt tttcaccat ctttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac actttttctg   3420
gtgtacagca ataagtgtca gactcccctg ggaatggctt ctggacacat tagagatttt   3480
cagattacag cttcaggaca atatggacag tgggccccaa agctggccag acttcattat   3540
tccggatcaa tcaatgcctg gagcaccaag gagccctttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata tttttaaccc tccaattatt gctcgataca tccgtttgca cccaactcat   3840
tatagcattc gcagcactct tcgcatggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga aagtcacagg agtaactact cagggagtaa aatctctgct taccagcatg   4140
tatgtgaagg agttcctcat ctccagcagt caagatggcc atcagtggac tctcttttt   4200
cagaatggca aagtaaaggt ttttcaggga aatcaagact ccttcacacc tgtggtgaac   4260
tctctagacc caccgttact gactcgctac cttcgaattc acccccagag ttgggtgcac   4320
cagattgccc tgaggatgga ggttctgggc tgcgaggcac aggacctcta cgacaaaact   4380
cacacatgcc caccgtgccc agcacctgaa ctcctgggag gaccgtcagt cttcctcttc   4440
cccccaaaac ccaaggacac cctcatgatc tcccggaccc ctgaggtcac atgcgtggtg   4500
gtggacgtga gccacgaaga ccctgaggtc aagttcaact ggtacgtgga cggcgtggag   4560
gtgcataatg ccaagacaaa gccgcgggag gagcagtaca acagcacgta ccgtgtggtc   4620
agcgtcctca ccgtcctgca ccaggactgg ctgaatggca aggagtacaa gtgcaaggtc   4680
tccaacaaag ccctcccagc ccccatcgag aaaaccatct ccaaagccaa agggcagccc   4740
```

cgagaaccac aggtgtacac cctgccccca tcccgcgatg agctgaccaa gaaccaggtc 4800
agcctgacct gcctggtcaa aggcttctat cccagcgaca tcgccgtgga gtgggagagc 4860
aatgggcagc cggagaacaa ctacaagacc acgcctcccg tgttggactc cgacggctcc 4920
ttcttcctct acagcaagct caccgtcgac aagagcaggt ggcagcaggg gaacgtcttc 4980
tcatgctccg tgatgcatga ggctctgcac aaccactaca cgcagaagag cctctccctg 5040
tctccgggta aacggcgccg ccggagcggt ggcggcggat caggtggggg tggatcaggc 5100
ggtggaggtt ccggtggcgg gggatccggc ggtggaggtt ccggtggggg tggatcaagg 5160
aagaggagga agagggcgca ggtgcagctg caggagtctg gggggaggctt ggtacagcct 5220
ggggggtccc tgagactctc ctgtgcagcc tctggattca tgtttagcag gtatgccatg 5280
agctgggtcc gccaggctcc agggaagggg ccagagtggg tctcaggtat tagtggtagt 5340
ggtggtagta catactacgc agactccgtg aagggccggt tcaccgtctc cagagacaat 5400
tccaagaaca cgctgtatct gcaaatgaac agcctgagag ccgaggacac ggctgtatat 5460
tactgcgccc ggggcgccac ctacaccagc cggagcgacg tgcccgacca gaccagcttc 5520
gactactggg gccagggaac cctggtcacc gtctcctcag ggagtgcatc cgccccaaag 5580
cttgaagaag gtgaattttc agaagcacgc gtatctgaac tgactcagga ccctgctgtg 5640
tctgtggcct tgggacagac agtcaggatc acatgccaag gagacagcct cagaaacttt 5700
tatgcaagct ggtaccagca gaagccagga caggccccta ctcttgtcat ctatggttta 5760
agtaaaaggc cctcagggat cccagaccga ttctctgcct ccagctcagg aaacacagct 5820
tccttgacca tcactggggc tcaggcggaa gatgaggctg actattactg cctgctgtac 5880
tacggcggcg gccagcaggg cgtgttcggc ggcggcacca agctgaccgt cctacgtcag 5940
cccaaggctg ccccctcggt cactctgttc ccgccctctt ctgcggccgg tggcggtggc 6000
tccggcggag gtgggtccgg tggcggcgga tcaggtgggg gtggatcagg cggtggaggt 6060
tccggtggcg ggggatcaga caaaactcac acatgcccac cgtgcccagc accggaactc 6120
ctgggcggac cgtcagtctt cctcttcccc ccaaaaccca aggacaccct catgatctcc 6180
cggacccctg aggtcacatg cgtggtggtg gacgtgagcc acgaagaccc tgaggtcaag 6240
ttcaactggt acgtggacgg cgtggaggtg cataatgcca agacaaagcc gcgggaggag 6300
cagtacaaca gcacgtaccg tgtggtcagc gtcctcaccg tcctgcacca ggactggctg 6360
aatggcaagg agtacaagtg caaggtctcc aacaaagccc tcccagcccc catcgagaaa 6420
accatctcca aagccaaagg gcagccccga gaaccacagg tgtacaccct gcccccatcc 6480
cgggatgagc tgaccaagaa ccaggtcagc ctgacctgcc tggtcaaagg cttctatccc 6540
agcgacatcg ccgtggagtg ggagagcaat gggcagccgg agaacaacta caagaccacg 6600
cctcccgtgt tggactccga cggctccttc ttcctctaca gcaagctcac cgtggacaag 6660
agcaggtggc agcaggggaa cgtcttctca tgctccgtga tgcatgaggc tctgcacaac 6720
cactacacgc agaagagcct ctccctgtct ccgggtaaat ga 6762

<210> SEQ ID NO 149
<211> LENGTH: 2253
<212> TYPE: PRT
<213> ORGANISM: Artificial Sequence
<220> FEATURE:
<223> OTHER INFORMATION: Synthetic construct: FVIII-108 amino acid
sequence

<400> SEQUENCE: 149

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415
```

-continued

```
Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
```

-continued

```
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230

Gly Lys  Lys Trp Gln Thr Tyr  Arg Gly Asn Ser Thr  Gly Thr Leu
    1235                1240                1245
```

-continued

```
Met Val  Phe Phe Gly Asn Val  Asp Ser Ser Gly Ile  Lys His Asn
    1250                 1255                 1260

Ile Phe  Asn Pro Pro Ile Ile  Ala Arg Tyr Ile Arg  Leu His Pro
    1265                 1270                 1275

Thr His  Tyr Ser Ile Arg Ser  Thr Leu Arg Met Glu  Leu Met Gly
    1280                 1285                 1290

Cys Asp  Leu Asn Ser Cys Ser  Met Pro Leu Gly Met  Glu Ser Lys
    1295                 1300                 1305

Ala Ile  Ser Asp Ala Gln Ile  Thr Ala Ser Ser Tyr  Phe Thr Asn
    1310                 1315                 1320

Met Phe  Ala Thr Trp Ser Pro  Ser Lys Ala Arg Leu  His Leu Gln
    1325                 1330                 1335

Gly Arg  Ser Asn Ala Trp Arg  Pro Gln Val Asn Asn  Pro Lys Glu
    1340                 1345                 1350

Trp Leu  Gln Val Asp Phe Gln  Lys Thr Met Lys Val  Thr Gly Val
    1355                 1360                 1365

Thr Thr  Gln Gly Val Lys Ser  Leu Leu Thr Ser Met  Tyr Val Lys
    1370                 1375                 1380

Glu Phe  Leu Ile Ser Ser Ser  Gln Asp Gly His Gln  Trp Thr Leu
    1385                 1390                 1395

Phe Phe  Gln Asn Gly Lys Val  Lys Val Phe Gln Gly  Asn Gln Asp
    1400                 1405                 1410

Ser Phe  Thr Pro Val Val Asn  Ser Leu Asp Pro Pro  Leu Leu Thr
    1415                 1420                 1425

Arg Tyr  Leu Arg Ile His Pro  Gln Ser Trp Val His  Gln Ile Ala
    1430                 1435                 1440

Leu Arg  Met Glu Val Leu Gly  Cys Glu Ala Gln Asp  Leu Tyr Asp
    1445                 1450                 1455

Lys Thr  His Thr Cys Pro Pro  Cys Pro Ala Pro Glu  Leu Leu Gly
    1460                 1465                 1470

Gly Pro  Ser Val Phe Leu Phe  Pro Pro Lys Pro Lys  Asp Thr Leu
    1475                 1480                 1485

Met Ile  Ser Arg Thr Pro Glu  Val Thr Cys Val Val  Val Asp Val
    1490                 1495                 1500

Ser His  Glu Asp Pro Glu Val  Lys Phe Asn Trp Tyr  Val Asp Gly
    1505                 1510                 1515

Val Glu  Val His Asn Ala Lys  Thr Lys Pro Arg Glu  Glu Gln Tyr
    1520                 1525                 1530

Asn Ser  Thr Tyr Arg Val Val  Ser Val Leu Thr Val  Leu His Gln
    1535                 1540                 1545

Asp Trp  Leu Asn Gly Lys Glu  Tyr Lys Cys Lys Val  Ser Asn Lys
    1550                 1555                 1560

Ala Leu  Pro Ala Pro Ile Glu  Lys Thr Ile Ser Lys  Ala Lys Gly
    1565                 1570                 1575

Gln Pro  Arg Glu Pro Gln Val  Tyr Thr Leu Pro Pro  Ser Arg Asp
    1580                 1585                 1590

Glu Leu  Thr Lys Asn Gln Val  Ser Leu Thr Cys Leu  Val Lys Gly
    1595                 1600                 1605

Phe Tyr  Pro Ser Asp Ile Ala  Val Glu Trp Glu Ser  Asn Gly Gln
    1610                 1615                 1620

Pro Glu  Asn Asn Tyr Lys Thr  Thr Pro Pro Val Leu  Asp Ser Asp
    1625                 1630                 1635
```

-continued

```
Gly Ser  Phe Phe Leu Tyr Ser  Lys Leu Thr Val Asp  Lys Ser Arg
    1640                 1645                 1650

Trp Gln  Gln Gly Asn Val Phe  Ser Cys Ser Val Met  His Glu Ala
    1655                 1660                 1665

Leu His  Asn His Tyr Thr Gln  Lys Ser Leu Ser Leu  Ser Pro Gly
    1670                 1675                 1680

Lys Arg  Arg Arg Arg Ser Gly  Gly Gly Gly Ser Gly  Gly Gly Gly
    1685                 1690                 1695

Ser Gly  Gly Gly Gly Ser Gly  Gly Gly Gly Ser Gly  Gly Gly Gly
    1700                 1705                 1710

Ser Gly  Gly Gly Gly Ser Arg  Lys Arg Arg Lys Arg  Ala Gln Val
    1715                 1720                 1725

Gln Leu  Gln Glu Ser Gly Gly  Gly Leu Val Gln Pro  Gly Gly Ser
    1730                 1735                 1740

Leu Arg  Leu Ser Cys Ala Ala  Ser Gly Phe Met Phe  Ser Arg Tyr
    1745                 1750                 1755

Ala Met  Ser Trp Val Arg Gln  Ala Pro Gly Lys Gly  Pro Glu Trp
    1760                 1765                 1770

Val Ser  Gly Ile Ser Gly Ser  Gly Gly Ser Thr Tyr  Tyr Ala Asp
    1775                 1780                 1785

Ser Val  Lys Gly Arg Phe Thr  Val Ser Arg Asp Asn  Ser Lys Asn
    1790                 1795                 1800

Thr Leu  Tyr Leu Gln Met Asn  Ser Leu Arg Ala Glu  Asp Thr Ala
    1805                 1810                 1815

Val Tyr  Tyr Cys Ala Arg Gly  Ala Thr Tyr Thr Ser  Arg Ser Asp
    1820                 1825                 1830

Val Pro  Asp Gln Thr Ser Phe  Asp Tyr Trp Gly Gln  Gly Thr Leu
    1835                 1840                 1845

Val Thr  Val Ser Ser Gly Ser  Ala Ser Ala Pro Lys  Leu Glu Glu
    1850                 1855                 1860

Gly Glu  Phe Ser Glu Ala Arg  Val Ser Glu Leu Thr  Gln Asp Pro
    1865                 1870                 1875

Ala Val  Ser Val Ala Leu Gly  Gln Thr Val Arg Ile  Thr Cys Gln
    1880                 1885                 1890

Gly Asp  Ser Leu Arg Asn Phe  Tyr Ala Ser Trp Tyr  Gln Gln Lys
    1895                 1900                 1905

Pro Gly  Gln Ala Pro Thr Leu  Val Ile Tyr Gly Leu  Ser Lys Arg
    1910                 1915                 1920

Pro Ser  Gly Ile Pro Asp Arg  Phe Ser Ala Ser Ser  Ser Gly Asn
    1925                 1930                 1935

Thr Ala  Ser Leu Thr Ile Thr  Gly Ala Gln Ala Glu  Asp Glu Ala
    1940                 1945                 1950

Asp Tyr  Tyr Cys Leu Leu Tyr  Tyr Gly Gly Gly Gln  Gln Gly Val
    1955                 1960                 1965

Phe Gly  Gly Gly Thr Lys Leu  Thr Val Leu Arg Gln  Pro Lys Ala
    1970                 1975                 1980

Ala Pro  Ser Val Thr Leu Phe  Pro Pro Ser Ser Ala  Ala Gly Gly
    1985                 1990                 1995

Gly Gly  Ser Gly Gly Gly Gly  Ser Gly Gly Gly Gly  Ser Gly Gly
    2000                 2005                 2010

Gly Gly  Ser Gly Gly Gly Gly  Ser Gly Gly Gly Gly  Ser Asp Lys
    2015                 2020                 2025

Thr His  Thr Cys Pro Pro Cys  Pro Ala Pro Glu Leu  Leu Gly Gly
```

2030 2035 2040

Pro Ser Val Phe Leu Phe Pro Pro Lys Pro Lys Asp Thr Leu Met
2045 2050 2055

Ile Ser Arg Thr Pro Glu Val Thr Cys Val Val Val Asp Val Ser
2060 2065 2070

His Glu Asp Pro Glu Val Lys Phe Asn Trp Tyr Val Asp Gly Val
2075 2080 2085

Glu Val His Asn Ala Lys Thr Lys Pro Arg Glu Glu Gln Tyr Asn
2090 2095 2100

Ser Thr Tyr Arg Val Val Ser Val Leu Thr Val Leu His Gln Asp
2105 2110 2115

Trp Leu Asn Gly Lys Glu Tyr Lys Cys Lys Val Ser Asn Lys Ala
2120 2125 2130

Leu Pro Ala Pro Ile Glu Lys Thr Ile Ser Lys Ala Lys Gly Gln
2135 2140 2145

Pro Arg Glu Pro Gln Val Tyr Thr Leu Pro Pro Ser Arg Asp Glu
2150 2155 2160

Leu Thr Lys Asn Gln Val Ser Leu Thr Cys Leu Val Lys Gly Phe
2165 2170 2175

Tyr Pro Ser Asp Ile Ala Val Glu Trp Glu Ser Asn Gly Gln Pro
2180 2185 2190

Glu Asn Asn Tyr Lys Thr Thr Pro Pro Val Leu Asp Ser Asp Gly
2195 2200 2205

Ser Phe Phe Leu Tyr Ser Lys Leu Thr Val Asp Lys Ser Arg Trp
2210 2215 2220

Gln Gln Gly Asn Val Phe Ser Cys Ser Val Met His Glu Ala Leu
2225 2230 2235

His Asn His Tyr Thr Gln Lys Ser Leu Ser Leu Ser Pro Gly Lys
2240 2245 2250

<210> SEQ ID NO 150
<211> LENGTH: 21
<212> TYPE: PRT
<213> ORGANISM: Artificial Sequence
<220> FEATURE:
<223> OTHER INFORMATION: Synthetic peptide

<400> SEQUENCE: 150

Ser Gly Gly Gly Gly Ser Gly Gly Gly Gly Ser Gly Gly Gly Gly Ser
1 5 10 15

Gly Gly Gly Gly Ser
20

<210> SEQ ID NO 151
<211> LENGTH: 5
<212> TYPE: PRT
<213> ORGANISM: Artificial Sequence
<220> FEATURE:
<223> OTHER INFORMATION: Synthetic peptide

<400> SEQUENCE: 151

Ala Leu Arg Pro Arg
1 5

<210> SEQ ID NO 152
<211> LENGTH: 4
<212> TYPE: PRT
<213> ORGANISM: Artificial Sequence
<220> FEATURE:

<223> OTHER INFORMATION: Synthetic peptide

<400> SEQUENCE: 152

Arg Arg Arg Arg
1

<210> SEQ ID NO 153
<211> LENGTH: 5
<212> TYPE: PRT
<213> ORGANISM: Artificial Sequence
<220> FEATURE:
<223> OTHER INFORMATION: Synthetic peptide

<400> SEQUENCE: 153

Leu Val Pro Arg Gly
1               5

<210> SEQ ID NO 154
<211> LENGTH: 12
<212> TYPE: PRT
<213> ORGANISM: Artificial Sequence
<220> FEATURE:
<223> OTHER INFORMATION: Synthetic peptide

<400> SEQUENCE: 154

Leu Gln Gln Ser Arg Lys Val Gly Asp Ser Pro Asn
1               5                   10

<210> SEQ ID NO 155
<211> LENGTH: 7
<212> TYPE: PRT
<213> ORGANISM: Artificial Sequence
<220> FEATURE:
<223> OTHER INFORMATION: Synthetic peptide

<400> SEQUENCE: 155

Glu Ala Ser Tyr Pro Gly Lys
1               5

<210> SEQ ID NO 156
<211> LENGTH: 271
<212> TYPE: PRT
<213> ORGANISM: Artificial Sequence
<220> FEATURE:
<223> OTHER INFORMATION: Synthetic

<400> SEQUENCE: 156

Ala Gln Val Gln Leu Gln Glu Ser Gly Gly Gly Leu Val Gln Pro Gly
1               5                   10                  15

Gly Ser Leu Arg Leu Ser Cys Ala Ala Ser Gly Phe Met Phe Ser Arg
            20                  25                  30

Tyr Ala Met Ser Trp Val Arg Gln Ala Pro Gly Lys Gly Pro Glu Trp
        35                  40                  45

Val Ser Gly Ile Ser Gly Ser Gly Gly Ser Thr Tyr Tyr Ala Asp Ser
    50                  55                  60

Val Lys Gly Arg Phe Thr Val Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Ala Thr Tyr Thr Ser Arg Ser Asp Val Pro Asp Gln
            100                 105                 110

Thr Ser Phe Asp Tyr Trp Gly Gln Gly Thr Leu Val Thr Val Ser Ser
        115                 120                 125

```
Gly Ser Ala Ser Ala Pro Lys Leu Glu Glu Gly Glu Phe Ser Glu Ala
    130                 135                 140

Arg Val Ser Glu Leu Thr Gln Asp Pro Ala Val Ser Val Ala Leu Gly
145                 150                 155                 160

Gln Thr Val Arg Ile Thr Cys Gln Gly Asp Ser Leu Arg Asn Phe Tyr
                165                 170                 175

Ala Ser Trp Tyr Gln Gln Lys Pro Gly Gln Ala Pro Thr Leu Val Ile
            180                 185                 190

Tyr Gly Leu Ser Lys Arg Pro Ser Gly Ile Pro Asp Arg Phe Ser Ala
        195                 200                 205

Ser Ser Ser Gly Asn Thr Ala Ser Leu Thr Ile Thr Gly Ala Gln Ala
    210                 215                 220

Glu Asp Glu Ala Asp Tyr Tyr Cys Leu Leu Tyr Tyr Gly Gly Gly Gln
225                 230                 235                 240

Gln Gly Val Phe Gly Gly Gly Thr Lys Leu Thr Val Leu Arg Gln Pro
                245                 250                 255

Lys Ala Ala Pro Ser Val Thr Leu Phe Pro Pro Ser Ser Ala Ala
            260                 265                 270
```

<210> SEQ ID NO 157
<211> LENGTH: 5
<212> TYPE: PRT
<213> ORGANISM: Artificial Sequence
<220> FEATURE:
<223> OTHER INFORMATION: Synthetic peptide

<400> SEQUENCE: 157

```
Val Val Gly Gly Ala
1               5
```

<210> SEQ ID NO 158
<211> LENGTH: 5859
<212> TYPE: DNA
<213> ORGANISM: Artificial Sequence
<220> FEATURE:
<223> OTHER INFORMATION: Synthetic construct

<400> SEQUENCE: 158

```
atgcaaatag agctctccac ctgcttcttt ctgtgccttt tgcgattctg ctttagtgcc      60

accagaagat actacctggg tgcagtggaa ctgtcatggg actatatgca aagtgatctc     120

ggtgagctgc ctgtggacgc aagatttcct cctagagtgc caaaatcttt tccattcaac     180

acctcagtcg tgtacaaaaa gactctgttt gtagaattca cggatcacct tttcaacatc     240

gctaagccaa ggccaccctg gatgggtctg ctaggtccta ccatccaggc tgaggtttat     300

gatacagtgg tcattacact taagaacatg gcttcccatc ctgtcagtct tcatgctgtt     360

ggtgtatcct actggaaagc ttctgaggga gctgaatatg atgatcagac cagtcaaagg     420

gagaaagaag atgataaagt cttccctggt ggaagccata catatgtctg gcaggtcctg     480

aaagagaatg gtccaatggc ctctgaccca ctgtgcctta cctactcata tctttctcat     540

gtggacctgg taaaagactt gaattcaggc ctcattggag ccctactagt atgtagagaa     600

gggagtctgg ccaaggaaaa gacacagacc ttgcacaaat ttatactact tttgctgta      660

tttgatgaag ggaaaagttg gcactcagaa acaaagaact ccttgatgca ggatagggat     720

gctgcatctg ctcgggcctg gcctaaaatg cacacagtca atggttatgt aaacaggtct     780

ctgccaggtc tgattggatg ccacaggaaa tcagtctatt ggcatgtgat tggaatgggc     840
```

-continued

```
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt ttttcaccat ctttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
```

attcatttca gtggacatgt gttcactgta cgaaaaaaag aggagtataa aatggcactg 3300
tacaatctct atccaggtgt ttttgagaca gtggaaatgt taccatccaa agctggaatt 3360
tggcgggtgg aatgccttat tggcgagcat ctacatgctg ggatgagcac actttttctg 3420
gtgtacagca ataagtgtca gactcccctg ggaatggctt ctggacacat tagagatttt 3480
cagattacag cttcaggaca atatggacag tgggccccaa agctggccag acttcattat 3540
tccggatcaa tcaatgcctg gagcaccaag gagccctttt cttggatcaa ggtggatctg 3600
ttggcaccaa tgattattca cggcatcaag acccagggtg cccgtcagaa gttctccagc 3660
ctctacatct ctcagtttat catcatgtat agtcttgatg ggaagaagtg gcagacttat 3720
cgaggaaatt ccactggaac cttaatggtc ttctttggca atgtggattc atctgggata 3780
aaacacaata tttttaaccc tccaattatt gctcgataca tccgtttgca cccaactcat 3840
tatagcattc gcagcactct tcgcatggag ttgatgggct gtgatttaaa tagttgcagc 3900
atgccattgg gaatggagag taaagcaata tcagatgcac agattactgc ttcatcctac 3960
tttaccaata tgtttgccac ctggtctcct tcaaaagctc gacttcacct ccaagggagg 4020
agtaatgcct ggagacctca ggtgaataat ccaaaagagt ggctgcaagt ggacttccag 4080
aagacaatga aagtcacagg agtaactact cagggagtaa aatctctgct taccagcatg 4140
tatgtgaagg agttcctcat ctccagcagt caagatggcc atcagtggac tctctttttt 4200
cagaatggca aagtaaaggt tttttcaggga aatcaagact ccttcacacc tgtggtgaac 4260
tctctagacc caccgttact gactcgctac cttcgaattc acccccagag ttgggtgcac 4320
cagattgccc tgaggatgga ggttctgggc tgcgaggcac aggacctcta cgacaaaact 4380
cacacatgcc caccgtgccc agcacctgaa ctcctgggag gaccgtcagt cttcctcttc 4440
cccccaaaac ccaaggacac cctcatgatc tcccggaccc ctgaggtcac atgcgtggtg 4500
gtggacgtga gccacgaaga ccctgaggtc aagttcaact ggtacgtgga cggcgtggag 4560
gtgcataatg ccaagacaaa gccgcgggag gagcagtaca acagcacgta ccgtgtggtc 4620
agcgtcctca ccgtcctgca ccaggactgg ctgaatggca aggagtacaa gtgcaaggtc 4680
tccaacaaag ccctcccagc ccccatcgag aaaaccatct ccaaagccaa agggcagccc 4740
cgagaaccac aggtgtacac cctgccccca tcccgcgatg agctgaccaa gaaccaggtc 4800
agcctgacct gcctggtcaa aggcttctat cccagcgaca tcgccgtgga gtgggagagc 4860
aatgggcagc cggagaacaa ctacaagacc acgcctcccg tgttggactc cgacggctcc 4920
ttcttcctct acagcaagct caccgtcgac aagagcaggt ggcagcaggg gaacgtcttc 4980
tcatgctccg tgatgcatga ggctctgcac aaccactaca cgcagaagag cctctccctg 5040
tctccgggta aacggcgccg ccggagcggt ggcggcggat caggtggggg tggatcaggc 5100
ggtggaggtt ccggtggcgg gggatccggc ggtggaggtt ccggtggggg tggatcaagg 5160
aagaggagga agagggacaa aactcacaca tgcccaccgt gcccagctcc agaactcctg 5220
ggcggaccgt cagtcttcct cttcccccca aaacccaagg acaccctcat gatctcccgg 5280
acccctgagg tcacatgcgt ggtggtggac gtgagccacg aagaccctga ggtcaagttc 5340
aactggtacg tggacggcgt ggaggtgcat aatgccaaga caaagccgcg ggaggagcag 5400
tacaacagca cgtaccgtgt ggtcagcgtc ctcaccgtcc tgcaccagga ctggctgaat 5460
ggcaaggagt acaagtgcaa ggtctccaac aaagccctcc cagcccccat cgagaaaacc 5520
atctccaaag ccaaagggca gccccgagaa ccacaggtgt acaccctgcc cccatcccgg 5580

```
gatgagctga ccaagaacca ggtcagcctg acctgcctgg tcaaaggctt ctatcccagc   5640

gacatcgccg tggagtggga gagcaatggg cagccggaga acaactacaa gaccacgcct   5700

cccgtgttgg actccgacgg ctccttcttc ctctacagca agctcaccgt ggacaagagc   5760

aggtggcagc aggggaacgt cttctcatgc tccgtgatgc atgaggctct gcacaaccac   5820

tacacgcaga agagcctctc cctgtctccg ggtaaatga                          5859


<210> SEQ ID NO 159
<211> LENGTH: 1952
<212> TYPE: PRT
<213> ORGANISM: Artificial Sequence
<220> FEATURE:
<223> OTHER INFORMATION: Synthetic construct

<400> SEQUENCE: 159

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320
```

-continued

```
Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735
```

```
Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
```

1145 1150 1155

Asp Phe Gln Ile Thr Ala Ser Gly Gln Tyr Gly Gln Trp Ala Pro
1160 1165 1170

Lys Leu Ala Arg Leu His Tyr Ser Gly Ser Ile Asn Ala Trp Ser
1175 1180 1185

Thr Lys Glu Pro Phe Ser Trp Ile Lys Val Asp Leu Leu Ala Pro
1190 1195 1200

Met Ile Ile His Gly Ile Lys Thr Gln Gly Ala Arg Gln Lys Phe
1205 1210 1215

Ser Ser Leu Tyr Ile Ser Gln Phe Ile Ile Met Tyr Ser Leu Asp
1220 1225 1230

Gly Lys Lys Trp Gln Thr Tyr Arg Gly Asn Ser Thr Gly Thr Leu
1235 1240 1245

Met Val Phe Phe Gly Asn Val Asp Ser Ser Gly Ile Lys His Asn
1250 1255 1260

Ile Phe Asn Pro Pro Ile Ile Ala Arg Tyr Ile Arg Leu His Pro
1265 1270 1275

Thr His Tyr Ser Ile Arg Ser Thr Leu Arg Met Glu Leu Met Gly
1280 1285 1290

Cys Asp Leu Asn Ser Cys Ser Met Pro Leu Gly Met Glu Ser Lys
1295 1300 1305

Ala Ile Ser Asp Ala Gln Ile Thr Ala Ser Ser Tyr Phe Thr Asn
1310 1315 1320

Met Phe Ala Thr Trp Ser Pro Ser Lys Ala Arg Leu His Leu Gln
1325 1330 1335

Gly Arg Ser Asn Ala Trp Arg Pro Gln Val Asn Asn Pro Lys Glu
1340 1345 1350

Trp Leu Gln Val Asp Phe Gln Lys Thr Met Lys Val Thr Gly Val
1355 1360 1365

Thr Thr Gln Gly Val Lys Ser Leu Leu Thr Ser Met Tyr Val Lys
1370 1375 1380

Glu Phe Leu Ile Ser Ser Ser Gln Asp Gly His Gln Trp Thr Leu
1385 1390 1395

Phe Phe Gln Asn Gly Lys Val Lys Val Phe Gln Gly Asn Gln Asp
1400 1405 1410

Ser Phe Thr Pro Val Val Asn Ser Leu Asp Pro Pro Leu Leu Thr
1415 1420 1425

Arg Tyr Leu Arg Ile His Pro Gln Ser Trp Val His Gln Ile Ala
1430 1435 1440

Leu Arg Met Glu Val Leu Gly Cys Glu Ala Gln Asp Leu Tyr Asp
1445 1450 1455

Lys Thr His Thr Cys Pro Pro Cys Pro Ala Pro Glu Leu Leu Gly
1460 1465 1470

Gly Pro Ser Val Phe Leu Phe Pro Pro Lys Pro Lys Asp Thr Leu
1475 1480 1485

Met Ile Ser Arg Thr Pro Glu Val Thr Cys Val Val Val Asp Val
1490 1495 1500

Ser His Glu Asp Pro Glu Val Lys Phe Asn Trp Tyr Val Asp Gly
1505 1510 1515

Val Glu Val His Asn Ala Lys Thr Lys Pro Arg Glu Glu Gln Tyr
1520 1525 1530

Asn Ser Thr Tyr Arg Val Val Ser Val Leu Thr Val Leu His Gln
1535 1540 1545

```
Asp Trp Leu Asn Gly Lys Glu Tyr Lys Cys Lys Val Ser Asn Lys
    1550                1555                1560

Ala Leu Pro Ala Pro Ile Glu Lys Thr Ile Ser Lys Ala Lys Gly
    1565                1570                1575

Gln Pro Arg Glu Pro Gln Val Tyr Thr Leu Pro Pro Ser Arg Asp
    1580                1585                1590

Glu Leu Thr Lys Asn Gln Val Ser Leu Thr Cys Leu Val Lys Gly
    1595                1600                1605

Phe Tyr Pro Ser Asp Ile Ala Val Glu Trp Glu Ser Asn Gly Gln
    1610                1615                1620

Pro Glu Asn Asn Tyr Lys Thr Thr Pro Pro Val Leu Asp Ser Asp
    1625                1630                1635

Gly Ser Phe Phe Leu Tyr Ser Lys Leu Thr Val Asp Lys Ser Arg
    1640                1645                1650

Trp Gln Gln Gly Asn Val Phe Ser Cys Ser Val Met His Glu Ala
    1655                1660                1665

Leu His Asn His Tyr Thr Gln Lys Ser Leu Ser Leu Ser Pro Gly
    1670                1675                1680

Lys Arg Arg Arg Arg Ser Gly Gly Gly Gly Ser Gly Gly Gly Gly
    1685                1690                1695

Ser Gly Gly Gly Gly Ser Gly Gly Gly Gly Ser Gly Gly Gly Gly
    1700                1705                1710

Ser Gly Gly Gly Gly Ser Arg Lys Arg Arg Lys Arg Asp Lys Thr
    1715                1720                1725

His Thr Cys Pro Pro Cys Pro Ala Pro Glu Leu Leu Gly Gly Pro
    1730                1735                1740

Ser Val Phe Leu Phe Pro Pro Lys Pro Lys Asp Thr Leu Met Ile
    1745                1750                1755

Ser Arg Thr Pro Glu Val Thr Cys Val Val Val Asp Val Ser His
    1760                1765                1770

Glu Asp Pro Glu Val Lys Phe Asn Trp Tyr Val Asp Gly Val Glu
    1775                1780                1785

Val His Asn Ala Lys Thr Lys Pro Arg Glu Glu Gln Tyr Asn Ser
    1790                1795                1800

Thr Tyr Arg Val Val Ser Val Leu Thr Val Leu His Gln Asp Trp
    1805                1810                1815

Leu Asn Gly Lys Glu Tyr Lys Cys Lys Val Ser Asn Lys Ala Leu
    1820                1825                1830

Pro Ala Pro Ile Glu Lys Thr Ile Ser Lys Ala Lys Gly Gln Pro
    1835                1840                1845

Arg Glu Pro Gln Val Tyr Thr Leu Pro Pro Ser Arg Asp Glu Leu
    1850                1855                1860

Thr Lys Asn Gln Val Ser Leu Thr Cys Leu Val Lys Gly Phe Tyr
    1865                1870                1875

Pro Ser Asp Ile Ala Val Glu Trp Glu Ser Asn Gly Gln Pro Glu
    1880                1885                1890

Asn Asn Tyr Lys Thr Thr Pro Pro Val Leu Asp Ser Asp Gly Ser
    1895                1900                1905

Phe Phe Leu Tyr Ser Lys Leu Thr Val Asp Lys Ser Arg Trp Gln
    1910                1915                1920
```

-continued

```
Gln Gly Asn Val Phe Ser Cys Ser Val Met His Glu Ala Leu His
    1925                1930                1935

Asn His Tyr Thr Gln Lys Ser Leu Ser Leu Ser Pro Gly Lys
    1940                1945                1950
```

CHIMERIC CLOTTING FACTORS

REFERENCE TO EARLIER FILED APPLICATIONS

This application is a continuation of U.S. application Ser. No. 13/809,289, which is the national phase application of International Application No. PCT/US2011/043597, filed Jul. 11, 2011 and published as WO 2012/006633, which claims the benefit of U.S. Provisional Application No. 61/363,183, filed Jul. 9, 2010; 61/363,186, filed Jul. 9, 2010; 61/442,055, filed Feb. 11, 2011; 61/442,150, filed Feb. 11, 2011; 61/442,029, filed Feb. 11, 2011; 61/467,880, filed Mar. 25, 2011; and 61/491,762, filed May 31, 2011, all of which are incorporated herein by reference in their entireties.

REFERENCE TO SEQUENCE LISTING SUBMITTED ELECTRONICALLY VIA EFS-WEB

The content of the electronically submitted sequence listing (Name: 2159_3750008_SEQUENCE_LISTING.txt, Size: 603,490 bytes; and Date of Creation: Jul. 27, 2016) was originally submitted in the International Application No. PCT/US2011/043597 and is incorporated herein by reference in its entirety.

BACKGROUND OF THE INVENTION

Initiation of the extrinsic clotting pathway is mediated by the formation of a complex between tissue factor, which is exposed as a result of injury to a vessel wall, and Factor VIIa. This complex then converts Factors IX and X to their active forms. Factor Xa converts limited amounts of prothrombin to thrombin on the tissue factor-bearing cell. This resulting thrombin is then able to diffuse away from the tissue-factor bearing cell and activate platelets, and Factors V and VIII, making Factors Va and VIIIa. During the propagation phase of coagulation, Factor Xa is generated by Factor IXa (in complex with factor VIIIa) on the surface of activated platelets. Factor Xa, in complex with the cofactor Factor Va, activates prothrombin into thrombin, generating a thrombin burst. The cascade culminates in the conversion of fibrinogen to fibrin by thrombin, which results in the formation of a fibrin clot. Factor VII and tissue factor are key players in the initiation of blood coagulation.

Factor VII is a plasma glycoprotein that circulates in blood as a single-chain zymogen. The zymogen is catalytically inactive. Although single-chain Factor VII may be converted to two-chain Factor VIIa by a variety of factors in vitro, Factor Xa is an important physiological activator of Factor VII. The conversion of zymogen Factor VII into the activated two-chain molecule occurs by cleavage of the peptide bond linking the Arginine residue at amino acid position 152 and the Ile residue at amino acid position 153. In the presence of tissue factor, phospholipids and calcium ions, the two-chain Factor VIIa activates Factor X or Factor IX. Factor VIIa is thought to be the physiologic initiator of the clotting cascade by acting at the surface of a TF-bearing cell, typically a damaged endothelial cell, and generating the initial amount of thrombin that then diffuses to platelets to activate them and prime them for the propagation phase of thrombin generation. Therapeutically, recombinant FVIIa acts by activating Factor X on the surface of activated platelets, bypassing the need for FIXa or FVIIIa to generate a thrombin burst during the propagation phase of coagulation. Since FVIIa has relatively low affinity for platelets, recombinant FVIIa is dosed at supra-physiological levels. This process is thought be tissue factor-independent.

Human factor IX circulates as a single-chain glycoprotein (mol wt 57,000). It is present in plasma as a zymogen and is converted to a serine protease, Factor IXaβ (more commonly referred to as FIXa), by Factor XIa (activated plasma thromboplastin antecedent) in the presence of calcium ions. In the activation reaction, two internal peptide bonds are hydrolyzed in Factor IX. These cleavages occur at a specific arginyl-alanine peptide bond and a specific arginyl-valine peptide bond. This results in the release of an activation peptide (mol wt approximately equal to 11,000) from the internal region of the precursor molecule and the generation of Factor IXaβ (mol wt approximately equal to 46,000). Factor IXaβ is composed of a light chain (mol wt approximately equal to 18,000) and a heavy chain (mol wt approximately equal to 28,000), and these chains are held together by a disulfide bond.

Factor X is also synthesized as a single-chain polypeptide containing the light and heavy chains connected by an Arg-Lys-Arg tripeptide. The single-chain molecule is then converted to the light and heavy chains by cleavage of two (or more) internal peptide bonds. In plasma, these two chains are linked together by a disulfide bond, forming Factor X. Activated Factor X, Factor Xa, participates in the final common pathway whereby prothrombin is converted to thrombin, which in turn converts fibrinogen to fibrin.

Clotting factors have been administered to patients to improve hemostasis for some time. The advent of recombinant DNA technology has significantly improved treatment for patients with clotting disorders, allowing for the development of safe and consistent protein therapeutics. For example, recombinant activated factor VII has become widely used for the treatment of major bleeding, such as that which occurs in patients having haemophilia A or B, deficiency of coagulation Factors XI or VII, defective platelet function, thrombocytopenia, or von Willebrand's disease. Recombinant factor IX is therapeutically useful as well.

Although such recombinant molecules are effective, there is a need for improved versions which localize the therapeutic to sites of coagulation, have improved pharmacokinetic properties, have reduced clearance rates, have improved manufacturability, have reduced thrombogenicity, or have enhanced activity, or more than one of these characteristics.

SUMMARY OF THE INVENTION

The instant invention relates to chimeric clotting factors which have enhanced activity. The present invention features inter alia methods for making chimeric clotting factors, the chimeric clotting factors made using these methods, and methods for improving hemostasis using these clotting factors. The chimeric clotting factors of the invention possess enhanced pharmacokinetic properties, have reduced clearance rates, have improved manufacturability, have reduced thrombogenicity, have enhanced activity, or more than one of these characteristics. In one embodiment, improved clotting factors of the invention have increased activity where needed, e.g., by targeting the clotting factor to platelets or by being present in a subject in an activatable form (a non-naturally occurring activatable form) that is activated at the site of clot formation.

In one aspect, the invention pertains to a chimeric clotting factor which comprises a clotting factor selected from the group consisting of FVII, FIX and FX and a targeting moiety which binds to platelets and optionally a spacer moiety between the clotting factor and the targeting moiety.

In one embodiment, the clotting factor comprises a structure represented by the formula A B C, wherein A is the clotting factor; wherein B is a spacer moiety; and wherein C is at least one targeting moiety which binds to platelets.

In one embodiment, the clotting factor comprises a structure from amino terminus to carboxy terminus represented by a formula selected from the group consisting of: A B C; C B A In one embodiment, the clotting factor exhibits increased generation of thrombin in the presence of platelets as compared to an appropriate control lacking the at least one targeting moiety.

In one embodiment, the clotting factor comprises a scaffold moiety and, optionally, a second spacer moiety.

In one embodiment, the clotting factor further comprises D and E, wherein D is a spacer moiety; and E is a scaffold moiety and wherein the chimeric clotting factor comprises a structure from amino terminus to carboxy terminus represented by a formula selected from the group consisting of: A B C D E; A D E B C; E D A B C; C B A D E; E D C B A; and C B E D A.

In one embodiment, E is a dimeric Fc region comprising a first Fc moiety, F1 and a second Fc moiety, F2.

In one embodiment, the clotting factor is expressed as a polypeptide comprising a cleavable scFc (cscFc) linker interposed between two Fc moieties, wherein the cscFc linker is adjacent to at least one enzymatic cleavage site which results in cleavage of the cscFc polypeptide linker.

In one embodiment, the cscFc linker is adjacent to at least one enzymatic cleavage site which results in cleavage of the cscFc linker.

In one embodiment, the chimeric clotting factor of claim 9, wherein the at least one enzymatic cleavage site is an intracellular processing site.

In one embodiment, wherein the polypeptide linker is flanked by two enzymatic cleavage sites which are recognized by the same or by different enzymes.

In one embodiment, the polypeptide linker has a length of about 10 to about 50 amino acids.

In one embodiment, the polypeptide linker has a length of about 20 to about 30 amino acids.

In one embodiment, the polypeptide linker comprises a gly/ser peptide.

In one embodiment, the gly/ser peptide is of the formula $(Gly_4Ser)n$, or $Ser(Gly_4Ser)n$ wherein n is a positive integer selected from the group consisting of 1, 2, 3, 4, 5, 6, 7, 8, 9 and 10. In one embodiment, the $(Gly_4\ Ser)n$ linker is selected from the group consisting of $(Gly_4\ Ser)6$, $Ser(Gly_4\ Ser)6$, $(Gly_4\ Ser)4$ and $Ser(Gly_4\ Ser)4$.

In one embodiment, the clotting factor comprises two polypeptide chains.

In one embodiment, the chimeric clotting factor has a structure selected from the group consisting of: A linked to F1 via a spacer moiety and C linked to F2; A linked to F1 via a spacer moiety and C linked to F2 via a spacer moiety; A linked to F1 and C is linked to F2 via a spacer moiety; A linked to F1 via a spacer moiety and C is linked to F2 via a spacer moiety.

In one embodiment, a chimeric clotting factor comprises two polypeptides wherein the first polypeptide comprises the moieties A B F1; A B F1; A B F1; or A B F1 D C and the second polypeptide comprises the moieties C F2; C D F2; F2 D C; or F2 D C, wherein the two polypeptide chains form an Fc region.

In one embodiment, the targeting moiety is fused to at least one of the polypeptide chains of the Fc region. In one embodiment, the targeting moiety is fused to at least one of F1 and F2 directly. In one embodiment, the targeting moiety is fused to at least one of F1 and F2 via a spacer moiety. In one embodiment, the targeting moiety is fused to at least one of F1 and F2 via a cleavable linker. In one embodiment, the targeting moiety is selected from the group consisting of: an antibody molecule, an antigen binding fragment of an antibody molecule, an scFv molecule, a receptor binding portion of a receptor, a peptide. In one embodiment, wherein the targeting moiety binds to resting platelets. In one embodiment, the targeting moiety selectively binds to activated platelets. In one embodiment, the targeting moiety selectively binds to a target selected from the group consisting of: GPIba, GPVI, and the nonactive form of GPIIb/IIIa. In one embodiment, the targeting moiety selectively binds to a target selected from the group consisting of: the active form of GPIIb/IIIa, P selectin, GMP-33, LAMP-1, LAMP-2, CD40L, and LOX-1. In one embodiment, the targeting moiety binds to the GPIb complex In one embodiment, the targeting moiety is a peptide selected from the group consisting of: PS4, OS1, and OS2. In one embodiment, the targeting moiety comprises an antibody variable regions from an antibody selected from the group consisting of: SCE5, MB9, and AP3.

In one embodiment, wherein the clotting factor is Factor VII.

In one embodiment, the clotting factor is a high specific activity variant of Factor VII. In one embodiment, the clotting factor is Factor IX. In one embodiment, the clotting factor is a high specific activity variant of Factor IX. In one embodiment, the clotting factor is Factor X. In one embodiment, clotting factor is a high specific activity variant of Factor X.

In one embodiment, the clotting factor is secreted by a cell in active form. In one embodiment, the clotting factor is activated in vivo.

In one embodiment, the chimeric clotting factor comprises a heterologous enzymatic cleavage site not naturally present in the clotting factor.

In one embodiment, the enzymatic cleavage site is genetically fused to the amino terminus of the heavy chain moiety of the clotting factor.

In one embodiment, the clotting factor comprises a scaffold moiety is a protein molecule which increases the hydrodynamic radius of the chimeric clotting factor. In one embodiment, the scaffold moiety, if present, is selected from the group consisting of albumin and XTEN®

In another aspect, the invention pertains to a polypeptide comprising FVII, which FVII comprises a heterologous enzymatic cleavage site activatable by a component of the clotting cascade.

In one embodiment, the polypeptide comprises a scaffold moiety and, optionally, a spacer moiety.

In one embodiment, the scaffold moiety is a dimeric Fc region comprising a first Fc moiety, F1 and a second Fc moiety, F2.

In one embodiment, the clotting factor comprises two polypeptide chains.

In one embodiment, the chimeric clotting factor has a structure selected from the group consisting of: the clotting factor linked to the first Fc moiety via a spacer moiety; the clotting factor linked to the second Fc moiety via a spacer moiety; the clotting factor is directly linked to F1; and the clotting factor is directly linked to F2.

In one embodiment, the chimeric clotting factor further comprises a targeting moiety.

In one embodiment, the chimeric clotting factor is synthesized as a single polypeptide chain comprising a cscFc linker. In one embodiment, the cscFc linker is linked to (e.g., directly linked or adjacent to) at least one enzymatic cleavage site which results in cleavage of the linker.

In one embodiment, the at least one enzymatic cleavage site is an intracellular processing site. In one embodiment, the cscFc linker is flanked by two enzymatic cleavage sites which are recognized by the same or by different enzymes. In one embodiment, the cscFc linker has a length of about 10 to about 50 amino acids. In one embodiment, the cscFc linker has a length of about 20 to about 30 amino acids.

In one embodiment, the cscFc linker comprises a gly/ser peptide.

In one embodiment, wherein the gly/ser peptide is of the formula $(Gly_4Ser)n$, or $Ser(Gly_4Ser)n$ wherein n is a positive integer selected from the group consisting of 1, 2, 3, 4, 5, 6, 7, 8, 9 and 10. In one embodiment, the $(Gly_4$ Ser)n linker is selected from the group consisting of $(Gly_4$ Ser)6, $Ser(Gly_4$ Ser)6, $(Gly_4$ Ser)4 and $Ser(Gly_4$ Ser)4.

In one embodiment, the clotting factor is a high specific activity variant of Factor VII. In one embodiment, the heterologous enzymatic cleavage site present in the chimeric clotting factor is cleaved at the site of clot formation. In one embodiment, the cleavage site is selected from the group consisting of: a factor XIa cleavage site, a factor Xa cleavage site, and a thrombin cleavage site. In one embodiment, the enzymatic cleavage site is genetically fused to the amino terminus of the heavy chain moiety of the clotting factor.

In one embodiment, the targeting moiety binds to resting platelets. In one embodiment, the targeting moiety selectively binds to activated platelets.

In one embodiment, wherein the targeting moiety selectively binds to a target selected from the group consisting of: GPIba, GPVI, and the nonactive form of GPIIb/IIIa. In one embodiment, the targeting moiety selectively binds to a target selected from the group consisting of: the active form of GPIIb/IIIa, P selectin, GMP-33, LAMP-1, LAMP-2, CD40L, and LOX-1.

In one embodiment, the scaffold moiety is a protein molecule which increases the hydrodynamic radius of the chimeric clotting factor. In one embodiment, the scaffold moiety, if present, is selected from the group consisting of albumin and XTEN®

In one aspect the invention pertains to a linear sequence of moieties from amino terminus to carboxy terminus selected from the group consisting of: A B C; C B A; A B C D E; A D E B C, E D A B C, C B A D E, E D C B A, C B E D A, wherein A an activatable clotting factor, B is absent or is a linker, C is a targeting moiety, D is absent or is a linker, and E is a scaffold moiety.

In one embodiment, the clotting factor comprises a light and heavy chain of a clotting factor and each of the light and heavy chains are expressed as separate polypeptide chains.

In one embodiment, the invention pertains to a nucleic acid molecule encoding a chimeric clotting factor of the invention. In one embodiment, the nucleic acid molecule is present in a vector. In one embodiment, the vector further comprises a nucleotide sequence encoding an enzyme which cleaves at least one of the enzymatic cleavage sites.

In one embodiment, the invention pertains to a host cell comprising the expression vector of the invention. In one embodiment, the host cell expresses an enzyme capable of intracellular processing. In one embodiment, the enzyme is endogenous to the cell. In one embodiment, the enzyme is heterologous to the cell.

In another embodiment, the invention pertains to a method for producing a chimeric clotting factor comprising culturing the host cell in culture and recovering the chimeric clotting factor from the medium.

In another embodiment, the invention pertains to a processed, heterodimeric polypeptide comprising two polypeptide chains, wherein said processed, heterodimeric polypeptide is made by expressing the vector in a cell cultured in cell culture medium and isolating the mature, heterodimeric polypeptide from the culture medium.

In one embodiment, the invention pertains to a composition comprising a chimeric clotting factor and a pharmaceutically acceptable carrier.

In another embodiment, the invention pertains to a composition comprising the nucleic acid molecule of the invention and a pharmaceutically acceptable carrier.

In another embodiment, the invention pertains to a method for improving hemostasis in a subject, comprising administering the composition of the invention.

in one aspect, the invention pertains to an chimeric clotting factor which comprises a light chain moiety and a heavy chain moiety of a clotting factor, and at least one targeting moiety, wherein said targeting moiety (i) specifically binds to platelets, (ii) is not interposed between the light and heavy chains of the clotting factor, and wherein said chimeric clotting factor exhibits increased generation of thrombin in the presence of platelets as compared to an appropriate control lacking the at least one targeting moiety.

In another aspect, the invention pertains to an chimeric clotting factor, which comprises the moieties A-B-C-D-E in linear sequence wherein A is a clotting factor, an activatable clotting factor, or an activated clotting factor; B is absent or is a linker; C is a targeting moiety; D is absent or is a linker; and E is absent or is a scaffold moiety.

In still another aspect, the invention pertains to an chimeric clotting factor, which comprises a linear sequence of moieties from amino terminus to carboxy terminus selected from the group consisting of: ABC; ABCDE; ADEBC, EDABC, CBADE, EDCBA, CBEDA, wherein A is a clotting factor, an activatable clotting factor or an activated clotting factor, B is absent or is a linker, C is a targeting moiety, D is absent or is a linker, and E is a scaffold moiety.

In yet another aspect, the invention pertains to an chimeric clotting factor, which comprises a linear sequence of moieties from amino terminus to carboxy terminus selected from the group consisting of: ABF1:F2; ABF1:CDF2; ABF1:F2DC, ABF1DC:F2DC, wherein A is a clotting factor, an activatable clotting factor or an activated clotting factor, B is absent or is a linker, C is a targeting moiety, D is absent or is a linker, and F1 and F2 are each an Fc moiety, and : represents dimerization mediated by the F1 and F2 chains of two polypeptide chains.

In still another aspect, the invention pertains to an chimeric clotting factor which comprises a light chain moiety and a heavy chain moiety of a clotting factor, and at least one targeting moiety, wherein said targeting moiety specifically binds to platelets, wherein the chimeric clotting factor comprises a disulfide linked Fc region which comprises two polypeptide chains.

BRIEF DESCRIPTION OF THE DRAWINGS

FIG. 24 shows the constructs used in the Western blot analysis of FVIIFc species following transient transfection of HEK 293 cells and protein A pulldown shown in FIG. 25.

FIG. 25 shows Western blot analysis of FVIIFc species following transient transfection of HEK 293 cells and protein A pulldown.

FIG. 26 shows Western blot of protein A immunoprecipitation following transient transfection of pSYN-FVII-024 with or without pSYN-PC5-003. Lane 1, pSYN-FVII-024, non reducing; lane 2, pSYN-FVII-024, non reducing; lane 3, pSYN-FVII-024, reducing; lane 4, pSYN-FVII-024, reducing.

FIG. 27 shows Western blot analysis (Fc western) of FVIIFc species following transient transfection of HEK 293 cells and protein A pulldown.

FIG. 39 shows the results of the control experiment which demonstrates that FX activation by FVIIaFc can be detected.

FIG. 41 illustrates exemplary activatable construct formats, including an activatable monomer structure used in FVII-118, FVII-119, and FVII-127.

FIG. 46A shows several targeted FVIIa constructs that target GPIb-alpha using peptides that bind to that molecule, specifically, the PS4, OS1, and OS2 peptides.

DETAILED DESCRIPTION OF THE INVENTION

Figure 1:
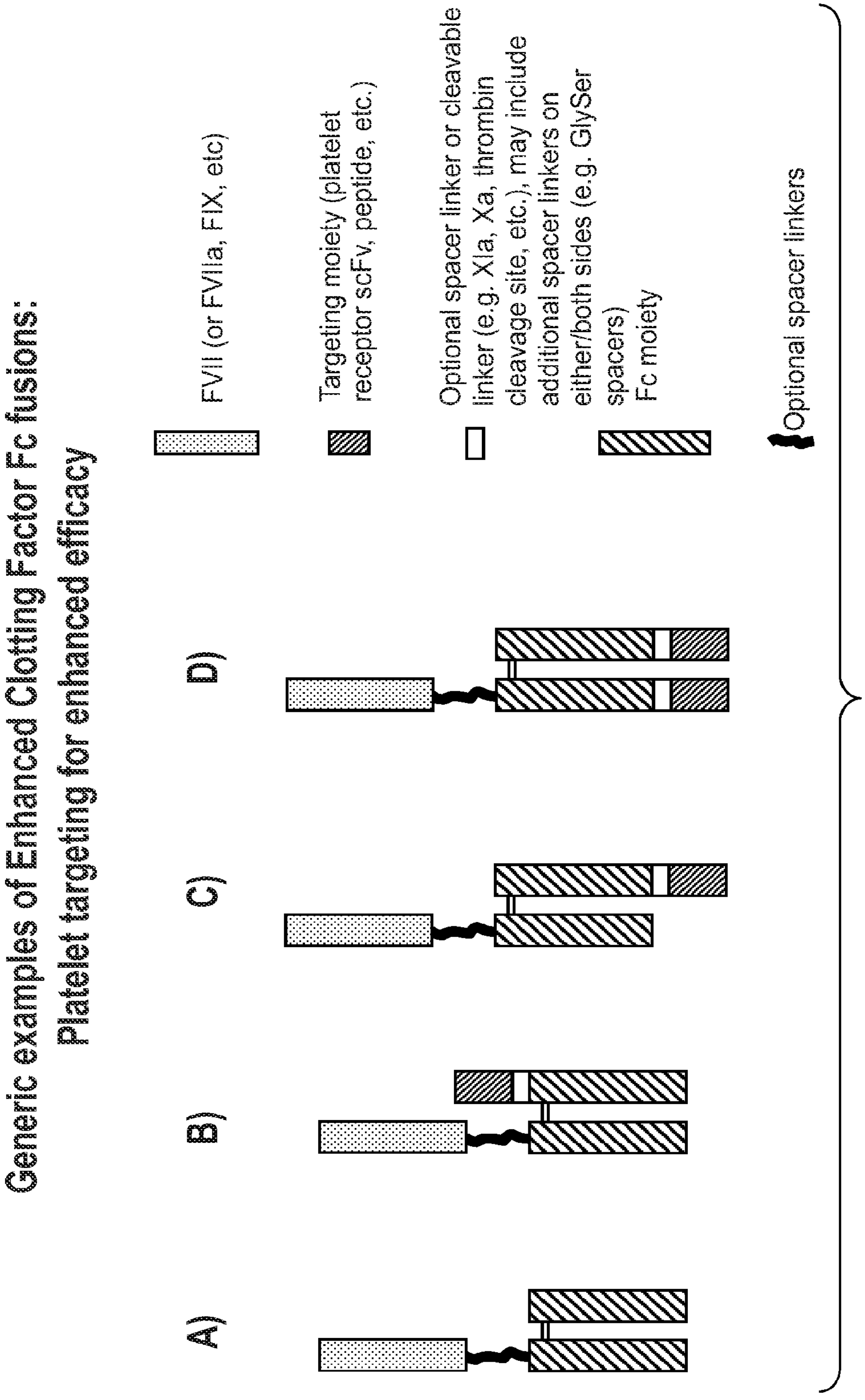
FIG. 1 illustrates exemplary chimeric clotting factor constructs comprising a targeting domain. These exemplary constructs comprise an Fc region.
Figure 2:
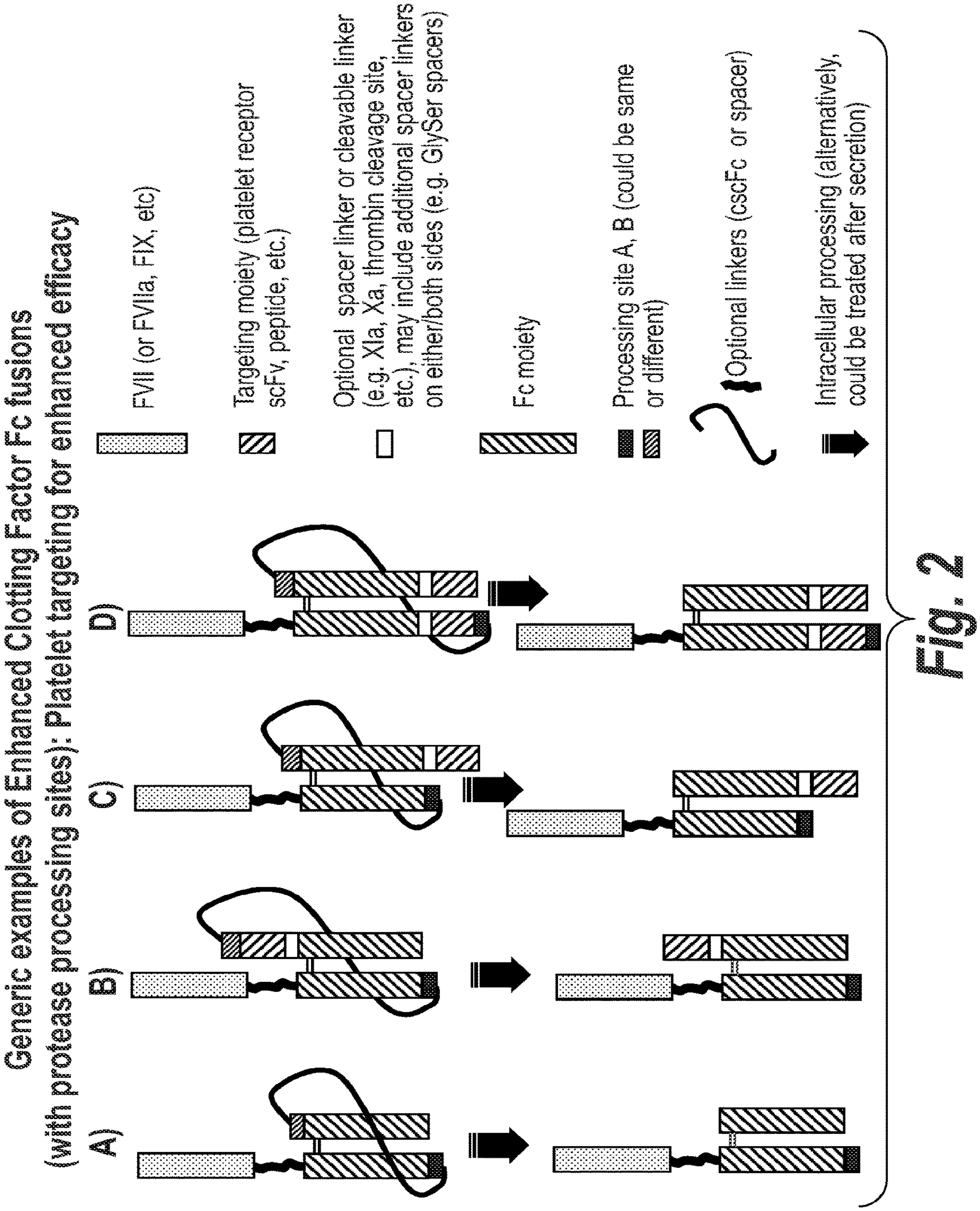
FIG. 2 illustrates exemplary chimeric clotting factor constructs comprising a targeting domain. These exemplary constructs comprise a cleavable single chain Fc (cscFc) in which the scFc linker is processed by a cell in which it is expressed to form a two chain Fc region.
Figure 3:
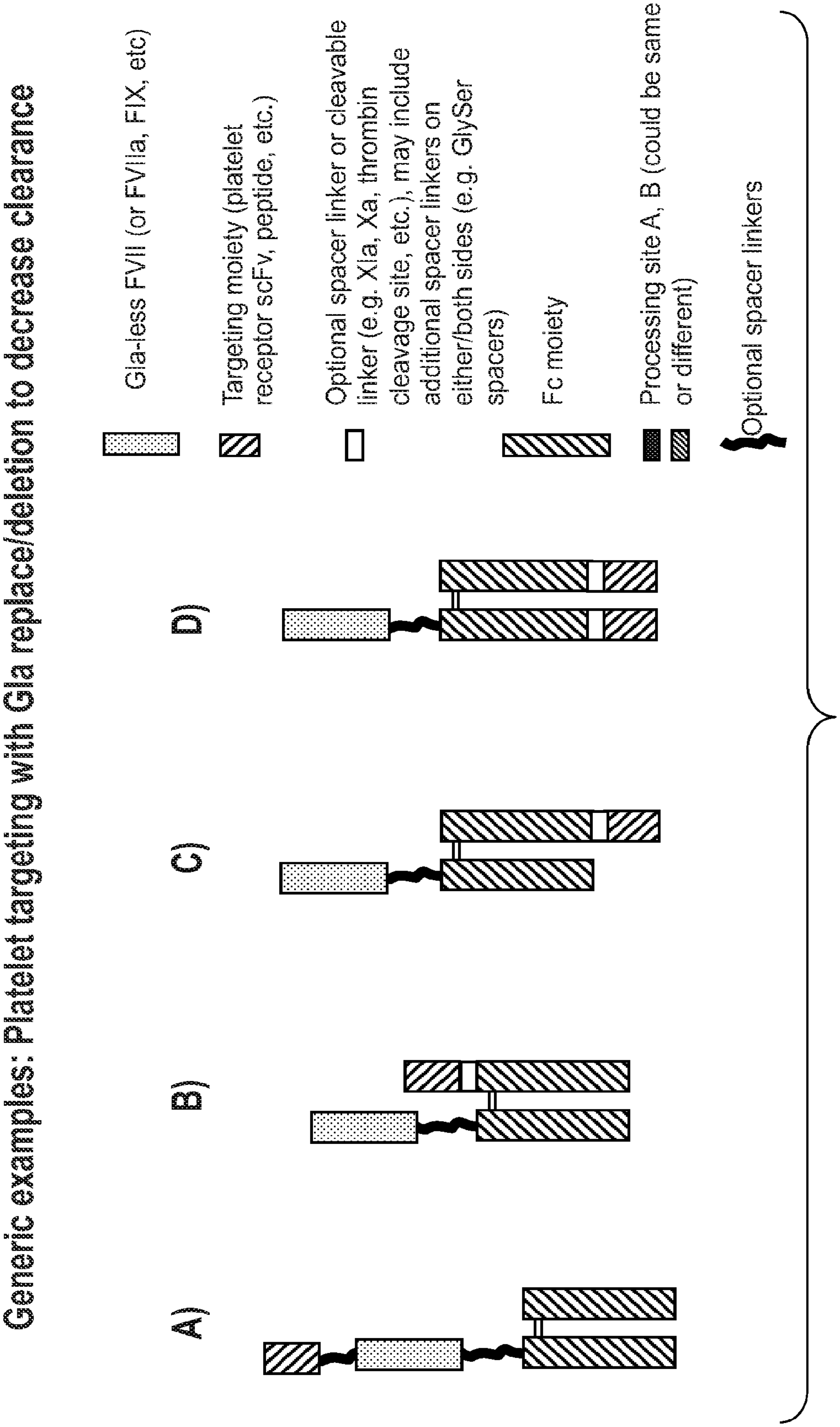
FIG. 3 illustrates exemplary chimeric clotting factor constructs which comprise a targeting domain and wherein the clotting factor moiety lacks a Gla domain. These exemplary constructs comprise an Fc region.
Figure 4:
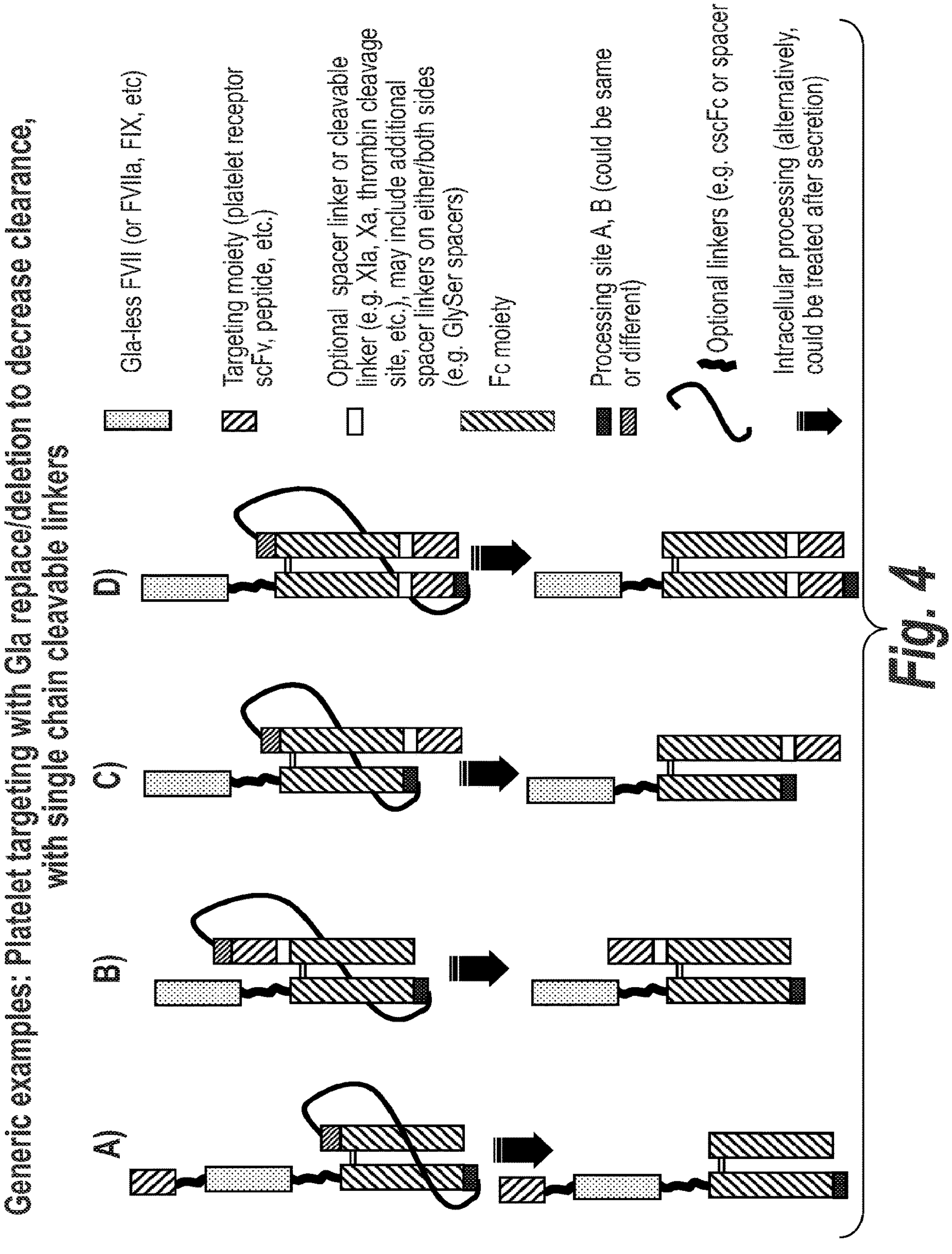
FIG. 4 illustrates exemplary chimeric clotting factor constructs which comprise a targeting domain and wherein the clotting factor moiety lacks a Gla domain. These exemplary constructs comprise a cleavable single chain Fc (cscFc) in which the scFc linker is processed by a cell in which it is expressed to form a two chain Fc region.
Figure 5:
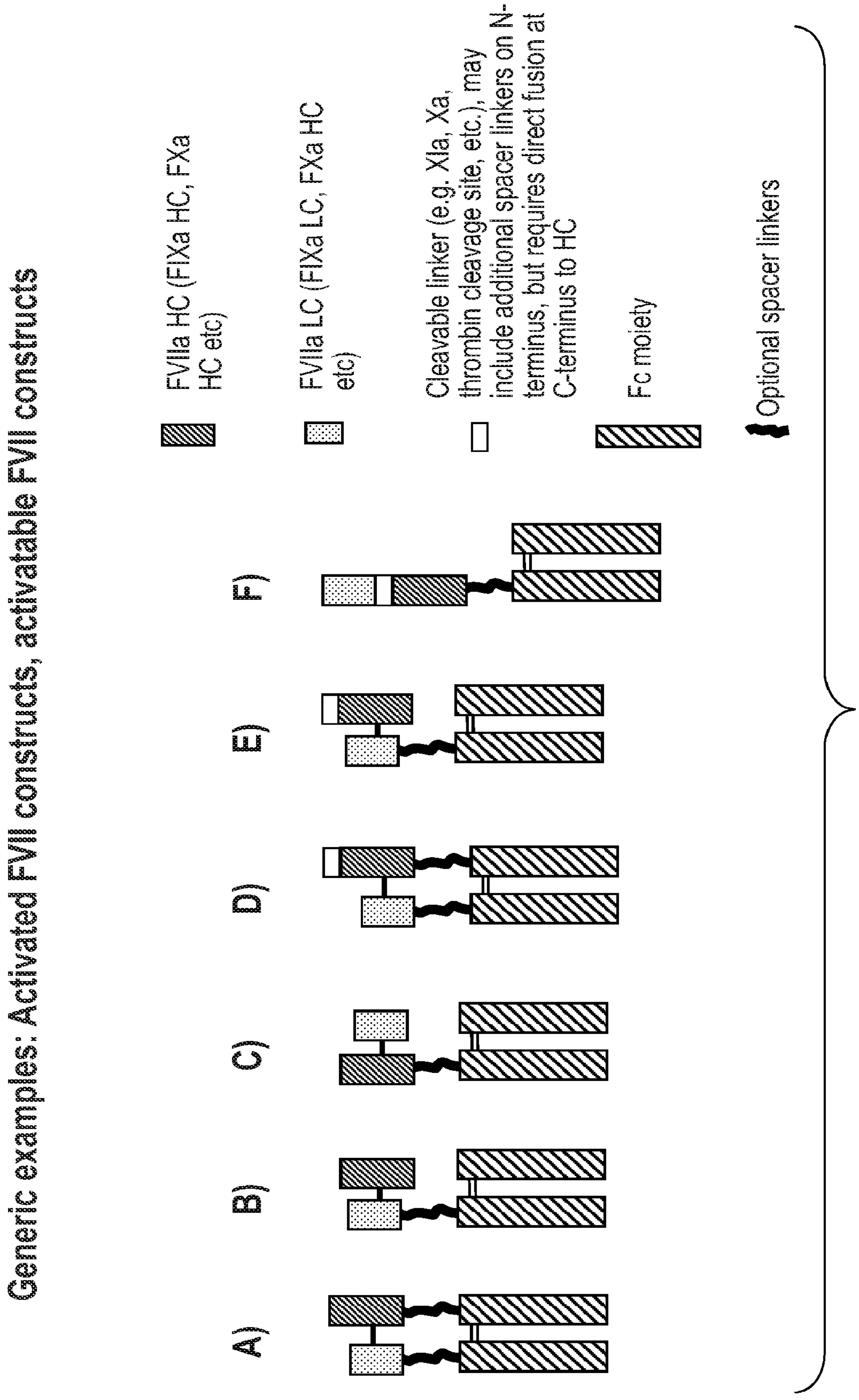
FIG. 5 illustrates exemplary chimeric clotting factor constructs which are activated (e.g., after activation in vitro or by separate expression of the light and heavy chains of the clotting factor) or which are activatable, i.e., comprise a moiety which is cleavable in vivo at the site of a clot (see panels D and E). These exemplary constructs comprise an Fc region. Constructs A, B, and C did not express well in early experiments.
Figure 6:
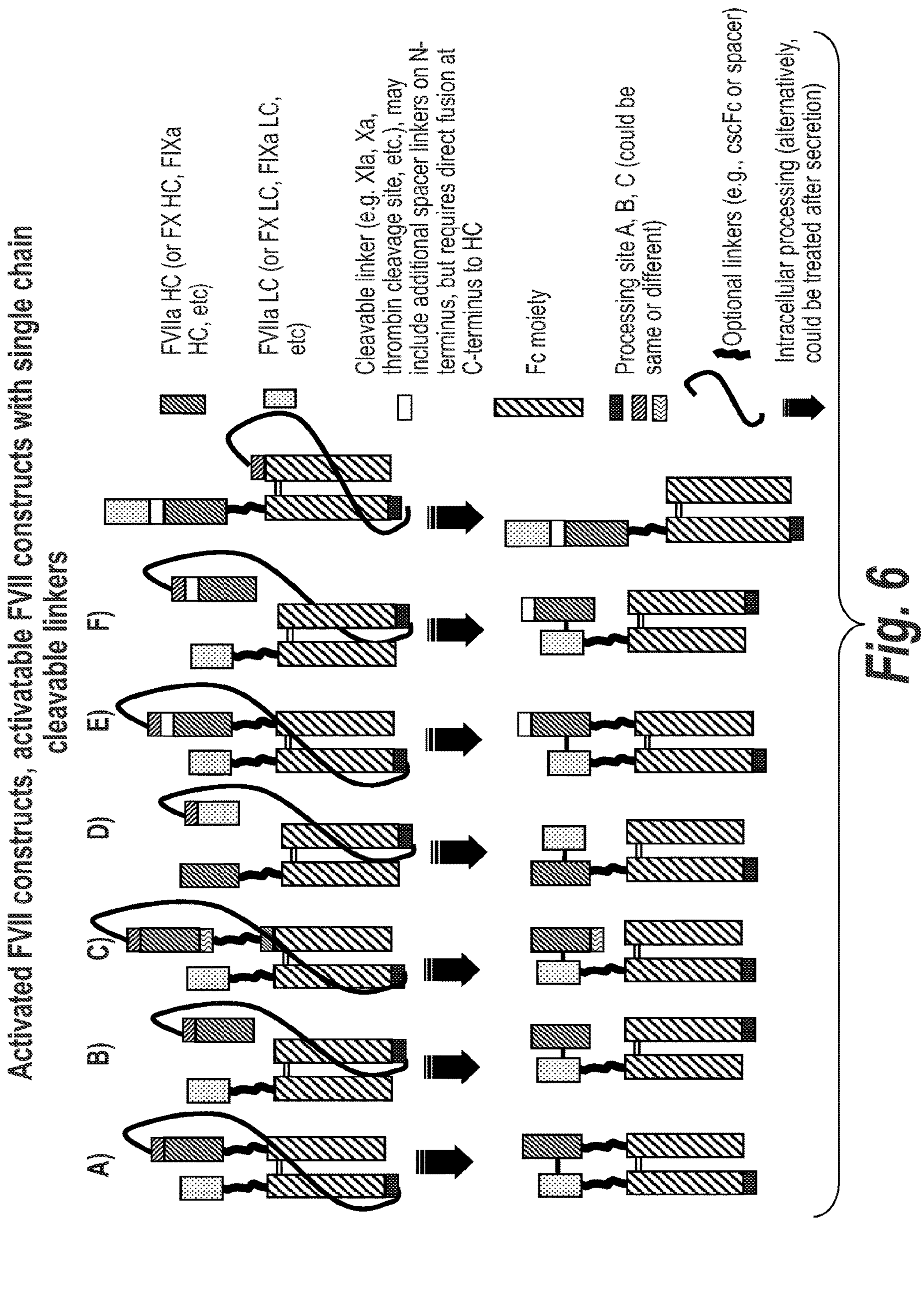
FIG. 6 illustrates exemplary chimeric clotting factor constructs which are activated (e.g., after activation in vitro or by separate expression of the light and heavy chains of the clotting factor) or which are activatable, i.e., comprise a moiety which is cleavable in vivo at the site of a clot. These exemplary constructs comprise a cleavable single chain Fc (cscFc) in which the scFc linker is processed by a cell in which it is expressed to form a two chain Fc region.
Figure 7:
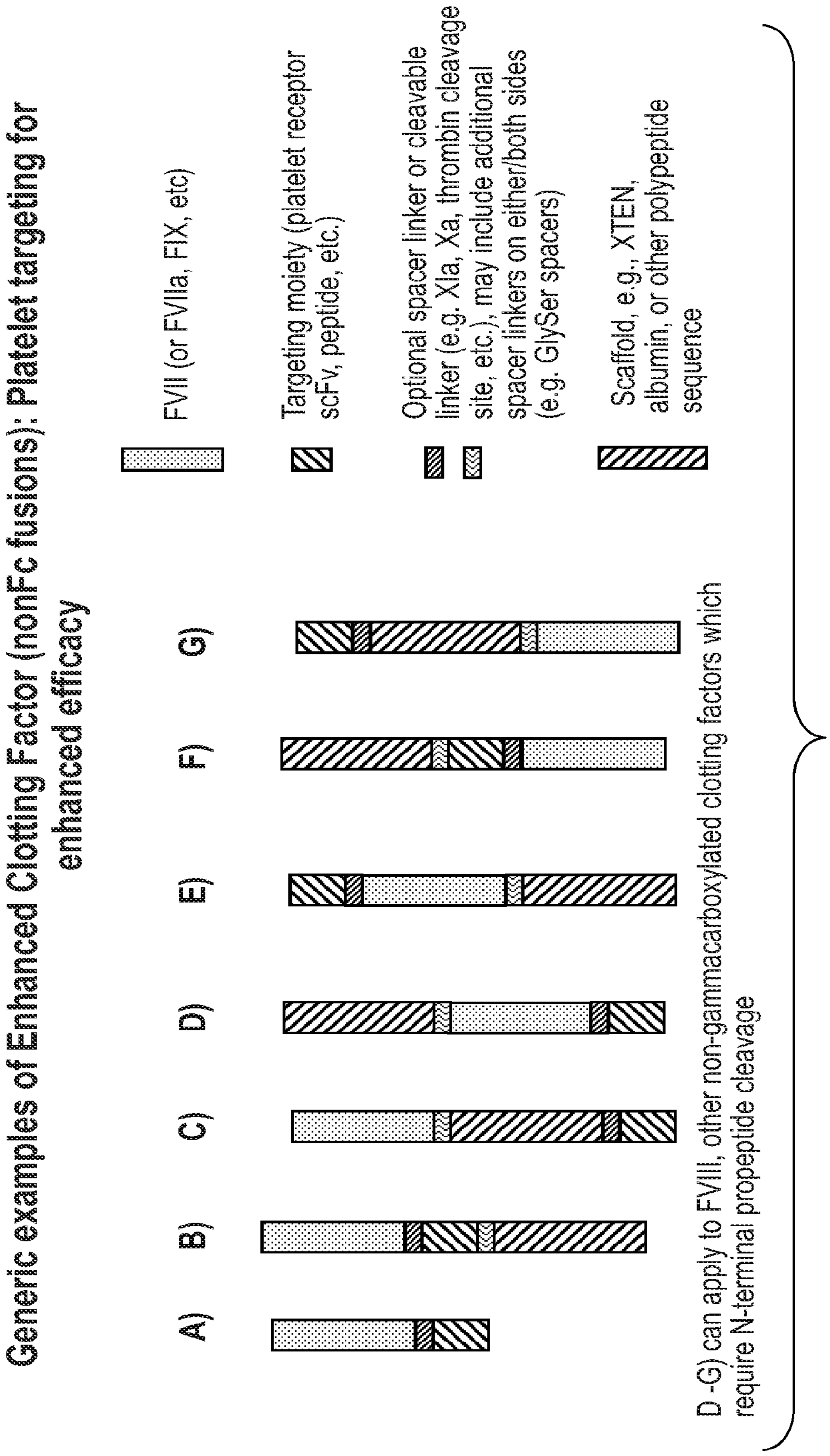
FIG. 7 illustrates exemplary chimeric clotting factor constructs comprising a targeting domain.
Figure 8:
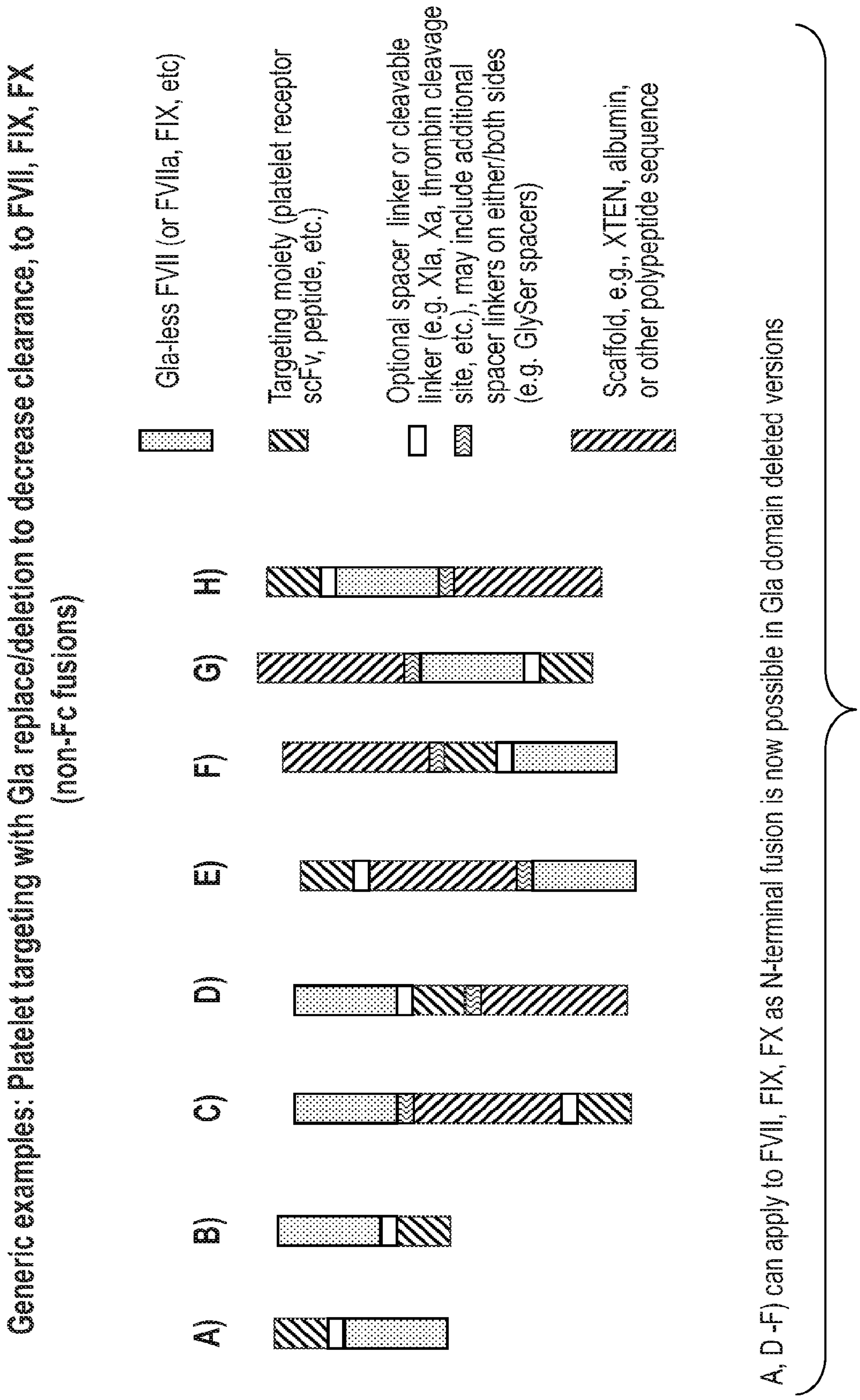
FIG. 8 illustrates exemplary chimeric clotting factor constructs which comprise a targeting domain and wherein the clotting factor moiety lacks a Gla domain.
Figure 9:
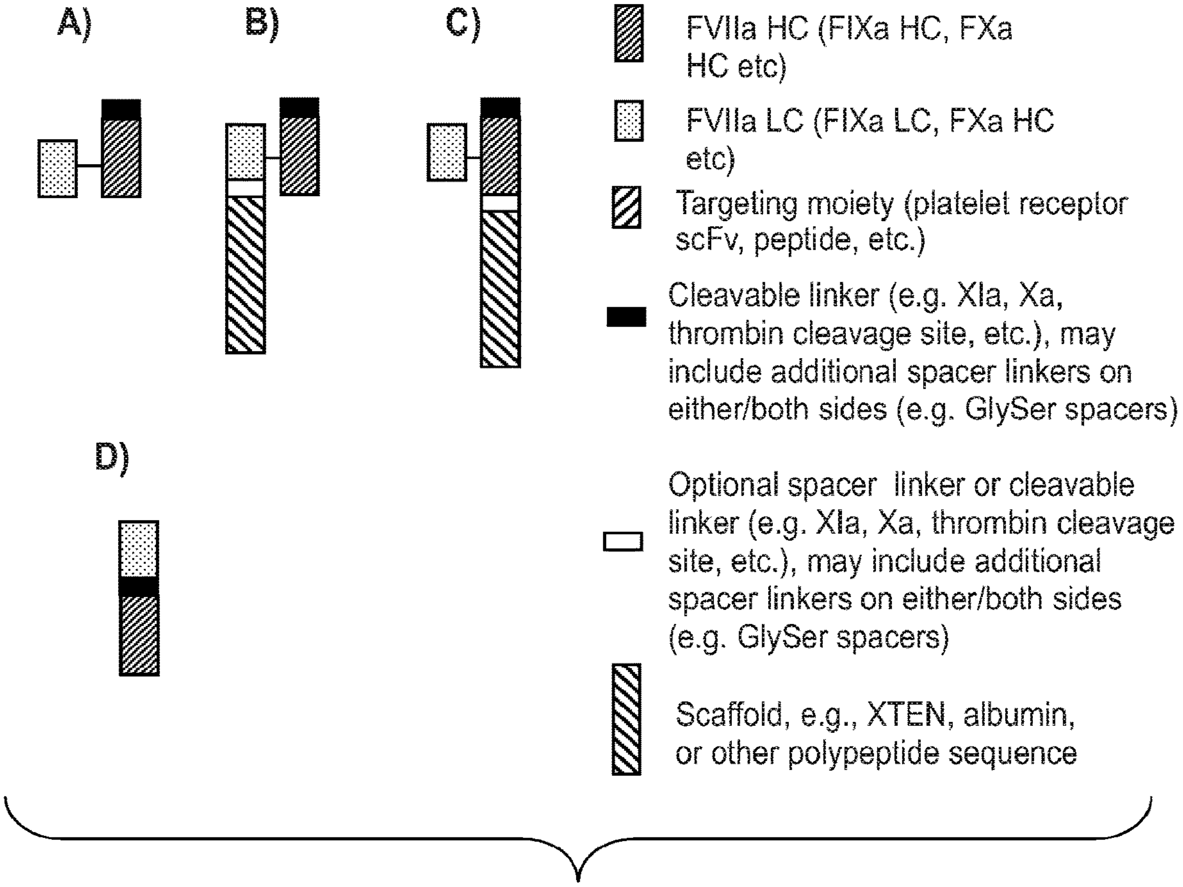
FIG. 9 illustrates exemplary chimeric clotting factor constructs which are activated (e.g., after activation in vitro or by separate expression of the light and heavy chains of the clotting factor) or which are activatable, i.e., comprise a moiety which is cleavable in vivo at the site of a clot.

The present invention relates to chimeric clotting factors. The present invention is based, at least in part, on the development of novel ways to enhance the efficacy, pharmacokinetic properties, and/or manufacturability of clotting factors. In one embodiment, improved clotting factors of the invention have increased activity where needed, e.g., by targeting the clotting factor to platelets or by being present in a subject in an activatable form (a non-naturally occurring activatable form) that is activated at the site of clot formation. This can be accomplished, e.g., by targeting the clotting factors or by making them in an activatable form.

In one embodiment, the subject clotting factors are targeted to the site of coagulation. By incorporating a targeting moiety which targets the clotting factor to resting or activated platelets, the activity of a clotting factor can be enhanced. For example, in the case of factor VII, unlike endogenous FVII that is likely activated by tissue factor (TF) at endothelial cell surfaces to generate activated factor X (FXa), exogenous FVIIa likely generates FXa/FIXa in a TF independent manner, most effective at the surface of activated platelets where other clotting factors are localized. However, physiologically FVIIa acts at the surface of a TF-bearing cell, such as an endothelial cell, and has low affinity for platelets. It has been hypothesized that therapeutic recombinant FVIIa acts by converting Factor X into Factor Xa on the surface of activated platelets. To overcome low platelet affinity and be effective at treating bleeds, recombinant FVIIa is dosed at supra-physiological levels. Therefore, in the case of FVIIa, targeting to platelet surfaces could significantly increase the efficacy of this molecule. Although other clotting factors (e.g. FIX, FVIII, FX) have higher affinity to platelets, these too may exhibit enhanced activity by incorporating platelet targeting moieties. In addition, FVIIa has a relatively short half-life (~2.3 hours) in humans. This short half-life likely contributes to the need to dose recombinant FVIIa multiple times to control a bleed. Thus, targeting clotting factors, and in particular FVIIa, to platelets improves efficiency.

The targeting moiety can be positioned at a number of places in a chimeric doting factor. Exemplary structures of targeted chimeric clotting factors are set forth, e.g., in FIGS. 1-4, 7, 8, 17, 19, 21, 44, 46, 49, 51, and 53.

In another embodiment, a chimeric clotting factor of the invention is made in a form that is activatable at the cite of coagulation. For use in bypass therapy exogenous clotting factors are only efficacious when given in the activated form. However, such activated clotting factors are rapidly inactivated by endogenous pathways (e.g. antithrombin III, TFPI), leading to clearance of the active form and a short effective half life. Giving higher doses does not solve this problem as it can result in thrombogenic effects. Thus, in one embodiment, the invention pertains to an "activatable" chimeric clotting factor constructs which comprise a heterologous enzymatic cleavage site not normally present in the clotting factor. These molecules circulate as enhanced zymogens and have a longer half life due to the lack of inactivation upon dosing, but can readily be activated at the site of clotting by cleavage by an enzyme. In one embodiment, such a heterologous enzymatic cleavage site is one for an enzyme produced during the clotting cascade. For example, in one embodiment, the heterologous cleavage site of an activatable construct comprises a Factor XIa, Xa, or thrombin cleavage site. Exemplary FXIa cleavage sites include, e.g.: TQSFNDFTR and SVSQTSKLTR. Exemplary thrombin cleavage sites include, e.g.: DFLAEGGGVR, TTKIKPR, and ALRPR. In one embodiment, a heterologous cleavage site is interposed between the light and heavy chains of the clotting factor. In another embodiment, a heterologous cleavage site is not interposed between the two chains of the clotting factor. In one embodiment, the heterologous cleavage site is amino terminal to the heavy chain of the clotting factor.

The heterologous cleavage site is present in a cleavable linker can be positioned at a number of places in a chimeric doting factor. Exemplary structures of activatable chimeric clotting factors are set forth, e.g., in FIGS. 5, 6, 9, 29, 27, 31, and 41. Exemplary such constructs are activated in the presence of clot formation and are described in more detail below.

In one embodiment, a chimeric clotting factor of the invention comprises a scaffold, e.g., to enhance the hydrodynamic radius of the molecule. For example, a chimeric clotting factor of the invention may be a fusion protein. Exemplary scaffolds include, e.g., FcRn binding moieties (e.g., complete Fc regions or portions thereof which bind to FcRn), single chain Fc regions (ScFc regions, e.g., as described in US 2008/0260738, WO 2008/012543, or WO 2008/1439545), cleaveable scFc regions (comprising a cscFc regions as described herein), less complicated proteins or portions thereof, e.g., XTen Polypeptides®, or albumin.

In one embodiment, a chimeric clotting factor of the invention employs an Fc region or an FcRn binding portion thereof as a scaffold moiety. In one embodiment, the Fc moiety to which the chimeric clotting factor is fused is a naturally occurring (or wild type (WT)) Fc moiety. In another embodiment, the Fc moiety comprises one or more variations in sequence.

In another embodiment, the Fc moiety is a scFc moiety (e.g., comprising a non-cleavable or a cscFc linker). In a construct comprising a cscFc linker an unprocessed molecule comprises a cleavable single chain Fc region in which the component Fc moieties are genetically-fused in a single polypeptide chain forming a functional, single chain, dimeric Fc region. The cscFc linker can link the Fc moieties that will comprise the dimeric Fc region of the polypeptide in tandem or may link one Fc moiety to a non-Fc moiety of the construct, e.g., a clotting factor or targeting moiety, which is, in turn, linked to a second Fc moiety. The cscFc linker is interposed between the Fc moieties that comprise the scFc region and is flanked by at least one enzymatic cleavage site, e.g., an intracellular enzymatic processing sites. In one embodiment, the scFc linker is flanked by two enzymatic cleavage sites resulting in the excision of the linker (e.g., all or substantially all of the linker) when the protein encoded by the nucleic acid molecule is processed in a cell, In another embodiment, the scFc linker is adjacent to at least one enzymatic cleavage site that allows for excision of the linker in vitro after the polypeptide has been secreted by a cell or comprises at least one enzymatic cleavage site that allows for cleavage of the linker in vivo after the construct is administered to a subject. Thus, in one embodiment, although the such a polypeptide comprises scFc region(s) encoded in a single open reading frame (ORF) as part of one contiguous nucleotide sequence in unprocessed form, the cscFc linker is enzymatically cleaved (e.g., prior to administration or in vivo after administration), resulting in a polypeptide which is a heterodimeric molecule comprising an Fc region which is not fused in a single amino acid chain, i.e., the resulting processed construct has a Fc region which comprises two polypeptide chains. In such embodiments, all or substantially all of the linker is excised, while in some embodiments, a portion of the cleavage site may remain, e.g., four arginines of the RRRR cleavage site.

In one embodiment, the scFc linker is flanked by two processing sites for cleavage. The two processing sites can be the same or different. In one embodiment, at least one processing site is a cluster of basic amino acid residues as recognized by arginine kex2/furin enzymes. Such enzymes cleave immediately C-terminal to an arginine residue. In another embodiment, at least one cleavage site is one that may be cleaved in vivo, for example a cleavage site recognized by thrombin.

In one embodiment, a chimeric clotting factor of the invention is manufactured in an activated form in the context of an scFc molecule comprising a csFc linker. For example, Factor VII, is generally produced recombinantly as a zymogen, and requires activation during manufacturing to produce the active form for administration. In one embodiment, a chimeric clotting factor of the invention is secreted from the cell in which it is expressed in active form to improve manufacturability. As is set forth in more detail below, such clotting factors can be produced by incorporating a single chain Fc region into the molecule. Single chain Fc regions are formed by dimerization of Fc moieties which are present in a single polypeptide chain. In one embodiment, such a construct comprises an scFc polypeptide linker linking the two Fc moieties of the scFc which is adjacent to at least one intracellular processing site. Cleavage of such a construct is delayed until late in the secretory pathway, e.g., when the protein colocalizes with active processing enzymes in the trans-Golgi apparatus.

In one embodiment, a cell expressing a construct encoding a polypeptide of the invention endogenously expresses an enzyme which cleaves the scFc linker at one or more processing sites resulting in a dimeric molecule comprising two polypeptide chains. In another embodiment, a cell expressing a construct encoding a polypeptide of the invention exogenously expresses an enzyme which cleaves the scFc linker at one or more processing sites.

In one embodiment, a chimeric clotting factor of the invention can combine two or more of these features to create an optimized construct e.g. targeting an activatable fusion protein construct to resting platelets, such that it can be activated efficiently as well as at a higher local concentration at the site of active coagulation. Exemplary such combination constructs include chimeric clotting factors that are both targeted and comprise an scFc linker for enhanced processing. In another embodiment, a construct of the invention is targeted and activatable.

Exemplary constructs of the invention are illustrated in the accompanying Figures and sequence listing. In one embodiment, the invention pertains to a polypeptide having the structure as set forth in the Figures. In another embodiment, the invention pertains to a polypeptide having the sequence set forth in the accompanying sequence listing or the nucleic acid molecule encoding such polypeptides. In one embodiment, the invention pertains to a mature form of a polypeptide having the sequence set forth in the accompanying sequence listing. It will be understood that these constructs and nucleic acid molecules encoding them can be used to improve hemostasis in a subject.

In order to provide a clear understanding of the specification and claims, the following definitions are provided below.

I. Definitions

As used herein, the term "protein" or "polypeptide" refers to a polymer of two or more of the natural amino acids or non-natural amino acids.

The term "amino acid" includes alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the invention and include norleucine, omithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art. As used herein, the term "polar amino acid" includes amino acids that have net zero charge, but have non-zero partial charges in different portions of their side chains (e.g. M, F, W, S, Y, N, Q, C). These amino acids can participate in hydrophobic interactions and electrostatic interactions. As used herein, the term "charged amino acid" include amino acids that can have non-zero net charge on their side chains (e.g. R, K, H, E, D). These amino acids can participate in hydrophobic interactions and electrostatic interactions.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions", can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

Polypeptides may be either monomers or multimers. For example, in one embodiment, a protein of the invention is a dimer. A dimeric polypeptide of the invention may comprise two polypeptide chains or may consist of one polypeptide chain (e.g., in the case of an scFc molecule). In one embodiment, the dimers of the invention are homodimers, comprising two identical monomeric subunits or polypeptides (e.g., two identical Fc moieties or two identical biologically active moieties). In another embodiment, the dimers of the invention are heterodimers, comprising two non-identical monomeric subunits or polypeptides (e.g., comprising two different clotting factors or portions thereof or one clotting factor only). See, e.g., U.S. Pat. No. 7,404,956, incorporated herein by reference.

As used herein, the term "polypeptide linkers" refers to a peptide or polypeptide sequence (e.g., a synthetic peptide or polypeptide sequence) which connects two domains in a linear amino acid sequence of a polypeptide chain. In one embodiment, the polypeptides of invention are encoded by nucleic acid molecules that encode polypeptide linkers which either directly or indirectly connect the two Fc moieties which make up the construct. These linkers are referred to herein as "scFc linkers" and the scFc linker is interposed between the two Fc moieties of a polypeptide which comprises it. If the scFc linker connects two Fc moieties contiguously in the linear polypeptide sequence, it is a "direct" linkage. In contract, the scFc linkers may link the first Fc moiety to a binding moiety which is, in turn, linked to the second Fc moiety, thereby forming an indirect linkage. These scFc linkers permit the formation of a single chain genetic construct. In one embodiment, the polypeptides also comprise enzymatic cleavage sites which result in the scFc linker being cleavable (a cscFc linker) and, in one embodiment, substantially excised (e.g., during processing by a cell). Thus, the resulting processed polypeptide is a dimeric molecule comprising at least two amino acid chains and substantially lacking extraneous linker amino acid sequences. In some embodiments, all or substantially all of the linker is excised, while in some embodiments, a portion of the cleavage site may remain, e.g., four arginines of the RRRR cleavage site.

In another embodiment, another type of polypeptide linker, herein referred to as a "spacer" may be used to connect different moieties, e.g., a clotting factor or targeting moiety to an Fc moiety on the polypeptide. This type of linker may provide flexibility to the polypeptide molecule. Spacers are not typically cleaved; however in certain embodiments, such cleavage may be desirable. Exemplary positions of spacers are shown in the accompanying drawings. Spacers can be located between the clotting factors, targeting moieties, and/or scaffolds, e.g., at the N or C terminus of these moieties. In one embodiment, these linkers are not removed during processing.

A third type of linker which may be present in a chimeric clotting factor of the invention is herein referred to as a "cleavable linker" which comprises a heterologous cleavage site (e.g., a factor XIa, Xa, or thrombin cleavage site) and which may include additional spacer linkers on either the N terminal of C terminal or both sides of the cleavage site. Exemplary locations for such sites are shown in the accompanying drawings and include, e.g., placement adjacent to targeting moieties. In another embodiment, such linkers may be adjacent to a clotting factor or portion thereof. For example, in one embodiment, a cleavable linker may be fused to the N terminus of the heavy chain of a clotting factor to make an activatable form of the clotting factor. In such cases, the cleavable linker may include additional spacer linkers at the N terminus of the cleavage site, but requires direct fusion at the C-terminus of the cleavage site to the amino terminus of the heavy chain of the clotting factor.

As used herein, the term "gly-ser polypeptide linker" refers to a peptide that consists of glycine and serine residues. An exemplary gly/ser polypeptide linker comprises the amino acid sequence $(Gly_4\ Ser)_n$. (SEQ ID NO:4) Another exemplary gly/ser polypeptide linker comprises the amino acid sequence $S(Gly_4\ Ser)_n$.

In one embodiment, n=1. In one embodiment, n=2. In another embodiment, n=3, i.e., $(Gly_4\ Ser)_3$. In another embodiment, n=4, i.e., $(Gly_4\ Ser)_4$ (SEQ ID NO:6). In another embodiment, n=5. In yet another embodiment, n=6. In another embodiment, n=7. In yet another embodiment, n=8. In another embodiment, n=9. In yet another embodiment, n=10. Another exemplary gly/ser polypeptide linker comprises the amino acid sequence $Ser(Gly_4Ser)_n$ (SEQ ID NO:26). In one embodiment, n=1. In one embodiment, n=2. In a preferred embodiment, n=3. In another embodiment, n=4. In another embodiment, n=5. In yet another embodiment, n=6.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence.

Polypeptides derived from another peptide may have one or more mutations relative to the starting polypeptide, e.g., one or more amino acid residues which have been substituted with another amino acid residue or which has one or more amino acid residue insertions or deletions. Preferably, the polypeptide comprises an amino acid sequence which is not naturally occurring. Such variants necessarily have less than 100% sequence identity or similarity with the starting antibody. In a preferred embodiment, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule. In one embodiment, there is one amino acid difference between a starting polypeptide sequence and the sequence derived therefrom. Identity or similarity with respect to this sequence is defined herein as the percentage of amino acid residues in the candidate sequence that are identical (i.e. same residue) with the starting amino acid residues, after aligning the sequences and introducing gaps, if necessary, to achieve the maximum percent sequence identity.

Preferred polypeptides of the invention comprise an amino acid sequence (e.g., at least one clotting factor or Fc moiety or domain) derived from a human protein sequence. However, polypeptides may comprise one or more amino acids from another mammalian species. For example, a clotting factor, Fc domain, or targeting moiety may be derived from a non-human species and included in the subject polypeptides. Alternatively, one or more amino acids may be present in a polypeptide which are derived from a non-human species. Preferred polypeptides of the invention are not immunogenic.

It will also be understood by one of ordinary skill in the art that the polypeptides of the invention may be altered such that they vary in amino acid sequence from the naturally occurring or native polypeptides from which they were derived, while retaining the desirable activity of the native polypeptides. For example, nucleotide or amino acid substitutions leading to conservative substitutions or changes at "non-essential" amino acid residues may be made. An isolated nucleic acid molecule encoding a non-natural variant of a polypeptide derived from an immunoglobulin (e.g., an Fc domain, moiety, or antigen binding site) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis.

The polypeptides of the invention may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a polypeptide may be replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into polypeptides of the invention and screened for their ability to bind to the desired target.

In the context of polypeptides, a "linear sequence" or a "sequence" is the order of amino acids in a polypeptide in an amino to carboxyl terminal direction in which residues that neighbor each other in the sequence are contiguous in the primary structure of the polypeptide.

As used herein, the terms "linked," "fused", or "fusion" refer to linkage via a peptide bonds (e.g., genetic fusion), chemical conjugation or other means. For example, one way in which molecules or moieties can be linked employs polypeptide linkers which link the molecules or moieties via peptide bonds. The terms "genetically fused," "genetically linked" or "genetic fusion" are used interchangeably and refer to the co-linear, covalent linkage or attachment of two or more proteins, polypeptides, or fragments thereof via their individual peptide backbones, through genetic expression of a single polynucleotide molecule encoding those proteins, polypeptides, or fragments. Such genetic fusion results in the expression of a single contiguous genetic sequence. Preferred genetic fusions are in frame, i.e., two or more open reading frames (ORFs) are fused to form a continuous longer ORF, in a manner that maintains the correct reading frame of the original ORFs. Thus, the resulting recombinant fusion protein is a single polypeptide containing two or more protein segments that correspond to polypeptides encoded by the original ORFs (which segments are not normally so joined in nature). In this case, the single polypeptide is cleaved during processing to yield dimeric molecules comprising two polypeptide chains.

As used herein, the term "Fc region" is defined as the portion of a polypeptide which corresponds to the Fc region of native immunoglobulin, i.e., as formed by the dimeric association of the respective Fc domains of its two heavy chains. A native Fc region is homodimeric and comprises two polypeptide chains. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

As used herein, the term "Fc domain" refers to the portion of a single immunoglobulin heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

As used herein, the term "Fc domain portion" or "Fc moiety" includes an amino acid sequence of an Fc domain or derived from an Fc domain. In certain embodiments, an Fc moiety comprises at least one of: a hinge (e.g., upper, middle, and/or lower hinge region) domain, a CH2 domain, a CH3 domain, a CH4 domain, or a variant, portion, or fragment thereof. In other embodiments, an Fc moiety comprises a complete Fc domain (i.e., a hinge domain, a CH2 domain, and a CH3 domain). In one embodiment, a Fc moiety comprises a hinge domain (or portion thereof) fused to a CH3 domain (or portion thereof). In another embodiment, an Fc moiety comprises a CH2 domain (or portion thereof) fused to a CH3 domain (or portion thereof). In another embodiment, an Fc moiety consists of a CH3 domain or portion thereof. In another embodiment, an Fc moiety consists of a hinge domain (or portion thereof) and a CH3 domain (or portion thereof). In another embodiment, a Fc moiety consists of a CH2 domain (or portion thereof) and a CH3 domain. In another embodiment, a Fc moiety consists of a hinge domain (or portion thereof) and a CH2 domain (or portion thereof). In one embodiment, an Fc moiety lacks at least a portion of a CH2 domain (e.g., all or part of a CH2 domain).

As used herein, the term "half-life" refers to a biological half-life of a particular polypeptide in vivo. Half-life may be represented by the time required for half the quantity administered to a subject to be cleared from the circulation and/or other tissues in the animal. When a clearance curve of a given polypeptide is constructed as a function of time, the curve is usually biphasic with a rapid $\alpha$-phase and longer $\beta$-phase. The $\alpha$-phase typically represents an equilibration of the administered Fc polypeptide between the intra- and extra-vascular space and is, in part, determined by the size of the polypeptide. The $\beta$-phase typically represents the catabolism of the polypeptide in the intravascular space. Therefore, in a preferred embodiment, the term half-life as used herein refers to the half-life of the polypeptide in the $\beta$-phase. The typical $\beta$ phase half-life of a human antibody in humans is 21 days.

As used herein the term "moiety" refers to a component part or constituent of a chimeric polypeptide.

As used herein, the term "targeting moiety" refers to a molecule, fragment thereof or a component of a polypeptide which localizes or directs the polypeptides of the invention to a desired site or cell. In one embodiment, a construct of the invention comprises a "targeting moiety" which enhances the activity of the polypeptide, e.g., by localizing the molecule to a desired site. Such a moiety may be, e.g., an antibody or variant thereof (e.g., and scFv) or a peptide. In another embodiment, such a targeting moiety may be a polypeptide, a receptor binding portion of a ligand, or a ligand binding portion of a receptor which is linked to a polypeptide of the invention and binds to the desired target, e.g., on a cell or tissue. The targeting moiety may be genetically fused to a construct, chemically conjugated to the construct or linked to the construct via a spacer. For example, targeting moieties may be attached to a construct of the invention by formation of a bond between the targeting moiety and an Fc moiety of a construct, where the targeting moiety comprises a first functional group and the Fc moiety comprises a second functional group, and where the first and second functional groups are capable of reacting with each other to form a chemical bond (see, e.g., U.S. Pat. No. 7,381,408). In one embodiment, a targeting moiety binds to platelets. Exemplary targeting moieties are described in more detail below.

In one embodiment a targeting moiety for use in a construct of the invention comprises an antibody variant. The term "antibody variant" or "modified antibody" includes an antibody which does not occur in nature and which has an amino acid sequence or amino acid side chain chemistry which differs from that of a naturally-derived antibody by at least one amino acid or amino acid modification as described herein. As used herein, the term "antibody variant" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules; single-chain antibodies; diabodies; triabodies; and antibodies with altered effector function and the like.

As used herein the term "scFv molecule" includes binding molecules which consist of one light chain variable domain (VL) or portion thereof, and one heavy chain variable domain (VH) or portion thereof, wherein each variable domain (or portion thereof) is derived from the same or different antibodies. scFv molecules preferably comprise an scFv linker interposed between the VH domain and the VL domain. ScFv molecules are known in the art and are described, e.g., in U.S. Pat. No. 5,892,019, Ho et al. 1989. Gene 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837.

A "scFv linker" as used herein refers to a moiety interposed between the VL and VH domains of the scFv. scFv linkers preferably maintain the scFv molecule in a antigen binding conformation. In one embodiment, a scFv linker comprises or consists of an scFv linker peptide. In certain embodiments, a scFv linker peptide comprises or consists of a gly-ser polypeptide linker. In other embodiments, a scFv linker comprises a disulfide bond.

The term "glycosylation" refers to the covalent linking of one or more carbohydrates to a polypeptide. Typically, glycosylation is a posttranslational event which can occur within the intracellular milieu of a cell or extract therefrom. The term glycosylation includes, for example, N-linked glycosylation (where one or more sugars are linked to an asparagine residue) and/or O-linked glycosylation (where one or more sugars are linked to an amino acid residue having a hydroxyl group (e.g., serine or threonine). In one embodiment, a molecule of the invention is glycosylated. In another embodiment, a molecule of the invention is aglycosylated. In yet another embodiment, a molecule of the invention has reduced glycosylation as compared to that in a wild type Fc region.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by native disulfide bonds and the two heavy chains are linked by two native disulfide bonds at positions corresponding to 239 and 242 using the Kabat numbering system (position 226 or 229, EU numbering system).

The term "vector" or "expression vector" is used herein to mean vectors used in accordance with the present invention as a vehicle for introducing into and expressing a desired polynucleotide in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed to produce the chimeric clotting factors of the invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. In one embodiment, an inducible expression system can be employed. Additional elements may also be needed for optimal synthesis of mRNA. These elements may include signal sequences, splice signals, as well as transcriptional promoters, enhancers, and termination signals. In one embodiment, a secretion signal, e.g., any one of several well characterized bacterial leader peptides (e.g., pelB, phoA, or ompA), can be fused in-frame to the N terminus of a polypeptide of the invention to obtain optimal secretion of the polypeptide. (Lei et al. (1988), *Nature,* 331:543; Better et al. (1988) *Science,* 240:1041; Mullinax et al., (1990). *PNAS,* 87:8095).

The term "host cell" refers to a cell that has been transformed with a vector constructed using recombinant DNA techniques and encoding at least one heterologous gene. In descriptions of processes for isolation of proteins from recombinant hosts, the terms "cell" and "cell culture" are used interchangeably to denote the source of protein unless it is clearly specified otherwise. In other words, recovery of protein from the "cells" may mean either from spun down whole cells, or from the cell culture containing both the medium and the suspended cells. The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), PerC6 cells), HAK (hamster kidney line), SP2/O (mouse myeloma), P3×63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature. The polypeptides of the invention can also be expressed in non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available including *Pichia pastoris*. For expression in *Saccharomyces*, the plasmid YRp7, for example, (Stinchcomb et al., (1979), *Nature,* 282:39; Kingsman et al., (1979), *Gene,* 7:141; Tschemper et al., (1980), *Gene,* 10:157) is commonly used. This plasmid already contains the TRP1 gene which provides a selection marker for a mutant strain of yeast lacking the ability to grow in tryptophan, for example ATCC No. 44076 or PEP4-1 (Jones, (1977), *Genetics,* 85:12). The presence of the trpl lesion as a characteristic of the yeast host cell genome then provides an effective environment for detecting transformation by growth in the absence of tryptophan.

As used herein the term "endogenous" refers to molecules (e.g. nucleic acid and/or protein molecules) that are naturally present in a cell. In contrast, the term "exogenous" or "heterologous" refers to such molecules that are not normally found in a given context, e.g., in a cell or in a polypeptide. For example, an exogenous or heterologous molecule may be introduced into a cell and are only present after manipulation of the cell, e.g., by transfection or other forms of genetic engineering or a heterologous amino acid sequence may be present in a protein in which it is not naturally found.

As used herein, the term "cleavage site" or "enzymatic cleavage site" refers to a site recognized by an enzyme. Certain enzymatic cleavage sites comprise an intracellular processing site. In one embodiment, a polypeptide has an enzymatic cleavage site cleaved by an enzyme that is activated during the clotting cascade, such that cleavage of such sites occurs at the site of clot formation. Exemplary such sites include e.g., those recognized by thrombin, Factor XIa or Factor Xa. Exemplary FXIa cleavage sites include, e.g., TQSFNDFTR and SVSQTSKLTR. Exemplary thrombin cleavage sites include, e.g., DFLAEGGGVR, TTKIKPR, LVPRG SEQ ID NO:35) and ALRPR. Other enzymatic cleavage sites are known in the art.

As used herein, the term "processing site" or "intracellular processing site" refers to a type of enzymatic cleavage site in a polypeptide which is the target for enzymes that function after translation of the polypeptide. In one embodiment, such enzymes function during transport from the Golgi lumen to the trans-Golgi compartment. Intracellular processing enzymes cleave polypeptides prior to secretion of the protein from the cell. Examples of such processing sites include, e.g., those targeted by the PACE/furin (where PACE is an acronym for Paired basic Amino acid Cleaving Enzyme) family of endopeptidases. These enzymes are localized to the Golgi membrane and cleave proteins on the carboxyterminal side of the sequence motif Arg-[any residue]-(Lys or Arg)-Arg. As used herein the "furin" family of enzymes includes, e.g., furin, PC2, PC1/Pc3, PC4, PACE4, PC5/PC6, and LPC/PC7/PC8/SPC7. Other processing sites are known in the art.

In constructs that include more than one processing or cleavage site, it will be understood that such sites may be the same or different.

In vitro production allows scale-up to give large amounts of the desired altered polypeptides of the invention. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, hydrophobic interaction chromatography (HIC, chromatography over DEAE-cellulose or affinity chromatography.

As used herein, the phrase "subject that would benefit from administration of a polypeptide" includes subjects, such as mammalian subjects, that would benefit from administration of polypeptides of the invention, e.g., to improve hemostasis.

A "chimeric protein" or "fusion protein", as used herein, refers to any protein comprised of a first amino acid sequence derived from a first source, bonded, covalently or non-covalently, to a second amino acid sequence derived from a second source, wherein the first and second source are not the same. A first source and a second source that are not the same can include two different biological entities, or two different proteins from the same biological entity, or a biological entity and a non-biological entity. A chimeric protein can include for example, a protein derived from at least 2 different biological sources. A biological source can include any non-synthetically produced nucleic acid or amino acid sequence (e.g. a genomic or cDNA sequence, a plasmid or viral vector, a native virion or a mutant or analog, as further described herein, of any of the above). A synthetic source can include a protein or nucleic acid sequence produced chemically and not by a biological system (e.g. solid phase synthesis of amino acid sequences). A chimeric protein can also include a protein derived from at least 2 different synthetic sources or a protein derived from at least one biological source and at least one synthetic source. A chimeric protein may also comprise a first amino acid sequence derived from a first source, covalently or non-covalently linked to a nucleic acid, derived from any source or a small organic or inorganic molecule derived from any source. The chimeric protein may comprise a linker molecule between the first and second amino acid sequence or between the first amino acid sequence and the nucleic acid, or between the first amino acid sequence and the small organic or inorganic molecule.

As used herein, the term "clotting factor," refers to molecules, or analogs thereof, naturally occurring or recombinantly produced which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot.

Clotting activity, as used herein, means the ability to participate in a cascade of biochemical reactions that culminates in the formation of a fibrin clot and/or reduces the severity, duration or frequency of hemorrhage or bleeding episode.

Hemostasis, as used herein, means the stopping or slowing of bleeding or hemorrhage; or the stopping or slowing of blood flow through a blood vessel or body part.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency), Von Willebrand disease, factor Xi deficiency (PTA deficiency), Factor XII deficiency, deficiencies or structural abnormalities in fibrinogen, prothrombin, Factor V, Factor VII, Factor X or factor XIII, Bernard-Soulier syndrome is a defect or deficiency in GPIb. GPIb, the receptor for vWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this may increase bleeding risk.

The chimeric molecules of the invention can be used prophylacticly. As used herein the term "prophylactic treatment" refers to the administration of a molecule prior to a bleeding episode. In one embodiment, the subject in need of a general hemostatic agent is undergoing, or is about to undergo, surgery. The chimeric protein of the invention can be administered prior to or after surgery as a prophylactic. The chimeric protein of the invention can be administered during or after surgery to control an acute bleeding episode. The surgery can include, but is not limited to, liver transplantation, liver resection, or stem cell transplantation On-demand treatment includes treatment for a bleeding episode, hemarthrosis, muscle bleed, oral bleed, hemorrhage, hemorrhage into muscles, oral hemorrhage, trauma, trauma capitis (head trauma), gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, peri-operative management, or treatment for surgery. Such surgeries include, e.g., minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

As used herein the term "acute bleeding" refers to a bleeding episode regardless of the underlying cause. For example, a subject may have trauma, uremia, a hereditary bleeding disorder (e.g., factor VII deficiency) a platelet disorder, or resistance owing to the development of antibodies to clotting factors.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, the prophylaxis of one or more symptoms associated with a disease or condition.

II. Clotting Factors

In particular, the invention pertains to improved versions of factors VII, IX, and X. These factors are all structurally related in that in each the amino terminal end of the light chain is not amenable to the incorporation of additional moieties. Similarly, the amino terminal end of the heavy chain of these three clotting factors is not amenable to the incorporation of additional moieties, with the exception of cleaveable moieties, i.e., moieties linked via a cleavage site or moieties which consist of a cleavage site. The chimeric clotting factor constructs of the invention were designed based on these shared properties and it will be understood that although factor VII is often shown to illustrate exemplary embodiments of the invention, the subject constructs may be made using factor VII, IX, or X. For example, one of skill in the art would understand that the FVII portion of a construct of the invention could be substituted with a FVIII, FIX or FX portion to make an enhanced version of one of these clotting factors.

Exemplary chimeric clotting factor constructs of the invention are set forth in the accompanying Figures. Although the Figures generally illustrate the clotting Factor as a single chain (in its zymogen form) it will be understood that the clotting factor may also be present in its active form in a construct of the invention, e.g. as a two chain, disulfide bonded form.

In one embodiment, a chimeric clotting factor of the invention is expressed by a cell in active form. In another embodiment, a chimeric clotting factor is expressed in inactive form and is subsequently activated under appropriate conditions in vitro such that the active form of the clotting factor is present in the construct. In another embodiment, a chimeric clotting factor of the invention comprises a clotting factor in inactive form and the clotting factor is activated in vivo after administration.

In one embodiment, an scFc scaffold can be used to produce an active form of a molecule. Certain clotting factors are produced recombinantly as zymogens and, therefore, require activation during manufacturing. Active forms of Factors VII, IX, and X are comprised of dimeric molecules in which the heavy and light chain are linked only by a disulfide bond.

In one embodiment, a chimeric clotting factor is activated prior to administration to a subject to improve hemostasis. Methods for activating clotting factors are known in the art. For example, in one embodiment, a chimeric clotting factor of the invention is contacted with media containing $CaCl_2$ at a concentration of approximately 5 mM.

In another embodiment, a chimeric clotting factor of the invention is secreted in active form by a cell in which it is expressed. In one embodiment, an active chimeric clotting factor is made by expressing the heavy and light chain of a clotting factor as separate polypeptides.

In another embodiment, the N-terminus of the heavy chain of the clotting factor is modified to comprise an intracellular processing site which delays the activation of the clotting factor during synthesis until later in the secretory pathway, (i.e. until protein colocalizes with active processing enzymes in the trans-Golgi network), leading to greater productivity. Exemplary such intracellular processing sites include those recognized by furin. Exemplary cleavage sites for this family of enzymes include an amino acid sequence comprising the motif Arg-Xaa-Lys/Arg-Arg.

In a preferred embodiment, an active construct of the invention is made in the context of an Fc fusion protein, e.g., using an scFc linker (e.g., a cscfc linker).

Exemplary constructs are shown in the accompanying figures.

In one embodiment, the invention pertains to processed (e.g., mature) polypeptides in which the at least one cleavage site adjacent to an scFc polypeptide linker has been cleaved such that the molecule is no longer a single polypeptide chain such that the polypeptide is comprised of at least two polypeptide chains (owing to cleavage at the enzymatic cleavage site(s) P1 and/or P2).

In one embodiment, such processed polypeptides comprise a clotting factor or portion thereof linked to the second Fc moiety (i.e., the second Fc moiety when counting from the amino terminus to the carboxy terminus prior to cleavage of the polypeptide linker) which has a free amino terminus after cleavage of the polypeptide linker.

In one embodiment, a clotting factor attached to the N-terminus of the second Fc moiety is catalytically active, e.g., has enzymatic activity. In another embodiment, a clotting factor attached to the N-terminus of the second Fc moiety is secreted by a cell as a zymogen requiring further enzymatic processing of the clotting factor in order to be fully activated.

In one embodiment, the invention pertains to clotting factors which are secreted from cells in active or activated form without the need for further activation during processing. For example, Factor VII is generally produced recombinantly as a zymogen and requires activation during manufacturing to produce the active form for administration. In one embodiment, a polypeptide of the invention is secreted from the cell in which it is expressed in active form to improve manufacturability. As is set forth in more detail below, such clotting factors can be produced by expressing the light chain of a clotting factor and the heavy chain of a clotting factor separately in the context of an scFc molecule comprising a cscFc linker. Activation of such a construct is delayed until late in the secretory pathway during processing, e.g., when the protein colocalizes with active processing enzymes in the trans-Golgi apparatus.

In one embodiment, a clotting factor of the invention is a mature form of Factor VII or a variant thereof. Factor VII (FVII, F7; also referred to as Factor 7, coagulation factor VII, serum factor VII, serum prothrombin conversion accelerator, SPCA, proconvertin and eptacog alpha) is a serine protease that is part of the coagulation cascade. FVII includes a Gla domain, two EGF domains (EGF-1 and EGF-2), and a serine protease domain (or peptidase S1 domain) that is highly conserved among all members of the peptidase S1 family of serine proteases, such as for example with chymotrypsin. FVII occurs as a single chain zymogen, an activated zymogen-like two-chain polypeptide and a fully activated two-chain form. As used herein, a "zymogen-like" protein or polypeptide refers to a protein that has been activated by proteolytic cleavage, but still exhibits properties that are associated with a zymogen, such as, for example, low or no activity, or a conformation that resembles the conformation of the zymogen form of the protein. For example, when it is not bound to tissue factor, the two-chain activated form of FVII is a zymogen-like protein; it retains a conformation similar to the uncleaved FVII zymogen, and, thus, exhibits very low activity. Upon binding to tissue factor, the two-chain activated form of FVII undergoes conformational change and acquires its full activity as a coagulation factor.

Exemplary FVII variants include those with increased specific activity, e.g., mutations that increase the activity of FVII by increasing its enzymatic activity (Kcat or Km). Such variants have been described in the art and include, e.g., mutant forms of the molecule as described for example in Persson et al. 2001. PNAS 98:13583; Petrovan and Ruf. 2001. J. Biol. Chem. 276:6616; Persson et al. 2001 J. Biol. Chem. 276:29195; Soejima et al. 2001. J. Biol. Chem. 276:17229; Soejima et al. 2002. J. Biol. Chem. 247:49027. In one embodiment, a variant form of FVII includes the mutations Exemplary mutations include V158D-E296V-M298Q. In another embodiment, a variant form of FVII includes a replacement of amino acids 608-619 (LQQSRKVGDSPN, corresponding to the 170-loop) from the FVII mature sequence with amino acids EASYPGK from the 170-loop of trypsin. High specific activity variants of FIX are also known in the art. Fir example, Simioni et al. (2009 N. E. Journal of Medicine 361:1671) describe an R338L mutation. Chang et al. (1988 JBC 273:12089) and Pierri et al. (2009 Human Gene Therapy 20:479) describe an R338A mutation. Other mutations are known in the art and include those described, e.g., in Zogg and Brandstetter. 2009 Structure 17:1669; Sichler et al. 2003. J. Biol. Chem. 278:4121; and Sturzebecher et al. 1997. FEBS Lett 412:295. The contents of these references are incorporated herein by reference.

Full activation, which occurs upon conformational change from a zymogen-like form, occurs upon binding to is co-factor tissue factor. Also, mutations can be introduced that result in the conformation change in the absence of tissue factor. Hence, reference to FVIIa includes both two-chain forms thereof, the zymogen-like form and the fully activated two-chain form.

In one embodiment, a clotting factor of the invention is a mature form of Factor VIII or a variant thereof. FVIII functions in the intrinsic pathway of blood coagulation as a cofactor to accelerate the activation of factor X by factor IXa, a reaction that occurs on a negatively charged phospholipid surface in the presence of calcium ions. FVIII is synthesized as a 2351 amino acid single-chain polypeptide having the domain structure A1-A2-B-A3-C1-C2. Wehar, G. A. et al., Nature 312:337-342 (1984) and Toole, J. J. et al., Nature 312:342-347 (1984). The domain structure of FVIII is identical to that of the homologous coagulation factor, factor V (FV). Kane, W. H. et al., PNAS (USA) 83:6800-6804 (1986) and Jenny, R. J. et al., PNAS (USA) 84:4846-4850 (1987). The FVIII A-domains are 330 amino acids and have 40% amino acid identity with each other and to the A-domain of FV and the plasma copper-binding protein ceruloplasmin. Takahashi, N. et al., PNAS (USA) 81:390-394 (1984). Each C-domain is 150 amino acids and exhibits 40% identity to the C-domains of FV, and to proteins that bind glycoconjugates and negatively charged phospholipids. Stubbs, J. D. et al., PNAS (USA) 87:8417-8421 (1990). The FVIII B-domain is encoded by a single exon and exhibits little homology to any known protein including FV B-domain. Gitschier, J. et al., Nature 312:326-330 (1984) and Cripe, L. D. et al., Biochemistry 31:3777-3785 (1992).

FVIII is secreted into plasma as a heterodimer of a heavy chain (domains A1-A2-B) and a light chain (domains A3-C1-C2) associated through a noncovalent divalent metal ion linkage between the A1- and A3-domains. In plasma, FVIII is stabilized by binding to von Willebrand factor. More specifically, the FVIII light chain is bound by noncovalent interactions to a primary binding site in the amino terminus of von Willebrand factor. Upon proteolytic activation by thrombin, FVIII is activated to a heterotrimer of 2 heavy chain fragments (A1, a 50 kDa fragment, and A2, a 43 kDa fragment) and the light chain (A3-C1-C2, a 73 kDa chain). The active form of FVIII (FVIIIa) thus consists of an A1-subunit associated through the divalent metal ion linkage to a thrombin-cleaved A3-C1-C2 light chain and a free A2 subunit associated with the A1 domain through an ion association. Eaton, D. et al., Biochemistry 25: 505 (1986); Lollar, P. et al., J. Biol. Chem. 266: 12481 (1991); and Fay, P. J. et al., J. Biol. Chem. 266: 8957 (1991). This FVIIIa heterotrimer is unstable and subject to rapid inactivation through dissociation of the A2 subunit under physiological conditions.

In one embodiment, a clotting factor comprises a B-domain deleted version of factor VIII. "B-domain" of Factor VIII, as used herein, is the same as the B-domain known in the art that is defined by internal amino acid sequence identity and sites of proteolytic cleavage, e.g., residues Ser741-Arg1648 of full-length human Factor VIII. The other human Factor VIII domains are defined by the following amino acid residues: A1, residues Ala1-Arg372; A2, residues Ser373-Arg740; A3, residues Ser1690-Asn2019; C1, residues Lys2020-Asn2172; C2, residues Ser2173-Tyr2332. The A3-C1-C2 sequence includes residues Ser1690-Tyr2332. The remaining sequence, residues Glu1649-Arg1689, is usually referred to as the a3 acidic region. The locations of the boundaries for all of the domains, including the B-domains, for porcine, mouse and canine Factor VIII are also known in the art. In one embodiment, the B domain of Factor VIII is deleted ("B-domain-deleted factor VIII" or "BDD FVIII"). An example of a BDD FVIII is REFACTO® (recombinant BDD FVIII with S743/Q1638 fusion), which is known in the art.

A "B-domain-deleted Factor VIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B-domain-deleted Factor VIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In another embodiment, a B-domain deleted Factor VIII is the S743/Q1638 B-domain deleted Factor VIII (SQ version Factor VIII) (e.g., Factor VIII having a deletion from amino acid 744 to amino acid 1637, e.g., Factor VIII having amino acids 1-743 and amino acids 1638-2332 of SEQ ID NO: 6, i.e., SEQ ID NO: 2). In some embodiments, a B-domain-deleted Factor VIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B-domain-deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B-domain-deleted Factor VIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some embodiments, a B-domain-deleted Factor VIII is constructed with a deletion of amino acids 747-1638, i.e., virtually a complete deletion of the B domain. Hoeben R. C., et al. *J. Biol. Chem.* 265 (13): 7318-7323 (1990), incorporated herein by reference in its entirety. A B-domain-deleted Factor VIII may also contain a deletion of amino acids 771-1666 or amino acids 868-1562 of Factor VIII. Meulien P., et al. *Protein Eng.* 2(4): 301-6 (1988), incorporated herein by reference in its entirety. Additional B domain deletions that are part of the invention include: deletion of amino acids 982 through 1562 or 760 through 1639 (Toole et al., *Proc. Natl. Acad. Sci. U.S.A.* (1986) 83, 5939-5942)), 797 through 1562 (Eaton, et al. *Biochemistry* (1986) 25:8343-8347)), 741 through 1646 (Kaufman (PCT published application No. WO 87/04187)), 747-1560 (Sarver, et al., *DNA* (1987) 6:553-564)), 741 though 1648 (Pasek (PCT application No. 88/00831)), or 816 through 1598 or 741 through 1648 (Lagner (Behring Inst. Mitt. (1988) No 82:16-25, EP 295597)), each of which is incorporated herein by reference in its entirety. Each of the foregoing deletions may be made in any Factor VIII sequence. In one embodiment, the invention pertains to a targeted version of FVIII, wherein the targeting (i) specifically binds to platelets, (ii) is not interposed between the light and heavy chains of the clotting factor, and wherein said chimeric clotting factor exhibits increased generation of thrombin in the presence of platelets as compared to an appropriate control lacking the at least one targeting moiety.

In one embodiment, a clotting factor of the invention is a mature form of Factor IX or a variant thereof. Factor IX circulates as a 415 amino acid, single chain plasma zymogen (A. Vysotchin et al., J. Biol. Chem. 268, 8436 (1993)). The zymogen of FIX is activated by FXIa or by the tissue factor/FVIIa complex. Specific cleavages between arginine-alanine 145-146 and arginine-valine 180-181 result in a light chain and a heavy chain linked by a single disulfide bond between cysteine 132 and cysteine 289 (S. Bajaj et al., Biochemistry 22, 4047 (1983)). The structural organization of FIX is similar to that of the vitamin K-dependent blood clotting proteins FVII, FX and protein C (B. Furie and B. Furie, supra). The approximately 45 amino acids of the amino terminus comprise the gamma-carboxyglutamic acid, or gla, domain. This is followed by two epidermal growth factor homology domains (EGF), an activation peptide and the catalytic "heavy chain" which is a member of the serine protease family (A. Vysotchin et al., J. Biol. Chem. 268, 8436 (1993); S. Spitzer et al., Biochemical Journal 265, 219 (1990); H. Brandstetter et al., Proc. Natl. Acad Sci. USA 92, 9796 (1995)).

In one embodiment, a clotting factor of the invention is a mature form of Factor X. Factor X is a vitamin-K dependent glycoprotein of a molecular weight of 58.5 kDa, which is secreted from liver cells into the plasma as a zymogen. Initially factor X is produced as a prepropeptide with a signal peptide consisting in total of 488 amino acids. The signal peptide is cleaved off by signal peptidase during export into the endoplasmatic reticulum, the propeptide sequence is cleaved off after gamma carboxylation took place at the first 11 glutamic acid residues at the N-terminus of the mature N-terminal chain. A further processing step occurs by cleavage between Arg182 and Ser183. This processing step also leads concomitantly to the deletion of the tripeptide Arg180-Lys181-Arg182. The resulting secreted factor X zymogen consists of an N-terminal light chain of 139 amino acids (M, 16,200) and a C-terminal heavy chain of 306 amino acids (M, 42,000) which are covalently linked via a disulfide bridge between Cys172 and Cys342. Further posttranslational processing steps include the .beta.-hydroxylation of Asp103 as well as N- and O-type glycosylation.

It will be understood that in addition to wild type (WT) versions of these clotting factors or biologically active portions thereof, the present invention may also employ precursor truncated forms thereof that have activity, allelic variants and species variants, variants encoded by splice variants, and other variants, including polypeptides that have at least 40%, 45%, 50%, 55%, 65%, 70%, 75%, 80%, 85%, 90%, 95%, 96%, 97%, 98%, 99% or more sequence identity to the mature form of the clotting factor and which retain the ability to promote clot formation. For example, modified FVII polypeptides and variants thereof which retain at least one activity of a FVII, such as TF binding, factor X binding, phospholipid binding, and/or coagulant activity of a FVII may be employed. By retaining activity, the activity can be altered, such as reduced or increased, as compared to a wild-type clotting factor so long as the level of activity retained is sufficient to yield a detectable effect. Exemplary sequences of clotting factors that can be used in the constructs of the invention are found in the accompanying sequence listing.

Exemplary modified polypeptides include, but are not limited to, tissue-specific isoforms and allelic variants thereof, synthetic molecules prepared by translation of nucleic acids, proteins generated by chemical synthesis, such as syntheses that include ligation of shorter polypeptides, through recombinant methods, proteins isolated from human and non-human tissue and cells, chimeric polypeptides and modified forms thereof. The instant clotting factors may also consist of fragments or portions of WT molecules that are of sufficient length or include appropriate regions to retain at least one activity (upon activation if needed) of a full-length mature polypeptide. Exemplary clotting factor variants are known in the art.

As used herein, the term "Gla domain" refers to the conserved membrane binding motif which is present In vitamin K-dependent proteins, such as prothrombin, coagulation factors VII, IX and X, proteins C, S, and Z. These proteins require vitamin K for the posttranslational synthesis of g-carboxyglutamic acid, an amino acid clustered in the N-terminal Gla domain of these proteins. All glutamic residues present in the domain are potential carboxylation sites and many of them are therefore modified by carboxylation. In the presence of calcium ions, the Gla domain interacts with phospholipid membranes that include phosphatidylserine. The Gla domain also plays a role in binding to the FVIIa cofactor, tissue factor (TF). Complexed with TF, the Gla domain of FVIIa is loaded with seven Ca2+ ions, projects three hydrophobic side chains in the direction of the cell membrane for interaction with phospholipids on the cell surface, and has significant contact with the C-terminal domain of TF.

The Gla domain of factor VII comprises the uncommon amino acid-carboxyglutamic acid (Gla), which plays a vital role in the binding of clotting factors to negatively charged phospholipid surfaces.

The GLA domain is responsible for the high-affinity binding of calcium ions. It starts at the N-terminal extremity of the mature form of proteins and ends with a conserved aromatic residue. A conserved Gla-x(3)-Gla-x-Cys motif is found in the middle of the domain which seems to be important for substrate recognition by the carboxylase.

Using stopped-flow fluorescence kinetic measurements in combination with surface plasmon resonance analysis, the Gla domain has been found to be important in the sequence of events whereby the protease domain of FVIIa initiates contact with sTF (Biochemical and Biophysical Research Communications. 2005. 337:1276). In addition, clearance of clotting factors may be significantly mediated through Gla interactions, e.g., on liver cells and clearance receptors, e.g., EPCR.

In one embodiment, targeted clotting factors are modified to lack a Gla domain. The Gla domain is responsible for mediating clearance of clotting factors via multiple pathways, such as binding to liver cells, clearance receptors such as EPCR, etc. Thus, eliminating the Gla domain has beneficial effects on half life of clotting factors. Though Gla domain is also generally required for activity by localizing clotting factors to sites of coagulation, the inclusion of a platelet targeting domain moiety targets the Gla deleted clotting factor to platelets. In one embodiment, a clotting factor of the invention comprises a targeting moiety and lacks a Gla domain. For example, in the case of Factor VII, the Gla domain is present at the amino terminus of the light chain and consists of amino acids 1-35. The Gla domains of exemplary clotting factors are indicated in the accompanying sequence listing. This domain can be removed using standard molecular biology techniques, replaced with a targeting domain, and the modified light chain incorporated into a construct of the invention. In one embodiment, a cleavage site may be introduced into constructs lacking a Gla domain to facilitate activation of the molecule. For example, in one embodiment, such a cleavage site may be introduced between the amino acids that are cleaved when the clotting factor is activated (e.g., between amino acids 152 and 153 in the case of Factor VII). Exemplary clotting factors lacking a Gla domain are shown in the accompanying figures In one embodiment, a cleavage site may be introduced into constructs lacking a Gla domain to facilitate activation of the molecule. For example, in one embodiment, such a cleavage site may be introduced between the amino acids that are cleaved when the clotting factor is activated (e.g., between amino acids 152 and 153 in the case of Factor VII). Exemplary clotting factors lacking a Gla domain are shown in the accompanying figures.

Exemplary clotting factors are those of mammalian, e.g., human, origin. The sequences of exemplary clotting factors are presented in the accompanying sequence listing, e.g., alone or in the context of a chimeric clotting factor construct.

III. Targeting Moieties

In one embodiment, a clotting factor of the invention is targeted to platelets to enhance its efficacy by localizing the clotting factor to the site of coagulation using a "targeting moiety" which binds to a target molecule expressed on platelets. Preferably the targeted molecules are not expressed on cells or tissues other than platelets, i.e., the targeting moieties specifically bind to platelets.

In one embodiment, receptors/conformations found on resting platelets are targeted. By doing so, sites for coagulation could be primed for enhanced efficacy. Targeting such molecule may also extend half life of the clotting factor and/or prevent clearance. Examples of such targets include GpIb of the GpIb/V/IX complex, and GpVI and nonactive form of GPIIb/IIIa.

In one embodiment, receptors/conformations only found on activated platelets are targeted in order to localize the clotting factor to site of active coagulation. Examples of such targets include, e.g., the active form of GpIIb/IIIa as well as CD62P.

In one embodiment, a polypeptide of the invention comprises a "targeting moiety" which has affinity for and binds to platelets. For example, in one embodiment, a targeting moiety binds to the GPIb complex, e.g., GPIb-alpha. Examples of such targeting moieties include the peptides PS4, OS1, and OS2 which bind to both active and nonactive platelets (Benard et al. 2008 Biochemistry 47:4674); In another embodiment, a targeting moiety binds to the active conformation of GPIIbIIIa. Examples of such targeting moieties include SCE5 and MB9 variable regions which bind active platelets only (Schwarz et al. 2004 FASEB Journal express article 10.1096/fj.04-1513fje; Schwarz et al. 2006 Circulation Research. 99:25-33; U.S. Patent publication 20070218067). In another embodiment, a targeting moiety binds to both the active/nonactive conformation of GPIIbIIIa. An example of such a targeting moiety is the variable region of the AP3 antibody (Peterson et al. 2003. Hemostasis, Thrombosis, and Vascular Biology 101:937; WO 2010115866). Other targets and targeting moieties are known in the art. Another version of factor IX (the triple mutant V86A/E277A/R338A) with augmented clotting activities has been described by Lin et al. 2010. Journal of Thrombosis and Haemostasis 8: 1773). The contents of these references are incorporated herein by this reference.

The chimeric clotting factors of the invention can comprise one or more than one targeting moiety. Exemplary configurations are set forth in the accompanying Figures. Additionally, two or more targeting moieties may be linked to each other (e.g., via a spacer) in series, and the tandem array operably linked to a construct of the invention. When two or more targeting moieties are present in a chimeric clotting factor of the invention, the moieties may be the same or different.

In one embodiment, a targeting moiety is fused to a chimeric clotting factor of the invention by a cleaveable linker which may be cleaved to remove the targeting moiety at the site of a clot. In another embodiment, a targeting moiety is not attached via a cleaveable linker and, therefore, is not cleaved at the site of a clot.

In one embodiment, the targeting moiety is located on the N- or C-terminus of factor VIII. In another embodiment, a targeting moiety is located on the C-terminus of FVII, FIX, FX, or the C-terminus of either or both chains of FVIIa, FIXa, of FXa. In embodiments in which an Fc region or portion thereof is employed, the targeting moiety may be positioned at the N or C terminus of the second Fc chain, or the C-terminus of either or both Fc chains.

In one embodiment, a targeting moiety is not genetically fused directly to a construct, but rather is linked via a spacer or a chemical bond to the construct. For example, targeting moieties may be attached to a construct of the invention by formation of a bond between the targeting moiety and an Fc moiety of a construct, where the targeting moiety comprises a first functional group and the Fc moiety comprises a second functional group, and where the first and second functional groups are capable of reacting with each other to form a chemical bond (see, e.g., U.S. Pat. No. 7,381,408).

In one embodiment, a polypeptide of the invention comprises at least one of an antigen binding site (e.g., an antigen binding site of an antibody, antibody variant, or antibody fragment), a polypeptide, a receptor binding portion of ligand, or a ligand binding portion of a receptor which specifically binds to platelets, e.g., resting or activated platelets. Exemplary targeting moieties include scFv molecules or peptides which bind to molecules to be targeted. Examples of targeting moieties are found in the instant examples and Figures. Other molecules useful as targeting moieties can readily be selected by one of skill in the art based upon the teaching herein.

A. Antigen Binding Sites which Bind to Platelets

In certain embodiments, a polypeptide of the invention comprises at least one antigen binding portion (e.g., binding site) of an antibody. In one embodiment, the antigen binding portion targets the polypeptide to platelets In other embodiments, a polypeptide of the invention may comprise an antigen binding portion. The term "antigen-binding portion" refers to a polypeptide fragment of an immunoglobulin, antibody, or antibody variant which binds antigen or competes with intact antibody (i.e., with the intact antibody from which they were derived) for antigen binding (i.e., specific binding). For example, said antigen binding portions can be derived from any of the antibodies or antibody variants described supra. Antigen binding portions can be produced by recombinant or biochemical methods that are well known in the art. Exemplary antigen-binding portions include Fv, Fab, Fab', and $(Fab')_2$ as well as scFv molecules.

In other embodiments, a chimeric clotting factor of the invention may comprise a binding site from single chain binding molecule (e.g., a single chain variable region or scFv). Techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain binding molecules. Single chain antibodies are formed by linking the heavy and light chain fragments of the Fv region via an amino acid bridge, resulting in a single chain antibody. Techniques for the assembly of functional Fv fragments in *E coli* may also be used (Skerra et al., *Science* 242:1038-1041 (1988)).

In certain embodiments, a polypeptide of the invention comprises one or more binding sites or regions comprising or consisting of a single chain variable region sequence (scFv). Single chain variable region sequences comprise a single polypeptide having one or more antigen binding sites, e.g., a $V_L$ domain linked by a flexible linker to a $V_H$ domain. The VL and/or VH domains may be derived from any of the antibodies or antibody variants described supra. ScFv molecules can be constructed in a $V_H$-linker-$V_L$ orientation or $V_L$-linker-$V_H$ orientation. The flexible linker that links the $V_L$ and $V_H$ domains that make up the antigen binding site preferably comprises from about 10 to about 50 amino acid residues. In one embodiment, the polypeptide linker is a gly-ser polypeptide linker. An exemplary gly/ser polypeptide linker is of the formula (Gly4Ser)n, wherein n is a positive integer (e.g., 1, 2, 3, 4, 5, or 6). Other polypeptide linkers are known in the art. Antibodies having single chain variable region sequences (e.g. single chain Fv antibodies) and methods of making said single chain antibodies are well-known in the art (see e.g., Ho et al. 1989. Gene 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837).

In certain embodiments, a scFv molecule employed in a polypeptide of the invention is a stabilized scFv molecule. In one embodiment, the stabilized cFv molecule may comprise a scFv linker interposed between a $V_H$ domain and a $V_L$ domain, wherein the $V_H$ and $V_L$ domains are linked by a disulfide bond between an amino acid in the $V_H$ and an amino acid in the $V_L$ domain. In other embodiments, the stabilized scFv molecule may comprise a scFv linker having an optimized length or composition. In yet other embodiments, the stabilized scFv molecule may comprise a $V_H$ or $V_L$ domain having at least one stabilizing amino acid substitution(s). In yet another embodiment, a stabilized scFv molecule may have at least two of the above listed stabilizing features.

Stabilized scFv molecules have improved protein stability or impart improved protein stability to the polypeptide to which it is operably linked. Preferred scFv linkers of the invention improve the thermal stability of a polypeptide of the invention by at least about 2° C. or 3° C. as compared to a conventional polypeptide Comparisons can be made, for example, between the scFv molecules of the invention. In certain preferred embodiments, the stabilized scFv molecule comprises a $(Gly_4Ser)_4$ scFv linker and a disulfide bond which links $V_H$ amino acid 44 and $V_L$ amino acid 100. Other exemplary stabilized scFv molecules which may be employed in the polypeptides of the invention are described in U.S. Provisional Patent Application No. 60/873,996, filed on Dec. 8, 2006 or U.S. patent application Ser. No. 11/725,970, filed on Mar. 19, 2007, each of which is incorporated herein by reference in its entirety.

Polypeptides of the invention may comprise a variable region or portion thereof (e.g. a VL and/or VH domain) derived from an antibody using art recognized protocols. For example, the variable domain may be derived from antibody produced in a non-human mammal, e.g., murine, guinea pig, primate, rabbit or rat, by immunizing the mammal with the antigen or a fragment thereof. See Harlow & Lane, supra, incorporated by reference for all purposes. The immunoglobulin may be generated by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes.

While the variable region may be derived from polyclonal antibodies harvested from the serum of an immunized mammal, it is often desirable to isolate individual lymphocytes from the spleen, lymph nodes or peripheral blood to provide homogenous preparations of monoclonal antibodies (MAbs) from which the desired variable region is derived. Rabbits or guinea pigs are typically used for making polyclonal antibodies. Mice are typically used for making monoclonal antibodies. Monoclonal antibodies can be prepared against a fragment by injecting an antigen fragment into a mouse, preparing "hybridomas" and screening the hybridomas for an antibody that specifically binds to the antigen. In this well known process (Kohler et al., (1975), *Nature,* 256:495) the relatively short-lived, or mortal, lymphocytes from the mouse which has been injected with the antigen are fused with an immortal tumor cell line (e.g. a myeloma cell line), thus, producing hybrid cells or "hybridomas" which are both immortal and capable of producing the antibody genetically encoded by the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunosorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, pp 59-103 (Academic Press, 1986)). It will further be appreciated that the monoclonal antibodies secreted by the subclones may be separated from culture medium, ascites fluid or serum by conventional purification procedures such as, for example, affinity chromatography (e.g., protein-A, protein-G, or protein-L affinity chromatography), hydroxylapatite chromatography, gel electrophoresis, or dialysis.

Optionally, antibodies may be screened for binding to platelets of a specific activation state or to a specific region or desired fragment of the antigen without binding to other nonoverlapping fragments of the antigen. The latter screening can be accomplished by determining binding of an antibody to a collection of deletion mutants of the antigen and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to the antigen. If the test and reference antibodies compete, then they bind to the same epitope or epitopes sufficiently proximal such that binding of one antibody interferes with binding of the other.

DNA encoding the desired monoclonal antibody or binding site thereof may be readily isolated and sequenced using any of the conventional procedures described supra for the isolation of constant region domain sequences (e.g., by using oligonucleotide probes that are capable of binding specifically to genes encoding the heavy and light chains of murine antibodies). The isolated and subcloned hybridoma cells serve as a preferred source of such DNA. More particularly, the isolated DNA (which may be synthetic as described herein) may be used to clone the desired variable region sequences for incorporation in the polypeptides of the invention.

In other embodiments, the binding site is derived from a fully human antibody. Human or substantially human antibodies may be generated in transgenic animals (e.g., mice) that are incapable of endogenous immunoglobulin production (see e.g., U.S. Pat. Nos. 6,075,181, 5,939,598, 5,591,669 and 5,589,369, each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

In other aspects, the polypeptides of the invention may comprise antigen binding sites, or portions thereof, derived from modified forms of antibodies. Exemplary such forms include, e.g., minibodies, diabodies, triabodies, nanobodies, camelids, Dabs, tetravalent antibodies, intradiabodies (e.g., Jendreyko et al. 2003. J. Biol. Chem. 278:47813), fusion proteins (e.g., antibody cytokine fusion proteins, proteins fused to at least a portion of an Fc receptor), and bispecific antibodies. Other modified antibodies are described, for example in U.S. Pat. No. 4,745,055; EP 256,654; Faulkner et al., Nature 298:286 (1982); EP 120,694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In another embodiment, a chimeric clotting factor of the invention comprises an antigen binding site or region which is a diabody or an antigen binding site derived therefrom. Diabodies are dimeric, tetravalent molecules each having a polypeptide similar to scFv molecules, but usually having a short (e.g., less than 10 and preferably 1-5) amino acid residue linker connecting both variable domains, such that the $V_L$ and $V_H$ domains on the same polypeptide chain cannot interact. Instead, the $V_L$ and $V_H$ domain of one polypeptide chain interact with the $V_H$ and $V_L$ domain (respectively) on a second polypeptide chain (see, for example, WO 02/02781). In one embodiment, a polypeptide of the invention comprises a diabody which is operably linked to the N-terminus and/or C-terminus of at least one genetically-fused Fc region (i.e., scFc region).

In certain embodiments, a polypeptide of the invention comprises a single domain binding molecule (e.g. a single domain antibody) as a targeting moiety. Exemplary single domain molecules include an isolated heavy chain variable domain ($V_H$) of an antibody, i.e., a heavy chain variable domain, without a light chain variable domain, and an isolated light chain variable domain ($V_L$) of an antibody, i.e., a light chain variable domain, without a heavy chain variable domain. Exemplary single-domain antibodies employed in the binding molecules of the invention include, for example, the Camelid heavy chain variable domain (about 118 to 136 amino acid residues) as described in Hamers-Casterman, et al., Nature 363:446-448 (1993), and Dumoulin, et al., Protein Science 11:500-515 (2002). Other exemplary single domain antibodies include single VH or VL domains, also known as Dabs® (Domantis Ltd., Cambridge, UK). Yet other single domain antibodies include shark antibodies (e.g., shark Ig-NARs). Shark Ig-NARs comprise a homodimer of one variable domain (V-NAR) and five C-like constant domains (C-NAR), wherein diversity is concentrated in an elongated CDR3 region varying from 5 to 23 residues in length. In camelid species (e.g., llamas), the heavy chain variable region, referred to as VHH, forms the entire antigen-binding domain. The main differences between camelid VHH variable regions and those derived from conventional antibodies (VH) include (a) more hydrophobic amino acids in the light chain contact surface of VH as compared to the corresponding region in VHH, (b) a longer CDR3 in VHH, and (c) the frequent occurrence of a disulfide bond between CDR1 and CDR3 in VHH. Methods for making single domain binding molecules are described in U.S. Pat. Nos. 6,005,079 and 6,765,087, both of which are incorporated herein by reference. Exemplary single domain antibodies comprising VHH domains include Nanobodies® (Ablynx NV, Ghent, Belgium).

Exemplary antibodies from which binding sites can be derived for use in the binding molecules of the invention are known in the art. Examples of such targeting moieties include SCE5 and MB9 variable regions which bind active platelets only (Schwarz et al. 2004 FASEB Journal express article 10.1096/fj.04-1513fje; Schwarz et al. 2006 Circulation Research. 99:25-33; U.S. Patent publication 20070218067). In another embodiment, a targeting moiety binds to both the active/nonactive conformation of GPIIbIIIa. An example of such a targeting moiety is the variable region of the AP3 antibody (Peterson et al. 2003. Hemostasis, Thrombosis, and Vascular Biology 101:937; WO 2010115866).

B. Non-Immunoglobulin Platelet Binding Molecules

In certain other embodiments, the polypeptides of the invention comprise one or more platelet binding sites derived from a non-immunoglobulin binding molecule. As used herein, the term "non-immunoglobulin binding molecules" are binding molecules whose binding sites comprise a portion (e.g., a scaffold or framework) which is derived from a polypeptide other than an immunoglobulin, but which may be engineered (e.g., mutagenized) to confer a desired binding specificity to a platelet target Other examples of binding molecules comprising binding sites not derived from antibody molecules include receptor binding sites and ligand binding sites which bind to platelets.

Non-immunoglobulin binding molecules may be identified by selection or isolation of a target-binding variant from a library of binding molecules having artificially diversified binding sites. Diversified libraries can be generated using completely random approaches (e.g., error-prone PCR, exon shuffling, or directed evolution) or aided by art-recognized design strategies. For example, amino acid positions that are usually involved when the binding site interacts with its cognate target molecule can be randomized by insertion of degenerate codons, trinucleotides, random peptides, or entire loops at corresponding positions within the nucleic acid which encodes the binding site (see e.g., U.S. Pub. No. 20040132028). The location of the amino acid positions can be identified by investigation of the crystal structure of the binding site in complex with the target molecule. Candidate positions for randomization include loops, flat surfaces, helices, and binding cavities of the binding site. In certain embodiments, amino acids within the binding site that are likely candidates for diversification can be identified using techniques known in the art. Following randomization, the diversified library may then be subjected to a selection or screening procedure to obtain binding molecules with the desired binding characteristics, e.g. specific binding platelets using methods known in the art. Selection can be achieved by art-recognized methods such as phage display, yeast display, or ribosome display. In one embodiment, molecules known in the art to bind to platelets may be employed in the constructs of the invention. For example, peptides which bind to GPIba as described in the art (e.g., PS4, OS1, or OS2) may be used (Benard et al. 2008. *Biochemistry* 47:4674-4682).

IV. Activatable Clotting Factors

Clotting factors given for bypass therapy are efficacious when given in the activated form, since exogenous clotting factors are often not activated with sufficient kinetics to be effective. However, they are also rapidly inactivated by endogenous pathways (e.g., by antithrombin III or TFPI), leading to clearance of the active form and a short effective half life. In one embodiment, a chimeric clotting factor of the invention is "activatable." Such activatable constructs circulate as an enhanced zymogen with a longer half life, but can be readily cleaved at the site of clotting when necessary.

In one embodiment, an activatable construct of the invention comprises a cleavable linker comprising, e.g., a factor XIa, Xa, or thrombin cleavage site (which is cleaved by factor XIa, Xa, or thrombin, respectively) leading to formation of the active form of the clotting factor at the site of a clot. Exemplary factor FXIa cleavage sites include, e.g., TQSFNDFTR and SVSQTSKLTR. Exemplary thrombin cleavage sites include, e.g., DFLAEGGGVR, TTKIKPR, and a sequence comprising or consisting of ALRPR (e.g. ALRPRVVGGA)).

In one embodiment, the cleavable linker may be flanked on one or more sides (upstream, downstream or both) by a spacer moiety.

In one embodiment, the cleavable linker is interposed between the light chain and heavy chain of the clotting factor. In another embodiment, the cleavable linker is not interposed between the light chain and heavy chain of the clotting factor. In one embodiment, the cleavable linker is located amino terminal to the heavy chain.

Exemplary activatable constructs are shown in the accompanying Figures and following Examples.

V. Scaffold Moieties

Some embodiments of the invention comprise a scaffold moiety, which can be selected from, e.g., a protein moiety, cscFc region, a Fc moiety, albumin, XTEN, etc.

A. Protein Moieties

In one embodiment, the scaffold is a protein moiety. Such a moiety may comprise a complete protein or a portion thereof, or a synthetic molecule. Preferred protein moieties are of a sufficient molecular size that they improve the half life of a chimeric clotting factor of the invention when incorporated into a construct. For example, in one embodiment, an artificial protein, XTEN, may be included in a construct as a scaffold (Schellenberger et al. 2009. 27:1186). In another embodiment, albumin (e.g., human serum albumin) may be included in a construct of the invention. For example, as known in the art, serum albumin (for example, HSA) can be used as a protein scaffold. In particular various domains and sub-domains of HSA, have a structure that is quite amenable to mutation or randomization for the generation of serum albumin scaffold-based protein libraries. Examples of albumin, e.g., fragments thereof, that may be used in the present invention are known. e.g., U.S. Pat. Nos. 7,592,010; 6,686,179; and Schulte, Thrombosis Res. 124 Suppl. 2:S6-S8 (2009), each of which is incorporated herein by reference in its entirety.

B. scFc Regions

In one embodiment, the invention provides for polypeptides comprising at least one genetically fused Fc region or portion thereof within a single polypeptide chain (i.e., polypeptides comprising a single-chain Fc (scFc) region) in one embodiment, comprising a cscFc.

In one embodiment, a chimeric clotting factor which comprises a clotting factor selected from the group consisting of FVII, FIX and FX and a targeting moiety which binds to platelets and optionally a spacer moiety between the clotting factor and the targeting moiety. In another embodiment, polypeptide comprising FVII, which FVII comprises a heterologous enzymatic cleavage site activatable by a component of the clotting cascade.

In one embodiment, the invention provides unprocessed polypeptides in which at least two Fc moieties or domains (e.g., 2, 3, 4, 5, 6, or more Fc moieties or domains) within the same linear polypeptide chain that are capable of folding (e.g., intramolecularly or intermolecularly folding) to form one functional scFc region which is linked by an Fc polypeptide linker. For example, in one preferred embodiment, a polypeptide of the invention is capable of binding, via its scFc region, to at least one Fc receptor (e.g. an FcRn, an FcγR receptor (e.g., FcγRIII), or a complement protein (e.g. C1q)) in order to improve half life or trigger an immune effector function (e.g., antibody-dependent cytotoxicity (ADCC), phagocytosis, or complement-dependent cytotoxicity (CDCC) and/or to improve manufacturability).

A variety of polypeptides of alternative designs are within the scope of the invention. For example, in one embodiment, a polypeptide comprises the moieties:

A-F1-P1-L-P2-B-F2 (I)

in linear sequence from the amino to carboxy terminus wherein A, if present, is a clotting factor or portion thereof, F1 is a first Fc moiety or domain, P1 is an enzymatic cleavage site, L is an ScFc linker, P2 is an enzymatic cleavage site B, if present, is a clotting factor or portion thereof, F2 is a second Fc moiety or domain and "-" represents a peptide bond. Formula (I) comprises at least an A or B and optionally both. A and B, if both present, can be the corresponding heavy and light chains of a clotting factor. Formula (I) comprises at least a P1 or P2 and optionally both. P1 and P2, if both present, can be the same or different. Formula (I) comprises at least a F1 and F2. F1 and F2, if both present, can be the same or different.

Exemplary polypeptides according to formula I include: A-F1-P1-L-P2-F2; F1-P1-L-P2-B-F2; A-F1-P1-L-F2; F1-P1-L-B-F2; A-F1-L-P2-F2; and F1-L-P2-B-F2.

In one embodiment, F1 and F2 each comprise a CH2 and CH3 moiety.

In one embodiment, after cleavage and substantial excision of the cscFc linker (L), a polypeptide of the invention comprises two polypeptide chains where the first polypeptide chain comprises A linked to a first Fc moiety and where the second polypeptide chain comprises B linked to a second Fc moiety, where F1 and F2 dimerize to form an Fc region. In one embodiment, A and B are optionally present and are clotting factors or portions thereof.

In one embodiment, A is the light chain of a clotting factor and B is the heavy chain of a clotting factor. In one embodiment, B is the light chain of a clotting factor and A is the heavy chain of a clotting factor. In one embodiment, when A and B associate in the polypeptide, the polypeptide then forms a functional clotting factor, e.g., FVII, FIX or FX. In one embodiment, such a polypeptide is enzymatically active upon secretion from a cell.

i) Fc Moieties or Domains

Fc moieties useful as F1 and F2 for producing the polypeptides of the present invention may be obtained from a number of different sources. In preferred embodiments, an Fc moiety of the polypeptide is derived from a human immunoglobulin. It is understood, however, that the Fc moiety may be derived from an immunoglobulin of another mammalian species, including for example, a rodent (e.g. a mouse, rat, rabbit, guinea pig) or non-human primate (e.g. chimpanzee, macaque) species. Moreover, the polypeptide Fc domain or portion thereof may be derived from any immunoglobulin class, including IgM, IgG, IgD, IgA and IgE, and any immunoglobulin isotype, including IgG1, IgG2, IgG3 and IgG4. In a preferred embodiment, the human isotype IgG1 is used.

A variety of Fc moiety gene sequences (e.g. human constant region gene sequences) are available in the form of publicly accessible deposits. Constant region domains comprising an Fc moiety sequence can be selected having a particular effector function (or lacking a particular effector function) or with a particular modification to reduce immunogenicity. Many sequences of antibodies and antibody-encoding genes have been published and suitable Fc moiety sequences (e.g. hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

Fc moiety sequences can be cloned, e.g., using the polymerase chain reaction and primers which are selected to amplify the domain of interest. To clone an Fc moiety sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

The polypeptides of the invention may comprise two or more Fc moieties (e.g., 2, 3, 4, 5, 6, 7, 8, 9, 10, or more Fc moieties). These two or more Fc moieties can form a Fc region. In one embodiment, the Fc moieties may be of different types. In one embodiment, at least one Fc moiety present in the polypeptide comprises a hinge domain or portion thereof. In another embodiment, the polypeptide of the invention comprises at least one Fc moiety which comprises at least one CH2 domain or portion thereof. In another embodiment, the polypeptide of the invention comprises at least one Fc moiety which comprises at least one CH3 domain or portion thereof. In another embodiment, the polypeptide of the invention comprises at least one Fc moiety which comprises at least one CH4 domain or portion thereof. In another embodiment, the polypeptide of the invention comprises at least one Fc moiety which comprises at least one hinge domain or portion thereof and at least one CH2 domain or portion thereof (e.g., in the hinge-CH2 orientation). In another embodiment, the polypeptide of the invention comprises at least one Fc moiety which comprises at least one CH2 domain or portion thereof and at least one CH3 domain or portion thereof (e.g., in the CH2-CH3 orientation). In another embodiment, the polypeptide of the invention comprises at least one Fc moiety comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, the polypeptide comprises at least one complete Fc region derived from one or more immunoglobulin heavy chains (e.g., an Fc domain including hinge, CH2, and CH3 domains, although these need not be derived from the same antibody). In other embodiments, the polypeptide comprises at least two complete Fc regions derived from one or more immunoglobulin heavy chains. In preferred embodiments, the complete Fc moiety is derived from a human IgG immunoglobulin heavy chain (e.g., human IgG1).

In another embodiment, a polypeptide of the invention comprises at least one Fc moiety comprising a complete CH3 domain (about amino acids 341-438 of an antibody Fc region according to EU numbering). In another embodiment, a polypeptide of the invention comprises at least one Fc moiety comprising a complete CH2 domain (about amino acids 231-340 of an antibody Fc region according to EU numbering). In another embodiment, a polypeptide of the invention comprises at least one Fc moiety comprising at least a CH3 domain, and at least one of a hinge region (about amino acids 216-230 of an antibody Fc region according to EU numbering), and a CH2 domain. In one embodiment, a polypeptide of the invention comprises at least one Fc moiety comprising a hinge and a CH3 domain. In another embodiment, a polypeptide of the invention comprises at least one Fc moiety comprising a hinge, a $CH_2$, and a $CH_3$ domain. In preferred embodiments, the Fc moiety is derived from a human IgG immunoglobulin heavy chain (e.g., human IgG1). In one embodiment, an Fc moiety comprises or consists of amino acids corresponding to EU numbers 221 to 447.

In another embodiment, a polypeptide of the invention comprises at least one Fc moiety comprising an FcRn binding partner. An FcRn binding partner is a molecule or portion thereof that can be specifically bound by the FcRn receptor with consequent active transport by the FcRn receptor of the FcRn binding partner. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or more preferably higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

The FcRn receptor has been isolated from several mammalian species including humans. The sequences of the human FcRn, monkey FcRn rat FcRn, and mouse FcRn are known (Story et al. 1994, J. Exp. Med. 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners of the present invention encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372: 379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda, Md.

The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. As an example, one specific embodiment, incorporates the N297A mutation, removing a highly conserved N-glycosylation site. In addition to alanine other amino acids may be substituted for the wildtype amino acids at the positions specified above. Mutations may be introduced singly into Fc giving rise to more than one hundred FcRn binding partners distinct from native Fc. Additionally, combinations of two, three, or more of these individual mutations may be introduced together, giving rise to hundreds more FcRn binding partners. Moreover, one of the FcRn binding partners of a construct of the invention may be mutated and the other FcRn binding partner not mutated at all, or they both may be mutated but with different mutations. Any of the mutations described herein, including N297A, may be used to modify Fc, regardless of the biologically active molecule (e.g., EPO, IFN, Factor VII, Factor IX, T20).

Certain of the above mutations may confer new functionality upon the FcRn binding partner. For example, one embodiment incorporates N297A, removing a highly conserved N-glycosylation site. The effect of this mutation is to reduce immunogenicity, thereby enhancing circulating half life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Mutations believed to impart an increased affinity for FcRn include T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In one embodiment, the FcRn binding partner is a polypeptide including the sequence PKNSSMISNTP (SEQ ID NO: 12) and optionally further including a sequence selected from HQSLGTQ (SEQ ID NO: 13), HQNLSDGK (SEQ ID NO: 14), HQNISDGK (SEQ ID NO: 24), or VISSHLGQ (SEQ ID NO: 25) (U.S. Pat. No. 5,739,277).

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the chimeric protein can be administered invasively, e.g., subcutaneously, intravenously.

The constant region domains or portions thereof making up an Fc moiety of a polypeptide of the invention may be derived from different immunoglobulin molecules. For example, a polypeptide of the invention may comprise a CH2 domain or portion thereof derived from an IgG1 molecule and a CH3 region or portion thereof derived from an IgG3 molecule. In another example, a polypeptide can comprise an Fc moiety comprising a hinge domain derived, in part, from an IgG1 molecule and, in part, from an IgG3 molecule. As set forth herein, it will be understood by one of ordinary skill in the art that an Fc moiety may be altered such that it varies in amino acid sequence from a naturally occurring antibody molecule.

In another embodiment, a polypeptide of the invention comprises an scFc region comprising one or more truncated Fc moieties that are nonetheless sufficient to confer Fc receptor (FcR) binding properties to the Fc region. For example, the portion of an Fc domain that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc moiety of a polypeptide of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In one embodiment, a polypeptide of the invention lacks one or more constant region domains of a complete Fc region, i.e., they are partially or entirely deleted. In a certain embodiments polypeptides of the invention will lack an entire CH2 domain (ΔCH2 constructs). Those skilled in the art will appreciate that such constructs may be preferred due to the regulatory properties of the CH2 domain on the catabolic rate of the antibody. In certain embodiments, polypeptides of the invention comprise CH2 domain-deleted Fc regions derived from a vector (e.g., from IDEC Pharmaceuticals, San Diego) encoding an $IgG_1$ human constant region domain (see, e.g., WO 02/060955A2 and WO02/096948A2). This exemplary vector is engineered to delete the CH2 domain and provide a synthetic vector expressing a domain-deleted $IgG_1$ constant region. It will be noted that these exemplary constructs are preferably engineered to fuse a binding CH3 domain directly to a hinge region of the respective Fc domain.

In other constructs it may be desirable to provide a spacer moiety between one or more constituent Fc moieties. For example, a spacer moiety may be placed between a hinge region and a CH2 domain and/or between a CH2 and a CH3 domains. For example, compatible constructs could be expressed wherein the CH2 domain has been deleted and the remaining CH3 domain (synthetic or unsynthetic) is joined to the hinge region with a 5-20 amino acid spacer moiety. Such a spacer moiety may be added, for instance, to ensure that the regulatory elements of the constant region domain remain free and accessible or that the hinge region remains flexible. Preferably, any linker peptide compatible with the instant invention will be relatively non-immunogenic and not prevent proper folding of the scFc region.

In certain embodiments, the polypeptides of the invention may comprise a dimeric Fc region comprising Fc moieties of the same, or substantially the same, sequence composition (herein termed a "homodimeric Fc region"). In other embodiments, the polypeptides of the invention may comprise a dimeric Fc region comprising at least two Fc moieties which are of different sequence composition (i.e., herein termed a "heterodimeric Fc region"). In one exemplary embodiment, the heterodimeric Fc region comprises an amino acid substitution in a first Fc moiety (e.g., an amino acid substitution of Asparagine at EU position 297), but not in a second Fc moiety.

In certain embodiments, the Fc region is hemi-glycosylated. For example, the heteromeric scFc region may comprise a first, glycosylated, Fc moiety (e.g., a glycosylated CH2 region) and a second, aglycosylated, Fc moiety (e.g., an aglycosylated CH2 region), wherein a linker is interposed between the glycosylated and aglycosylated Fc moieties. In other embodiments, the Fc region is fully glycosylated, i.e., all of the Fc moieties are glycosylated. In still further embodiments, the Fc region may be aglycosylated, i.e., none of the Fc moieties are glycosylated.

In certain embodiments, an Fc moiety employed in a polypeptide of the invention is altered, e.g., by amino acid mutation (e.g., addition, deletion, or substitution). For example, in one embodiment, an Fc moiety has at least one amino acid substitution as compared to the wild-type Fc from which the Fc moiety is derived. For example, wherein the Fc moiety is derived from a human IgG1 antibody, a variant comprises at least one amino acid mutation (e.g., substitution) as compared to a wild type amino acid at the corresponding position of the human IgG1 Fc region.

The amino acid substitution(s) of an Fc variant may be located at a position within the Fc moiety referred to as corresponding to the position number that that residue would be given in an Fc region in an antibody (as set forth using the EU numbering convention). One of skill in the art can readily generate alignments to determine what the EU number corresponding to a position in an Fc moiety would be.

In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

In certain embodiments, the polypeptides of the invention comprise an Fc variant comprising more than one amino acid substitution. The polypeptides of the invention may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In certain embodiments, the Fc variant confers a change in at least one effector function imparted by an Fc region comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue The polypeptides of the invention may employ art-recognized Fc variants which is known to impart a change (e.g., an enhancement or reduction) in effector function and/or FcR or FcRn binding. Specifically, a binding molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

In certain embodiments, a polypeptide of the invention comprises an amino acid substitution to an Fc moiety which alters the antigen-independent effector functions of the antibody, in particular the circulating half-life of the antibody.

Such polypeptides exhibit either increased or decreased binding to FcRn when compared to polypeptides lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder (see, e.g., U.S. Pat. Nos. 7,348,004, 7,404,956, and 7,862,820). In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the polypeptides of the invention exhibit reduced transport across the epithelium of kidney glomeruli from the vasculature. In another embodiment, the polypeptides of the invention exhibit reduced transport across the blood brain barrier (BBB) from the brain, into the vascular space. In one embodiment, a polypeptide with altered FcRn binding comprises at least one Fc moiety (e.g., one or two Fc moieties) having one or more amino acid substitutions within the "FcRn binding loop" of an Fc moiety. The FcRn binding loop is comprised of amino acid residues 280-299 (according to EU numbering) of a wild-type, full-length, Fc moiety. In other embodiments, a polypeptide of the invention having altered FcRn binding affinity comprises at least one Fc moiety (e.g., one or two Fc moieties) having one or more amino acid substitutions within the 15 Å FcRn "contact zone." As used herein, the term 15 Å FcRn "contact zone" includes residues at the following positions of a wild-type, full-length Fc moiety: 243-261, 275-280, 282-293, 302-319, 336-348, 367, 369, 372-389, 391, 393, 408, 424, 425-440 (EU numbering). In preferred embodiments, a polypeptide of the invention having altered FcRn binding affinity comprises at least one Fc moiety (e.g., one or two Fc moieties) having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered FcRn binding activity are disclosed in International PCT Publication No. WO05/047327 which is incorporated by reference herein.

A polypeptide of the invention may also comprise an art recognized amino acid substitution which alters the glycosylation of the polypeptide. For example, the scFc region of the binding polypeptide may comprise an Fc moiety having a mutation leading to reduced glycosylation (e.g., N- or O-linked glycosylation) or may comprise an altered glycoform of the wild-type Fc moiety (e.g., a low fucose or fucose-free glycan).

In other embodiments, a polypeptide of the invention comprises at least one Fc moiety having engineered cysteine residue or analog thereof which is located at the solvent-exposed surface. Preferably the engineered cysteine residue or analog thereof does not interfere with an effector function conferred by the scFc region. More preferably, the alteration does not interfere with the ability of the scFc region to bind to Fc receptors (e.g. FcγRI, FcγRII, or FcγRIII) or complement proteins (e.g. C1q), or to trigger immune effector function (e.g., antibody-dependent cytotoxicity (ADCC), phagocytosis, or complement-dependent cytotoxicity (CDCC)).

In one embodiment, an unprocessed polypeptide of the invention may comprise a genetically fused Fc region (i.e., scFc region) having two or more of its constituent Fc moieties independently selected from the Fc moieties described herein. In one embodiment, the Fc moieties of a dimeric Fc region are the same. In another embodiment, at least two of the Fc moieties are different. For example, the Fc moieties of the polypeptides of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc moieties of the polypeptides of the invention may differ in sequence at one or more amino acid positions. For example, at least two of the Fc moieties may differ at about 5 amino acid positions (e.g., 1, 2, 3, 4, or 5 amino acid positions), about 10 positions, about 15 positions, about 20 positions, about 30 positions, about 40 positions, or about 50 positions).

VI. Polypeptide Linkers

As used herein, the term "polypeptide linkers" refers to a peptide or polypeptide sequence (e.g., a synthetic peptide or polypeptide sequence) which connects two domains in a linear amino acid sequence of a polypeptide chain. The polypeptides of invention are encoded by nucleic acid molecules that encode polypeptide linkers which either directly or indirectly connect the two Fc moieties which make up the construct. These linkers are referred to herein as "scFc linkers". If the scFc linker connects two Fc moieties contiguously in the linear polypeptide sequence, it is a "direct" linkage. In contract, the scFc linkers may link the first Fc moiety to a binding moiety which is, in turn, linked to the second Fc moiety, thereby forming an indirect linkage. These scFc linkers (L) result in the formation of a single chain genetic construct. However, in one embodiment, the scFc polypeptides also comprise enzymatic cleavage sites which result in the scFc linker being cleavable (an cscFc linker) and, in one embodiment, substantially excised (e.g., during processing by a cell). Thus, the processed molecule is a dimeric molecule comprising at least two amino acid chains and substantially lacking extraneous linker amino acid sequences. In some embodiments, all or substantially all of the linker is excised, while in some embodiments, a portion of the cleavage site may remain, e.g., four arginines of the RRRR cleavage site.

In another embodiment, another type of polypeptide linker, herein referred to as a "spacer" may be used to connect different moieties, e.g., a clotting factor or a targeting moiety to an Fc moiety. This type of polypeptide linker may provide flexibility to the polypeptide molecule. Spacers are not typically cleaved, however such cleavage may be desirable. Exemplary positions of spacers are shown in the accompanying drawings. Spacers can be located between the clotting factors, targeting moieties, and/or scaffolds, e.g., at the N or C terminus of these moieties. In one embodiment, these linkers are not removed during processing.

A third type of linker which may be present in a chimeric clotting factor of the invention is a cleavable linker which comprises a cleavage site (e.g., a factor XIa, Xa, or thrombin cleavage site) and which may include additional spacer linkers on either the N terminal of C terminal or both sides of the cleavage site. These cleavable linkers when incorporated into a clotting factor result in a chimeric molecule having a heterologous cleavage site. Exemplary locations for such sites are shown in the accompanying drawings and include, e.g., adjacent to targeting moieties, In another embodiment, such linkers may be adjacent to a clotting factor or portion thereof. For example, in one embodiment, a cleavable linker may be fused to the N terminus of the heavy chain of a clotting factor to make an activatable form of the clotting factor. In such cases, the cleavable linker may include additional spacer linkers at the N terminus of the cleavage site, but require direct fusion at the C-terminus of the cleavage site to the amino terminus of the heavy chain of the clotting factor.

In one embodiment, an unprocessed polypeptide of the instant invention comprises two or more Fc domains or moieties linked via a cscFc linker to form an Fc region comprised in a single polypeptide chain. The cscFc linker is flanked by at least one enzymatic cleavage site, e.g., a site for processing by an intracellular enzyme. Cleavage of the polypeptide at the at least one enzymatic cleavage site results in a polypeptide which comprises at least two polypeptide chains. In one embodiment, an cscFc linker links F1 or F2 to, e.g., a clotting factor, optionally via a cleavage site.

As is set forth above, other polypeptide linkers may optionally be used in a construct of the invention, e.g., to connect a clotting factor or targeting moiety to an Fc moiety. One type of polypeptide linker is referred to here as spacers. Some exemplary locations of spacers that can be used in connection with the invention include, e.g., polypeptides comprising GlySer amino acids such as those set forth in the accompanying figures and described in more detail below. In one embodiment, a spacer may be adjacent to one or more moieties each independently selected from clotting factor, scaffold moiety, e.g., Fc, cleavage site, and a targeting moiety.

In one embodiment, the polypeptide linker is synthetic, i.e., non-naturally occurring. In one embodiment, a polypeptide linker includes peptides (or polypeptides) (which may or may not be naturally occurring) which comprise an amino acid sequence that links or genetically fuses a first linear sequence of amino acids to a second linear sequence of amino acids to which it is not naturally linked or genetically fused in nature. For example, in one embodiment the polypeptide linker may comprise non-naturally occurring polypeptides which are modified forms of naturally occurring polypeptides (e.g., comprising a mutation such as an addition, substitution or deletion). In another embodiment, the polypeptide linker may comprise non-naturally occurring amino acids. In another embodiment, the polypeptide linker may comprise naturally occurring amino acids occurring in a linear sequence that does not occur in nature. In still another embodiment, the polypeptide linker may comprise a naturally occurring polypeptide sequence.

For example, in certain embodiments, a polypeptide linker can be used to fuse identical Fc moieties, thereby forming a homomeric scFc region. In other embodiments, a polypeptide linker can be used to fuse different Fc moieties (e.g. a wild-type Fc moiety and an Fc moiety variant), thereby forming a heteromeric scFc region.

In another embodiment, a polypeptide linker comprises or consists of a gly-ser linker. In one embodiment, an scFc or cscFc linker comprises at least a portion of an immunoglobulin hinge and a gly-ser linker. As used herein, the term "gly-ser linker" refers to a peptide that consists of glycine and serine residues. An exemplary gly/ser linker comprises an amino acid sequence of the formula $(Gly_4Ser)n$ (SEQ ID NO: 4), wherein is a positive integer (e.g., 1, 2, 3, 4, 5, 6, 7, 8, 9, or 10). A preferred gly/ser linker is $(Gly_4Ser)_2$ (SEQ ID NO:29), $(Gly_4Ser)_4$ (SEQ ID NO:6), or $(Gly_4Ser)_6$. (SEQ ID NO: 5) Another exemplary gly-ser linker is GGGSSGGGSG (SEQ ID NO: 30). In certain embodiments, said gly-ser linker may be inserted between two other sequences of the polypeptide linker (e.g., any of the polypeptide linker sequences described herein). In other embodiments, a gly-ser linker is attached at one or both ends of another sequence of the polypeptide linker (e.g., any of the polypeptide linker sequences described herein). In yet other embodiments, two or more gly-ser linker are incorporated in series in a polypeptide linker. In one embodiment, a polypeptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues (e.g., a gly/ser linker such as $(Gly_4Ser)n)$ (SEQ ID NO:4)).

Polypeptide linkers of the invention are at least one amino acid in length and can be of varying lengths. In one embodiment, a polypeptide linker of the invention is from about 1 to about 50 amino acids in length. As used in this context, the term "about" indicates +/− two amino acid residues. Since linker length must be a positive integer, the length of from about 1 to about 50 amino acids in length, means a length of from 1-3 to 48-52 amino acids in length. In another embodiment, a polypeptide linker of the invention is from about 10-20 amino acids in length. In another embodiment, a polypeptide linker of the invention is from about 15 to about 50 amino acids in length. In another embodiment, a polypeptide linker of the invention is from about 20 to about 45 amino acids in length. In another embodiment, a polypeptide linker of the invention is from about 15 to about 35 or about 20 to about 30 amino acids in length. In another embodiment, a polypeptide linker of the invention is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 amino acids in length. In one embodiment, a peptide linker of the invention is 20 or 30 amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

VIII. Enzymatic Cleavage Sites

In one embodiment, one or more enzymatic cleavage site(s) is linked to e.g., flanks or is adjacent to, a cscFc linker (L) of an unprocessed polypeptide of the invention. Such cleavage sites can be upstream or downstream of the cscFc liner or both. For example, in one embodiment of a construct encoding a polypeptide of the invention, a cleavage site is linked (e.g., directly or indirectly) to one or both ends of a cscFc linker (L).

For example, in one embodiment, a nucleic acid molecule of the invention specifies a polypeptide represented by the formula:

A-F1-P1-L-P2-B-F2 (I)

in linear sequence from the amino to carboxy terminus wherein A, if present, is a clotting factor or portion thereof, F1 is a first Fc moiety or domain, P1 is an enzymatic cleavage site, L is a cscFc linker, P2 is an enzymatic cleavage site B, if present, is a clotting factor or portion thereof, F2 is a second Fc moiety or domain and "-" represents a peptide bond. Formula (I) comprises at least an A or B and optionally both. A and B, if both present, can be the corresponding heavy and light chains of a clotting factor. Formula (I) comprises at least a P1 or P2 and optionally both. P1 and P2, if both present, can be the same or different. Formula (I) comprises at least a F1 and F2. F1 and F2, if both present, can be the same or different.

In another embodiment, a Factor XIa or Xa cleavage site may be incorporated into a construct of the invention, e.g., in a cleavable linker. Exemplary FXIa cleavage sites include, e.g., TQSFNDFTR and SVSQTSKLTR. Exemplary thrombin cleavage sites include, e.g., DFLAEGGGVR, TTKIKPR, LVPRG SEQ ID NO:35) and ALRPRVVGGA Other useful cleavage sites are known in the art.

In one embodiment, some portion of the linker may remain after cleavage at the at least one enzymatic cleavage site. In order to minimize the presence of extraneous amino acid sequences, two cleavage sites may be included in a polypeptide of the invention. In some embodiments, all or substantially all of the linker is excised, while in some embodiments, a portion of the cleavage site may remain, e.g., four arginines of the RRRR cleavage site.

Preparation of Polypeptides

A variety of methods are available for recombinantly producing a chimeric clotting factor of the invention. In one embodiment, the invention relates to a nucleic acid construct comprising a nucleic acid sequence encoding the chimeric proteins of the invention. It will be understood that because of the degeneracy of the code, a variety of nucleic acid sequences will encode the amino acid sequence of the polypeptide. The desired polynucleotide can be produced by de novo solid-phase DNA synthesis or by PCR mutagenesis of an earlier prepared polynucleotide.

Oligonucleotide-mediated mutagenesis is one method for preparing a substitution, in-frame insertion, or alteration (e.g., altered codon) to introduce a codon encoding an amino acid substitution (e.g., into an Fc variant moiety). For example, the starting polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide encoding a polypeptide of the invention.

For recombinant production, a polynucleotide sequence encoding the chimeric protein is inserted into an appropriate expression vehicle, i.e., a vector which contains the necessary elements for the transcription and translation of the inserted coding sequence, or in the case of an RNA viral vector, the necessary elements for replication and translation.

The nucleic acid encoding the chimeric protein is inserted into the vector in proper reading frame. The expression vector is then transfected into a suitable target cell which will express the polypeptide. Transfection techniques known in the art include, but are not limited to, calcium phosphate precipitation (Wigler et al. 1978, Cell 14:725) and electroporation (Neumann et al. 1982, EMBO, J. 1:841). A variety of host-expression vector systems may be utilized to express the chimeric proteins described herein in eukaryotic cells. In one embodiment, the eukaryotic cell is an animal cell, including mammalian cells (e.g. 293 cells, PerC6, CHO, BHK, Cos, HeLa cells). When the chimeric protein is expressed in a eukaryotic cell the DNA encoding the chimeric protein may also code for a signal sequence that will permit the chimeric protein to be secreted. One skilled in the art will understand that while the protein is translated the signal sequence is cleaved by the cell to form the mature chimeric protein. Various signal sequences are known in the art e.g., native factor Vll signal sequence, native factor IX signal sequence and the mouse IgK light chain signal sequence. Alternatively, where a signal sequence is not included the chimeric protein can be recovered by lysing the cells.

The chimeric protein of the invention can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, Proc. Natl. Acad. Sci. USA 82:4438). Methods of producing transgenic animals are known in the art. including transgenics that produce immunoglobulin molecules (Wagner et al. 1981, Proc. Natl. Acad. Sci. USA 78: 6376; McKnight et al. 1983, Cell 34:335; Brinster et al. 1983, Nature 306: 332; Ritchie et al. 1984, Nature 312: 517; Baldassarre et al. 2003, Theriogenology 59:831; Robl et al. 2003, Theriogenology 59: 107; Malassagne et al. 2003, Xenotransplantation 10 (3): 267).

The expression vectors can encode for tags that permit for easy purification or identification of the recombinantly produced protein. Examples include, but are not limited to, vector pUR278 (Ruther et al. 1983, EMBO J. 2: 1791) in which the chimeric protein described herein coding sequence may be ligated into the vector in frame with the lac z coding region so that a hybrid protein is produced; pGEX vectors may be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e.g. PreCission Protease (Pharmacia, Peapack, N.J.)) for easy removal of the tag after purification.

For the purposes of this invention, numerous expression vector systems may be employed. These expression vectors are typically replicable in the host organisms either as episomes or as an integral part of the host chromosomal DNA. Expression vectors may include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors may also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

A preferred expression vector is NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the polypeptides of the invention of the instant invention may be expressed using polycistronic constructs. In these expression systems, multiple gene products of interest such as multiple polypeptides of multimer binding protein may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No.

6,193,980 which is also incorporated herein. Those skilled in the art will appreciate that such expression systems may be used to effectively produce the full range of polypeptides disclosed in the instant application.

More generally, once the vector or DNA sequence encoding a polypeptide has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte), PerC6, and 293 (human kidney). Host cell lines are typically available from commercial services, the American Tissue Culture Collection or from published literature.

In one embodiment, a host cell endogenously expresses an enzyme (or the enzymes) necessary to cleave an scFc linker (e.g., if such a linker is present and contains intracellular processing site(s)) during processing to form the mature polypeptide. During this processing, the scFc linker may be substantially removed to reduce the presence of extraneous amino acids. In another embodiment of the invention, a host cell is transformed to express one or more enzymes which are exogenous to the cell such that processing of an scFc linker occurs or is improved.

In one embodiment an enzyme which may be endogenously or exogenously expressed by a cell is a member of the furin family of enzymes. Complete cDNA and amino acid sequences of human furin (i.e., PACE) were published in 1990. Van den Ouweland A M et al. (1990) Nucleic Acids Res. 18:664; Erratum in: Nucleic Acids Res. 18:1332 (1990).

U.S. Pat. No. 5,460,950, issued to Barr et al., describes recombinant PACE and the coexpression of PACE with a substrate precursor polypeptide of a heterologous protein to improve expression of active, mature heterologous protein.

U.S. Pat. No. 5,935,815, issued to van de Ven et al., likewise describes recombinant human furin (i.e., PACE) and the coexpression of furin with a substrate precursor polypeptide of a heterologous protein to improve expression of active, mature heterologous protein. Possible substrate precursors disclosed in this patent include a precursor of Factor IX. Other family members in the mammalian furin/subtilisin/Kex2p-like proprotein convertase (PC) family in addition to PACE are reported to include PC1/PC3, PC2, PC4, PC5/6 (hereinafter referred to simply as PC5), PACE4, and LPC/PC7/PC8/SPC7. While these various members share certain conserved overall structural features, they differ in their tissue distribution, subcellular localization, cleavage specificities, and preferred substrates. For a review, see Nakayama K (1997) Biochem J. 327:625-35. Similar to PACE, these proprotein convertases generally include, beginning from the amino terminus, a signal peptide, a propeptide (that may be autocatalytically cleaved), a subtilisin-like catalytic domain characterized by Asp, His, Ser, and Asn/Asp residues, and a Homo B domain that is also essential for catalytic activity and characterized by an Arg-Gly-Asp (RGD) sequence. PACE, PACE4, and PC5 also include a Cys-rich domain, the function of which is unknown. In addition, PC5 has isoforms with and without a transmembrane domain; these different isoforms are known as PC5B and PC5A, respectively. Comparison between the amino acid sequence of the catalytic domain of PACE and the amino acid sequences of the catalytic domains of other members of this family of proprotein convertases reveals the following degrees of identity: 70 percent for PC4; 65 percent for PACE4 and PC5; 61 percent for PC1/PC3; 54 percent for PC2; and 51 percent for LPC/PC7/PC8/SPC7. Nakayama K (1997) Biochem J. 327:625-35.

PACE and PACE4 have been reported to have partially overlapping but distinct substrates. In particular, PACE4, in striking contrast to PACE, has been reported to be incapable of processing the precursor polypeptide of FIX. Wasley L C et al. (1993) J Biol Chem. 268:8458-65; Rehemtulla A et al. (1993) Biochemistry. 32:11586-90.

U.S. Pat. No. 5,840,529, issued to Seidah et al., discloses nucleotide and amino acid sequences for human PC7 and the notable ability of PC7, as compared to other PC family members, to cleave HIV gp160 to gp120 and gp41.

Nucleotide and amino acid sequences of rodent PC5 were first described as PC5 by Lusson J et al. (1993) Proc Natl Acad Sci USA 90:6691-5 and as PC6 by Nakagawa T et al. (1993) J Biochem (Tokyo) 113:132-5. U.S. Pat. No. 6,380,171, issued to Day et al., discloses nucleotide and amino acid sequences for human PC5A, the isoform without the transmembrane domain. The sequences of these enzymes and method of cloning them are known in the art.

Genes encoding the polypeptides of the invention can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan. Other yeast hosts such *Pichia* may also be employed. Yeast expression vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Alternatively, polypeptide-coding nucleotide sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for polypeptides in operable linkage with a promoter and enhancer from a mammary gland specific gene, such as casein or beta lactoglobulin.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein. An affinity tag sequence (e.g. a His(6) tag) may optionally be attached or included within the polypeptide sequence to facilitate downstream purification.

In one embodiment, a host cell of the invention comprises a genetic construct encoding a polypeptide comprising an scFc scaffold and one or more enzymes that can process a cscFc linker. The construct and the enzyme(s) can be expressed using a single vector or two vectors.

In one embodiment, the invention pertains to nucleic acid molecules which encode a polypeptide of the invention. In one embodiment, the nucleic acid molecule encodes a chimeric clotting factor selected from the group consisting of FVII, FIX and FX and which comprises a targeting moiety which binds to platelets and optionally a spacer moiety between the clotting factor and the targeting moiety.

In another embodiment, the invention pertains to a nucleic acid molecule encoding a polypeptide comprising FVII, which FVII which comprises a heterologous enzymatic cleavage site activatable by a component of the clotting cascade.

Once expressed, the chimeric clotting factor can be purified according to standard procedures of the art, including ammonium sulfate precipitation, affinity column chromatography, HPLC purification, gel electrophoresis and the like (see generally Scopes, Protein Purification (Springer-Verlag, N.Y., (1982)) and see specifically the methods used in the instant Examples. Substantially pure proteins of at least about 90 to 95% homogeneity are preferred, and 98 to 99% or more homogeneity most preferred, for pharmaceutical uses.

IX. Methods of Administering Polypeptides of the Invention

In another embodiment, the invention relates to a method of treating a subject with a hemostatic disorder comprising administering a therapeutically effective amount of an enhanced clotting factor of the Invention.

Compositions for administration to a subject include nucleic acid molecules which comprise a nucleotide sequence encoding a chimeric clotting factor of the invention (for gene therapy applications) as well as polypeptide molecules.

In one embodiment, an enhanced doting factor composition of the invention is administered in combination with at least one other agent that promotes hemostasis. Said other agent that promotes hemostasis Is a therapeutic with demonstrated clotting activity. As an example, but not as a limitation, hemostatic agent can include Factor V, Factor VII, Factor VIII, Factor IX, Factor X, Factor XI, Factor XII, Factor XIII, prothrombin, or fibrinogen or activated forms of any of the preceding. The clotting factor of hemostatic agent can also include anti-fibrinolytic drugs, e.g., epsilon-amino-caproic acid, tranexamic acid.

In one embodiment of the invention, the composition (e.g., the polypeptide or nucleic acid molecule encoding the polypeptide) is one in which the clotting factor is present in active form when administered to a subject. Such an activated molecule may be expressed by a cell in active form or may be activated in vitro prior to administration to a subject. In another embodiment, the composition is one in which the clotting factor is present in activatable form and the clotting factor is activated in vivo at the site of clotting after administration to a subject.

The chimeric clotting factor of the invention can be administered intravenously, subcutaneously, intramuscularly, or via any mucosal surface, e.g., orally, sublingually, buccally, sublingually, nasally, rectally, vaginally or via pulmonary route. The chimeric protein can be implanted within or linked to a biopolymer solid support that allows for the slow release of the chimeric protein to the desired site.

For oral administration, the pharmaceutical composition can take the form of tablets or capsules prepared by conventional means. The composition can also be prepared as a liquid for example a syrup or a suspension. The liquid can include suspending agents (e.g. sorbitol syrup, cellulose derivatives or hydrogenated edible fats), emulsifying agents (lecithin or acacia), non-aqueous vehicles (e.g. almond oil, oily esters, ethyl alcohol, or fractionated vegetable oils), and preservatives (e.g. methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration the composition may take the form of tablets, lozenges or fast dissolving films according to conventional protocols.

For administration by inhalation, the compounds for use according to the present invention are conveniently delivered in the form of an aerosol spray from a pressurized pack or nebulizer (e.g. in PBS), with a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In one embodiment, the route of administration of the polypeptides of the invention is parenteral. The term parenteral as used herein includes intravenous, intraarterial, intraperitoneal, intramuscular, subcutaneous, rectal or vaginal administration. The intravenous form of parenteral administration is preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will preferably have labels or package inserts indicating that the associated compositions are useful for treating a subject suffering from, or predisposed to clotting disorders.

The pharmaceutical composition can also be formulated for rectal administration as a suppository or retention enema, e.g., containing conventional suppository bases such as cocoa butter or other glycerides.

Effective doses of the compositions of the present invention, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

In one embodiment, the dose of a biologically active moiety (e.g., comprising FIX) can range from about 25 to 100 IU/kg, e.g., 0.417 mg/kg to 1.67 mg/kg. In another embodiment, the dose of a biologically active moiety (e.g., comprising FVIII) can range from about 25 to 65 IU/kg, e.g., 0.003125 mg/kg to 0.008125 mg/kg. In another embodiment, the dose of a biologically active moiety (e.g., comprising FVII), can range from about 90 to 270 ug/kg or 0.090 to 0.270 mg/kg.

Dosages can range from 1000 ug/kg to 0.1 ng/kg body weight. In one embodiment, the dosing range is 1 ug/kg to 100 ug/kg. The protein can be administered continuously or at specific timed intervals. In vitro assays may be employed to determine optimal dose ranges and/or schedules for administration. In vitro assays that measure clotting factor activity are known in the art, e.g., STA-CLOT VIIa-rTF clotting assay. Additionally, effective doses may be extrapolated from dose-response curves obtained from animal models, e.g., a hemophiliac dog (Mount et al. 2002, Blood 99 (8): 2670).

Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. In some methods, two or more polypeptides may be administered simultaneously, in which case the dosage of each polypeptide administered falls within the ranges indicated.

Polypeptides of the invention can be administered on multiple occasions. Intervals between single dosages can be daily, weekly, monthly or yearly. Intervals can also be irregular as indicated by measuring blood levels of modified polypeptide or antigen in the patient. Alternatively, polypeptides can be administered as a sustained release formulation, in which case less frequent administration is required. Dosage and frequency vary depending on the half-life of the polypeptide in the patient.

The dosage and frequency of administration can vary depending on whether the treatment is prophylactic or therapeutic. In prophylactic applications, compositions containing the polypeptides of the invention or a cocktail thereof are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

Polypeptides of the invention can optionally be administered in combination with other agents that are effective in treating the disorder or condition in need of treatment (e.g., prophylactic or therapeutic).

As used herein, the administration of polypeptides of the invention in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen may be timed to enhance the overall effectiveness of the treatment. A skilled artisan (e.g. a physician) would be readily be able to discern effective combined therapeutic regimens without undue experimentation based on the selected adjunct therapy and the teachings of the instant specification.

It will further be appreciated that the polypeptides of the instant invention may be used in conjunction or combination with an agent or agents (e.g. to provide a combined therapeutic regimen). Exemplary agents with which a polypeptide of the invention may be combined include agents that represent the current standard of care for a particular disorder being treated. Such agents may be chemical or biologic in nature. The term "biologic" or "biologic agent" refers to any pharmaceutically active agent made from living organisms and/or their products which is intended for use as a therapeutic.

The amount of agent to be used in combination with the polypeptides of the instant invention may vary by subject or may be administered according to what is known in the art. See for example, Bruce A Chabner et al., *Antineoplastic Agents, in* Goodman & Gilman's The Pharmacological Basis of Therapeutics 1233-1287 ((Joel G. Hardman et al., eds., 9$^{th}$ ed. 1996). In another embodiment, an amount of such an agent consistent with the standard of care is administered.

As previously discussed, the polypeptides of the present invention, may be administered in a pharmaceutically effective amount for the in vivo treatment of clotting disorders. In this regard, it will be appreciated that the polypeptides of the invention can be formulated to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. Of course, the pharmaceutical compositions of the present invention may be administered in single or multiple doses to provide for a pharmaceutically effective amount of the polypeptide.

In one embodiment, a chimeric clotting factor of the invention can be administered as a nucleic acid molecule. Nucleic acid molecules can be administered using techniques known in the art, including via vector, plasmid, liposome, DNA injection, electroporation, gene gun, intravenously injection or hepatic artery infusion. Vectors for use in gene therapy embodiments are known in the art.

In keeping with the scope of the present disclosure, the chimeric clotting factors of the invention may be administered to a human or other animal in accordance with the aforementioned methods of treatment in an amount sufficient to produce a therapeutic or prophylactic effect.

The chimeric proteins of the invention have many uses as will be recognized by one skilled in the art, including, but not limited to methods of treating a subject with a disease or condition. The disease or condition can include, but is are not limited to, hemostatic disorders.

In one embodiment, the invention relates to a method of treating a subject having a hemostatic disorder comprising administering a therapeutically effective amount of at least one chimeric clotting factor of the invention.

The chimeric clotting factors of the invention treat or prevent a hemostatic disorder by promoting the formation of a fibrin clot. The chimeric clotting factor of the invention can activate any member of a coagulation cascade. The clotting factor can be a participant in the extrinsic pathway, the intrinsic pathway or both.

A chimeric clotting factor of the invention can be used to treat hemostatic disorders, e.g., those known to be treatable with the particular clotting factor present in the chimeric clotting factor. The hemostatic disorders that may be treated by administration of the chimeric protein of the invention include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII In one embodiment, the hemostatic disorder is an inherited disorder. In one embodiment, the subject has hemophilia A, and the chimeric protein comprises Factor VII or Factor VIIIa. In another embodiment, the subject has hemophilia A and the chimeric clotting factor comprises Factor VII or Factor VIIa. In another embodiment, the subject has hemophilia B and the chimeric clotting factor comprises Factor IX or Factor IXa. In another embodiment, the subject has hemophilia B and the chimeric protein comprises Factor VII or Factor VIIa. In another embodiment, the subject has inhibitory antibodies to Factor VII or Factor VIIIa and the chimeric clotting factor comprises Factor VII or Factor VIIa. In yet another embodiment, the subject has inhibitory antibodies against Factor IX or Factor IXa and the chimeric protein comprises Factor VII or Factor VIIa.

The chimeric clotting factor of the invention can be used to prophylactically treat a subject with a hemostatic disorder. The chimeric clotting factor of the invention can be used to treat an acute bleeding episode in a subject with a hemostatic disorder.

In one embodiment, the hemostatic disorder is the result of a deficiency in a clotting factor, e.g., Factor IX, Factor VIII. In another embodiment, the hemostatic disorder can be the result of a defective clotting factor.

In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g. cancer chemotherapy).

The invention also relates to methods of treating a subject that does not have a hemostatic disorder or a secondary disease or condition resulting in acquisition of a hemostatic disorder. The invention thus relates to a method of treating a subject in need of a general hemostatic agent comprising administering a therapeutically effective amount of at least one chimeric clotting factor of the invention. For example, in one embodiment, the subject in need of a general hemostatic agent is undergoing, or is about to undergo, surgery. The chimeric clotting factor of the invention can be administered prior to or after surgery as a prophylactic. The chimeric clotting factor of the invention can be administered during or after surgery to control an acute bleeding episode. The surgery can include, but is not limited to, liver transplantation, liver resection, or stem cell transplantation.

In another embodiment, the chimeric clotting factor of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

This invention is further illustrated by the following examples which should not be construed as limiting. The contents of all references, patents and published patent applications cited throughout this application are incorporated herein by reference.

EXAMPLES

Throughout the examples, the following materials and methods were used unless otherwise stated.

General Materials and Methods

In general, the practice of the present invention employs, unless otherwise indicated, conventional techniques of chemistry, biophysics, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., CS.H.L. Press, Pub. (1999); and Current Protocols in Molecular Biology, eds. Ausubel et al., John Wiley & Sons (1992).

Example 1. Heterodimeric Constructs Comprising FVII-Fc and MB9-Fc at the Amino Terminus of the Second Fc Chain Cloning of pSYN-FVII-027

The FVII-027 construct comprises cscFc for cleavage when processed during manufacture in a cell. The construct comprises a targeting moiety, a scFv moiety that binds to GPIIbIIIa, MB9.

Plasmid (pSYN-FVII-027) was generated for the expression FVII-Fc and MB9-Fc heterodimer, where MB9 is a scFv previously shown to bind to receptor GPIIb/IIIa on activated platelets. Protein from pSYN-FVII-027 is expressed in the cell as a single polypeptide where the C-terminus of the FVII-Fc subunit is linked to the N-terminus of the MB9-Fc subunit by a $(GGGGS)_{6x}$ polypeptide linker. Furthermore, RRRRS and RKRRKR sequences were inserted at the 5' and 3' end of the polypeptide linker, respectively, for intracellular cleavage by proprotein convertases following the last Arg at each sequence. Consequently, cells will express a 2 chain FVII-Fc/MB9-Fc heterodimer where the FVII-Fc chain has a RRRRS sequence at the C-terminus, but the remainder of the linker and the RKRRKR sequence have otherwise been removed.

As a first step a series of intermediate plasmid were generated using the following primers:

```
HindIII-SalI-BpsEI-Fc-F
AGTCAAGCTTGTCGACTCCGGAACTCCTGGGCGGACC

BamHI-linker-Fc-R
CATCGGATCCCCCGCCACCGGAACCTCCACCGCCTGATCCACCCCCACC
TGATCCGCCGCCACCTTTACCCGGAGACAGGGAGAGG

BclI-Fc-F
CAGTCTTGATCAGACAAAACTCACACATGCCCACC

scFc-EcoRI-R
ACTGACGAATTCTCATTTACCCGGAGACAGGGAG

HindIII-Kozak-FVII-F:
CGACAAGCTTGCCGCCACCATGGTCTCCCAGGCCCTCAGG

FVII-HC-BspEI -R:
AGGAGTTCCGGAGCTGGGCACGGTGGGCATGTGTGAGTTTTGTCGGATCC

CCCGCCACCGGAACCTCCACCGCCTGATCCACCCCCACCTGATCCGCCGC

CACCGGACCCACCTCCGCCGGAGCCACCGCCACCGGGAAATGGGGCTCGC

AGGAGG
```

A 50 ul PCR reaction was carried out with 25 pmol of HindIII-SalI-BpEI-Fc-F and BamHI-linker-Fc-R and template pSYN-Fc-001 using the following cycle: 95° C. 2 minutes; 30 cycles of (95° C. 30 seconds, 54° C. 30 seconds, 72° C. 1 minute). The expected sized band (~700 bp) was gel purified with a Gel Extraction kit (Qiagen, Valencia, Calif.) and cloned into the HindIII and BamHI restriction sites of pBUDCE4 (Invitrogen, Carlsbad, Calif.) to generate intermediate pSYN-FVII-007. Primers HindIII-SalI-BpEI-Fc-F and BamHI-linker-Fc-R amplify the Fc region starting at amino acid 221 (EU numbering) and add a HindIII and a SalI restriction enzyme site immediately upstream of site Fc region, as well as a DNA fragment encoding a $(GGGGS)_{4x}$ linker followed by a BamHI site immediately downstream of the Fc coding region. Next, a 50 ul reaction was carried out with 25 pmol of BclI-Fc-F and scFc-EcoRI-R, and template pSYN-Fc-011 using the same cycles as above. The expected sized band (~700 bp) was gel purified as above, cut with restriction enzymes BamHI and EcoRI, and cloned in the BclI/EcoRI restriction sites of pSYN-FVII-007 to generate the intermediate plasmid pSYN-FVII-008. The primer pair BclI-Fc-F and scFc-EcoRI-R amplifies the Fc region while adding a BclI and EcoRI restriction sites immediately upstream and downstream of the Fc coding region, respectively. To generate the last intermediate plasmid, a 50 ul PCR reaction was carried out with 25 pmol of HindIII-Kozak-FVII-F and FVII-HC-BspEI-R and template pSYN-FVII-001 using the following cycle: 95° C. 2 minutes; 30 cycles of (95° C. 30 seconds, 55° C. 30 seconds, 72° C. 90 seconds). The primer pair amplifies the FVII coding region while adding a DNA fragment at the 3' end of the molecule encoding a $(GGGGS)_{6x}$ polypeptide linker followed by a fragment of the Fc region ending at amino acid 221 (EU numbering). Primer HindIII-Kozak-FVII-F generates a HindIII restriction site at the 5' of the molecule followed by a Kozak sequence directly upstream of the FVII coding region. The FVII-HC-BspEI-R primer introduces DNA encoding the polypeptide linker as well as the Fc portion. The expected sized band (~1500 bp) was gel purified as above and cloned into the HindIII/BspEI sites of pSYN-FVII-008 to generate pSYN-FVII-011.

Next, 2 DNA fragments were synthesized: Genescript-FVII-027-1 and Genscript-FVII-026-2. Genescript-FVII-027-1 consists of a DNA fragment encoding a portion of the Fc region (starting at nucleotide 1306, EU numbering) followed by the sequence RRRRS-$(GGGGS)_{6x}$-RKRRKR followed by a portion of the MB9 scFv (residues 1-142). An EcoRI site was introduced in the coding sequence of MB9 using the degeneracy of the genetic code to preserve the proper amino acid sequence and overlaps the last 6 bases of Genescript-FVII-027-1. In addition, the first 6 bases at the 5' include a SapI site found within the Fc region. Genscript-FVII-026-2 consists of a DNA fragment encoding a portion of the MB9 (residues 143-273) followed by a $(GGGGS)_{6x}$ polypeptide linker followed by the Fc region and an EcoRI site. An EcoRI site was introduced in the coding sequence of MB9 using the degeneracy of the genetic code to preserve the proper amino acid sequence and overlaps the first 6 bases of Genescript-FVII-026-2.

Genescript-FVII-027-1 was cloned into the SapI and EcoRI sites of pSYN-FVII-011 to generate pSYN-FVII-036. Next, Genscript-FVII-026-2 was cloned into the EcoRI site of pSYN-FVII-036 to generate pSYN-FVII-027. Correct orientation of the last cloning step was confirmed by restriction enzyme analysis and DNA sequencing.

Example 2. Heterodimeric Constructs Comprising FVII-Fc AND MB9-Fc, MB9 at the Carboxy Terminus of the Second Fc Chain Cloning of FVII-037

The FVII-037 construct is made using an scFc scaffold which is not cleaved during processing. In this construct the targeting moiety, again the MB9 scFv which binds to GPIIbIIIa is attached to the c-terminus of the second Fc moiety.

Synthesis of DNA fragment Genscript-FVII-037 was outsourced (Genscript) This fragment comprises a portion of the Fc region (residues 434 to 447, EU numbering) followed by a (GGGGS)4× polypeptide linker and the MB9 scFv. A SapI/EcoRI fragment of Genscript-FVII-037 was subcloned into the SapI/EcoRI of pSYN-FVII-011 (refer to P0830) to generate and intermediate construct. A SapI fragment from pSYN-FVII-011 was subcloned into the SapI sites of the intermediate construct to generate pSYNFVII-037.

Example 3. Heterodimeric Constructs Comprising FVII-Fc and a Peptide Against GPIb at the Carboxy Terminus of the Second Fc Chain Cloning of THE pSYN-FVII-041 Intermediate Construct.

In order to make this construct, the FVII-041 construct was first made as an intermediate. Synthesis of DNA molecule Genscript-FVII-041 was outsourced (Genscript). This fragment was digested with SapI and cloned into SapI sites of pSYN-FVII-011 to generate pSYN-FVII-041. This process introduces a unique SalI site (residues 412-413 EU numbering, GTG GAC to GTC GAC) in the second Fc.

Cloning of pSYN-FVII-044-, -045 and -046.

The FVII-041 construct was used as the starting material to generate several constructs that comprise targeting moieties which are peptides that bind to GPIb. The PS4 peptide is used in the -044 construct, the OS1 peptide in the -045 construct, ad the OS2 peptide in the -046 construct. In these constructs an scFc scaffold is used and the peptides are attached via a linker to the C-terminus of the second Fc moiety.

Synthesis of Genscript-FVII-044, -045 and -046 was outsourced (Genscript). These DNA fragments were cleaved with SalI/EcoRI and subcloned into the SalI/EcoRI sites of pSYN-FVII-041 to generate pSYN-FVII-044, -045 and -046.

Example 4. Heterodimeric Constructs Comprising FVII-Fc and a Peptide Against GPIb at the Amino Terminus of the Second Fc Chain Cloning of the pSYN-FVII-043 Intermediate.

In order to make this construct, the FVII-043 construct was first made as an intermediate. Synthesis of DNA fragment Genscript-FVII-043 was outsourced (Genscript). This fragment comprises a DNA molecule encoding a portion of the Fc region (residues 232 to 447, EU numbering) followed by a (GGGGS)4× polypeptide linker and another portion of the Fc region (residues 221 to 238, EU numbering). This DNA fragment was digested with BspEI and RsrII and subcloned into the BspEI/RsrII sites of pSYN-FVII-042 to generate pSYN-FVII-050. This process introduces a unique SalI site (residues 412-413 EU numbering, GTG GAC to GTC GAC) in the first Fc. A HindIII/EcoRI fragment of pSYNFVII-050 was subcloned into the HindIII/EcoRI sites of pSYN-FVII-011 to generate pSYN-FVII-043.

Cloning of pSYN-FVII-047, -048 and -049.

The FVII-043 construct was used as the starting material to generate several constructs that comprise targeting moieties which are peptides that bind to GPIb. The PS4 peptide is used in the -047 construct, the OS1 peptide in the -048 construct, and the OS2 peptide in the -049 construct. In these constructs an scFc scaffold is used and the peptides are interposed between the scFc linker and a linker which is attached to the N-terminus of the second Fc moiety.

Synthesis of DNA molecules Genscript-FVII-047, -048 and -049 was outsourced (Genscript). A Sal/RsrII fragment from Genscript-FVII-047, -048 and -049 was subcloned into SalI/RsrII sites of pSYN-FVII-043 to generate pSYN-FVII-047, -048 and 049, respectively.

Example 5. Heterodimeric Constructs Comprising a Gla-Deleted FVII-Fc and a Targeting Molecule Cloning of the FVII-028 Intermediate In order to make this construct, the FVII-028 construct was first made as an intermediate. Synthesis of DNA fragment Genscript-FVII-028 was outsourced (Genscript). This fragment was cut with HindIII/XbaI and subcloned into pSYN-FVII-011 to generate p SYN-FVII-028.

Cloning of FVII-053

The FVII-028 construct was used as the starting material to generate a construct that comprises a targeting moiety and employs a clotting factor that lacks a Gla domain. For this construct, amino acids 1-35 were removed from FVII and an RKRRKR insertion was added after residue R152 (WT FVII numbering) to facilitate intracellular activation. The MB9 scFv served as the targeting moiety.

DNA molecule Genscript-FVII-025 was outsourced and an XbaI/BsiWI fragment from this molecule was subcloned into XbaI/BsiWI sites of pSYN-FVII-028 to generate p SYN-FVII-053.

Example 6. Heterodimeric Constructs Comprising a Factor VII Heavy and Light Chains as Two Separate Polypeptides Cloning of pSYN-FVII-024 Intermediate Construct The FVII-024 construct is one in which the heavy and light chains of factor FVII are not contiguous in a single chain molecule. The construct employs cscFc such that the cscFc linker is cleaved by proteases in the trans-Golgi network This cleavage results in linker removal as well as activation of FVII, resulting in the expression of activated FVIIaFc.

The coding sequence of FVII was obtained by reverse transcription coupled to polymerase chain reaction from a human liver mRNA library (Ambion, Austin, Tex.) using the following primers:

```
FVII-F1
GGGAATGTCAACAGGCAGGG

FVII-R1
CTTGGCTTTCTCTCCACAGGC
```

A 50 μl reaction was carried out with 10 pmol of each primer using the Superscript One-step RT-PCR with Platinum Taq system (Invitrogen, Carlsbad, Calif.) according to the manufacturer's standard protocol in a MJ thermocycler. The cycle used was 50° C. for 30 minutes for the reverse transcription followed by denaturing at 94° C. for 2 minutes and 30 cycles of (94° C. 30 seconds, 53° C. 30 seconds, 72° C. 90 seconds) followed by 10 minutes at 72° C. The expected sized band (~1400 bp) was gel-purified with a Gel Extraction kit (Qiagen, Valencia, Calif.) and cloned in pCR2.1 TOPO using the TOPO TA Cloning kit (Invitrogen, Carlsbad, Calif.) to produce the intermediate plasmid pSYN-FVII-001. To construct a plasmid for the expression of a two-chain FVII-Fc and Fc heterodimer, the FVII coding sequence was PCR-amplified using the following primers:

```
HindIII-Kozak-FVII-F
CGACAAGCTTGCCGCCACCATGGTCTCCCAGGCCCTCAGG

BspeI-Fc-FVII-R
CGACTCCGGAGCTGGGCACGGTGGGCATGTGTGAGTTTTGTCGGGAAATG
GGGCTCGCAGG
```

The forward primer HindIII-Kozak-FVII-F adds a HindIII restriction site followed by a Kozak sequence immediately upstream of the FVII coding region. The reverse primer BspeI-Fc-FVII-R adds a fragment of the constant region of IgG1 (the Fc region) comprising amino acids 221-233 (EU numbering). This process also incorporates a BspEI restriction site at amino acids 231-233 using the degeneracy of the genetic code to preserve the correct amino acid sequence (EU numbering). A 50 ul reaction was carried out with 15 pmol of each primer and template pSYN-FVII-001 using Platinum Pfx DNA Polymerase system according to manufacturer's protocol in a MJ Thermocycler using the following cycles: 95° C. 2 minutes; 30 cycles of (95° C. 15 seconds, 49° C. 30 seconds, 68° C. 90 seconds); 68° C. 10 minutes. Plasmid pSYN-FIX-027 (pBUD FIXFc/Fc) was digested with HindIII and BspEI and the expected sized band for the vector (approximately 5800 bp) was purified away from the FIX insert (expected size band approximately 1480 bp) with a Gel Extraction kit (Qiagen, Valencia, Calif.). Next, the PCR-amplified FVII sequence was subcloned into HindIII and EcoRI sites of the vector derived from pSYN-FIX-027 after removing the FIX insert. This generated pSYN-FVII-002 (pBUD FVIIFc/Fc). Next, A $(GGGGS)_{6x}$ polypeptide linker was added between FVII and the Fc region coding sequences in pSYN-FVII-002 using the following primers:

```
FVII-linker-F:
CATCCCCAGCACGTACGTCC

FVII-Linker-R:
GGGCATGTGTGAGTTTTGTCTGATCCCCCGCCACCGGAACCTCCACCGCCT
GATCCACCCCCACCTGATCCGCCGCCACCGGACCCACCTCCGCCGGAGCCA
CCGCCACCGGGAAATGGGGCTCGCAGGAGG

Fc-linker-F:
GACAAAACTCACACATGCCCACC

Fc-linker-R:
GCAGAATTCTCATTTACCCGGAG
```

Two 12 μl PCR reactions were carried out with either 12 pmol of FVII-linker-F and FVII-Linker-R (reaction 1) or Fc-linker-F and Fc-linker-R (reaction 2) using Expand High Fidelity System (Boehringer Mannheim, Indianapolis, Ind.) according to manufacturer's standard protocol in a MJ Thermocycler. The first and second reactions were carried out with 1 μg of pSYN-FVII-002 as template using the following cycle: 94° C. 2 minutes; 14 cycles of (94° C. 30 seconds, 55° C. 30 seconds, 72° C. 2 minutes); 72° C. 10 minutes. The expected sized bands (532 bp for reaction 1 and 670 bp for reaction 2) were gel purified with a Gel Extraction kit (Qiagen, Valencia, Calif.), then combined in a PCR reaction with 25 pmol of FVII-linker-F and Fc-linker-R as before, but with 30 rounds of amplification. The expected sized band (1200 bp) was gel purified with a Gel Extraction kit (Qiagen, Valencia, Calif.) and digested with restriction enzymes KpnI and EcoRI. The expected sized band (920 bp) was gel purified as before and cloned into the KpnI/EcoRI sites of pSYN-FVII-002 to generate pSYN-FVII-003 (pBUD FVIIFc/6×(GGGGS)/Fc).

Cloning of pSYN-FVII-024 to Express a Two-Chain Heterodimer

Plasmid (pSYN-FVII-024) was generated for the expression of a two-chain heterodimer where one chain consists of the FVII light chain (residues 1-152) followed by a $(GGGGS)_{6x}$ linker followed by the Fc region, while the other chain contains a FVII heavy chain (residues 153 to 406) followed by a $(GGGGS)_{6x}$ linker followed by the Fc region. The plasmid is designed to express the heterodimer as a single polypeptide where the C-terminus of the FVII heavy chain-linker-Fc chain is connected to the N-terminus of the heavy chain-linker-Fc chain by the following polypeptide sequence: RRRRS-$(GGGGS)_{6x}$-RKRRKR, where the RRRRS and RKRRKR sequences are proprotein convertase cleavage sites. Intracellular cleavage by proprotein convertases following the last Arg at each cleavage site can result in removal of the polypeptide linker. Consequently, cells will express a 2 chain heterodimer where the FVII light chain-linker-Fc chain has a RRRRS sequence at the C-terminus, but the remainder of the linker and the RKRRKR sequence have otherwise been removed. Construction of the pSYN-FVII-024 and several intermediate plasmids required the use of the following primers:

```
HindIII-SalI-BpEI-Fc-F
AGTCAAGCTTGTCGACTCCGGAACTCCTGGGCGGACC

BamHI-linker (PACE1)-Fc-R
CATCGGATCCCCCGCCACCGGAACCTCCACCGCCTGATCCACCCCCACCT
GATCCGCCGCCACCGCTCCGGCGGCGCCGTTTACCCGGAGACAGGGAGAG
G

HindIII-Kozak-FVII-F
CGACAAGCTTGCCGCCACCATGGTCTCCCAGGCCCTCAGG

BspEI-Fc-linker-FVIILC-R
GAGTTCCGGAGCTGGGCACGGTGGGCATGTGTGAGTTTTGTCTGATCCCC

CGCCACCGGAACCTCCACCGCCTGATCCACCCCCACCTGATCCGCCGCCA

CCGGACCCACCTCCGCCGGAGCCACCGCCACCTCGGCCTTGGGGTTTGCT

GG

BamHI-2xlink-pace-HC-F
CAGTCTGGATCCGGCGGTGGAGGTTCCGGTGGGGGTGGATCAAGGAAGAG
GAGGAAGAGGATTGTGGGGGGCAAGGTGTGCC

Fc-EcoRI-R
ATGTCTGAATTCTCATTTACCCGGAGACAGGGAGAGG
```

To generate the first intermediate plasmid, a PCR reaction was performed with 25 pmol of primers HindIII-SalI-BpEI-Fc-F and BamHI-linker(PACE1)-Fc-R and template pSYN-Fc-001 using Expand High Fidelity System (Boehringer Mannheim, Indianapolis, Ind.) according to manufacturer's standard protocol in a MJ Thermocycler. The following cycles were used: 95° C. 2 minutes; 30 cycles of (95° C. 30 seconds, 58° C. 30 seconds, and 72° C. 1 minute); 72° C. 10 minutes. The correct sized band (approximately 730 bp) was gel purified as above and cloned into the HindIII/BamHI sites of pBUDCE4 vector (Invitrogen, Carlsbad, Calif.), generating pSYN-FVII-014. PCR amplification with primers HindIII-SalI-BpEI-Fc-F and BamHI-linker(PACE1)-Fc-R generated a DNA fragment encoding a portion of the Fc region (Amino A X-Y) followed by an RRRRS sequence and $(GGGGS)_{2x}$ polypeptide linker. Primer HindIII-SalI-BpEI-Fc-F introduces a HindIII and SalI restriction site at the 5' end of the molecule, while primer BamHI-linker (PACE1)-Fc-R introduces a BamHI at the 3' end that overlaps the codons encoding the last 2 residues of the GGGGS linker (residues GS with codons GGA TCC). Next, another PCR reaction was performed as above with primers HindIII-Kozak-FVII-F and BspEI-Fc-linker-FVIILC-R and template pSYN-FVII-002 using the same conditions described for cloning of pSYN-FVII-014, but with an annealing temperature of 57° C. The expected sized band (approximately 700 bp) was gel purified and cloned into the HindIII and BspEI sites of pSYN-FVII-014 to generate pSYN-FVII-023. Primers HindIII-Kozak-FVII-F and BspEI-Fc-linker-FVIILC-R amplified a DNA fragment encoding the FVII light chain followed by a $(GGGGS)_{6x}$ polypeptide linker and a portion of the Fc region up to amino acid 232 (EU numbering). Primer HindIII-Kozak-FVII-F introduces a HindIII restriction site at the 5' end of the molecule followed by a Kozak sequence while primer BspEI-Fc-linker-FVIILC-R adds a BspeI site at the 3' end of the molecule.

In the final step a PCR reaction was carried out as above with primers BamHI-2×link-pace-HC-F and Fc-EcoRI-R and template pSYN-FVII-003 with the following cycles: 95° C. 2 minutes; 30 cycles of (95° C. 30 seconds, 55° C. 30 seconds, and 72° C. 2 minute); 72° C. 7 minutes. This PCR reaction generated a DNA molecule encoding a $(GGGGS)_{2x}$ polypeptide linker followed by a RKRRKR sequence followed by the FVII heavy chain. Primers BamHI-2×link-pace-HC-F and Fc-EcoRI-R introduce a BamHI site and an EcoRI site at the 5' and 3' end of the molecule, respectively. The expected sized band (approximately 1600 bp) was cloned into the BamHI and EcoRI sites of pSYN-FVII-023 to generate pSYN-FVII-024.

Cloning of Intermediate pSYN-FVII-073

A silent mutation was introduced in the first Fc moiety of FVII-024 by PCR-based site-directed mutagenesis methods, resulting in the generation of a SalI site at DNA region encoding amino acids in position 412 and 413 (EU numbering). This generated the intermediate construct FVII-073.

Cloning of pSYN-FVII-057

The synthesis of the DNA sequence comprising nucleotides from the SalI to BsiWI sites of pSYN-FVII-057 was outsourced. This DNA was subcloned into the SalI/BsiWI sites of pSYN-FVII-073 to generate pSYN-FVII-057.

Cloning of pSYN-FVII-058, pSYN-FVII-059, pSYN-FVII-060, pSYN-FVII-061 and pSYN-FVII-062

These constructs were cloned as described for pSYN-FVII-057 (outsourced synthesis of DNA from SalI to BsiWI and subcloned into pSYN-FVII-073).

Cloning of pSYN-FVII-066

The synthesis of the DNA sequence comprising nucleotides from the SalI to RsrII sites of pSYN-FVII-066 was outsourced. This DNA was subcloned into the SalI/RsrII sites of pSYN-FVII-043 to generate pSYN-FVII-066.

Cloning of pSYN-FVII-067

The synthesis of the DNA sequence comprising nucleotides from the SalI to EcoRI sites of pSYN-FVII-067 was outsourced. This DNA was subcloned into the SalI/EcoRI sites of pSYN-FVII-041 to generate pSYN-FVII-067.

Cloning of pSYN-FVII-090

The synthesis of the DNA sequence comprising nucleotides from the BamHI to BsiWI sites of pSYN-FVII-090 was outsourced. This DNA was subcloned into pSYN-FVII-061 by 3-way ligation (where the outsourced DNA was cut with BamHI/BsiWI and pSYN-FVII-061 with BamHI/BsiWI/NotI) to generate pSYN-FVII-090.

Cloning of pSYN-FVII-100

A portion (amino acids 311 to 322 of the FVII mature sequence) of the 170 loop of FVII was replaced with the 170 loop of trypsin (amino acids EASYPGK). This mutation was introduced by standard overlapping PCR methods using the pSYN-FVII-090 as template and backbone structure to generate pSYN-FVII-100.

Cloning of pSYN-FVII-115

A triple point mutation (V158D, E296V and M298Q; mature FVII sequence numbering) was introduced into the FVII coding region of pSYN-FVII-090 by PCR-based site-directed mutagenesis to generate pSYN-FVII-115.

Cloning of pSYN-FVII-118

The synthesis of the DNA sequence comprising nucleotides from the XbaI to BsiWI sites of pSYN-FVII-118 was outsourced. This DNA was subcloned into the XbaI/BsiWI sites of pSYN-FVII-011 to generate pSYN-FVII-118.

Cloning of pSYN-FVII-119

The synthesis of the DNA sequence comprising nucleotides from the XbaI to BsiWI sites of pSYN-FVII-119 was outsourced. This DNA was subcloned into the XbaI/BsiWI sites of pSYN-FVII-011 to generate pSYN-FVII-119.

Cloning of pSYN-FVII-127

A DNA fragment comprising the 170 loop of trypsin was generated by PCR using pSYN-FVII-100 as template. This PCR reaction generated BsiWI and BspEI restriction sites at the 5' and 3', respectively. The DNA fragment was subcloned into the BsiWI/BspEI sites of pSYN-FVII-118 to generate pSYN-FVII-127.

Cloning of pSYN-FIX-042

A HindIII/BspEI fragment from pSYN-FIX-030 (as described in U.S. Pat. No. 7,566,565) was subcloned into the HindIII/BspEI sites of pSYN-FVII-011 to generate pSYN-FIX-042.

Cloning of pSYN-FIX-068

A HindIII/BspEI fragment from pSYN-FIX-030 (plasmid described in full in U.S. Pat. No. 7,566,565) was subcloned into the HindIII/BspEI sites of pSYN-FVII-066 to generate pSYN-FIX-068.

Cloning of pSYN-FIX-088

A BspEI-EcoRI fragment from pSYN-FIX-067 was subcloned into BspEI-EcoRI sites of pSYN-FIX-053 to generate pSYN-FIX-088.

Cloning of pSYN-FIX-089

A BspEI-EcoRI fragment from pSYN-FIX-048 was subcloned into BspEI-EcoRI sites of pSYN-FIX-053 to generate pSYN-FIX-089.

Cloning of pSYN-FIX-090

A DNA fragment comprising the FIX coding region from the XbaI site to the C-terminus of the protein followed by a 6×(GGGGGS) linker, the SCE5 coding sequence and an EcoRI site was outsourced for synthesis and subcloned into the XbaI/EcoRI sites of pSYN-FIX-053 to generate pSYN-FIX-090. The SCE5 sequence is set forth below:

```
AQVQLQESGGGLVQPGGSLRLSCAASGEMESRYAMSWVRQAPGKGPEWVS

GISGSGGSTYYADSVKGRFTVSRDNSKNTLYLQMNSLRAEDTAVYYCARG

ATYTSRSDVPDQTSFDYWGQGTLVTVSSGSASAPKLEEGEFSEARVSELT

QDPAVSVALGQTVRITCQGDSLRNFYASWYQQKPGQAPTLVIYGLSKRPS

GIPDRFSASSSGNTASLTITGAQAEDEADYYCLLYYGGGQQGVFGGGTKL

TVLRQPKAAPSVTLFPPSSAA
```

Cloning of pSYN-FVII-094

A DNA fragment comprising a sequence encoding a 6×(GGGGS) linker followed by the SCE5 coding sequence was synthesized (outsourced) and cloned into the EcoRV/EcoRI sites of a pSYN-FVII-011 variant that had been previously modified to generate an EcoRV site at the C-terminus of the FVII coding region.

Cloning of pSYN-FVII-088

The synthesis of the DNA sequence comprising nucleotides from the SalI to RsrII sites of pSYN-FVII-088 was outsourced. This DNA was subcloned into the SalI/RsrII sites of pSYN-FVII-066 to generate pSYN-FVII-088.

Cloning of pSYN-FVII-125

A DNA fragment was PCR amplified from pSYN-FVII-088, comprising the AP3 region and part of the linker. This PCR reaction generated BamHI and EcoRI sites at the 5' and 3' of the DNA fragment, respectively. This DNA fragment was subcloned into the BamHI/EcoRI sites of pSYN-FVII-011 to generate pSYN-FVII-125.

Cloning of pSYN-FVIII-041

The coding sequence of human recombinant B-domain deleted FVIII was obtained by reverse transcription-polymerase chain reaction (RT-PCR) from human liver poly A RNA (Clontech) using FVIII-specific primers. The FVIII sequence includes the native signal sequence for FVIII. The B-domain deletion starts after serine 743 (S743; 2287 bp) and ends before glutamine 1638 (Q1638; 4969 bp) for a total deletion of 2682 bp (SQ version).

The coding sequence for human recombinant Fc was obtained by RT-PCR from a human leukocyte cDNA library (Clontech) using Fc specific primers. Primers were designed such that the B-domain deleted FVIII sequence was fused directly to the N-terminus of the Fc sequence with no intervening linker. The FVIIIFc DNA sequence was cloned into the mammalian dual expression vector pBUDCE4.1 (Invitrogen) under control of the CMV promoter.

A second identical Fc sequence including the mouse Igk signal sequence was obtained by RT-PCR and cloned downstream of the second promoter, EF1α, in the expression vector pBUDCE4.1. This final construct was designated pSYN-FVIII-013.

A second plasmid was created from similar constructs using PCR and standard molecular biology techniques, in order to express rFVIIMDD-Fc-Fc in which the rFVIIIBDDFc coding sequence was fused to the second Fc sequence with a (GGGGS)4 linker, allowing for production of only the rFVIIIBDD-Fc monomer-dimer hybrid in transient transfection. This construct was designated pSYN-FVIII-041.

Cloning of pSYN-FVIII-049

Generated intermediate pSYN-FVIII-048 by cloning NheI/XhoI fragment from pBUD-CE4.1 into pSYN-FVIII-013. The synthesis of a DNA fragment comprising the region from RsrII to XbaI sites of pSYN-FVIII-049 was outsourced. This fragment was subcloned into the RsrII/XbaI sites of pSYN-FVIII-048 to generate p SYN-FVIII-049.

Cloning of pSYN-FVIII-108

A SalI/RsrII fragment from pSYN-FVII-066 was subcloned into pSYN-FVIII-049 to generate pSYN-FVIII-108.

Example 7. Additional Attempts at Expression of Activated Constructs

Several other constructs were made with the goal of expressing activated FVII. However, these constructs did not successfully express activated molecules. By Western blot it was demonstrated that that the FVII heavy chain cannot be expressed with a free N terminus using a common method of fusing a heterologous signal peptide to the N-terminus of the heavy chain.

Cloning of pSYN-FVII-010

The FVII-010 construct is one in which the heavy chain of factor VII was expressed in the context of an scFc scaffold and the light chain was expressed separately.

PCR-amplify with primer pairs FVII-HC-Hind3-IggKss-F/FVII-HC-BspEI-R, using pSYN-FVII-001 (see supra.). Clone in BspEI/HindIII sites of pSYN-FVII-008 (see supra), generating pSYN-FVII-009.

PCR amplify FVII light chain from pSYN-FVII-003 (refer to P0830) with primers FVII-LC-NotI-F/FVII-LC-XhoI-R and clone in pSYN-FVII-009 to generate pSYN-FVII-010.

Primers

```
FVII-HC-BspEI-R
AGGAGTTCCGGAGCTGGGCACGGTGGGCATGTGTGAGTTTTGTCGGATCC

CCCGCCACCGGAACCTCCACCGCCTGATCCACCCCCACCTGATCCGCCGC

CACCGGACCCACCTCCGCCGGAGCCACCGCCACCGGGAAATGGGGCTCGC

AGGAGG

FVII-HC-Hind3-IggKss-f
ACTGACAAGCTTGCCGCCACCATGGAGACAGACACACTCCTGCTATGGGT
ACTGCTGCTCTGGGTTCCAGGTTCCACTGGTATTGTGGGGGGCAAGGTGT
GC

FVII-LC-NotI-F
ACTGACGCGGCCGCGCCGCCACCATGGTCTCCCAGG

FVII-LC-XhoI-R
ACTGACCTCGAGTTATCGGCCTTGGGGTTTGCTGG
```

Cloning of pSYN-FVII-013

The FVII-013 construct is one in which the light chain was expressed in the context of an scFc scaffold and the heavy chain was expressed separately.

PCR-amplify with primer pair FVII-LC-linker-BamHI-R/HindIII-Kozak-FVII-F from pSYN-FVII-001 (refer to P0830) and clone in BamHI/HindIII sites of pSYN-FVII-011, generating pSYN-FVII-012. PCR-amplify FVII-HC from pSYN-FVII-009 using primer pair FVII-HC-NotI-F/FVII-HC-XhoI-R ad subclone in pSYN-FVII-012 to generate pSYN-FVII-013.

Primers

```
FVII-LC-6xlinker-BamHI
RACTGACGGATCCCCCGCCACCGGAACCTCCACCGCCTGATCCACCCCCA
CCTGATCCGCCGCCACCGGACCCACCTCCGCCGGAGCCACCGCCACCTCG
GCCTTGGGGTTTGCTGGC

HindIII-Kozak-FVII-F
CGACAAGCTTGCCGCCACCATGGTCTCCCAGGCCCTCAGG

FVII-HC-NotI-F
ACTGACGCGGCCGCGCCGCCACCATGGAGACAGAC

FVII-HC-XhoI-R
ACTGACCTCGAGTTAGGGAAATGGGGCTCGCAGGAG
```

Cloning of pSYN-FVII-018

For the FVII-018 construct, the heavy chain of FVII was expressed as an Fc fusion protein and the light chain of FVII was separately expressed as a separate Fc fusion protein.

Primers FVII-HC-Hind3-IggKss-F/scFc-EcoRI-R were used to PCR amplify HCFVII-linker-Fc, using pSYN-FVII-010 as template. Subclone in HindIII/EcoRI sites of pBUDCE4. This makes pSYN-FVII-017. Next, PCR-amplify from pSYN-FVII-013 with primers FVII-LC-NotI-F/FC-XHOI-R and subclone in XhoI/NotI sites of FVII-017. This makes PSYN-FVII-018.

Primers

```
scFc-EcoRI-R
ACTGACGAATTCTCATTTACCCGGAGACAGGGAG

Fc-XhoI-R
AGCTCTCGAGTCATTTACCCGGAGACAGGG
```

Example 8. Attempts at Expression of Activatable Constructs

Cloning of FVII-039, -040

Several constructs were made in an attempt to generate constructs in which Factor VII can be activated in vivo at the site of clotting using an appropriate cleavage site, in this case the DFTR Factor XIa cleavage site.

The 039 construct was made in the context of an scFc scaffold. The construct included the FVII light chain, the FXIa cleavage site, and the FVII heavy chain with a I153V mutation in linear sequence attached to the N-terminus of the first Fc moiety.

The 040 construct was also made in the context of an scFc scaffold. The construct included the FVII light chain with an R152 deletion, the FXIa cleavage site, and the FVII heavy chain with an I153V mutation in linear sequence attached to the N-terminus of the first Fc moiety. The DFTR cleavage sequence is a natural FXIa sequence found in FIX. In FIX, the DFTR sequence is followed by a valine, so an I152V mutation was introduced in pSYN-FVII-039, -040 to increase FXIa cleavage efficiency.

Synthesis of DNA molecule Genscript-FVII-039 and -040 was outsourced (Genscript). An XbaI/BsiWI fragment from Genscript-FVII-039 and -040 was subcloned into XbaI/BsiWI sites of pSYN-FVII-011 to generate pSYN-FVII-039 and -040, respectively.

Example 9. Transient Transfection of Constructs

For expression of constructs, HEK-293-F cells were grown in suspension in Freestyle media (Invitrogen) supplemented with vitamin K3 (For FVII and FIX transfections only) (Sigma Aldrich, St. Louis, Mo.) to 2 μg/liter (growth media) as suspension cells at 37° C./10% $CO_2$. Cells we subcultured every three to four days by seeding at cell density of $5\times10^5$ cells/ml.

Twenty-four hours prior to transfection cells were seeded at a density of $7\times10^5$ cells/ml in growth media supplemented with LONG™R3IGF-1 (Sigma Aldrich, St. Louis, Mo.) to 20 μg/liter (transfection media). On the day of transfection, a transfection solution was made with a volume equal to 5% of the total volume of the cell culture to be transfected. In the transfection solution DNA was added (final concentration 20 mg/L) to a freshly made solution of PEI (60 mg/L) in transfection media. The solution was swirled for 30 seconds and incubated for five minutes at room temperature before adding directly to the cell culture. Four hours later a volume equal to the cell culture volume of OptiCHO (Invitrogen) supplemented with vitamin K3, LONG™R3IGF-1 and 200 mM L-glutamine was added to the cells. The cell culture was allowed to grow as shown above and daily media samples were taken to assess protein expression. On the day of harvest, the cells were spun down and the media filtered in preparation for protein purification or protein analysis by protein A pulldown/western blot.

Example 10. Protein Purification of FVIIFc Molecules (Except FVII-028 and FVII-053) and FIXFc Molecules FVIIFc molecules were purified from conditioned media using the following columns: 1) Anion exchange chromatography with pseudo-affinity elution (e.g. Q sepharose 4FF (GE Healthcare) followed by elution with varying levels of $CaCl_2$ to selectively elute the most active species), followed by 2) shFcRn (soluble human FcRn) affinity (NHS-coupled shFcRn with sepharose 4FF beads) chromatography, binding Fc-containing proteins at low pH (e.g. pH 6.2) and eluting at neutral pH (e.g. pH 8.0). In some cases, an additional step was included utilizing cation exchange chromatography with NaCl elution. These purification steps utilized standard methods known to those in the art to generate purified proteins of >95% purity by SEC analysis and SDS-PAGE. FIXFc proteins were purified as previously described in U.S. Pat. No. 7,566,565.

Example 11. Protein Purification of FVII-028 and FVII-053

FVII-028 and -053 were purified from conditioned media using the following columns: 1) Hydrophobic interaction chromatography (e.g. Phenyl FF (high sub) (GE Healthcare)), followed by 2) Anion/cation exchange chromatography with salt elution. These purification steps utilized standard methods known to those in the art to generate purified proteins of >95% purity by SEC analysis and SDS-PAGE.

Example 12. Purification of FIX-090

FIX-090 was purified through a 2-step chromatography process, first using an immunoaffinity chromatography step with an anti-GLA domain antibody, followed by anion exchange chromatography using pseudoaffinity elution similar to FIXFc proteins described above. These purification steps utilized standard methods known to those in the art to generate purified proteins of >95% purity by SEC analysis and SDS-PAGE.

Example 13. Purification of FVIIIFc Proteins

FVIIIFc proteins were purified from clarified and chemically defined harvest media using a two or three column purification process, including a FVIII-specific affinity purification step (McCue 2009) followed by a combination of anion exchange with standard NaCl elution and/or shFcRn (soluble human FcRn) affinity (NHS-coupled shFcRn with sepharose 4FF beads) chromatography, binding Fc-containing proteins at low pH (e.g. pH 6.2) and eluting at neutral pH (e.g. pH 8.0). These purification steps utilized standard methods known to those in the art to generate purified proteins of >95% purity by SEC analysis and SDS-PAGE.

Example 14. Activation of FVII Constructs

Figure 10:
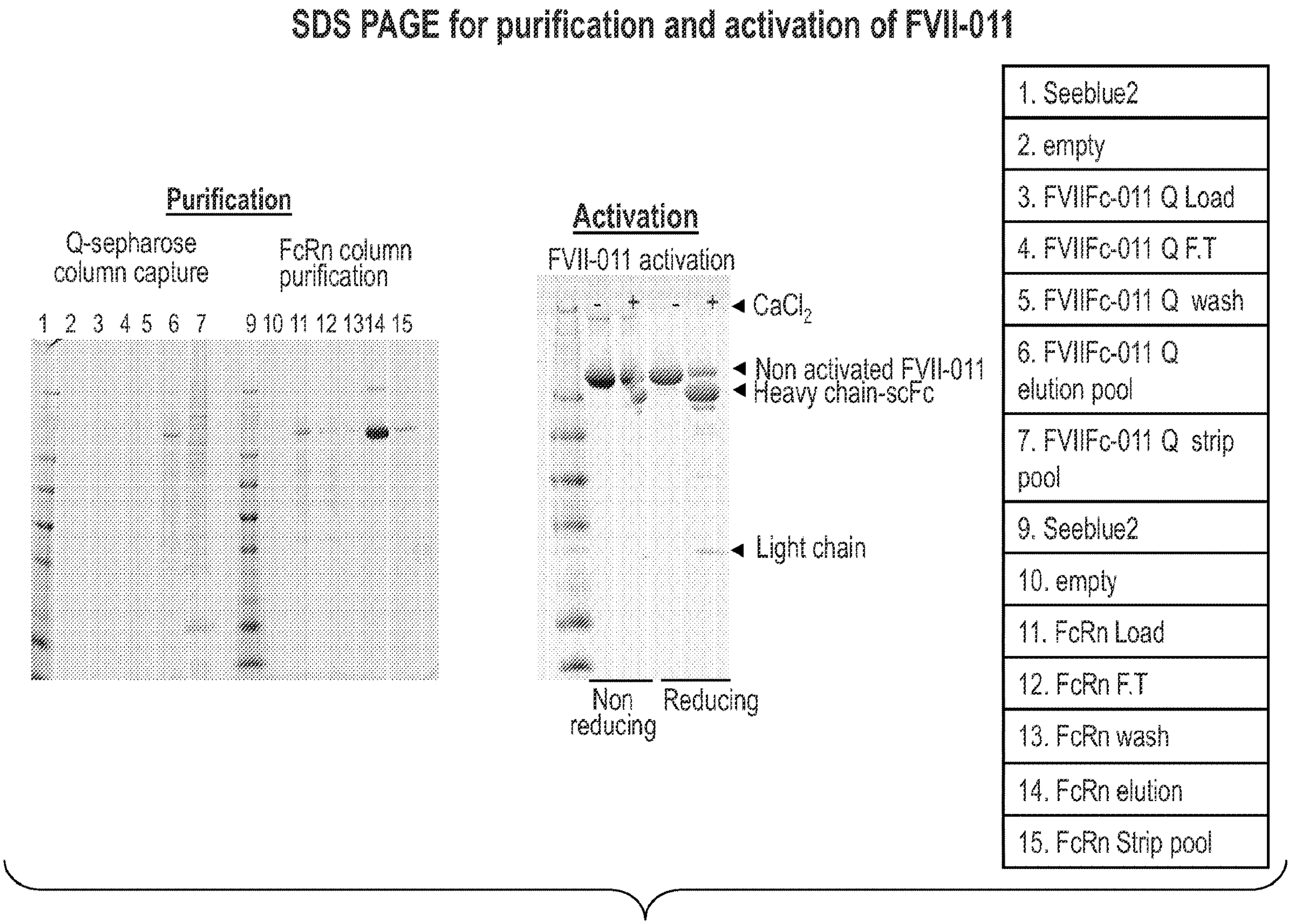
FIG. 10 shows SDS PAGE for purification and activation of FVII-011.
Figure 11:
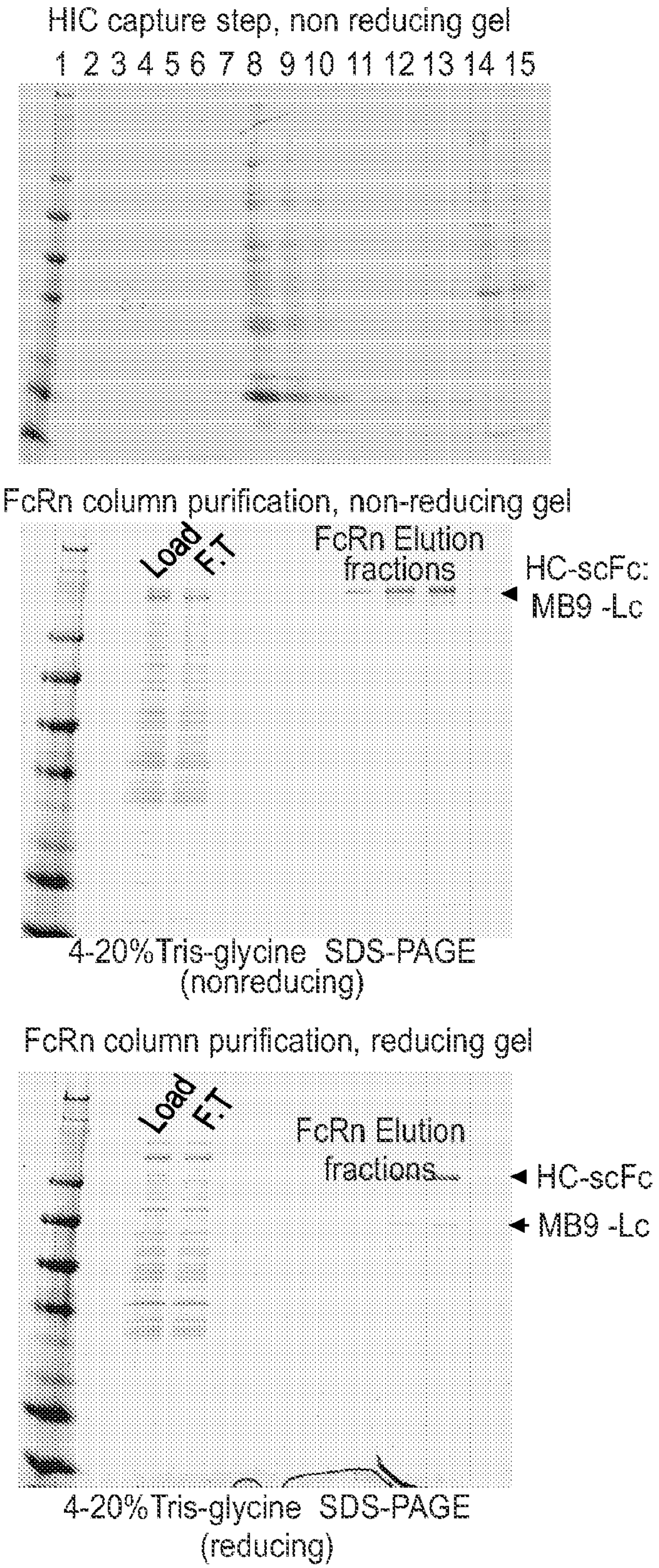
FIG. 11 shows SDS PAGE for purification of active FVII-053.

Fractions eluted from the FcRn column containing FVIIFc were pooled, and total protein was concentrated to 4 mg/ml. The $CaCl_2$ concentration was raised to 5 mM and the sample was incubated at 4° C. for 24 to 48 hours until at least 80% of FVIIFc was activated. The extent of activation was assessed by SDS PAGE (FIG. 10).

Example 15. FVIIa Activity Assays, Soluble Tissue Factor Method

Specific activity of the FVIIaFc variants was determined by the soluble tissue factor method. Unlike lipidated full length tissue factor, soluble tissue factor (extracellular portion of tissue factor) can't activate FVII into FVIIa, but it acts as an activator of the conversion of factor X into factor Xa by FVIIa. To determine the specific activity of FVIIaFc variants, A STACLOT® FVII-rTF kit (Diagnostica Stago, Asnieres, France) was used following manufacturer's recommendations. Table 1 summarizes the data and shows comparable specific activity for all variants.

TABLE 1

Specific activity of FVIIaFc variants based on the soluble tissue factor method

| FVIIaFc | IU/nM |
|---|---|
| FVII-011 | 991 |
| FVII-024 | 929 |
| FVII-027 | 790 |
| FVII-037 | 1131 |
| FVII-044 | 1300 |
| FVII-045 | 906 |
| FVII-046 | 1145 |
| FVII-047 | 924 |
| FVII-048 | 973 |
| FVII-049 | 1130 |
| FVII-053 | 929 |

Example 16. FACs Assays to Study Binding of FVIIaFc and Platelets

In this example, the following reagents and methods were used:

Reagents

ADP: Sigma Aldrich, cat #A2754, stock 1 mM, working concentration 10 uM

SFLLRN peptide: in-house synthesis, stock concentration 5 mg/ml (6.7 mM), working concentration 50 ug/ml (67 uM)

FVII antibody-FITC-labeled: Affinity Biologicals SAFVII-APFTC

Platelet buffer: 15 mM HEPES, 138 mM NaCl, 2.7 mM KCl, 1 mM MgCl2, 5 mM CaCl2, 5.5 mM dextrose and mg/ml BSA, pH 7.4

Method

Count Platelets

Add 20 ul of ~2-4×$10^8$ cells/ml gel-purified platelets to 1 ml of platelet buffer Make 100 ul aliquot for each sample Add agonist and FVIIaFc (to desired concentration) as needed Incubate at 37 C for 15 minutes Add equal volume of HBS/5 mM $CaCl_2$/1.5% formaldehyde, incubate 20' at RT Spin 15' at 3000 g Wash in HBS/5 mM CaCl2/1 mg/ml BSA, spin again and resuspend in 100 ul of platelet buffer.

Add 2.5 ul of FVII antibody-FITC-labeled and incubate for 30 at room temperature.

Analyze by FACs

Example 17. Thrombin Generation Assay

In this example, the following reagents and methods were used:

Reagents

FV: HTI, cat #HCV-0100, lot #Z0413, 5.1 mg/ml

Prothrombin: HTI, cat #HCP-0010, lot #Z0128, 4.8 mg/ml

FX: HTI, cat #HCX-0050, lot #X0401, 5.4 mg/ml

ATIII: HTI, cat #HCATIII-0120, lot #Y0401, 8.2 mg/ml

TFPI: American Diagnostica, cat #4900PC, lot #081031, 100 ug/ml

Reader: Fluorskan, Thermo Electron Fluorometer

Thrombin Calibrator: Thrombinoscope, cat #TS20.00

Fluca: Thrombinoscope, cat #TS50.00

Platelet buffer: 15 mM Hepes pH 7.4, 138 mM NaCl, 2.7 mM KCl, 1 mM MgCl2, 5.5 mM Dextrose, supplemented with 1 mg/ml BSA before using ADP: Sigma Aldrich, cat #A2754, stock 1 mM, working concentration 10 uM SFLLRN peptide: in-house synthesis, stock concentration 5 mg/ml (6.7 mM), working concentration 50 ug/ml (67 uM)

| | Primary stock (mg/ml) | Working solution (ug/ml) | [final] ug/ml |
|---|---|---|---|
| FV | 5.1 | 105.6 | 4.4 |
| FII | 4.8 | 1200 | 54 |
| FX | 5.4 | 120 | 5 |
| ATIII | 8.2 | 1800 | 75 |
| TFPI | 0.1 | 1.44 | 0.06 |
| Platelet | 2-10E8 | 1.74E8 | 0.6E8 |
| FVIIaFc | 1 mg/ml (10 uM) | 1200 nM | 200 nM |
| FVIIaFc | 1 mg/ml (10 uM) | 200 nM | 62.5 nM |
| FVIIaFc | 1 mg/ml (10 uM) | 62.5 nM | 12.5 nM |

Method

Set up software according to manufacturer's recommendations

Prewarm water and Fluca buffer

Make clotting factor mix. Dilute stock concentration of FV, FII, FX, ATIII and TFPI to make working solution. Need 5 ul/well, so for a 30 well assay prepare 180 ul of each Mix all the clotting factor solutions in a single bulk solution Premake FVIIaFc dilutions. Make 1200 nM solution (12 ul into 88 ul of buffer) in 100 ul and dilute 4-fold twice (25 ul into 75 ul of buffer) to obtain 200 nM and 62.5 nM solutions Make calibrator solution (1 ml of warm water in calibrator vial)

Add 20 ul of buffer or calibrator to the wells

Add 25 ul of clotting factor mix to the wells (or 25 ul of buffer to calibrator wells)

Add 20 ul of FVIIaFc to the wells (or buffer to calibrator wells)

Add 35 ul of platelets (previously add ADP and SFLLRN). Add platelets to calibrator well Put plate in instrument, prepare Fluca buffer and start reaction (add 20 ul Fluca/well) 5 minutes after putting plate into instrument.

Example 18. Analysis of Protein Generated from Transient Transfections

For analysis of protein from transient transfections, conditioned media from transfections of pSYN-FVII-010, 011, -013, -018, -003, -019-020 and -024 were subjected to protein A immunoprecipitation. Briefly, cell culture supernatant was mixed with approximately 50 ul of protein A-Sepharose 50% slurry and incubated at 4° C. with rocking for 1 hour, then centrifuged to pellet the protein A beads. Beads were washed twice by resuspending in 1 ml of PBS, spinning and aspirating. The beads were resuspended with sodium dodecylsulfate-polyacrylamide gel electrophoresis (SDS-PAGE) under reducing or nonreducing conditions, heated for 5 minutes at 100° C., spun down and loaded on SDS-PAGE gels and run according to standard protocols. Gels were transferred to nitrocellulose membranes and Western blots were performed to detect the Fc region or the FVII light chain. For Fc detection, the antibody used was a goat anti-human IgG (Fc specific)-horseradish peroxidase conjugate (Pierce ImmunoPure antibody, catalog #31413). For FVII light chain detection an anti light chain monoclonal antibody was used (Green Mountain, clone 6MA-219). The antibodies were diluted 1:15,000 (for Fc detection) or 1:200 (for light chain detection) in PBST (PBS with 0.1% Tween-20) with 5% nonfat dry milk and incubated with the membrane for 1 hour at room temperature. The membrane was then washed in PBST 3 times for 10 minutes and signal was detected by a chemiluminescent method for Fc detection. For FVII light chain detection, the membrane was further incubated for one hour in a solution containing HRP-labeled goat anti-mouse antibody (Southern Biotech, #1010-05) diluted 1:5000 in PBST. The membrane was also washed in PBST 3 times for 10 minutes and the signal was detected by a chemiluminescent method. Chemiluminescent detection was performed using ECL Plus Western Blotting Detection System (Amersham Biosciences catalog #RPN2132) according to manufacturer's protocol. Signal was visualized in a Storm 840 Phosphorimager (Molecular Devices).

The effect of PC5 on the processing of the proprotein convertase cleavage sites in the FVII-024 linker was tested as shown in FIG. 26. Under nonreducing conditions the effect of PC5 on cleavage site processing can not be detected because the FVII light chain-Fc and FVII heavy chain-Fc subunits remain linked via 2 disulfide bonds in the Fc region (lanes 2 and 3). Under reducing conditions we observed partial processing of FVII-024 generated from cells not cotransfected with PC5 (lane 4), but full processing when the cells were cotransfected with PC5 (lane 5). Full processing of the linker results in secretion of activated FVII (FVIIa), since a free N-terminus of the heavy chain is required and sufficient to activate the protein Example 19. Cleavage of FVII-039 and FVII-040 by FXIa The activation FVII-039 and FVII-040 by FXIa, as a result of the FXIa cleavage site inserted immediately upstream of the FVII light chain in these proteins, was characterized in vitro. A 1.5 μM solution of FVII-039, FVII-040 or FVII-011 (non activated) containing 15 nM FXIa in 50 mM Tris-HCl, 100 mM NaCl, 10 mM $CaCl_2$, pH 7.4 was incubated for 5 or 20 minutes, and cleavage of FVIIFc was determined by SDS PAGE under reducing conditions, followed by SYPRO Ruby staining (Invitrogen). FXIa failed to cleave FVII-039, FVII-040 and nonactivated FVII-011, as shown in FIG. 28.

Example 20. Alternative Activatable FVIIFc Constructs

Failure of FXIa to cleave FVII-039 and FVII-040 may have been caused by inaccessibility of the protease to the cleavage site by steric hindrance. To improve FXIa or thrombin cleavage site accessibility, the sites will be placed upstream of the heavy chain in a structure where the heavy chain is not preceded by the light chain (Light chain-linker-Fc-scFclinker-FXIa/thrombin cleavage site-heavy chain-linker-Fc). In some embodiment, the heavy chain will comprise the I152V mutation. Once the best cleavage site is determined, a cscFc will be introduced so that the cell secretes a heterodimeric protein with the following structure: light chain-linker-Fc which is disulfide bonded to a second chain: FXIa/thrombin cleavage site-heavy chain-linker Fc.

Figure 28:
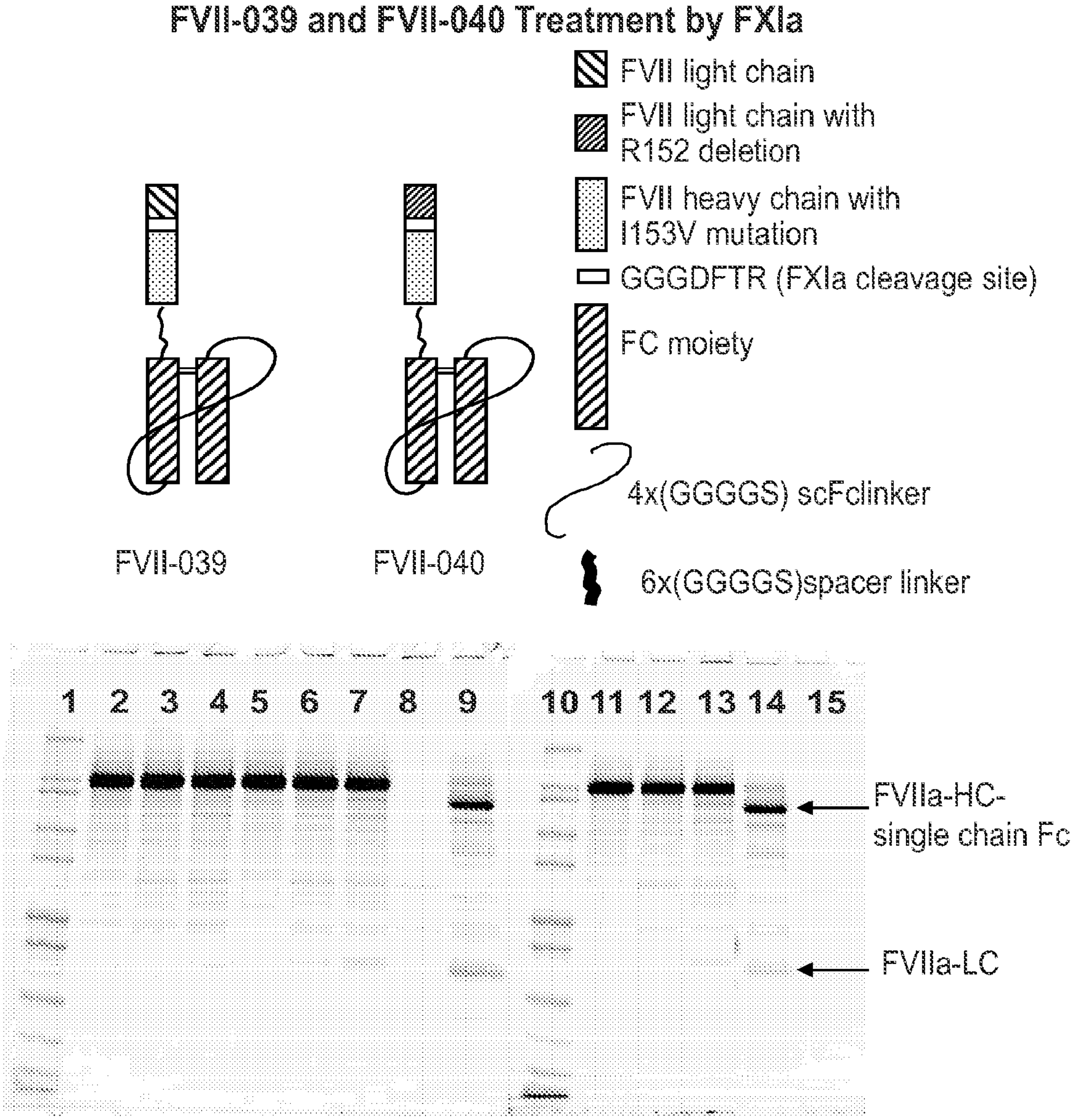
FIG. 28 shows FVII-039 and FVII-040 treatment by FXIa.
Figure 31:
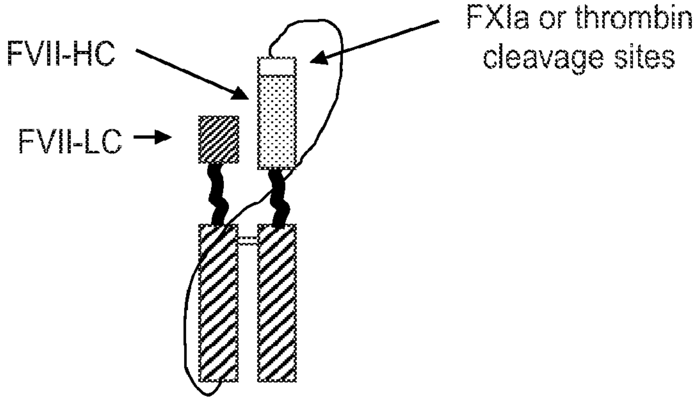
FIG. 31 shows exemplary cleavage sites and illustrative positions of such cleavage sites in activatable clotting factor constructs. In this Figure FVII is used as an example.
Figure 32:
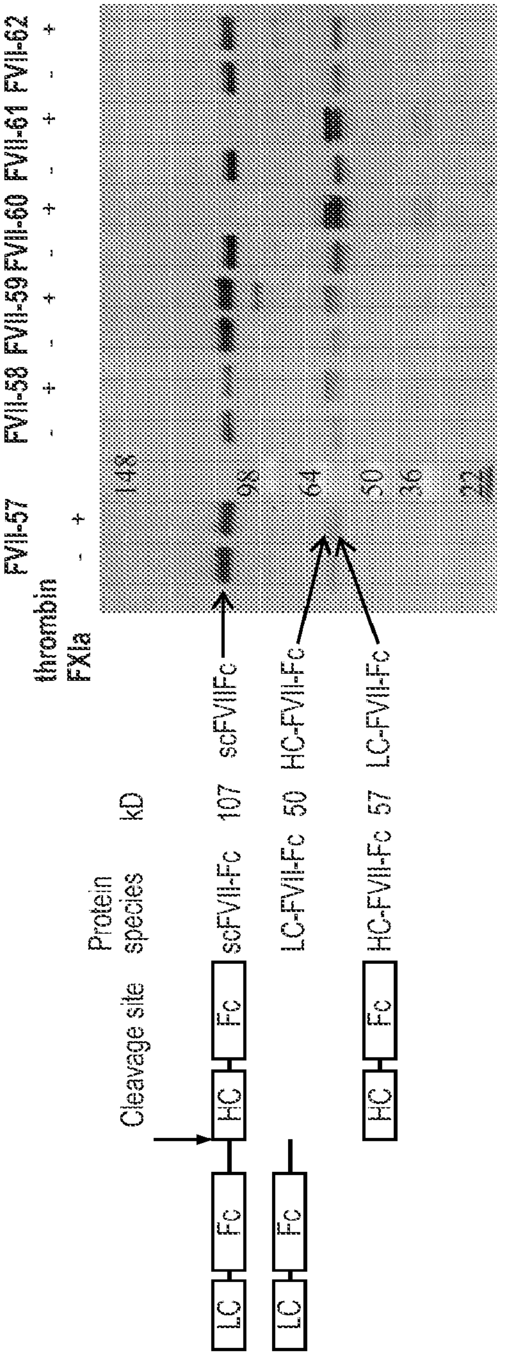
FIG. 32 shows cleavage of the constructs illustrated in FIG. 31.

In order to improve the level of activation observed with the constructs shown in FIG. 28, a second generation of activatable variants illustrated in FIG. 31 (similar in structure to those shown in FIG. 6E) was used to increase accessibility of the cleavage site. In this example, FXIa and thrombin cleavage sites were used for these constructs (See FIG. 31). Constructs were transiently transfected as previously described. FVIIFc was captured from media with protein A. FVIIFc bound to the beads was put in buffer and FXIa or thrombin was added and incubated. FVIIFc was eluted from beads with SDS PAGE loading buffer at 100 C for 5 minutes. The gel was loaded and western blot performed to detect Fc as previously described and the results are shown in FIG. 32. As shown in FIG. 32, both the thrombin and factor XIa cleavage sites could be cleaved to yield FVII heavy and light chain molecules in the presence of the appropriate enzyme. Best cleavage was observed for constructs FVII-060 and FVII-061, while no cleavage was observed for the negative control (FVII-062) in the presence of thrombin.

Example 21. A Factor VII Activatable Construct

Figure 33:
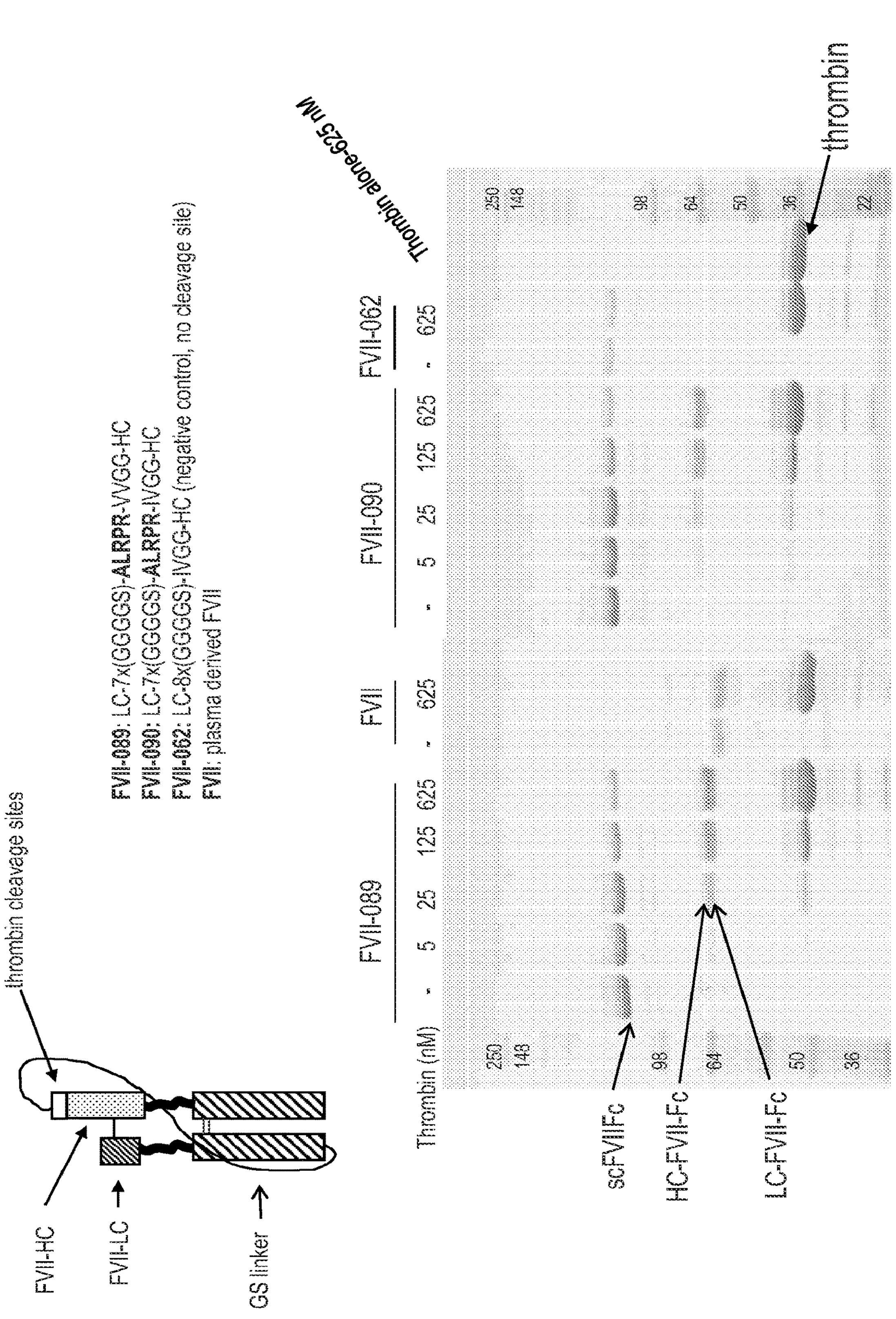
FIG. 33 shows additional activatable constructs and a Western blot illustrating their cleavage.

The constructs depicted in FIG. 33 were (FVII-090, FVII-089 and FVII-062) were cloned, expressed and purificated as previously described (these proteins do not require activation). Due to a cloning error a "VVGGA" sequence was inserted after the ALRPR thrombin cleavage sequence of FVII-060 and FVII-061, but while this insertion would be expected to affect the activity, it would not be predicted to affect the assessment of cleavage by thrombin in SDS-PAGE based assays. This sequence was removed in FVII-089 and FVII-090. To 125 nM of FVII-090, FVII-089, FVII-062, or plasma-derived FVII (FVII) increasing concentrations of thrombin were added and incubated for 10 minutes at 37° C. The mixture was run on SDS-PAGE gel to determine cleavage by thrombin (FIG. 33). Generation of FVII light chain-Fc and FVII heavy chain-Fc was observed for FVII-089 and FVII-090 after incubation with thrombin. The fact that there was no cleavage of plasma-derived FVII or the FVII-062 negative control by thrombin shows specificity. No significant difference in cleavage efficiency was observed for FVII-089 and FVII-090.

Figure 34:
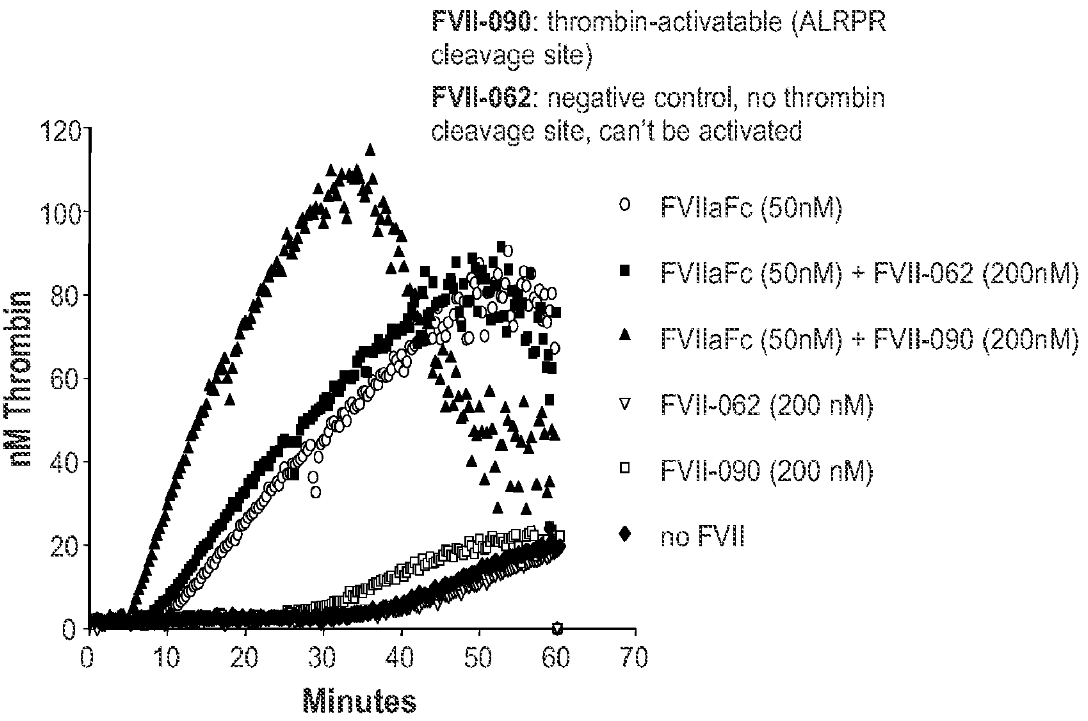
FIG. 34 shows the results of a thrombin generation assay using the FVII-062 and -090 constructs. FVII-062 is a negative control which lacks a thrombin cleavage site, so the construct cannot be activated. FVII-090 contains the ALRPR cleavage site and so is activatable by thrombin.

Thrombin generation assays were used to measure activity of activatable variant FVII-090. A thrombin generation assays in FVIII-deficient platelet-rich plasma was performed as previously described, but replacing clotting factors and platelets with FVIII-deficient platelet-rich plasma. The results depicted in FIG. 34 are from an assay in which thrombin generation was activated with 50 nM of FVIIaFc. As shown in FIG. 34, thrombin is generated by 50 nM of FVIIaFc. The addition of 200 nM FVII-090 (not FVII-062, the negative control) to 50 nM of FVIIaFc results in a significant increase in thrombin generation, suggesting that FVI-090 becomes activated by thrombin generated by FVIIaFc. FVII-090 in the absence of any FVIIaFc activation also shows increased thrombin generation relative to FVII-062 in the absence of activation. This could be caused by activation of FVII-090 from small amounts of thrombin generated by residual levels of tissue factor or contact pathway activation.

Example 22. A High Specific Activity Factor VII Activatable Construct

To make the high specific activity version of Factor VII, FVII-100, amino acids 311 to 322 of the FVII mature sequence (LQQSRKVGDSPN, corresponding to the 170-loop) from FVII-090, were replaced with amino acids EASYPGK from the 170-loop of trypsin. This substitution has been shown to confer high specific activity.

An additional high specific activity version of Factor VII, FVII-115, was constructed. In this version, the 170 loop is wild type, but there are three point mutations in the heavy chain of FVII, V158D, E296V and M298Q. FVII-100 and FVII-115 are illustrated in FIG. 41.

In a soluble tissue factor assay, the specific activity of FVII-011(wild type FVIIaFc) is 10,000 IU/mg. FVII-090 has a specific activity of 0.32 IU/mg, FVII-100 has a specific activity of 0.25 IU/mg, and FVII-115 has a specific activity of 14 IU/mg. Thus, each of the activatable forms (prior to activation by the appropriate enzyme) is essentially inactive in this assay.

In the context of activated FVII, such high specific activity variants have the potential to be more efficacious, but also to be more susceptible to inhibition by proteins such as antithrombin. This inhibition depends on FVIIa being active; therefore, high specific activity variants which are activatable (dosed as nonactive proteins) should be more resistant to antithrombin inhibition while having the potential to have high specific activity once activated at the site of injury.

Figure 35:
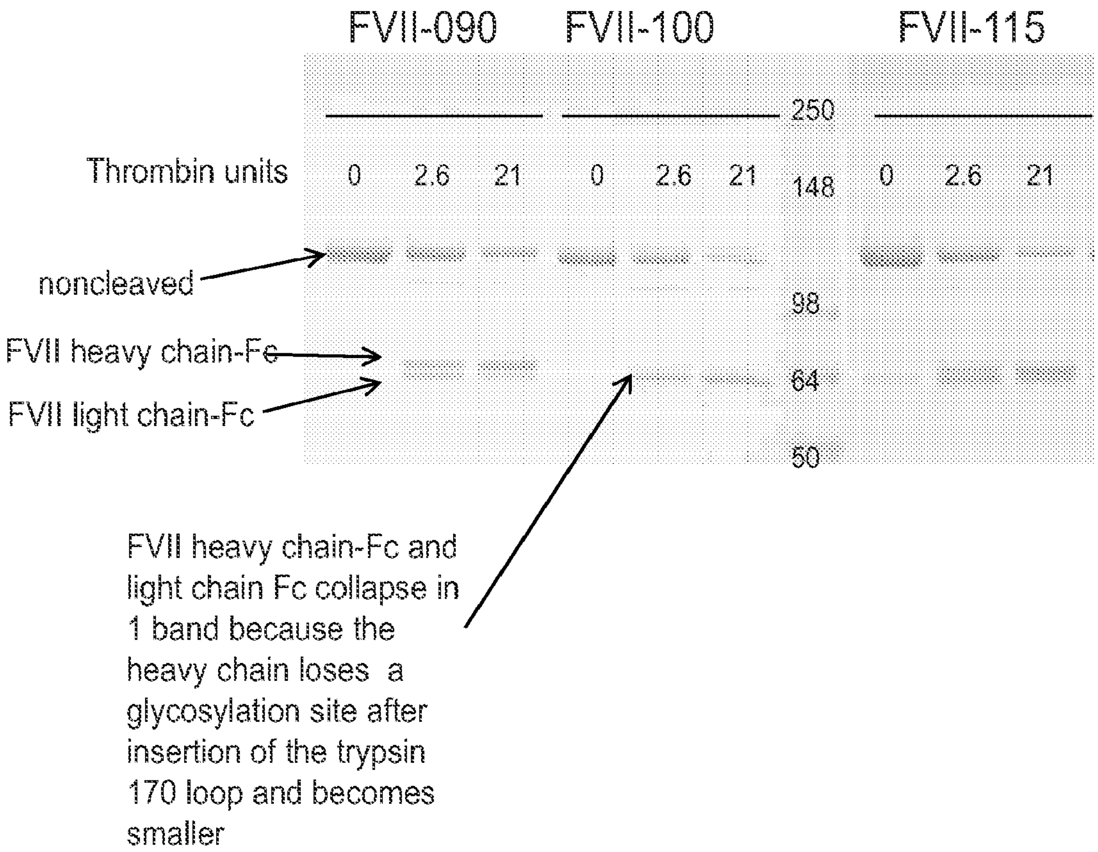
FIG. 35 illustrates the cleavage of high specific activity FVII variants. FVII heavy chain-Fc and light chain Fc collapse in 1 band because the heavy chain loses a glycosylation site after insertion of the trypsin 170 loop and becomes smaller.

The cleavage of purified FVII-090 and FVII-100 and 115 (high specific activity variants) by thrombin was tested as previously described. The results are shown in FIG. 35. SDS PAGE analysis showed how the 3 proteins were cleaved by thrombin with comparable efficiency. For FVII-100, FVII heavy chain-Fc and light chain Fc collapse in 1 band because a glycosylation site is removed from the heavy chain after insertion of the trypsin 170 loop, reducing the mass of the FVII HC-Fc band which therefore migrates faster on the gel and comigrates with the FVII LC-Fc band. Thrombin generation assays were used to measure activity of activatable variant FVII-090 and high specific activity variant FVII-100. As set forth previously herein, thrombin generation was tested in a reconstituted system with human platelets, Factor X, Factor V, prothrombin, antithrombin and tissue-factor pathway inhibitor. Activity was measured with or without 5 nM thrombin activation.

Figure 36:
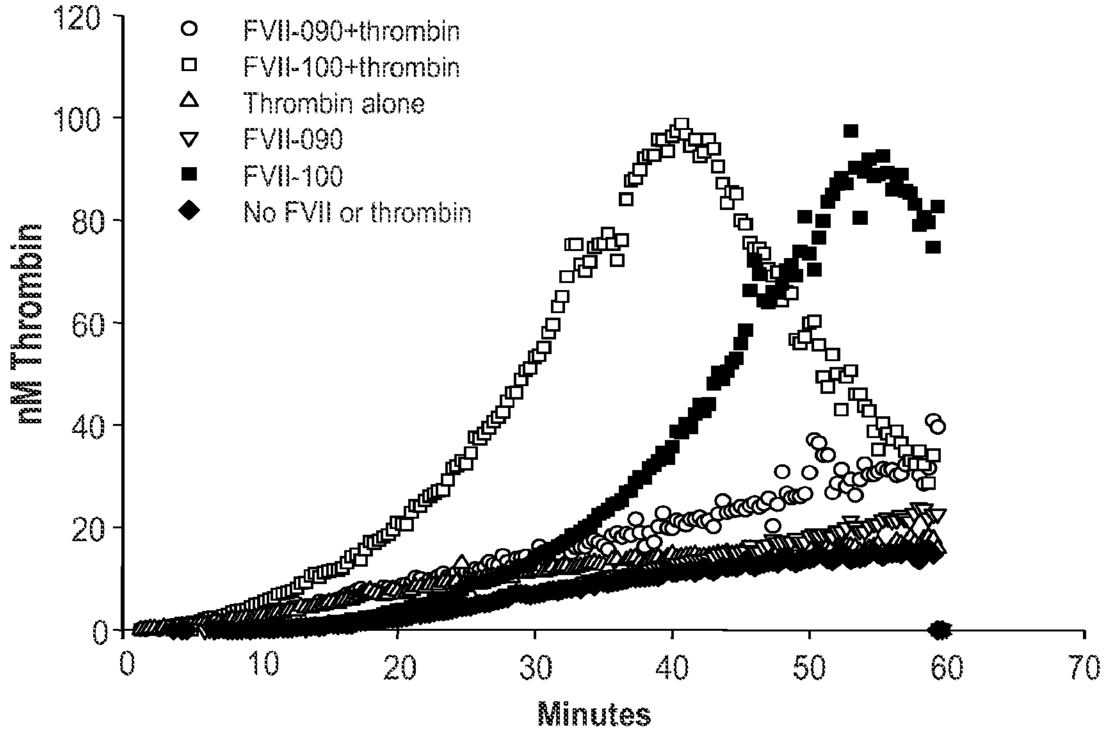
FIG. 36 illustrates the results of a thrombin generation assay using FVII-090 and FVII-100.
Figure 37:
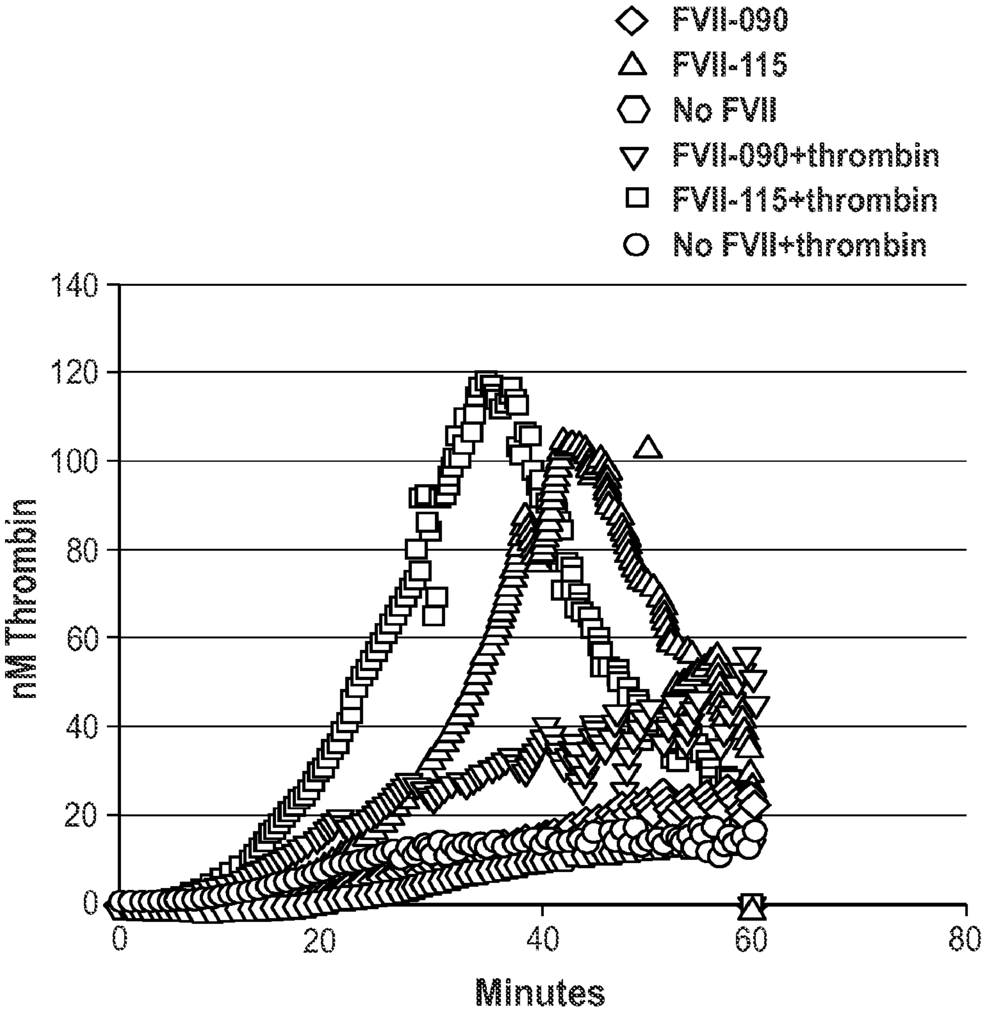
FIG. 37 illustrates the results of a thrombin generation assay using FVII-090 and FVII-115.

As shown in FIG. 36, activity of FVII-090 is enhanced in the presence of thrombin, suggesting activation of FVII-090 by thrombin. However, activity is significantly increased in the context of the high specific activity variant FVII-100 with thrombin activation. High activity with longer initiation time for FVII-100 in the absence of thrombin, suggests that residual levels of tissue factor, thrombin or contact pathway activation can generate enough thrombin to activate FVII-100 without exogenous addition of thrombin. FIG. 37 shows that similar results were obtained for the other high specific activity variant, FVII-115.

Example 23. Confirmation of Activity of Activatable Variants Using Various Assays In this example, chromogenic assays were used to measure FVII activity. One of the assays used measures the amidolytic activity of FVIIaFc by measuring the cleavage of a chromogenic substrate by FVIIa. Another of these measures the FX activation activity by measuring the ability of FVIIa to activate FX, as determined by measuring levels of a chromogenic substrate that is cleaved by activated FX (FXa).

In amidolytic assays, the chromogenic substrate Chromozyme t-PA was used. FVIIa cleaves this substrate in a dose dependent manner. The substrate is also cleaved by thrombin, but the cleavage by thrombin can be inhibited by hirudin (data not shown).

Figure 38:
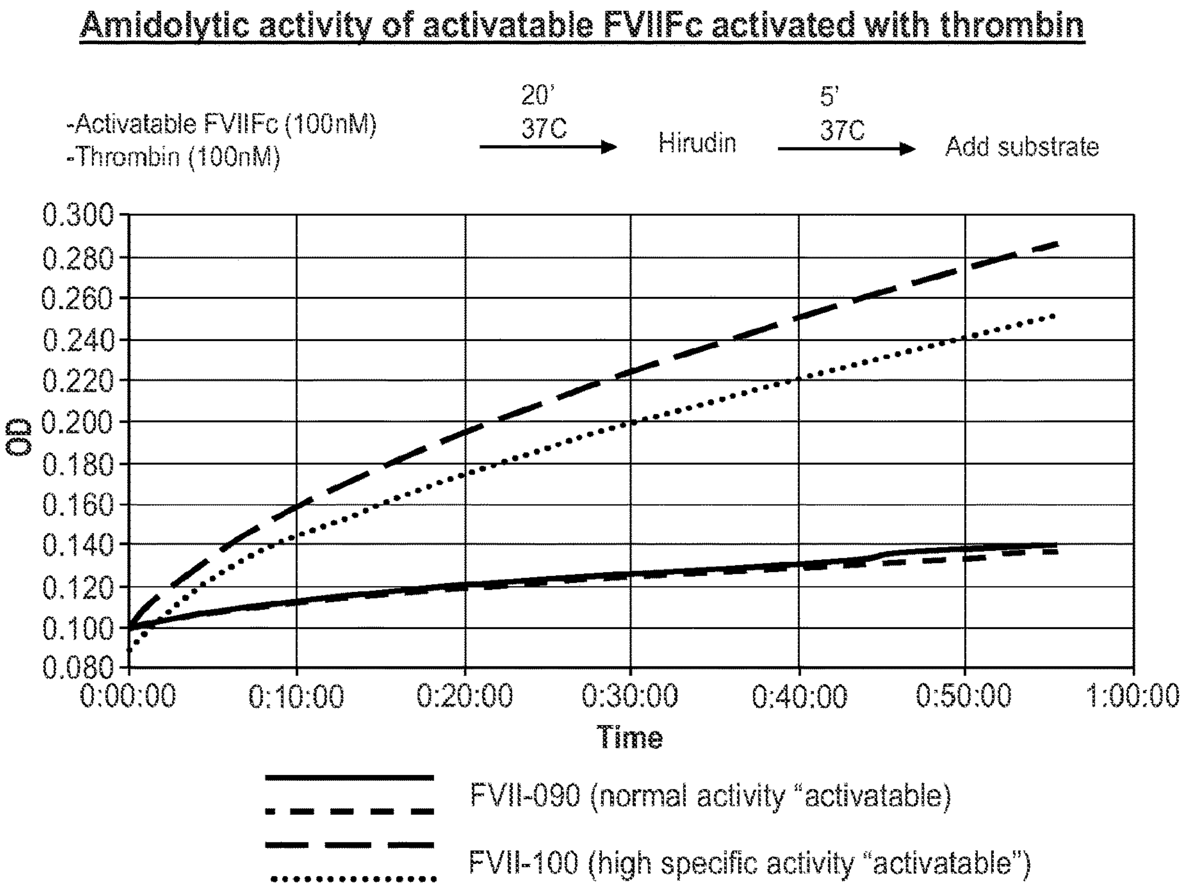
FIG. 38 illustrates amidolytic activity of activatable FVIIFC activated with thrombin. Amidolytic activity of the activatable variants can be measured following thrombin activation and there is increased amidolytic activity for the high specific activity variants as compared to FVII-090. In these assays, after activation of the activatable molecule by thrombin, hirudin is added to inhibit thrombin cleavage of the chromogenic substrate. In this manner, the thrombin does not interfere with the ability to detect FVIIa activity.

As shown in FIG. 38, amidolytic activity of the activatable variants can be measured following thrombin activation and there is increased amidolytic activity for the high specific activity variants as compared to FVII-090. In these assays, after activation of the activatable molecule by thrombin, hirudin is added to inhibit thrombin cleavage of the chromogenic substrate. In this manner, the thrombin does not interfere with the ability to detect FVIIa activity.

Figure 39:
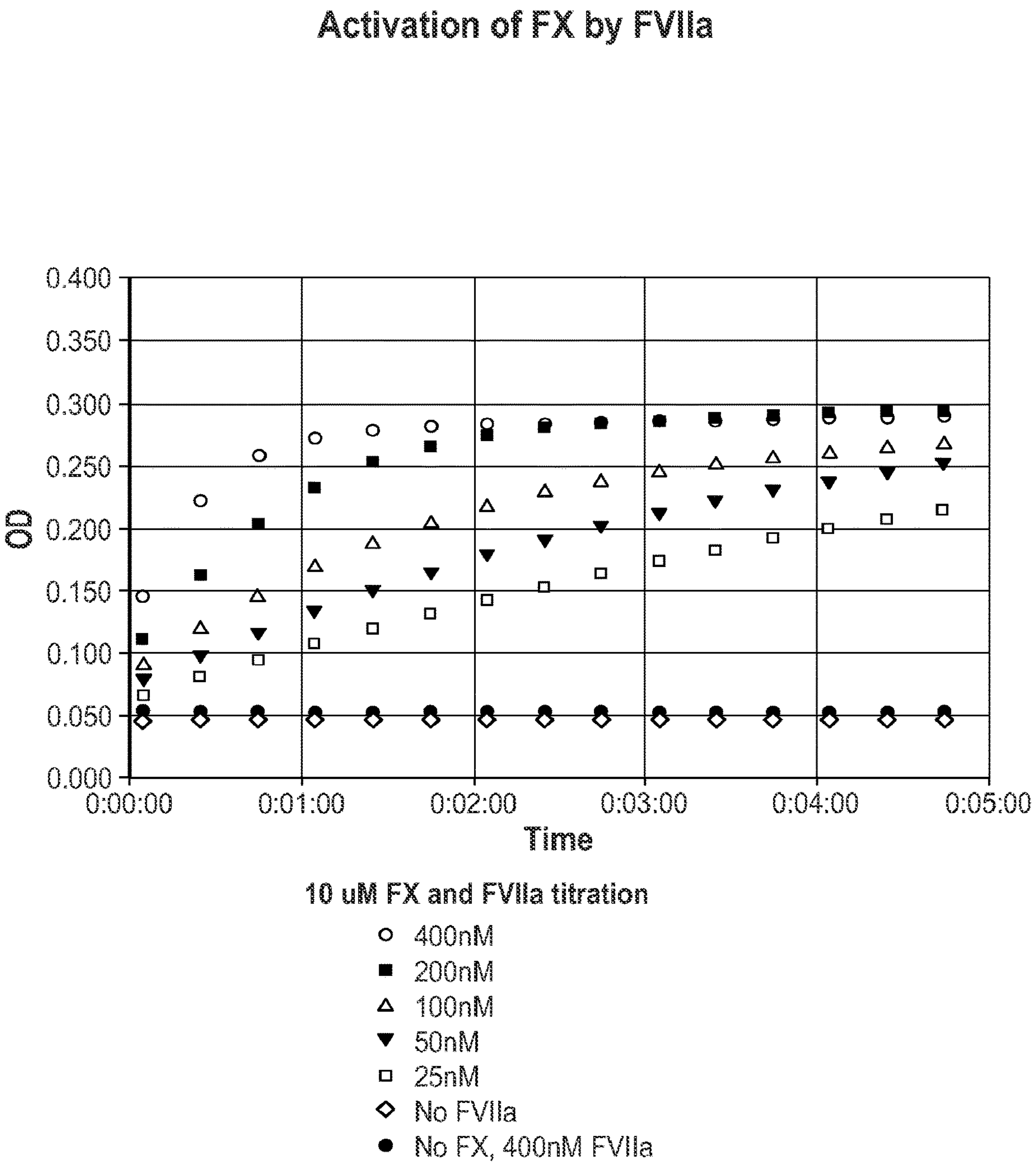
FIG. 39 illustrates the results of an assay measuring activation of FX by FVIIa using substrate S2765, which is not cleaved by FVIIa. In this assay, 10 uM of FX was incubated with FVIIaFc for 15 minutes at 37° C. The reaction was quenched with EDTA and substrate was added.

The activation of FX by FVIIa is also enhanced in the high specific activity FVII activatable variants. To measure activation of FX by FVIIa, substrate S2765 was used. This chromogenic substrate is also recognized by FX. In the assay, 10 uM of FX was incubated with FVIIaFc for 15 minutes and the reaction was quenched with EDTA. FIG. 39 shows the results of the control experiment which demonstrates that FX activation by FVIIaFc can be detected.

Figure 40:
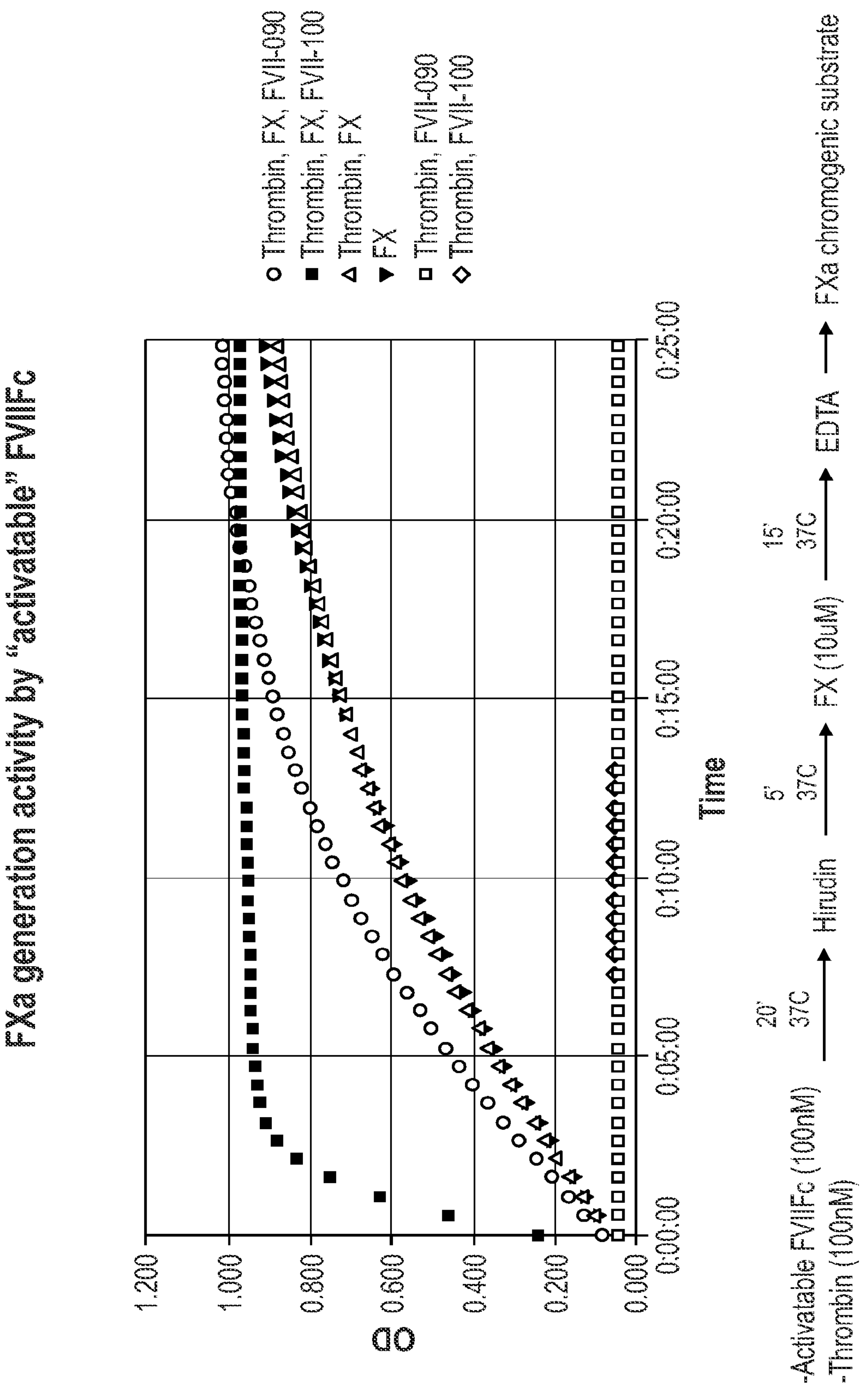
FIG. 40 shows FXa generation activity by "activatable FVIIFc." The experiment shown in FIG. 40 shows that there is an increase in FX activation activity for the high specific activity variants. In this experiment, FVIIFc (100 nM) was activated with thrombin (100 nM) Hirudin was added to inhibit the thrombin. FX (10 uM) was added, followed by EDTA to inhibit the reaction. The activity of FX was measured by detecting the FXa substrate.

The experiment shown in FIG. 40 shows that there is an increase in FX activation activity for the high specific activity activatable variant FVII-100. In this experiment, FVIIFc (100 nM) was activated with thrombin (100 nM) for 20 minutes at 37 C. Hirudin was added to inhibit the thrombin. FX (10 uM) was added and incubated for 15 minutes at 37 C, followed by EDTA to inhibit the reaction. S2765 substrate was added and FXa generation was detected by monitoring substrate cleavage.

Example 24. Monomeric Fc Molecules can Also be Synthesized in Activatable Form Three monomeric constructs were made as shown in FIG. 41. In FVII-118, an ALRPR cleavage site was inserted between the light chain and heavy chain. In FVII-119, the sequence GGGGS-ALRPR was inserted between the light chain and heavy chain. For FVII-127, the construct was made like FVII-118, but with the same high specific activity mutation used in FVII-100. The specific activity of the non-activated purified forms of these constructs was tested in a soluble tissue factor assay and compared to FVII-011 (wild type FVIIaFc which had an activity of 10,000 IU/mg). FVII-118 had an activity of 4.5 IU/mg and FVII-127 had an activity of 1.8 IU/mg, demonstrating that these molecules had essentially no activity in their activatable form.

Figure 42:
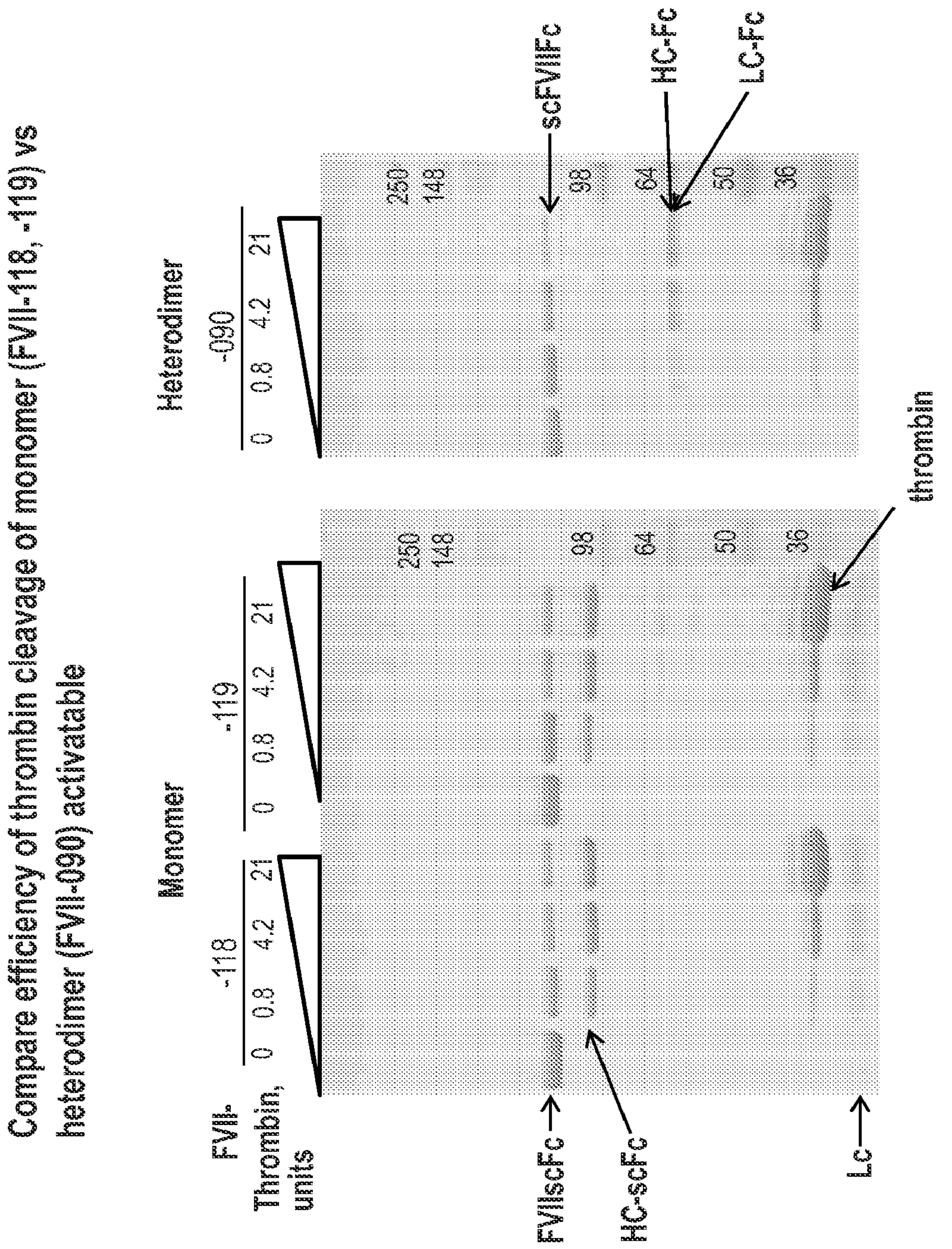
FIG. 42 illustrates the efficiency of thrombin cleavage of activatable constructs, specifically monomeric (FVII-118 and -119) as compared to the heterodimeric (FVII-090).

Thrombin cleavage reactions of FVII-118, FVII-119 and FVII-090 followed by SDS PAGE analysis were performed as previously described. As shown in FIG. 42, the cleavage site in an activatable construct can be cleaved in the context of both the monomer and heterodimer Fc molecules. In the figure, the decrease in the intensity of the nonactivated FVIIFc band with increasing thrombin concentration is similar for the FVII-118, FVII-119, and FVII-090 constructs.

Figure 43:
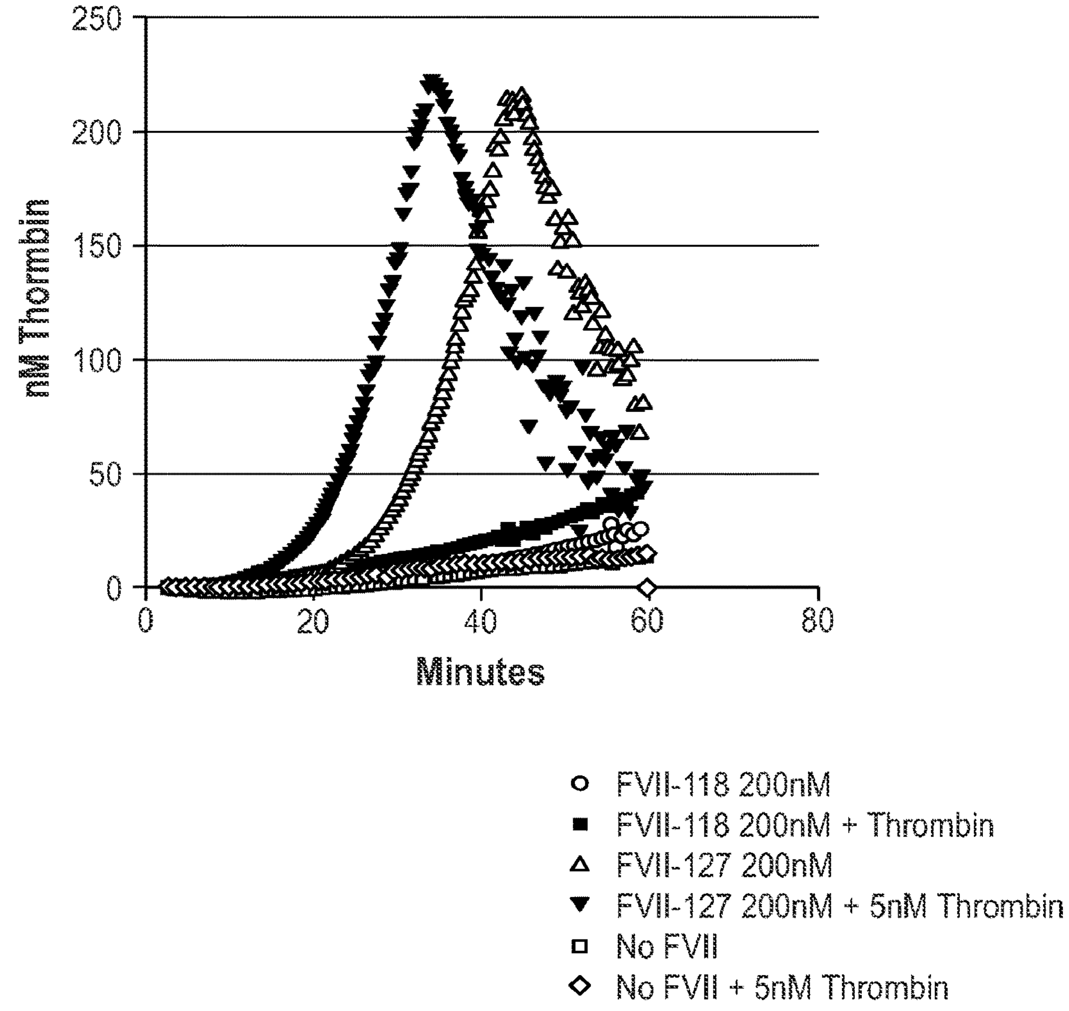
FIG. 43 illustrates the results of a thrombin generation assay to compare wild type activatable FVIIFc (FVII-118) to the high specific activity variant (FVII-127).

Another activatable monomeric construct, FVII-127, was made and tested. FVII-127 has the backbone of FVII-118, but the same 170 loop substitution used in FVII-100 to confer high specific activity. As shown in FIG. 43, the activity of FVII-127 is significantly increased as compared to FVII-118 lacking the high specific activity amino acid substitution. High activity with longer initiation time for FVII-127 in the absence of thrombin, suggests that residual levels of tissue factor, thrombin or contact pathway activation can generate enough thrombin to activate FVII-127 without exogenous addition of thrombin. FVII-127 activity is accelerated by thrombin.

Example 25. FVIIaFc Variants Targeted to the Active Form of GPIIbIIIa

Figure 29:
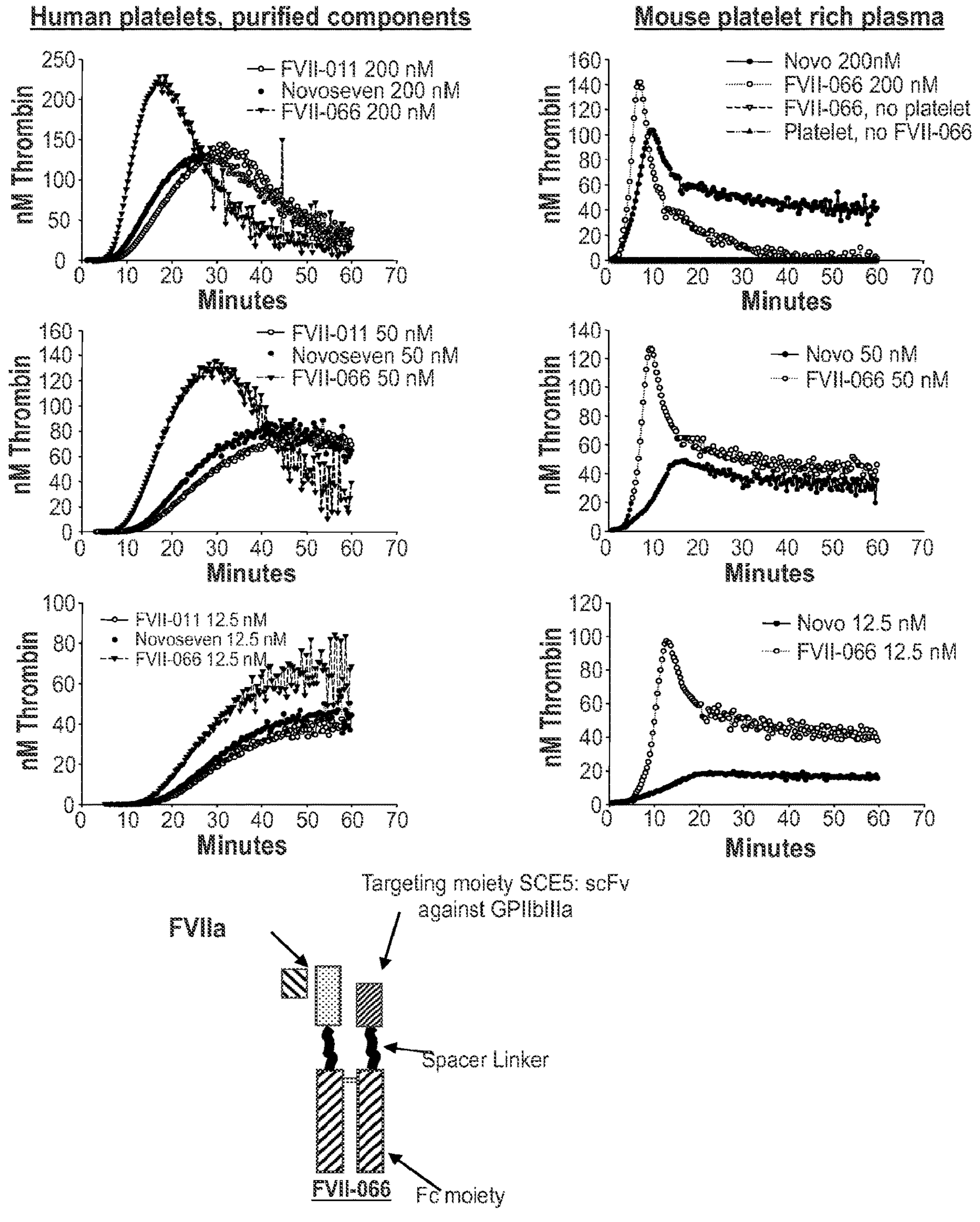
FIG. 29 shows that an FVIIaFc variant targeted to active form of GPIIbIIIa shows an increased rate of thrombin generation.
Figure 44A:
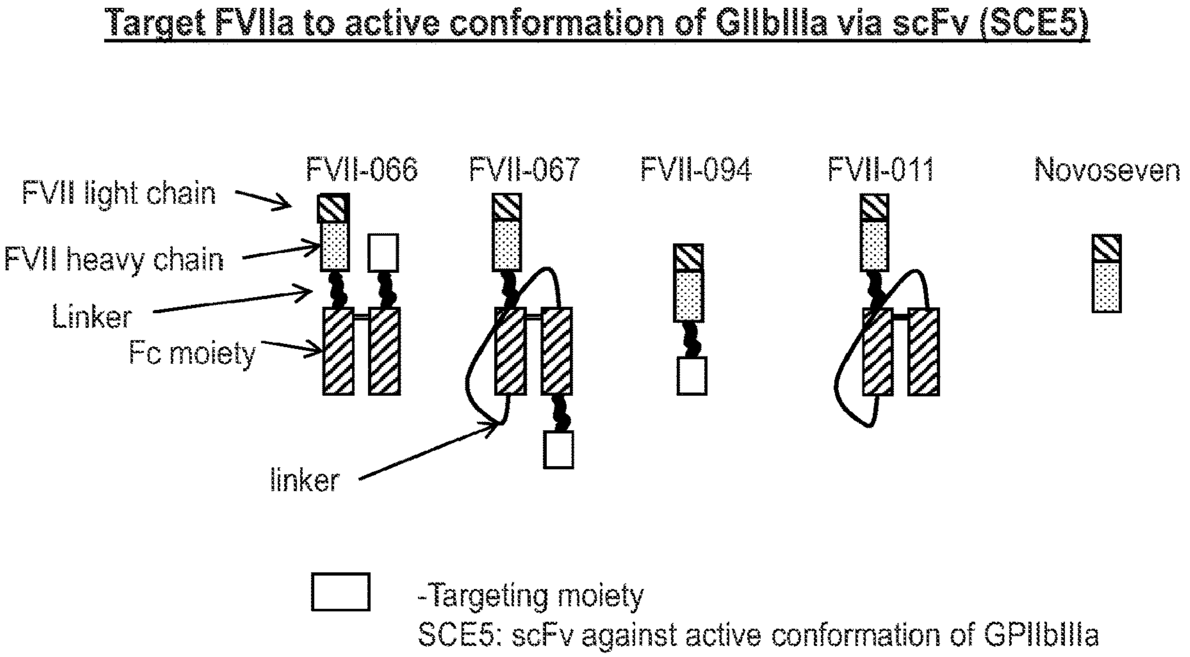
FIG. 44A illustrates several targeted constructs. In this instance, an SCE5 scFv which binds to the active conformation of GPIIbIIIa was included at various sites in the construct.
Figure 44B:
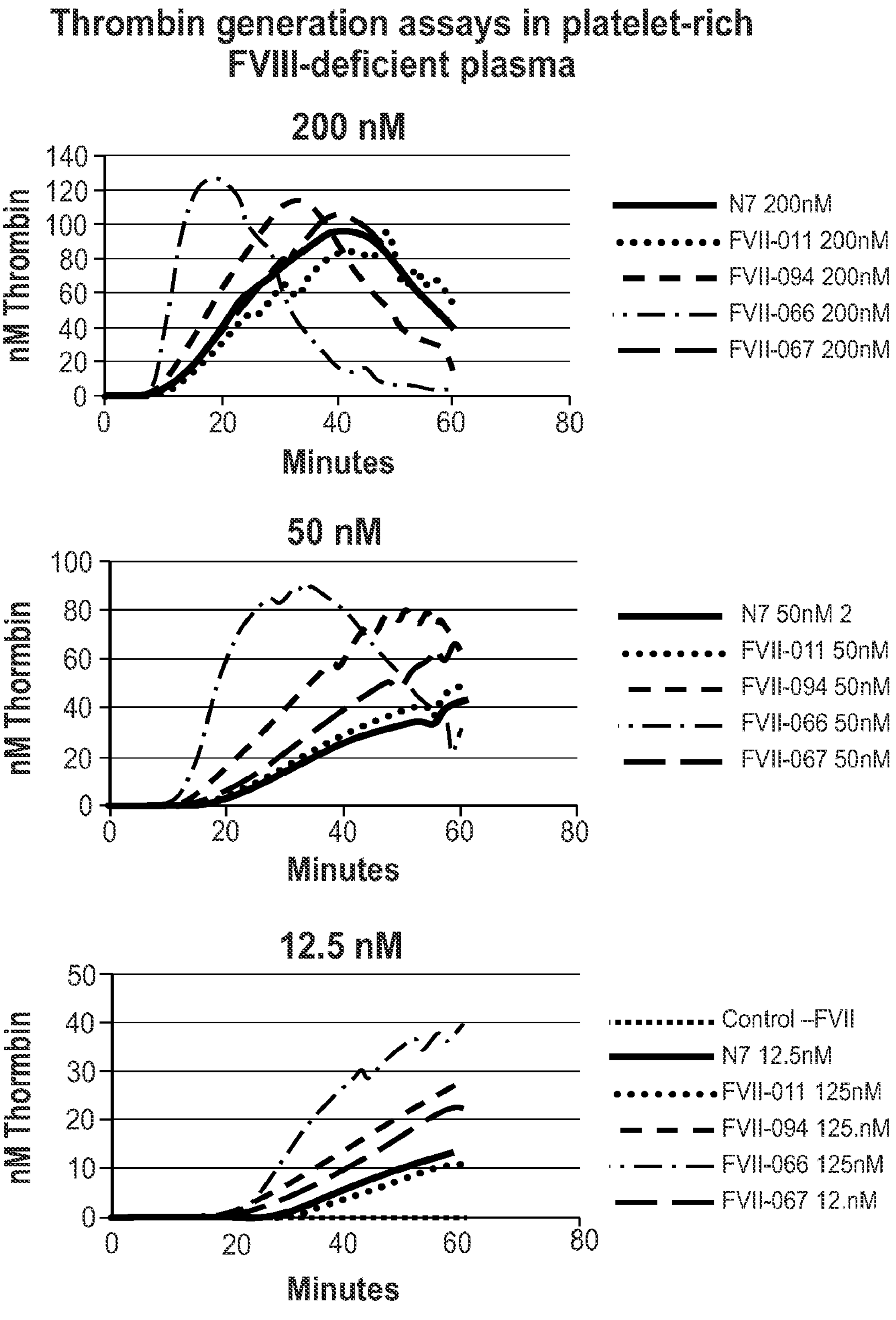
FIG. 44B illustrates the results of thrombin generation assays in platelet-rich FVIII-deficient plasma using these constructs. N7 is the NOVOSEVEN® control.
Figure 44C:
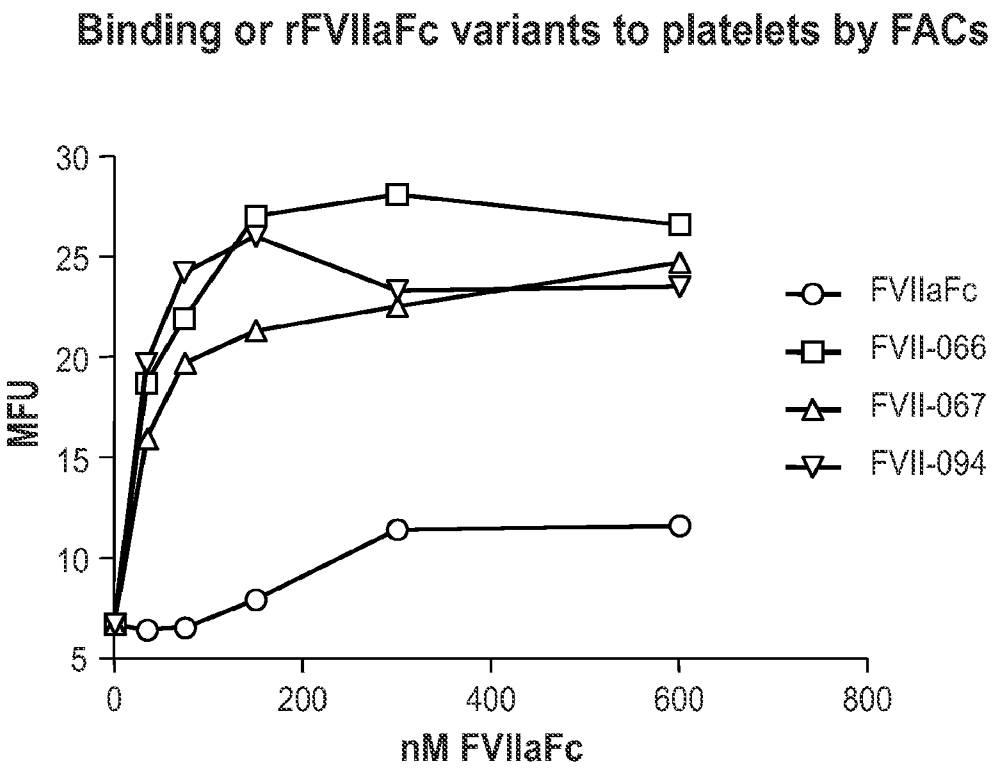
FIG. 44C illustrates the binding of recombinant FVIIaFc variants to platelets by FACs.

In this example the constructs illustrated in FIG. 44A were cloned, transiently expressed, purified and activated as previously described. FVII-066 was cotransfected with PC5 to fully process the cscFc linker, described in the protein sequence, connecting the first Fc moiety to the platelet targeting moiety. These constructs employed the targeting moiety SCE5, a scFv against the active conformation of GPIIbIIIa. SCE5 has been shown to crossreact with mouse and human receptor. The SCE5 targeting moiety was placed at the N-terminus (FVII-066) or C terminus (FVII-067) of the second Fc moiety of FVIIaFc. In addition, the SCE5 was placed at the C-terminus of FVIIa (FVII-094). FVIIaFc (FVII-011) and NOVOSEVEN® were used as controls. As shown in FIG. 44B, these proteins were tested by thrombin generation assays in FVIII-deficient human plasma as previously described. These experiments revealed increased rates of thrombin generation for all the proteins containing the SCE5 targeting moiety relative to the controls. The highest rates of thrombin generation were observed for FVII-066, followed by FVII-094 and FVII-067, suggesting that the placement of the SCE5 targeting moiety can have a significant effect on the activity of the protein. Binding of these proteins to activated human platelets was determined by FACS assays as previously described (FIG. 44C). All the FVIIa proteins containing the SCE5 targeting moiety showed increased binding to platelets relative to the FVIIaFc control. This shows that attaching the SCE5 targeting moiety to FVIIa can increase its affinity from platelets. Since the SCE5 targeting moiety has been shown to interact with the mouse GPIIbIIIa receptor, FVII-066 was tested in thrombin generation assays using mouse FVIII-deficient platelet rich plasma, as well as in a reconstituted system using human purified components and platelets, as previously described (FIG. 29). We observed increased rates of thrombin generation for FVII-066 relative to the controls in both systems.

Figure 12A:
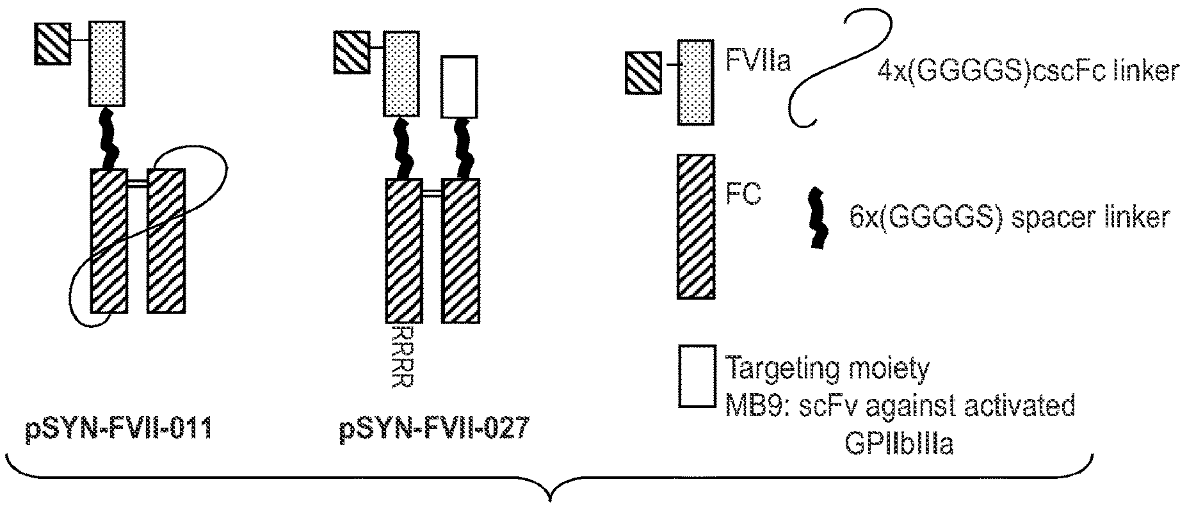
FIG. 12A shows schematics of FVII-011 and FVII-102.
Figure 12B:
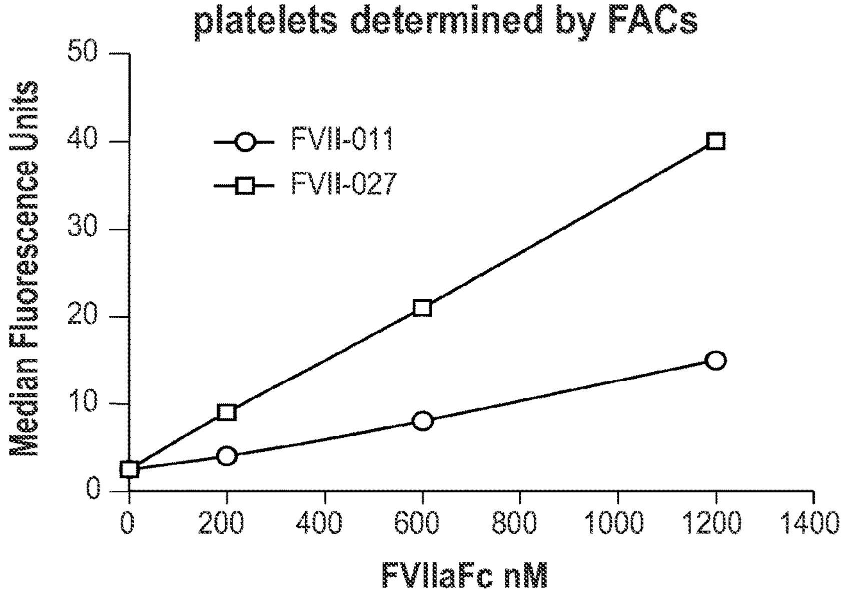
FIG. 12B shows binding of FVIII-011 and FVII-027 to activated platelets determined by FACS.
Figure 13A:
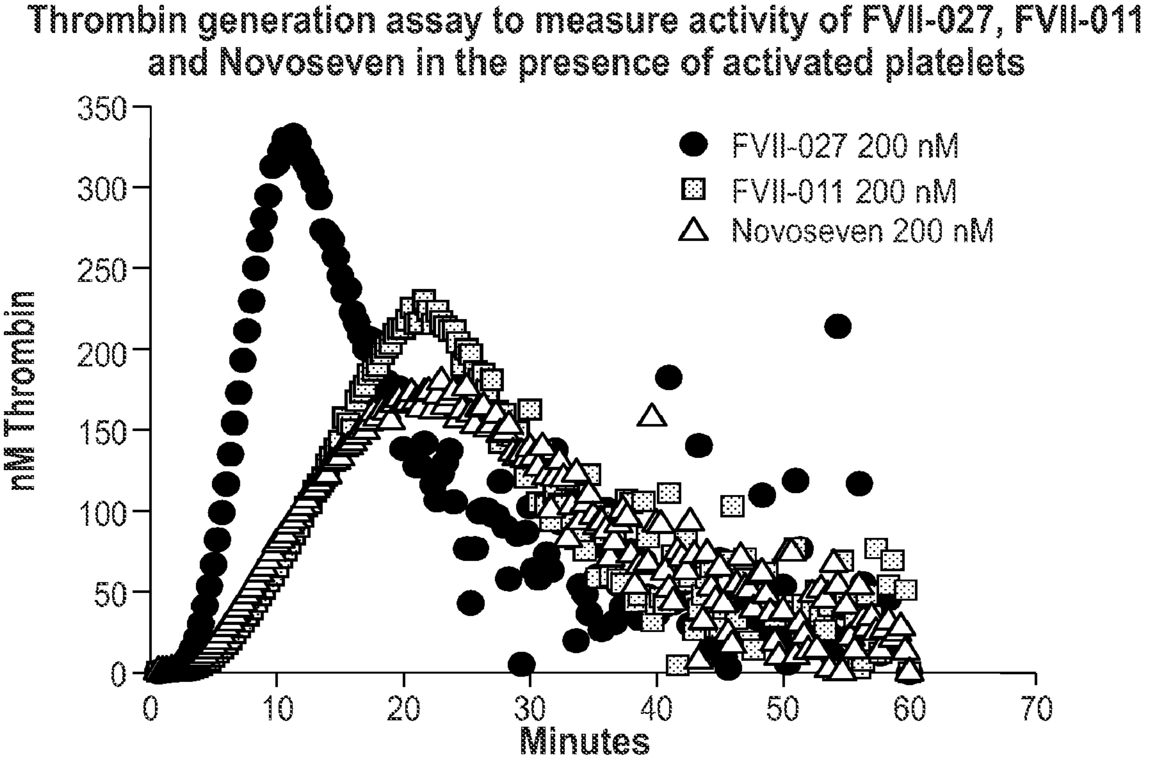
FIGS. 13A, 13B, 13C, and 13D show thrombin generation assays to measure activity of FVII-027, FVII-011 and NOVOSEVEN® in the presence of activated platelets.
Figure 13B:
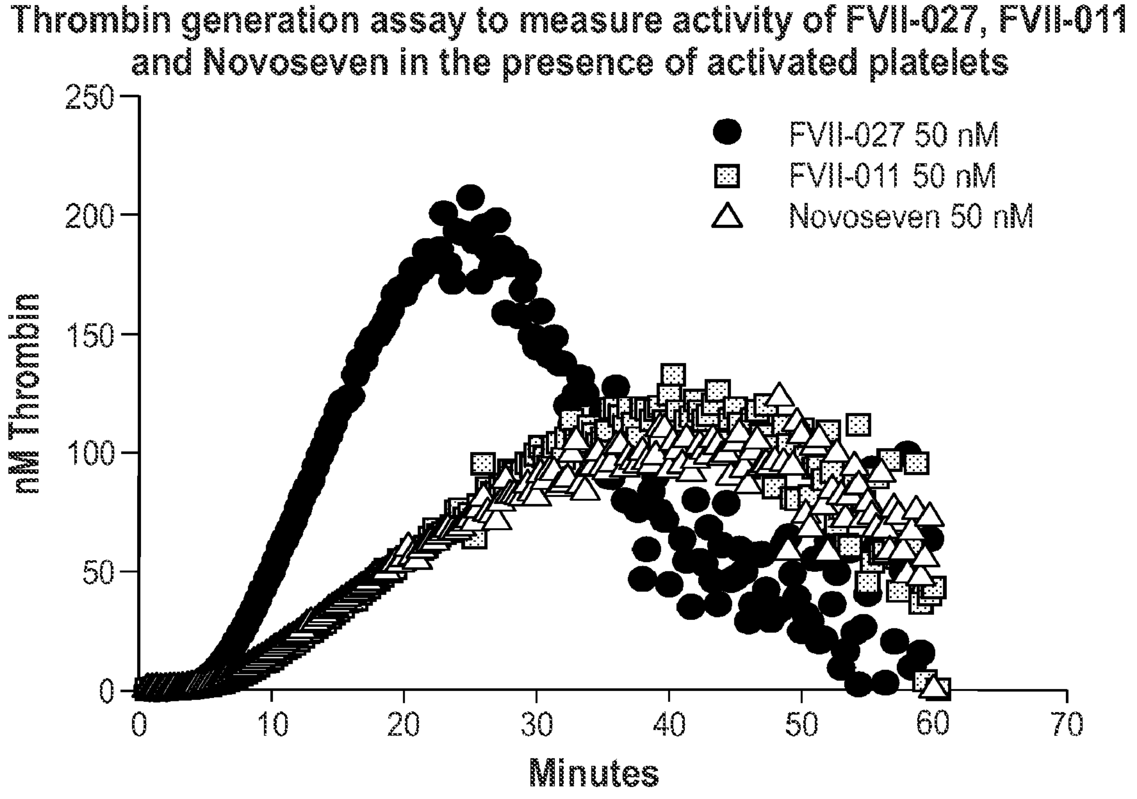
Figure 13C:
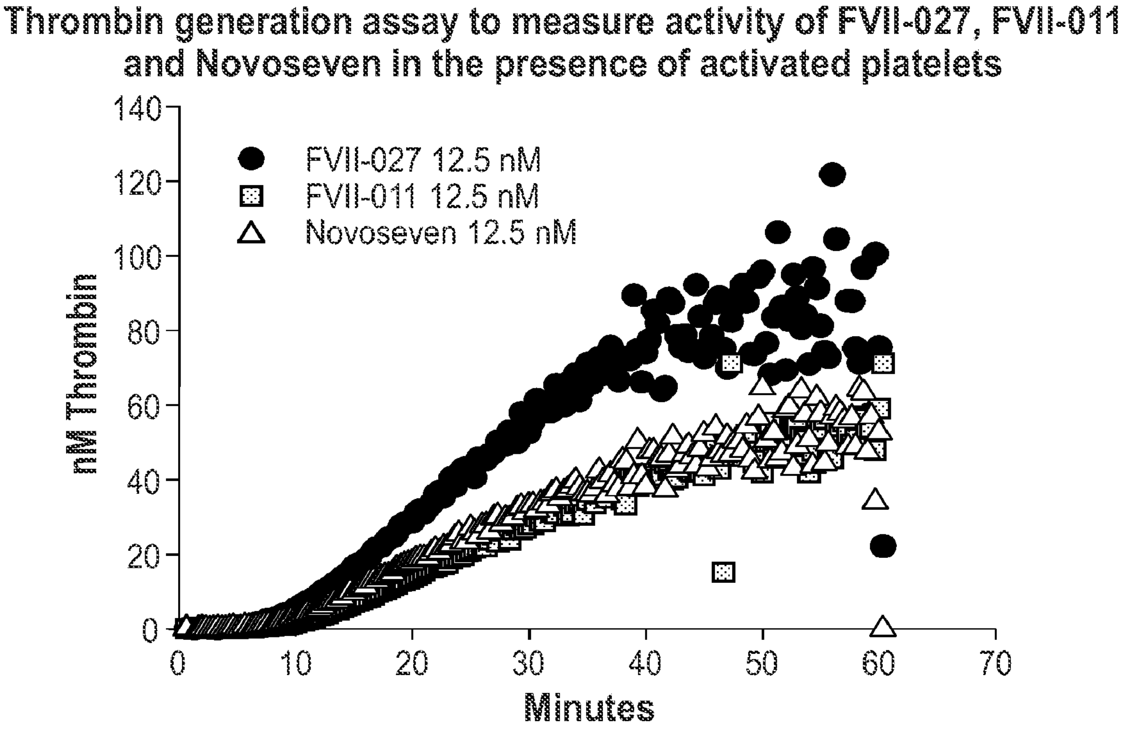
Figure 13D:
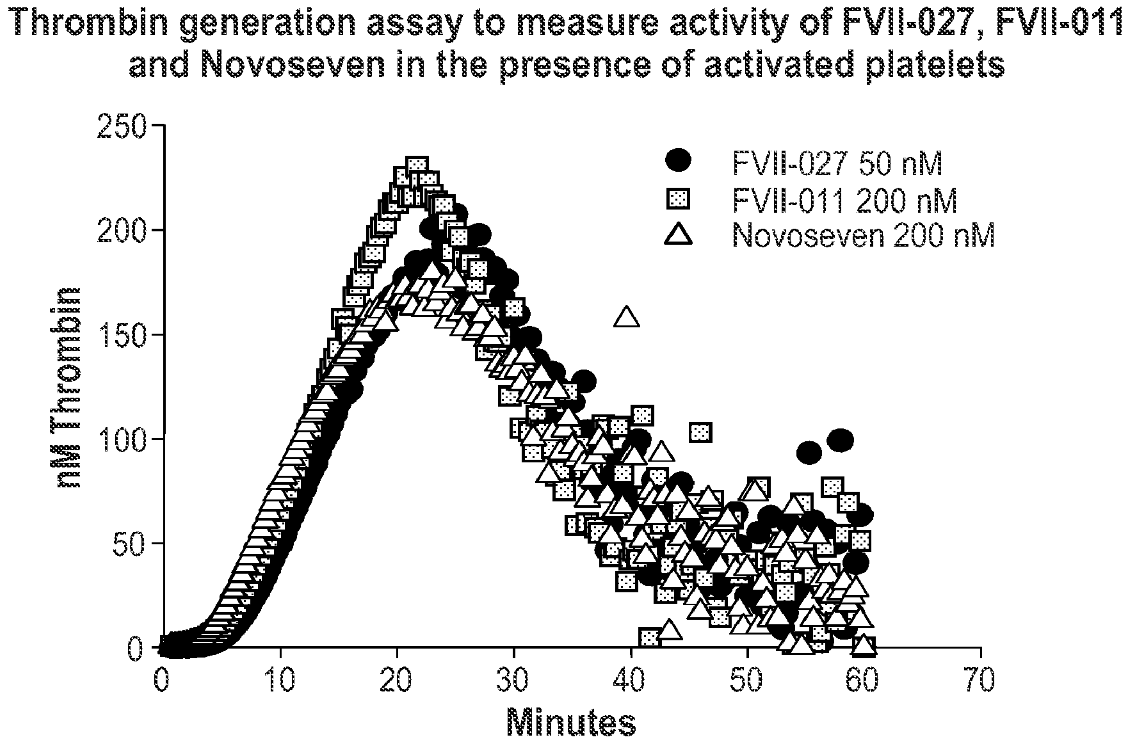
Figure 14A:
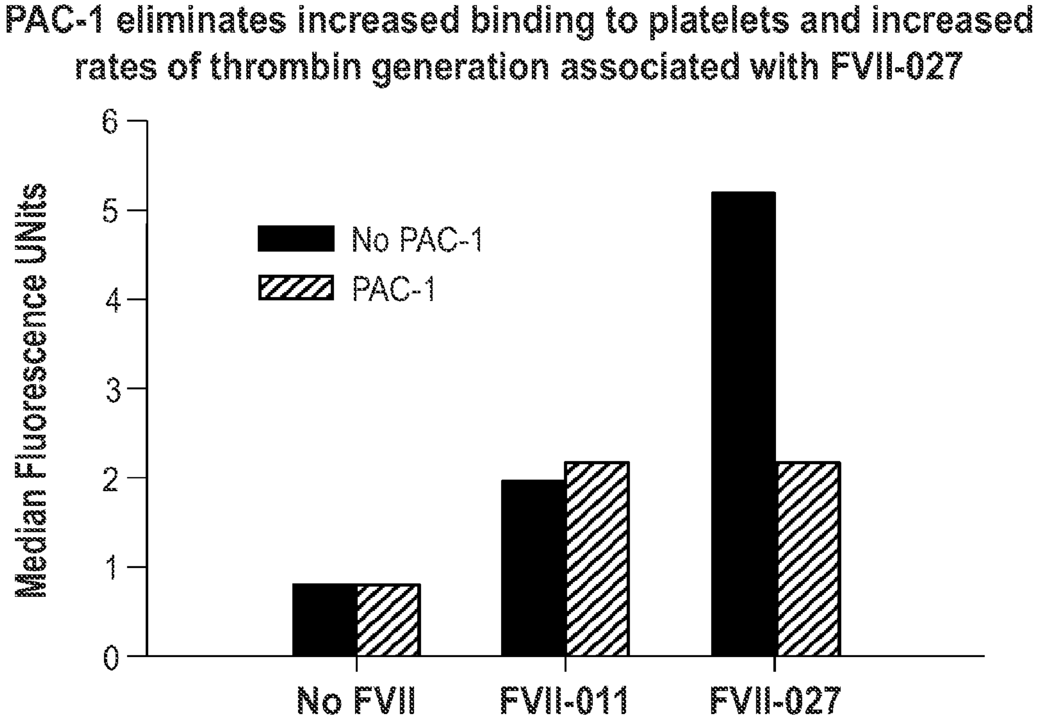
FIG. 14A shows that PAC-1 eliminates increased binding to platelets associated with FVII-027.
Figure 14B:
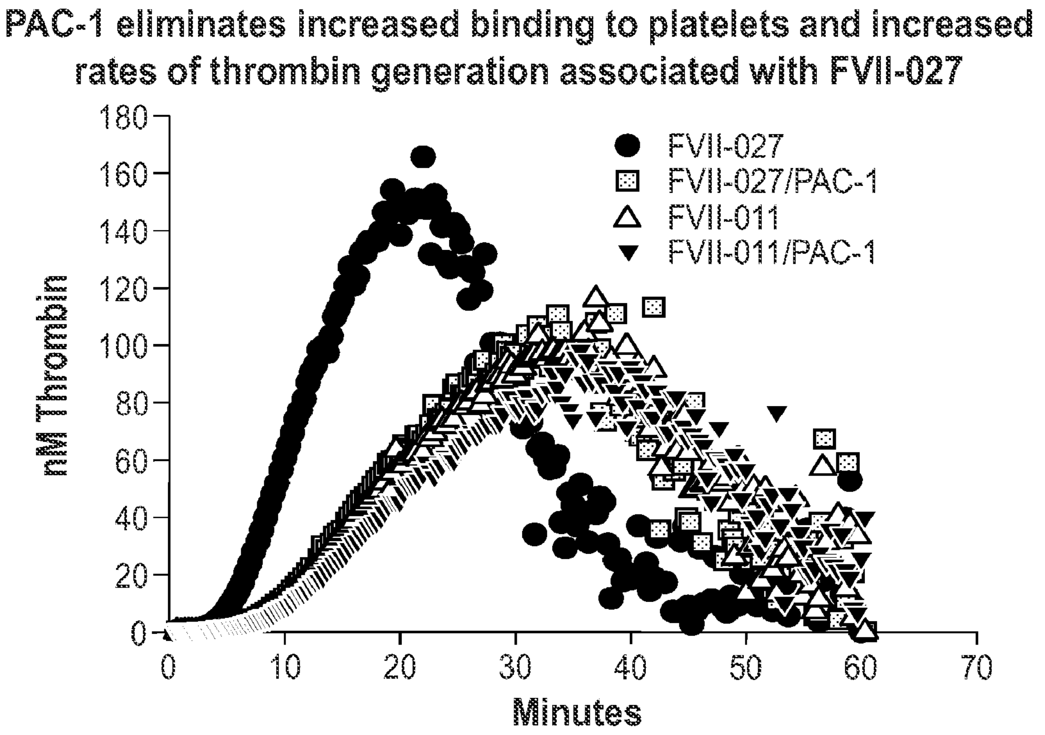
FIG. 14B shows that PAC-1 eliminates increased rates of thrombin generation associated with FVII-027.
Figure 15:
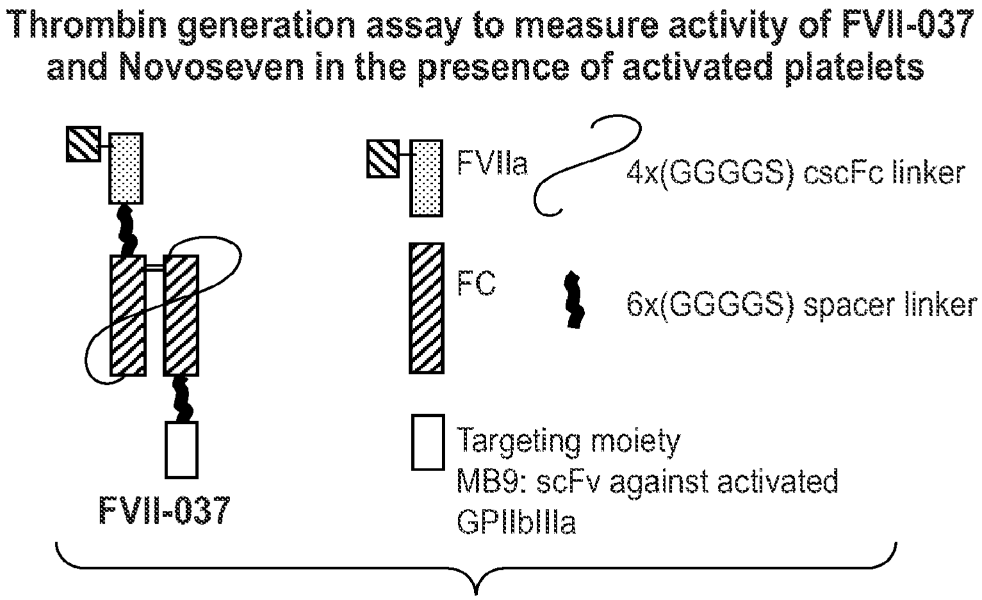
FIG. 15 shows constructs used in a thrombin generation assay to measure activity of FVII-037 and NOVOSEVEN® in the presence of activated platelets.

Example 26. Additional FVIIaFc Variants Targeted to the Active Form of GPIIbIIIa In this example, construct FVII-027 illustrated in FIG. 12A was cloned, expressed (with PC5 cotransfection to fully process the cscFc linker, described in the protein sequence, connecting the first Fc moiety to the platelet targeting moiety), purified and activated as previously described. This construct employs the targeting moiety MB9, a scFv that has been shown to bind to the active conformation of GPIIbIIIa. FACS assays were performed as previously described to assess binding to activated platelets, and FVII-027 was shown to bind to activated platelets with higher affinity than the FVII-011 control (FIG. 12B). Thrombin generation assays were performed with reconstituted purified human proteins and platelets as previously described (FIGS. 13A, 13B and 13C). FVII-027 showed increased rates of thrombin generation relative to the controls. FIG. 13D illustrates that FVII-027 has four times more activity than FVII-011 or NOVOSEVEN®, based on thrombin generation assays. FIGS. 14A and 14B illustrate that the enhanced platelet binding and thrombin generation activity of FVII-027 were abrogated by PAC1, an antibody that competes with MB9 for binding to the activated form of GPIIbIIIa, demonstrating the effects are mediated by the interaction of MB9 with the activated form of GPIIbIIIa. The MB9 targeting moiety was also placed at the C-terminus of the second Fc moiety of FVIIaFc to generate FVII-037 illustrated in FIG. 15.

Figure 16A:
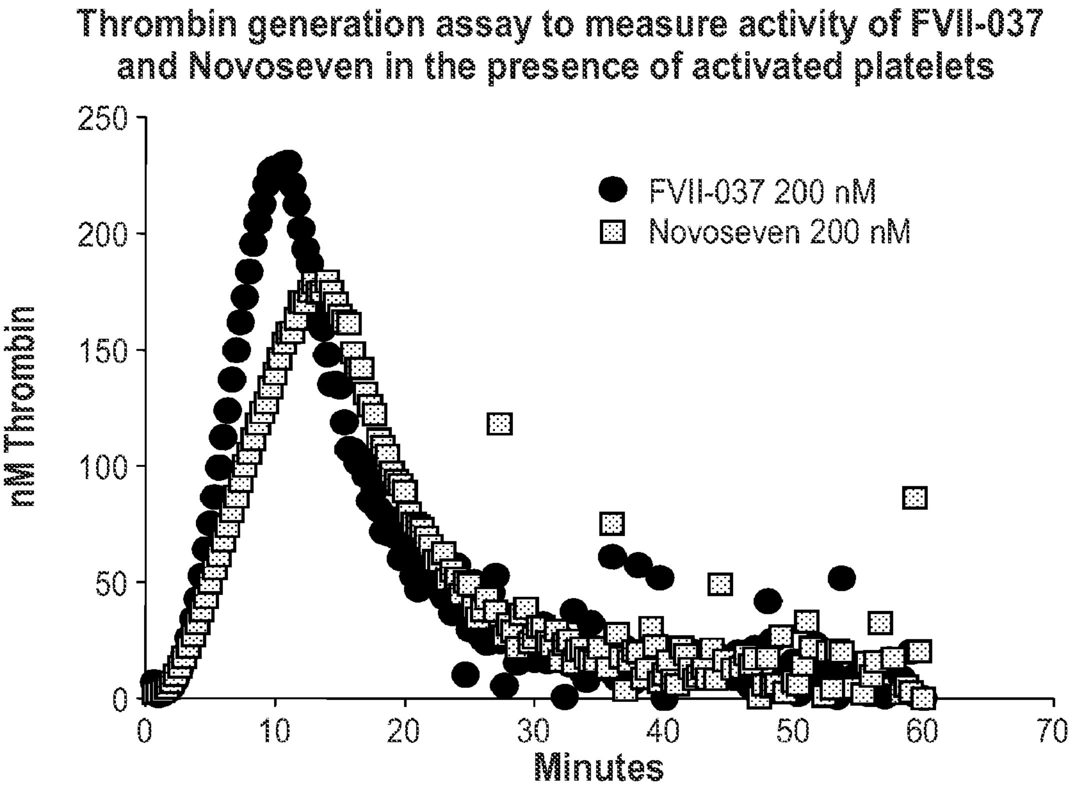
FIGS. 16A, 16B, and 16C show thrombin generation assays to measure activity of FVII-037 and NOVOSEVEN® in the presence of activated platelets.
Figure 16B:
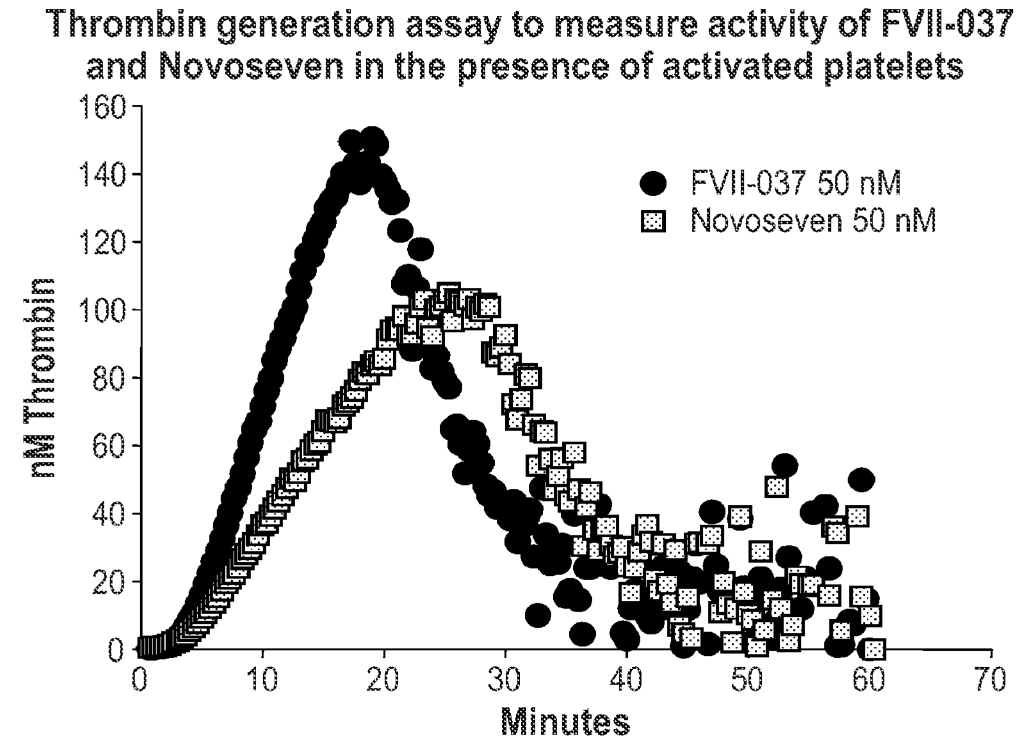
Figure 16C:
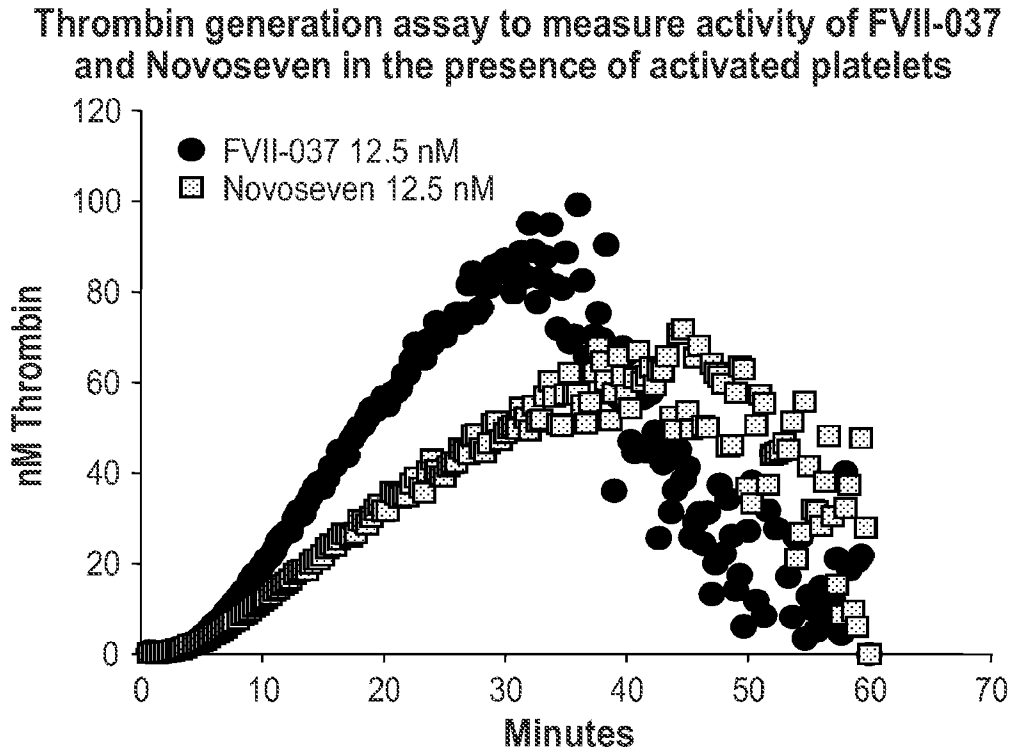
Figure 17:
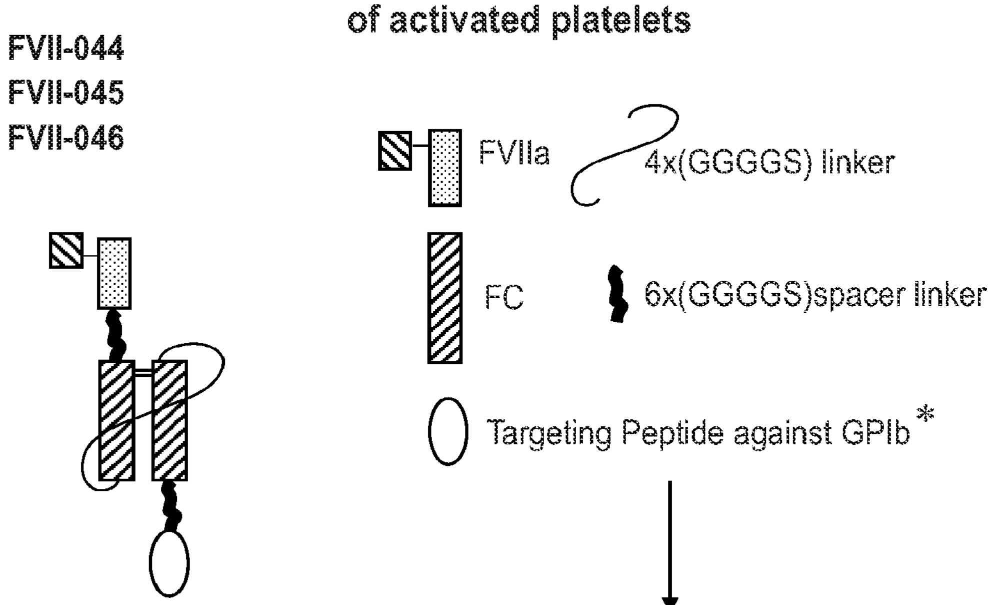
FIG. 17 shows the constructs used in the thrombin generation assay to measure activity of FVII-044, FVII-045, FVII-046, FVII-011 and NOVOSEVEN® in the presence of activated platelets shown in FIGS. 18A, 18B, 18C, and 18D.
Figure 18A:
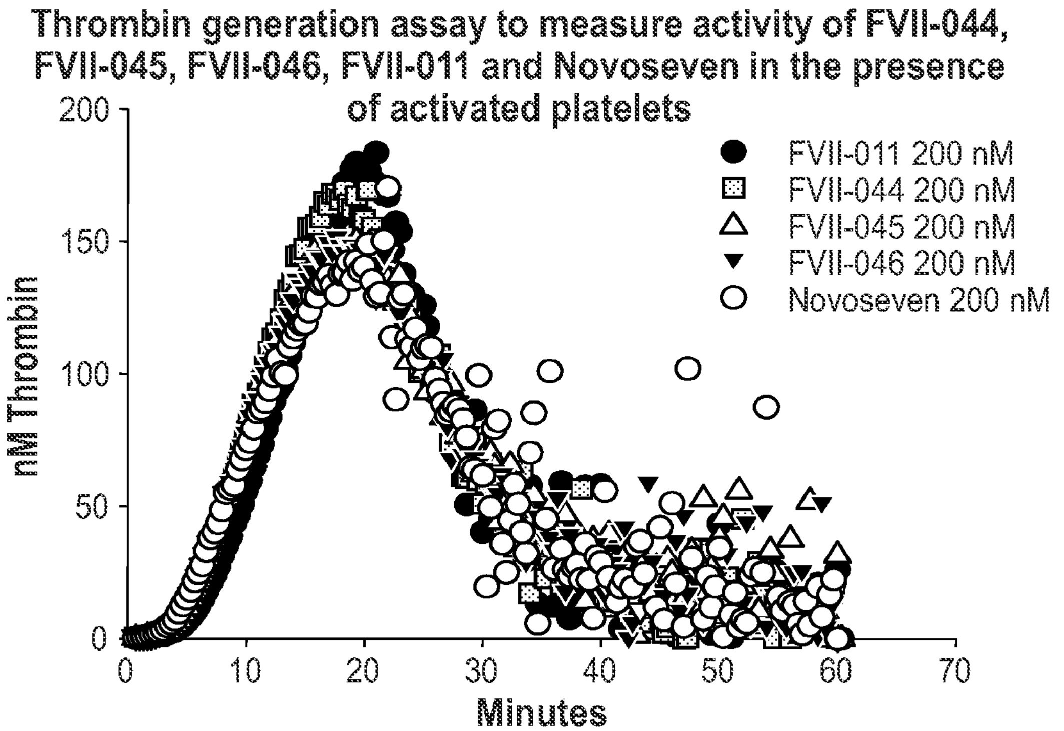
FIGS. 18A, 18B, 18C, and 18D show thrombin generation assays to measure activity of FVII-044, FVII-045, FVII-046, FVII-011 and NOVOSEVEN® in the presence of activated platelets.
Figure 18B:
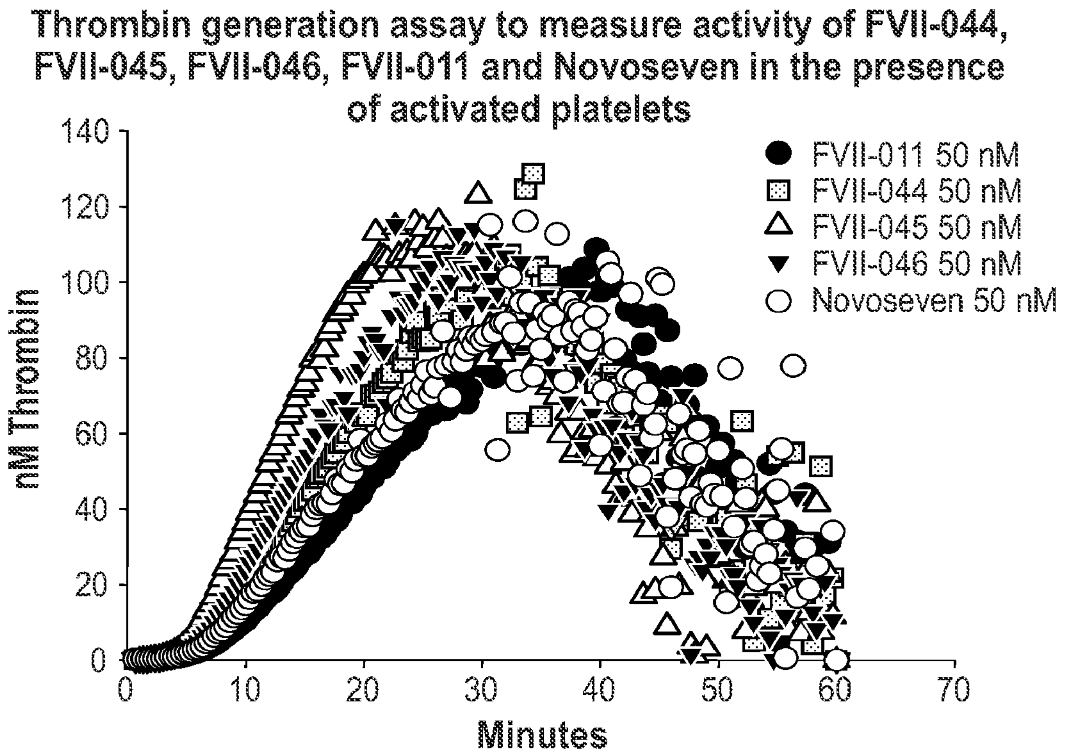
Figure 18C:
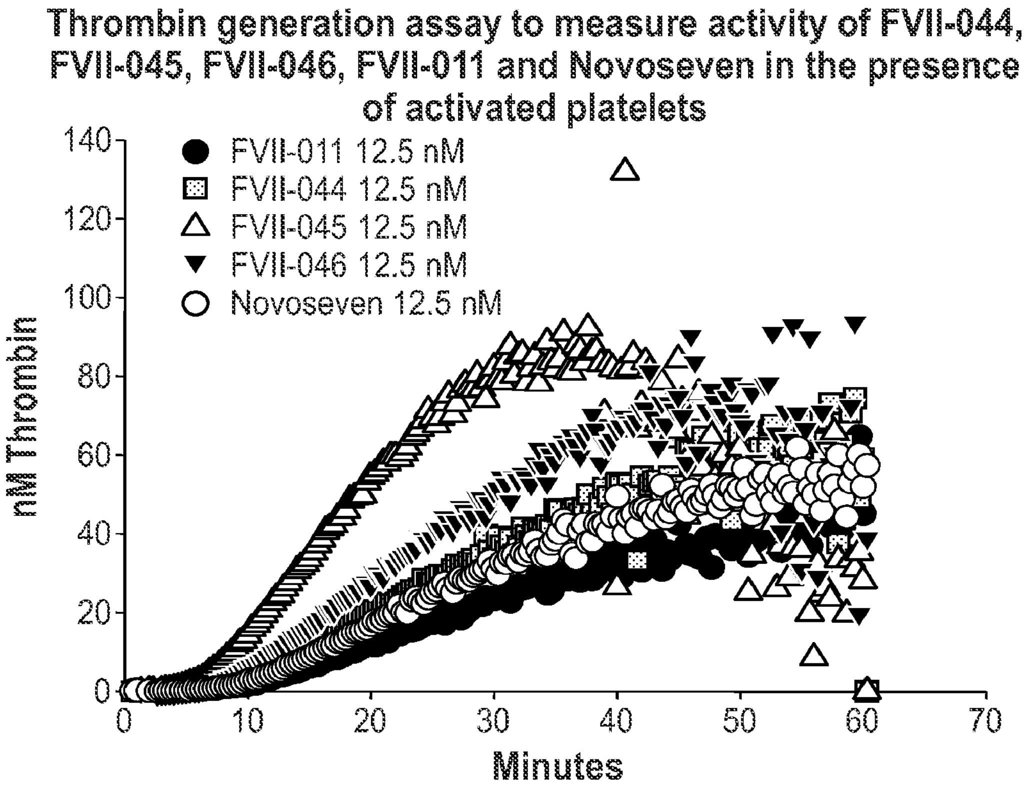
Figure 18D:
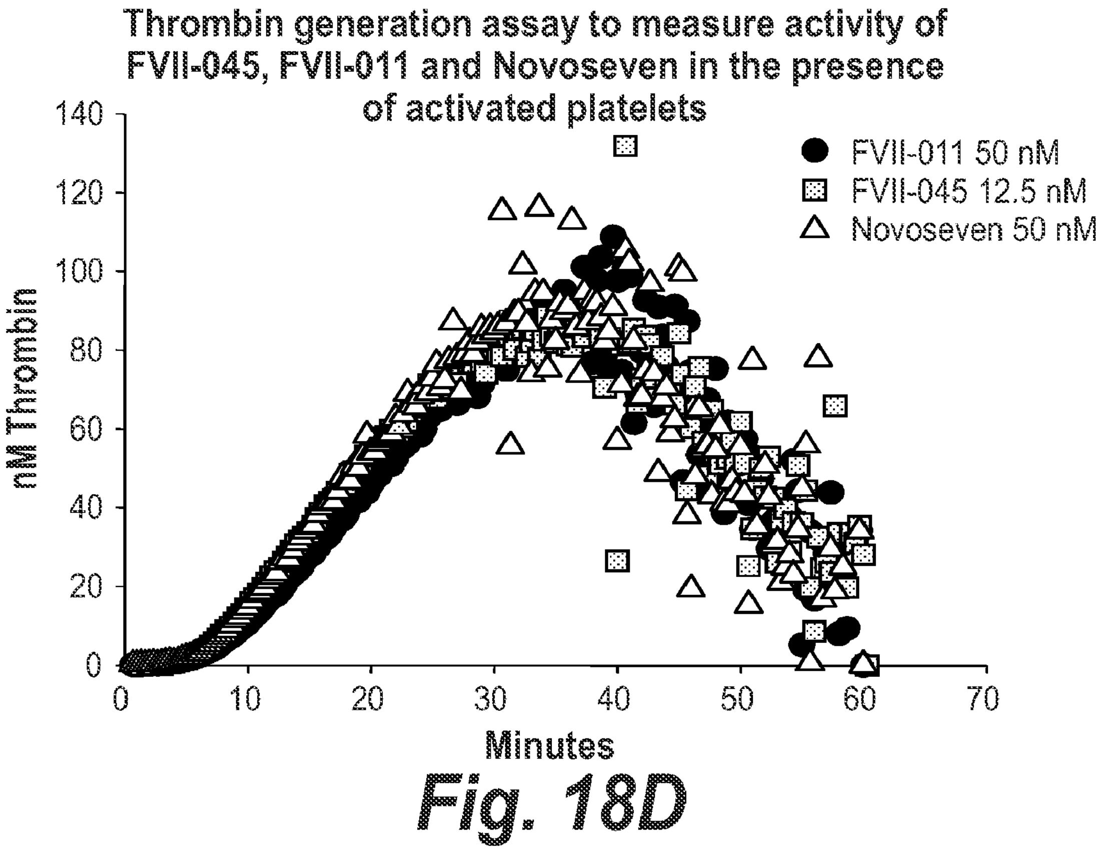
Figure 19:
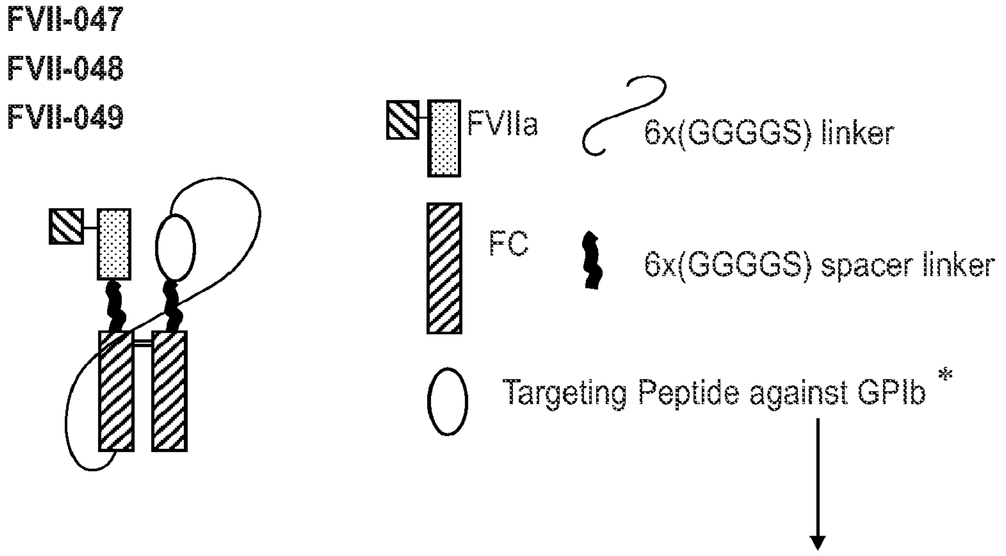
FIG. 19 shows the constructs used in the thrombin generation assay to measure activity of FVII-047, FVII-048, FVII-049, FVII-011 and NOVOSEVEN® in the presence of activated platelets shown in FIGS. 20A, 20B, 20C, and 20D.
Figure 20A:
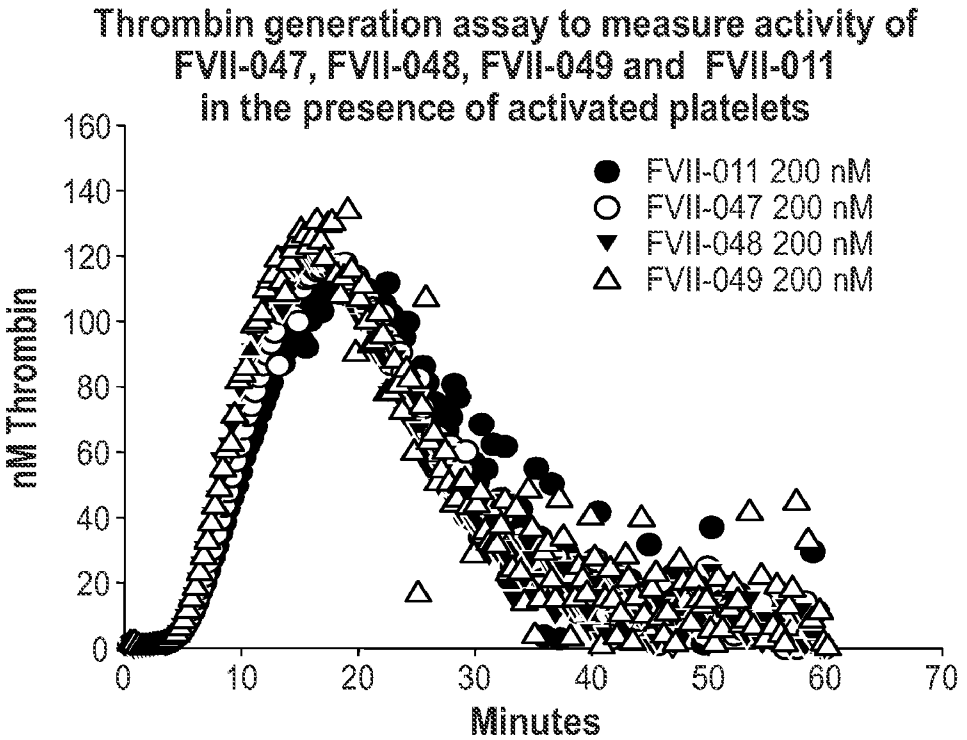
FIGS. 20A, 20B, 20C, and 20D show thrombin generation assays to measure activity of FVII-047, FVII-048, FVII-049, FVII-011 and NOVOSEVEN® in the presence of activated platelets.
Figure 20B:
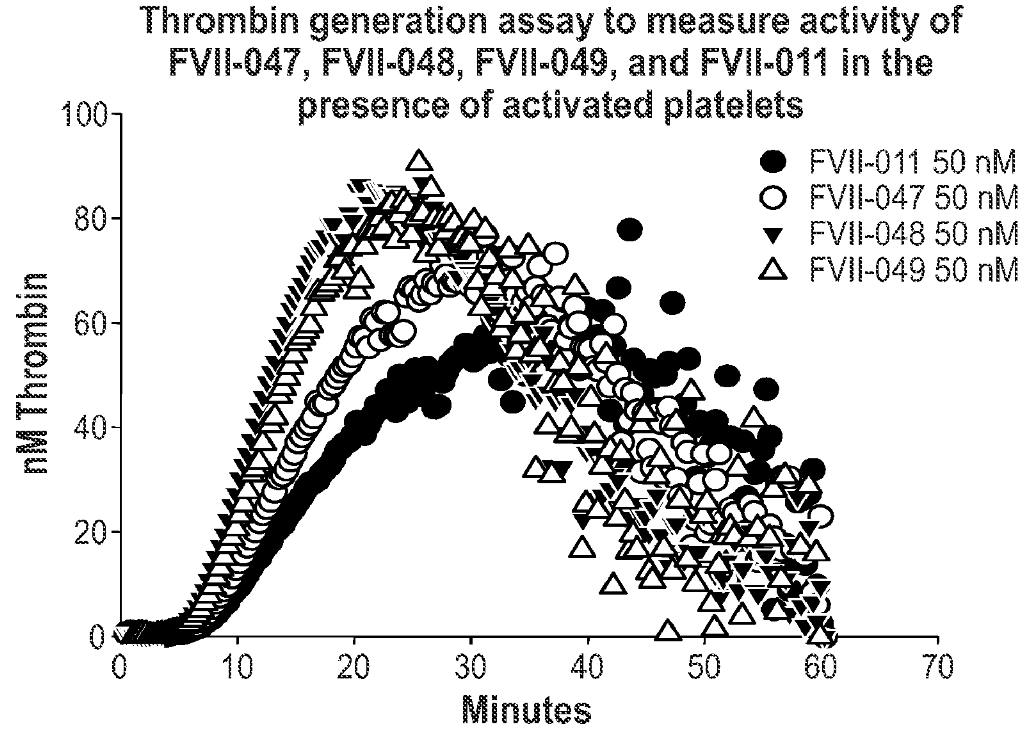
Figure 20C:
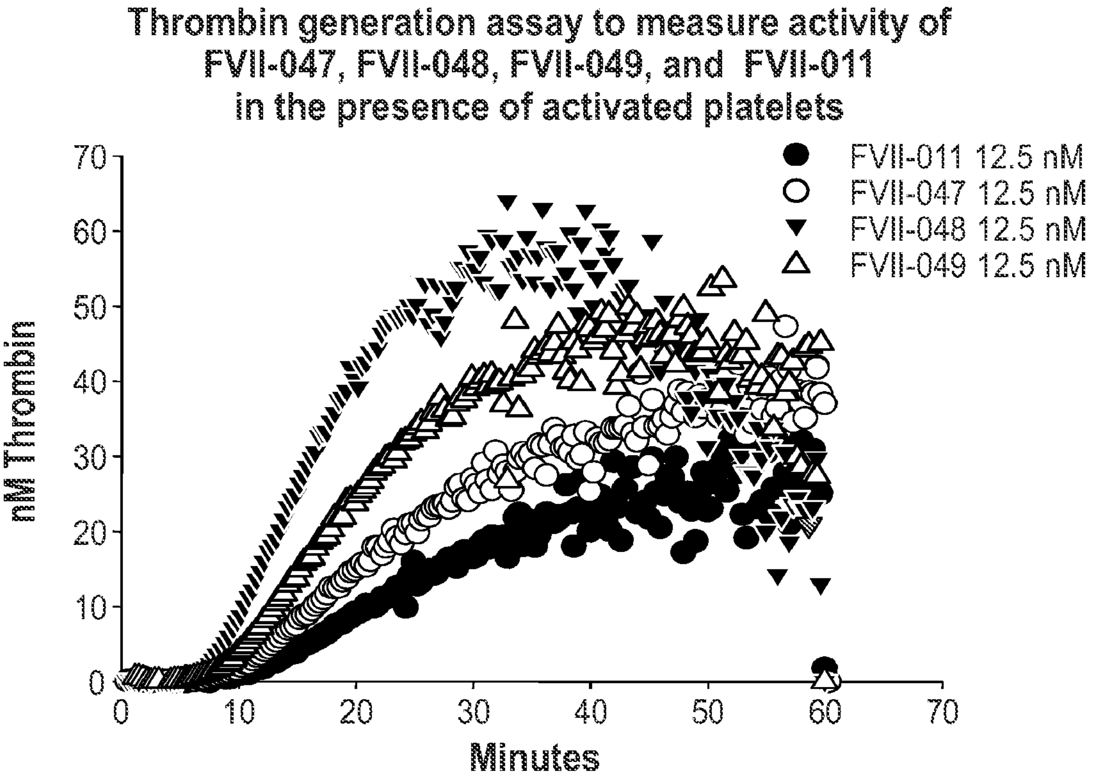
Figure 20D:
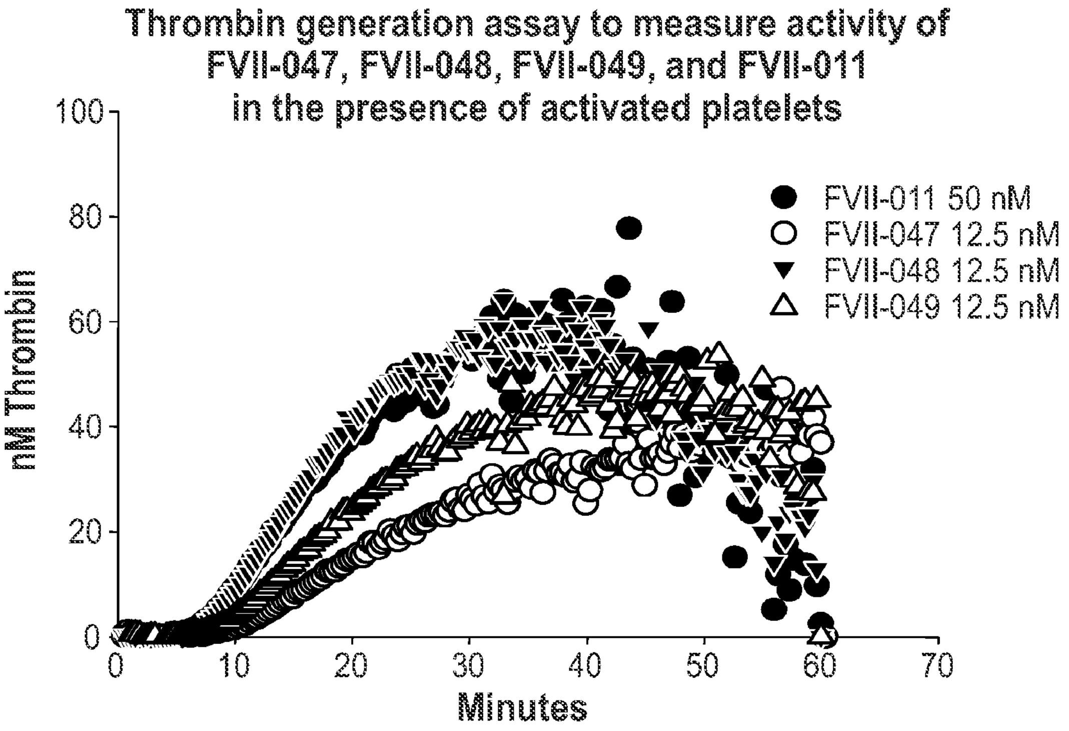
Figure 21:
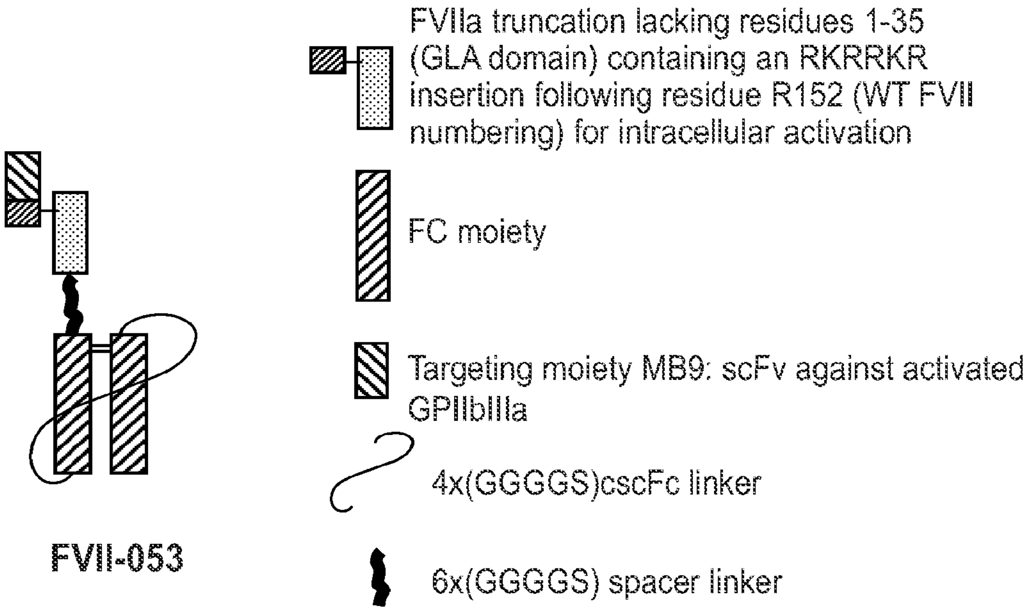
FIG. 21 shows the construct used in the thrombin generation assay to measure activity of FVII-053 and FVII-011 in the presence of activated platelets shown in FIGS. 22A, 22B, 22C, and 22D.

Thombin generation assays in a FVIII-deficient reconstituted system with platelets revealed increased rates of thrombin generation for FVII-037 relative to the NOVOSEVEN® control (FIGS. 16A, 16B, and 16C).

Figure 45A:
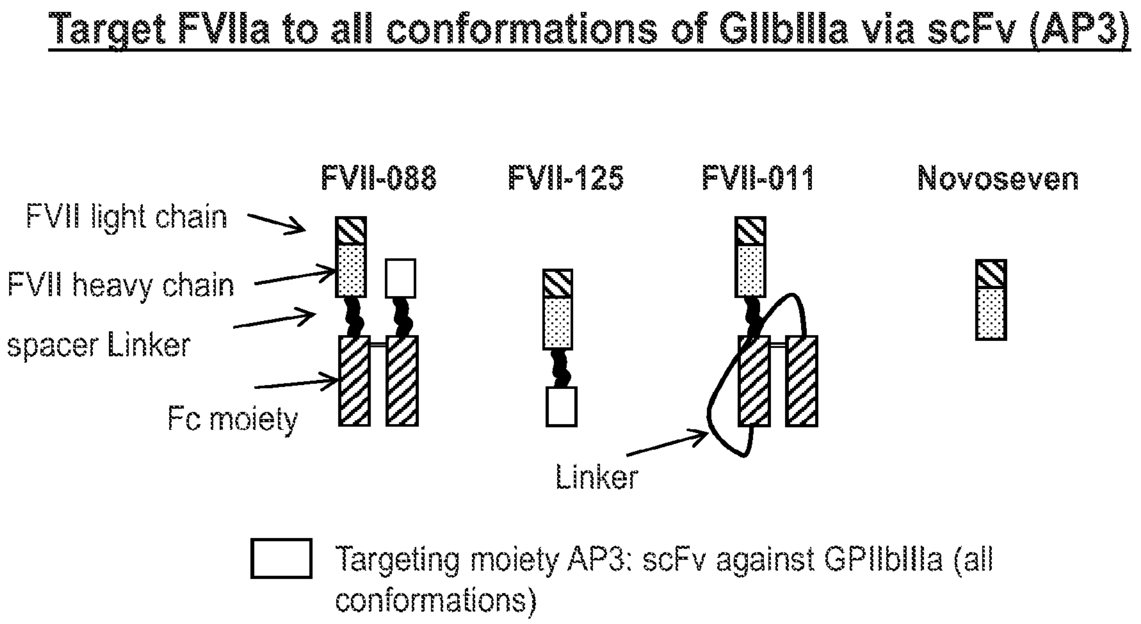
FIG. 45A illustrates several targeted FVIIa constructs which include AP3, an scFv against GPIIbIIIa present on resting and activated platelets.
Figure 45B:
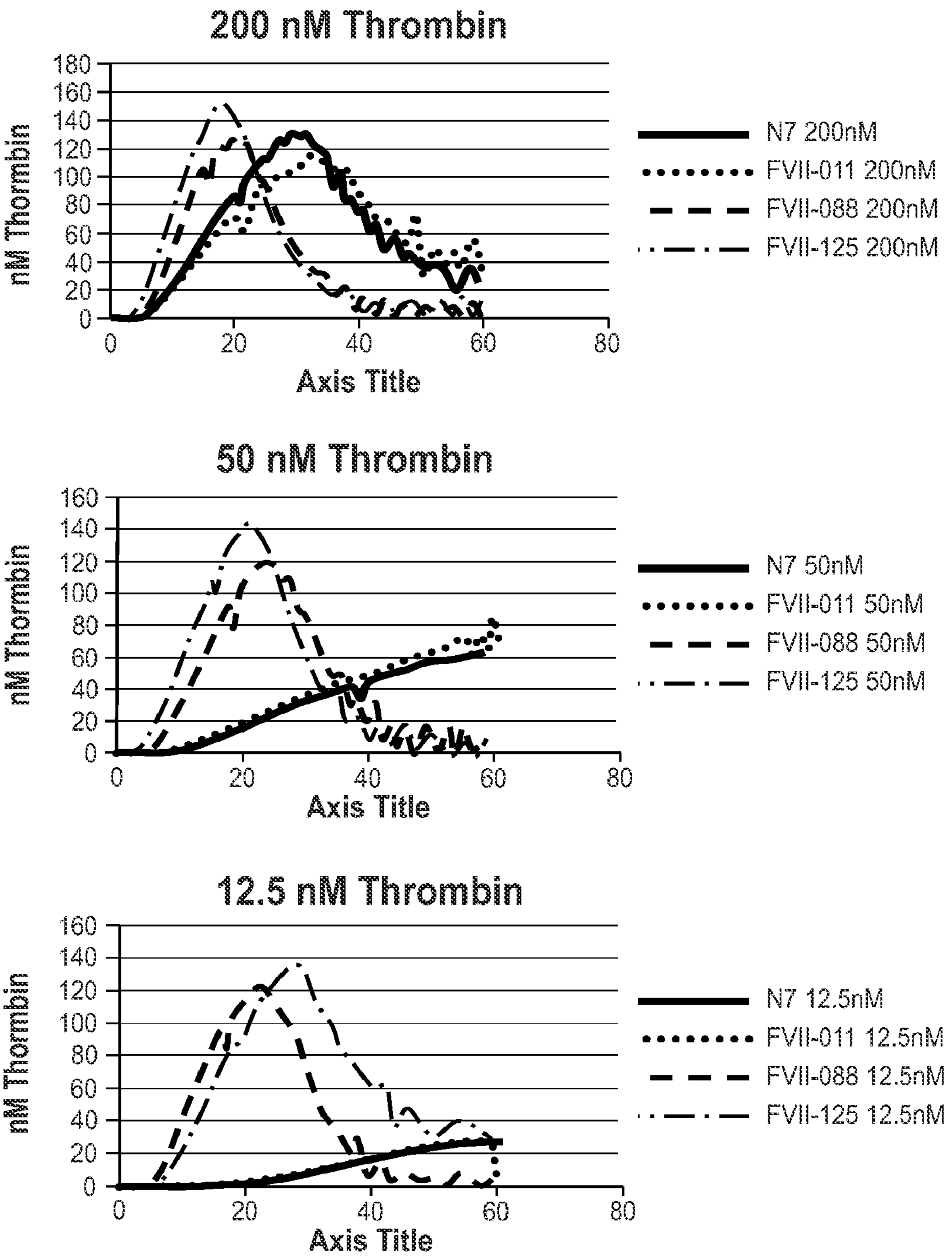
FIG. 45B shows the results of thrombin generation assays in platelet-rich FVIII-deficient plasma.
Figure 45C:
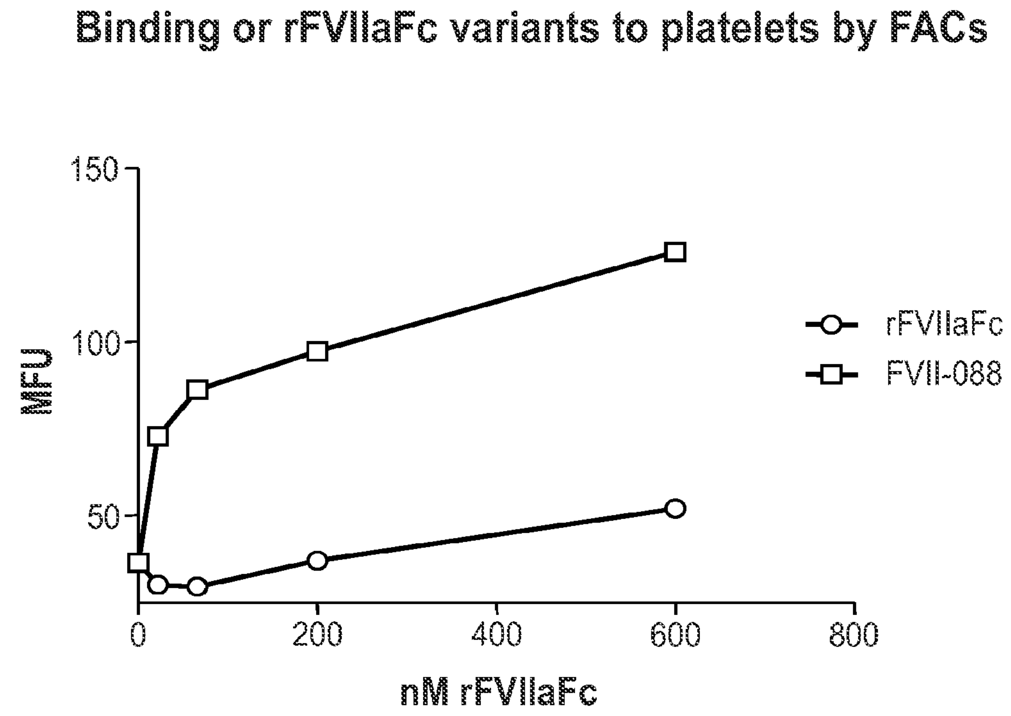
FIG. 45C shows the results of binding of rFVIIaFc variants to platelets by FACS.

Example 27. Factor VII Constructs Targeted to Both Activated and Nonactivated Platelets In this example, the constructs illustrated in FIG. 45A were cloned, expressed, purified and activated as previously described. FVII-088 was cotransfected with PC5 to fully process the cscFc linker, described in the protein sequence, connecting the first Fc moiety to the platelet targeting moiety. FVII-088 and FVII-125 employed the AP3 targeting moiety, a scFv that binds to both active and nonactive conformations of human GPIIbIIIa. The results in FIG. 45B show thrombin generation assays in FVIII-deficient platelet-rich plasma, and both FVII-088 and FVII-125 showed increased rates of thrombin generation relative to the controls, demonstrating that targeting FVIIaFc or FVIIa to the active and nonactive conformation of GPIIbIIIa results in increased activity. Binding of FVII-088 and FVIIaFc to activated human platelets was tested by FACS (FIG. 45C). These data reveal that FVII-088 binds to platelets with higher affinity than FVIIaFc (FVII-011), showing that the AP3 targeting moiety can increase the affinity of FVIIaFc for platelets.

Figure 30:
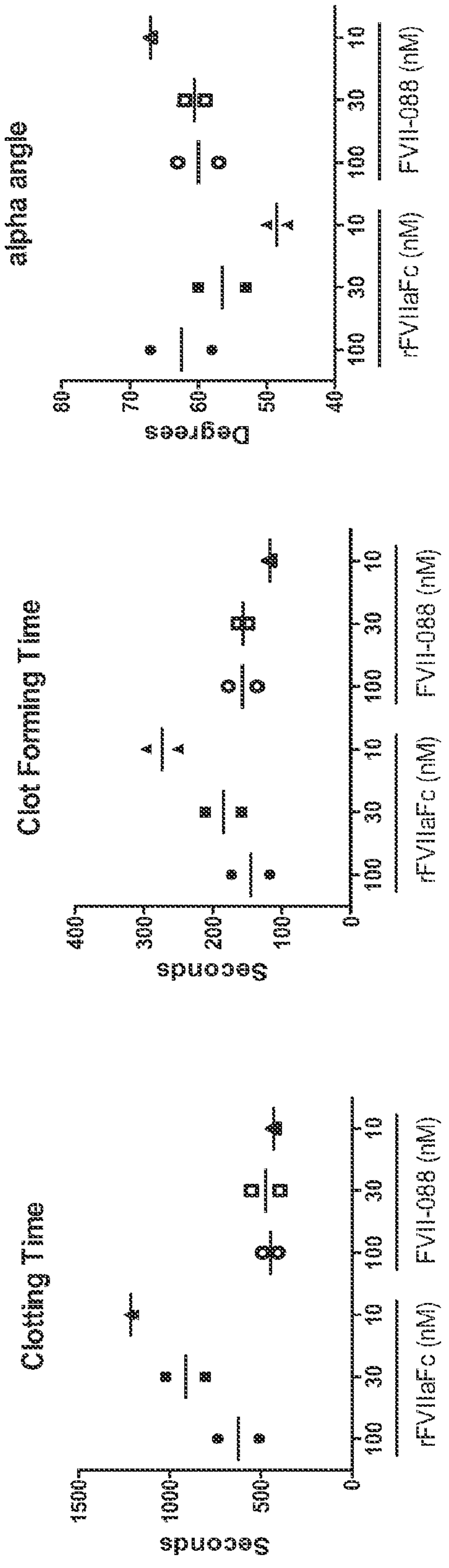
FIG. 30 shows a Rotation Thromoboelastometry (ROTEM) assay to measure the activity of FVII-088 and wild type recombinant FVIIaFc in hemophilia A human blood. Clotting Time, Clot Forming Time and Alpha Angle parameters are shown.

Rotation Thromboelastometry (ROTEM®, Pentapharm GmbH, Munich, Germany) is another method to evaluate platelet-targeted FVIIa constructs, since it allows for the characterization of several coagulation parameters in whole blood (in the presence of platelets). The ability of FVII-088 and wild type recombinant FVIIaFc (rFVIIaFc) to form firm and stable clots was evaluated by ROTEM with Calcium Chloride as activator (NATEM) following manufacturer's recommendations. Hemophilia A blood from a human donor was spiked with FVIIFc to a final concentration of 100, 30 or 10 nM. The NATEM reaction was initiated by the addition of $CaCl_2$. Coagulation parameters, including Clotting Time (relates to coagulation initiation time), Clot Formation Time (relates to rates of coagulation) and Alpha Angle (relates to rates of coagulation) were assessed as shown in FIG. 30. FVII-088 showed a significant reduction in the Clotting Time and Clot Forming Time and an increase in the alpha angle relative to wild type rFVIIaFc, consistent with enhanced coagulation kinetics for FVII-088. These data demonstrate that FVII-088 has enhanced activity relative to wild type FVIIaFc in agreement with the thrombin generation assay data.

Example 28. Use of Peptides for Targeting FVIIa to Platelets

Figure 46B:
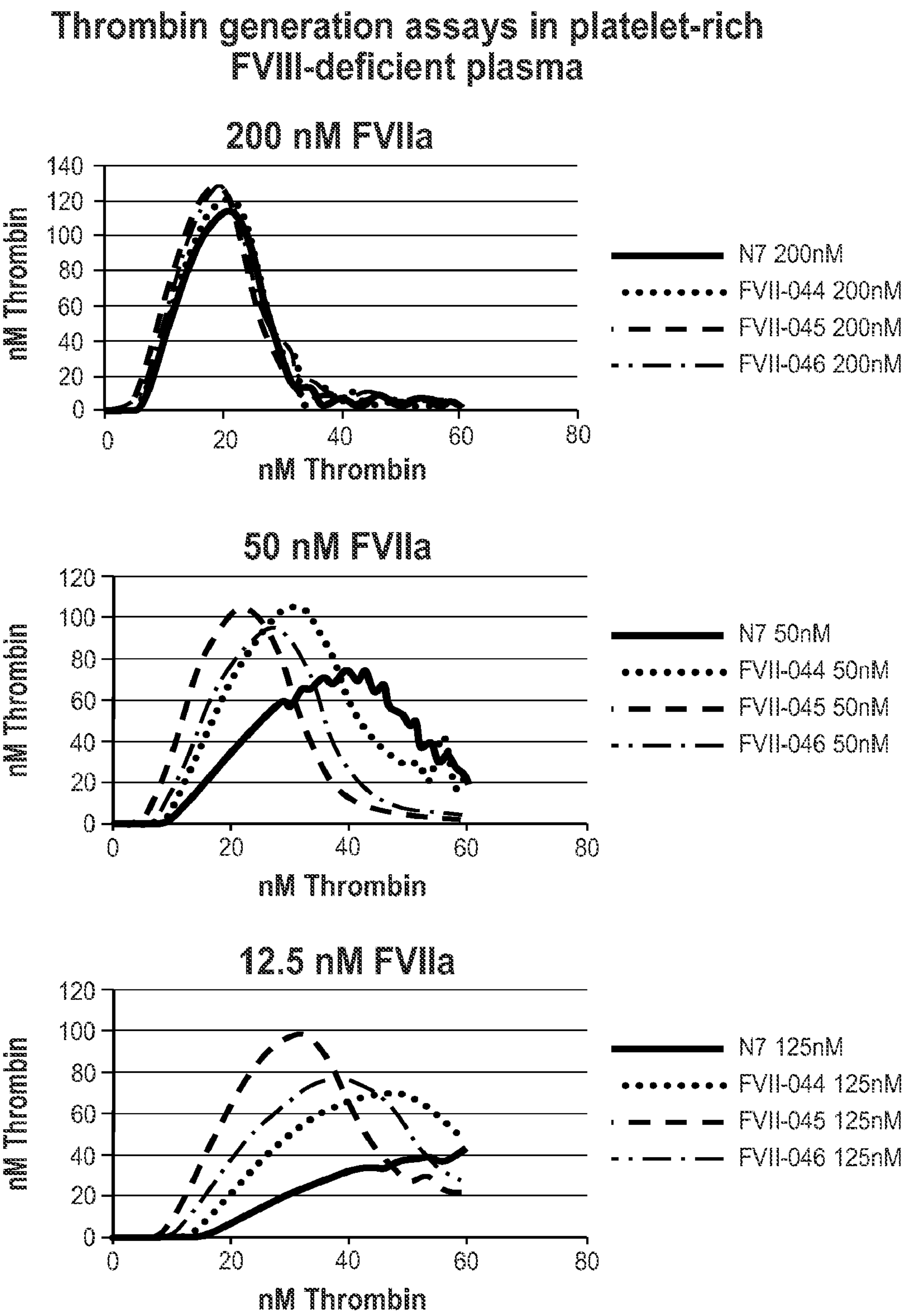
FIG. 46B shows the results of thrombin generation assays in platelet-rich FVIII-deficient plasma using the C terminal peptide constructs shown in FIG. 46A.
Figure 47A:
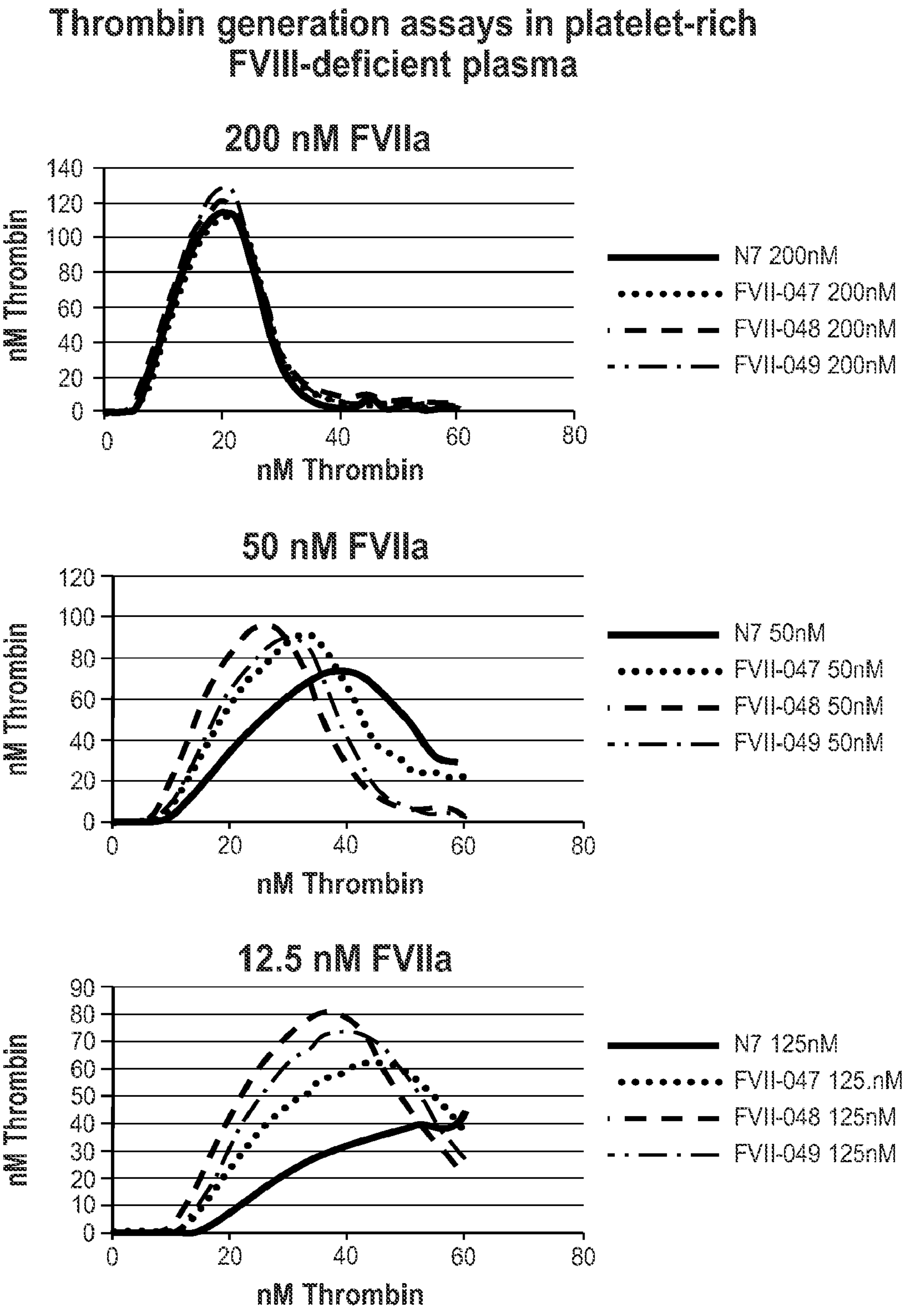
FIG. 47A shows the results of thrombin generation assays in platelet-rich FVIII-deficient plasma using the N terminal peptide constructs shown in FIG. 46A.
Figure 47B:
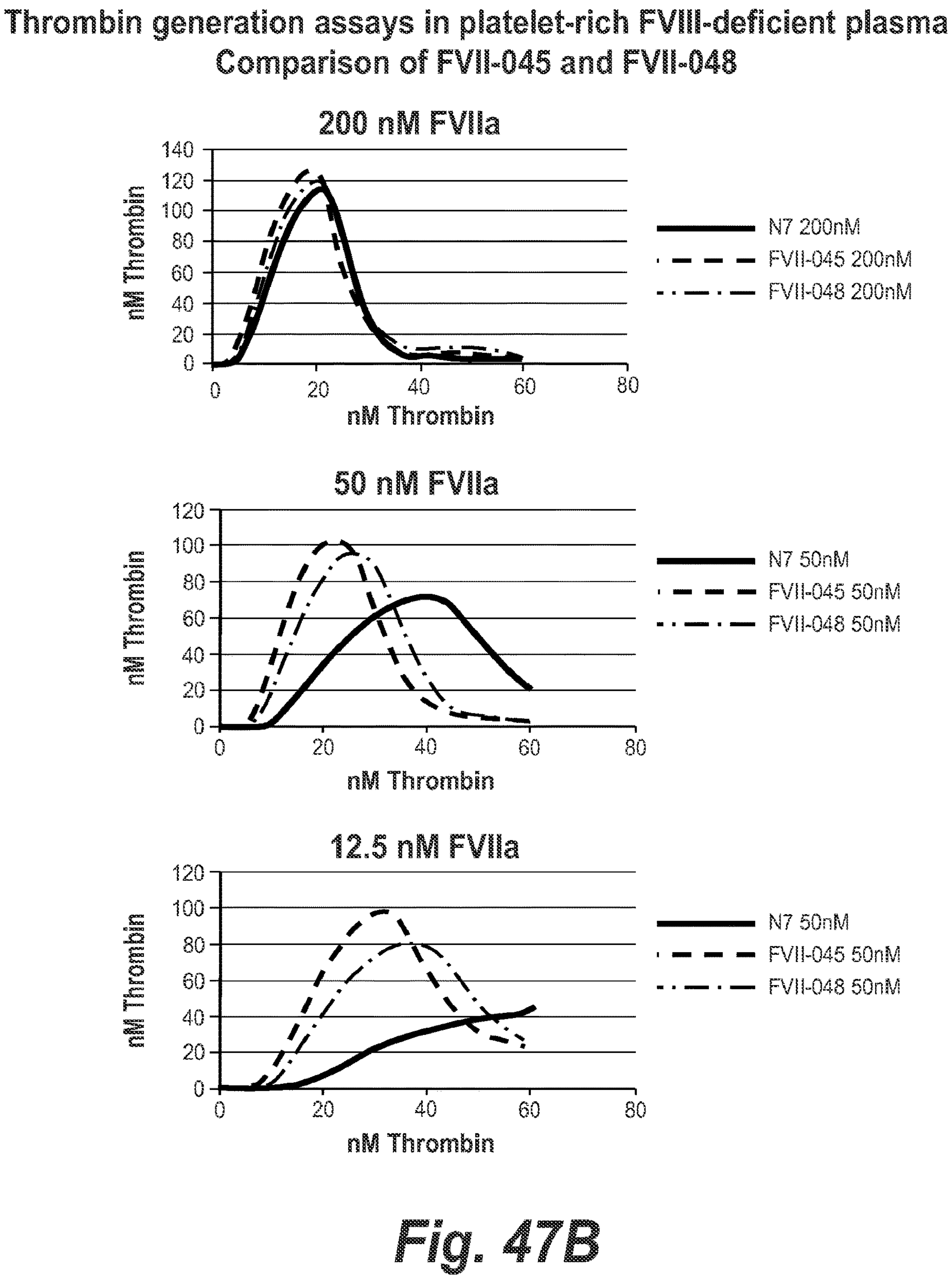
FIG. 47B shows a direct comparison of FVII-045 and FVII-048.
Figure 48:
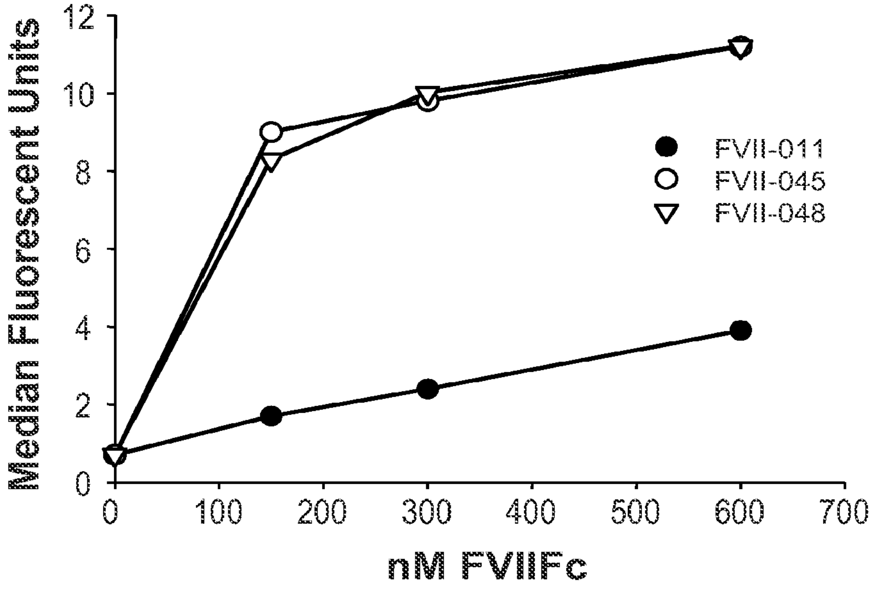
FIG. 48 shows the binding of FVII-045 and FVII-048 and wild type FVIIaFc to platelets as determined by FACS. The figure also shows the affinity of the targeting peptides as reported in Bernard et al. Biochemistry 2008, 47:4674-4682.
Figure 49A:
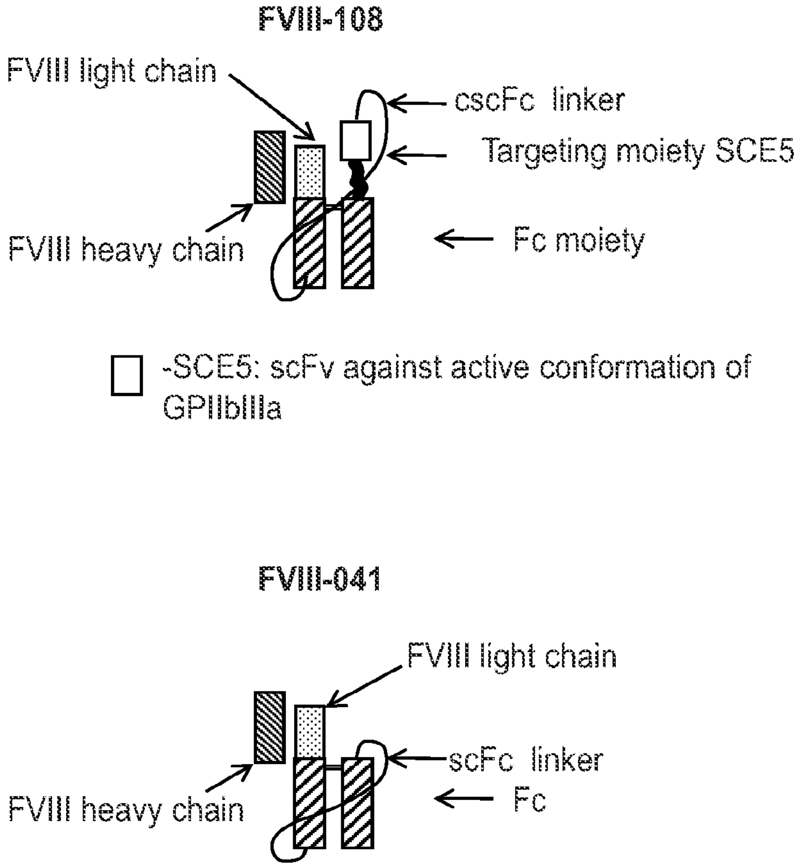
FIG. 49A shows an exemplary targeted FVIII construct.
Figure 49B:
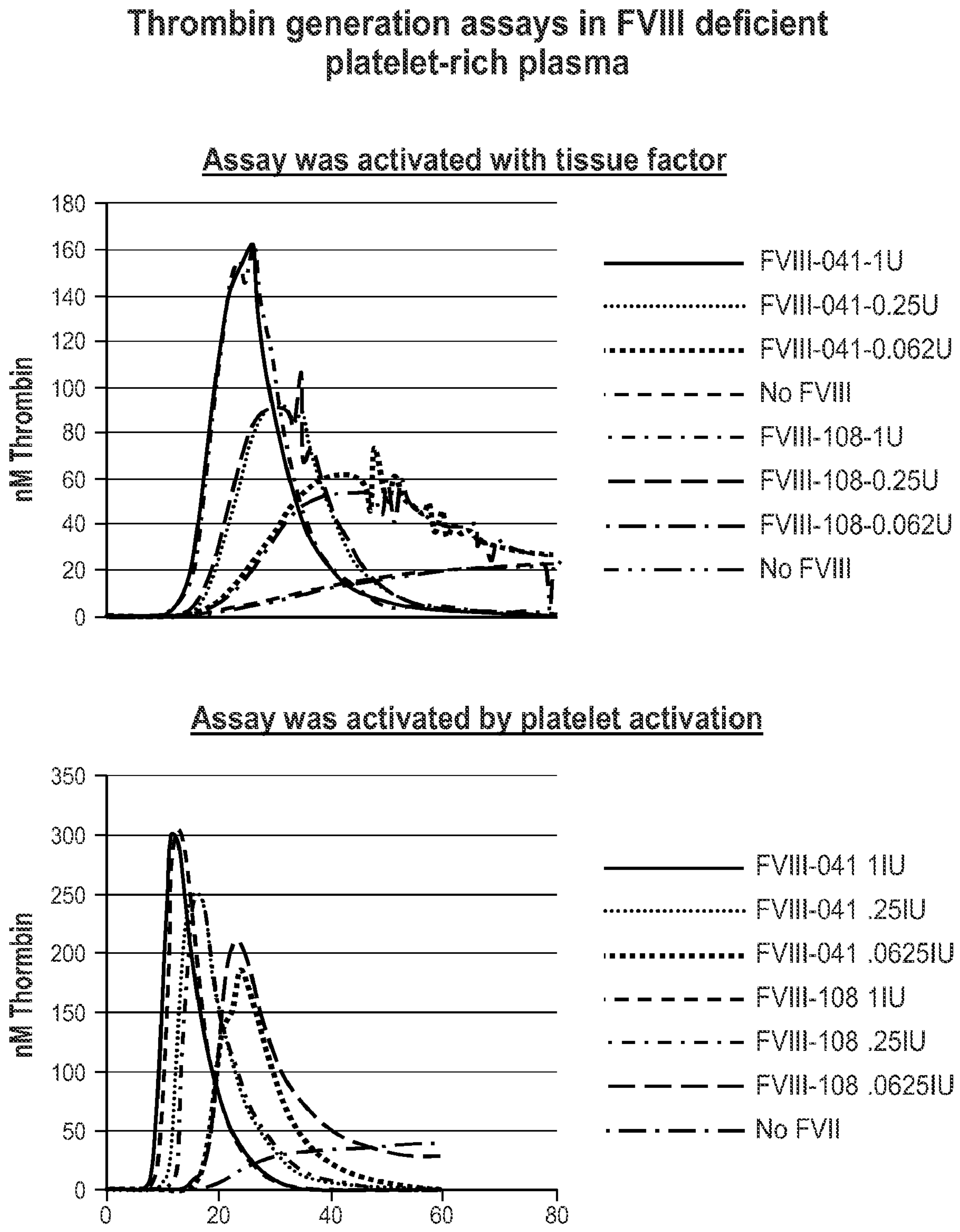
FIG. 49B shows the results of a thrombin generation assay in FVIII deficient platelet-rich plasma. In this experiment, the assay was activated with tissue factor (top panel) or by platelet activation (bottom panel).

The constructs illustrated in FIG. 46A were cloned, expressed, purified and activated as previously described. These proteins were made using peptides that bind to platelet receptor GPIb-alpha (found in both activated and nonactivated platelets), specifically PS4, OS1, and OS2 as platelet targeting moieties. In making these molecules the peptide was attached to either the N or the C terminus of the second Fc moiety of the construct. The FVII-044 construct employed the PS4 peptide attached to the C terminus of the second Fc moiety of the construct; FVII-045 employed the OS1 peptide attached to the C terminus of the second Fc moiety of the construct; and the FVII-046 construct employed the OS2 molecule attached to the C terminus of the second Fc moiety of the construct. In contrast, the FVII-047 construct employed the PS4 peptide attached to the N terminus of the second Fc moiety of the construct; the FVII-048 molecule employed the OS1 peptide attached to the N-terminus of the second Fc moiety of the construct; and the FVII-049 molecule employed the OS2 peptide attached to the N-terminus of the second Fc moiety of the construct. Thrombin generation assays were performed using FVIII-deficient platelet rich plasma as previously described. As shown in FIG. 46B, when the assay was performed with limiting concentrations of FVIIa, each of the FVII-044, FVII-045, and FVII-046 C-terminal fusion constructs exhibited enhanced thrombin generation as compared to the NOVOSEVEN® control. A similar result is shown in FIG. 47A for the N-terminal fusion constructs. FIG. 47B shows that the FVII-045 construct may be marginally better than the FVII-048 construct in this assay, but that again both the N and C terminal fusions are better than the NOVOSEVEN® control. In addition, there is a correlation between the published GPIb-alpha affinity for each peptide (FIG. 48) and the increase in the activity associated with that peptide when recombinantly fused to FVIIaFc. FIG. 48 shows the binding of FVII-049, FVII-048 and wild type FVIIaFc (FVII-011 control) to activated platelets as determined by FACS as well as the affinity for the targeting peptides reported in Bernard et al. Biochemistry 2008. 47:4674-4682. FACS data revealed increased affinity of FVII-045 and FVII-048 for platelets relative to the FVII-011 control Example 29. An FVIIIFc Variant Targeted to the Active Form of GPIIbIIIa The constructs illustrated in FIG. 49A were made as previously described. FVIII-041 is wild type FVIIIFc, while FVIII-108 has a SCE5 platelet targeting moiety at the N-terminus of the second Fc moiety. For expression, FVIII-108 was cotransfected with PC5 to fully process the cscFc linker, described in the protein sequence, connecting the first Fc moiety to the platelet targeting moiety. These proteins were tested in thrombin generation assays using FVIII deficient platelet rich plasma as previously described, but in addition the thrombin generation assay was also activated with tissue factor As shown in FIG. 49B, no significant improvement was seen using the targeted version of FVIIIFc. It is noteworthy that the thrombin generation assays described herein measure thrombin generation on the surface of platelets and, therefore, are an accurate measure of activity.

Figure 22A:
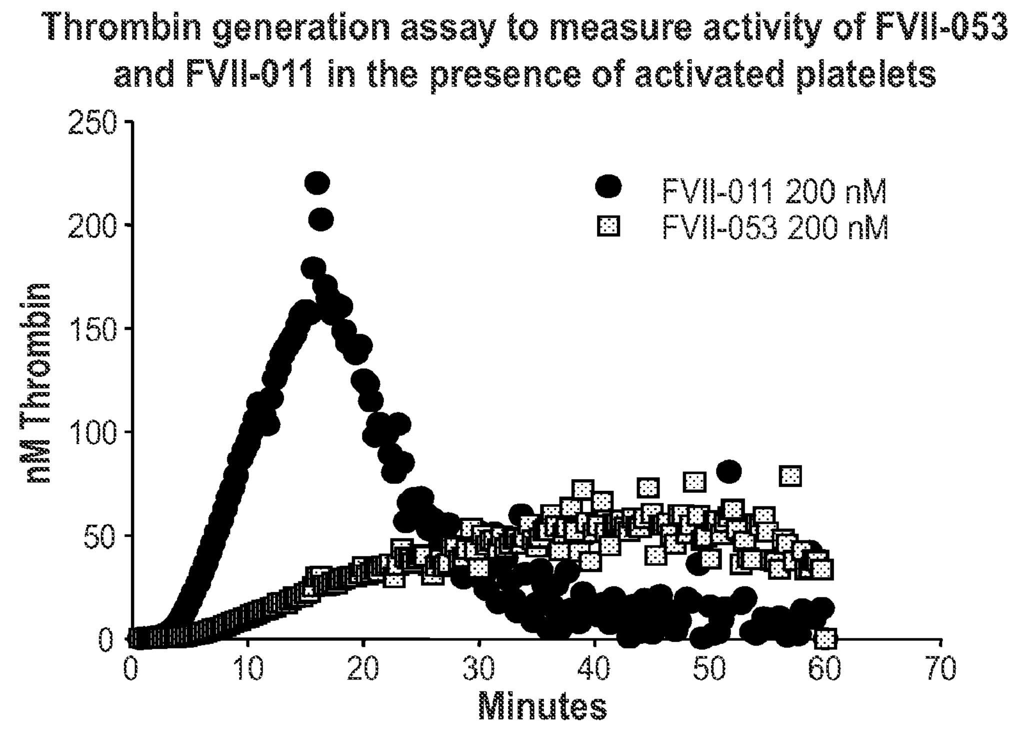
FIGS. 22A, 22B, 22C, and 22D show thrombin generation assays to measure activity of FVII-053 and FVII-011 in the presence of activated platelets.
Figure 22B:
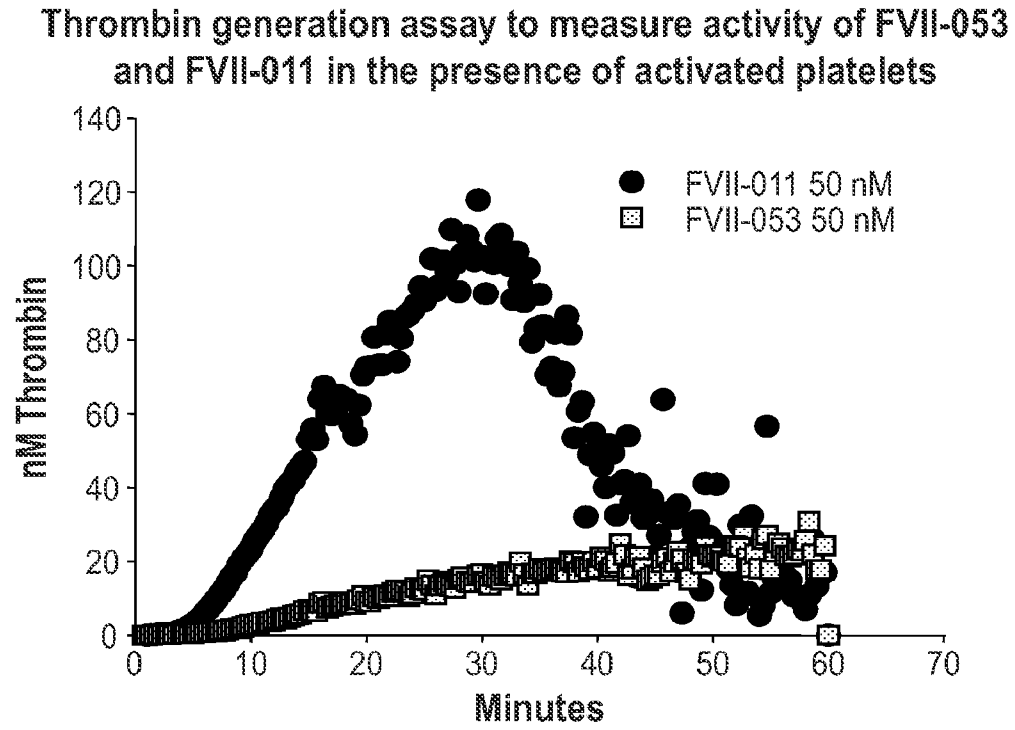
Figure 22C:
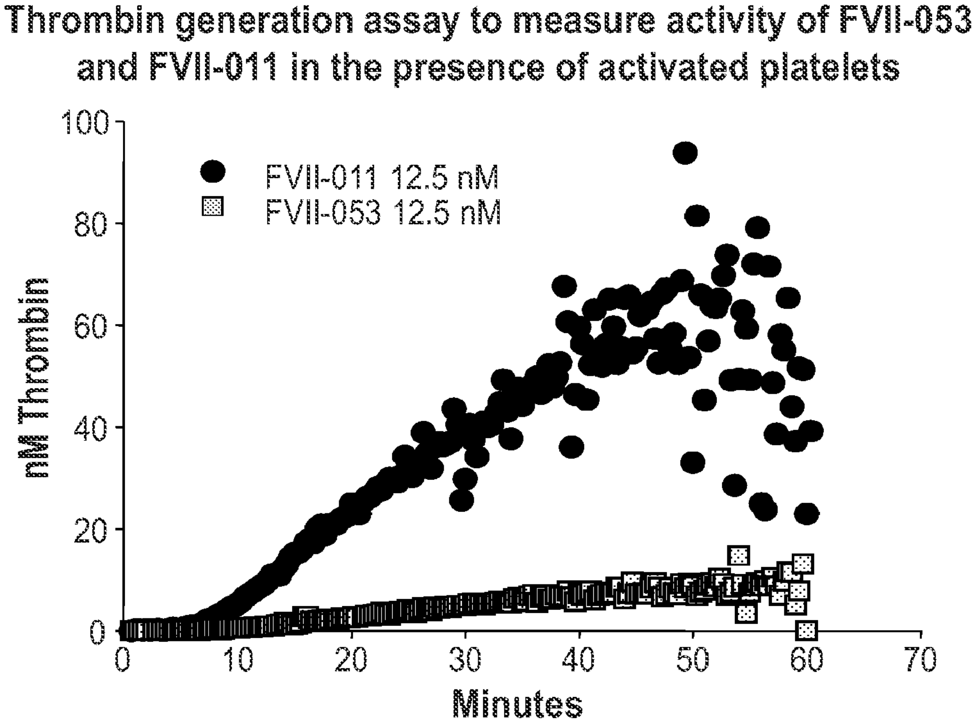
Figure 22D:
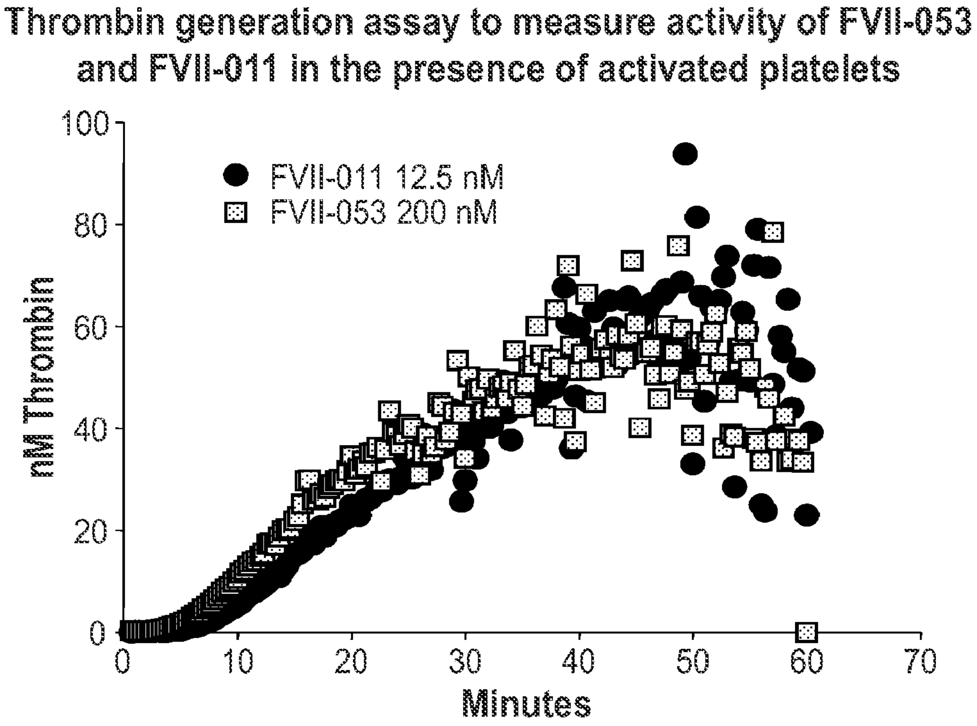
Figure 23A:
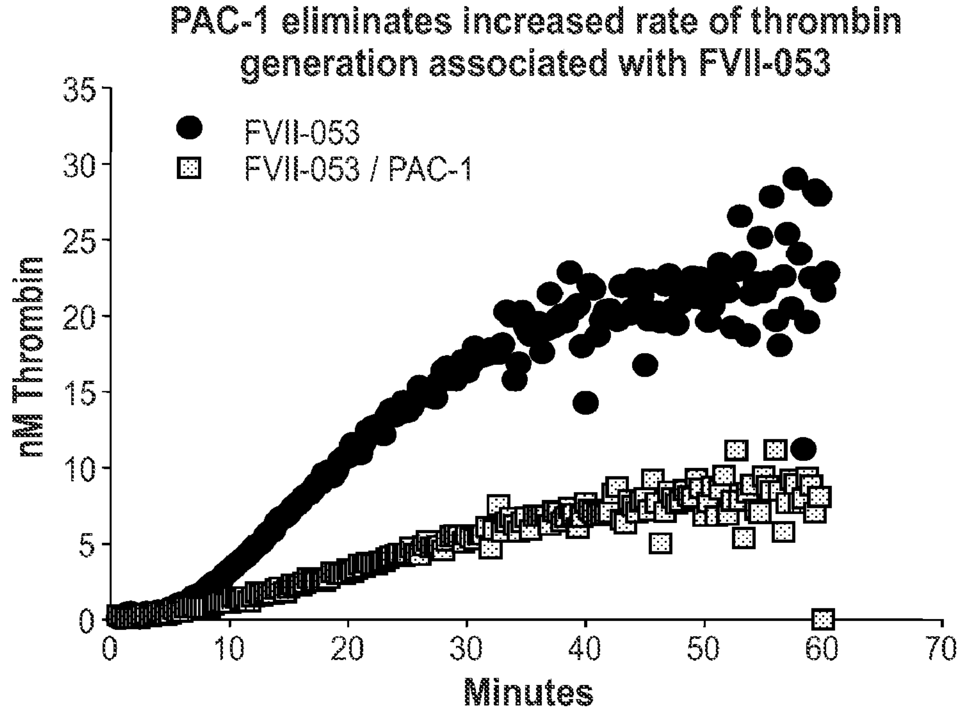
FIGS. 23A and 23B show that PAC-1 eliminates increased rate of thrombin generation associated with FVII-053.
Figure 23B:
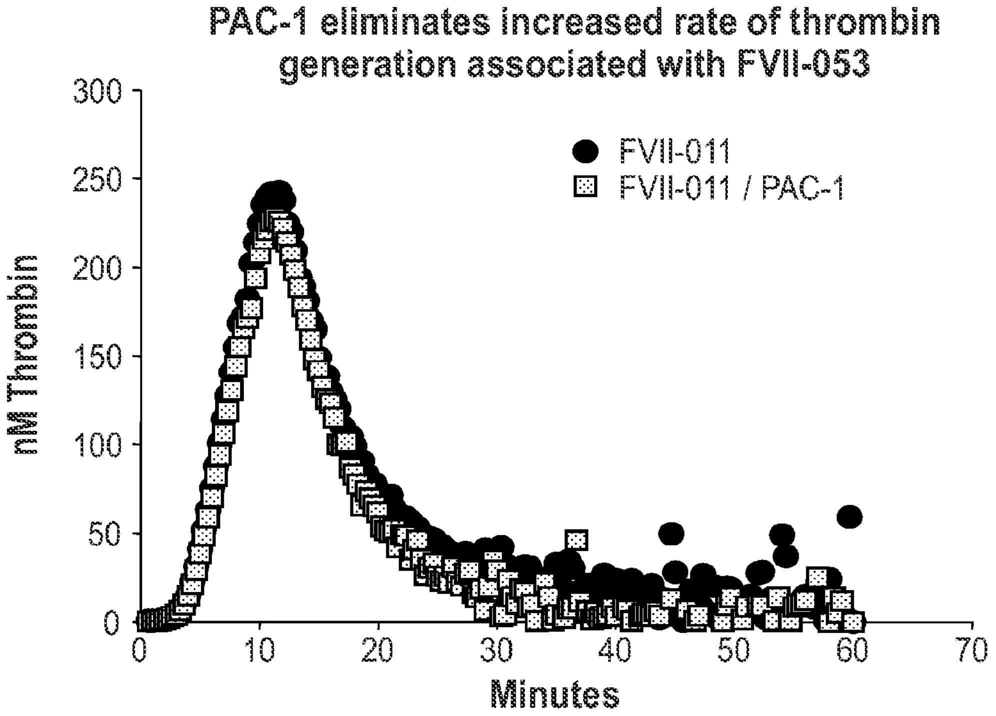

Example 30. Making and Testing a Version of FVII Targeted to Platelets that Lacks a Gla Domain In this example a version of FVIIaFc illustrated in FIG. 21 was generated. This protein has the MB9 scFv at the N-terminus and a deletion that removes the Gla domain. FVII-053 contains an RKRRKR sequence inserted between the light and heavy chain for intracellular activation. FVII-053 was transiently expressed (cotransfected with PC5 for processing of the RKRRKR sequence which results in activation of the protein) and purified as previously described. Thrombin generation assays with purified components and platelets reveal that FVII-053 has some activity (FIGS. 22A, 22B, 22C, and 22D), even though this activity is compromised relative to the FVII-011 control (FIG. 22D). Data in FIGS. 23A and 23B show how the PAC1 antibody, which competes with MB9 for GPIIbIIIa binding, inhibits thrombin generation activity associated with FVII-053, suggesting that platelet targeting is important for activity.

Figure 50:
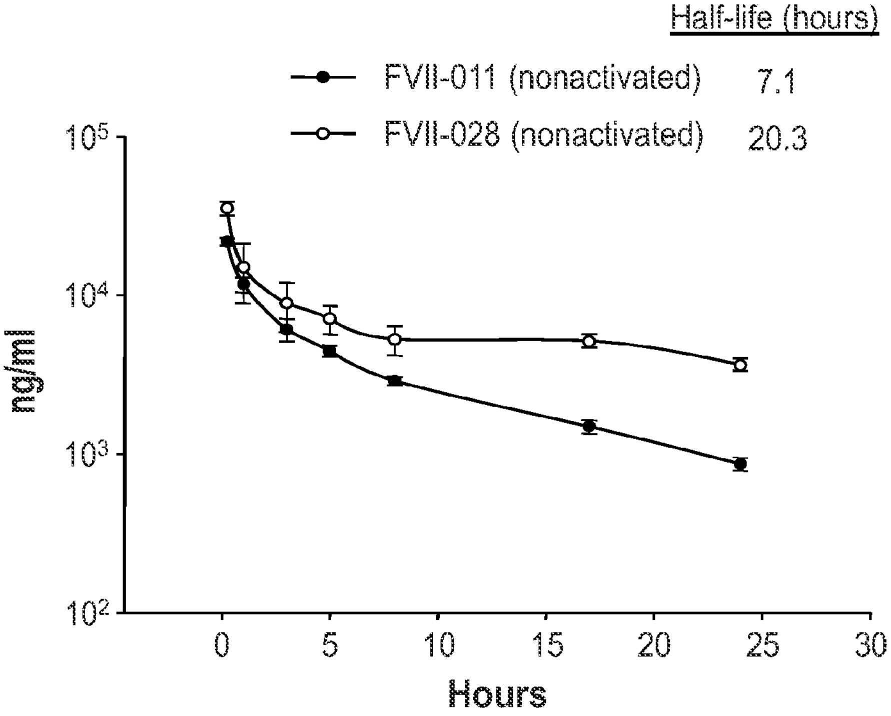
FIG. 50 shows results of an experiment measuring half life of a targeted FVII construct comprising a gla domain (FVII-011) and lacking a gla domain (FVII-028).

Another construct identical to FVII-053, but without the RKRRKR insertion was generated (FVII-028) and tested in a Pk study in the nonactivated together with nonactivated FVII-011. As shown in FIG. 50, the terminal half-life of the targeted, Gla-less FVII-028 molecule was nearly three times longer (20.3 hours) than that of the FVII-011 control (7.1 hours), suggesting that removing the Gla domain increases the terminal half-life of FVIIFc.

Example 31. Platelet Targeted FIX Molecules

Figure 51A:
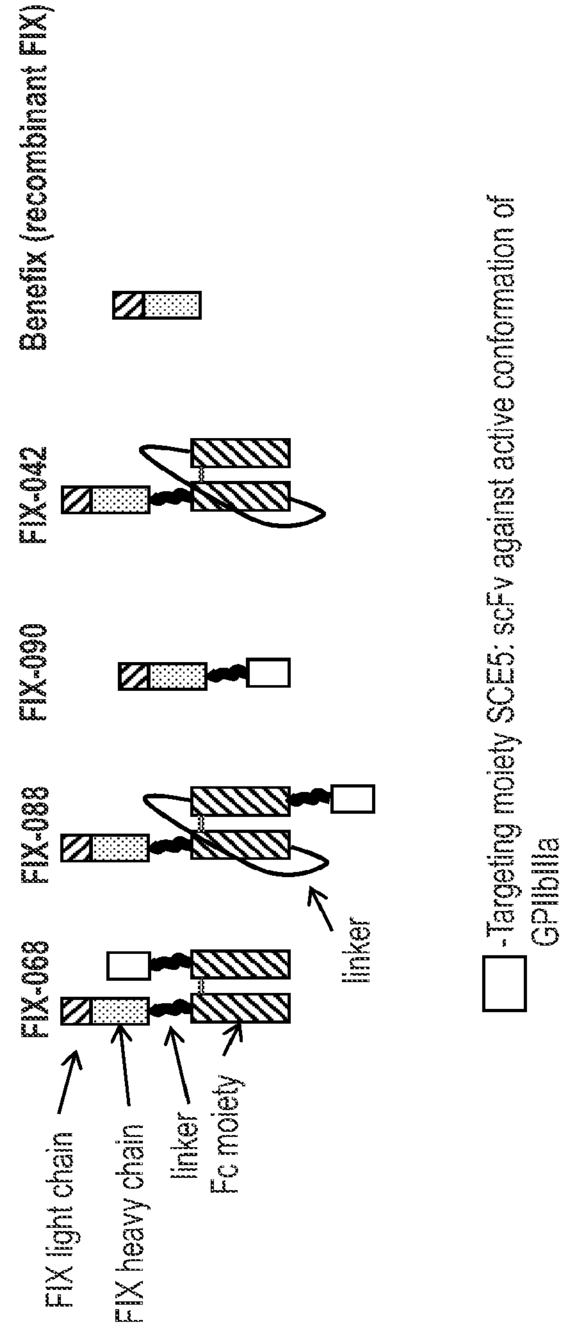
FIG. 51A shows several FIX construct comprising targeting moieties, in this case SCE5 scFv.
Figure 51B:
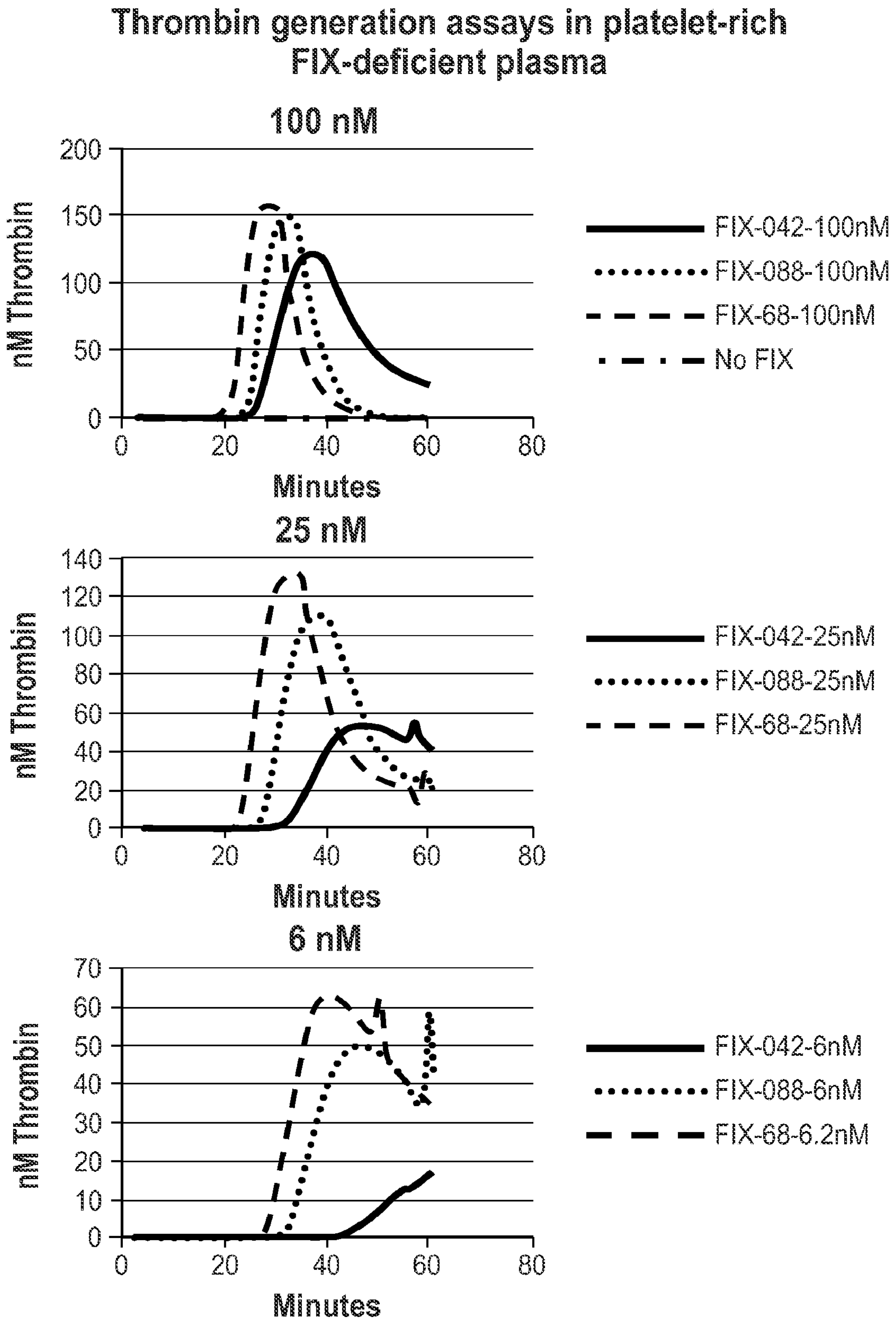
FIG. 51B shows the results of thrombin generation assays in platelet-rich FIX-deficient plasma using the constructs of FIG. 51A.
Figure 51C:
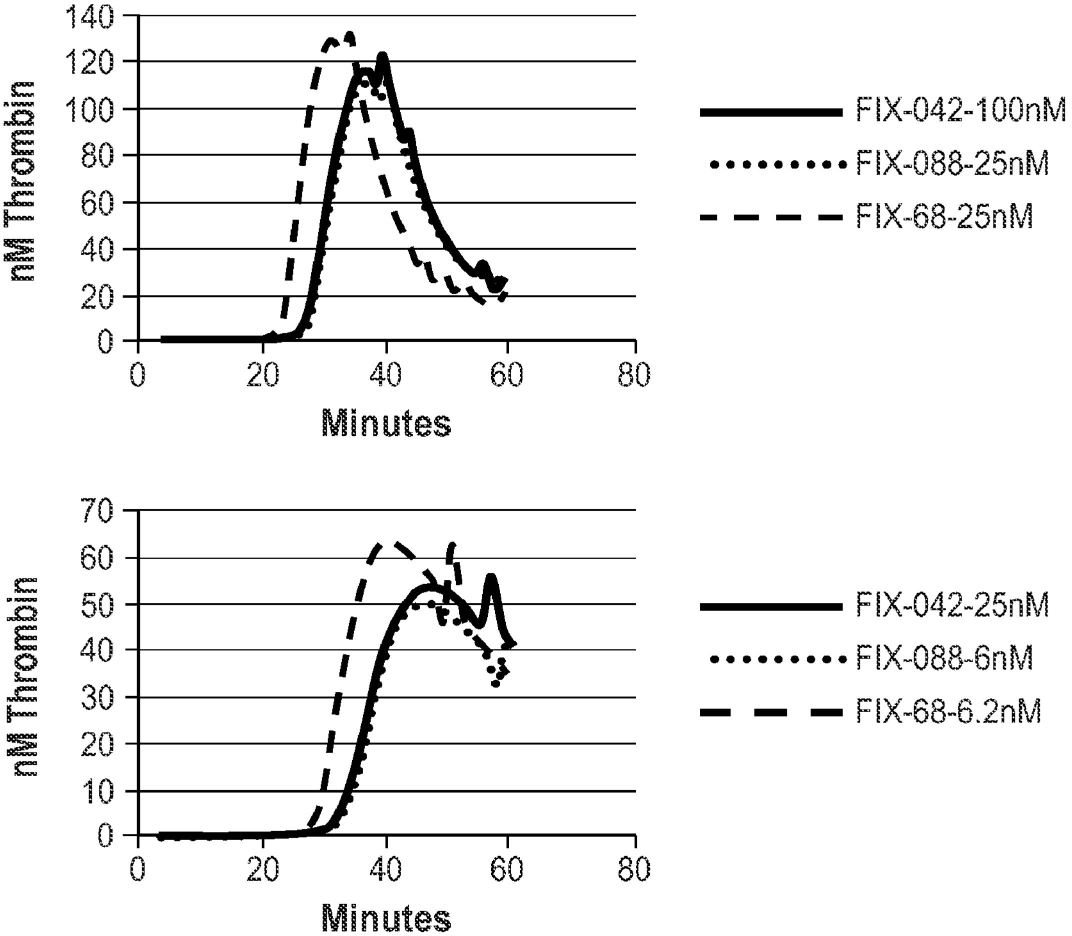
FIG. 51C illustrates that both FIX-068 and FIX-088 have at least 4 times more activity than FIX-042 as measured by Thrombin generation.

In this example, the FIX constructs illustrated in FIG. 51A were made and tested. FIX-068 was cotransfected with PC5 to fully process the cscFc linker, described in the protein sequence, connecting the first Fc moiety to the platelet targeting moiety. FIX-068 has the SCE5 platelet targeting moiety at the N-terminus of the second Fc moiety, while FIX-088 has SCE5 at the C-terminus of the second Fc moiety. FIX-090 is a FIX construct without an Fc domain and has the SCE5 moiety attached at the C-terminus of the FIX protein. FIX-042 is a FIXFc as a single chain Fc without a targeting moiety and was made as a control. BENEFIX® (Pfizer) was also used as a control. To remove trace amounts of activated FIX (FIXa) from the BENEFIX® sample that cause misleading results in thrombin generation assays, the BENEFIX® sample was treated with the irreversible active site inhibitor glutamyl-glycyl-arginyl-chloromethylketone (Hematologic Technologies). BENEFIX® was incubated with an excess amount of the inhibitor for 180 minutes at room temperature. The sample was then dialyzed to remove unbound inhibitor. The treated BENEFIX® is hereafter referred to as BENEFIX®. The specific activities of the molecules made were FIX-042, 6 IU/nmol; FIX068, 5.1 IU/nmol; FIX-088, 3.5 IU/nmol; FIX-090, 13.8 IU/nmol, and BENEFIX®, 12 IU/nmol. When these constructs (FIX-068, FIX-088 and FIX-042) were tested in a thrombin generation assay in platelet-rich FIX-deficient plasma as shown in FIG. 51B, each of the targeted molecules had a higher activity than the FIX-042 control. FIG. 51C illustrates that both FIX-068 and FIX-088 have at least 4 times more activity than FIX-042 as measured by thrombin generation. Since the specific activity of FIX-042 is higher than FIX-068 and FIX-088, the increased activity observed in the thrombin generation assays may be underestimated, and therefore the increased activity by platelet targeting may be greater than 4-fold.

Figure 52A:
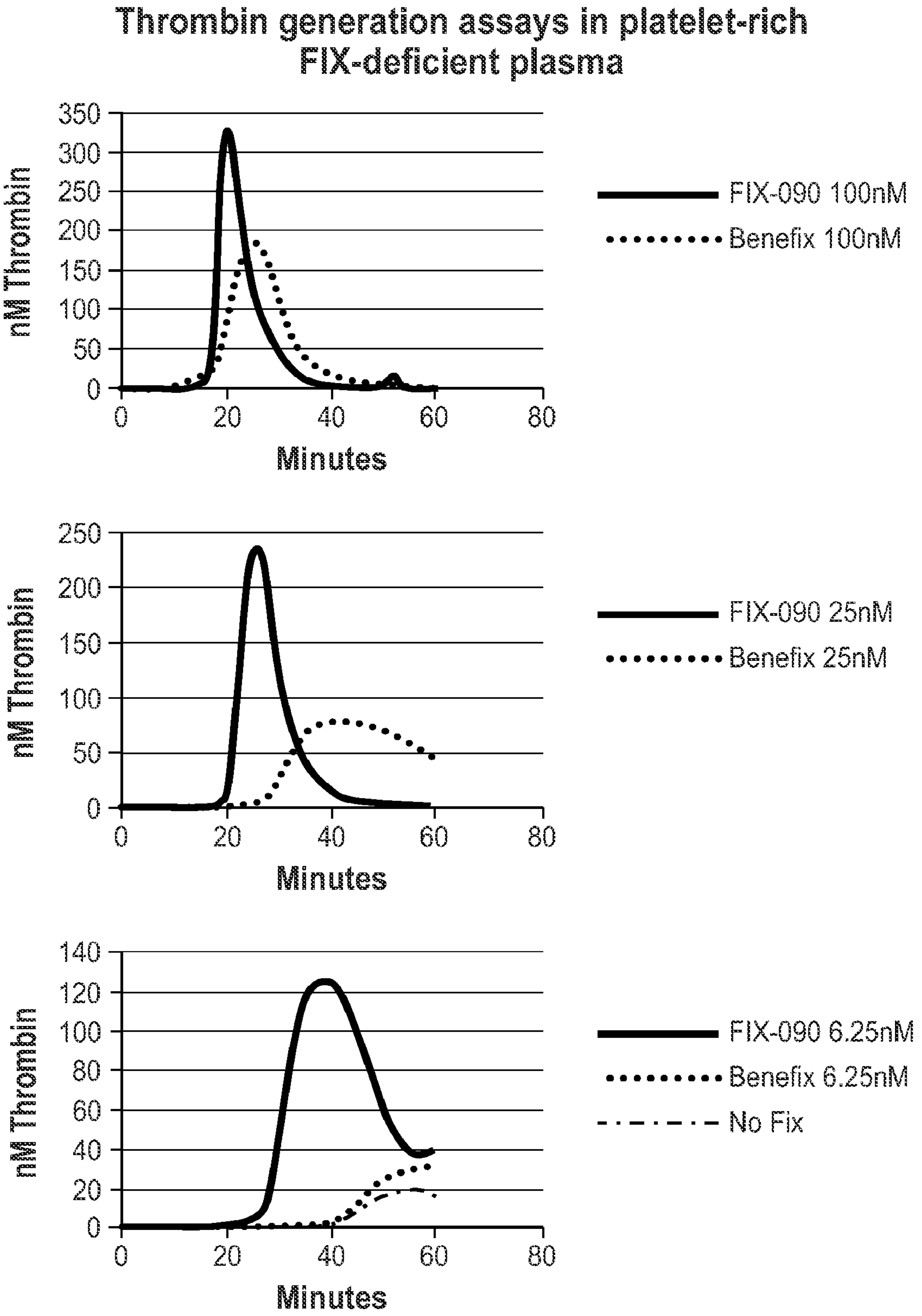
FIG. 52A shows the results of a thrombin generation assay comparing FIX-090 and BENEFIX®.
Figure 52B:
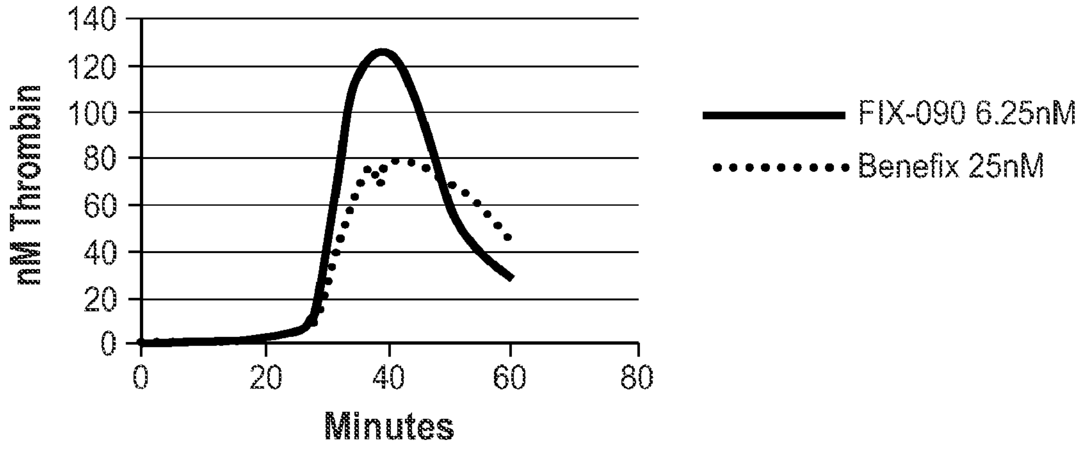
FIG. 52B shows that the activity of FIX-090 is almost 4 times that of BENEFIX®.

As shown in FIG. 52A, FIX-090 (which lacks an Fc) also shows increased activity relative to BENEFIX®, suggesting that targeting FIX to platelets in the absence of Fc also increases activity. FIG. 52B shows that the activity of FIX-090 is at least 4 times that of BENEFIX®. Since both FIX-090 and BENEFIX® have similar specific activities, the 4-fold increase in activity in thrombin generations assays must be caused by the platelet targeting effect.

Example 32. Use of Peptides for Targeting FIX to Platelets

Figure 53A:
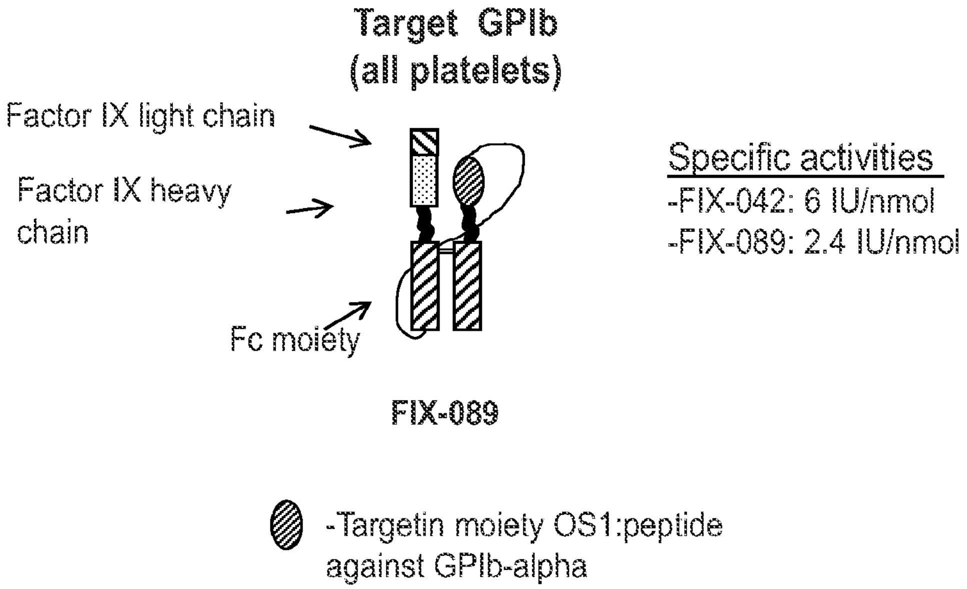
FIG. 53A shows a targeted FIX construct comprising a peptide that binds to GPIb, present on resting and activated platelets.

In this example, the FIX-089 construct illustrated in FIG. 53A was cloned, transiently expressed and purified as previously described. The molecule comprises the OS1 peptide, which binds to GPIb-alpha receptor, attached to the N-terminus of the second Fc moiety of the construct. The specific activity of the FIX-089 construct was 2.4 IU/nmol as compared to 6 IU/nmol for the control FIX-042 molecule.

Figure 53B:
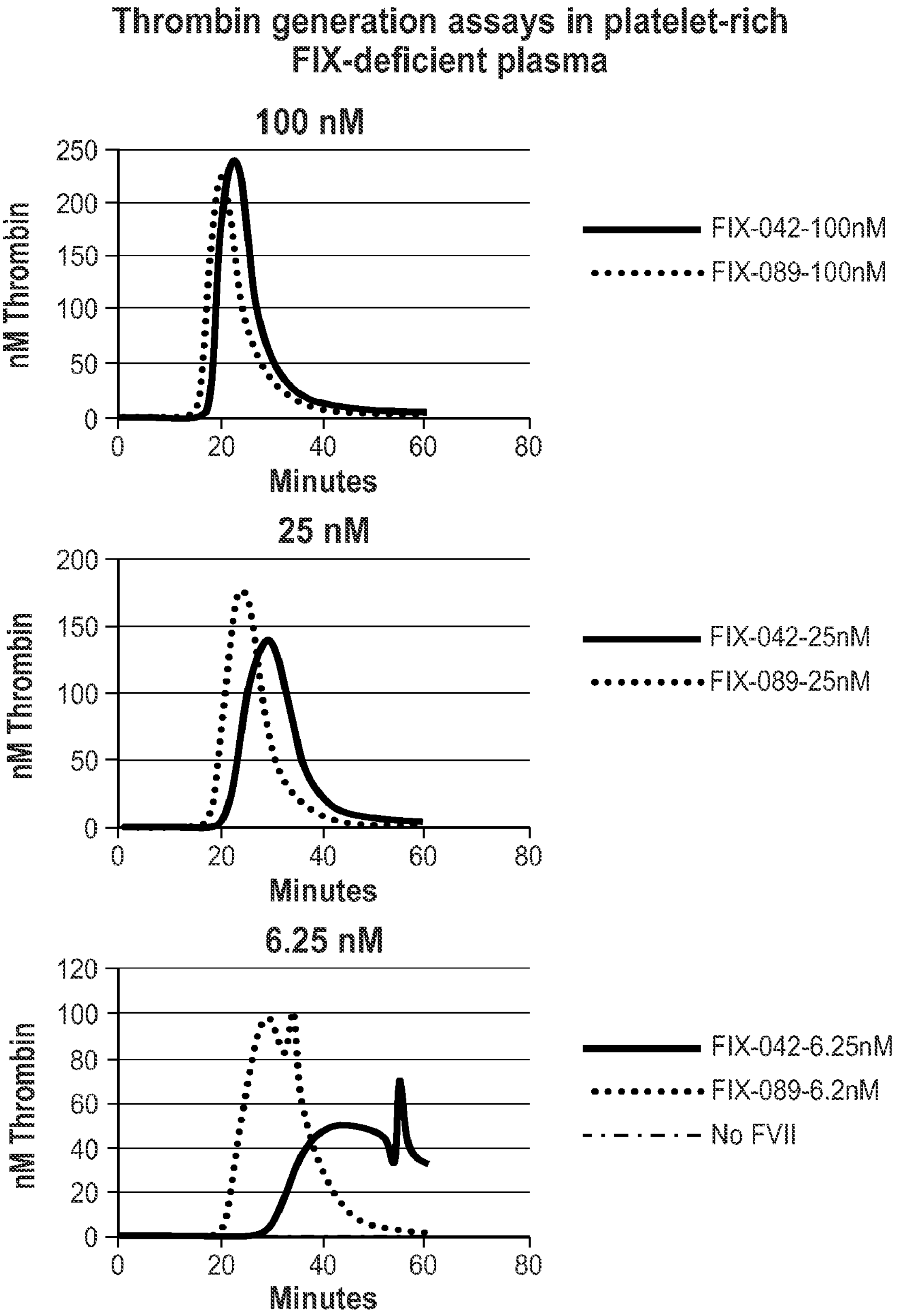
FIG. 53 B shows the results of thrombin generation assays in platelet-rich FIX deficient plasma.
FIG. 53C demonstrates that FIX-089 is roughly 4-times stronger than FIX-042 as measured by thrombin generation, while having a lower specific activity.
Figure 53C:
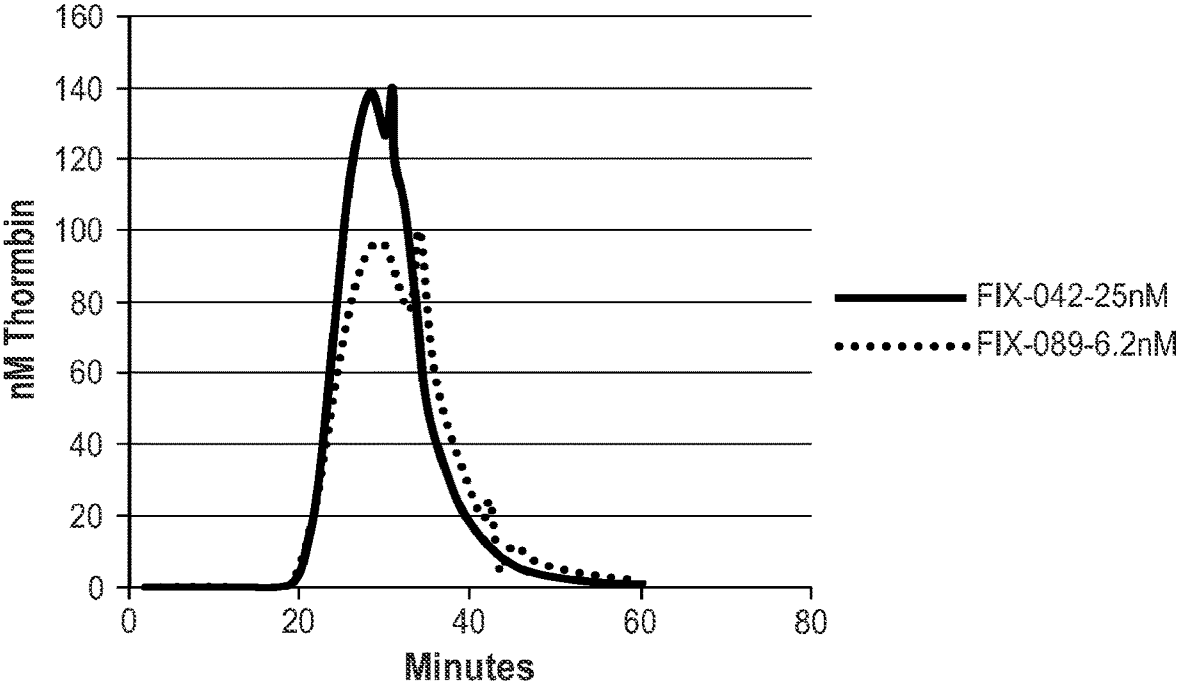

As shown in FIG. 53B, the FIX-089 molecule is more active than the FIX-042 control in thrombin generation assays with FIX-platelet rich plasma; this is particularly evident at limiting concentrations of FIX. FIG. 53C demonstrates that FIX-089 is roughly 4-times stronger than FIX-042 as measured by thrombin generation, while having a lower specific activity. This further suggests that targeting to GPIb increases the activity of FIXFc.

DRAFT SEQUENCE LISTING

FVII-027 amino acid sequence. Signal sequence is shown in dotted underline, propeptide is double underlined, linker region connecting FVII or MB9 to Fc region is underlined, and linker with proprotein convertase processing sites is shown in bold MVSQALRLLC LLLGLQGCLA AVFVTQEEAH GVLHRRRRAN AFLEELRPGS LERECKEEQC
SFEEAREIFK DAERTKLFWI SYSDGDQCAS SPCQNGGSCK DQLQSYICFC LPAFEGRNCE
THKDDQLICV NENGGCEQYC SDHTGTKRSC RCHEGYSLLA DGVSCTPTVE YPCGKIPILE
KRNASKPQGR IVGGKVCPKG ECPWQVLLLV NGAQLCGGTL INTIWVVSAA HCFDKIKNWR
NLIAVLGEHD LSEHDGDEQS RRVAQVIIPS TYVPGTTNHD IALLRLHQPV VLTDHVVPLC
LPERTFSERT LAFVRFSLVS GWGQLLDRGA TALELMVLNV PRLMTQDCLQ QSRKVGDSPN
ITEYMFCAGY SDGSKDSCKG DSGGPHATHY RGTWYLTGIV SWGQGCATVG HFGVYTRVSQ
YIEWLQKLMR SEPRPGVLLR APFPGGGGSG GGGSGGGGSG GGGSGGGGSG GGGSDKTHTC
PPCPAPELLG GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP
QVYTLPPSRD ELTKNQVSLT CLVKGFYPSD IAVEWESNGQ PENNYKTTPP VLDSDGSFFL
YSKLTVDKSR WQQGNVFSCS VMHEALHNHY TQKSLSLSPG KRRRRSGGGG SGGGGSGGGG
SGGGGSGGGG SGGGGSRKRR KRAEVQLVQS GAEVNKPGAS VKVSCKASGY TFTGYYMHWV
RQAPGQGLEW MGWINPNSGG TNYAQKFQGW VTMTRDTSIS TAYMELSRLR SDDTAVYYCA
RGRALYNRND RSPNWFDPWG QGTLVTVSSG SASAPTLKLE EGEFSEARVQ AVLTQPPSVS
VAPGQTARIT CGGNNIGSKS VQWYQQKPGQ APVLVVYDDS DRPSGIPERF SGSNSGNMAT
LTISRVEAGD EADYYCQVWD SSSDHVVFGG GTKLTVLGQP KAAPSVTLFP PSAAAGGGGS
GGGGSGGGGS GGGGSGGGGS GGGGSDKTHT CPPCPAPELL GGPSVFLFPP KPKDTLMISR
TPEVTCVVVD VSHEDPEVKF NWYVDGVEVH NAKTKPREEQ YNSTYRVVSV LTVLHQDWLN
GKEYKCKVSN KALPAPIEKT ISKAKGQPRE PQVYTLPPSR DELTKNQVSL TCLVKGFYPS
DIAVEWESNG QPENNYKTTP PVLDSDGSFF LYSKLTVDKS RWQQGNVFSC SVMHEALHNH
YTQKSLSLSP GK DNA sequence of FVII-027 atggtctccc aggccctcag gctcctctgc cttctgcttg ggcttcaggg ctgcctggct
gcagtcttcg taacccagga ggaagcccac ggcgtcctgc accggcgccg gcgcgccaac
gcgttcctgg aggagctgcg gccgggctcc ctggagaggg agtgcaagga ggagcagtgc
tccttcgagg aggcccggga gatcttcaag gacgcggaga ggacgaagct gttctggatt
tcttacagtg atggggacca gtgtgcctca agtccatgcc agaatggggg ctcctgcaag
gaccagctcc agtcctatat ctgcttctgc ctccctgcct tcgagggccg gaactgtgag -continued

DRAFT SEQUENCE LISTING acgcacaagg atgaccagct gatctgtgtg aacgagaacg gcggctgtga gcagtactgc
agtgaccaca cgggcaccaa gcgctcctgt cggtgccacg aggggtactc tctgctggca
gacggggtgt cctgcacacc cacagttgaa tatccatgtg gaaaaatacc tattctagaa
aaaagaaatg ccagcaaacc ccaaggccga attgtggggg gcaaggtgtg ccccaaaggg
gagtgtccat ggcaggtcct gttgttggtg aatggagctc agttgtgtgg ggggaccctg
atcaacacca tctgggtggt ctccgcggcc cactgtttcg acaaaatcaa gaactggagg
aacctgatcg cggtgctggg cgagcacgac ctcagcgagc acgacgggga tgagcagagc
cggcgggtgg cgcaggtcat catccccagc acgtacgtcc cgggcaccac caaccacgac
atcgcgctgc tccgcctgca ccagcccgtg gtcctcactg accatgtggt gcccctctgc
ctgcccgaac ggacgttctc tgagaggacg ctggccttcg tgcgcttctc attggtcagc
ggctggggcc agctgctgga ccgtggcgcc acggccctgg agctcatggt cctcaacgtg
ccccggctga tgacccagga ctgcctgcag cagtcacgga aggtgggaga ctccccaaat
atcacggagt acatgttctg tgccggctac tcggatggca gcaaggactc ctgcaagggg
gacagtggag gcccacatgc cacccactac cggggcacgt ggtacctgac gggcatcgtc
agctggggcc agggctgcgc aaccgtgggc cactttgggg tgtacaccag ggtctcccag
tacatcgagt ggctgcaaaa gctcatgcgc tcagagccac gcccaggagt cctcctgcga
gccccatttc ccggtggcgg tggctccggc ggaggtgggt ccggtggcgg cggatcaggt
gggggtggat caggcggtgg aggttccggt ggcgggggat ccgacaaaac tcacacatgc
ccaccgtgcc cagctccgga actcctgggc ggaccgtcag tcttcctctt ccccccaaaa
cccaaggaca ccctcatgat ctcccggacc cctgaggtca catgcgtggt ggtggacgtg
agccacgaag accctgaggt caagttcaac tggtacgtgg acggcgtgga ggtgcataat
gccaagacaa agccgcggga ggagcagtac aacagcacgt accgtgtggt cagcgtcctc
accgtcctgc accaggactg gctgaatggc aaggagtaca agtgcaaggt ctccaacaaa
gccctcccag cccccatcga gaaaaccatc tccaaagcca aagggcagcc ccgagaacca
caggtgtaca ccctgccccc atcccgggat gagctgacca agaaccaggt cagcctgacc
tgcctggtca aaggcttcta tcccagcgac atcgccgtgg agtgggagag caatgggcag
ccggagaaca actacaagac cacgcctccc gtgttggact ccgacggctc cttcttcctc
tacagcaagc tcaccgtgga caagagcagg tggcagcagg ggaacgtctt ctcatgctcc
gtgatgcatg aggctctgca caaccactac acgcagaaga gcctctccct gtctccgggt
aaacggcgcc gccggagcgg tggcggcgga tcaggtgggg gtggatcagg cggtggaggt
tccggtggcg gggggatccgg cggtggaggt tccggtgggg gtggatcaag gaagaggagg
aagagggcgg aagtgcagct ggtgcagtct ggagctgagg tgaataagcc tggggcctca
gtgaaggtct cctgcaaggc ttctggatac accttcaccg gctactatat gcactgggtg
cgacaggccc ctggacaagg gcttgagtgg atgggatgga tcaaccctaa cagtggtggc
acaaactatg cacagaagtt tcagggctgg gtcaccatga ccagggacac gtccatcagc
accgcctaca tggagctgag caggctgaga tctgacgaca cggccgtgta ttactgtgcg
agaggccgtg ctttgtataa ccggaacgac cggtccccca actggttcga cccctggggc
cagggaaccc tggtcaccgt ctcctcaggg agtgcatccg ccccaaccct taagcttgaa
gaaggtgaat tctcagaagc acgcgtacag gctgtgctga ctcagccgcc ctcggtgtca
gtggccccag gacagacggc caggattacc tgtgggggaa acaacattgg aagtaaaagt
gtgcagtggt accagcagaa gccaggccag gcccctgtgc tggtcgtcta tgatgatagc
gaccggccct cagggatccc tgagcgattc tctggctcca actctgggaa catggccacc
ctgaccatca gcagggtcga agccggggat gaggccgact attactgtca ggtgtgggat
agtagtagtg atcatgtggt attcggcgga gggaccaagc tgaccgtcct aggtcagccc
aaggctgccc cctcggtcac tctgttcccg ccgtccgcgg ccgctggtgg cggtggctcc
ggcggaggtg ggtccggtgg cggcggatca ggtgggggtg gatcaggcgg tggaggttcc
ggtggcgggg gatcagacaa aactcacaca tgcccaccgt gcccagcacc tgaactcctg
ggaggaccgt cagtcttcct cttcccccca aaacccaagg acaccctcat gatctcccgg
acccctgagg tcacatgcgt ggtggtggac gtgagccacg aagaccctga ggtcaagttc
aactggtacg tggacggcgt ggaggtgcat aatgccaaga caaagccgcg ggaggagcag
tacaacagca cgtaccgtgt ggtcagcgtc ctcaccgtcc tgcaccagga ctggctgaat
ggcaaggagt acaagtgcaa ggtctccaac aaagccctcc cagcccccat cgagaaaacc
atctccaaag ccaaagggca gccccgagaa ccacaggtgt acaccctgcc cccatcccgc
gatgagctga ccaagaacca ggtcagcctg acctgcctgg tcaaaggctt ctatcccagc
gacatcgccg tggagtggga gagcaatggg cagccggaga acaactacaa gaccacgcct
cccgtgttgg actccgacgg ctccttcttc ctctacagca agctcaccgt ggacaagagc
aggtggcagc aggggaacgt cttctcatgc tccgtgatgc atgaggctct gcacaaccac
tacacgcaga agagcctctc cctgtctccg ggtaaatga Genscript-FVII-027-1 DNA sequence
gaagagcctc tccctgtctc cgggtaaacg gcgccgccgg agcggtggcg gcggatcagg
tgggggtgga tcaggcggtg gaggttccgg tggcggggga tccggcggtg gaggttccgg
tgggggtgga tcaaggaaga ggaggaagag ggcggaagtg cagctggtgc agtctggagc
tgaggtgaat aagcctgggg cctcagtgaa ggtctcctgc aaggcttctg gatacacctt
caccggctac tatatgcact gggtgcgaca ggcccctgga caagggcttg agtggatggg
atggatcaac cctaacagtg gtggcacaaa ctatgcacag aagtttcagg gctgggtcac
catgaccagg gacacgtcca tcagcaccgc ctacatggag ctgagcaggc tgagatctga
cgacacggcc gtgtattact gtgcgagagg ccgtgctttg tataaccgga acgaccggtc
ccccaactgg ttcgacccct ggggccaggg aaccctggtc accgtctcct cagggagtgc
atccgcccca acccttaagc ttgaagaagg tgaattc Genscript-FVII-026-2 DNA sequence
gaattctcag aagcacgcgt acaggctgtg ctgactcagc cgccctcggt gtcagtggcc
ccaggacaga cggccaggat tacctgtggg ggaaacaaca ttggaagtaa aagtgtgcag
tggtaccagc agaagccagg ccaggcccct gtgctggtcg tctatgatga tagcgaccgg
ccctcaggga tccctgagcg attctctggc tccaactctg ggaacatggc caccctgacc
atcagcaggg tcgaagccgg ggatgaggcc gactattact gtcaggtgtg ggatagtagt -continued

DRAFT SEQUENCE LISTING agtgatcatg tggtattcgg cggagggacc aagctgaccg tcctaggtca gcccaaggct
gccccctcgg tcactctgtt cccgccgtcc gcggccgctg gtggcggtgg ctccggcgga
ggtgggtccg gtggcggcgg atcaggtggg ggtggatcag gcggtggagg ttccggtggc
gggggatcag acaaaactca cacatgccca ccgtgcccag cacctgaact cctgggagga
ccgtcagtct tcctcttccc cccaaaaccc aaggacaccc tcatgatctc ccggacccct
gaggtcacat gcgtggtggt ggacgtgagc cacgaagacc ctgaggtcaa gttcaactgg
tacgtggacg gcgtggaggt gcataatgcc aagacaaagc cgcgggagga gcagtacaac
agcacgtacc gtgtggtcag cgtcctcacc gtcctgcacc aggactggct gaatggcaag
gagtacaagt gcaaggtctc caacaaagcc ctcccagccc ccatcgagaa aaccatctcc
aaagccaaag ggcagccccg agaaccacag gtgtacaccc tgcccccatc ccgcgatgag
ctgaccaaga accaggtcag cctgacctgc ctggtcaaag gcttctatcc cagcgacatc
gccgtggagt gggagagcaa tgggcagccg gagaacaact acaagaccac gcctcccgtg
ttggactccg acggctcctt cttcctctac agcaagctca ccgtggacaa gagcaggtgg
cagcagggga acgtcttctc atgctccgtg atgcatgagg ctctgcacaa ccactacacg
cagaagagcc tctccctgtc tccgggtaaa tgagaattc FVII-037 amino acid sequence. Signal sequence is shown in dotted underline, propeptide is double underlined, linker region connecting FVII or MB9 to Fc region is underlined, and linker connecting both Fcs sites is shown in bold MVSQALRLLC LLLGLQGCLA AVFVTQEEAH GVLHRRRRAN AFLEELRPGS LERECKEEQC
SFEEAREIFK DAERTKLFWI SYSDGDQCAS SPCQNGGSCK DQLQSYICFC LPAFEGRNCE
HKDDQLICV NENGGCEQYC SDHTGTKRSC RCHEGYSLLA DGVSCTPTVE YPCGKIPILE
KRNASKPQGR IVGGKVCPKG ECPWQVLLLV NGAQLCGGTL INTIWVVSAA HCFDKIKNWR
NLIAVLGEHD LSEHDGDEQS RRVAQVIIPS TYVPGTTNHD IALLRLHQPV VLTDHVVPLC
LPERTFSERT LAFVRFSLVS GWGQLLDRGA TALELMVLNV PRLMTQDCLQ QSRKVGDSPN
ITEYMFCAGY SDGSKDSCKG DSGGPHATHY RGTWYLTGIV SWGQGCATVG HFGVYTRVSQ
YIEWLQKLMR SEPRPGVLLR APFPGGGGSG GGGSGGGGSG GGGSGGGGSG GGGSDKTHTC
PPCPAPELLG GPSVFLFPKK PKDTLMISRT PEVTCVVVDV SHEDPEVKFN WYVDGVEVHN
AKTKPREEQY NSTYRVVSVL TVLHQDWLNG KEYCKCVSNK ALPAPIEKTI SKAKGQPREP
QVYTLPPSRD ELTKNQVSLT CLVKGFYPSD IAVEWESNGQ PENNYKTTPP VLDSDGSFFL
YSKLTVDKSR WQQGNVFSCS VMHEALHNHY TQKSLSLSPG KGGGGSGGGG SGGGGSGGGG
SDKTHTCPPC PAPELLGGPS VFLFPPKPKD TLMISRTPEV TCVVVDVSHE DPEVKFNWYV
DGVEVHNAKT KPREEQYNST YRVVSVLTVL HQDWLNGKEY KCKVSNKALP APIEKTISKA
KGQPREPQVY TLPPSRKELT KNQVSLTCLV KGFYPSDIAV EWESNGQPEN NYKTTPPVLD
SDGSFFLYSK LTVDKSRWQQ GNVFSCSVMH EALHNHYTQK SLSLSPGKGG GGSGGGGSGG
GGSGGGGSGG GGSGGGGSAE VQLVQSGAEV NKPGASVKVS CKASGYTFTG YYMHWVRQAP
GQGLEWMGWI NPNSGGTNYA QKFQGWVTMT RDTSISTAYM ELSRLRSDDT AVYYCARGRA
LYNRNDRSPN WFDPWGQGTL VTVSSGSASA PTLKLEEGEF SEARVQAVLT QPPSVSVAPG
QTARITCGGN NIGSKSVQWY QQKPGQAPVL VVYDDSDRPS GIPERFSGSN SGNMATLTIS
RVEAGDEADY YCQVWDSSSD HVVFGGGTKL TVLGQPKAAP SVTLFPPSAA A FIX-037 DNA sequence atggtctccc aggccctcag gctcctctgc cttctgcttg ggcttcaggg ctgcctggct
gcagtcttcg taacccagga ggaagcccac ggcgtcctgc accggcgccg gcgcgccaac
gcgttcctgg aggagctgcg gccgggctcc ctggagaggg agtgcaagga ggagcagtgc
tccttcgagg aggcccggga gatcttcaag gacgcggaga ggacgaagct gttctggatt
tcttacagtg atggggacca gtgtgcctca agtccatgcc agaatggggg ctcctgcaag
gaccagctcc agtcctatat ctgcttctgc ctccctgcct tcgagggccg gaactgtgag
acgcacaagg atgaccagct gatctgtgtg aacgagaacg gcggctgtga gcagtactgc
agtgaccaca cgggcaccaa gcgctcctgt cggtgccacg aggggtactc tctgctggca
gacggggtgt cctgcacacc cacagttgaa tatccatgtg gaaaaatacc tattctagaa
aaaagaaatg ccagcaaacc ccaaggccga attgtggggg gcaaggtgtg ccccaaaggg
gagtgtccat ggcaggtcct gttgttggtg aatggagctc agttgtgtgg ggggaccctg
atcaacacca tctgggtggt ctccgcggcc cactgtttcg acaaaatcaa gaactggagg
aacctgatcg cggtgctggg cgagcacgac ctcagcgagc acgacgggga tgagcagagc
cggcgggtgg cgcaggtcat catccccagc acgtacgtcc cgggcaccac caaccacgac
atcgcgctgc tccgcctgca ccagcccgtg gtcctcactg accatgtggt gcccctctgc
ctgcccgaac ggacgttctc tgagaggacg ctggccttcg tgcgcttctc attggtcagc
ggctggggcc agctgctgga ccgtggcgcc acggccctgg agctcatggt cctcaacgtg
ccccggctga tgacccagga ctgcctgcag cagtcacgga aggtgggaga ctccccaaat
atcacggagt acatgttctg tgccggctac tcggatggca gcaaggactc ctgcaagggg
gacagtggag gcccacatgc cacccactac cggggcacgt ggtacctgac gggcatcgtc
agctggggcc agggctgcgc aaccgtgggc cactttgggg tgtacaccag ggtctcccag
tacatcgagt ggctgcaaaa gctcatgcgc tcagagccac gcccaggagt cctcctgcga
gccccatttc ccggtggcgg tggctccggc ggaggtgggt ccggtggcgg cggatcaggt
gggggtggat caggcggtgg aggttccggt ggcgggggat ccgacaaaac tcacacatgc
ccaccgtgcc cagctccgga actcctgggc ggaccgtcag tcttcctctt ccccccaaaa
cccaaggaca ccctcatgat ctcccggacc cctgaggtca catgcgtggt ggtggacgtg
agccacgaag accctgaggt caagttcaac tggtacgtgg acggcgtgga ggtgcataat
gccaagacaa agccgcggga ggagcagtac aacagcacgt accgtgtggt cagcgtcctc
accgtcctgc accaggactg gctgaatggc aaggagtaca agtgcaaggt ctccaacaaa
gccctcccag cccccatcga gaaaaccatc tccaaagcca aagggcagcc ccgagaacca
caggtgtaca ccctgccccc atcccgggat gagctgacca agaaccaggt cagcctgacc
tgcctggtca aaggcttcta tcccagcgac atcgccgtgg agtgggagag caatgggcag
ccggagaaca actacaagac cacgcctccc gtgttggact ccgacggctc cttcttcctc
tacagcaagc tcaccgtgga caagagcagg tggcagcagg ggaacgtctt ctcatgctcc
gtgatgcatg aggctctgca caaccactac acgcagaaga gcctctccct gtctccgggt
aaaggtggcg gcggatcagg tgggggtgga tcaggcggtg gaggttccgg tggcggggga -continued

DRAFT SEQUENCE LISTING tcagacaaaa ctcacacatg cccaccgtgc ccagcacctg aactcctggg aggaccgtca
gtcttcctct tccccccaaa acccaaggac accctcatga tctcccggac ccctgaggtc
acatgcgtgg tggtggacgt gagccacgaa gaccctgagg tcaagttcaa ctggtacgtg
gacggcgtgg aggtgcataa tgccaagaca aagccgcggg aggagcagta caacagcacg
taccgtgtgg tcagcgtcct caccgtcctg caccaggact ggctgaatgg caaggagtac
aagtgcaagg tctccaacaa agccctccca gcccccatcg agaaaaccat ctccaaagcc
aaagggcagc cccgagaacc acaggtgtac accctgcccc catcccgcga tgagctgacc
aagaaccagg tcagcctgac ctgcctggtc aaaggcttct atcccagcga catcgccgtg
gagtgggaga gcaatgggca gccggagaac aactacaaga ccacgcctcc cgtgttggac
tccgacggct ccttcttcct ctacagcaag ctcaccgtcg acaagagcag gtggcagcag
gggaacgtct tctcatgctc cgtgatgcat gaggctctgc acaaccacta cacgcagaag
agcctctccc tgtctccggg taaaggtggc ggtggctccg gcggaggtgg gtccggtggc
ggcggatcag gtgggggtgg atcaggcggt ggaggttccg gtggcggggg atcagcggaa
gtgcagctgg tgcagtctgg agctgaggtg aataagcctg gggcctcagt gaaggtctcc
tgcaaggctt ctggatacac cttcaccggc tactatatgc actgggtgcg acaggcccct
ggacaagggc ttgagtggat gggatggatc aaccctaaca gtggtggcac aaactatgca
cagaagtttc agggctgggt caccatgacc agggacacgt ccatcagcac cgcctacatg
gagctgagca ggctgagatc tgacgacacg gccgtgtatt actgtgcgag aggccgtgct
ttgtataacc ggaacgaccg gtcccccaac tggttcgacc cctggggcca gggaaccctg
gtcaccgtct cctcagggag tgcatccgcc ccaaccctta agcttgaaga aggtgaattt
tcagaagcac gcgtacaggc tgtgctgact cagccgccct cggtgtcagt ggccccagga
cagacggcca ggattacctg tgggggaaac aacattggaa gtaaaagtgt gcagtggtac
cagcagaagc caggccaggc ccctgtgctg gtcgtctatg atgatagcga ccggccctca
gggatccctg agcgattctc tggctccaac tctgggaaca tggccaccct gaccatcagc
agggtcgaag ccggggatga ggccgactat tactgtcagg tgtgggatag tagtagtgat
catgtggtat tcggcggagg gaccaagctg accgtcctag gtcagcccaa ggctgccccc
tcggtcactc tgttcccgcc gtccgcggcc gcttga FVII-053 amino acid sequence. Signal sequence is shown in dotted underline, linker region connecting FVII to Fc region is underlined, linker connecting both Fcs sites is shown in bold, and MB9 is italicized MVSQALRLLC LLLGLQGCLA *AEVQLVQSGA EVNKPGASVK VSCKASGYTF TGYYMHWVRQ*
*APGQGLEWMG WINPNSGGTN YAQKFQGWVT MTRDTSISTA YMELSRLRSD DTAVYYCARG*
*RALYNRNDRS PNWFDPWGQG TLVTVSSGSA SAPTLKLEEG EFSEARVQAV LTQPPSVSVA*
*PGQTARITCG GNNIGSKSVQ WYQQKPGQAP VLVVYDDSDR PSGIPERFSG SNSGNMATLT*
*ISRVEAGDEA DYYCQVWDSS SDHVVFGGGT KLTVLGQPKA APSVTLFPPS* AAARTKLFWI
SYSDGDQCAS SPCQNGGSCK DQLQSYICFC LPAFEGRNCE THKDDQLICV NENGGCEQYC
SDHTGTKRSC RCHEGYSLLA DGVSCTPTVE YPCGKIPILE KRNASKPQGR RKRRKRIVGG
KVCPKGECPW QVLLLVNGAQ LCGGTLINTI WVVSAAHCFD KIKNWRNLIA VLGEHDLSEH
DGDEQSRRVA QVIIPSTYVP GTTNHDIALL RLHQPVVLTD HVVPLCLPER TFSERTLAFV
RFSLVSGWGQ LLDRGATALE LMVLNVPRLM TQDCLQQSRK VGDSPNITEY MFCAGYSDGS
KDSCKGDSGG PHATHYRGTW YLTGIVSWGQ GCATVGHFGV YTRVSQYIEW LQKLMRSEPR
PGVLLRAPFP GGGGSGGGGS GGGGSGGGGS GGGGSGGGGS DKTHTCPPCP APELLGGPSV
FLFPPKPKDT LMISRTPEVT CVVVDVSHED PEVKFNWYVD GVEVHNAKTK PREEQYNSTY
RVVSVLTVLH QDWLNGKEYK CKVSNKALPA PEIKTISKAK GQPREPQVYT LPPSRDELTK
NQVSLTCLVK GFYPSDIAVE WESNGQPENN YKTTPPVLDS DGSFFLYSKL TVDKSRWQQG
NVFSCSVMHE ALHNHYTQKS LSLSPGKGGG GSGGGGSGGG GSGGGGSDKT HTCPPCPAPE
LLGGPSVFLF PPKPKDTLMI SRTPEVTCVV VDVSHEDPEV KFNWYVDGVE VHNAKTKPRE
EQYNSTYRVV SVLTVLHQDW LNGKEYKCKV SNKALPAPIE KTISKAKGQP REPQVYTLPP
SRDELTKNQV SLTCLVKGFY PSDIAVEWES NGQPENNYKT TPPVLDSDGS FFLYSKLTVD
KSRWQQGNVF SCSVMHEALH NHYTQKSLSL SPGK FVII-053 DNA sequence atggtctccc aggccctcag gctcctctgc cttctgcttg ggcttcaggg ctgcctggct
gcggaagtgc agctggtgca gtctggagct gaggtgaata agcctggggc ctcagtgaag
gtctcctgca aggcttctgg atacaccttc accggctact atatgcactg ggtgcgacag
gcccctggac aagggcttga gtggatggga tggatcaacc ctaacagtgg tggcacaaac
tatgcacaga agtttcaggg ctgggtcacc atgaccaggg acacgtccat cagcaccgcc
tacatggagc tgagcaggct gagatctgac gacacggccg tgtattactg tgcgagaggc
cgtgctttgt ataaccggaa cgaccggtcc cccaactggt tcgacccctg gggccaggga
accctggtca ccgtctcctc agggagtgca tccgccccaa cccttaaact tgaagaaggt
gaattttcag aagcacgcgt acaggctgtg ctgactcagc cgccctcggt gtcagtggcc
ccaggacaga cggccaggat tacctgtggg ggaaacaaca ttggaagtaa aagtgtgcag
tggtaccagc agaagccagg ccaggcccct gtgctggtcg tctatgatga tagcgaccgg
ccctcaggga tccctgagcg attctctggc tccaactctg ggaacatggc caccctgacc
atcagcaggg tcgaagccgg ggatgaggcc gactattact gtcaggtgtg ggatagtagt
agtgatcatg tggtattcgg cggagggacc aagctgaccg tcctaggtca gcccaaggct
gcccccctcgg tcactctgtt cccgccgtcc gcggccgcta ggacgaagct gttctggatt
tcttacagtg atggggacca gtgtgcctca agtccatgcc agaatggggg ctcctgcaag
gaccagctcc agtcctatat ctgcttctgc ctccctgcct tcgagggccg gaactgtgag
acgcacaagg atgaccagct gatctgtgtg aacgagaacg gcggctgtga gcagtactgc
agtgaccaca cgggcaccaa gcgctcctgt cggtgccacg aggggtactc tctgctggca
gacggggtgt cctgcacacc cacagttgaa tatccatgtg gaaaaatacc tattctagaa
aaaagaaatg ccagcaaacc ccaaggccga aggaagagga ggaagaggat tgtgggggc
aaggtgtgcc ccaaagggga gtgtccatgg caggtcctgt tgttggtgaa tggagctcag
ttgtgtgggg ggaccctgat caacaccatc tgggtggtct ccgcggccca ctgtttcgac
aaaatcaaga actggaggaa cctgatcgcg gtgctgggcg agcacgacct cagcgagcac
gacggggatg agcagagccg gcgggtggcg caggtcatca tccccagcac gtacgtcccg -continued

DRAFT SEQUENCE LISTING

```
ggcaccacca accacgacat cgcgctgctc cgcctgcacc agcccgtggt cctcactgac
catgtggtgc ccctctgcct gcccgaacgg acgttctctg agaggacgct ggccttcgtg
cgcttctcat tggtcagcgg ctggggccag ctgctggacc gtggcgccac ggccctggag
ctcatggtcc tcaacgtgcc ccggctgatg acccaggact gcctgcagca gtcacggaag
gtgggagact ccccaaatat cacggagtac atgttctgtg ccggctactc ggatggcagc
aaggactcct gcaaggggga cagtggaggc ccacatgcca cccactaccg gggcacgtgg
tacctgacgg gcatcgtcag ctggggccag ggctgcgcaa ccgtgggcca ctttggggtg
tacaccaggg tctcccagta catcgagtgg ctgcaaaagc tcatgcgctc agagccacgc
ccaggagtcc tcctgcgagc cccatttccc ggtggcggtg gctccggcgg aggtgggtcc
ggtggcggcg gatcaggtgg gggtggatca ggcggtggag gttccggtgg cgggggatcc
gacaaaactc acacatgccc accgtgccca gctccggaac tcctgggcgg accgtcagtc
ttcctcttcc ccccaaaacc caaggacacc ctcatgatct cccggacccc tgaggtcaca
tgcgtggtgg tggacgtgag ccacgaagac cctgaggtca agttcaactg gtacgtggac
ggcgtggagg tgcataatgc caagacaaag ccgcgggagg agcagtacaa cagcacgtac
cgtgtggtca gcgtcctcac cgtcctgcac caggactggc tgaatggcaa ggagtacaag
tgcaaggtct ccaacaaagc cctcccagcc cccatcgaga aaaccatctc caaagccaaa
gggcagcccc gagaaccaca ggtgtacacc ctgcccccat cccgggatga gctgaccaag
aaccaggtca gcctgacctg cctggtcaaa ggcttctatc ccagcgacat cgccgtggag
tgggagagca atgggcagcc ggagaacaac tacaagacca cgcctcccgt gttggactcc
gacggctcct tcttcctcta cagcaagctc accgtggaca agagcaggtg gcagcagggg
aacgtcttct catgctccgt gatgcatgag gctctgcaca accactacac gcagaagagc
ctctccctgt ctccgggtaa aggtggcggc ggatcaggtg gggtggatc aggcggtgga
ggttccggtg gcgggggatc cgacaaaact cacacatgcc caccgtgccc agcacctgaa
ctcctgggag gaccgtcagt cttcctcttc cccccaaaac ccaaggacac cctcatgatc
tcccggaccc ctgaggtcac atgcgtggtg gtggacgtga gccacgaaga ccctgaggtc
aagttcaact ggtacgtgga cggcgtggag gtgcataatg ccaagacaaa gccgcgggag
gagcagtaca acagcacgta ccgtgtggtc agcgtcctca ccgtcctgca ccaggactgg
ctgaatggca aggagtacaa gtgcaaggtc tccaacaaag ccctcccagc ccccatcgag
aaaaccatct ccaaagccaa agggcagccc cgagaaccac aggtgtacac cctgccccca
tcccgcgatg agctgaccaa gaaccaggtc agcctgacct gcctggtcaa aggcttctat
cccagcgaca tcgccgtgga gtgggagagc aatgggcagc cggagaacaa ctacaagacc
acgcctcccg tgttggactc cgacggctcc ttcttcctct acagcaagct caccgtggac
aagagcaggt ggcagcaggg gaacgtcttc tcatgctccg tgatgcatga ggctctgcac
aaccactaca cgcagaagag cctctccctg tctccgggta aatga
```

FVII-044 amino acid sequence. Signal sequence is shown in dotted underline, propeptide is double underlined, linker region connecting FVII or PS4 or Fc region is underlined, linker connecting both Fcs sites is shown in bold, and PS4 peptide is italicized MVSQALRLLC LLLGLQGCLA AVFVTQEEAH GVLHRRRRAN AFLEELRPGS LERECKEEQC
SFEEAREIFK DAERTKLFWI SYSDGDQCAS SPCQNGGSCK DQLQSYICFC LPAFEGRNCE
THKDDQLICV NENGGCEQYC SDHTGTKRSC RCHEGYSLLA DGVSCTPTVE YPCGKIPILE
KRNASKPQGR IVGGKVCPKG ECPWQVLLLV NGAQLCGGTL INTIWVVSAA HCFDKIKVWR
NLIAVLGEED LSEEDGDEQS RRVAQVIIPS TYVPGTTNHD IALLRLHQPV VLTDHVVPLC
LPERTFSERT LAFVRFSLVS GWGQLLDRGA TALELMVLNV PRLMTQDCLQ QSRKVGDSPM
ITEYMFCAGY SDGSKDSCKG DSGGPHATHY RGTWYLTGIV SWGQGCATVG HFGVYTRVSQ
YIEWLQKLMR SEPRPGVLLR APFPGGGGSG GGGSGGGGSG GGGSGGGGSG GGGSDKTHTC
PPCPAPELLG GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP
QVYTLPPSRD ELTKNQVSLT CLVKGFYPSD IAVEWESNGQ PENNYKTTPP VLDSDGSFFL
YSKLTVDKSR WQQGNVFSCS VMHEALHNHY TQKSLSLSPG KGGGGSGGGG SGGGGSGGGG
SDKTHTCPPC PAPELLGGPS VFLFPPKPKD TLMISRTPEV TCVVVDVSHE DPEVKFNWYV
DGVEVHNAKT KPREEQYNST YRVVSVLTVL HQDWLNGKEY KCKVSNKALP APIEKTISKA
KGQPREPQVY TLPPSRDELT KNQVSLTCLV KGFYPSDIAV EWESNGQPEN NYKTTPPVLD
SDGSFFLYSK LTVDKSRWQQ GNVFSCSVMH EALHNHYTQK SLSLSPGKGG GGSGGGGSGG
GGSGGGG*SAC TERWALHNLC GG*

FVII-044 DNA sequence

```
atggtctccc aggccctcag gctcctctgc cttctgcttg ggcttcaggg ctgcctggct
gcagtcttcg taacccagga ggaagcccac ggcgtcctgc accggcgccg gcgcgccaac
gcgttcctgg aggagctgcg gccgggctcc ctggagaggg agtgcaagga ggagcagtgc
tccttcgagg aggcccggga gatcttcaag gacgcggaga ggacgaagct gttctggatt
tcttacagtg atggggacca gtgtgcctca agtccatgcc agaatggggg ctcctgcaag
gaccagctcc agtcctatat cygcttctgc ctccctgcct tcgagggccg gaactgtgag
acgcacaagg atgaccagct gatctgtgtg aacgagaacg gcggctgtga gcagtactgc
agtgaccaca cgggcaccaa gcgctcctgt cggtgccacg aggggtactc tctgctggca
gacggggtgt cctgcacacc cacagttgaa tatccatgtg gaaaaatacc tattctagaa
aaaagaaatg ccagcaaacc ccaaggccga attgtggggg gcaaggtgtg ccccaaaggg
gagtgtccat ggcaggtcct gttgttggtg aatggagctc agttgtgtgg ggggaccctg
atcaacacca tctgggtggt ctccgcggcc cactgtttcg acaaaatcaa gaactggagg
aacctgatcg cggtgctggg cgagcacgac ctcagcgagc acgacgggga tgagcagagc
cggcgggtgg cgcaggtcat catccccagc acgtacgtcc cgggcaccac caaccacgac
atcgcgctgc tccgcctgca ccagcccgtg gtcctcactg accatgtggt gcccctctgc
ctgcccgaac ggacgttctc tgagaggacg ctggccttcg tgcgcttctc attggtcagc
ggctggggcc agctgctgga ccgtggcgcc acggccctgg agctcatggt cctcaacgtg
ccccggctga tgacccagga ctgcctgcag cagtcacgga aggtgggaga ctccccaaat
atcacggagt acatgttctg tgccggctac tcggatggca gcaaggactc ctgcaagggg
gacagtggag gcccacatgc cacccactac cggggcacgt ggtacctgac gggcatcgtc
```

-continued

DRAFT SEQUENCE LISTING agctggggcc agggctgcgc aaccgtgggc cactttgggg tgtacaccag ggtctcccag
tacatcgagt ggctgcaaaa gctcatgcgc tcagagccac gcccaggagt cctcctgcga
gccccatttc ccggtggcgg tggctccggc ggaggtgggt ccggtggcgg cggatcaggt
gggggtggat caggcggtgg aggttccggt ggcgggggat ccgacaaaac tcacacatgc
ccaccgtgcc cagctccgga actcctgggc ggaccgtcag tcttcctctt ccccccaaaa
cccaaggaca ccctcatgat ctcccggacc cctgaggtca catgcgtggt ggtggacgtg
agccacgaag accctgaggt caagttcaac tggtacgtgg acggcgtgga ggtgcataat
gccaagacaa agccgcggga ggagcagtac aacagcacgt accgtgtggt cagcgtcctc
accgtcctgc accaggactg gctgaatggc aaggagtaca agtgcaaggt ctccaacaaa
gccctcccag cccccatcga gaaaaccatc tccaaagcca aagggcagcc ccgagaacca
caggtgtaca ccctgccccc atcccgggat gagctgacca agaaccaggt cagcctgacc
tgcctggtca aaggcttcta tcccagcgac atcgccgtgg agtgggagag caatgggcag
ccggagaaca actacaagac cacgcctccc gtgttggact ccgacggctc cttcttcctc
tacagcaagc tcaccgtgga caagagcagg tggcagcagg ggaacgtctt ctcatgctcc
gtgatgcatg aggctctgca caaccactac acgcagaaga gcctctccct gtctccgggt
aaaggtggcg gcggatcagg tgggggtgga tcaggcggtg gaggttccgg tggcggggga
tcagacaaaa ctcacacatg cccaccgtgc ccagcacctg aactcctggg aggaccgtca
gtcttcctct tccccccaaa acccaaggac accctcatga tctcccggac ccctgaggtc
acatgcgtgg tggtggacgt gagccacgaa gaccctgagg tcaagttcaa ctggtacgtg
gacggcgtgg aggtgcataa tgccaagaca aagccgcggg aggagcagta caacagcacg
taccgtgtgg tcagcgtcct caccgtcctg caccaggact ggctgaatgg caaggagtac
aagtgcaagg tctccaacaa agccctccca gcccccatcg agaaaaccat ctccaaagcc
aaagggcagc cccgagaacc acaggtgtac accctgcccc catcccgcga tgagctgacc
aagaaccagg tcagcctgac ctgcctggtc aaaggcttct atcccagcga catcgccgtg
gagtgggaga gcaatgggca gccggagaac aactacaaga ccacgcctcc cgtgttggac
tccgacggct ccttcttcct ctacagcaag ctcaccgtcg acaagagcag gtggcagcag
gggaacgtct tctcatgctc cgtgatgcat gaggctctgc acaaccacta cacgcagaag
agcctctccc tgtctccggg taaaggtggc ggcggatcag gtgggggtgg atcaggcggt
ggaggttccg gtggcggggg atcagcctgc accgagcggt gggccctgca caacctgtgc
ggcgggtga FVII-045 amino acid sequence. Signal sequence is shown in dotted underline, propeptide is double underlined, linker region connecting FVII or OSI to Fc region is underlined, linker connecting both Fcs sites is shown in bold, and OSI peptide is italicized MVSQALRLLC LLLGLQGCLA AVFVTQEEAH GVLHRRRRAN AFLEELRPGS LERECKEEQC
SFEEAREIFK DAERTKLFWI SYSDGDQCAS SPCQNGGSCK DQLQSYICFC LPAFEGRNCE
THKDDQLICV NENGGCEQYC SDHTGTKRSC RCHEGYSLLA DGVSCTPTVE YPCGKIPILE
KRNASKPQGR IVGGKVCPKG ECPWQVLLLV NGAQLCGGTL INTIWVVSAA HCFDKIKNWR
NLIAVLGEHD LSEHDGDEQS RRVAQVIIPS TYVPGTTNHD IALLRLHQPV VLTDHVVPLC
LPERTFSERT LAFVRFSLVS GWGQLLDRGA TALELMVLNV PRLMTQDCLQ QSRKVGDSPN
ITEYMFCAGY SDGSKDSCKG DSGGPHATHY RGTWYLTGIV SWGQGCATVG HFGVYTRVSQ
YIEWLQKLMR SEPRPGVLLR APFPGGGGSG GGGSGGGGSG GGGSGGGGSG GGGSDKTHTC
PPCPAPELLG GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP
QVYTLPPSRD ELTKNQVSLT CLVKGFYPSD IAVEWESNGQ PENNYKTTPP VLDSDGSFFL
YSKLTVDKSR WQQGNVFSCS VMHEALHNHY TQKSLSLSPG KGGGGSGGGG SGGGGSGGGG
SDKTHTCPPC PAPELLGGPS VFLFPPKPKD TLMISRTPEV TCVVVDVSHE DPEVKFVWYV
DGVEVHNAKT KPREEQYNST YRVVSVLTVL HQDWLNGKEY KCKVSNKALP APIEKTISKA
KGQPREPQVY TLPPSRDELT KNQVSLTCLV KGFYPSDIAV EWESNGQPEN NYKTTPPVLD
SDGSFFLYSK LTVDKSRWQQ GNVFSCSVMH EALHNHYTQK SLSLSPGKGG GGSGGGGSGG
GGSGGGGS*AC TERMALHNLC GG*

FVII-045 DNA sequence atggtctccc aggccctcag gctcctctgc cttctgcttg ggcttcaggg ctgcctggct
gcagtcttcg taacccagga ggaagcccac ggcgtcctgc accggcgccg gcgcgccaac
gcgttcctgg aggagctgcg gccgggctcc ctggagaggg agtgcaagga ggagcagtgc
tccttcgagg aggcccggga gatcttcaag gacgcggaga ggacgaagct gttctggatt
tcttacagtg atggggacca gtgtgcctca agtccatgcc agaatggggg ctcctgcaag
gaccagctcc agtcctatat ctgcttctgc ctccctgcct tcgagggccg gaactgtgag
acgcacaagg atgaccagct gatctgtgtg aacgagaacg gcggctgtga gcagtactgc
agtgaccaca cgggcaccaa gcgctcctgt cggtgccacg aggggtactc tctgctggca
gacggggtgt cctgcacacc cacagttgaa tatccatgtg gaaaaatacc tattctagaa
aaaagaaatg ccagcaaacc ccaaggccga attgtggggg gcaaggtgtg ccccaaaggg
gagtgtccat ggcaggtcct gttgttggtg aatggagctc agttgtgtgg ggggaccctg
atcaacacca tctgggtggt ctccgcggcc cactgtttcg acaaaatcaa gaactggagg
aacctgatcg cggtgctggg cgagcacgac ctcagcgagc acgacgggga tgagcagagc
cggcgggtgg cgcaggtcat catccccagc acgtacgtcc cgggcaccac caaccacgac
atcgcgctgc tccgcctgca ccagcccgtg gtcctcactg accatgtggt gcccctctgc
ctgcccgaac ggacgttctc tgagaggacg ctggccttcg tgcgcttctc attggtcagc
ggctggggcc agctgctgga ccgtggcgcc acggccctgg agctcatggt cctcaacgtg
ccccggctga tgacccagga ctgcctgcag cagtcacgga aggtgggaga ctccccaaat
atcacggagt acatgttctg tgccggctac tcggatggca gcaaggactc ctgcaagggg
gacagtggag gcccacatgc cacccactac cggggcacgt ggtacctgac gggcatcgtc
agctggggcc agggctgcgc aaccgtgggc cactttgggg tgtacaccag ggtctcccag
tacatcgagt ggctgcaaaa gctcatgcgc tcagagccac gcccaggagt cctcctgcga
gccccatttc ccggtggcgg tggctccggc ggaggtgggt ccggtggcgg cggatcaggt
gggggtggat caggcggtgg aggttccggt ggcgggggat ccgacaaaac tcacacatgc -continued

DRAFT SEQUENCE LISTING ccaccgtgcc cagctccgga actcctgggc ggaccgtcag tcttcctctt ccccccaaaa
cccaaggaca ccctcatgat ctcccggacc cctgaggtca catgcgtggt ggtggacgtg
agccacgaag accctgaggt caagttcaac tggtacgtgg acggcgtgga ggtgcataat
gccaagacaa agccgcggga ggagcagtac aacagcacgt accgtgtggt cagcgtcctc
accgtcctgc accaggactg gctgaatggc aaggagtaca agtgcaaggt ctccaacaaa
gccctcccag cccccatcga gaaaaccatc tccaaagcca aagggcagcc ccgagaacca
caggtgtaca ccctgccccc atcccgggat gagctgacca agaaccaggt cagcctgacc
tgcctggtca aaggcttcta tcccagcgac atcgccgtgg agtgggagag caatgggcag
ccggagaaca actacaagac cacgcctccc gtgttggact ccgacggctc cttcttcctc
tacagcaagc tcaccgtgga caagagcagg tggcagcagg ggaacgtctt ctcatgctcc
gtgatgcatg aggctctgca caaccactac acgcagaaga gcctctccct gtctccgggt
aaaggtggcg gcggatcagg tgggggtgga tcaggcggtg gaggttccgg tggcggggga
tcagacaaaa ctcacacatg cccaccgtgc ccagcacctg aactcctggg aggaccgtca
gtcttcctct tccccccaaa acccaaggac accctcatga tctcccggac ccctgaggtc
acatgcgtgg tggtggacgt gagccacgaa gaccctgagg tcaagttcaa ctggtacgtg
gacggcgtgg aggtgcataa tgccaagaca aagccgcggg aggagcagta caacagcacg
taccgtgtgg tcagcgtcct caccgtcctg caccaggact ggctgaatgg caaggagtac
aagtgcaagg tctccaacaa agccctccca gcccccatcg agaaaaccat ctccaaagcc
aaagggcagc cccgagaacc acaggtgtac accctgcccc catcccgcga tgagctgacc
aagaaccagg tcagcctgac ctgcctggtc aaaggcttct atcccagcga catcgccgtg
gagtgggaga gcaatgggca gccggagaac aactacaaga ccacgcctcc cgtgttggac
tccgacggct ccttcttcct ctacagcaag ctcaccgtcg acaagagcag gtggcagcag
gggaacgtct tctcatgctc cgtgatgcat gaggctctgc acaaccacta cacgcagaag
agcctctccc tgtctccggg taaaggtggc ggcggatcag gtgggggtgg atcaggcggt
ggaggttccg gtggcggggg atcagcctgc accgagcgga tggccctgca caacctgtgc
ggcgggtga FVII-046 amino acid sequence. Signal sequence is shown in dotted underline, propeptide is double underlined, linker region connecting FVII or OS2 to Fc region is underlined, linker connecting both Fcs sites is shown in bold, and OS2 peptide is italicized MVSQALRLLC LLLGLQGCLA AVFVTQEEAH GVLHRRRRAN AFLEELRPGS LERECKEEQC
SFEEAREIFK DAERTKLFWI SYSDGDQCAS SPCQNGGSCK DQLQSYICFC LPAFEGRNCE
THKDDQLICV NENGGCEQYC SDHTGTKRSC RCHEGYSLLA DGVSCTPTVE YPCGKIPILE
KRNASKPQGR IVGGKVCPKG ECPWQVLLLV NGAQLCGGTL INTIWVVSAA HCFDKIKNWR
NLIAVLGEHD LSEHDGDEQS RRVAQVIIPS TYVPGTTNHD IALLRLHQPV VLTDHVVPLC
LPERTFSERT LAFVRFSLVS GWGQLLDRGA TALELMVLNV PRLMTQDCLQ QSRKVGDSPN
ITEYMFCAGY SDGSKDSCKG DSGGPHATHY RGTWYLTGIV SWGQGCATVG HFGVYTRVSQ
YIEWLQKLMR SEPRPGVLLR APFPGGGGSG GGGSGGGGSG GGGSGGGGSG GGGSDKTHTC
PPCPAPELLG GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP
QVYTLPPSRD ELTKNQVSLT CLVKGFYPSD IAVEWESNGQ PENNYKTTPP VLDSDGSFFL
YSKLTVDKSR WQQGNVFSCS VMHEALHNHY TQKSLSLSPG KGGGGSGGGG SGGGGSGGGG
SDKTHTCPPC PAPELLGGPS VFLFPPKPKD TLMISRTPEV TCVVVDVSHE DPEVKFNWYV
DGVEVHNAKT KPREEQYNST YRVVSVLTVL HQDWLNGKEY KCKVSNKALP APIEKTISKA
KGQPREPQVY TLPPSRDELT KNQVSLTCLV KGFYPSDIAV EWESNGQPEN NYKTTPPVLD
SDGSFFLYSK LTVDKSRWQQ GNVFSCSVMH EALHNHYTQK SLSLSPGKGG GGSGGGGSGG
GGSGGGGS*AC TERDALHNLC GG*

FVII-046 DNA sequence atggtctccc aggccctcag gctcctctgc cttctgcttg ggcttcaggg ctgcctggct
gcagtcttcg taacccagga ggaagcccac ggcgtcctgc accggcgccg gcgcgccaac
gcgttcctgg aggagctgcg gccgggctcc ctggagaggg agtgcaagga ggagcagtgc
tccttcgagg aggcccggga gatcttcaag gacgcggaga ggacgaagct gttctggatt
tcttacagtg atggggacca gtgtgcctca agtccatgcc agaatggggg ctcctgcaag
gaccagctcc agtcctatat ctgcttctgc ctccctgcct tcgagggccg gaactgtgag
acgcacaagg atgaccagct gatctgtgtg aacgagaacg gcggctgtga gcagtactgc
agtgaccaca cgggcaccaa gcgctcctgt cggtgccacg aggggtactc tctgctggca
gacggggtgt cctgcacacc cacagttgaa tatccatgtg gaaaaatacc tattctagaa
aaaagaaatg ccagcaaacc ccaaggccga attgtggggg gcaaggtgtg ccccaaaggg
gagtgtccat ggcaggtcct gttgttggtg aatggagctc agttgtgtgg ggggaccctg
atcaacacca tctgggtggt ctccgcggcc cactgtttcg acaaaatcaa gaactggagg
aacctgatcg cggtgctggg cgagcacgac ctcagcgagc acgacgggga tgagcagagc
cggcgggtgg cgcaggtcat catccccagc acgtacgtcc cgggcaccac caaccacgac
atcgcgctgc tccgcctgca ccagcccgtg gtcctcactg accatgtggt gcccctctgc
ctgcccgaac ggacgttctc tgagaggacg ctggccttcg tgcgcttctc attggtcagc
ggctggggcc agctgctgga ccgtggcgcc acggccctgg agctcatggt cctcaacgtg
ccccggctga tgacccagga ctgcctgcag cagtcacgga aggtgggaga ctccccaaat
atcacggagt acatgttctg tgccggctac tcggatggca gcaaggactc ctgcaagggg
gacagtggag gcccacatgc cacccactac cggggcacgt ggtacctgac gggcatcgtc
agctggggcc agggctgcgc aaccgtgggc cactttgggg tgtacaccag ggtctcccag
tacatcgagt ggctgcaaaa gctcatgcgc tcagagccac gcccaggagt cctcctgcga
gccccatttc ccggtggcgg tggctccggc ggaggtgggt ccggtggcgg cggatcaggt
gggggtggat caggcggtgg aggttccggt ggcgggggat ccgacaaaac tcacacatgc
ccaccgtgcc cagctccgga actcctgggc ggaccgtcag tcttcctctt ccccccaaaa
cccaaggaca ccctcatgat ctcccggacc cctgaggtca catgcgtggt ggtggacgtg
agccacgaag accctgaggt caagttcaac tggtacgtgg acggcgtgga ggtgcataat
gccaagacaa agccgcggga ggagcagtac aacagcacgt accgtgtggt cagcgtcctc
accgtcctgc accaggactg gctgaatggc aaggagtaca agtgcaaggt ctccaacaaa

DRAFT SEQUENCE LISTING gccctcccag cccccatcga gaaaaccatc tccaaagcca aagggcagcc ccgagaacca
caggtgtaca ccctgccccc atcccgggat gagctgacca agaaccaggt cagcctgacc
tgcctggtca aaggcttcta tcccagcgac atcgccgtgg agtgggagag caatgggcag
ccggagaaca actacaagac cacgcctccc gtgttggact ccgacggctc cttcttcctc
tacagcaagc tcaccgtgga caagagcagg tggcagcagg ggaacgtctt ctcatgctcc
gtgatgcatg aggctctgca caaccactac acgcagaaga gcctctccct gtctccgggt
aaaggtggcg gcggatcagg tgggggtgga tcaggcggtg gaggttccgg tggcggggga
tcagacaaaa ctcacacatg cccaccgtgc ccagcacctg aactcctggg aggaccgtca
gtcttcctct tccccccaaa acccaaggac accctcatga tctcccggac ccctgaggtc
acatgcgtgg tggtggacgt gagccacgaa gaccctgagg tcaagttcaa ctggtacgtg
gacggcgtgg aggtgcataa tgccaagaca aagccgcggg aggagcagta caacagcacg
taccgtgtgg tcagcgtcct caccgtcctg caccaggact ggctgaatgg caaggagtac
aagtgcaagg tctccaacaa agccctccca gcccccatcg agaaaaccat ctccaaagcc
aaagggcagc cccgagaacc acaggtgtac accctgcccc catcccgcga tgagctgacc
aagaaccagg tcagcctgac ctgcctggtc aaaggcttct atcccagcga catcgccgtg
gagtgggaga gcaatgggca gccggagaac aactacaaga ccacgcctcc cgtgttggac
tccgacggct ccttcttcct ctacagcaag ctcaccgtcg acaagagcag gtggcagcag
gggaacgtct tctcatgctc cgtgatgcat gaggctctgc acaaccacta cacgcagaag
agcctctccc tgtctccggg taaaggtggc ggcggatcag gtgggggtgg atcaggcggt
ggaggttccg gtggcggggg atcagcctgc accgagcggg acgccctgca caacctgtgc
ggcgggtga FVII-047 amino acid sequence. Signal sequence is shown in dotted underline, propeptide is double underlined, linker region connecting FVII or PS4 to Fc regions is underlined, and PS4 peptide is italicized <u>MVSQALRLLC LLLGLQGCLA</u> <u>AVFVTQEEAH GVLHRRRR</u>AN AFLEELRPGS LERECKEEQC
SFEEAREIFK DAERTKLFWI SYSDGDQCAS SPCQNGGSCK DQLQSYICFC LPAFEGRNCE
THKDDQLICV NENGGCEQYC SDHTGTKRSC RCHEGYSLLA DGVSCTPTVE YPCGKIPILE
KRNASKPQGR IVGGKVCPKG ECPWQVLLLV NGAQLCGGTL INTIWVVSAA HCFDKIKNWR
NLIAVLGEHD LSEHDGDEQS RRVAQVIIPS TYVPGTTNHD IALLRLHQPV VLTDHVVPLC
LPERTFSERT LAFVRFSLVS GWGQLLDRGA TALELMVLNV PRLMTQDCLQ QSRKVGDSPN
ITEYMFCAGY SDGSKDSCKG DSGGPHATHY RGTWYLTGIV SWGQGCATVG HFGVYTRVSQ
YIEWLQKLMR SEPRPGVLLR APF<u>PGGGGSG GGGSGGGGSG GGGSGGGGSG GGGS</u>DKTHTC
PPCPAPELLG GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP
QVYTLPPSRD ELTKNQVSLT CLVKGFYPSD IAVEWESNGQ PENNYKTTPP VLDSDGSFFL
YSKLTVDKSR WQQGNVFSCS VMHEALHNHY TQKSLSLSPG K<u>GGGGSGGGG SGGGGSGGGG</u>
<u>SGGGGSGGGG S</u>*ACTERWALH NLC*<u>GGGGSGG GGSGGGGSGG GGSGGGGSGG GGSD</u>KTHTCP
PCPAPELLGG PSVFLFPPKP KDTLMISRTP EVTCVVVDVS HEDPEVKFNW YVDGVEVHNA
KTKPREEQYN STYRVVSVLT VLHQDWLNGK EYKCKVSNKA LPAPIEKTIS KAKGQPREPQ
VYTLPPSRDE LTKNQVSLTC LVKGFYPSDI AVEWESNGQP ENNYKTTPPV LDSDGSFFLY
SKLTVDKSRW QQGNVFSCSV MHEALHNHYT QKSLSLSPGK FVII-047 DNA sequence atggtctccc aggccctcag gctcctctgc cttctgcttg ggcttcaggg ctgcctggct
gcagtcttcg taacccagga ggaagcccac ggcgtcctgc accggcgccg gcgcgccaac
gcgttcctgg aggagctgcg gccgggctcc ctggagaggg agtgcaagga ggagcagtgc
tccttcgagg aggcccggga gatcttcaag gacgcggaga ggacgaagct gttctggatt
tcttacagtg atggggacca gtgtgcctca agtccatgcc agaatggggg ctcctgcaag
gaccagctcc agtcctatat ctgcttctgc ctccctgcct tcgagggccg gaactgtgag
acgcacaagg atgaccagct gatctgtgtg aacgagaacg gcggctgtga gcagtactgc
agtgaccaca cgggcaccaa gcgctcctgt cggtgccacg aggggtactc tctgctggca
gacggggtgt cctgcacacc cacagttgaa tatccatgtg gaaaaatacc tattctagaa
aaaagaaatg ccagcaaacc ccaaggccga attgtggggg gcaaggtgtg ccccaaaggg
gagtgtccat ggcaggtcct gttgttggtg aatggagctc agttgtgtgg ggggaccctg
atcaacacca tctgggtggt ctccgcggcc cactgtttcg acaaaatcaa gaactggagg
aacctgatcg cggtgctggg cgagcacgac ctcagcgagc acgacgggga tgagcagagc
cggcgggtgg cgcaggtcat catccccagc acgtacgtcc cgggcaccac caaccacgac
atcgcgctgc tccgcctgca ccagcccgtg gtcctcactg accatgtggt gcccctctgc
ctgcccgaac ggacgttctc tgagaggacg ctggccttcg tgcgcttctc attggtcagc
ggctggggcc agctgctgga ccgtggcgcc acggccctgg agctcatggt cctcaacgtg
ccccggctga tgacccagga ctgcctgcag cagtcacgga aggtgggaga ctccccaaat
atcacggagt acatgttctg tgccggctac tcggatggca gcaaggactc ctgcaagggg
gacagtggag gcccacatgc caccactac cggggcacgt ggtacctgac gggcatcgtc
agctggggcc agggctgcgc aaccgtgggc cactttgggg tgtacaccag ggtctcccag
tacatcgagt ggctgcaaaa gctcatgcgc tcagagccac gcccaggagt cctcctgcga
gccccatttc ccggtggcgg tggctccggc ggaggtgggt ccggtggcgg cggatcaggt
gggggtggat caggcggtgg aggttccggt ggcgggggat ccgacaaaac tcacacatgc
ccaccgtgcc cagctccgga actcctggga ggaccgtcag tcttcctctt ccccccaaaa
cccaaggaca ccctcatgat ctcccggacc cctgaggtca catgcgtggt ggtggacgtg
agccacgaag accctgaggt caagttcaac tggtacgtgg acggcgtgga ggtgcataat
gccaagacaa agccgcggga ggagcagtac aacagcacgt accgtgtggt cagcgtcctc
accgtcctgc accaggactg gctgaatggc aaggagtaca agtgcaaggt ctccaacaaa
gccctcccag cccccatcga gaaaaccatc tccaaagcca aagggcagcc ccgagaacca
caggtgtaca ccctgccccc atcccgggat gagctgacca agaaccaggt cagcctgacc
tgcctggtca aaggcttcta tcccagcgac atcgccgtgg agtgggagag caatgggcag
ccggagaaca actacaagac cacgcctccc gtgttggact ccgacggctc cttcttcctc
tacagcaagc tcaccgtcga caagagcagg tggcagcagg ggaacgtctt ctcatgctcc -continued

DRAFT SEQUENCE LISTING gtgatgcatg aggctctgca caaccactac acgcagaaga gcctctccct gtctccgggt
aaaggcggtg gcggttcagg tggaggaggg tcaggcggtg gtggatccgg cgggggcgga
tccggtggcg gagggtcagg cggtggcgga tcagcctgca ccgagcggtg ggccctgcac
aacctgtgcg gtggcggtgg ctccggcgga ggtgggtccg gtggcggcgg atcaggtggg
ggtggatcag gcggtggagg ttccggtggc gggggatccg acaaaactca cacatgccca
ccgtgcccag caccggaact cctgggcgga ccgtcagtct tcctcttccc cccaaaaccc
aaggacaccc tcatgatctc ccggacccct gaggtcacat gcgtggtggt ggacgtgagc
cacgaagacc ctgaggtcaa gttcaactgg tacgtggacg gcgtggaggt gcataatgcc
aagacaaagc cgcgggagga gcagtacaac agcacgtacc gtgtggtcag cgtcctcacc
gtcctgcacc aggactggct gaatggcaag gagtacaagt gcaaggtctc caacaaagcc
ctcccagccc ccatcgagaa aaccatctcc aaagccaaag ggcagccccg agaaccacag
gtgtacaccc tgcccccatc ccgggatgag ctgaccaaga accaggtcag cctgacctgc
ctggtcaaag gcttctatcc cagcgacatc gccgtggagt gggagagcaa tgggcagccg
gagaacaact acaagaccac gcctcccgtg ttggactccg acggctcctt cttcctctac
agcaagctca ccgtggacaa gagcaggtgg cagcagggga acgtcttctc atgctccgtg
atgcatgagg ctctgcacaa ccactacacg cagaagagcc tctccctgtc tccgggtaaa
tga FVII-048 amino acid sequence. Signal sequence is shown in dotted underline, propeptide is double underlined, linker region connecting FVII or OS1 to Fc regions is underlined, and OS1 peptide is italicized MVSQALRLLC LLLGLQGCLA AVFVTQEEAH GVLHRRRRAN AFLEELRPGS LERECKEEQC
SFEEAREIFK DAERTKLFWI SYSDGDQCAS SPCQNGGSCK DQLQSYICFC LPAFEGRNCE
THKDDQLICV NENGGCEQYC SDHTGTKRSC RCHEGYSLLA DGVSCTPTVE YPCGKIPILE
KRNASKPQGR IVGGKVCPKG ECPWQVLLLV NGAQLCGGTL INTIWVVSAA HCFDKIKNWR
NLIAVLGEHD LSEHDGDEQS RRVAQVIIPS TYVPGTTNHD IALLRLHQPV VLTDHVVPLC
LPERTFSERT LAFVRFSLVS GWGQLLDRGA TALELMVLNV PRLMTQDCLQ QSRKVGDSPN
ITEYMFCAGY SDGSKDSCKG DSGGPHATHY RGTWYLTGIV SWGQGCATVG HFGVYTRVSQ
YIEWLQKLMR SEPRPGVLLR APFPGGGGSG GGGSGGGGSG GGGSGGGGSG GGGSDKTHTC
PPCPAPELLG GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP
QVYTLPPSRD ELTKNQVSLT CLVKGFYPSD IAVEWESNGQ PENNYKTTPP VLDSDGSFFL
YSKLTVDKSR WQQGNVFSCS VMHEALHNHY TQKSLSLSPG KGGGGSGGGG SGGGGSGGGG
SGGGGSGGGG S*ACTERMALH NLC*GGGGSGG GGSGGGGSGG GGSGGGGSGG GGSDKTHTCP
PCPAPELLGG PSVFLFPPKP KDTLMISRTP EVTCVVVDVS HEDPEVKFNW YVDGVEVHNA
KTKPREEQYN STYRVVSVLT VLHQDWLNGK EYKCKVSNKA LPAPIEKTIS KAKGQPREPQ
VYTLPPSRDE LTKNQVSLTC LVKGFYPSDI AVEWESNGQP ENNYKTTPPV LDSDGSFFLY
SKLTVDKSRW QQGNVFSCSV MHEALHNHYT QKSLSLSPGK DNA sequence of FVII-048 atggtctccc aggccctcag gctcctctgc cttctgcttg ggcttcaggg ctgcctggct
gcagtcttcg taacccagga ggaagcccac ggcgtcctgc accggcgccg gcgcgccaac
gcgttcctgg aggagctgcg gccgggctcc ctggagaggg agtgcaagga ggagcagtgc
tccttcgagg aggcccggga gatcttcaag gacgcggaga ggacgaagct gttctggatt
tcttacagtg atggggacca gtgtgcctca agtccatgcc agaatggggg ctcctgccag
gaccagctcc agtcctatat ctgcttctgc ctccctgcct tcgagggccg gaactgtgag
acgcacaagg atgaccagct gatctgtgtg aacgagaacg gcggctgtga gcagtactgc
agtgaccaca cgggcaccaa gcgctcctgt cggtgccacg aggggtactc tctgctggca
gacggggtgt cctgcacacc cacagttgaa tatccatgtg gaaaaatacc tattctagaa
aaaagaaatg ccagcaaacc ccaaggccga attgtggggg gcaaggtgtg ccccaaaggg
gagtgtccat ggcaggtcct gttgttggtg aatggagctc agttgtgtgg ggggaccctg
atcaacacca tctgggtggt ctccgcggcc cactgtttcg acaaaatcaa gaactggagg
aacctgatcg cggtgctggg cgagcacgac ctcagcgagc acgacgggga tgagcagagc
cggcgggtgg cgcaggtcat catccccagc acgtacgtcc cgggcaccac caaccacgac
atcgcgctgc tccgcctgca ccagcccgtg gtcctcactg accatgtggt gcccctctgc
ctgcccgaac ggacgttctc tgagaggacg ctggccttcg tgcgcttctc attggtcagc
ggctggggcc agctgctgga ccgtggcgcc acggccctgg agctcatggt cctcaacgtg
ccccggctga tgacccagga ctgcctgcag cagtcacgga aggtgggaga ctccccaaat
atcacggagt acatgttctg tgccggctac tcggatggca gcaaggactc ctgcaagggg
gacagtggag gcccacatgc cacccactac cggggcacgt ggtacctgac gggcatcgtc
agctggggcc agggctgcgc aaccgtgggc cactttgggg tgtacaccag ggtctcccag
tacatcgagt ggctgcaaaa gctcatgcgc tcagagccac gcccaggagt cctcctgcga
gccccatttc ccggtggcgg tggctccggc ggaggtgggt ccggtggcgg cggatcaggt
gggggtggat caggcggtgg aggttccggt ggcgggggat ccgacaaaac tcacacatgc
ccaccgtgcc cagctccgga actcctggga ggaccgtcag tcttcctctt ccccccaaaa
cccaaggaca ccctcatgat ctcccggacc cctgaggtca catgcgtggt ggtggacgtg
agccacgaag accctgaggt caagttcaac tggtacgtgg acggcgtgga ggtgcataat
gccaagacaa agccgcggga ggagcagtac aacagcacgt accgtgtggt cagcgtcctc
accgtcctgc accaggactg gctgaatggc aaggagtaca agtgcaaggt ctccaacaaa
gccctcccag cccccatcga gaaaaccatc tccaaagcca aagggcagcc ccgagaacca
caggtgtaca ccctgccccc atcccgggat gagctgacca agaaccaggt cagcctgacc
tgcctggtca aaggcttcta tcccagcgac atcgccgtgg agtgggagag caatgggcag
ccggagaaca actacaagac cacgcctccc gtgttggact ccgacggctc cttcttcctc
tacagcaagc tcaccgtcga caagagcagg tggcagcagg ggaacgtctt ctcatgctcc
gtgatgcatg aggctctgca caaccactac acgcagaaga gcctctccct gtctccgggt
aaaggcggtg gcggttcagg tggaggaggg tcaggcggtg gtggatccgg cgggggcgga
tccggtggcg gagggtcagg cggtggcgga tcagcctgca ccgagcggat ggccctgcac
aacctgtgcg gtggcggtgg ctccggcgga ggtgggtccg gtggcggcgg atcaggtggg -continued

DRAFT SEQUENCE LISTING

```
ggtggatcag gcggtggagg ttccggtggc gggggatccg acaaaactca cacatgccca
ccgtgcccag caccggaact cctgggcgga ccgtcagtct tcctcttccc cccaaaaccc
aaggacaccc tcatgatctc ccggacccct gaggtcacat gcgtggtggt ggacgtgagc
cacgaagacc ctgaggtcaa gttcaactgg tacgtggacg gcgtggaggt gcataatgcc
aagacaaagc cgcgggagga gcagtacaac agcacgtacc gtgtggtcag cgtcctcacc
gtcctgcacc aggactggct gaatggcaag gagtacaagt gcaaggtctc caacaaagcc
ctcccagccc ccatcgagaa aaccatctcc aaagccaaag ggcagccccg agaaccacag
gtgtacaccc tgcccccatc ccgggatgag ctgaccaaga accaggtcag cctgacctgc
ctggtcaaag gcttctatcc cagcgacatc gccgtggagt gggagagcaa tgggcagccg
gagaacaact acaagaccac gcctcccgtg ttggactccg acggctcctt cttcctctac
agcaagctca ccgtggacaa gagcaggtgg cagcagggga acgtcttctc atgctccgtg
atgcatgagg ctctgcacaa ccactacacg cagaagagcc tctccctgtc tccgggtaaa
tga
```

FVII-049 amino acid sequence. Signal sequence is shown in dotted underline, propeptide is double underlined, linker region connecting FVII or OS2 to Fc regions is underlined, and OS2 peptide is italicized

```
MVSQALRLLC LLLGLQGCLA AVFVTQEEAH GVLHRRRRAN AFLEELRPGS LERECKEEQC
SFEEAREIFK DAERTKLFWI SYSDGDQCAS SPCQNGGSCK DQLQSYICFC LPAFEGRNCE
THKDDQLICV NENGGCEQYC SDHTGTKRSC RCHEGYSLLA DGVSCTPTVE YPCGKIPILE
KRNASKPQGR IVGGKVCPKG ECPWQVLLLV NGAQLCGGTL INTIWVVSAA HCFDKIKNWR
NLIAVLGEHD LSEHDGDEQS RRVAQVIIPS TYVPGTTNHD IALLRLHQPV VLTDHVVPLC
LPERTFSERT LAFVRFSLVS GWGQLLDRGA TALELMVLNV PRLMTQDCLQ QSRKVGDSPN
ITEYMFCAGY SDGSKDSCKG DSGGPHATHY RGTWYLTGIV SWGQGCATVG HFGVYTRVSQ
YIEWLQKLMR SEPRPGVLLR APFPGGGGSG GGGSGGGGSG GGGSGGGGSG GGGSDKTHTC
PPCPAPELLG GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP
QVYTLPPSRD ELTKNQVSLT CLVKGFYPSD IAVEWESNGQ PENNYKTTPP VLDSDGSFFL
YSKLTVDKSR WQQGNVFSCS VMHEALHNHY TQKSLSLSPG KGGGGSGGGG SGGGGSGGGG
SGGGGSGGGG SACTERDALH NLCGGGGSGG GGSGGGGSGG GGSGGGGSGG GGSDKTHTCP
PCPAPELLGG PSVFLFPPKP KDTLMISRTP EVTCVVVDVS HEDPEVKFNW YVDGVEVHNA
KTKPREEQYN STYRVVSVLT VLHQDWLNGK EYKCKVSNKA LPAPIEKTIS KAKGQPREPQ
VYTLPPSRDE LTKNQVSLTC LVKGFYPSDI AVEWESNGQP ENNYKTTPPV LDSDGSFFLY
SKLTVDKSRW QQGNVFSCSV MHEALHNHYT QKSLSLSPGK
```

DNA sequence of FVII-049

```
atggtctccc aggccctcag gctcctctgc cttctgcttg ggcttcaggg ctgcctggct
gcagtcttcg taacccagga ggaagcccac ggcgtcctgc accggcgccg gcgcgccaac
gcgttcctgg aggagctgcg gccgggctcc ctggagaggg agtgcaagga ggagcagtgc
tccttcgagg aggcccggga gatcttcaag gacgcggaga ggacgaagct gttctggatt
tcttacagtg atggggacca gtgtgcctca agtccatgcc agaatggggg ctcctgcaag
gaccagctcc agtcctatat ctgcttctgc ctccctgcct tcgagggccg gaactgtgag
acgcacaagg atgaccagct gatctgtgtg aacgagaacg gcggctgtga gcagtactgc
agtgaccaca cgggcaccaa gcgctcctgt cggtgccacg aggggtactc tctgctggca
gacggggtgt cctgcacacc cacagttgaa tatccatgtg gaaaaatacc tattctagaa
aaaagaaatg ccagcaaacc ccaaggccga attgtggggg gcaaggtgtg ccccaaaggg
gagtgtccat ggcaggtcct gttgttggtg aatggagctc agttgtgtgg ggggaccctg
atcaacacca tctgggtggt ctccgcggcc cactgtttcg acaaaatcaa gaactggagg
aacctgatcg cggtgctggg cgagcacgac ctcagcgagc acgacgggga tgagcagagc
cggcgggtgg cgcaggtcat catccccagc acgtacgtcc cgggcaccac caaccacgac
atcgcgctgc tccgcctgca ccagcccgtg gtcctcactg accatgtggt gcccctctgc
ctgcccgaac ggacgttctc tgagaggacg ctggccttcg tgcgcttctc attggtcagc
ggctggggcc agctgctgga ccgtggcgcc acggccctgg agctcatggt cctcaacgtg
ccccggctga tgacccagga ctgcctgcag cagtcacgga aggtgggaga ctccccaaat
atcacggagt acatgttctg tgccggctac tcggatggca gcaaggactc ctgcaagggg
gacagtggag gcccacatgc cacccactac cggggcacgt ggtacctgac gggcatcgtc
agctggggcc agggctgcgc aaccgtgggc cactttgggg tgtacaccag ggtctcccag
tacatcgagt ggctgcaaaa gctcatgcgc tcagagccac gcccaggagt cctcctgcga
gccccatttc ccggtggcgg tggctccggc ggaggtgggt ccggtggcgg cggatcaggt
gggggtggat caggcggtgg aggttccggt ggcgggggat ccgacaaaac tcacacatgc
ccaccgtgcc cagctccgga actcctggga ggaccgtcag tcttcctctt ccccccaaaa
cccaaggaca ccctcatgat ctcccggacc cctgaggtca catgcgtggt ggtggacgtg
agccacgaag accctgaggt caagttcaac tggtacgtgg acggcgtgga ggtgcataat
gccaagacaa agccgcggga ggagcagtac aacagcacgt accgtgtggt cagcgtcctc
accgtcctgc accaggactg gctgaatggc aaggagtaca agtgcaaggt ctccaacaaa
gccctcccag cccccatcga gaaaaccatc tccaaagcca aagggcagcc ccgagaacca
caggtgtaca ccctgccccc atcccgggat gagctgacca agaaccaggt cagcctgacc
tgcctggtca aaggcttcta tcccagcgac atcgccgtgg agtgggagag caatgggcag
ccggagaaca actacaagac cacgcctccc gtgttggact ccgacggctc cttcttcctc
tacagcaagc tcaccgtcga caagagcagg tggcagcagg ggaacgtctt ctcatgctcc
gtgatgcatg aggctctgca caaccactac acgcagaaga gcctctccct gtctccgggt
aaaggcggtg gcggttcagg tggaggaggg tcaggcggtg gtggatccgg cgggggcgga
tccggtggcg gagggtcagg cggtggcgga tcagcctgca ccgagcggga cgccctgcac
aacctgtgcg gtggcggtgg ctccggcgga ggtgggtccg gtggcggcgg atcaggtggg
ggtggatcag gcggtggagg ttccggtggc gggggatccg acaaaactca cacatgccca
ccgtgcccag caccggaact cctgggcgga ccgtcagtct tcctcttccc cccaaaaccc
aaggacaccc tcatgatctc ccggacccct gaggtcacat gcgtggtggt ggacgtgagc
cacgaagacc ctgaggtcaa gttcaactgg tacgtggacg gcgtggaggt gcataatgcc
```

-continued

DRAFT SEQUENCE LISTING aagacaaagc cgcgggagga gcagtacaac agcacgtacc gtgtggtcag cgtcctcacc
gtcctgcacc aggactggct gaatggcaag gagtacaagt gcaaggtctc caacaaagcc
ctcccagccc ccatcgagaa aaccatctcc aaagccaaag ggcagccccg agaaccacag
gtgtacaccc tgcccccatc ccgggatgag ctgaccaaga accaggtcag cctgacctgc
ctggtcaaag gcttctatcc cagcgacatc gccgtggagt gggagagcaa tgggcagccg
gagaacaact acaagaccac gcctcccgtg ttggactccg acggctcctt cttcctctac
agcaagctca ccgtggacaa gagcaggtgg cagcagggga acgtcttctc atgctccgtg
atgcatgagg ctctgcacaa ccactacacg cagaagagcc tctccctgtc tccgggtaaa
tga FVII-011 amino acid sequence. Signal sequence is shown in dotted underline, propeptide is double underlined, Gla domain is italicized, linker region connecting FVII to Fc region is underlined, and linker connecting both Fcs sites is shown in bold MVSQALRLLC LLLGLQGCLA AVFVTQEEAH GVLHRRRR*AN AFLEELRPGS LERECKEEQC*
*SFEEAREIFK DAE*RTKLFWI SYSDGDQCAS SPCQNGGSCK DQLQSYICFC LPAFEGRNCE
THKDDQLICV NENGGCEQYC SDHTGTKRSC RCHEGYSLLA DGVSCTPTVE YPCGKIPILE
KRNASKPQGR IVGGKVCPKG ECPWQVLLLV NGAQLCGGTL INTIWVVSAA HCFDKIKNWR
NLIAVLGEHD LSEHDGDEQS RRVAQVIIPS TYVPGTTNHD IALLRLHQPV VLTDHVVPLC
LPERTFSERT LAFVRFSLVS GWGQLLDRGA TAKELMVLNV PRLMTQDCLQ QSRKVGDSPN
ITEYMFCAGY SDGSKDSCKG DSGGPHATHY RGTWYLTGIV SWGQGCATVG HFGVYTRVSQ
YIEWLQKLMR SEPRPGVLLR APFPGGGGSF GGGSGGGGSG GGGSGGGGSG GGGSDKTHTC
PPCPAPELLG GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP
QVYTLPPSRD ELTKNQVSLT CLVKGFYPSD IAVEWESNGQ PENNYKTTPP VLDSDGSFFL
YSKLTVDKSR WQQGNVFSCS VMHEALHNHY TQKSLSLSPG KGGGGSGGGG SGGGGSGGGG
SDKTHTCPPC PAPELLGGPS VFLFPPKPKD TLMISRTPEV TCVVVDVSHE DPEVKFNWYV
DGVEVHNAKT KPREEQYNST YRVVSVLTVL HQDWLNGKEY KCKVSNKALP APIEKTISKA
KGQPREPQVY TLPPSRDELT KNQVSLTCLV KGFYPSDIAV EWESNGQPEN NYKTTPPVLD
SDGSFFLYSK LTVDKSRWQQ GNVFSCSVMH EALHNHYTQK SLSLSPGK FVII-011 DNA sequence
atggtctccc aggccctcag gctcctctgc cttctgcttg ggcttcaggg ctgcctggct
gcagtcttcg taacccagga ggaagcccac ggcgtcctgc accggcgccg gcgcgccaac
gcgttcctgg aggagctgcg gccgggctcc ctggagaggg agtgcaagga ggagcagtgc
tccttcgagg aggcccggga gatcttcaag gacgcggaga ggacgaagct gttctggatt
tcttacagtg atggggacca gtgtgcctca agtccatgcc agaatggggg ctcctgcaag
gaccagctcc agtcctatat ctgcttctgc ctccctgcct tcgagggccg gaactgtgag
acgcacaagg atgaccagct gatctgtgtg aacgagaacg gcggctgtga gcagtactgc
agtgaccaca cgggcaccaa gcgctcctgt cggtgccacg aggggtactc tctgctggca
gacggggtgt cctgcacacc cacagttgaa tatccatgtg gaaaaatacc tattctagaa
aaaagaaatg ccagcaaacc ccaaggccga attgtggggg gcaaggtgtg ccccaaaggg
gagtgtccat ggcaggtcct gttgttggtg aatggagctc agttgtgtgg ggggaccctg
atcaacacca tctgggtggt ctccgcggcc cactgtttcg acaaaatcaa gaactggagg
aacctgatcg cggtgctggg cgagcacgac ctcagcgagc acgacgggga tgagcagagc
cggcgggtgg cgcaggtcat catccccagc acgtacgtcc cgggcaccac caaccacgac
atcgcgctgc tccgcctgca ccagcccgtg gtcctcactg accatgtggt gcccctctgc
ctgcccgaac ggacgttctc tgagaggacg ctggccttcg tgcgcttctc attggtcagc
ggctggggcc agctgctgga ccgtggcgcc acggccctgg agctcatggt cctcaacgtg
ccccggctga tgacccagga ctgcctgcag cagtcacgga aggtgggaga ctccccaaat
atcacggagt acatgttctg tgccggctac tcggatggca gcaaggactc ctgcaagggg
gacagtggag gcccacatgc cacccactac cggggcacgt ggtacctgac gggcatcgtc
agctggggcc agggctgcgc aaccgtgggc cactttgggg tgtacaccag ggtctcccag
tacatcgagt ggctgcaaaa gctcatgcgc tcagagccac gcccaggagt cctcctgcga
gccccatttc ccggtggcgg tggctccggc ggaggtgggt ccggtggcgg cggatcaggt
gggggtggat caggcggtgg aggttccggt ggcgggggat ccgacaaaac tcacacatgc
ccaccgtgcc cagctccgga actcctgggc ggaccgtcag tcttcctctt ccccccaaaa
cccaaggaca ccctcatgat ctcccggacc cctgaggtca catgcgtggt ggtggacgtg
agccacgaag accctgaggt caagttcaac tggtacgtgg acggcgtgga ggtgcataat
gccaagacaa agccgcggga ggagcagtac aacagcacgt accgtgtggt cagcgtcctc
accgtcctgc accaggactg gctgaatggc aaggagtaca agtgcaaggt ctccaacaaa
gccctcccag cccccatcga gaaaaccatc tccaaagcca aagggcagcc ccgagaacca
caggtgtaca ccctgccccc atcccgggat gagctgacca agaaccaggt cagcctgacc
tgcctggtca aaggcttcta tcccagcgac atcgccgtgg agtgggagag caatgggcag
ccggagaaca actacaagac cacgcctccc gtgttggact ccgacggctc cttcttcctc
tacagcaagc tcaccgtgga caagagcagg tggcagcagg ggaacgtctt ctcatgctcc
gtgatgcatg aggctctgca caaccactac acgcagaaga gcctctccct gtctccgggt
aaaggtggcg gcggatcagg tgggggtgga tcaggcggtg gaggttccgg tggcggggga
tcagacaaaa ctcacacatg cccaccgtgc ccagcacctg aactcctggg aggaccgtca
gtcttcctct tccccccaaa acccaaggac accctcatga tctcccggac ccctgaggtc
acatgcgtgg tggtggacgt gagccacgaa gaccctgagg tcaagttcaa ctggtacgtg
gacggcgtgg aggtgcataa tgccaagaca aagccgcggg aggagcagta caacagcacg
taccgtgtgg tcagcgtcct caccgtcctg caccaggact ggctgaatgg caaggagtac
aagtgcaagg tctccaacaa agccctccca gcccccatcg agaaaaccat ctccaaagcc
aaagggcagc cccgagaacc acaggtgtac accctgcccc catcccgcga tgagctgacc
aagaaccagg tcagcctgac ctgcctggtc aaaggcttct atcccagcga catcgccgtg
gagtgggaga gcaatgggca gccggagaac aactacaaga ccacgcctcc cgtgttggac
tccgacggct ccttcttcct ctacagcaag ctcaccgtgg acaagagcag gtggcagcag -continued

DRAFT SEQUENCE LISTING gggaacgtct tctcatgctc cgtgatgcat gaggctctgc acaaccacta cacgcagaag
agcctctccc tgtctccggg taaatga B domain deleted FVIII amino acid sequence: Signal peptide underlined; 14 amino acid linker (containing the remaining B domain) between the HC and LC sequence is double underlined, with the S743/Q1638 fusion site indicated in bold.

1 MQIELSTCFF LCLLRFCFSA TRRYYLGAVE LSWDYMQSDL GELPVDARFP
51 PRVPKSFPFN TSVVYKKTLF VEFTDHLFNI AKPRPPWMGL LGPTIQAEVY
101 DTVVITLKNM ASHPVSLHAV GVSYWKASEG AEYDDQTSQR EKEDDKVFPG
151 GSHTYVWQVL KENGPMASDP LCLTYSYLSH VDLVKDLNSG LIGALLVCRE
201 GSLAKEKTQT LHKFILLFAV FDEGKSWHSE TKNSLMQDRD AASARAWPKM
251 HTVNGYVNRS LPGLIGCHRK SVYWHVIGMG TTPEVHSIFL EGHTFLVRNH
301 RQASLEISPI TFLTAQTLLM DLGQFLLFCH ISSHQHDGME AYVKVDSCPE
351 EPQLRMKNNE EAEDYDDDLT DSEMDVVRFD DDNSPSFIQI PSVAKKHPKT
401 WVHYIAAEEE DWDYAPLVLA PDDRSYKSQY LNNGPQRIGR KYKKVRFMAY
451 TDETFKTREA IQHESGILGP LLYGEVGDTL LIIFKNQASR PYNIYPHGIT
501 DVRPLYSRRL PKGVKHLKDF PILPGEIFKY KWTVTVEDGP TKSDPRCLTR
551 YYSSFVNMER DLASGLIGPL LICYKESVDQ RGNQIMSDKR NVILFSVFDE
601 NRSWYLTENI QRFLPNPAGV QLEDPEFQAS NIMHSINGYV FDSLQLSVCL
651 HEVAYWYILS IGAQTDFLSV FFSGYTFKHK MVYEDTLTLF PFSGETVFMS
701 MENPGLWILG CHNSDFRNRG MTALLKVSSC DKNTGDYYED SYEDISAYLL
751 SKNNAIEPRS FSQNPPVLKR HQREITRTTL QSDQEEIDYD DTISVEMKKE
801 DFDIYDEDEN QSPRSFQKKT RHYFIAAVER LWDYGMSSSP HVLRNRAQSG
851 SVPQFKKVVF QEFTDGSFTQ PLYRGELNEH LGLLGPYIRA EVEDNIMVTF
901 RNQASRPYSF YSSLISYEED QRQGAEPRKN FVKPNETKTY FWKVQHHMAP
951 TKDEFDCKAW AYFSDVDLEK DVHSGLIGPL LVCHTNTLNP AHGRQVTVQE
1001 FALFFTIFDE TKSWYFTENM ERNCRAPCNI QMEDPTFKEN YRFHAINGYI
1051 MDTLPGLVMA QDQRIRWYLL SMGSNENIHS IHFSGHVFTV RKKEEYKMAL
1101 YNLYPGVFET VEMLPSKAGI WRVECLIGEH LHAGMSTLFL VYSNKCQTPL
1151 GMASGHIRDF QITASGQYGQ WAPKLARLHY SGISNAWSTK EPFSWIKVDL
1201 LAPMIIHGIK TQGARQKFSS LYISQFIIMY SLDGKKWQTY RGNSTGTLMV
1251 FFGNVDSSGI KHNIFNPPII ARYIRLHPTH YSIRSTLRME LMGCDLNSCS
1301 MPLGMESKAI SDAQITASSY FTNMFATWSP SKARLHLQGR SNAWRPQVNN
1351 PKEWLQVDFQ KTMKVTGVTT QGVKSLLTSM YVKEFLISSS QDGHQWTLFF
1401 QNGKVKVFQG NQDSFTPVVN SLDPPLLTRY LRIHPQSWVH QIALRMEVLG
1451 CEAQDLY

Full length FVIII amino acid sequence: Signal peptide underlined

1 MQIELSTCFF LCLLRFCFSA TRRYYLGAVE LSWDYMQSDL GELPVDARFP
51 PRVPKSFPFN TSVVYKKTLF VEFTDHLFNI AKPRPPWMGL LGPTIQAEVY
101 DTVVITLKNM ASHPVSLHAV GVSYWKASEG AEYDDQTSQR EKEDDKVFPG
151 GSHTYVWQVL KENGPMASDP LCLTYSYLSH VDLVKDLNSG LIGALLVCRE
201 GSLAKEKTQT LHKFILLFAV FDEGKSWHSE TKNSLMQDRD AASARAWPKM
251 HTVNGYVNRS LPGLIGCHRK SVYWHVIGMG TTPEVHSIFL EGHTFLVRNH
301 RQASLEISPI TFLTAQTLLM DLGQFLLFCH ISSHQHDGME AYVKVDSCPE
351 EPQLRMKNNE EAEDYDDDLT DSEMDVVRFD DDNSPSFIQI RSVAKKHPKT
401 WVHYIAAEEE DWDYAPLVLA PDDRSYKSQY LNNGPQRIGR KYKKVRFMAY
451 TDETFKTREA IQHESGILGP LLYGEVGDTL LIIFKNQASR PYNIYPHGIT
501 DVRPLYSRRL PKGVKHLKDF PILPGEIFKY KWTVTVEDGP TKSDPRCLTR
551 YYSSFVNMER DLASGLIGPL LICYKESVDQ RGNQIMSDKR NVILFSVFDE
601 NRSWYLTENI QRFLPNPAGV QLEDPEFQAS NIMHSINGYV FDSLQLSVCL
651 HEVAYWYILS IGAQTDFLSV FFSGYTFKHK MVYEDTLTLF PFSGETVFMS
701 MENPGLWILG CHNSDFRNRG MTALLKVSSC DKNTGDYYED SYEDISAYLL
751 SKNNAIEPRS FSQNSRHPST RQKQFNATTI PENDIEKTDP WFAHRTPMPK
801 IQNVSSSDLL MLLRQSPTPH GLSLSDLQEA KYETFSDDPS PGAIDSNNSL
851 SEMTHFRPQL HHSGDMVFTP ESGLQLRLNE KLGTTAATEL KKLDFKVSST
901 SNNLISTIPS DNLAAGTDNT SSLGPPSMPV HYDSQLDTTL FGKKSSPLTE
951 SGGPLSLSEE NNDSKLLESG LMNSQESSWG KNVSSTESGR LFKGKRAHGP
1001 ALLTKDNALF KVSISLLKTN KTSNNSATNR KTHIDGPSLL IENSPSVWQN
1051 ILESDTEFKK VTPLIHDRML MDKNATALRL NHMSNKTTSS KNMEMVQQKK
1101 EGPIPPDAQN PDMSFFKMLF LPESARWIQR THGKNSLNSG QGPSPKQLVS
1151 LGPEKSVEGQ NFLSEKNKVV VGKGEFTKDV GLKEMVFPSS RNLFLTNLDN
1201 LHENNTHNQE KKIQEEIEKK ETLIQENVVL PQIHTVTGTK NFMKNLFLLS
1251 TRQNVEGSYD GAYAPVLQDF RSLNDSTNRT KKHTAHFSKK GEEENLEGLG
1301 NQTKQIVEKY ACTTRISPNT SQQNFVTQRS KRALKQFRLP LEETELEKRI
1351 IVDDTSTQWS KNMKHLTPST LTQIDYNEKE KGAITQSPLS DCLTRSHSIP
1401 QANRSPLPIA KVSSFPSIRP IYLTRVLFQD NSSHLPAASY RKKDSGVQES
1451 SHFLQGAKKN NLSLAILTLE MTGDQREVGS LGTSATNSVT YKKVENTVLP
1501 KPDLPKTSGK VELLPKVHIY QKDLFPTETS NGSPGHLDLV EGSLLQGTEG
1551 AIKWNEANRP GKVPFLRVAT ESSAKTPSKL LDPLAWDNHY GTQIPKEEWK
1601 SQEKSPEKTA FKKKDTILSL NACESNHAIA AINEGQNKPE IEVTWAKQGR
1651 TERLCSQNPP VLKRHQREIT RTTLQSDQEE IDYDDTISVE MKKEDFDIYD
1701 EDENQSPRSF QKKTRHYFIA AVERLWDYGM SSSPHVLRNR AQSGSVPQFK
1751 KVVFQEFTDG SFTQPLYRGE LNEHLGLLGP YIRAEVEDNI MVTFRNQASR
1801 PYSFYSSLIS YEEDQRQGAE PRKNFVKPNE TKTYFWKVQH HMAPTKDEFD
1851 CKAWAYFSDV DLEKDVHSGL IGPLLVCHTN TLNPAHGRQV TVQEFALFFT

-continued

DRAFT SEQUENCE LISTING

```
1901 IFDETKSWYF TENMERNCRA PCNIQMEDPT FKENYRFHAI NGYIMDTLPG
1951 LVMAQDQRIR WYLLSMGSNE NIHSIHFSGH VFTVRKKEEY KMALYNLYPG
2001 VFETVEMLPS KAGIWRVECL IGEHLHAGMS TLFLVYSNKC QTPLGMASGH
2051 IRDFQITASG QYGQWAPKLA RLHYSGSINA WSTKEPFSWI KVDLLAPMII
2101 HGIKTQGARQ KFSSLYISQF IIMYSLDGKK WQTYRGNSTG TLMVFFGNVD
2151 SSGIKHNIFN PPIIARYIRL HPTHYSIRST LRMELMGCDL NSCSMPLGME
2201 SKAISDAQIT ASSYFTNMFA TWSPSKARLH LQGRSNAWRP QVNNPKEWLQ
2251 VDFQKTMKVT GVTTQGVKSL LTSMYVKEFL ISSSQDGHQW TLFFQNGKVK
2301 VFQGNQDSFT PVVNSLDPPL LTRYLRIHPQ SWVHQIALRM EVLGCEAQDL
2351 Y
```

FIX amino acid sequence. Signal sequence is shown in dotted underline, propeptide is double underlined

```
MQRVNMIMAE SPGLITICLL GYLLSAECTV FLDHENANKI LNRPKRYNSG KLEEFVQGNL
ERECMEEKCS FEEAREVFEN TERTTEFWKQ YVDGDQCESN PCLNGGSCKD DINSYECWCP
FGFEGKNCEL DVTCNIKNGR CEQFCKNSAD NKVVCSCTEG YRLAENQKSC EPAVPFPCGR
VSVSQTSKLT RAETVFPDVD YVNSTEAETI LDNITQSTQS FNDFTRVVGG EDAKPGQFPW
QVVLNGKVDA FCGGSIVNEK WIVTAAHCVE TGVKITVVAG EHNIEETEHT EQKRNVIRII
PHHNYNAAIN KYNHDIALLE LDEPLVLNSY VTPICIADKE YTNIFLKFGS GYVSGWGRVF
HKGRSALVLQ YLRVPLVDRA TCLRSTKFTI YNNMFCAGFH EGGRDSCQGD SGGPHVTEVE
GTSFLTGIIS WGEECAMKGK YGIYTKVSRY VNWIKEKTKL T
```

FIX DNA sequence

```
atgcagcgcg tgaacatgat catggcagaa tcaccaggcc tcatcaccat ctgcctttta
ggatatctac tcagtgctga atgtacagtt tttcttgatc atgaaaacgc acaaaatt
ctgaatcggc caaagaggta taattcaggt aaattggaag agtttgttca agggaatcta
gagagagaat gtatggaaga aaagtgtagt tttgaagaag cacgagaagt tttgaaaac
actgaaagaa caactgaatt ttggaagcag tatgttgatg gagatcagtg tgagtccaat
ccatgtttaa atggcggcag ttgcaaggat gacattaatt cctatgaatg ttggtgtccc
tttggatttg aaggaaagaa ctgtgaatta gatgtaacat gtaacattaa gaatggcaga
tgcgagcagt tttgtaaaaa tagtgctgat aacaaggtgg tttgctcctg tactgaggga
tatcgacttg cagaaaacca gaagtcctgt gaaccagcag tgccatttcc atgtggaaga
gtttctgttt cacaaacttc taagctcacc cgtgctgaga ctgtttttcc tgatgtggac
tatgtaaatt ctactgaagc tgaaaccatt ttggataaca tcactcaaag cacccaatca
tttaatgact tcactcgggt tgttggtgga gaagatgcca aaccaggtca attcccttgg
caggttgttt tgaatggtaa agttgatgca ttctgtggag gctctatcgt taatgaaaaa
tggattgtaa ctgctgccca ctgtgttgaa actggtgtta aaattacagt tgtcgcaggt
gaacataata ttgaggagac agaacataca gagcaaaagc gaaatgtgat tcgaattatt
cctcaccaca actacaatgc agctattaat aagtacaacc atgacattgc ccttctggaa
ctggacgaac ccttagtgct aaacagctac gttacaccta tttgcattgc tgacaaggaa
tacacgaaca tcttcctcaa atttggatct ggctatgtaa gtggctgggg aagagtcttc
cacaaaggga gatcagcttt agttcttcag taccttagag ttccacttgt tgaccgagcc
acatgtcttc gatctacaaa gttcaccatc tataacaaca tgttctgtgc tggcttccat
gaaggaggta gagattcatg tcaaggagat agtgggggac cccatgttac tgaagtggaa
gggaccagtt tcttaactgg aattattagc tggggtgaag agtgtgcaat gaaaggcaaa
tatggaatat ataccaaggt atcccggtat gtcaactgga ttaaggaaaa aacaaagctc
acttga
```

FX amino acid sequence. Signal sequence is shown in dotted underline, propeptide is double underlined

```
MGRPLHLVLL SASLAGLLLL GESLFIRREQ ANNILARVTR ANSFLEEMKK GHLERECMEE
TCSYEEAREV FEDSDKTNEF WNKYKDGDQC ETSPCQNQGK CKDGLGEYTC TCLEGFEGKN
CELFTRKLCS LDNGDCDQFC HEEQNSVVCS CARGYTLADN GKACIPTGPY PCGKQTLERR
KRSVAQATSS SGEAPDSITW KPYDAADLDP TENPFDLLDF NQTQPERGDN NLTRIVGGQE
CKDGECPWQA LLINEENEGF CGGTILSEFY ILTAAHCLYQ AKRFKVRVGD RNTEQEEGGE
AVHEVEVVIK HNRFTKETYD FDIAVLRLKT PITFRMVNAP ACLPERDWAE STLMTQKTGI
VSGFGRTHEK GRQSTRLKML EVPYVDRNSC KLSSSFIITQ NMFCAGYDTK QEDACQGDSG
GPHVTRFKDT YFVTGIVSWG EGCARGKGYG IYTKVTAFLK WIDRSMKTRG LPKAKSHAPE
VITSSPLK
```

FX DNA sequence

```
atggggcgcc cactgcacct cgtcctgctc agtgcctccc tggctggcct cctgctgctc
ggggaaagtc tgttcatccg cagggagcag gccaacaaca tcctggcgag ggtcacgagg
gccaattcct ttcttgaaga gatgaagaaa ggacacctcg aaagagagtg catggaagag
acctgctcat acgaagaggc ccgcgaggtc tttgaggaca gcgacaagac gaatgaattc
tggaataaat acaaagatgg cgaccagtgt gagaccagtc cttgccagaa ccagggcaaa
tgtaaagacg gcctcgggga atacacctgc acctgtttag aaggattcga aggcaaaaac
tgtgaattat tcacacggaa gctctgcagc ctggacaacg gggactgtga ccagttctgc
cacgaggaac agaactctgt ggtgtgctcc tgcgcccgcg ggtacaccct ggctgacaac
ggcaaggcct gcattcccac agggccctac ccctgtggga aacagaccct ggaacgcagg
aagaggtcag tggcccaggc caccagcagc agcggggagg cccctgacag catcacatgg
aagccatatg atgcagccga cctggacccc accgagaacc ccttcgacct gcttgacttc
aaccagacgc agcctgagag gggcgacaac aacctcacca ggatcgtggg aggccaggaa
tgcaaggacg gggagtgtcc ctggcaggcc ctgctcatca atgaggaaaa cgagggtttc
tgtggtggaa ccattctgag cgagttctac atcctaacgg cagcccactg tctctaccaa
gccaagagat tcaaggtgag ggtaggggac cggaacacgg agcaggagga gggcggtgag
gcggtgcacg aggtggaggt ggtcatcaag cacaaccggt tcacaaagga gacctatgac
ttcgacatcg ccgtgctccg gctcaagacc cccatcacct tccgcatgaa cgtggcgcct
```

-continued

DRAFT SEQUENCE LISTING

```
gcctgcctcc ccgagcgtga ctgggccgag tccacgctga tgacgcagaa gacggggatt
gtgagcggct tcgggcgcac ccacgagaag ggccggcagt ccaccaggct caagatgctg
gaggtgccct acgtggaccg caacagctgc aagctgtcca gcagcttcat catcacccag
aacatgttct gtgccggcta cgacaccaag caggaggatg cctgccaggg ggacagcggg
ggcccgcacg tcacccgctt caaggacacc tacttcgtga caggcatcgt cagctgggga
gagggctgtg cccgtaaggg gaagtacggg atctacacca aggtcaccgc cttcctcaag
tggatcgaca ggtccatgaa aaccaggggc ttgcccaagg ccaagagcca tgccccggag
gtcataacgt cctctccatt aaagtga
```

DNA sequence of FVII-066

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CAGAGTTGAA TATCCATGTG GAAAAATACC TATTCTAGAA
 541 AAAAGAAATG CCAGCAAACC CCAAGGCCGA ATTGTGGGGG GCAAGGTGTG CCCCAAAGGG
 601 GAGTGTCCAT GGCAGGTCCT GTTGTTGGTG AATGGAGCTC AGTTGTGTGG GGGGACCCTG
 661 ATCAACACCA TCTGGGTGGT CTCCGCGGCC CACTGTTTCG ACAAAATCAA GAACTGGAGG
 721 AACCTGATCG CGGTGCTGGG CGAGCACGAC CTCAGCGAGC ACGACGGGGA TGAGCAGAGC
 781 CGGCGGGTGG CGCAGGTCAT CATCCCCAGC ACGTACGTCC CGGGCACCAC CAACCACGAC
 841 ATCGCGCTGC TCCGCCTGCA CCAGCCCGTG GTCCTCACTG ACCATGTGGT GCCCCTCTGC
 901 CTGCCCGAAC GGACGTTCTC TGAGAGGACG CTGGCCTTCG TGCGCTTCTC ATTGGTCAGC
 961 GGCTGGGGCC AGCTGCTGGA CCGTGGCGCC ACGGCCCTGG AGCTCATGGT CCTCAACGTG
1021 CCCCGGCTGA TGACCCAGGA CTGCCTGCAG CAGTCACGGA AGGTGGGAGA CTCCCCAAAT
1081 ATCACGGAGT ACATGTTCTG TGCCGGCTAC TCGGATGGCA GCAAGGACTC CTGCAAGGGG
1141 GACAGTGGAG GCCCACATGC CACCCACTAC CGGGGCACGT GGTACCTGAC GGGCATCGTC
1201 AGCTGGGGCC AGGGCTGCGC AACCGTGGGC CACTTTGGGG TGTACACCAG GGTCTCCCAG
1261 TACATCGAGT GGCTGCAAAA GCTCATGCGC TCAGAGCCAC GCCCAGGAGT CCTCCTGCGA
1321 GCCCCATTTC CCGGTGGCGG TGGCTCCGGC GGAGGTGGGT CCGGTGGCGG CGGATCAGGT
1381 GGGGGTGGAT CAGGCGGTGG AGGTTCCGGT GGCGGGGGAT CCGACAAAAC TCACACATGC
1441 CCACCGTGCC CAGCTCCGGA ACTCCTGGGA GGACCGTCAG TCTTCCTCTT CCCCCCAAAA
1501 CCCAAGGACA CCCTCATGAT CTCCCGGACC CCTGAGGTCA CATGCGTGGT GGTGGACGTG
1561 AGCCACGAAG ACCCTGAGGT CAAGTTCAAC TGGTACGTGG ACGGCGTGGA GGTGCATAAT
1621 GCCAAGACAA AGCCGCGGGA GGAGCAGTAC AACAGCACGT ACCGTGTGGT CAGCGTCCTC
1681 ACCGTCCTGC ACCAGGACTG GCTGAATGGC AAGGAGTACA AGTGCAAGGT CTCCAACAAA
1741 GCCCTCCCAG CCCCCATCGA GAAAACCATC TCCAAAGCCA AAGGGCAGCC CCGAGAACCA
1801 CAGGTGTACA CCCTGCCCCC ATCCCGGGAT GAGCTGACCA AGAACCAGGT CAGCCTGACC
1861 TGCCTGGTCA AAGGCTTCTA TCCCAGCGAC ATCGCCGTGG AGTGGGAGAG CAATGGGCAG
1921 CCGGAGAACA ACTACAAGAC CACGCCTCCC GTGTTGGACT CCGACGGCTC CTTCTTCCTC
1981 TACAGCAAGC TCACCGTCGA CAAGAGCAGG TGGCAGCAGG GGAACGTCTT CTCATGCTCC
2041 GTGATGCATG AGGCTCTGCA CAACCACTAC ACGCAGAAGA GCCTCTCCCT GTCTCCGGGT
2101 AAACGGCGCC GCCGGAGCGG TGGCGGCGGA TCAGGTGGGG GTGGATCAGG CGGTGGAGGT
2161 TCCGGTGGCG GGGGATCCGG CGGTGGAGGT TCCGGTGGGG GTGGATCAAG GAAGAGGAGG
2221 AAGAGGGCGC AGGTGCAGCT GCAGGAGTCT GGGGGAGGCT TGGTACAGCC TGGGGGGTCC
2281 CTGAGACTCT CCTGTGCAGC CTCTGGATTC ATGTTTAGCA GGTATGCCAT GAGCTGGGTC
2341 CGCCAGGCTC CAGGGAAGGG GCCAGAGTGG GTCTCAGGTA TTAGTGGTAG TGGTGGTAGT
2401 ACATACTACG CAGACTCCGT GAAGGGCCGG TTCACCGTCT CCAGAGACAA TTCCAAGAAC
2461 ACGCTGTATC TGCAAATGAA CAGCCTGAGA GCCGAGGACA CGGCTGTATA TTACTGCGCC
2521 CGGGGCGCCA CCTACACCAG CCGGAGCGAC GTGCCCGACC AGACCAGCTT CGACTACTGG
2581 GGCCAGGGAA CCCTGGTCAC CGTCTCCTCA GGGAGTGCAT CCGCCCCAAA GCTTGAAGAA
2641 GGTGAATTTT CAGAAGCACG CGTATCTGAA CTGACTCAGG ACCCTGCTGT GTCTGTGGCC
2701 TTGGGACAGA CAGTCAGGAT CACATGCCAA GGAGACAGCC TCAGAAACTT TTATGCAAGC
2761 TGGTACCAGC AGAAGCCAGG ACAGGCCCCT ACTCTTGTCA TCTATGGTTT AAGTAAAAGG
2821 CCCTCAGGGA TCCCAGACCG ATTCTCTGCC TCCAGCTCAG GAAACACAGC TTCCTTGACC
2881 ATCACTGGGG CTCAGGCGGA AGATGAGGCT GACTATTACT GCCTGCTGTA CTACGGCGGC
2941 GGCCAGCAGG GCGTGTTCGG CGGCGGCACC AAGCTGACCG TCCTACGTCA GCCCAAGGCT
3001 GCCCCCTCGG TCACTCTGTT CCCGCCCTCT TCTGCGGCCG GTGGCGGTGG CTCCGGCGGA
3061 GGTGGGTCCG GTGGCGGCGG ATCAGGTGGG GGTGGATCAG GCGGTGGAGG TTCCGGTGGC
3121 GGGGGATCAG ACAAAACTCA CACATGCCCA CCGTGCCCAG CACCGGAACT CCTGGGCGGA
3181 CCGTCAGTCT TCCTCTTCCC CCCAAAACCC AAGGACACCC TCATGATCTC CCGGACCCCT
3241 GAGGTCACAT GCGTGGTGGT GGACGTGAGC CACGAAGACC CTGAGGTCAA GTTCAACTGG
3301 TACGTGGACG GCGTGGAGGT GCATAATGCC AAGACAAAGC CGCGGGAGGA GCAGTACAAC
3361 AGCACGTACC GTGTGGTCAG CGTCCTCACC GTCCTGCACC AGGACTGGCT GAATGGCAAG
3421 GAGTACAAGT GCAAGGTCTC CAACAAAGCC CTCCCAGCCC CCATCGAGAA AACCATCTCC
3481 AAAGCCAAAG GGCAGCCCCG AGAACCACAG GTGTACACCC TGCCCCCATC CCGGGATGAG
3541 CTGACCAAGA ACCAGGTCAG CCTGACCTGC CTGGTCAAAG GCTTCTATCC CAGCGACATC
3601 GCCGTGGAGT GGGAGAGCAA TGGGCAGCCG GAGAACAACT ACAAGACCAC GCCTCCCGTG
3661 TTGGACTCCG ACGGCTCCTT CTTCCTCTAC AGCAAGCTCA CCGTGGACAA GAGCAGGTGG
3721 CAGCAGGGGA ACGTCTTCTC ATGCTCCGTG ATGCATGAGG CTCTGCACAA CCACTACACG
3781 CAGAAGAGCC TCTCCCTGTC TCCGGGTAAA TGA
```

-continued

DRAFT SEQUENCE LISTING

FVII-066 amino acid sequence. Signal is shown in dotted underline, propeptide is double underlined, linker region connecting FVII or SCE5 to Fc region is underlined, and linker with proprotein convertase processing sites is shown in bold 1 MVSQALRLLC LLLGLQGCLA AVFVTQEEAH GVLHRRRRAN AFLEELRPGS LERECKEEQC
61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR IVGGKVCPKG ECPWQVLLLV NGAQLCGGTL INTIWVVSAA HCFDKIKNWR
241 NLIAVLGEHD LSEHDGDEQS RRVAQVIIPS TYVPGTTNHD IALLRLHQPV VLTDHVVPLC
301 LPERTFSERT LAFVRFSLVS GWGQLLDRGA TALELMVLNV PRLMTQDCLQ QSRKVGDSPN
361 ITEYMFCAGY SDGSKDSCKG DSGGPHATHY RGTWYLTGIV SWGQGCATVG HFGVYTRVSQ
421 YIEWLQKLMR SEPRPGVLLR APFPGGGGSG GGGSGGGGSG GGGSGGGGSG GGGSDKTHTC
481 PPCPAPELLG GPSVFLFPPK PKDTLMISRT PEVTCVVVDV SHEDPEVKFN WYVDGVEVHN
541 AKTKPREEQY NSTYRVVSVL TVLHQDWLNG KEYKCKVSNK ALPAPIEKTI SKAKGQPREP
601 QVYTLPPSRD ELTKNQVSLT CLVKGFYPSD IAVEWESNGQ PENNYKTTPP VLDSDGSFFL
661 YSKLTVDKSR WQQGNVFSCS VMHEALHNHY TQKSLSLSPG KRRRRSGGGG SGGGGSGGGG
721 SGGGGSGGGG SGGGGGSRKRR KRAQVQLQES GGGLVQPGGS LRLSCAASGF MFSRYAMSWV
781 RQAPGKGPEW VSGISGSGGS TYYADSVKGR FTVSRDNSKN TLYLQMNSLR AEDTAVYYCA
841 RGATYTSRSD VPDQTSFDYW GQGTLVTVSS GSASAPKLEE GEFSEARVSE LTQDPAVSVA
901 LGQTVRITCQ GDSLRNFYAS WYQQKPGQAP TLVIYGLSKR PSGIPDRFSA SSSGNTASLT
961 ITGAQAEDEA DYYCLLYYGG GQQGVFGGGT KLTVLRQPKA APSVTLFPPS SAAGGGGSGG
1021 GGSGGGGSGG GGSGGGGSGG GGSDKTHTCP PCPAPELLGG PSVFLFPPKP KDTLMISRTP
1081 EVTCVVVDVS HEDPEVKFNW YVDGVEVHNA KTKPREEQYN STYRVVSVLT VLHQDWLNGK
1141 EYKCKVSNKA LPAPIEKTIS KAKGQPREPQ VYTLPPSRDE LTKNQVSLTC LVKGFYPSDI
1201 AVEWESNGQP ENNYKTTPPV LDSDGSFFLY SKLTVDKSRW QQGNVFSCSV MHEALHNHYT
1261 QKSLSLSPGK *

DNA sequence for FVII-057

1 ATGGTCTCCC AGGCCCTCAG GCTCCTCTGC CTTCTGCTTG GGCTTCAGGG CTGCCTGGCT
61 GCAGTCTTCG TAACCCAGGA GGAAGCCCAC GGCGTCCTGC ACCGGCGCCG GCGCGCCAAC
121 GCGTTCCTGG AGGAGCTGCG GCCGGGCTCC CTGGAGAGGG AGTGCAAGGA GGAGCAGTGC
181 TCCTTCGAGG AGGCCCGGGA GATCTTCAAG GACGCGGAGA GGACGAAGCT GTTCTGGATT
241 TCTTACAGTG ATGGGGACCA GTGTGCCTCA AGTCCATGCC AGAATGGGGG CTCCTGCAAG
301 GACCAGCTCC AGTCCTATAT CTGCTTCTGC CTCCCTGCCT TCGAGGGCCG GAACTGTGAG
361 ACGCACAAGG ATGACCAGCT GATCTGTGTG AACGAGAACG GCGGCTGTGA GCAGTACTGC
421 AGTGACCACA CGGGCACCAA GCGCTCCTGT CGGTGCCACG AGGGGTACTC TCTGCTGGCA
481 GACGGGGTGT CCTGCACACC CACAGTTGAA TATCCATGTG GAAAAATACC TATTCTAGAA
541 AAAAGAAATG CCAGCAAACC CCAAGGCCGA GGTGGCGGTG GCTCCGGCGG AGGTGGGTCC
601 GGTGGCGGCG GATCAGGTGG GGGTGGATCA GGCGGTGGAG GTTCCGGTGG CGGGGGATCC
661 GACAAAACTC ACACATGCCC ACCGTGCCCA GCTCCGGAAC TCCTGGGAGG ACCGTCAGTC
721 TTCCTCTTCC CCCCAAAACC CAAGGACACC CTCATGATCT CCCGGACCCC TGAGGTCACA
781 TGCGTGGTGG TGGACGTGAG CCACGAAGAC CCTGAGGTCA AGTTCAACTG GTACGTGGAC
841 GGCGTGGAGG TGCATAATGC CAAGACAAAG CCGCGGGAGG AGCAGTACAA CAGCACGTAC
901 CGTGTGGTCA GCGTCCTCAC CGTCCTGCAC CAGGACTGGC TGAATGGCAA GGAGTACAAG
961 TGCAAGGTCT CCAACAAAGC CCTCCCAGCC CCCATCGAGA AAACCATCTC CAAAGCCAAA
1021 GGGCAGCCCC GAGAACCACA GGTGTACACC CTGCCCCCAT CCCGGGATGA GCTGACCAAG
1081 AACCAGGTCA GCCTGACCTG CCTGGTCAAA GGCTTCTATC CCAGCGACAT CGCCGTGGAG
1141 TGGGAGAGCA ATGGGCAGCC GGAGAACAAC TACAAGACCA CGCCTCCCGT GTTGGACTCC
1201 GACGGCTCCT TCTTCCTCTA CAGCAAGCTC ACCGTCGACA AGAGCAGGTG GCAGCAGGGG
1261 AACGTCTTCT CATGCTCCGT GATGCATGAG GCTCTGCACA ACCACTACAC GCAGAAGAGC
1321 CTCTCCCTGT CTCCGGGTAA AGGTGGCGGC GGATCAGGTG GGGGTGGATC AGGCGGTGGA
1381 GGTTCCGGTG GCGGGGGATC CGGCGGTGGA GGTTCCGGTG GGGGTGGATC AGGAGGAGGT
1441 GGTTCAAGCG TGAGCCAGAC CAGCAAGCTG ACCCGGATTG TGGGGGGCAA GGTGTGCCCC
1501 AAAGGGGAGT GTCCATGGCA GGTCCTGTTG TTGGTGAATG GAGCTCAGTT GTGTGGGGGG
1561 ACCCTGATCA ACACCATCTG GGTGGTCTCC GCGGCCCACT GTTTCGACAA AATCAAGAAC
1621 TGGAGGAACC TGATCGCGGT GCTGGGCGAG CACGACCTCA GCGAGCACGA CGGGGATGAG
1681 CAGAGCCGGC GGGTGGCGCA GGTCATCATC CCCAGCACGT ACGTCCCGGG CACCACCAAC
1741 CACGACATCG CGCTGCTCCG CCTGCACCAG CCCGTGGTCC TCACTGACCA TGTGGTGCCC
1801 CTCTGCCTGC CCGAACGGAC GTTCTCTGAG AGGACGCTGG CCTTCGTGCG CTTCTCATTG
1861 GTCAGCGGCT GGGGCCAGCT GCTGGACCGT GGCGCCACGG CCCTGGAGCT CATGGTCCTC
1921 AACGTGCCCC GGCTGATGAC CCAGGACTGC CTGCAGCAGT CACGGAAGGT GGGAGACTCC
1981 CCAAATATCA CGGAGTACAT GTTCTGTGCC GGCTACTCGG ATGGCAGCAA GGACTCCTGC
2041 AAGGGGGACA GTGGAGGCCC ACATGCCACC CACTACCGGG GCACGTGGTA CCTGACGGGC
2101 ATCGTCAGCT GGGGCCAGGG CTGCGCAACC GTGGGCCACT TTGGGGTGTA CACCAGGGTC
2161 TCCCAGTACA TCGAGTGGCT GCAAAAGCTC ATGCGCTCAG AGCCACGCCC AGGAGTCCTC
2221 CTGCGAGCCC CATTTCCCGG TGCCGGTGGC TCCGGCGGAG GTGGGTCCGG TGGCGGCGGA
2281 TCAGGTGGGG GTGGATCAGG CGGTGGAGGT TCCGGTGGCG GGGGATCAGA CAAAACTCAC
2341 ACATGCCCAC CGTGCCCAGC ACCTGAACTC CTGGGAGGAC CGTCAGTCTT CCTCTTCCCC
2401 CCAAAACCCA AGGACACCCT CATGATCTCC CGGACCCCTG AGGTCACATG CGTGGTGGTG
2461 GACGTGAGCC ACGAAGACCC TGAGGTCAAG TTCAACTGGT ACGTGGACGG CGTGGAGGTG
2521 CATAATGCCA AGACAAAGCC GCGGGAGGAG CAGTACAACA GCACGTACCG TGTGGTCAGC
2581 GTCCTCACCG TCCTGCACCA GGACTGGCTG AATGGCAAGG AGTACAAGTG CAAGGTCTCC
2641 AACAAAGCCC TCCCAGCCCC CATCGAGAAA ACCATCTCCA AAGCCAAAGG GCAGCCCCGA
2701 GAACCACAGG TGTACACCCT GCCCCCATCC CGGGATGAGC TGACCAAGAA CCAGGTCAGC
2761 CTGACCTGCC TGGTCAAAGG CTTCTATCCC AGCGACATCG CCGTGGAGTG GGAGAGCAAT
2821 GGGCAGCCGG AGAACAACTA CAAGACCACG CCTCCCGTGT TGGACTCCGA CGGCTCCTTC

-continued

DRAFT SEQUENCE LISTING

2881 TTCCTCTACA GCAAGCTCAC CGTGGACAAG AGCAGGTGGC AGCAGGGGAA CGTCTTCTCA
2941 TGCTCCGTGA TGCATGAGGC TCTGCACAAC CACTACACGC AGAAGAGCCT CTCCCTGTCT
3001 CCGGGTAAAT GA

FVII-057 amino acid sequence. Signal sequence is shown in dotted underline, propeptide is double underlined, linker region connecting FVII light chain or heavy chain to Fc region is underlined, linker region connecting the Fc and the Factor XIa cleavage site is shown in bold, and the Factor XIa cleavage site is shown in dashed underline 1 MVSQALRLLC LLLGLQGCLA AVFVTQEEAH GVLHRRRRAN AFLEELRPGS LERECKEEQC
61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR GGGGSGGGGS GGGGSGGGGS GGGGSGGGGS DKTHTCPPCP APELLGGPSV
241 FLFPPKPKDT LMISRTPEVT CVVVDVSHED PEVKFNWYVD GVEVHNAKTK PREEQYNSTY
301 RVVSVLTVLH QDWLNGKEYK CKVSNKALPA PIEKTISKAK GQPREPQVYT LPPSRDELTK
361 NQVSLTCLVK GFYPSDIAVE WESNGQPENN YKTTPPVLDS DGSFFLYSKL TVDKSRWQQG
421 NVFSCSVMHE ALHNHYTQKS LSLSPGKGGG GSGGGGSGGG GSGGGGSGGG GSGGGGSGGG
481 GSSVSQTSKL TRIVGGKVCP KGECPWQVLL LVNGAQLCGG TLINTIWVVS AAHCFDKIKN
541 WRNLIAVLGE HDLSEHDGDE QSRRVAQVII PSTYVPGTTN HDIALLRLHQ PVVLTDHVVP
601 LCLPERTFSE RTLAFVRFSL VSGWGQLLDR GATALELMVL NVPRLMTQDC LQQSRKVGDS
661 PNITEYMFCA GYSDGSKDSC KGDSGGPHAT HYRGTWYLTG IVSWGQGCAT VGHFGVYTRV
721 SQYIEWLQKL MRSEPRPGVL LRAPFPGGGG SGGGGSGGGG SGGGGSGGGG SGGGGSDKTH
781 TCPPCPAPEL LGGPSVFLFP PKPKDTLMIS RTPEVTCVVV DVSHEDPEVK FNWYVDGVEV
841 HNAKTKPREE QYNSTYRVVS VLTVLHQDWL NGKEYKCKVS NKALPAPIEK TISKAKGQPR
901 EPQVYTLPPS RDELTKNQVS LTCLVKGFYP SDIAVEWESN GQPENNYKTT PPVLDSDGSF
961 FLYSKLTVDK SRWQQGNVFS CSVMHEALHN HYTQKSLSLS PGK*

DNA sequence for FVII-058

1 ATGGTCTCCC AGGCCCTCAG GCTCCTCTGC CTTCTGCTTG CTGCCTGGCT CTGCCTGGCT
61 GCAGTCTTCG TAACCCAGGA GGAAGCCCAC GGCGTCCTGC ACCGGCGCCG GCGCGCCAAC
121 GCGTTCCTGG AGGAGCTGCG GCCGGGCTCC CTGGAGAGGG AGTGCAAGGA GGAGCAGTGC
181 TCCTTCGAGG AGGCCCGGGA GATCTTCAAG GACGCGGAGA GGACGAAGCT GTTCTGGATT
241 TCTTACAGTG ATGGGGACCA GTGTGCCTCA AGTCCATGCC AGAATGGGGG CTCCTGCAAG
301 GACCAGCTCC AGTCCTATAT CTGCTTCTGC CTCCCTGCCT TCGAGGGCCG GAACTGTGAG
361 ACGCACAAGG ATGACCAGCT GATCTGTGTG AACGAGAACG GCGGCTGTGA GCAGTACTGC
421 AGTGACCACA CGGGCACCAA GCGCTCCTGT CGGTGCCACG AGGGGTACTC TCTGCTGGCA
481 GACGGGGTGT CCTGCACACC CACAGTTGAA TATCCATGTG GAAAAATACC TATTCTAGAA
541 AAAAGAAATG CCAGCAAACC CCAAGGCCGA GGTGGCGGTG GCTCCGGCGG AGGTGGGTCC
601 GGTGGCGGCG GATCAGGTGG GGGTGGATCA GGCGGTGGAG GTTCCGGTGG CGGGGGATCC
661 GACAAAACTC ACACATGCCC ACCGTGCCCA GCTCCGGAAC TCCTGGGAGG ACCGTCAGTC
721 TTCCTCTTCC CCCCAAAACC CAAGGACACC CTCATGATCT CCCGGACCCC TGAGGTCACA
781 TGCGTGGTGG TGGACGTGAG CCACGAAGAC CCTGAGGTCA AGTTCAACTG GTACGTGGAC
841 GGCGTGGAGG TGCATAATGC CAAGACAAAG CCGCGGGAGG AGCAGTACAA CAGCACGTAC
901 CGTGTGGTCA GCGTCCTCAC CGTCCTGCAC CAGGACTGGC TGAATGGCAA GGAGTACAAG
961 TGCAAGGTCT CCAACAAAGC CCTCCCAGCC CCCATCGAGA AAACCATCTC CAAAGCCAAA
1021 GGGCAGCCCC GAGAACCACA GGTGTACACC CTGCCCCCAT CCCGGGATGA GCTGACCAAG
1081 AACCAGGTCA GCCTGACCTG CCTGGTCAAA GGCTTCTATC CCAGCGACAT CGCCGTGGAG
1141 TGGGAGAGCA ATGGGCAGCC GGAGAACAAC TACAAGACCA CGCCTCCCGT GTTGGACTCC
1201 GACGGCTCCT TCTTCCTCTA CAGCAAGCTC ACCGTCGACA AGAGCAGGTG GCAGCAGGGG
1261 AACGTCTTCT CATGCTCCGT GATGCATGAG GCTCTGCACA ACCACTACAC GCAGAAGAGC
1321 CTCTCCCTGT CTCCGGGTAA AGGTGGCGGC GGATCAGGTG GGGGTGGATC AGGCGGTGGA
1381 GGTTCCGGTG GCGGGGGATC CGGCGGTGGA GGTTCCGGTG GGGGTGGATC AGGAGGAGGT
1441 GGTTCAGACT TCCTGGCCGA GGGCGGCGGC GTGCGGATTG TGGGGGGCAA GGTGTGCCCC
1501 AAAGGGGAGT GTCCATGGCA GGTCCTGTTG TTGGTGAATG GAGCTCAGTT GTGTGGGGGG
1561 ACCCTGATCA ACACCATCTG GGTGGTCTCC GCGGCCCACT GTTTCGACAA AATCAAGAAC
1621 TGGAGGAACC TGATCGCGGT GCTGGGCGAG CACGACCTCA GCGAGCACGA CGGGGATGAG
1681 CAGAGCCGGC GGGTGGCGCA GGTCATCATC CCCAGCACGT ACGTCCCGGG CACCACCAAC
1741 CACGACATCG CGCTGCTCCG CCTGCACCAG CCCGTGGTCC TCACTGACCA TGTGGTGCCC
1801 CTCTGCCTGC CCGAACGGAC GTTCTCTGAG AGGACGCTGG CCTTCGTGCG CTTCTCATTG
1861 GTCAGCGGCT GGGGCCAGCT GCTGGACCGT GGCGCCACGG CCCTGGAGCT CATGGTCCTC
1921 AACGTGCCCC GGCTGATGAC CCAGGACTGC CTGCAGCAGT CACGGAAGGT GGGAGACTCC
1981 CCAAATATCA CGGAGTACAT GTTCTGTGCC GGCTACTCGG ATGGCAGCAA GGACTCCTGC
2041 AAGGGGGACA GTGGAGGCCC ACATGCCACC CACTACCGGG GCACGTGGTA CCTGACGGGC
2101 ATCGTCAGCT GGGGCCAGGG CTGCGCAACC GTGGGCCACT TTGGGGTGTA CACCAGGGTC
2161 TCCCAGTACA TCGAGTGGCT GCAAAAGCTC ATGCGCTCAG AGCCACGCCC AGGAGTCCTC
2221 CTGCGAGCCC CATTTCCCGG TGGCGGTGGC TCCGGCGGAG GTGGGTCCGG TGGCGGCGGA
2281 TCAGGTGGGG GTGGATCAGG CGGTGGAGGT TCCGGTGGCG GGGGATCAGA CAAAACTCAC
2341 ACATGCCCAC CGTGCCCAGC ACCTGAACTC CTGGGAGGAC CGTCAGTCTT CCTCTTCCCC
2401 CCAAAACCCA AGGACACCCT CATGATCTCC CGGACCCCTG AGGTCACATG CGTGGTGGTG
2461 GACGTGAGCC ACGAAGACCC TGAGGTCAAG TTCAACTGGT ACGTGGACGG CGTGGAGGTG
2521 CATAATGCCA AGACAAAGCC GCGGGAGGAG CAGTACAACA GCACGTACCG TGTGGTCAGC
2581 GTCCTCACCG TCCTGCACCA GGACTGGCTG AATGGCAAGG AGTACAAGTG CAAGGTCTCC
2641 AACAAAGCCC TCCCAGCCCC CATCGAGAAA ACCATCTCCA AAGCCAAAGG GCAGCCCCGA
2701 GAACCACAGG TGTACACCCT GCCCCCATCC CGGGATGAGC TGACCAAGAA CCAGGTCAGC
2761 CTGACCTGCC TGGTCAAAGG CTTCTATCCC AGCGACATCG CCGTGGAGTG GGAGAGCAAT
2821 GGGCAGCCGG AGAACAACTA CAAGACCACG CCTCCCGTGT TGGACTCCGA CGGCTCCTTC
2881 TTCCTCTACA GCAAGCTCAC CGTGGACAAG AGCAGGTGGC AGCAGGGGAA CGTCTTCTCA
2941 TGCTCCGTGA TGCATGAGGC TCTGCACAAC CACTACACGC AGAAGAGCCT CTCCCTGTCT
3001 CCGGGTAAAT GA

-continued

DRAFT SEQUENCE LISTING

FVII-058 amino acid sequence. Signal sequence is shown in dotted underline, propeptide is double underlined, linker region connecting FVII light chain or heavy chain to Fc region is underlined, linker region connecting the Fc and the thrombin cleavage site is shown in bold, and the thrombin cleavage site is shown in dashed underline

```
  1 MVSQALRLLC LLLGLQGCLA AVFVTQEEAH GVLHRRRRAN AFLEELRPGS LERECKEEQC
 61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR GGGGSGGGGS GGGGSGGGGS GGGGSGGGGS DKTHTCPPCP APELLGGPSV
241 FLFPPKPKDT LMISRTPEVT CVVVDVSHED PEVKFNWYVD GVEVHNAKTK PREEQYNSTY
301 RVVSVLTVLH QDWLNGKEYK CKVSNKALPA PIEKTISKAK GQPREPQVYT LPPSRDELTK
361 NQVSLTCLVK GFYPSDIAVE WESNGQPENN YKTTPPVLDS DGSFFLYSKL TVDKSRWQQG
421 NVFSCSVMHE ALHNHYTQKS LSLSPGKGGG GSGGGGSGGG GSGGGGSGGG GSGGGGSGGG
481 GSDFLAEGGG VRIVGGKVCP KGECPWQVLL LVNGAQLCGG TLINTIWVVS AAHCFDKIKN
541 WRNLIAVLGE HDLSEHDGDE QSRRVAQVII PSTYVPGTTN HDIALLRLHQ PVVLTDHVVP
601 LCLPERTFSE RTLAFVRFSL VSGWGQLLDR GATALELMVL NVPRLMTQDS LQQSRKVGDS
661 PNITEYMFCA GYSDGSKDSC KGDSGGPHAT HYRGTWYLTG IVSWGQGCAT VGHFGVYTRV
721 SQYIEWLQKL MRSEPRPGVL LRAPFPGGGG SGGGGSGGGG SGGGGSGGGG SGGGGSDKTH
781 TCPPCPAPEL LGGPSVFLFP PKPKDTLMIS RTPEVTCVVV DVSHEDPEVK FNWYVDGVEV
841 HNAKTKPREE QYNSTYRVVS VLTVLHQDWL NGKEYKCKVS NKALPAPIEK TISKAKGQPR
901 EPQVYTLPPS RDELTKNQVS LTCLVKGFYP SDIAVEWESN GQPENNYKTT PPVLDSDGSF
961 FLYSKLTVDK SRWQQGNVFS CSVMHEALHN HYTQKSLSLS PGK*
```

DNA sequence for FVII-059

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCCGA GGTGGCGGTG GCTCCGGCGG AGGTGGGTCC
 601 GGTGGCGGCG GATCAGGTGG GGGTGGATCA GGCGGTGGAG GTTCCGGTGG CGGGGGATCC
 661 GACAAAACTC ACACATGCCC ACCGTGCCCA GCTCCGGAAC TCCTGGGAGG ACCGTCAGTC
 721 TTCCTCTTCC CCCCAAAACC CAAGGACACC CTCATGATCT CCCGGACCCC TGAGGTCACA
 781 TGCGTGGTGG TGGACGTGAG CCACGAAGAC CCTGAGGTCA AGTTCAACTG GTACGTGGAC
 841 GGCGTGGAGG TGCATAATGC CAAGACAAAG CCGCGGGAGG AGCAGTACAA CAGCACGTAC
 901 CGTGTGGTCA GCGTCCTCAC CGTCCTGCAC CAGGACTGGC TGAATGGCAA GGAGTACAAG
 961 TGCAAGGTCT CCAACAAAGC CCTCCCAGCC CCCATCGAGA AAACCATCTC CAAAGCCAAA
1021 GGGCAGCCCC GAGAACCACA GGTGTACACC CTGCCCCCAT CCCGGGATGA GCTGACCAAG
1081 AACCAGGTCA GCCTGACCTG CCTGGTCAAA GGCTTCTATC CCAGCGACAT CGCCGTGGAG
1141 TGGGAGAGCA ATGGGCAGCC GGAGAACAAC TACAAGACCA CGCCTCCCGT GTTGGACTCC
1201 GACGGCTCCT TCTTCCTCTA CAGCAAGCTC ACCGTCGACA AGAGCAGGTG GCAGCAGGGG
1261 AACGTCTTCT CATGCTCCGT GATGCATGAG GCTCTGCACA ACCACTACAC GCAGAAGAGC
1321 CTCTCCCTGT CTCCGGGTAA AGGTGGCGGC GGATCAGGTG GGGGTGGATC AGGCGGTGGA
1381 GGTTCCGGTG GCGGGGGATC CGGCGGTGGA GGTTCCGGTG GGGGTGGATC AGGAGGAGGT
1441 GGTTCAACCA CCAAGATCAA GCCCCGGATT GTGGGGGGCA AGGTGTGCCC CAAAGGGGAG
1501 TGTCCATGGC AGGTCCTGTT GTTGGTGAAT GGAGCTCAGT TGTGTGGGGG GACCCTGATC
1561 AACACCATCT GGGTGGTCTC CGCGGCCCAC TGTTTCGACA AAATCAAGAA CTGGAGGAAC
1621 CTGATCGCGG TGCTGGGCGA GCACGACCTC AGCGAGCACG ACGGGGATGA GCAGAGCCGG
1681 CGGGTGGCGC AGGTCATCAT CCCCAGCACG TACGTCCCGG GCACCACCAA CCACGACATC
1741 GCGCTGCTCC GCCTGCACCA GCCCGTGGTC CTCACTGACC ATGTGGTGCC CCTCTGCCTG
1801 CCCGAACGGA CGTTCTCTGA GAGGACGCTG GCCTTCGTGC GCTTCTCATT GGTCAGCGGC
1861 TGGGGCCAGC TGCTGGACCG TGGCGCCACG GCCCTGGAGC TCATGGTCCT CAACGTGCCC
1921 CGGCTGATGA CCCAGGACTG CCTGCAGCAG TCACGGAAGG TGGGAGACTC CCCAAATATC
1981 ACGGAGTACA TGTTCTGTGC CGGCTACTCG GATGGCAGCA AGGACTCCTG CAAGGGGGAC
2041 AGTGGAGGCC CACATGCCAC CCACTACCGG GGCACGTGGT ACCTGACGGG CATCGTCAGC
2101 TGGGGCCAGG GCTGCGCAAC CGTGGGCCAC TTTGGGGTGT ACACCAGGGT CTCCCAGTAC
2161 ATCGAGTGGC TGCAAAAGCT CATGCGCTCA GAGCCACGCC CAGGAGTCCT CCTGCGAGCC
2221 CCATTTCCCG GTGGCGGTGG CTCCGGCGGA GGTGGGTCCG GTGGCGGCGG ATCAGGTGGG
2281 GGTGGATCAG GCGGTGGAGG TTCCGGTGGC GGGGGATCAG ACAAAACTCA CACATGCCCA
2341 CCGTGCCCAG CACCTGAACT CCTGGGAGGA CCGTCAGTCT TCCTCTTCCC CCCAAAACCC
2401 AAGGACACCC TCATGATCTC CCGGACCCCT GAGGTCACAT GCGTGGTGGT GGACGTGAGC
2461 CACGAAGACC CTGAGGTCAA GTTCAACTGG TACGTGGACG GCGTGGAGGT GCATAATGCC
2521 AAGACAAAGC CGCGGGAGGA GCAGTACAAC AGCACGTACC GTGTGGTCAG CGTCCTCACC
2581 GTCCTGCACC AGGACTGGCT GAATGGCAAG GAGTACAAGT GCAAGGTCTC CAACAAAGCC
2681 CTCCCAGCCC CCATCGAGAA AACCATCTCC AAAGCCAAAG GGCAGCCCCG AGAACCACAG
2701 GTGTACACCC TGCCCCCATC CCGGGATGAG CTGACCAAGA ACCAGGTCAG CCTGACCTGC
2761 CTGGTCAAAG GCTTCTATCC CAGCGACATC GCCGTGGAGT GGGAGAGCAA TGGGCAGCCG
2821 GAGAACAACT ACAAGACCAC GCCTCCCGTG TTGGACTCCG ACGGCTCCTT CTTCCTCTAC
2881 AGCAAGCTCA CCGTGGACAA GAGCAGGTGG CAGCAGGGGA ACGTCTTCTC ATGCTCCGTG
2941 ATGCATGAGG CTCTGCACAA CCACTACACG CAGAAGAGCC TCTCCCTGTC TCCGGGTAAA
3001 TGA
```

-continued

DRAFT SEQUENCE LISTING

FVII-059 amino acid sequence. Signal sequence is shown in dotted underline, propeptide is double underlined, linker region connecting FVII light chain or heavy chain to Fc region is underlined, linker region connecting the Fc and the thrombin cleavage site is shown in bold, and the thrombin cleavage site is shown in dashed underline

```
  1 MVSQALRLLC LLLGLQGCLA AVFVTQEEAH GVLHRRRRAN AFLEELRPGS LERECKEEQC
 61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR GGGGSGGGGS GGGGSGGGGS GGGGSGGGGS DKTHTCPPCP APELLGGPSV
241 FLFPPKPKDT LMISRTPEVT CVVVDVSHED PEVKFNWYVD GVEVHNAKTK PREEQYNSTY
301 RVVSVLTVLH QDWLNGKEYK CKVSNKALPA PIEKTISKAK GQPREPQVYT LPPSRDELTK
361 NQVSLTCLVK GFYPSDIAVE WESNGQPENN YKTTPPVLDS DGSFFLYSKL TVDKSRWQQG
421 NVFSCSVMHE ALHNHYTQKS LSLSPGKGGG GSGGGGSGGG GSGGGGSGGG GSGGGGSGGG
481 GSTTKIKPRI VGGKVCPKGE CPWQVLLLVN GAQLCGGTLI NTIWVVSAAH CFDKIKNWRN
541 LIAVLGEHDL SEHDGDEQSR RVAQVIIPST YVPGTTNHDI ALLRLHQPVV LTDHVVPLCL
601 PERTFSERTL AFVRFSLVSG WGQLLDRGAT ALELMVLNVP RLMTQDCLQQ SRKVGDSPNI
661 TEYMFCAGYS DGSKDSCKGD SGGPHATHYR GTWYLTGIVS WGQGCATVGH FGVYTRVSQY
721 IEWLQKLMRS EPRPGVLLRA PFPGGGGSGG GGSGGGGSGG GGSGGGGSGG GGSDKTHTCP
781 PCPAPELLGG PSVFLFPPKP KDTLMISRTP EVTCVVVDVS HEDPEVKFNW YVDGVEVHNA
841 KTKPREEQYN STYRVVSVLT VLHQDWLNGK EYKCKVSNKA LPAPIEKTIS KAKGQPREPQ
901 VYTLPPSRDE LTKNQVSLTC LVKGFYPSDI AVEWESNGQP ENNYKTTPPV LDSDGSFFLY
961 SKLTVDKSRW QQGNVFSCSV MHEALHNHYT QKSLSLSPGK *
```

DNA sequence for FVII-060

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCCGA GGTGGCGGTG GCTCCGGCGG AGGTGGGTCC
 601 GGTGGCGGCG GATCAGGTGG GGGTGGATCA GGCGGTGGAG GTTCCGGTGG CGGGGGATCC
 661 GACAAAACTC ACACATGCCC ACCGTGCCCA GCTCCGGAAC TCCTGGGAGG ACCGTCAGTC
 721 TTCCTCTTCC CCCCAAAACC CAAGGACACC CTCATGATCT CCCGGACCCC TGAGGTCACA
 781 TGCGTGGTGG TGGACGTGAG CCACGAAGAC CCTGAGGTCA AGTTCAACTG GTACGTGGAC
 841 GGCGTGGAGG TGCATAATGC CAAGACAAAG CCGCGGGAGG AGCAGTACAA CAGCACGTAC
 901 CGTGTGGTCA GCGTCCTCAC CGTCCTGCAC CAGGACTGGC TGAATGGCAA GGAGTACAAG
 961 TGCAAGGTCT CCAACAAAGC CCTCCCAGCC CCCATCGAGA AAACCATCTC CAAAGCCAAA
1021 GGGCAGCCCC GAGAACCACA GGTGTACACC CTGCCCCCAT CCCGGGATGA GCTGACCAAG
1081 AACCAGGTCA GCCTGACCTG CCTGGTCAAA GGCTTCTATC CCAGCGACAT CGCCGTGGAG
1141 TGGGAGAGCA ATGGGCAGCC GGAGAACAAC TACAAGACCA CGCCTCCCGT GTTGGACTCC
1201 GACGGCTCCT TCTTCCTCTA CAGCAAGCTC ACCGTCGACA AGAGCAGGTG GCAGCAGGGG
1261 AACGTCTTCT CATGCTCCGT GATGCATGAG GCTCTGCACA ACCACTACAC GCAGAAGAGC
1321 CTCTCCCTGT CTCCGGGTAA AGGTGGCGGC GGATCAGGTG GGGGTGGATC AGGCGGTGGA
1381 GGTTCCGGTG GCGGGGGATC CGGCGGTGGA GGTTCCGGTG GGGGTGGATC AGGAGGAGGT
1441 GGTTCAGCCC TGCGGCCCCG GGTGGTGGGC GGCGCCGTGG TGGGGGGCAA GGTGTGCCCC
1501 AAAGGGGAGT GTCCATGGCA GGTCCTGTTG TTGGTGAATG GAGCTCAGTT GTGTGGGGGG
1561 ACCCTGATCA ACACCATCTG GGTGGTCTCC GCGGCCCACT GTTTCGACAA AATCAAGAAC
1621 TGGAGGAACC TGATCGCGGT GCTGGGCGAG CACGACCTCA GCGAGCACGA CGGGGATGAG
1681 CAGAGCCGGC GGGTGGCGCA GGTCATCATC CCCAGCACGT ACGTCCCGGG CACCACCAAC
1741 CACGACATCG CGCTGCTCCG CCTGCACCAG CCCGTGGTCC TCACTGACCA TGTGGTGCCC
1801 CTCTGCCTGC CCGAACGGAC GTTCTCTGAG AGGACGCTGG CCTTCGTGCG CTTCTCATTG
1861 GTCAGCGGCT GGGGCCAGCT GCTGGACCGT GGCGCCACGG CCCTGGAGCT CATGGTCCTC
1921 AACGTGCCCC GGCTGATGAC CCAGGACTGC CTGCAGCAGT CACGGAAGGT GGGAGACTCC
1981 CCAAATATCA CGGAGTACAT GTTCTGTGCC GGCTACTCGG ATGGCAGCAA GGACTCCTGC
2041 AAGGGGGACA GTGGAGGCCC ACATGCCACC CACTACCGGG GCACGTGGTA CCTGACGGGC
2101 ATCGTCAGCT GGGGCCAGGG CTGCGCAACC GTGGGCCACT TTGGGGTGTA CACCAGGGTC
2161 TCCCAGTACA TCGAGTGGCT GCAAAAGCTC ATGCGCTCAG AGCCACGCCC AGGAGTCCTC
2221 CTGCGAGCCC CATTTCCCGG TGGCGGTGGC TCCGGCGGAG GTGGGTCCGG TGGCGGCGGA
2281 TCAGGTGGGG GTGGATCAGG CGGTGGAGGT TCCGGTGGCG GGGGATCAGA CAAAACTCAC
2341 ACATGCCCAC CGTGCCCAGC ACCTGAACTC CTGGGAGGAC CGTCAGTCTT CCTCTTCCCC
2401 CCAAAACCCA AGGACACCCT CATGATCTCC CGGACCCCTG AGGTCACATG CGTGGTGGTG
2461 GACGTGAGCC ACGAAGACCC TGAGGTCAAG TTCAACTGGT ACGTGGACGG CGTGGAGGTG
2521 CATAATGCCA AGACAAAGCC GCGGGAGGAG CAGTACAACA GCACGTACCG TGTGGTCAGC
2581 GTCCTCACCG TCCTGCACCA GGACTGGCTG AATGGCAAGG AGTACAAGTG CAAGGTCTCC
2641 AACAAAGCCC TCCCAGCCCC CATCGAGAAA ACCATCTCCA AAGCCAAAGG GCAGCCCCGA
2701 GAACCACAGG TGTACACCCT GCCCCCATCC CGGGATGAGC TGACCAAGAA CCAGGTCAGC
2761 CTGACCTGCC TGGTCAAAGG CTTCTATCCC AGCGACATCG CCGTGGAGTG GGAGAGCAAT
2821 GGGCAGCCGG AGAACAACTA CAAGACCACG CCTCCCGTGT TGGACTCCGA CGGCTCCTTC
2881 TTCCTCTACA GCAAGCTCAC CGTGGACAAG AGCAGGTGGC AGCAGGGGAA CGTCTTCTCA
2941 TGCTCCGTGA TGCATGAGGC TCTGCACAAC CACTACACGC AGAAGAGCCT CTCCCTGTCT
3001 CCGGGTAAAT GA
```

-continued

DRAFT SEQUENCE LISTING

FVII-060 amino acid sequence. Signal sequence is shown in dotted underline, propeptide is double underlined, linker region connecting FVII light chain or heavy chain to Fc region is underlined, linker region connecting the Fc and the thrombin cleavage site is shown in bold, and the thrombin cleavage site is shown in dashed underline

```
  1 MVSQALRLLC LLLGLQGCLA AVFVTQEEAH GVLHRRRRAN AFLEELRPGS LERECKEEQC
 61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR GGGGSGGGGS GGGGSGGGGS GGGGSGGGGS DKTHTCPPCP APELLGGPSV
241 FLFPPKPKDT LMISRTPEVT CVVVDVSHED PEVKFNWYVD GVEVHNAKTK PREEQYNSTY
301 RVVSVLTVLH QDWLNGKEYK CKVSNKALPA PIEKTISKAK GQPREPQVYT LPPSRDELTK
361 NQVSLTCLVK GFYPSDIAVE WESNGQPENN YKTTPPVLDS DGSFFLYSKL TVDKSRWQQG
421 NVFSCSVMHE ALHNHYTQKS LSLSPGKGGG GSGGGGSGGG GSGGGGSGGG GSGGGGSGGG
481 GSALRPRVVG GAVVGGKVCP KGECPWQVLL LVNGAQLCGG TLINTIWVVS AAHCFDKIKN
541 WRNLIAVLGE HDLSEHDGDE QSRRVAQVII PSTYVPGTTN HDIALLRLHQ PVVLTDHVVP
601 LCLPERTFSE RTLAFVRFSL VSGWGQLLDR GATALEILML NVPRLMTQDC LQQSRKVGDS
661 PNITEYMFCA GYSDGSKDSC KGDSGGPHAT HYRGTWYLTG IVSWGQGCAT VGHFGVYTRV
721 SQYIEWLQKL MRSEPRPGVL LRAPFPGGGG SGGGGSGGGG SGGGGSGGGG SGGGGSDKTH
781 TCPPCPAPEL LGGPSVFLFP PKPKDTLMIS RTPEVTCVVV DVSHEDPEVK FNWYVDGVEV
841 HNAKTKPREE QYNSTYRVVS VLTVLHQSWL NGKEYKCKVS NKALPAPIEK TISKAKGQPR
901 EPQVYTLPPS RDELTKNQVS LTCLVKGFYP SDIAVEWESN GQPENNYKTT PPVLDSDGSF
961 FLYSKLTVDK SRWQQGNVFS CSVMHEALHN HYTQKSLSLS PGK*
```

DNA sequence for FVII-061

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCCGA GGTGGCGGTG GCTCCGGCGG AGGTGGGTCC
 601 GGTGGCGGCG GATCAGGTGG GGGTGGATCA GGCGGTGGAG GTTCCGGTGG CGGGGGATCC
 661 GACAAAACTC ACACATGCCC ACCGTGCCCA GCTCCGGAAC TCCTGGGAGG ACCGTCAGTC
 721 TTCCTCTTCC CCCCAAAACC CAAGGACACC CTCATGATCT CCCGGACCCC TGAGGTCACA
 781 TGCGTGGTGG TGGACGTGAG CCACGAAGAC CCTGAGGTCA AGTTCAACTG GTACGTGGAC
 841 GGCGTGGAGG TGCATAATGC CAAGACAAAG CCGCGGGAGG AGCAGTACAA CAGCACGTAC
 901 CGTGTGGTCA GCGTCCTCAC CGTCCTGCAC CAGGACTGGC TGAATGGCAA GGAGTACAAG
 961 TGCAAGGTCT CCAACAAAGC CCTCCCAGCC CCCATCGAGA AAACCATCTC CAAAGCCAAA
1021 GGGCAGCCCC GAGAACCACA GGTGTACACC CTGCCCCCAT CCCGGGATGA GCTGACCAAG
1081 AACCAGGTCA GCCTGACCTG CCTGGTCAAA GGCTTCTATC CCAGCGACAT CGCCGTGGAG
1141 TGGGAGAGCA ATGGGCAGCC GGAGAACAAC TACAAGACCA CGCCTCCCGT GTTGGACTCC
1201 GACGGCTCCT TCTTCCTCTA CAGCAAGCTC ACCGTCGACA AGAGCAGGTG GCAGCAGGGG
1261 AACGTCTTCT CATGCTCCGT GATGCATGAG GCTCTGCACA ACCACTACAC GCAGAAGAGC
1321 CTCTCCCTGT CTCCGGGTAA AGGTGGCGGC GGATCAGGTG GGGGTGGATC AGGCGGTGGA
1381 GGTTCCGGTG GCGGGGGATC CGGCGGTGGA GGTTCCGGTG GGGGTGGATC AGGAGGAGGT
1441 GGTTCAGCCC TGCGGCCCCG GGTGGTGGGC GGCGCCATTG TGGGGGGCAA GGTGTGCCCC
1501 AAAGGGGAGT GTCCATGGCA GGTCCTGTTG TTGGTGAATG GAGCTCAGTT GTGTGGGGGG
1561 ACCCTGATCA ACACCATCTG GGTGGTCTCC GCGGCCCACT GTTTCGACAA AATCAAGAAC
1621 TGGAGGAACC TGATCGCGGT GCTGGGCGAG CACGACCTCA GCGAGCACGA CGGGGATGAG
1681 CAGAGCCGGC GGGTGGCGCA GGTCATCATC CCCAGCACGT ACGTCCCGGG CACCACCAAC
1741 CACGACATCG CGCTGCTCCG CCTGCACCAG CCCGTGGTCC TCACTGACCA TGTGGTGCCC
1801 CTCTGCCTGC CCGAACGGAC GTTCTCTGAG AGGACGCTGG CCTTCGTGCG CTTCTCATTG
1861 GTCAGCGGCT GGGGCCAGCT GCTGGACCGT GGCGCCACGG CCCTGGAGCT CATGGTCCTC
1921 AACGTGCCCC GGCTGATGAC CCAGGACTGC CTGCAGCAGT CACGGAAGGT GGGAGACTCC
1981 CCAAATATCA CGGAGTACAT GTTCTGTGCC GGCTACTCGG ATGGCAGCAA GGACTCCTGC
2041 AAGGGGGACA GTGGAGGCCC ACATGCCACC CACTACCGGG GCACGTGGTA CCTGACGGGC
2101 ATCGTCAGCT GGGGCCAGGG CTGCGCAACC GTGGGCCACT TTGGGGTGTA CACCAGGGTC
2161 TCCCAGTACA TCGAGTGGCT GCAAAAGCTC ATGCGCTCAG AGCCACGCCC AGGAGTCCTC
2221 CTGCGAGCCC CATTTCCCGG TGGCGGTGGC TCCGGCGGAG GTGGGTCCGG TGGCGGCGGA
2281 TCAGGTGGGG GTGGATCAGG CGGTGGAGGT TCCGGTGGCG GGGGATCAGA CAAAACTCAC
2341 ACATGCCCAC CGTGCCCAGC ACCTGAACTC CTGGGAGGAC CGTCAGTCTT CCTCTTCCCC
2401 CCAAAACCCA AGGACACCCT CATGATCTCC CGGACCCCTG AGGTCACATG CGTGGTGGTG
2461 GACGTGAGCC ACGAAGACCC TGAGGTCAAG TTCAACTGGT ACGTGGACGG CGTGGAGGTG
2521 CATAATGCCA AGACAAAGCC GCGGGAGGAG CAGTACAACA GCACGTACCG TGTGGTCAGC
2581 GTCCTCACCG TCCTGCACCA GGACTGGCTG AATGGCAAGG AGTACAAGTG CAAGGTCTCC
2641 AACAAAGCCC TCCCAGCCCC CATCGAGAAA ACCATCTCCA AAGCCAAAGG GCAGCCCCGA
2701 GAACCACAGG TGTACACCCT GCCCCCATCC CGGGATGAGC TGACCAAGAA CCAGGTCAGC
2761 CTGACCTGCC TGGTCAAAGG CTTCTATCCC AGCGACATCG CCGTGGAGTG GGAGAGCAAT
2821 GGGCAGCCGG AGAACAACTA CAAGACCACG CCTCCCGTGT TGGACTCCGA CGGCTCCTTC
```

-continued

DRAFT SEQUENCE LISTING

2881 TTCCTCTACA GCAAGCTCAC CGTGGACAAG AGCAGGTGGC AGCAGGGGAA CGTCTTCTCA
2941 TGCTCCGTGA TGCATGAGGC TCTGCACAAC CACTACACGC AGAAGAGCCT CTCCCTGTCT
3001 CCGGGTAAAT GA

FVII-061 amino acid sequence. Signal sequence is shown in dotted underline, propeptide is double underlined, linker region connecting FVII light chain or heavy chain to Fc region is underlined, linker region connecting the Fc and the thrombin cleavage site is shown in bold, and the thrombin cleavage site is shown in dashed underline 1 MVSQALRLLC LLLGLQGCLA AVFVTQEEAH GVLHRRRRAN AFLEELRPGS LERECKEEQC
61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR GGGGSGGGGS GGGGSGGGGS GGGGSGGGGS DKTHTCPPCP APELLGGPSV
241 FLFPPKPKDT LMISRTPEVT CVVVDVSHED PEVKFNWYVD GVEVHNAKTK PREEQYNSTY
301 RVVSVLTVLH QDWLNGKEYK CKVSNKALPA PIEKTISKAK GQPREPQVYT LPPSRDELTK
361 NQVSLTCLVK GFYPSDIAVE WESNGQPENN YKTTPPVLDS DGSFFLYSKL TVDKSRWQQG
421 NVFSCSVMHE ALHNHYTQKS LSLSPGKGGG GSGGGGSGGG GSGGGGSGGG GSGGGGSGGG
481 GSALRPRVVG GAIVGGKVCP KGECPWQVLL LVNGAQLCGG TLINTIWVVS AAHCFDKIKN
541 WRNLIAVLGE HDLSEHDGDE QSRRVAQVII PSTYVPGTTN DHIALLRLHQ PVVLTDHVVP
601 LCLPERTFSE RTLAFVRFSL VSGWGQLLDR GATALELMVL NVPRLMTQDC LQQSRKVGDS
661 PNITEYMFCA GYSDGSKDSC KGDSGGPHAT HYRGTWYLTG IVSWGQGCAT VGHFGVYTRV
721 SQYIEWLQKL MRSEPRPGVL LRAPFPGGGG SGGGGSGGGG SGGGGSGGGG SGGGGSDKTH
781 TCPPCPAPEL LGGPSVFLFP PKPKDTLMIS RTPEVTCVVV DVSHEDPEVK FNWYVDGVEV
841 HNAKTKPREE QYNSTYRVVS VLTVLHQDWL NGKEYKCKVS NKALPAPIEK TISKAKGQPR
901 EPQVYTLPPS RDELTKNQVS LTCLVKGFYP SDIAVEWESN GQPENNYKTT PPVLDSDGSF
961 FLYSKLTVDK SRWQQGNVFS CSVMHEALHN HYTQKSLSLS PGK*

DNA sequence for FVII-062

1 ATGGTCTCCC AGGCCCTCAG GCTCCTCTGC CTTCTGCTTG GGCTTCAGGG CTGCCTGGCT
61 GCAGTCTTCG TAACCCAGGA GGAAGCCCAC GGCGTCCTGC ACCGGCGCCG GCGCGCCAAC
121 GCGTTCCTGG AGGAGCTGCG GCCGGGCTCC CTGGAGAGGG AGTGCAAGGA GGAGCAGTGC
181 TCCTTCGAGG AGGCCCGGGA GATCTTCAAG GACGCGGAGA GGACGAAGCT GTTCTGGATT
241 TCTTACAGTG ATGGGGACCA GTGTGCCTCA AGTCCATGCC AGAATGGGGG CTCCTGCAAG
301 GACCAGCTCC AGTCCTATAT CTGCTTCTGC CTCCCTGCCT TCGAGGGCCG GAACTGTGAG
361 ACGCACAAGG ATGACCAGCT GATCTGTGTG AACGAGAACG GCGGCTGTGA GCAGTACTGC
421 AGTGACCACA CGGGCACCAA GCGCTCCTGT CGGTGCCACG AGGGGTACTC TCTGCTGGCA
481 GACGGGGTGT CCTGCACACC CACAGTTGAA TATCCATGTG GAAAAATACC TATTCTAGAA
541 AAAAGAAATG CCAGCAAACC CCAAGGCCGA GGTGGCGGTG GCTCCGGCGG AGGTGGGTCC
601 GGTGGCGGCG GATCAGGTGG GGGTGGATCA GGCGGTGGAG GTTCCGGTGG CGGGGGATCA
661 GACAAAACTC ACACATGCCC ACCGTGCCCA GCTCCGGAAC TCCTGGGCGG ACCGTCAGTC
721 TTCCTCTTCC CCCCAAAACC CAAGGACACC CTCATGATCT CCCGGACCCC TGAGGTCACA
781 TGCGTGGTGG TGGACGTGAG CCACGAAGAC CCTGAGGTCA AGTTCAACTG GTACGTGGAC
841 GGCGTGGAGG TGCATAATGC CAAGACAAAG CCGCGGGAGG AGCAGTACAA CAGCACGTAC
901 CGTGTGGTCA GCGTCCTCAC CGTCCTGCAC CAGGACTGGC TGAATGGCAA GGAGTACAAG
961 TGCAAGGTCT CCAACAAAGC CCTCCCAGCC CCCATCGAGA AAACCATCTC CAAAGCCAAA
1021 GGGCAGCCCC GAGAACCACA GGTGTACACC CTGCCCCCAT CCCGGGATGA GCTGACCAAG
1081 AACCAGGTCA GCCTGACCTG CCTGGTCAAA GGCTTCTATC CCAGCGACAT CGCCGTGGAG
1141 TGGGAGAGCA ATGGGCAGCC GGAGAACAAC TACAAGACCA CGCCTCCCGT GTTGGACTCC
1201 GACGGCTCCT TCTTCCTCTA CAGCAAGCTC ACCGTCGACA AGAGCAGGTG GCAGCAGGGG
1261 AACGTCTTCT CATGCTCCGT GATGCATGAG GCTCTGCACA ACCACTACAC GCAGAAGAGC
1321 CTCTCCCTGT CTCCGGGTAA AGGTGGCGGC GGATCAGGTG GGGGTGGATC AGGCGGTGGA
1381 GGTTCCGGTG GCGGGGGATC CGGCGGTGGA GGTTCCGGTG GGGGTGGATC AGGAGGAGGT
1441 GGTTCAGGTG GTGGAGGATC CATTGTGGGG GGCAAGGTGT GCCCCAAAGG GGAGTGTCCA
1501 TGGCAGGTCC TGTTGTTGGT GAATGGAGCT CAGTTGTGTG GGGGGACCCT GATCAACACC
1561 ATCTGGGTGG TCTCCGCGGC CCACTGTTTC GACAAAATCA AGAACTGGAG GAACCTGATC
1621 GCGGTGCTGG GCGAGCACGA CCTCAGCGAG CACGACGGGG ATGAGCAGAG CCGGCGGGTG
1681 GCGCAGGTCA TCATCCCCAG CACGTACGTC CCGGGCACCA CCAACCACGA CATCGCGCTG
1741 CTCCGCCTGC ACCAGCCCGT GGTCCTCACT GACCATGTGG TGCCCCTCTG CCTGCCCGAA
1801 CGGACGTTCT CTGAGAGGAC GCTGGCCTTC GTGCGCTTCT CATTGGTCAG CGGCTGGGGC
1861 CAGCTGCTGG ACCGTGGCGC CACGGCCCTG GAGCTCATGG TCCTCAACGT GCCCCGGCTG
1921 ATGACCCAGG ACTGCCTGCA GCAGTCACGG AAGGTGGGAG ACTCCCCAAA TATCACGGAG
1981 TACATGTTCT GTGCCGGCTA CTCGGATGGC AGCAAGGACT CCTGCAAGGG GGACAGTGGA
2041 GGCCCACATG CCACCCACTA CCGGGGCACG TGGTACCTGA CGGGCATCGT CAGCTGGGGC
2101 CAGGGCTGCG CAACCGTGGG CCACTTTGGG GTGTACACCA GGGTCTCCCA GTACATCGAG
2161 TGGCTGCAAA AGCTCATGCG CTCAGAGCCA CGCCCAGGAG TCCTCCTGCG AGCCCCATTT
2221 CCCGGTGGCG GTGGCTCCGG CGGAGGTGGG TCCGGTGGCG GCGGATCAGG TGGGGGTGGA
2281 TCAGGCGGTG GAGGTTCCGG TGGCGGGGGA TCAGACAAAA CTCACACATG CCCACCGTGC
2341 CCAGCACCTG AACTCCTGGG AGGACCGTCA GTCTTCCTCT TCCCCCCAAA ACCCAAGGAC
2401 ACCCTCATGA TCTCCCGGAC CCCTGAGGTC ACATGCGTGG TGGTGGACGT GAGCCACGAA
2461 GACCCTGAGG TCAAGTTCAA CTGGTACGTG GACGGCGTGG AGGTGCATAA TGCCAAGACA
2521 AAGCCGCGGG AGGAGCAGTA CAACAGCACG TACCGTGTGG TCAGCGTCCT CACCGTCCTG
2581 CACCAGGACT GGCTGAATGG CAAGGAGTAC AAGTGCAAGG TCTCCAACAA AGCCCTCCCA
2641 GCCCCCATCG AGAAAACCAT CTCCAAAGCC AAAGGGCAGC CCCGAGAACC ACAGGTGTAC
2701 ACCCTGCCCC CATCCCGGGA TGAGCTGACC AAGAACCAGG TCAGCCTGAC CTGCCTGGTC
2761 AAAGGCTTCT ATCCCAGCGA CATCGCCGTG GAGTGGGAGA GCAATGGGCA GCCGGAGAAC
2821 AACTACAAGA CCACGCCTCC CGTGTTGGAC TCCGACGGCT CCTTCTTCCT CTACAGCAAG
2881 CTCACCGTGG ACAAGAGCAG GTGGCAGCAG GGGAACGTCT TCTCATGCTC CGTGATGCAT
2941 GAGGCTCTGC ACAACCACTA CACGCAGAAG AGCCTCTCCC TGTCTCCGGG TAAATGA

-continued

DRAFT SEQUENCE LISTING

FVII-062 amino acid sequence. Signal sequence is shown in dotted underline, propeptide is double underlined, linker region connecting FVIIa light chain or heavy chain to Fc region is underlined, and linker region connecting the Fc and the FVIIa heavy chain is shown in bold

```
  1 MVSQALRLLC LLLGLQGCLA AVFVTQEEAH GVLHRRRRAN AFLEELRPGS LERECKEEQC
 61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR GGGGSGGGGS GGGGSGGGGS GGGGSGGGGS DKTHTCPPCP APELLGGPSV
241 FLFPPKPKDT LMISRTPEVT CVVVDVSHED PEVKFNWYVD GVEVHNAKTK PREEQYNSTY
301 RVVSVLTVLH QDWLNGKEYK CKVSNKALPA PIEKTISKAK GQPREPQVYT LPPSRDELTK
361 NQVSLTCLVK GFYPSDIAVE WESNGQPENN YKTTPPVLDS DGSFFLYSKL TVDKSRWQQG
421 NVFSCSVMHE ALHNHYTQKS LSLSPGKGGG GSGGGGSGGG GSGGGGSGGG GSGGGGSGGG
481 GSGGGGSIVG GKVCPKGECP WQVLLLVNGA QLCGGTLINT IWVVSAAHCF DKIKNWRNLI
541 AVLGEHDLSE HDGDEQSRRV AQVIIPSTYV PGTTNHDIAL LRLHQPVVLT DHVVPLCLPE
601 RTFSERTLAF VRFSLVSGWG QLLDRGATAL ELMVLNVPRL MTQDCLQQSR KVGDSPNITE
661 YMFCAGYSDG SKDSCKGDSG GPHATHYRGT WYLTGIVSWG QGCATVGHFG VYTRVSQYIE
721 WLQKLMRSEP RPGVLLRAPF PGGGGSGGGG SGGGGSGGGG SGGGGSGGGG SDKTHTCPPC
781 PAPELLGGPS VFLFPPKRKD TLMISRTPEV TCVVVDVSHE DPEVKFNWYV DGVEVHNAKT
841 KPREEQYNST YRVVSVLTVL HQDWLNGKEY KCKVSNKALP APIEKTISKA KGQPREPQVY
901 TLPPSRDELT KNQVSLTCLV KGFYPSDIAV EWESNGQPEN NYKTTPPVLD SDGSFFLYSK
961 LTVDKSRWQQ GNVFSCSVMH EALHNHYTQK SLSLSPGK*
```

DNA sequence for FVII-090

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCCGA GGTGGCGGTG GCTCCGGCGG AGGTGGGTCC
 601 GGTGGCGGCG GATCAGGTGG GGGTGGATCA GGCGGTGGAG GTTCCGGTGG CGGGGGATCA
 661 GACAAAACTC ACACATGCCC ACCGTGCCCA GCTCCGGAAC TCCTGGGCGG ACCGTCAGTC
 721 TTCCTCTTCC CCCCAAAACC CAAGGACACC CTCATGATCT CCCGGACCCC TGAGGTCACA
 781 TGCGTGGTGG TGGACGTGAG CCACGAAGAC CCTGAGGTCA AGTTCAACTG GTACGTGGAC
 841 GGCGTGGAGG TGCATAATGC CAAGACAAAG CCGCGGGAGG AGCAGTACAA CAGCACGTAC
 901 CGTGTGGTCA GCGTCCTCAC CGTCCTGCAC CAGGACTGGC TGAATGGCAA GGAGTACAAG
 961 TGCAAGGTCT CCAACAAAGC CCTCCCAGCC CCCATCGAGA AAACCATCTC CAAAGCCAAA
1021 GGGCAGCCCC GAGAACCACA GGTGTACACC CTGCCCCCAT CCCGGGATGA GCTGACCAAG
1081 AACCAGGTCA GCCTGACCTG CCTGGTCAAA GGCTTCTATC CCAGCGACAT CGCCGTGGAG
1141 TGGGAGAGCA ATGGGCAGCC GGAGAACAAC TACAAGACCA CGCCTCCCGT GTTGGACTCC
1201 GACGGCTCCT TCTTCCTCTA CAGCAAGCTC ACCGTCGACA AGAGCAGGTG GCAGCAGGGG
1261 AACGTCTTCT CATGCTCCGT GATGCATGAG GCTCTGCACA ACCACTACAC GCAGAAGAGC
1321 CTCTCCCTGT CTCCGGGTAA AGGTGGCGGC GGATCAGGTG GGGGTGGATC AGGCGGTGGA
1381 GGTTCCGGTG GCGGGGGATC CGGCGGTGGA GGTTCCGGTG GGGGTGGATC AGGAGGAGGT
1441 GGTTCAGCCC TGCGGCCCCG GATTGTGGGG GGCAAGGTGT GCCCCAAAGG GGAGTGTCCA
1501 TGGCAGGTCC TGTTGTTGGT GAATGGAGCT CAGTTGTGTG GGGGGACCCT GATCAACACC
1561 ATCTGGGTGG TCTCCGCGGC CCACTGTTTC GACAAAATCA AGAACTGGAG GAACCTGATC
1621 GCGGTGCTGG GCGAGCACGA CCTCAGCGAG CACGACGGGG ATGAGCAGAG CCGGCGGGTG
1681 GCGCAGGTCA TCATCCCCAG CACGTACGTC CCGGGCACCA CCAACCACGA CATCGCGCTG
1741 CTCCGCCTGC ACCAGCCCGT GGTCCTCACT GACCATGTGG TGCCCCTCTG CCTGCCCGAA
1801 CGGACGTTCT CTGAGAGGAC GCTGGCCTTC GTGCGCTTCT CATTGGTCAG CGGCTGGGGC
1861 CAGCTGCTGG ACCGTGGCGC CACGGCCCTG GAGCTCATGG TCCTCAACGT GCCCCGGCTG
1921 ATGACCCAGG ACTGCCTGCA GCAGTCACGG AAGGTGGGAG ACTCCCCAAA TATCACGGAG
1981 TACATGTTCT GTGCCGGCTA CTCGGATGGC AGCAAGGACT CCTGCAAGGG GGACAGTGGA
2041 GGCCCACATG CCACCCACTA CCGGGGCACG TGGTACCTGA CGGGCATCGT CAGCTGGGGC
2101 CAGGGCTGCG CAACCGTGGG CCACTTTGGG GTGTACACCA GGGTCTCCCA GTACATCGAG
2161 TGGCTGCAAA AGCTCATGCG CTCAGAGCCA CGCCCAGGAG TCCTCCTGCG AGCCCCATTT
2221 CCCGGTGGCG GTGGCTCCGG CGGAGGTGGG TCCGGTGGCG GCGGATCAGG TGGGGGTGGA
2281 TCAGGCGGTG GAGGTTCCGG TGGCGGGGGA TCAGACAAAA CTCACACATG CCCACCGTGC
2341 CCAGCACCTG AACTCCTGGG AGGACCGTCA GTCTTCCTCT TCCCCCCAAA ACCCAAGGAC
2401 ACCCTCATGA TCTCCCGGAC CCCTGAGGTC ACATGCGTGG TGGTGGACGT GAGCCACGAA
2461 GACCCTGAGG TCAAGTTCAA CTGGTACGTG GACGGCGTGG AGGTGCATAA TGCCAAGACA
2521 AAGCCGCGGG AGGAGCAGTA CAACAGCACG TACCGTGTGG TCAGCGTCCT CACCGTCCTG
2581 CACCAGGACT GGCTGAATGG CAAGGAGTAC AAGTGCAAGG TCTCCAACAA AGCCCTCCCA
2641 GCCCCCATCG AGAAAACCAT CTCCAAAGCC AAAGGGCAGC CCCGAGAACC ACAGGTGTAC
2701 ACCCTGCCCC CATCCCGGGA TGAGCTGACC AAGAACCAGG TCAGCCTGAC CTGCCTGGTC
2761 AAAGGCTTCT ATCCCAGCGA CATCGCCGTG GAGTGGGAGA GCAATGGGCA GCCGGAGAAC
2821 AACTACAAGA CCACGCCTCC CGTGTTGGAC TCCGACGGCT CCTTCTTCCT CTACAGCAAG
2881 CTCACCGTGG ACAAGAGCAG GTGGCAGCAG GGGAACGTCT TCTCATGCTC CGTGATGCAT
2941 GAGGCTCTGC ACAACCACTA CACGCAGAAG AGCCTCTCCC TGTCTCCGGG TAAATGA
```

-continued

DRAFT SEQUENCE LISTING

FVII-090 amino acid sequence. Signal sequence is shown in dotted underline, propeptide is double underlined, linker region connecting FVII light chain or heavy chain to Fc region is underlined, linker region connecting the Fc and the thrombin cleavage site is shown in bold, and the thrombin cleavage site is shown in dashed underline

```
  1 MVSQALRLLC LLLGLQGCLA AVFVTQEEAH GVLHRRRRAN AFLEELRPGS LERECKEEQC
 61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR GGGGSGGGGS GGGGSGGGGS GGGGSGGGGS DKTHTCPPCP APELLGGPSV
241 FLFPPKPKDT LMISRTPEVT CVVVDVSHED PEVKFNWYVD GVEVHNAKTK PREEQYNSTY
301 RVVSVLTVLH QDWLNGKEYK CKVSNKALPA PIEKTISKAK GQPREPQVYT LPPSRDELTK
361 NQVSLTCLVK GFYPSDIAVE WESNGQPENN YKTTPPVLDS DGSFFLYSKL TVDKSRWQQG
421 NVFSCSVMHE ALHNHYTQKS LSLSPGKGGG GSGGGGSGGG GSGGGGSGGG GSGGGGSGGG
481 GSALRPRIVG GKVCPKGECP WQVLLLVNGA QLCGGTLINT IWVVSAAHCF DKIKNWRNLI
541 AVLGEHDLSE HDGDEQSRRV AQVIIPSTYV PGTTNHDIAL LRLHQPVVLT DHVVPLCLPE
601 RTFSERTLAF VRFSLVSGWG QLLDRGATAL ELMVLNVPRL MTQDCLQQSR KVGDSPNITE
661 YMFCAGYSDG SKDSCKGDSG GPHATHYRGT WYLTGIVSWG QGCATVGHFG VYTRVSQYIE
721 WLQKLMRSEP RPGVLLRAPF PGGGGSGGGG SGGGGSGGGG SGGGGSGGGG SDKTHTCPPC
781 PAPELLGGPS VFLFPPKPKD TLMISRTPEV TCVVVDVSHE DPEVKFNWYV DGVEVHNAKT
841 KPREEQYNST YRVVSVLTVL HQDWLNGKEY KCKVSNKALP APIEKTISKA KGQPREPQVY
901 TLPPSRDELT KNQVSLTCLV KGFYPSDIAV EWESNGQPEN NYKTTPPVLD SDGSFFLYSK
961 LTVDKSRWQQ GNVFSCSVMH EALHNHYTQK SLSLSPGK*
```

DNA sequence for FVII-100

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCCGA GGTGGCGGTG GCTCCGGCGG AGGTGGGTCC
 601 GGTGGCGGCG GATCAGGTGG GGGTGGATCA GGCGGTGGAG GTTCCGGTGG CGGGGGATCC
 661 GACAAAACTC ACACATGCCC ACCGTGCCCA GCTCCGGAAC TCCTGGGAGG ACCGTCAGTC
 721 TTCCTCTTCC CCCCAAAACC CAAGGACACC CTCATGATCT CCCGGACCCC TGAGGTCACA
 781 TGCGTGGTGG TGGACGTGAG CCACGAAGAC CCTGAGGTCA AGTTCAACTG GTACGTGGAC
 841 GGCGTGGAGG TGCATAATGC CAAGACAAAG CCGCGGGAGG AGCAGTACAA CAGCACGTAC
 901 CGTGTGGTCA GCGTCCTCAC CGTCCTGCAC CAGGACTGGC TGAATGGCAA GGAGTACAAG
 961 TGCAAGGTCT CCAACAAAGC CCTCCCAGCC CCCATCGAGA AAACCATCTC CAAAGCCAAA
1021 GGGCAGCCCC GAGAACCACA GGTGTACACC CTGCCCCCAT CCCGGGATGA GCTGACCAAG
1081 AACCAGGTCA GCCTGACCTG CCTGGTCAAA GGCTTCTATC CCAGCGACAT CGCCGTGGAG
1141 TGGGAGAGCA ATGGGCAGCC GGAGAACAAC TACAAGACCA CGCCTCCCGT GTTGGACTCC
1201 GACGGCTCCT TCTTCCTCTA CAGCAAGCTC ACCGTCGACA AGAGCAGGTG GCAGCAGGGG
1261 AACGTCTTCT CATGCTCCGT GATGCATGAG GCTCTGCACA ACCACTACAC GCAGAAGAGC
1321 CTCTCCCTGT CTCCGGGTAA AGGTGGCGGC GGATCAGGTG GGGGTGGATC AGGCGGTGGA
1381 GGTTCCGGTG GCGGGGGATC CGGCGGTGGA GGTTCCGGTG GGGGTGGATC AGGAGGAGGT
1441 GGTTCAGCCC TGCGGCCCCG GATTGTGGGG GGCAAGGTGT GCCCCAAAGG GGAGTGTCCA
1501 TGGCAGGTCC TGTTGTTGGT GAATGGAGCT CAGTTGTGTG GGGGGACCCT GATCAACACC
1561 ATCTGGGTGG TCTCCGCGGC CCACTGTTTC GACAAAATCA AGAACTGGAG GAACCTGATC
1621 GCGGTGCTGG GCGAGCACGA CCTCAGCGAG CACGACGGGG ATGAGCAGAG CCGGCGGGTG
1681 GCGCAGGTCA TCATCCCCAG CACGTACGTC CCGGGCACCA CCAACCACGA CATCGCGCTG
1741 CTCCGCCTGC ACCAGCCCGT GGTCCTCACT GACCATGTGG TGCCCCTCTG CCTGCCCGAA
1801 CGGACGTTCT CTGAGAGGAC GCTGGCCTTC GTGCGCTTCT CATTGGTCAG CGGCTGGGGC
1861 CAGCTGCTGG ACCGTGGCGC CACGGCCCTG GAGCTCATGG TCCTCAACGT GCCCCGGCTG
1921 ATGACCCAGG ACTGCGAGGC CAGCTACCCC GGCAAGATCA CGGAGTACAT GTTCTGTGCC
1981 GGCTACTCGG ATGGCAGCAA GGACTCCTGC AAGGGGGACA GTGGAGGCCC ACATGCCACC
2041 CACTACCGGG GCACGTGGTA CCTGACGGGC ATCGTCAGCT GGGGCCAGGG CTGCGCAACC
2101 GTGGGCCACT TTGGGGTGTA CACCAGGGTC TCCCAGTACA TCGAGTGGCT GCAAAAGCTC
2161 ATGCGCTCAG AGCCACGCCC AGGAGTCCTC CTGCGAGCCC CATTTCCCGG TGGCGGTGGC
2221 TCCGGCGGAG GTGGGTCCGG TGGCGGCGGA TCAGGTGGGG GTGGATCAGG CGGTGGAGGT
2281 TCCGGTGGCG GGGGATCAGA CAAAACTCAC ACATGCCCAC CGTGCCCAGC ACCTGAACTC
2341 CTGGGAGGAC CGTCAGTCTT CCTCTTCCCC CCAAAACCCA AGGACACCCT CATGATCTCC
2401 CGGACCCCTG AGGTCACATG CGTGGTGGTG GACGTGAGCC ACGAAGACCC TGAGGTCAAG
2461 TTCAACTGGT ACGTGGACGG CGTGGAGGTG CATAATGCCA AGACAAAGCC GCGGGAGGAG
2521 CAGTACAACA GCACGTACCG TGTGGTCAGC GTCCTCACCG TCCTGCACCA GGACTGGCTG
2581 AATGGCAAGG AGTACAAGTG CAAGGTCTCC AACAAAGCCC TCCCAGCCCC CATCGAGAAA
2641 ACCATCTCCA AAGCCAAAGG GCAGCCCCGA GAACCACAGG TGTACACCCT GCCCCCATCC
2701 CGGGATGAGC TGACCAAGAA CCAGGTCAGC CTGACCTGCC TGGTCAAAGG CTTCTATCCC
2761 AGCGACATCG CCGTGGAGTG GGAGAGCAAT GGGCAGCCGG AGAACAACTA CAAGACCACG
2821 CCTCCCGTGT TGGACTCCGA CGGCTCCTTC TTCCTCTACA GCAAGCTCAC CGTGGACAAG
2881 AGCAGGTGGC AGCAGGTGGC CGTCTTCTCA TGCTCCGTGA TGCATGAGGC TCTGCACAAC
2941 CACTACACGC AGAAGAGCCT CTCCCTGTCT CCGGGTAAAT GA
```

-continued

DRAFT SEQUENCE LISTING

FVII-100 amino acid sequence. Signal sequence is shown in dotted underline, propeptide is double underlined, linker region connecting FVII light chain or heavy chain to Fc region is underlined, linker region connecting the Fc and the thrombin cleavage site is shown in bold, the thrombin cleavage site is shown in dashed underline, and the trypsin 170 loop region is wave underlined 1 MVSQALRLLC LLLGLQGCLA AVFVTQEEAH GVLHRRRRAN AFLEELRPGS LERECKEEQC
61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR GGGGSGGGGS GGGGSGGGGS GGGGSGGGGS DKTHTCPPCP APELLGGPSV
241 FLFPPKPKDT LMISRTPEVT CVVVDVSHED PEVKFNWYVD GVEVHNAKTK PREEQYNSTY
301 RVVSVLTVLH QDWLNGKEYK CKVSNKALPA PIEKTISKAK GQPREPQVYT LPPSRDELTK
361 NQVSLTCLVK GFYPSDIAVE WESNGQPENN YKTTPPVLDS DGSFFLYSKL TVDKSRWQQG
421 NVFSCSVMHE ALHNHYTQKS LSLSPGKGGG GSGGGGSGGG GSGGGGSGGG GSGGGGSGGG
481 GSALRPRIVG GKVCPKGECP WQVLLLVNGA QLCGGTLINT IWVVSAAHCF DKIKNWRNLI
541 AVLGEHDLSE HDGDEQSRRV AQVIIPSTYV PGTTNHDIAL LRLHQPVVLT DHVVPLCLPE
601 RTFSERTLAF VRFSLVSGWG QLLDRGATAL ELMVLNVPRL MTQDCEASYP GKITEYMFCA
661 GYSDGSKDSC KGDSGGPHAT HYRGTWYLTG IVSWGQGCAT VGHFGVYTRV SQYIEWLQKL
721 MRSEPRPGVL LRAPFPGGGG SGGGGSGGGG SGGGGSGGGG SGGGGSDKTH TCPPCPAPEL
781 LGGPSVFLFP PKPKDTLMIS RTPEVTCVVV DVSHEDPEVK FNWYVDGVEV HANKTKPREE
841 QYNSTYRVVS VLTVLHQDWL NGKEYKCKVS NKALPAPIEK TISKAKGQPR EPQVYTLPPS
901 RDELTKNQVS LTCLVKGFYP SDIAVEWESN GQPENNYKTT PPVLDSDGSF FLYSKLTVDK
961 SRWQQGNVFS CSVMHEALHN HYTQKSLSLS PGK*

DNA sequence for FVII-115

1 ATGGTCTCCC AGGCCCTCAG GCTCCTCTGC CTTCTGCTTG GGCTTCAGGG CTGCCTGGCT
61 GCAGTCTTCG TAACCCAGGA GGAAGCCCAC GGCGTCCTGA ACCGGCGCCG GCGCGCCAAC
121 GCGTTCCTGG AGGAGCTGCG GCCGGGCTCC CTGGAGAGGG AGTGCAAGGA GGAGCAGTGC
181 TCCTTCGAGG AGGCCCGGGA GATCTTCAAG GACGCGGAGA GGACGAAGCT GTTCTGGATT
241 TCTTACAGTG ATGGGGACCA GTGTGCCTCA AGTCCATGCC AGAATGGGGG CTCCTGCAAG
301 GACCAGCTCC AGTCCTATAT CTGCTTCTGC CTCCCTGCCT TCGAGGGCCG GAACTGTGAG
361 ACGCACAAGG ATGACCAGCT GATCTGTGTG AACGAGAACG GCGGCTGTGA GCAGTACTGC
421 AGTGACCACA CGGGCACCAA GCGCTCCTGT CGGTGCCACG AGGGGTACTC TCTGCTGGCA
481 GACGGGGTGT CCTGCACACC CACAGTTGAA TATCCATGTG GAAAAATACC TATTCTAGAA
541 AAAAGAAATG CCAGCAAACC CCAAGGCCGA GGTGGCGGTG GCTCCGGCGG AGGTGGGTCC
601 GGTGGCGGCG GATCAGGTGG GGGTGGATCA GGCGGTGGAG GTTCCGGTGG CGGGGGATCA
661 GACAAAACTC ACACATGCCC ACCGTGCCCA GCTCCGGAAC TCCTGGGCGG ACCGTCAGTC
721 TTCCTCTTCC CCCCAAAACC CAAGGACACC CTCATGATCT CCCGGACCCC TGAGGTCACA
781 TGCGTGGTGG TGGACGTGAG CCACGAAGAC CCTGAGGTCA AGTTCAACTG GTACGTGGAC
841 GGCGTGGAGG TGCATAATGC CAAGACAAAG CCGCGGGAGG AGCAGTACAA CAGCACGTAC
901 CGTGTGGTCA GCGTCCTCAC CGTCCTGCAC CAGGACTGGC TGAATGGCAA GGAGTACAAG
961 TGCAAGGTCT CCAACAAAGC CCTCCCAGCC CCCATCGAGA AAACCATCTC CAAAGCCAAA
1021 GGGCAGCCCC GAGAACCACA GGTGTACACC CTGCCCCCAT CCCGGGATGA GCTGACCAAG
1081 AACCAGGTCA GCCTGACCTG CCTGGTCAAA GGCTTCTATC CCAGCGACAT CGCCGTGGAG
1141 TGGGAGAGCA ATGGGCAGCC GGAGAACAAC TACAAGACCA CGCCTCCCGT GTTGGACTCC
1201 GACGGCTCCT TCTTCCTCTA CAGCAAGCTC ACCGTCGACA AGAGCAGGTG GCAGCAGGGG
1261 AACGTCTTCT CATGCTCCGT GATGCATGAG GCTCTGCACA ACCACTACAC GCAGAAGAGC
1321 CTCTCCCTGT CTCCGGGTAA AGGTGGCGGC GGATCAGGTG GGGGTGGATC AGGCGGTGGA
1381 GGTTCCGGTG GCGGGGGATC CGGCGGTGGA GGTTCCGGTG GGGGTGGATC AGGAGGAGGT
1441 GGTTCAGCCC TGCGGCCCCG GATTGTGGGG GGCAAGGACT GCCCCAAAGG GGAGTGTCCA
1501 TGGCAGGTCC TGTTGTTGGT GAATGGAGCT CAGTTGTGTG GGGGGACCCT GATCAACACC
1561 ATCTGGGTGG TCTCCGCGGC CCACTGTTTC GACAAAATCA AGAACTGGAG GAACCTGATC
1621 GCGGTGCTGG GCGAGCACGA CCTCAGCGAG CACGACGGGG ATGAGCAGAG CCGGCGGGTG
1681 GCGCAGGTCA TCATCCCCAG CACGTACGTC CCGGGCACCA CCAACCACGA CATCGCGCTG
1741 CTCCGCCTGC ACCAGCCCGT GGTCCTCACT GACCATGTGG TGCCCCTCTG CCTGCCCGAA
1801 CGGACGTTCT CTGAGAGGAC GCTGGCCTTC GTGCGCTTCT CATTGGTCAG CGGCTGGGGC
1861 CAGCTGCTGG ACCGTGGCGC CACGGCCCTG GTACTCCAAG TCCTCAACGT GCCCCGGCTG
1921 ATGACCCAGG ACTGCCTGCA GCAGTCACGG AAGGTGGGAG ACTCCCCAAA TATCACGGAG
1981 TACATGTTCT GTGCCGGCTA CTCGGATGGC AGCAAGGACT CCTGCAAGGG GGACAGTGGA
2041 GGCCCACATG CCACCCACTA CCGGGGCACG TGGTACCTGA CGGGCATCGT CAGCTGGGGC
2101 CAGGGCTGCG CAACCGTGGG CCACTTTGGG GTGTACACCA GGGTCTCCCA GTACATCGAG
2161 TGGCTGCAAA AGCTCATGCG CTCAGAGCCA CGCCCAGGAG TCCTCCTGCG AGCCCCATTT
2221 CCCGGTGGCG GTGGCTCCGG CGGAGGTGGG TCCGGTGGCG GCGGATCAGG TGGGGGTGGA
2281 TCAGGCGGTG GAGGTTCCGG TGGCGGGGGA TCAGACAAAA CTCACACATG CCCACCGTGC
2341 CCAGCACCTG AACTCCTGGG AGGACCGTCA GTCTTCCTCT TCCCCCCAAA ACCCAAGGAC
2401 ACCCTCATGA TCTCCCGGAC CCCTGAGGTC ACATGCGTGG TGGTGGACGT GAGCCACGAA
2461 GACCCTGAGG TCAAGTTCAA CTGGTACGTG GACGGCGTGG AGGTGCATAA TGCCAAGACA
2521 AAGCCGCGGG AGGAGCAGTA CAACAGCACG TACCGTGTGG TCAGCGTCCT CACCGTCCTG
2581 CACCAGGACT GGCTGAATGG CAAGGAGTAC AAGTGCAAGG TCTCCAACAA AGCCCTCCCA
2641 GCCCCCATCG AGAAAACCAT CTCCAAAGCC AAAGGGCAGC CCCGAGAACC ACAGGTGTAC
2701 ACCCTGCCCC CATCCCGGGA TGAGCTGACC AAGAACCAGG TCAGCCTGAC CTGCCTGGTC
2761 AAAGGCTTCT ATCCCAGCGA CATCGCCGTG GAGTGGGAGA GCAATGGGCA GCCGGAGAAC
2821 AACTACAAGA CCACGCCTCC CGTGTTGGAC TCCGACGGCT CCTTCTTCCT CTACAGCAAG
2881 CTCACCGTGG ACAAGAGCAG GTGGCAGCAG GGGAACGTCT TCTCATGCTC CGTGATGCAT
2941 GAGGCTCTGC ACAACCACTA CACGCAGAAG AGCCTCTCCC TGTCTCCGGG TAAATGA

-continued

DRAFT SEQUENCE LISTING

FVII-115 amino acid sequence. Signal sequence is shown in dotted underline, propeptide is double underlined, linker region connecting FVII light chain or heavy chain to Fc region is underlined, linker region connecting the Fc and the thrombin cleavage site is shown in bold, the thrombin cleavage site is shown in dashed underline, and the three point mutations in FVIIa (V158D, E296V and M298Q) are in bold and underlined

```
  1 MVSQALRLLC LLLGLQGCLA AVFVTQEEAH GVLHRRRRAN AFLEELRPGS LERECKEEQC
 61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR GGGGSGGGGS GGGGSGGGGS GGGGSGGGGS DKTHTCPPCP APELLGGPSV
241 FLFPPKPKDT LMISRTPEVT CVVVDVSHED PEVKFNWYVD GVEVHNAKTK PREEQYNSTY
301 RVVSVLTVLH QDWLNGKEYK CKVSNKALPA PEIKTISKAK GQPREPQVYT LPPSRDELTK
361 NQVSLTCLVK GFYPSDIAVE WESNGQPENN YKTTPPVLDS DGSFFLYSKL TVDKSRWQQG
421 NVFSCSVMHE ALHNHYTQKS LSLSPGKGGG GSGGGGSGGG GSGGGGSGGG GSGGGGSGGG
481 GSALRPRIVG GKDCPKGECP WQVLLLVNGA QLCGGTLINT IWVVSAAHCF DKIKNWRNLI
541 AVLGEHDLSE HDGDEQSRRV AQVIIPSTYV PGTTNHDIAL LRLHQPVVLT DHVVPLCLPE
601 RTFSERTLAF VRFSLVSGWG QLLDRGATAL VLQVLNVPRL MTQDCLQQSR KVGDSPNITE
661 YMFCAGYSDG SKDSCKGDSG GPHATHYRGT WYLTGIVSWG QGCATVGHFG VYTRVSQYIE
721 WLQKLMRSEP RPGVLLRAPF PGGGGSGGGG SGGGGSGGGG SGGGGSGGGG SDKTHTCPPC
781 PAPELLGGPS VFLFPPKPKD TLMISRTPEV TCVVVDVSHE DPEVKFNWYV DGVEVHNAKT
841 KPREEQYNST YRVVSVLTVL HQDWLNGKEY KCKVSNKALP APIEKTISKA KGQPREPQVY
901 TLPPSRDELT KNQVSLTCLV KGFYPSDIAV EWESNGQPEN NYKTTPPVLD SDGSFFLYSK
961 LTVDKSRWQQ GNVFSCSVMH EALHNHYTQK SLSLSPGK*
```

DNA sequence for FVII-118

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCGCC CTGCGGCCCC GGATTGTGGG GGGCAAGGTG
 601 TGCCCCAAAG GGGAGTGTCC ATGGCAGGTC CTGTTGTTGG TGAATGGAGC TCAGTTGTGT
 661 GGGGGGACCC TGATCAACAC CATCTGGGTG GTCTCCGCGG CCCACTGTTT CGACAAAATC
 721 AAGAACTGGA GGAACCTGAT CGCGGTGCTG GGCGAGCACG ACCTCAGCGA GCACGACGGG
 781 GATGAGCAGA GCCGGCGGGT GGCGCAGGTC ATCATCCCCA GCACGTACGT CCCGGGCACC
 841 ACCAACCACG ACATCGCGCT GCTCCGCCTG CACCAGCCCG TGGTCCTCAC TGACCATGTG
 901 GTGCCCCTCT GCCTGCCCGA ACGGACGTTC TCTGAGAGGA CGCTGGCCTT CGTGCGCTTC
 961 TCATTGGTCA GCGGCTGGGG CCAGCTGCTG GACCGTGGCG CCACGGCCCT GGAGCTCATG
1021 GTCCTCAACG TGCCCCGGCT GATGACCCAG GACTGCCTGC AGCAGTCACG GAAGGTGGGA
1081 GACTCCCCAA ATATCACGGA GTACATGTTC TGTGCCGGCT ACTCGGATGG CAGCAAGGAC
1141 TCCTGCAAGG GGGACAGTGG AGGCCCACAT GCCACCCACT ACCGGGGCAC GTGGTACCTG
1201 ACGGGCATCG TCAGCTGGGG CCAGGGCTGC GCAACCGTGG GCCACTTTGG GGTGTACACC
1261 AGGGTCTCCC AGTACATCGA GTGGCTGCAA AAGCTCATGC GCTCAGAGCC ACGCCCAGGA
1321 GTCCTCCTGC GAGCCCCATT TCCCGGTGGC GGTGGCTCCG GCGGAGGTGG GTCCGGTGGC
1381 GGCGGATCAG GTGGGGGTGG ATCAGGCGGT GGAGGTTCCG GTGGCGGGGG ATCCGACAAA
1441 ACTCACACAT GCCCACCGTG CCCAGCTCCG GAACTCCTGG GCGGACCGTC AGTCTTCCTC
1501 TTCCCCCCAA AACCCAAGGA CACCCTCATG ATCTCCCGGA CCCCTGAGGT CACATGCGTG
1561 GTGGTGGACG TGAGCCACGA AGACCCTGAG GTCAAGTTCA ACTGGTACGT GGACGGCGTG
1621 GAGGTGCATA ATGCCAAGAC AAAGCCGCGG GAGGAGCAGT ACAACAGCAC GTACCGTGTG
1681 GTCAGCGTCC TCACCGTCCT GCACCAGGAC TGGCTGAATG GCAAGGAGTA CAAGTGCAAG
1741 GTCTCCAACA AAGCCCTCCC AGCCCCCATC GAGAAAACCA TCTCCAAAGC CAAAGGGCAG
1801 CCCCGAGAAC CACAGGTGTA CACCCTGCCC CCATCCCGGG ATGAGCTGAC CAAGAACCAG
1861 GTCAGCCTGA CCTGCCTGGT CAAAGGCTTC TATCCCAGCG ACATCGCCGT GGAGTGGGAG
1921 AGCAATGGGC AGCCGGAGAA CAACTACAAG ACCACGCCTC CCGTGTTGGA CTCCGACGGC
1981 TCCTTCTTCC TCTACAGCAA GCTCACCGTG GACAAGAGCA GGTGGCAGCA GGGGAACGTC
2041 TTCTCATGCT CCGTGATGCA TGAGGCTCTG CACAACCACT ACACGCAGAA GAGCCTCTCC
2101 CTGTCTCCGG GTAAAGGTGG CGGCGGATCA GGTGGGGGTG GATCAGGCGG TGGAGGTTCC
2161 GGTGGCGGGG GATCAGACAA AACTCACACA TGCCCACCGT GCCCAGCACC TGAACTCCTG
2221 GGAGGACCGT CAGTCTTCCT CTTCCCCCCA AAACCCAAGG ACACCCTCAT GATCTCCCGG
2281 ACCCCTGAGG TCACATGCGT GGTGGTGGAC GTGAGCCACG AAGACCCTGA GGTCAAGTTC
2341 AACTGGTACG TGGACGGCGT GGAGGTGCAT AATGCCAAGA CAAAGCCGCG GGAGGAGCAG
2401 TACAACAGCA CGTACCGTGT GGTCAGCGTC CTCACCGTCC TGCACCAGGA CTGGCTGAAT
2461 GGCAAGGAGT ACAAGTGCAA GGTCTCCAAC AAAGCCCTCC CAGCCCCCAT CGAGAAAACC
2521 ATCTCCAAAG CCAAAGGGCA GCCCCGAGAA CCACAGGTGT ACACCCTGCC CCCATCCCGC
2581 GATGAGCTGA CCAAGAACCA GGTCAGCCTG ACCTGCCTGG TCAAAGGCTT CTATCCCAGC
2641 GACATCGCCG TGGAGTGGGA GAGCAATGGG CAGCCGGAGA ACAACTACAA GACCACGCCT
2701 CCCGTGTTGG ACTCCGACGG CTCCTTCTTC CTCTACAGCA AGCTCACCGT GGACAAGAGC
2761 AGGTGGCAGC AGGGGAACGT CTTCTCATGC TCCGTGATGC ATGAGGCTCT GCACAACCAC
2821 TACACGCAGA AGAGCCTCTC CCTGTCTCCG GGTAAATGA
```

-continued

DRAFT SEQUENCE LISTING

FVII-118 amino acid sequence. Signal sequence is shown in dotted underline, propeptide is double underlined, the thrombin cleavage site is shown in dashed underline, the linker region connecting FVII heavy chain to Fc region is underlined, and the linker region connecting the Fc regions is shown in bold

```
  1 MVSQALRLLC LLLGLQGCLA AVFVTQEEAH GVLHRRRRAN AFLEELRPGS LERECKEEQC
 61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGA LRPRIVGGKV CPKGECPWQV LLLVNGAQLC GGTLINTIWV VSAAHCFDKI
241 KNWRNLIAVL GEHDLSEHDG DEQSRRVAQV IIPSTYVPGT TNHDIALLRL HQPVVLTDHV
301 VPLCLPERTF SERTLAFVRF SLVSGWGQLL DRGATALELM VLNVPRLMTQ DCLQQSRKVG
361 DSPNITEYMF CAGYSDGSKD SCKGDSGGPH ATHYRGTWYL TGIVSWGQGC ATVGHFGVYT
421 RVSQYIEWLQ KLMRSEPRPG VLLRAPFPGG GGSGGGGSGG GGSGGGGSGG GGSGGGGSDK
481 THTCPPCPAP ELLGGPSVFL FPPKPKDTLM ISRTPEVTCV VVDVSHEDPE VKFNWYVDGV
541 EVHNAKTKPR EEQYNSTYRV VSVLTVLHQD WLNGKEYKCK VSNKALPAPI EKTISKAKGQ
601 PREPQVYTLP PSRDELTKNQ VSLTCLVKGF YPSDIAVEWE SNGQPENNYK TTPPVLDSDG
661 SFFLYSKLTV DKSRWQQGNV FSCSVMHEAL HNHYTQKSLS LSPGKGGGGS GGGGSGGGGS
721 GGGGSDKTHT CPPCPAPELL GGPSVFLFPP KPKDTLMISR TPEVTCVVVD VSHEDPEVKF
781 NWYVDGVEVH NAKTKPREEQ YNSTYRVVSV LTVLHQDWLN GKEYKCKVSN KALPAPIEKT
841 ISKAKGQPRE PQVYTLPPSR DELTKNQVSL TCLVKGFYPS DIAVEWESNG QPENNYKTTP
901 PVLDSDGSFF LYSKLTVDKS RWQQGNVFSC SVMHEALHNH YTQKSLSLSP GK*
```

DNA sequence for FVII-119

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCGGA GGAGGTGGTT CAGCCCTGCG GCCCCGGATT
 601 GTGGGGGGCA AGGTGTGCCC CAAAGGGGAG TGTCCATGGC AGGTCCTGTT GTTGGTGAAT
 661 GGAGCTCAGT TGTGTGGGGG GACCCTGATC AACACCATCT GGGTGGTCTC CGCGGCCCAC
 721 TGTTTCGACA AAATCAAGAA CTGGAGGAAC CTGATCGCGG TGCTGGGCGA GCACGACCTC
 781 AGCGAGCACG ACGGGGATGA GCAGAGCCGG CGGGTGGCGC AGGTCATCAT CCCCAGCACG
 841 TACGTCCCGG GCACCACCAA CCACGACATC GCGCTGCTCC GCCTGCACCA GCCCGTGGTC
 901 CTCACTGACC ATGTGGTGCC CCTCTGCCTG CCCGAACGGA CGTTCTCTGA GAGGACGCTG
 961 GCCTTCGTGC GCTTCTCATT GGTCAGCGGC TGGGGCCAGC TGCTGGACCG TGGCGCCACG
1021 GCCCTGGAGC TCATGGTCCT CAACGTGCCC CGGCTGATGA CCCAGGACTG CCTGCAGCAG
1081 TCACGGAAGG TGGGAGACTC CCCAAATATC ACGGAGTACA TGTTCTGTGC CGGCTACTCG
1141 GATGGCAGCA AGGACTCCTG CAAGGGGGAC AGTGGAGGCC CACATGCCAC CCACTACCGG
1201 GGCACGTGGT ACCTGACGGG CATCGTCAGC TGGGGCCAGG GCTGCGCAAC CGTGGGCCAC
1261 TTTGGGGTGT ACACCAGGGT CTCCCAGTAC ATCGAGTGGC TGCAAAAGCT CATGCGCTCA
1321 GAGCCACGCC CAGGAGTCCT CCTGCGAGCC CCATTTCCCG GTGGCGGTGG CTCCGGCGGA
1381 GGTGGGTCCG GTGGCGGCGG ATCAGGTGGG GGTGGATCAG GCGGTGGAGG TTCCGGTGGC
1441 GGGGGATCCG ACAAAACTCA CACATGCCCA CCGTGCCCAG CTCCGGAACT CCTGGGCGGA
1501 CCGTCAGTCT TCCTCTTCCC CCCAAAACCC AAGGACACCC TCATGATCTC CCGGACCCCT
1561 GAGGTCACAT GCGTGGTGGT GGACGTGAGC CACGAAGACC CTGAGGTCAA GTTCAACTGG
1621 TACGTGGACG GCGTGGAGGT GCATAATGCC AAGACAAAGC CGCGGGAGGA GCAGTACAAC
1681 AGCACGTACC GTGTGGTCAG CGTCCTCACC GTCCTGCACC AGGACTGGCT GAATGGCAAG
1741 GAGTACAAGT GCAAGGTCTC CAACAAAGCC CTCCCAGCCC CCATCGAGAA AACCATCTCC
1801 AAAGCCAAAG GGCAGCCCCG AGAACCACAG GTGTACACCC TGCCCCCATC CCGGGATGAG
1861 CTGACCAAGA ACCAGGTCAG CCTGACCTGC CTGGTCAAAG GCTTCTATCC CAGCGACATC
1921 GCCGTGGAGT GGGAGAGCAA TGGGCAGCCG GAGAACAACT ACAAGACCAC GCCTCCCGTG
1981 TTGGACTCCG ACGGCTCCTT CTTCCTCTAC AGCAAGCTCA CCGTGGACAA GAGCAGGTGG
2041 CAGCAGGGGA ACGTCTTCTC ATGCTCCGTG ATGCATGAGG CTCTGCACAA CCACTACACG
2101 CAGAAGAGCC TCTCCCTGTC TCCGGGTAAA GGTGGCGGCG GATCAGGTGG GGGTGGATCA
2161 GGCGGTGGAG GTTCCGGTGG CGGGGGATCA GACAAAACTC ACACATGCCC ACCGTGCCCA
2221 GCACCTGAAC TCCTGGGAGG ACCGTCAGTC TTCCTCTTCC CCCCAAAACC CAAGGACACC
2281 CTCATGATCT CCCGGACCCC TGAGGTCACA TGCGTGGTGG TGGACGTGAG CCACGAAGAC
2341 CCTGAGGTCA AGTTCAACTG GTACGTGGAC GGCGTGGAGG TGCATAATGC CAAGACAAAG
2401 CCGCGGGAGG AGCAGTACAA CAGCACGTAC CGTGTGGTCA GCGTCCTCAC CGTCCTGCAC
2461 CAGGACTGGC TGAATGGCAA GGAGTACAAG TGCAAGGTCT CCAACAAAGC CCTCCCAGCC
2521 CCCATCGAGA AAACCATCTC CAAAGCCAAA GGGCAGCCCC GAGAACCACA GGTGTACACC
2581 CTGCCCCCAT CCCGCGATGA GCTGACCAAG AACCAGGTCA GCCTGACCTG CCTGGTCAAA
2641 GGCTTCTATC CCAGCGACAT CGCCGTGGAG TGGGAGAGCA ATGGGCAGCC GGAGAACAAC
2701 TACAAGACCA CGCCTCCCGT GTTGGACTCC GACGGCTCCT TCTTCCTCTA CAGCAAGCTC
```

-continued

DRAFT SEQUENCE LISTING

```
2761 ACCGTGGACA AGAGCAGGTG GCAGCAGGGG AACGTCTTCT CATGCTCCGT GATGCATGAG
2821 GCTCTGCACA ACCACTACAC GCAGAAGAGC CTCTCCCTGT CTCCGGGTAA ATGA
```

FVII-119 amino acid sequence. Signal sequence is shown in dotted underline, propeptide is double underlined, the thrombin cleavage site with GGGS linker is shown in dashed underline, the linker region connecting FVII heavy chain to Fc region is underlined, and the linker region connecting the Fc regions is shown in bold

```
  1 MVSQALRLLC LLLGLQGCLA AVFVTQEEAH GVLHRRRRAN AFLEELRPGS LERECKEEQC
 61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGG GGGSALRPRI VGGKVCPKGE CPWQVLLLVN GAQLCGGTLI NTIWVVSAAH
241 CFDKIKNWRN LIAVLGEHDL SEHDGDEQSR RVAQVIIPST YVPGTTNHDI ALLRLHQPVV
301 LTDHVVPLCL PERTFSERTL AFVRFSLVSG WGQLLDRGAT ALELMVLNVP RLMTQDCLQQ
361 SRKVGDSPNI TEYMFCAGYS DGSKDSCKGD SGGPHATHYR GTWYLTGIVS WGQGCATVGH
421 FGVYTRVSQY IEWLQKLMRS EPRPGVLLRA PFPGGGGSGG GGSGGGGSGG GGSGGGGSGG
481 GGSDKTHTCP PCPAPELLGG PSVFLFPPKP KDTLMISRTP EVTCVVVDVS HEDPEVKFNW
541 YVDGVEVHNA KTKPREEQYN STYRVVSVLT VLHQDWLNGK EYKCKVSNKA LPAPIEKTIS
601 KAKGQPREPQ VYTLPPSRDE LTKNQVSLTC LVKGFYPSDI AVEWESNGQP ENNYKTTPPV
661 LDSDGSFFLY SKLTVDKSRW QQGNVFSCSV MHEALHNHYT QKSLSLSPGK GGGGSGGGGS
721 GGGGSGGGGS DKTHTCPPCP APELLGGPSV FLFPPKPKDT LMISRTPEVT CVVVDVSHED
781 PEVKFNWYVD GVEVHNAKTK PREEQYNSTY RVVSVLTVLH QDWLNGKEYK CKVSNKALPA
841 PIEKTISKAK GQPREPQVYT LPPSRDELTK NQVSLTCLVK GFYPSDIAVE WESNGQPENN
901 YKTTPPVLDS DGSFFLYSKL TVDKSRWQQG NVFSCSVMHE ALHNHYTQKS LSLSPGK*
```

DNA sequence for FVII-127

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCGCC CTGCGGCCCC GGATTGTGGG GGGCAAGGTG
 601 TGCCCCAAAG GGGAGTGTCC ATGGCAGGTC CTGTTGTTGG TGAATGGAGC TCAGTTGTGT
 661 GGGGGGACCC TGATCAACAC CATCTGGGTG GTCTCCGCGG CCCACTGTTT CGACAAAATC
 721 AAGAACTGGA GGAACCTGAT CGCGGTGCTG GGCGAGCACG ACCTCAGCGA GCACGACGGG
 781 GATGAGCAGA GCCGGCGGGT GGCGCAGGTC ATCATCCCCA GCACGTACGT CCCGGGCACC
 841 ACCAACCACG ACATCGCGCT GCTCCGCCTG CACCAGCCCG TGGTCCTCAC TGACCATGTG
 901 GTGCCCCTCT GCCTGCCCGA ACGGACGTTC TCTGAGAGGA CGCTGGCCTT CGTGCGCTTC
 961 TCATTGGTCA GCGGCTGGGG CCAGCTGCTG GACCGTGGCG CCACGGCCCT GGAGCTCATG
1021 GTCCTCAACG TGCCCCGGCT GATGACCCAG GACTGCGAGG CCAGCTACCC CGGCAAGATC
1081 ACGGAGTACA TGTTCTGTGC CGGCTACTCG GATGGCAGCA AGGACTCCTG CAAGGGGGAC
1141 AGTGGAGGCC CACATGCCAC CCACTACCGG GGCACGTGGT ACCTGACGGG CATCGTCAGC
1201 TGGGGCCAGG GCTGCGCAAC CGTGGGCCAC TTTGGGGTGT ACACCAGGGT CTCCCAGTAC
1261 ATCGAGTGGC TGCAAAAGCT CATGCGCTCA GAGCCACGCC CAGGAGTCCT CCTGCGAGCC
1321 CCATTTCCCG GTGGCGGTGG CTCCGGCGGA GGTGGGTCCG GTGGCGGCGG ATCAGGTGGG
1381 GGTGGATCAG GCGGTGGAGG TTCCGGTGGC GGGGGATCAG ACAAAACTCA CACATGCCCA
1441 CCGTGCCCAG CTCCGGAACT CCTGGGCGGA CCGTCAGTCT TCCTCTTCCC CCCAAAACCC
1501 AAGGACACCC TCATGATCTC CCGGACCCCT GAGGTCACAT GCGTGGTGGT GGACGTGAGC
1561 CACGAAGACC CTGAGGTCAA GTTCAACTGG TACGTGGACG GCGTGGAGGT GCATAATGCC
1621 AAGACAAAGC CGCGGGAGGA GCAGTACAAC AGCACGTACC GTGTGGTCAG CGTCCTCACC
1681 GTCCTGCACC AGGACTGGCT GAATGGCAAG GAGTACAAGT GCAAGGTCTC CAACAAAGCC
1741 CTCCCAGCCC CCATCGAGAA AACCATCTCC AAAGCCAAAG GGCAGCCCCG AGAACCACAG
1801 GTGTACACCC TGCCCCCATC CCGGGATGAG CTGACCAAGA ACCAGGTCAG CCTGACCTGC
1861 CTGGTCAAAG GCTTCTATCC CAGCGACATC GCCGTGGAGT GGGAGAGCAA TGGGCAGCCG
1921 GAGAACAACT ACAAGACCAC GCCTCCCGTG TTGGACTCCG ACGGCTCCTT CTTCCTCTAC
1981 AGCAAGCTCA CCGTGGACAA GAGCAGGTGG CAGCAGGGGA ACGTCTTCTC ATGCTCCGTG
2041 ATGCATGAGG CTCTGCACAA CCACTACACG CAGAAGAGCC TCTCCCTGTC TCCGGGTAAA
2101 GGTGGCGGCG GATCAGGTGG GGGTGGATCA GGCGGTGGAG GTTCCGGTGG CGGGGGATCA
2161 GACAAAACTC ACACATGCCC ACCGTGCCCA GCACCTGAAC TCCTGGGAGG ACCGTCAGTC
2221 TTCCTCTTCC CCCCAAAACC CAAGGACACC CTCATGATCT CCCGGACCCC TGAGGTCACA
2281 TGCGTGGTGG TGGACGTGAG CCACGAAGAC CCTGAGGTCA AGTTCAACTG GTACGTGGAC
2341 GGCGTGGAGG TGCATAATGC CAAGACAAAG CCGCGGGAGG AGCAGTACAA CAGCACGTAC
2401 CGTGTGGTCA GCGTCCTCAC CGTCCTGCAC CAGGACTGGC TGAATGGCAA GGAGTACAAG
2461 TGCAAGGTCT CCAACAAAGC CCTCCCAGCC CCCATCGAGA AAACCATCTC CAAAGCCAAA
2521 GGGCAGCCCC GAGAACCACA GGTGTACACC CTGCCCCCAT CCCGCGATGA GCTGACCAAG
2581 AACCAGGTCA GCCTGACCTG CCTGGTCAAA GGCTTCTATC CCAGCGACAT CGCCGTGGAG
2641 TGGGAGAGCA ATGGGCAGCC GGAGAACAAC TACAAGACCA CGCCTCCCGT GTTGGACTCC
2701 GACGGCTCCT TCTTCCTCTA CAGCAAGCTC ACCGTGGACA AGAGCAGGTG GCAGCAGGGG
2761 AACGTCTTCT CATGCTCCGT GATGCATGAG GCTCTGCACA ACCACTACAC GCAGAAGAGC
2821 CTCTCCCTGT CTCCGGGTAA ATGA
```

-continued

DRAFT SEQUENCE LISTING

FVII-127 amino acid sequence. Signal sequence is shown in dotted underline, propeptide is double underlined, the thrombin cleavage site is shown in dashed underline, the trypsin 170 loop region is wave underlined, the linker region connecting FVII heavy chain to Fc region is underlined, and the linker region connecting the Fc regions is shown in bold 1 MVSQALRLLC LLLGLQGCLA AVFVTQEEAH GVLHRRRRAN AFLEELRPGS LERECKEEQC
61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGA LRPRIVGGKV CPKGECPWQV LLLVNGAQLC GGTLINTIWV VSAAHCFDKI
241 KNWRNLIAVL GEHDLSEHDG DEQSRRVAQV IIPSTYVPGT TNHDIALLRL HQPVVLTDHV
301 VPLCLPERTF SERTLAFVRF SLVSGWGQLL DRGATALELM VLNVPRLMTQ DCEASYPGKI
361 TEYMFCAGYS DGSKDSCKGD SGGPHATHYR GTWYLTGIVS WGQGCATVGH FGVYTRVSQY
421 IEWLQKLMRS EPRPGVLLRA PFPGGGGSGG GGSGGGGSGG GGSGGGGSGG GGSDKTHTCP
481 PCPAPELLGG PSVFLFPPKP KDTLMISRTP EVTCVVVDVS HEDPEVKFNW YVDGVEVHNA
541 KTKPREEQYN STYRVVSVLT VLHQDWLNGK EYKCKVSNKA LPAPIEKTIS KAKGQPREPQ
601 VYTLPPSRDE LTKNQVSLTC LVKGFYPSDI AVEWESNGQP ENNYKTTPPV LDSDGSFFLY
661 SKLTVDKSRW QQGNVFSCSV MHEALHNHYT QKSLSLSPGK GGGGSGGGGS GGGGSGGGGS
721 DKTHTCPPCP APELLGGPSV FLFPPKPKDT LMISRTPEVT CVVVDVSHED PEVKFNWYVD
781 GVEVHNAKTK PREEQYNSTY RVVSVLTVLH QDWLNGKEYK CKVSNKALPA PEIKTISKAK
841 GQPREPQVYT LPPSRDELTK NQVSLTCLVK GFYPSDIAVE WESNGQPENN YKTTPPVLDS
901 DGSFFLYSKL TVDKSRWQQG NVFSCSVMHE ALHNHYTQKS LSLSPGK*

DNA sequence for FVII-125

1 ATGGTCTCCC AGGCCCTCAG GCTCCTCTGC CTTCTGCTTG GGCTTCAGGG CTGCCTGGCT
61 GCAGTCTTCG TAACCCAGGA GGAAGCCCAC GGCGTCCTGC ACCGGCGCCG GCGCGCCAAC
121 GCGTTCCTGG AGGAGCTGCG GCCGGGCTCC CTGGAGAGGG AGTGCAAGGA GGAGCAGTGC
181 TCCTTCGAGG AGGCCCGGGA GATCTTCAAG GACGCGGAGA GGACGAAGCT GTTCTGGATT
241 TCTTACAGTG ATGGGGACCA GTGTGCCTCA AGTCCATGCC AGAATGGGGG CTCCTGCAAG
301 GACCAGCTCC AGTCCTATAT CTGCTTCTGC CTCCCTGCCT TCGAGGGCCG GAACTGTGAG
361 ACGCACAAGG ATGACCAGCT GATCTGTGTG AACGAGAACG GCGGCTGTGA GCAGTACTGC
421 AGTGACCACA CGGGCACCAA GCGCTCCTGT CGGTGCCACG AGGGGTACTC TCTGCTGGCA
481 GACGGGGTGT CCTGCACACC CACAGTTGAA TATCCATGTG GAAAAATACC TATTCTAGAA
541 AAAAGAAATG CCAGCAAACC CCAAGGCCGA ATTGTGGGGG GCAAGGTGTG CCCCAAAGGG
601 GAGTGTCCAT GGCAGGTCCT GTTGTTGGTG AATGGAGCTC AGTTGTGTGG GGGGACCCTG
661 ATCAACACCA TCTGGGTGGT CTCCGCGGCC CACTGTTTCG ACAAAATCAA GAACTGGAGG
721 AACCTGATCG CGGTGCTGGG CGAGCACGAC CTCAGCGAGC ACGACGGGGA TGAGCAGAGC
781 CGGCGGGTGG CGCAGGTCAT CATCCCCAGC ACGTACGTCC CGGGCACCAC CAACCACGAC
841 ATCGCGCTGC TCCGCCTGCA CCAGCCCGTG GTCCTCACTG ACCATGTGGT GCCCCTCTGC
901 CTGCCCGAAC GGACGTTCTC TGAGAGGACG CTGGCCTTCG TGCGCTTCTC ATTGGTCAGC
961 GGCTGGGGCC AGCTGCTGGA CCGTGGCGCC ACGGCCCTGG AGCTCATGGT CCTCAACGTG
1021 CCCCGGCTGA TGACCCAGGA CTGCCTGCAG CAGTCACGGA AGGTGGGAGA CTCCCCAAAT
1081 ATCACGGAGT ACATGTTCTG TGCCGGCTAC TCGGATGGCA GCAAGGACTC CTGCAAGGGG
1141 GACAGTGGAG GCCCACATGC CACCCACTAC CGGGGCACGT GGTACCTGAC GGGCATCGTC
1201 AGCTGGGGCC AGGGCTGCGC AACCGTGGGC CACTTTGGGG TGTACACCAG GGTCTCCCAG
1261 TACATCGAGT GGCTGCAAAA GCTCATGCGC TCAGAGCCAC GCCCAGGAGT CCTCCTGCGA
1321 GCCCCATTTC CCGGTGGCGG TGGCTCCGGC GGAGGTGGGT CCGGTGGCGG CGGATCAGGT
1381 GGGGGTGGAT CAGGCGGTGG AGGTTCCGGT GGCGGGGGAT CCGACATCGT GATGACCCAG
1441 GCCGCCCCCA GCGTGCCCGT GACCCCCGGC GAGAGCGTGA GCATCAGCTG CCGGAGCAGC
1501 CGGAGCCTGC TGCACAGCAA CGGCAACACC TACCTGTGCT GGTTCCTGCA GCGGCCCGGC
1561 CAGAGCCCCC AGCTGCTGAT CTACCGGATG AGCAACCTGG CCAGCGGCGT GCCCGACCGG
1621 TTCAGCGGCA GCGGCAGCGG CACCGCCTTC ACCCTGCGGA TCAGCCGGGT GGAGGCCGAG
1681 GACGTGGGCG TGTACTACTG CATGCAGCAC CTGGAGTACC CCTTCACCTT CGGCAGCGGC
1741 ACCAAGCTGG AGATCAAGCG GGGCGGCGGC GGCAGCGGCG GCGGCGGCAG CGGCGGCGGC
1801 GGCAGCCAGG TGCAGCTGCA GCAGAGCGGC GCCGAGCTGG TGCGGCCCGG CACCAGCGTG
1861 AAGATCAGCT GCAAGGCCAG CGGCTACACC TTCACCAACT ACTGGCTGGG CTGGGTGAAG
1921 CAGCGGCCCG GCCACGGCCT GGAGTGGATC GGCGACATCT ACCCCGGCGG CGGCTACAAC
1981 AAGTACAACG AGAACTTCAA GGGCAAGGCC ACCCTGACCG CCGACACCAG CAGCAGCACC
2041 GCCTACATGC AGCTGAGCAG CCTGACCAGC GAGGACAGCG CCGTGTACTT CTGCGCCCGG
2101 GAGTACGGCA ACTACGACTA CGCCATGGAC AGCTGGGGCC AGGGCACCAG CGTGACCGTG
2161 AGCAGCTGA

FVII-125 amino acid sequence. Signal sequence is shown in dotted underline, propeptide is double underlined, and linker region connecting FVII to AP3 is bold, and AP3 scFv is italicized 1 MVSQALRLLC LLLGLQGCLA AVGVTQEEAH GVLHRRRRAN AFLEELRPGS LERECKEEQC
61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR IVGGKVCPKG ECPWQVLLLV NGAQLCGGTL INTIWVVSAA HCFDKIKNWR
241 NLIAVLGEHD LSEHDGDEQS RRVAQVIIPS TYVPGTTNHD IALLRLHQPV VLTDHVVPLC
301 LPERTFSERT LAFVRFSLVS GWGQLLDRGA TALELMVLNV PRLMTQDCLQ QSRKVGDSPN
361 ITEYMFCAGY SDGSKDSCKG DSGGPHATHY RGTWYLTGIV SWGQGCATVG HFGVYTRVSQ
421 YIEWLQKLMR SEPRPGVLLR APFPGGGGSG GGGSGGGGSG GGGSGGGGSG GGGS*DIVMTQ*
481 *AAPSVPVTPG ESVSISCRSS RSLLHSNGNT YLCWFLQRPG QSPQLLIYRM SNLASGVPDR*
541 *FSGSGSGTAF TLRISRVEAE DVGVYYCMQH LEYPFTFGSG TKLEIKRGGG GSGGGGSGGG*
601 *GSQVQLQQSG AELVRPGTSV KISCKASGYT FTNYWLGWVK QRPGHGLEWI GDIYPGGGYN*
661 *KYNENFKGKA TLTADTSSST AYMQLSSLTS EDSAVYFCAR EYGNYDYAMD SWGQGTSVTV*
721 *SS**

-continued

DRAFT SEQUENCE LISTING

DNA sequence for FVII-067

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCCGA ATTGTGGGGG GCAAGGTGTG CCCCAAAGGG
 601 GAGTGTCCAT GGCAGGTCCT GTTGTTGGTG AATGGAGCTC AGTTGTGTGG GGGGACCCTG
 661 ATCAACACCA TCTGGGTGGT CTCCGCGGCC CACTGTTTCG ACAAAATCAA GAACTGGAGG
 721 AACCTGATCG CGGTGCTGGG CGAGCACGAC CTCAGCGAGC ACGACGGGGA TGAGCAGAGC
 781 CGGCGGGTGG CGCAGGTCAT CATCCCCAGC ACGTACGTCC CGGGCACCAC CAACCACGAC
 841 ATCGCGCTGC TCCGCCTGCA CCAGCCCGTG GTCCTCACTG ACCATGTGGT GCCCCTCTGC
 901 CTGCCCGAAC GGACGTTCTC TGAGAGGACG CTGGCCTTCG TGCGCTTCTC ATTGGTCAGC
 961 GGCTGGGGCC AGCTGCTGGA CCGTGGCGCC ACGGCCCTGG AGCTCATGGT CCTCAACGTG
1021 CCCCGGCTGA TGACCCAGGA CTGCCTGCAG CAGTCACGGA AGGTGGGAGA CTCCCCAAAT
1081 ATCACGGAGT ACATGTTCTG TGCCGGCTAC TCGGATGGCA GCAAGGACTC CTGCAAGGGG
1141 GACAGTGGAG GCCCACATGC CACCCACTAC CGGGGCACGT GGTACCTGAC GGGCATCGTG
1201 AGCTGGGGCC AGGGCTGCGC AACCGTGGGC CACTTTGGGG TGTACACCAG GGTCTCCCAG
1261 TACATCGAGT GGCTGCAAAA GCTCATGCGC TCAGAGCCAC GCCCAGGAGT CCTCCTGCGA
1321 GCCCCATTTC CCGGTGGCGG TGGCTCCGGC GGAGGTGGGT CCGGTGGCGG CGGATCAGGT
1381 GGGGGTGGAT CAGGCGGTGG AGGTTCCGGT GGCGGGGGAT CCGACAAAAC TCACACATGC
1441 CCACCGTGCC CAGCTCCGGA ACTCCTGGGC GGACCGTCAG TCTTCCTCTT CCCCCCAAAA
1501 CCCAAGGACA CCCTCATGAT CTCCCGGACC CCTGAGGTCA CATGCGTGGT GGTGGACGTG
1561 AGCCACGAAG ACCCTGAGGT CAAGTTCAAC TGGTACGTGG ACGGCGTGGA GGTGCATAAT
1621 GCCAAGACAA AGCCGCGGGA GGAGCAGTAC AACAGCACGT ACCGTGTGGT CAGCGTCCTC
1681 ACCGTCCTGC ACCAGGACTG GCTGAATGGC AAGGAGTACA AGTGCAAGGT CTCCAACAAA
1741 GCCCTCCCAG CCCCCATCGA GAAAACCATC TCCAAAGCCA AAGGGCAGCC CCGAGAACCA
1801 CAGGTGTACA CCCTGCCCCC ATCCCGGGAT GAGCTGACCA AGAACCAGGT CAGCCTGACC
1861 TGCCTGGTCA AAGGCTTCTA TCCCAGCGAC ATCGCCGTGG AGTGGGAGAG CAATGGGCAG
1921 CCGGAGAACA ACTACAAGAC CACGCCTCCC GTGTTGGACT CCGACGGCTC CTTCTTCCTC
1981 TACAGCAAGC TCACCGTGGA CAAGAGCAGG TGGCAGCAGG GGAACGTCTT CTCATGCTCC
2041 GTGATGCATG AGGCTCTGCA CAACCACTAC ACGCAGAAGA GCCTCTCCCT GTCTCCGGGT
2101 AAAGGTGGCG GCGGATCAGG TGGGGGTGGA TCAGGCGGTG GAGGTTCCGG TGGCGGGGGA
2161 TCAGACAAAA CTCACACATG CCCACCGTGC CCAGCACCTG AACTCCTGGG AGGACCGTCA
2221 GTCTTCCTCT TCCCCCCAAA ACCCAAGGAC ACCCTCATGA TCTCCCGGAC CCCTGAGGTC
2281 ACATGCGTGG TGGTGGACGT GAGCCACGAA GACCCTGAGG TCAAGTTCAA CTGGTACGTG
2341 GACGGCGTGG AGGTGCATAA TGCCAAGACA AAGCCGCGGG AGGAGCAGTA CAACAGCACG
2401 TACCGTGTGG TCAGCGTCCT CACCGTCCTG CACCAGGACT GGCTGAATGG CAAGGAGTAC
2461 AAGTGCAAGG TCTCCAACAA AGCCCTCCCA GCCCCCATCG AGAAAACCAT CTCCAAAGCC
2521 AAAGGGCAGC CCCGAGAACC ACAGGTGTAC ACCCTGCCCC CATCCCGCGA TGAGCTGACC
2581 AAGAACCAGG TCAGCCTGAC CTGCCTGGTC AAAGGCTTCT ATCCCAGCGA CATCGCCGTG
2641 GAGTGGGAGA GCAATGGGCA GCCGGAGAAC AACTACAAGA CCACGCCTCC CGTGTTGGAC
2701 TCCGACGGCT CCTTCTTCCT CTACAGCAAG CTCACCGTCG ACAAGAGCAG GTGGCAGCAG
2761 GGGAACGTCT TCTCATGCTC CGTGATGCAT GAGGCTCTGC ACAACCACTA CACGCAGAAG
2821 AGCCTCTCCC TGTCTCCGGG TAAAGGTGGC GGTGGCTCCG GCGGAGGTGG GTCCGGTGGC
2881 GGCGGATCAG GTGGGGGTGG ATCAGGCGGT GGAGGTTCCG GTGGCGGGGG ATCAGCGCAG
2941 GTGCAGCTGC AGGAGTCTGG GGGAGGCTTG GTACAGCCTG GGGGGTCCCT GAGACTCTCC
3001 TGTGCAGCCT CTGGATTCAT GTTTAGCAGG TATGCCATGA GCTGGGTCCG CCAGGCTCCA
3061 GGGAAGGGGC CAGAGTGGGT CTCAGGTATT AGTGGTAGTG GTGGTAGTAC ATACTACGCA
3121 GACTCCGTGA AGGGCCGGTT CACCGTCTCC AGAGACAATT CCAAGAACAC GCTGTATCTG
3181 CAAATGAACA GCCTGAGAGC CGAGGACACG GCTGTATATT ACTGCGCCCG GGGCGCCACC
3241 TACACCAGCC GGAGCGACGT GCCCGACCAG ACCAGCTTCG ACTACTGGGG CCAGGGAACC
3301 CTGGTCACCG TCTCCTCAGG GAGTGCATCC GCCCCAAAGC TTGAAGAAGG TGAATTTTCA
3361 GAAGCACGCG TATCTGAACT GACTCAGGAC CCTGCTGTGT CTGTGGCCTT GGGACAGACA
3421 GTCAGGATCA CATGCCAAGG AGACAGCCTC AGAAACTTTT ATGCAAGCTG GTACCAGCAG
3481 AAGCCAGGAC AGGCCCCTAC TCTTGTCATC TATGGTTTAA GTAAAAGGCC CTCAGGGATC
3541 CCAGACCGAT TCTCTGCCTC CAGCTCAGGA AACACAGCTT CCTTGACCAT CACTGGGGCT
3601 CAGGCGGAAG ATGAGGCTGA CTATTACTGC CTGCTGTACT ACGGCGGCGG CCAGCAGGGC
3661 GTGTTCGGCG GCGGCACCAA GCTGACCGTC CTACGTCAGC CCAAGGCTGC CCCCTCGGTC
3721 ACTCTGTTCC CGCCCTCTTC TGCGGCCTGA
```

-continued

DRAFT SEQUENCE LISTING

FVII-067 amino acid sequence. Signal sequence is shown in dotted underline, propeptide is double underlined, linker region connecting FVIIa to Fc region is underlined, linker connecting both Fc regions is dashed underlined and linker connecting the Fc region to SCE5 is in bold

```
   1 MVSQALRLLC LLLGLQGCLA AVFVTQEEAH GVLHRRRRAN AFLEELRPGS LERECKEEQC
  61 SFEEAREIFK DAERTKLFWI SYSDGDQCAS SPCQNGGSCK DQLQSYICFC LPAFEGRNCE
 121 THKDDQLICV NENGGCEQYC SDHTGTKRSC RCHEGYSLLA DGVSCTPTVE YPCGKIPILE
 181 KRNASKPQGR IVGGKVCPKG ECPWQVLLLV NGAQLCGGTL INTIWVVSAA HCFDKIKNWR
 241 NLIAVLGEHD LSEHDGDEQS RRVAQVIIPS TYVPGTTNHD IALLRLHQPV VLTDHVVPLC
 301 LPERTFSERT LAFVRFSLVS GWGQLLDRGA TALELMVLNV PRLMTQDCLQ QSRKVGDSPN
 361 ITEYMFCAGY SDGSKDSCKG DSGGPHATHY RGTWYLTGIV SWGQGCATVG HFGVYTRVSQ
 421 YIEWLQKLMR SEPRPGVLLR APFPGGGGSG GGGSGGGGSG GGGSGGGGSG GGGSDKTHTC
 481 PPCPAPELLG GPSVFLFPPK PKDTLMISRT PEVTCVVVDV SHEDPEVKFN WYVDGVEVHN
 541 AKTKPREEQY NSTYRVVSVL TVLHQDWLNG KEYKCKVSNK ALPAPIEKTI SKAKGQPREP
 601 QVYTLPPSRD ELTKNQVSLT CLVKGFYPSD IAVEWESNGQ PENNYKTTPP VLDSDGSFFL
 661 YSKLTVDKSR WQQGNVFSCS VMHEALHNHY TQKSLSLSPG KGGGGSGGGG SGGGGSGGGG
 721 SDKTHTCPPC PAPELLGGPS VFLFPPKPKD TLMISRTPEV TCVVVDVSHE DPEVKFNWYV
 781 DGVEVHNAKT KPREEQYNST YRVVSVLTVL HQDWLNGKEY KCKVSNKALP APIEKTISKA
 841 KGQPREPQVY TLPPSRDELT KNQVSLTCLV KGFYPSDIAV EWESNGQPEN NYKTTPPVLD
 901 SDGSFFLYSK LTVDKSRWQQ GNVFSCSVMH EALHNHYTQK SLSLSPGKGG GGSGGGGSGG
 961 GGSGGGGSGG GGSGGGGSAQ VQLQESGGGL VQPGGSLRLS CAASGFMFSR YAMSWVRQAP
1021 GKGPEWVSGI SGSGGSTYYA DSVKGRFTVS RDNSKNTLYL QMNSLRAEDT AVYYCARGAT
1081 YTSRSDVPDQ TSFDYWGQGT LVTVSSGSAS APKLEEGEFS EARVSELTQD PAVSVALGQT
1141 VRITCQGDSL RNFYASWYQQ DPGQAPTLVI YGLSKRPSGI PDRFSASSSG NTASLTITGA
1201 QAEDEADYYC LLYYGGGQQG VFGGGTKLTV LRQPKAAPSV TLFPPSSAA*
```

DNA sequence for FVII-094

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCCGA ATTGTGGGGG GCAAGGTGTG CCCCAAAGGG
 601 GAGTGTCCAT GGCAGGTCCT GTTGTTGGTG AATGGAGCTC AGTTGTGTGG GGGGACCCTG
 661 ATCAACACCA TCTGGGTGGT CTCCGCGGCC CACTGTTTCG ACAAAATCAA GAACTGGAGG
 721 AACCTGATCG CGGTGCTGGG CGAGCACGAC CTCAGCGAGC ACGACGGGGA TGAGCAGAGC
 781 CGGCGGGTGG CGCAGGTCAT CATCCCCAGC ACGTACGTCC CGGGCACCAC CAACCACGAC
 841 ATCGCGCTGC TCCGCCTGCA CCAGCCCGTG GTCCTCACTG ACCATGTGGT GCCCCTCTGC
 901 CTGCCCGAAC GGACGTTCTC TGAGAGGACG CTGGCCTTCG TGCGCTTCTC ATTGGTCAGC
 961 GGCTGGGGCC AGCTGCTGGA CCGTGGCGCC ACGGCCCTGG AGCTCATGGT CCTCAACGTG
1021 CCCCGGCTGA TGACCCAGGA CTGCCTGCAG CAGTCACGGA AGGTGGGAGA CTCCCCAAAT
1081 ATCACGGAGT ACATGTTCTG TGCCGGCTAC TCGGATGGCA GCAAGGACTC CTGCAAGGGG
1141 GACAGTGGAG GCCCACATGC CACCCACTAC CGGGGCACGT GGTACCTGAC GGGCATCGTC
1201 AGCTGGGGCC AGGGCTGCGC AACCGTGGGC CACTTTGGGG TGTACACCAG GGTCTCCCAG
1261 TACATCGAGT GGCTGCAAAA GCTCATGCGC TCAGAGCCAC GCCCAGGAGT CCTCCTGCGA
1321 GCCCCATTTC CCGATATCGG TGGCGGTGGC TCCGGCGGAG GTGGGTCCGG TGGCGGCGGA
1381 TCAGGTGGGG GTGGATCAGG CGGTGGAGGT TCCGGTGGCG GGGGATCAGC GCAGGTGCAG
1441 CTGCAGGAGT CTGGGGGAGG CTTGGTACAG CCTGGGGGGT CCCTGAGACT CTCCTGTGCA
1501 GCCTCTGGAT TCATGTTTAG CAGGTATGCC ATGAGCTGGG TCCGCCAGGC TCCAGGGAAG
1561 GGGCCAGAGT GGGTCTCAGG TATTAGTGGT AGTGGTGGTA GTACATACTA CGCAGACTCC
1621 GTGAAGGGCC GGTTCACCGT CTCCAGAGAC AATTCCAAGA ACACGCTGTA TCTGCAAATG
1681 AACAGCCTGA GAGCCGAGGA CACGGCTGTA TATTACTGCG CCCGGGGCGC CACCTACACC
1741 AGCCGGAGCG ACGTGCCCGA CCAGACCAGC TTCGACTACT GGGGCCAGGG AACCCTGGTC
1801 ACCGTCTCCT CAGGGAGTGC ATCCGCCCCA AAGCTTGAAG AAGGTGAATT TTCAGAAGCA
1861 CGCGTATCTG AACTGACTCA GGACCCTGCT GTGTCTGTGG CCTTGGGACA GACAGTCAGG
1921 ATCACATGCC AAGGAGACAG CCTCAGAAAC TTTTATGCAA GCTGGTACCA GCAGAAGCCA
1981 GGACAGGCCC CTACTCTTGT CATCTATGGT TTAAGTAAAA GGCCCTCAGG GATCCCAGAC
2041 CGATTCTCTG CCTCCAGCTC AGGAAACACA GCTTCCTTGA CCATCACTGG GGCTCAGGCG
2101 GAAGATGAGG CTGACTATTA CTGCCTGCTG TACTACGGCG GCGGCCAGCA GGGCGTGTTC
2161 GGCGGCGGCA CCAAGCTGAC CGTCCTACGT CAGCCCAAGG CTGCCCCCTC GGTCACTCTG
2221 TTCCCGCCCT CTTCTGCGGC CTGA
```

-continued

DRAFT SEQUENCE LISTING

FVII-094 amino acid sequence. Signal sequence is shown in dotted underline, propeptide is double underlined, and linker region connecting FVII to SCE5 is underlined

```
  1 MVSQALRLLC LLLGLQGCLA AVFVTQEEAH GVLHRRRRAN AFLEELRPGS LERECKEEQC
 61 SFEEAREIFK DAERTLKFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR IVGGKVCPKG ECPWQVLLLV NGAQLCGGTL INTIWVVSAA HCFDKIKNWR
241 NLIAVLGEHD LSEHDGDEQS RRVAQVIIPS TYVPGTTNHD IALLRLHQPV VLTDHVVPLC
301 LPERTFSERT LAFVRFSLVS GWGQLLDRGA TALELMVLNV PRLMTQDCLQ QSRKVGDSPN
361 ITEYMFCAGY SDGSKDSCKG DSGGPHATHY RGTWYLTGIV SWGQGCATVG HFGVYTRVSQ
421 YIEWLQKLMR SEPRPGVLLR APFPDIGGGG SGGGGSGGGG SGGGGSGGGG SGGGGSAQVQ
481 LQESGGGLVQ PGGSLRLSCA ASGFMFSRYA MSWVRQAPGK GPEWVSGISG SGGSTYYADS
541 VKGRFTVSRD NSKNTLYLQM NSLRAEDTAV YYCARGATYT SRSDVPDQTS FDYWGQGTLV
601 TVSSGSASAP KLEEGEFSEA RVSELTQDPA VSVALGQTVR ITCQGDSLRN FYASWYQQKP
661 GQAPTLVIYG LSKRPSGIPD RFSASSSGNT ASLTITGAQA EDEADYYCLL YYGGGQQGVF
721 GGGTKLTVLR QPKAAPSVTL FPPSSAA*
```

DNA sequence for FVII-028

```
   1 ATGGTCTCCC AGGCCCTCAG GCTCCTCTGC CTTCTGCTTG GGCTTCAGGG CTGCCTGGCT
  61 GCGGAAGTGC AGCTGGTGCA GTCTGGAGCT GAGGTGAATA AGCCTGGGGC CTCAGTGAAG
 121 GTCTCCTGCA AGGCTTCTGG ATACACCTTC ACCGGCTACT ATATGCACTG GGTGCGACAG
 181 GCCCCTGGAC AAGGGCTTGA GTGGATGGGA TGGATCAACC CTAACAGTGG TGGCACAAAC
 241 TATGCACAGA AGTTTCAGGG CTGGGTCACC ATGACCAGGG ACACGTCCAT CAGCACCGCC
 301 TACATGGAGC TGAGCAGGCT GAGATCTGAC GACACGGCCG TGTATTACTG TGCGAGAGGC
 361 CGTGCTTTGT ATAACCGGAA CGACCGGTCC CCCAACTGGT TCGACCCCTG GGGCCAGGGA
 421 ACCCTGGTCA CCGTCTCCTC AGGGAGTGCA TCCGCCCCAA CCCTTAAACT TGAAGAAGGT
 481 GAATTTTCAG AAGCACGCGT ACAGGCTGTG CTGACTCAGC CGCCCTCGGT GTCAGTGGCC
 541 CCAGGACAGA CGGCCAGGAT TACCTGTGGG GGAAACAACA TTGGAAGTAA AAGTGTGCAG
 601 TGGTACCAGC AGAAGCCAGG CCAGGCCCCT GTGCTGGTCG TCTATGATGA TAGCGACCGG
 661 CCCTCAGGGA TCCCTGAGCG ATTCTCTGGC TCCAACTCTG GGAACATGGC CACCCTGACC
 721 ATCAGCAGGG TCGAAGCCGG GGATGAGGCC GACTATTACT GTCAGGTGTG GGATAGTAGT
 781 AGTGATCATG TGGTATTCGG CGGAGGGACC AAGCTGACCG TCCTAGGTCA GCCCAAGGCT
 841 GCCCCTCGGS TCACTCTGTT CCCGCCGTCC GCGGCCGCTA GGACGAAGCT GTTCTGGATT
 901 TCTTACAGTG ATGGGGACCA GTGTGCCTCA AGTCCATGCC AGAATGGGGG CTCCTGCAAG
 961 GACCAGCTCC AGTCCTATAT CTGCTTCTGC CTCCCTGCCT TCGAGGGCCG GAACTGTGAG
1021 ACGCACAAGG ATGACCAGCT GATCTGTGTG AACGAGAACG GCGGCTGTGA GCAGTACTGC
1081 AGTGACCACA CGGGCACCAA GCGCTCCTGT CGGTGCCACG AGGGGTACTC TCTGCTGGCA
1141 GACGGGGTGT CCTGCACACC CACAGTTGAA TATCCATGTG GAAAAATACC TATTCTAGAA
1201 AAAAGAAATG CCAGCAAACC CCAAGGCCGA ATTGTGGGGG GCAAGGTGTG CCCCAAAGGG
1201 GAGTGTCCAT GGCAGGTCCT GTTGTTGGTG AATGGAGCTC AGTTGTGTGG GGGGACCCTG
1321 ATCAACACCA TCTGGGTGGT CTCCGCGGCC CACTGTTTCG ACAAAATCAA GAACTGGAGG
1381 AACCTGATCG CGGTGCTGGG CGAGCACGAC CTCAGCGAGC ACGACGGGGA TGAGCAGAGC
1441 CGGCGGGTGG CGCAGGTCAT CATCCCCAGC ACGTACGTCC CGGGCACCAC CAACCACGAC
1501 ATCGCGCTGC TCCGCCTGCA CCAGCCCGTG GTCCTCACTG ACCATGTGGT GCCCCTCTGC
1561 CTGCCCGAAC GGACGTTCTC TGAGAGGACG CTGGCCTTCG TGCGCTTCTC ATTGGTCAGC
1621 GGCTGGGGCC AGCTGCTGGA CCGTGGCGCC ACGGCCCTGG AGCTCATGGT CCTCAACGTG
1681 CCCCGGCTGA TGACCCAGGA CTGCCTGCAG CAGTCACGGA AGGTGGGAGA CTCCCCAAAT
1741 ATCACGGAGT ACATGTTCTG TGCCGGCTAC TCGGATGGCA GCAAGGACTC CTGCAAGGGG
1801 GACAGTGGAG GCCCACATGC CACCCACTAC CGGGGCACGT GGTACCTGAC GGGCATCGTC
1861 AGCTGGGGCC AGGGCTGCGC AACCGTGGGC CACTTTGGGG TGTACACCAG GGTCTCCCAG
1921 TACATCGAGT GGCTGCAAAA GCTCATGCGC TCAGAGCCAC GCCCAGGAGT CCTCCTGCGA
1981 GCCCCATTTC CCGGTGGCGG TGGCTCCGGC GGAGGTGGGT CCGGTGGCGG CGGATCAGGT
2041 GGGGGTGGAT CAGGCGGTGG AGGTTCCGGT GGCGGGGGAT CCGACAAAAC TCACACATGC
2101 CCACCGTGCC CAGCTCCGGA ACTCCTGGGC GGACCGTCAG TCTTCCTCTT CCCCCCAAAA
2161 CCCAAGGACA CCCTCATGAT CTCCCGGACC CCTGAGGTCA CATGCGTGGT GGTGGACGTG
2221 AGCCACGAAG ACCCTGAGGT CAAGTTCAAC TGGTACGTGG ACGGCGTGGA GGTGCATAAT
2281 GCCAAGACAA AGCCGCGGGA GGAGCAGTAC AACAGCACGT ACCGTGTGGT CAGCGTCCTC
2341 ACCGTCCTGC ACCAGGACTG GCTGAATGGC AAGGAGTACA AGTGCAAGGT CTCCAACAAA
2401 GCCCTCCCAG CCCCCATCGA GAAAACCATC TCCAAAGCCA AAGGGCAGCC CCGAGAACCA
2461 CAGGTGTACA CCCTGCCCCC ATCCCGGGAT GAGCTGACCA AGAACCAGGT CAGCCTGACC
2521 TGCCTGGTCA AAGGCTTCTA TCCCAGCGAC ATCGCCGTGG AGTGGGAGAG CAATGGGCAG
2581 CCGGAGAACA ACTACAAGAC CACGCCTCCC GTGTTGGACT CCGACGGCTC CTTCTTCCTC
2641 TACAGCAAGC TCACCGTGGA CAAGAGCAGG TGGCAGCAGG GGAACGTCTT CTCATGCTCC
2701 GTGATGCATG AGGCTCTGCA CAACCACTAC ACGCAGAAGA GCCTCTCCCT GTCTCCGGGT
2761 AAAGGTGGCG GCGGATCAGG TGGGGGTGGA TCAGGCGGTG GAGGTTCCGG TGGCGGGGGA
2821 TCCGACAAAA CTCACACATG CCCACCGTGC CCAGCACCTG AACTCCTGGG AGGACCGTCA
2881 GTCTTCCTCT TCCCCCCAAA ACCCAAGGAC ACCCTCATGA TCTCCCGGAC CCCTGAGGTC
2941 ACATGCGTGG TGGTGGACGT GAGCCACGAA GACCCTGAGG TCAAGTTCAA CTGGTACGTG
3001 GACGGCGTGG AGGTGCATAA TGCCAAGACA AAGCCGCGGG AGGAGCAGTA CAACAGCACG
3061 TACCGTGTGG TCAGCGTCCT CACCGTCCTG CACCAGGACT GGCTGAATGG CAAGGAGTAC
3121 AAGTGCAAGG TCTCCAACAA AGCCCTCCCA GCCCCCATCG AGAAAACCAT CTCCAAAGCC
3181 AAAGGGCAGC CCCGAGAACC ACAGGTGTAC ACCCTGCCCC CATCCCGCGA TGAGCTGACC
3241 AAGAACCAGG TCAGCCTGAC CTGCCTGGTC AAAGGCTTCT ATCCCAGCGA CATCGCCGTG
3301 GAGTGGGAGA GCAATGGGCA GCCGGAGAAC AACTACAAGA CCACGCCTCC CGTGTTGGAC
3361 TCCGACGGCT CCTTCTTCCT CTACAGCAAG CTCACCGTGG ACAAGAGCAG GTGGCAGCAG
3421 GGGAACGTCT TCTCATGCTC CGTGATGCAT GAGGCTCTGC ACAACCACTA CACGCAGAAG
3481 AGCCTCTCCC TGTCTCCGGG TAAATGA
```

-continued

DRAFT SEQUENCE LISTING

FVII-028 amino acid sequence. Signal sequence is shown in dotted underline, linker region connecting FVII to Fc region is underlined, linker connecting both Fcs sites is shown in bold, and MB9 is italicized

```
   1 MVSQALRLLC LLLGLQGCLA AEVQLVQSGA EVNKPGASVK VSCKASGYTF TGYYMHWVRQ
  61 APGQGLEWMG WINPNSGGTN YAQKFQGWVT MTRDTSISTA YMELSRLRSD DTAVYYCARG
 121 RALYNRNDRS PNWFDPWGQG TLVTVSSGSA SAPTLKLEEG EFSEARVQAV LTQPPSVSVA
 181 PGQTARITCG GNNIGSKSVQ WYQQKPGQAP VLVVYDDSDR PSGIPERFSG SNSGNMATLT
 241 ISRVEAGDEA DYYCQVWDSS SDHVVFGGGT KLTVLGQPKA APSVTLFPPS AAARTKLFWI
 301 SYSDGDQCAS SPCQNGGSCK DQLQSYICFC LPAFEGRNCE THKDDQLICV NENGGCEQYC
 361 SDHTGTKRSC RCHEGYSLLA DGVSCTPTVE YPCGKIPILE KRNASKPQGR IVGGKVCPKG
 421 ECPWQVLLLV NGAQLCGGTL INTIWVVSAA HCFDKIKNWR NLIAVLGEHD LSEHDGDEQS
 481 RRVAQVIIPS TYVPGTTNHD IALLRLHQPV VLTDHVVPLC LPERTFSERT LAFVRFSLVS
 541 GWGQLLDRGA TALELMVLNV PRLMTQDCLQ QSRKVGDSPN ITEYMFCAGY SDGSKDSCKG
 601 DSGGPHATHY RGTWYLTGIV SWGQGCATVG HFGVYTRVSQ YIEWLQKLMR SEPRPGVLLR
 661 APFPGGGGSG GGGSGGGGSG GGGSGGGGSG GGGSDKTHTC PPCPAPELLG GPSVFLFPPK
 721 PKDTLMISRT PEVTCVVVDV SHEDPEVKFN WYVDGVEVHN AKTKPREEQY NSTYRVVSVL
 781 TVLHQDWLNG KEYKCKVSNK ALPAPIEKTI SKAKGQPREP AVYTLPPSRD ELTKNQVSLT
 841 CLVKGFYPSD IAVEWESNGQ PENNYKTTPP VLDSDGSFFL YSKLTVDKSR WQQGNVFSCS
 901 VMHEALHNHY TQKSLSLSPG KGGGGSGGGG SGGGGSGGGG SDKTHTCPPC PAPELLGGPS
 961 VFLFPPKPKD TLMISRTPEV TCVVVDVSHE DPEVKFNWYV DGVEVHNAKT KPREEQYNST
1021 YRVVSVLTVL HQDWLNGKEY KCKVSNKALP APIEKTISKA KGQPREPQVY TLPPSRDELT
1081 KNQVSLTCLV KGFYPSDIAV EWESNGQPEN NYKTTPPVLD SDGSFFLYSK LTVDKSRWQQ
1141 GNVFSCSVMH EALHNHYTQK SLSLSPGK*
```

DNA sequence FVII-039

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCCGA GGCGGAGGAG ACTTCACTCG GGTTGTGGGG
 601 GGCAAGGTGT GCCCCAAAGG GGAGTGTCCA TGGCAGGTCC TGTTGTTGGT GAATGGAGCT
 661 CAGTTGTGTG GGGGGACCCT GATCAACACC ATCTGGGTGG TCTCCGCGGC CCACTGTTTC
 721 GACAAAATCA AGAACTGGAG GAACCTGATC GCGGTGCTGG GCGAGCACGA CCTCAGCGAG
 781 CACGACGGGG ATGAGCAGAG CCGGCGGGTG GCGCAGGTCA TCATCCCCAG CACGTACGTC
 841 CCGGGCACCA CCAACCACGA CATCGCGCTG CTCCGCCTGC ACCAGCCCGT GGTCCTCACT
 901 GACCATGTGG TGCCCCTCTG CCTGCCCGAA CGGACGTTCT CTGAGAGGAC GCTGGCCTTC
 961 GTGCGCTTCT CATTGGTCAG CGGCTGGGGC CAGCTGCTGG ACCGTGGCGC CACGGCCCTG
1021 GAGCTCATGG TCCTCAACGT GCCCCGGCTG ATGACCCAGG ACTGCCTGCA GCAGTCACGG
1081 AAGGTGGGAG ACTCCCCAAA TATCACGGAG TACATGTTCT GTGCCGGCTA CTCGGATGGC
1141 AGCAAGGACT CCTGCAAGGG GGACAGTGGA GGCCCACATG CCACCCACTA CCGGGGCACG
1201 TGGTACCTGA CGGGCATCGT CAGCTGGGGC CAGGGCTGCG CAACCGTGGG CCACTTTGGG
1261 GTGTACACCA GGGTCTCCCA GTACATCGAG TGGCTGCAAA AGCTCATGCG CTCAGAGCCA
1321 CGCCCAGGAG TCCTCCTGCG AGCCCCATTT CCCGGTGGCG GTGGCTCCGG CGGAGGTGGG
1381 TCCGGTGGCG GCGGATCAGG TGGGGGTGGA TCAGGCGGTG GAGGTTCCGG TGGCGGGGGA
1441 TCCGACAAAA CTCACACATG CCCACCGTGC CCAGCTCCGG AACTCCTGGG CGGACCGTCA
1501 GTCTTCCTCT TCCCCCCAAA ACCCAAGGAC ACCCTCATGA TCTCCCGGAC CCCTGAGGTC
1561 ACATGCGTGG TGGTGGACGT GAGCCACGAA GACCCTGAGG TCAAGTTCAA CTGGTACGTG
1621 GACGGCGTGG AGGTGCATAA TGCCAAGACA AAGCCGCGGG AGGAGCAGTA CAACAGCACG
1681 TACCGTGTGG TCAGCGTCCT CACCGTCCTG CACCAGGACT GGCTGAATGG CAAGGAGTAC
1741 AAGTGCAAGG TCTCCAACAA AGCCCTCCCA GCCCCCATCG AGAAAACCAT CTCCAAAGCC
1801 AAAGGGCAGC CCCGAGAACC ACAGGTGTAC ACCCTGCCCC CATCCCGGGA TGAGCTGACC
1861 AAGAACCAGG TCAGCCTGAC CTGCCTGGTC AAAGGCTTCT ATCCCAGCGA CATCGCCGTG
1921 GAGTGGGAGA GCAATGGGCA GCCGGAGAAC AACTACAAGA CCACGCCTCC CGTGTTGGAC
1981 TCCGACGGCT CCTTCTTCCT CTACAGCAAG CTCACCGTGG ACAAGAGCAG GTGGCAGCAG
2041 GGGAACGTCT TCTCATGCTC CGTGATGCAT GAGGCTCTGC ACAACCACTA CACGCAGAAG
2101 AGCCTCTCCC TGTCTCCGGG TAAAGGTGGC GGCGGATCAG GTGGGGGTGG ATCAGGCGGT
2161 GGAGGTTCCG GTGGCGGGGG ATCAGACAAA ACTCACACAT GCCCACCGTG CCCAGCACCT
2221 GAACTCCTGG GAGGACCGTC AGTCTTCCTC TTCCCCCCAA AACCCAAGGA CACCCTCATG
2281 ATCTCCCGGA CCCCTGAGGT CACATGCGTG GTGGTGGACG TGAGCCACGA AGACCCTGAG
2341 GTCAAGTTCA ACTGGTACGT GGACGGCGTG GAGGTGCATA ATGCCAAGAC AAAGCCGCGG
2401 GAGGAGCAGT ACAACAGCAC GTACCGTGTG GTCAGCGTCC TCACCGTCCT GCACCAGGAC
2461 TGGCTGAATG GCAAGGAGTA CAAGTGCAAG GTCTCCAACA AAGCCCTCCC AGCCCCCATC
2521 GAGAAAACCA TCTCCAAAGC CAAAGGGCAG CCCCGAGAAC CACAGGTGTA CACCCTGCCC
2581 CCATCCCGCG ATGAGCTGAC CAAGAACCAG GTCAGCCTGA CCTGCCTGGT CAAAGGCTTC
2641 TATCCCAGCG ACATCGCCGT GGAGTGGGAG AGCAATGGGC AGCCGGAGAA CAACTACAAG
2701 ACCACGCCTC CCGTGTTGGA CTCCGACGGC TCCTTCTTCC TCTACAGCAA GCTCACCGTG
2761 GACAAGAGCA GGTGGCAGCA GGGGAACGTC TTCTCATGCT CCGTGATGCA TGAGGCTCTG
2821 CACAACCACT ACACGCAGAA GAGCCTCTCC CTGTCTCCGG GTAAATGA
```

-continued

DRAFT SEQUENCE LISTING

FVII-039 amino acid sequence. Signal sequence is shown in dotted underline, propeptide is double underlined, the FXIa cleavage site is shown in dashed underline, the linker region connecting FVII heavy chain to Fc region is underlined, and the linker region connecting the Fc regions is shown in bold 1 MVSQALRLLC LLLGLQGCLA AVFVTQEEAH GVLHRRRRAN AFLEELRPGS LERECKEEQC
61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR GGGDFTRVVG GKVCPKGECP WQVLLLVNGA QLCGGTLINT IWVVSAAHCF
241 DKIKNWRNLI AVLGEHDLSE HDGDEQSRRV AQVIIPSTYV PGTTNHDIAL LRLHQPVVLT
301 DHVVPLCLPE RTFSERTLAF VRFSLVSGWG QLLDRGATAL ELMVLNVPRL MTQDCLQQSR
361 KVGDSPNITE YMFCAGYSDG SKDSCKGDSG GPHATHYRGT WYLTGIVSWG QGCATVGHFG
421 VYTRVSQYIE WLQKLMRSEP RPGVLLRAPF PGGGGSGGGG SGGGGSGGGG SGGGGSGGGG
481 SDKTHTCPPC PAPELLGGPS VFLFPPKPKD TLMISRTPEV TCVVVDVSHE DPEVKFNWYV
541 DGVEVHNAKT KPREEQYNST YRVVSVLTVL HQDWLNGKEY KCKVSNKALP APIEKTISKA
601 KGQPREPQVY TLPPSRDELT KNQVSLTCLV KGFYPSDIAV EWESNGQPEN NYKTTPPVLD
661 SDGSFFLYSK LTVDKSRWQQ GNVFSCSVMH EALHNHYTQK SLSLSPGKGG GGSGGGGSGG
721 GGSGGGGSDK THTCPPCPAP ELLGGPSVFL FPPKPKDTLM ISRTPEVTCV VVDVSHEDPE
781 VKFNWYVDGV EVHNAKTKPR EEQYNSTYRV VSVLTVLHQD WLNGKEYKCK VSNKALPAPI
841 EKTISKAKGQ PREPQVYTLP PSRDELTKNQ VSLTCLVKGF YPSDIAVEWE SNGQPENNYK
901 TTPPVLDSDG SFFLYSKLTV DKSRWQQGNV FSCSVMHEAL HNHYTQKSLS LSPGK*

DNA sequence for FVII-040
1 ATGGTCTCCC AGGCCCTCAG GCTCCTCTGC CTTCTGCTTG GGCTTCAGGG CTGCCTGGCT
61 GCAGTCTTCG TAACCCAGGA GGAAGCCCAC GGCGTCCTGC ACCGGCGCCG GCGCGCCAAC
121 GCGTTCCTGG AGGAGCTGCG GCCGGGCTCC CTGGAGAGGG AGTGCAAGGA GGAGCAGTGC
181 TCCTTCGAGG AGGCCCGGGA GATCTTCAAG GACGCGGAGA GGACGAAGCT GTTCTGGATT
241 TCTTACAGTG ATGGGGACCA GTGTGCCTCA AGTCCATGCC AGAATGGGGG CTCCTGCAAG
301 GACCAGCTCC AGTCCTATAT CTGCTTCTGC CTCCCTGCCT TCGAGGGCCG GAACTGTGAG
361 ACGCACAAGG ATGACCAGCT GATCTGTGTG AACGAGAACG GCGGCTGTGA GCAGTACTGC
421 AGTGACCACA CGGGCACCAA GCGCTCCTGT CGGTGCCACG AGGGGTACTC TCTGCTGGCA
481 GACGGGGTGT CCTGCACACC CACAGTTGAA TATCCATGTG GAAAAATACC TATTCTAGAA
541 AAAAGAAATG CCAGCAAACC CCAAGGCGGC GGAGGAGACT TCACTCGGGT TGTGGGGGGC
601 AAGGTGTGCC CCAAAGGGGA GTGTCCATGG CAGGTCCTGT TGTTGGTGAA TGGAGCTCAG
661 TTGTGTGGGG GGACCCTGAT CAACACCATC TGGGTGGTCT CCGCGGCCCA CTGTTTCGAC
721 AAAATCAAGA ACTGGAGGAA CCTGATCGCG GTGCTGGGCG AGCACGACCT CAGCGAGCAC
781 GACGGGGATG AGCAGAGCCG GCGGGTGGCG CAGGTCATCA TCCCCAGCAC GTACGTCCCG
841 GGCACCACCA ACCACGACAT CGCGCTGCTC CGCCTGCACC AGCCCGTGGT CCTCACTGAC
901 CATGTGGTGC CCCTCTGCCT GCCCGAACGG ACGTTCTCTG AGAGGACGCT GGCCTTCGTG
961 CGCTTCTCAT TGGTCAGCGG CTGGGGCCAG CTGCTGGACC GTGGCGCCAC GGCCCTGGAG
1021 CTCATGGTCC TCAACGTGCC CCGGCTGATG ACCCAGGACT GCCTGCAGCA GTCACGGAAG
1081 GTGGGAGACT CCCCAAATAT CACGGAGTAC ATGTTCTGTG CCGGCTACTC GGATGGCAGC
1141 AAGGACTCCT GCAAGGGGGA CAGTGGAGGC CCACATGCCA CCCACTACCG GGGCACGTGG
1201 TACCTGACGG GCATCGTCAG CTGGGGCCAG GGCTGCGCAA CCGTGGGCCA CTTTGGGGTG
1261 TACACCAGGG TCTCCCAGTA CATCGAGTGG CTGCAAAAGC TCATGCGCTC AGAGCCACGC
1321 CCAGGAGTCC TCCTGCGAGC CCCATTTCCC GGTGGCGGTG GCTCCGGCGG AGGTGGGTCC
1381 GGTGGCGGCG GATCAGGTGG GGGTGGATCA GGCGGTGGAG GTTCCGGTGG CGGGGGATCC
1441 GACAAAACTC ACACATGCCC ACCGTGCCCA GCTCCGGAAC TCCTGGGCGG ACCGTCAGTC
1501 TTCCTCTTCC CCCCAAAACC CAAGGACACC CTCATGATCT CCCGGACCCC TGAGGTCACA
1561 TGCGTGGTGG TGGACGTGAG CCACGAAGAC CCTGAGGTCA AGTTCAACTG GTACGTGGAC
1621 GGCGTGGAGG TGCATAATGC CAAGACAAAG CCGCGGGAGG AGCAGTACAA CAGCACGTAC
1681 CGTGTGGTCA GCGTCCTCAC CGTCCTGCAC CAGGACTGGC TGAATGGCAA GGAGTACAAG
1741 TGCAAGGTCT CCAACAAAGC CCTCCCAGCC CCCATCGAGA AAACCATCTC CAAAGCCAAA
1801 GGGCAGCCCC GAGAACCACA GGTGTACACC CTGCCCCCAT CCCGGGATGA GCTGACCAAG
1861 AACCAGGTCA GCCTGACCTG CCTGGTCAAA GGCTTCTATC CCAGCGACAT CGCCGTGGAG
1921 TGGGAGAGCA ATGGGCAGCC GGAGAACAAC TACAAGACCA CGCCTCCCGT GTTGGACTCC
1981 GACGGCTCCT TCTTCCTCTA CAGCAAGCTC ACCGTGGACA AGAGCAGGTG GCAGCAGGGG
2041 AACGTCTTCT CATGCTCCGT GATGCATGAG GCTCTGCACA ACCACTACAC GCAGAAGAGC
2101 CTCTCCCTGT CTCCGGGTAA AGGTGGCGGC GGATCAGGTG GGGGTGGATC AGGCGGTGGA
2161 GGTTCCGGTG GCGGGGGATC AGACAAAACT CACACATGCC CACCGTGCCC AGCACCTGAA
2221 CTCCTGGGAG GACCGTCAGT CTTCCTCTTC CCCCCAAAAC CCAAGGACAC CCTCATGATC
2281 TCCCGGACCC CTGAGGTCAC ATGCGTGGTG GTGGACGTGA GCCACGAAGA CCCTGAGGTC
2341 AAGTTCAACT GGTACGTGGA CGGCGTGGAG GTGCATAATG CCAAGACAAA GCCGCGGGAG
2401 GAGCAGTACA ACAGCACGTA CCGTGTGGTG AGCGTCCTCA CCGTCCTGCA CCAGGACTGG
2461 CTGAATGGCA AGGAGTACAA GTGCAAGGTC TCCAACAAAG CCCTCCCAGC CCCCATCGAG
2521 AAAACCATCT CCAAAGCCAA AGGGCAGCCC CGAGAACCAC AGGTGTACAC CCTGCCCCCA
2581 TCCCGCGATG AGCTGACCAA GAACCAGGTC AGCCTGACCT GCCTGGTCAA AGGCTTCTAT
2641 CCCAGCGACA TCGCCGTGGA GTGGGAGAGC AATGGGCAGC CGGAGAACAA CTACAAGACC
2701 ACGCCTCCCG TGTTGGACTC CGACGGCTCC TTCTTCCTCT ACAGCAAGCT CACCGTGGAC -continued

DRAFT SEQUENCE LISTING

```
2761 AAGAGCAGGT GGCAGCAGGG GAACGTCTTC TCATGCTCCG TGATGCATGA GGCTCTGCAC
2821 AACCACTACA CGCAGAAGAG CCTCTCCCTG TCTCCGGGTA AATGA
```

FVII-040 amino acid sequence. Signal sequence is shown in dotted underline, propeptide is double underlined, the FXIa cleavage site is shown in dashed underline, the linker region connecting FVII heavy chain to Fc region is underlined, and the linker region connecting the Fc regions is shown in bold

```
  1 MVSQALRLLC LLLGLQGCLA AVFVTQEEAH GVLHRRRRAN AFLEELRPGS LERECKEEQC
 61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGG GGDFTRVVGG KVCPKGECPW QVLLLVNGAQ LCGGTLINTI WVVSAAHCFD
241 KIKNWRNLIA VLGEHDLSEH DGDEQSRRVA QVIIPSTYVP GTTNHDIALL RLHQPVVLTD
301 HVVPLCLPER TFSERTLFAV RFSLVSGWGQ LLDRGATALE LMVLNVPRLM TQDCLQQSRK
361 VGDSPNITEY MFCAGYSDGS KDSCKGDSGG PHATHYRGTW YLTGIVSWGQ GCATVGHFGV
421 YTRVSQYIEW LQKLMRSEPR PGVLLRAPFP GGGGSGGGGS GGGGSGGGGS GGGGSGGGGS
481 DKTHTCPPCP APELLGGPSV FLFPPKPKDT LMISRTPEVT CVVVDVSHED PEVKFNWYVD
541 GVEVHNAKTK PREEQYNSTY RVVSVLTVLH QDWLNGKEYK CKVSNKALPA PEIKTISKAK
601 GQPREPQVYT LPPSRDELTK NQVSLTCLVK GFYPSDIAVE WESNGQPENN YKTTPPVLDS
661 DGSFFLYSKL TVDKSRWQQG NVFSCSVMHE ALHNHYTQKS LSLSPGKGGG GSGGGGSGGG
721 GSGGGGSDKT HTCPPCPAPE LLGGPSVFLF PPKPKDTLMI SRTPEVTCVV VDVSHEDPEV
781 KFNWYVDGVE VHNAKTKPRE EQYNSTYRVV SVLTVLHQDW LNGKEYKCKV SNKALPAPIE
841 KTISKAKGQP REPQVYTLPP SRDELTKNQV SLTCLVKGFY PSDIAVEWES NGQPENNYKT
901 TPPVLDSDGS FFLYSKLTVD KSRWQQGNVF SCSVMHEALH NHYTQKSLSL SPGK*
```

DNA sequence for FIX-042

```
   1 ATGCAGCGCG TGAACATGAT CATGGCAGAA TCACCAGGCC TCATCACCAT CTGCCTTTTA
  61 GGATATCTAC TCAGTGCTGA ATGTACAGGT TTGTTTCCTT TTTTAAAATA CATTGAGTAT
 121 GCTTGCCTTT TAGATATAGA AATATCTGAT GCTGTCTTCT TCACTAAATT TTGATTACAT
 181 GATTTGACAG CAATATTGAA GAGTCTAACA GCCAGCACGC AGGTTGGTAA GTACTGTGGG
 241 AACATCACAG ATTTTGGCTC CATGCCCTAA AGAGAAATTG GCTTTCAGAT TATTTGGATT
 301 AAAAACAAAG ACTTTCTTAA GAGATGTAAA ATTTTCATGA TGTTTTCTTT TTTGCTAAAA
 361 CTAAAGAATT ATTCTTTTAC ATTTCAGTTT TTCTTGATCA TGAAAACGCC AACAAAATTC
 421 TGAATCGGCC AAAGAGGTAT AATTCAGGTA AATTGGAAGA GTTTGTTCAA GGGAATCTAG
 481 AGAGAGAATG TATGGAAGAA AAGTGTAGTT TTGAAGAAGC ACGAGAAGTT TTTGAAAACA
 541 CTGAAAGAAC AACTGAATTT TGGAAGCAGT ATGTTGATGG AGATCAGTGT GAGTCCAATC
 601 CATGTTTAAA TGGCGGCAGT TGCAAGGATG ACATTAATTC CTATGAATGT TGGTGTCCCT
 661 TTGGATTTGA AGGAAAGAAC TGTGAATTAG ATGTAACATG TAACATTAAG AATGGCAGAT
 721 GCGAGCAGTT TTGTAAAAAT AGTGCTGATA ACAAGGTGGT TTGCTCCTGT ACTGAGGGAT
 781 ATCGACTTGC AGAAAACCAG AAGTCCTGTG AACCAGCAGT GCCATTTCCA TGTGGAAGAG
 841 TTTCTGTTTC ACAAACTTCT AAGCTCACCC GTGCTGAGAC TGTTTTTCCT GATGTGGACT
 901 ATGTAAATTC TACTGAAGCT GAAACCATTT TGGATAACAT CACTCAAAGC ACCCAATCAT
 961 TTAATGACTT CACTCGGGTT GTTGGTGGAG AAGATGCCAA ACCAGGTCAA TTCCCTTGGC
1021 AGGTTGTTTT GAATGGTAAA GTTGATGCAT TCTGTGGAGG CTCTATCGTT AATGAAAAAT
1081 GGATTGTAAC TGCTGCCCAC TGTGTTGAAA CTGGTGTTAA AATTACAGTT GTCGCAGGTG
1141 AACATAATAT TGAGGAGACA GAACATACAG AGCAAAAGCG AAATGTGATT CGAATTATTC
1201 CTCACCACAA CTACAATGCA GCTATTAATA AGTACAACCA TGACATTGCC CTTCTGGAAC
1261 TGGACGAACC CTTAGTGCTA AACAGCTACG TTACACCTAT TTGCATTGCT GACAAGGAAT
1321 ACACGAACAT CTTCCTCAAA TTTGGATCTG GCTATGTAAG TGGCTGGGGA AGAGTCTTCC
1381 ACAAAGGGAG ATCAGCTTTA GTTCTTCAGT ACCTTAGAGT TCCACTTGTT GACCGAGCCA
1441 CATGTCTTCG ATCTACAAAG TTCACCATCT ATAACAACAT GTTCTGTGCT GGCTTCCATG
1501 AAGGAGGTAG AGATTCATGT CAAGGAGATA GTGGGGGACC CCATGTTACT GAAGTGGAAG
1561 GGACCAGTTT CTTAACTGGA ATTATTAGCT GGGGTGAAGA GTGTGCAATG AAAGGCAAAT
1621 ATGGAATATA TACCAAGGTG TCCCGGTATG TCAACTGGAT TAAGGAAAAA ACAAAGCTCA
1681 CTGACAAAAC TCACACATGC CCACCGTGCC CAGCTCCGGA ACTCCTGGGC GGACCGTCAG
1741 TCTTCCTCTT CCCCCCAAAA CCCAAGGACA CCCTCATGAT CTCCCGGACC CCTGAGGTCA
1801 CATGCGTGGT GGTGGACGTG AGCCACGAAG ACCCTGAGGT CAAGTTCAAC TGGTACGTGG
1861 ACGGCGTGGA GGTGCATAAT GCCAAGACAA AGCCGCGGGA GGAGCAGTAC AACAGCACGT
1921 ACCGTGTGGT CAGCGTCCTC ACCGTCCTGC ACCAGGACTG GCTGAATGGC AAGGAGTACA
1981 AGTGCAAGGT CTCCAACAAA GCCCTCCCAG CCCCCATCGA GAAAACCATC TCCAAAGCCA
2041 AAGGGCAGCC CCGAGAACCA CAGGTGTACA CCCTGCCCCC ATCCCGGGAT GAGCTGACCA
2101 AGAACCAGGT CAGCCTGACC TGCCTGGTCA AAGGCTTCTA TCCCAGCGAC ATCGCCGTGG
2161 AGTGGGAGAG CAATGGGCAG CCGGAGAACA ACTACAAGAC CACGCCTCCC GTGTTGGACT
2221 CCGACGGCTC CTTCTTCCTC TACAGCAAGC TCACCGTGGA CAAGAGCAGG TGGCAGCAGG
2281 GGAACGTCTT CTCATGCTCC GTGATGCATG AGGCTCTGCA CAACCACTAC ACGCAGAAGA
2341 GCCTCTCCCT GTCTCCGGGT AAAGGTGGCG GCGGATCAGG TGGGGGTGGA TCAGGCGGTG
2401 GAGGTTCCGG TGGCGGGGGA TCAGACAAAA CTCACACATG CCCACCGTGC CCAGCACCTG
2461 AACTCCTGGG AGGACCGTCA GTCTTCCTCT TCCCCCCAAA ACCCAAGGAC ACCCTCATGA
2521 TCTCCCGGAC CCCTGAGGTC ACATGCGTGG TGGTGGACGT GAGCCACGAA GACCCTGAGG
2581 TCAAGTTCAA CTGGTACGTG GACGGCGTGG AGGTGCATAA TGCCAAGACA AAGCCGCGGG
2641 AGGAGCAGTA CAACAGCACG TACCGTGTGG TCAGCGTCCT CACCGTCCTG CACCAGGACT
2701 GGCTGAATGG CAAGGAGTAC AAGTGCAAGG TCTCCAACAA AGCCCTCCCA GCCCCCATCG
2761 AGAAAACCAT CTCCAAAGCC AAAGGGCAGC CCCGAGAACC ACAGGTGTAC ACCCTGCCCC
2821 CATCCCGCGA TGAGCTGACC AAGAACCAGG TCAGCCTGAC CTGCCTGGTC AAAGGCTTCT
2881 ATCCCAGCGA CATCGCCGTG GAGTGGGAGA GCAATGGGCA GCCGGAGAAC AACTACAAGA
2941 CCACGCCTCC CGTGTTGGAC TCCGACGGCT CCTTCTTCCT CTACAGCAAG CTCACCGTGG
3001 ACAAGAGCAG GTGGCAGCAG GGGAACGTCT TCTCATGCTC CGTGATGCAT GAGGCTCTGC
3061 ACAACCACTA CACGCAGAAG AGCCTCTCCC TGTCTCCGGG TAAATGA
```

-continued

DRAFT SEQUENCE LISTING

FIX-042 amino acid sequence. Signal sequence is shown in dotted underline, propeptide is double underlined, and linker region connecting the Fc regions is underlined

```
  1 MQRVNMIMAE SPGLITICLL GYLLSAECTV FLDHENANKI LNRPKRYNSG KLEEFVQGNL
 61 ERECMEEKCS FEEAREVFEN TERTTEFWKQ YVDGDQCESN PCLNGGSCKD DINSYECWCP
121 FGFEGKNCEL DVTCNIKNGR CEQFCKNSAD NKVVCSCTEG YRLAENQKSC EPAVPFPCGR
181 VSVSQTSKLT RAETVFPDVD YVNSTEAETI LDNITQSTQS FNDFTRVVGG EDAKPGQFPW
241 QVVLNGKVDA FCGGSIVNEK WIVTAAHCVE TGVKITVVAG EHNIEETEHT EQKRNVIRII
301 PHHNYNAAIN KYNHDIALLE LDEPLVLNSY VTPICIADKE YTNIFLKFGS GYVSGWGRVF
361 HKGRSALVLQ YLRVPLVDRA TCLRSTKFTI YNNMFCAGFH EGGRDSCQGD SGGPHVTEVE
421 GTSFLTGIIS WGEECAMKGK YGIYTKVSRY VNWIKEKTKL TDKTHTCPPC PAPELLGGPS
481 VFLFPPKPKD TLMISRTPEV TCVVVDVSHE DPEVKFNWYV DGVEVHNAKT KPREEQYNST
541 YRVVSVLTVL HQDWLNGKEY KCKVSNKALP APIEKTISKA KGQPREPQVY TLPPSRDELT
601 KNQVSLTCLV KGFYPSDIAV EWESNGQPEN NYKTTPPVLD SDGSFFLYSK LTVDKSRWQQ
661 GNVFSCSVMH EALHNHYTQK SLSLSPGKGG GGSGGGGSGG GGSGGGGSDK THTCPPCPAP
721 ELLGGPSVFL FPPKPKDTLM ISRTPEVTCV VVDVSHEDPE VKFNWYVDGV EVHNAKTKPR
781 EEQYNSTYRV VSVLTVLHQD WLNGKEYKCK VSNKALPAPI EKTISKAKGQ PREPQVYTLP
841 PSRDELTKNQ VSLTCLVKGF YPSDIAVEWE SNGQPENNYK TTPPVLDSDG SFFLYSKLTV
901 DKSRWQQGNV FSCSVMHEAL HNHYTQKSLS LSPGK*
```

DNA sequence for FIX-068

```
   1 ATGCAGCGCG TGAACATGAT CATGGCAGAA TCACCAGGCC TCATCACCAT CTGCCTTTTA
  61 GGATATCTAC TCAGTGCTGA ATGTACAGGT TTGTTTCCTT TTTTAAAATA CATTGAGTAT
 121 GCTTGCCTTT TAGATATAGA AATATCTGAT GCTGTCTTCT TCACTAAATT TTGATTACAT
 181 GATTTGACAG CAATATTGAA GAGTCTAACA GCCAGCACGC AGGTTGGTAA GTACTGTGGG
 241 AACATCACAG ATTTTGGCTC CATGCCCTAA AGAGAAATTG GCTTTCAGAT TATTTGGATT
 301 AAAAACAAAG ACTTTCTTAA GAGATGTAAA ATTTTCATGA TGTTTTCTTT TTTGCTAAAA
 361 CTAAAGAATT ATTCTTTTAC ATTTCAGTTT TTCTTGATCA TGAAAACGCC AACAAAATTC
 421 TGAATCGGCC AAAGAGGTAT AATTCAGGTA AATTGGAAGA GTTTGTTCAA GGGAATCTAG
 481 AGAGAGAATG TATGGAAGAA AAGTGTAGTT TTGAAGAAGC ACGAGAAGTT TTTGAAAACA
 541 CTGAAAGAAC AACTGAATTT TGGAAGCAGT ATGTTGATGG AGATCAGTGT GAGTCCAATC
 601 CATGTTTAAA TGGCGGCAGT TGCAAGGATG ACATTAATTC CTATGAATGT TGGTGTCCCT
 661 TTGGATTTGA AGGAAAGAAC TGTGAATTAG ATGTAACATG TAACATTAAG AATGGCAGAT
 721 GCGAGCAGTT TTGTAAAAAT AGTGCTGATA ACAAGGTGGT TTGCTCCTGT ACTGAGGGAT
 781 ATCGACTTGC AGAAAACCAG AAGTCCTGTG AACCAGCAGT GCCATTTCCA TGTGGAAGAG
 841 TTTCTGTTTC ACAAACTTCT AAGCTCACCC GTGCTGAGAC TGTTTTTCCT GATGTGGACT
 901 ATGTAAATTC TACTGAAGCT GAAACCATTT TGGATAACAT CACTCAAAGC ACCCAATCAT
 961 TTAATGACTT CACTCGGGTT GTTGGTGGAG AAGATGCCAA ACCAGGTCAA TTCCCTTGGC
1021 AGGTTGTTTT GAATGGTAAA GTTGATGCAT TCTGTGGAGG CTCTATCGTT AATGAAAAAT
1081 GGATTGTAAC TGCTGCCCAC TGTGTTGAAA CTGGTGTTAA AATTACAGTT GTCGCAGGTG
1141 AACATAATAT TGAGGAGACA GAACATACAG AGCAAAAGCG AAATGTGATT CGAATTATTC
1201 CTCACCACAA CTACAATGCA GCTATTAATA AGTACAACCA TGACATTGCC CTTCTGGAAC
1261 TGGACGAACC CTTAGTGCTA AACAGCTACG TTACACCTAT TTGCATTGCT GACAAGGAAT
1321 ACACGAACAT CTTCCTCAAA TTTGGATCTG GCTATGTAAG TGGCTGGGGA AGAGTCTTCC
1381 ACAAAGGGAG ATCAGCTTTA GTTCTTCAGT ACCTTAGAGT TCCACTTGTT GACCGAGCCA
1441 CATGTCTTCG ATCTACAAAG TTCACCATCT ATAACAACAT GTTCTGTGCT GGCTTCCATG
1501 AAGGAGGTAG AGATTCATGT CAAGGAGATA GTGGGGGACC CCATGTTACT GAAGTGGAAG
1561 GGACCAGTTT CTTAACTGGA ATTATTAGCT GGGGTGAAGA GTGTGCAATG AAAGGCAAAT
1621 ATGGAATATA TACCAAGGTG TCCCGGTATG TCAACTGGAT TAAGGAAAAA ACAAAGCTCA
1681 CTGACAAAAC TCACACATGC CCACCGTGCC CAGCTCCGGA ACTCCTGGGC GGACCGTCAG
1741 TCTTCCTCTT CCCCCCAAAA CCCAAGGACA CCCTCATGAT CTCCCGGACC CCTGAGGTCA
1801 CATGCGTGGT GGTGGACGTG AGCCACGAAG ACCCTGAGGT CAAGTTCAAC TGGTACGTGG
1861 ACGGCGTGGA GGTGCATAAT GCCAAGACAA AGCCGCGGGA GGAGCAGTAC AACAGCACGT
1921 ACCGTGTGGT CAGCGTCCTC ACCGTCCTGC ACCAGGACTG GCTGAATGGC AAGGAGTACA
1981 AGTGCAAGGT CTCCAACAAA GCCCTCCCAG CCCCCATCGA GAAAACCATC TCCAAAGCCA
2041 AAGGGCAGCC CCGAGAACCA CAGGTGTACA CCCTGCCCCC ATCCCGGGAT GAGCTGACCA
2101 AGAACCAGGT CAGCCTGACC TGCCTGGTCA AAGGCTTCTA TCCCAGCGAC ATCGCCGTGG
2161 AGTGGGAGAG CAATGGGCAG CCGGAGAACA ACTACAAGAC CACGCCTCCC GTGTTGGACT
2221 CCGACGGCTC CTTCTTCCTC TACAGCAAGC TCACCGTCGA CAAGAGCAGG TGGCAGCAGG
2281 GGAACGTCTT CTCATGCTCC GTGATGCATG AGGCTCTGCA CAACCACTAC ACGCAGAAGA
2341 GCCTCTCCCT GTCTCCGGGT AAACGGCGCC GCCGGAGCGG TGGCGGCGGA TCAGGTGGGG
2401 GTGGATCAGG CGGTGGAGGT TCCGGTGGCG GGGGATCCGG CGGTGGAGGT TCCGGTGGGG
2461 GTGGATCAAG GAAGAGGAGG AAGAGGGCGC AGGTGCAGCT GCAGGAGTCT GGGGGAGGCT
2521 TGGTACAGCC TGGGGGGTCC CTGAGACTCT CCTGTGCAGC CTCTGGATTC ATGTTTAGCA
2581 GGTATGCCAT GAGCTGGGTC CGCCAGGCTC CAGGGAAGGG GCCAGAGTGG GTCTCAGGTA
2641 TTAGTGGTAG TGGTGGTAGT ACATACTACG CAGACTCCGT GAAGGGCCGG TTCACCGTCT
2701 CCAGAGACAA TTCCAAGAAC ACGCTGTATC TGCAAATGAA CAGCCTGAGA GCCGAGGACA
2761 CGGCTGTATA TTACTGCGCC CGGGGCGCCA CCTACACCAG CCGGAGCGAC GTGCCCGACC
2821 AGACCAGCTT CGACTACTGG GGCCAGGGAA CCCTGGTCAC CGTCTCCTCA GGGAGTGCAT
2881 CCGCCCCAAA GCTTGAAGAA GGTGAATTTT CAGAAGCACG CGTATCTGAA CTGACTCAGG
2941 ACCCTGCTGT GTCTGTGGCC TTGGGACAGA CAGTCAGGAT CACATGCCAA GGAGACAGCC
3001 TCAGAAACTT TTATGCAAGC TGGTACCAGC AGAAGCCAGG ACAGGCCCCT ACTCTTGTCA
3061 TCTATGGTTT AAGTAAAAGG CCCTCAGGGA TCCCAGACCG ATTCTCTGCC TCCAGCTCAG
3121 GAAACACAGC TTCCTTGACC ATCACTGGGG CTCAGGCGGA AGATGAGGCT GACTATTACT
3181 GCCTGCTGTA CTACGGCGGC GGCCAGCAGG GCGTGTTCGG CGGCGGCACC AAGCTGACCG
3241 TCCTACGTCA GCCCAAGGCT GCCCCCTCGG TCACTCTGTT CCCGCCCTCT TCTGCGGCCG
3301 GTGGCGGTGG CTCCGGCGGA GGTGGGTCCG GTGGCGGCGG ATCAGGTGGG GGTGGATCAG
```

-continued

DRAFT SEQUENCE LISTING

3361 GCGGTGGAGG TTCCGGTGGC GGGGGATCAG ACAAAACTCA CACATGCCCA CCGTGCCCAG
3421 CACCGGAACT CCTGGGCGGA CCGTCAGTCT TCCTCTTCCC CCCAAAACCC AAGGACACCC
3481 TCATGATCTC CCGGACCCCT GAGGTCACAT GCGTGGTGGT GGACGTGAGC CACGAAGACC
3541 CTGAGGTCAA GTTCAACTGG TACGTGGACG GCGTGGAGGT GCATAATGCC AAGACAAAGC
3601 CGCGGGAGGA GCAGTACAAC AGCACGTACC GTGTGGTCAG CGTCCTCACC GTCCTGCACC
3661 AGGACTGGCT GAATGGCAAG GAGTACAAGT GCAAGGTCTC CAACAAAGCC CTCCCAGCCC
3721 CCATCGAGAA AACCATCTCC AAAGCCAAAG GGCAGCCCCG AGAACCACAG GTGTACACCC
3781 TGCCCCCATC CCGCGATGAG CTGACCAAGA ACCAGGTCAG CCTGACCTGC CTGGTCAAAG
3841 GCTTCTATCC CAGCGACATC GCCGTGGAGT GGGAGAGCAA TGGGCAGCCG GAGAACAACT
3901 ACAAGACCAC GCCTCCCGTG TTGGACTCCG ACGGCTCCTT CTTCCTCTAC AGCAAGCTCA
3961 CCGTGGACAA GAGCAGGTGG CAGCAGGGGA ACGTCTTCTC ATGCTCCGTG ATGCATGAGG
4021 CTCTGCACAA CCACTACACG CAGAAGAGCC TCTCCCTGTC TCCGGGTAAA TGA

FIX-068 amino acid sequence. Signal sequence is shown in dotted underline, propeptide is double underlined, linker region connecting SCE5 to Fc region is underlined, and linker with proprotein convertase processing sites is shown in bold 1 MQRVNMIMAE SPGLITICLL GYLLSAECTV FLDHENANKI LNRPKRYNSG KLEEFVQGNL
61 ERECMEEKCS FEEAREVFEN TERTTEFWKQ YVDGDQCESN PCLNGGSCKD DINSYECWCP
121 FGFEGKNCEL DVTCNIKNGR CEQFCKNSAD NKVVCSCTEG YRLAENQKSC EPAVPFPCGR
181 VSVSQTSKLT RAETVFPDVD YVNSTEAETI LDNITQSTQS FNDFTRVVGG EDAKPGQFPW
241 QVVLNGKVDA FCGGSIVNEK WIVTAAHCVE TGVKITVVAG EHNIEETEHT EQKRNVIRII
301 PHHNYNAAIN KYNHDIALLE LDEPLVLNSY VTPICIADKE YTNIFLKFGS GYVSGWGRVF
361 HKGRSALVLQ YLRVPLVDRA TCLRSTKFTI YNNMFCAGFH EGGRDSCQGD SGGPHVTEVE
421 GTSFLTGIIS WGEECAMKGK YGIYTKVSRY VNWIKEKTKL TDKTHTCPPC PAPELLGGPS
481 VFLFPPKPKD TLMISRTPEV TCVVVDVSHE DPEVKFNWYV DGVEVHNAKT KPREEQYNST
541 YRVVSVLTVL HQDWLNGKEY KCKVSNKALP APIEKTISKA KGQPREPQVY TLPPSRDELT
601 KNQVSLTCLV KGFYPSDIAV EWESNGQPEN NYKTTPPVLD SDGSFFLYSK LTVDKSRWQQ
661 GNVFSCSVMH EALHNHYTQK SLSLSPGKRR RRSGGGGSGG GGSGGGGSGG GGSGGGGSGG
721 GGSRKRRKRA QVQLQESGGG LVQPGGSLRL SCAASGFMFS RYAMSWVRQA PGKGPEWVSG
781 ISGSGGSTYY ADSVKGRFTV SRDNSKNTLY LQMNSLRAED TAVYYCARGA TYTSRSDVPD
841 QTSFDYWGQG TLVTVSSGSA SAPKLEEGEF SEARVSELTQ DPAVSVALGQ TVRITCQGDS
901 LRNFYASWYQ QKPGQAPTLV IYGLSKRPSG IPDRFSASSS GNTASLTITG AQAEDEADYY
961 CLLYYGGGQQ GVFGGGTKLT VLRQPKAAPS VTLFPPSSAA GGGGSGGGGS GGGGSGGGGS
1021 GGGGSGGGGS DKTHTCPPCP APELLGGPSV FLFPPKPKDT LMISRTPEVT CVVVDVSHED
1081 PEVKFNWYVD GVEVHNAKTK PREEQYNSTY RVVSVLTVLH QDWLNGKEYK CKVSNKALPA
1141 PIEKTISKAK GQPREPQVYT LPPSRDELTK NQVSLTCLVK GFYPSDIAVE WESNGQPENN
1201 YKTTPPVLDS DGSFFLYSKL TVDKSRWQQG NVFSCSVMHE ALHNHYTQKS LSLSPGK*

DNA sequence for FIX-088

1 ATGCAGCGCG TGAACATGAT CATGGCAGAA TCACCAGGCC TCATCACCAT CTGCCTTTTA
61 GGATATCTAC TCAGTGCTGA ATGTACAGGT TTGTTTCCTT TTTTAAAATA CATTGAGTAT
121 GCTTGCCTTT TAGATATAGA AATATCTGAT GCTGTCTTCT TCACTAAATT TTGATTACAT
181 GATTTGACAG CAATATTGAA GAGTCTAACA GCCAGCACGC AGGTTGGTAA GTACTGTGGG
241 AACATCACAG ATTTTGGCTC CATGCCCTAA AGAGAAATTG GCTTTCAGAT TATTTGGATT
301 AAAAACAAAG ACTTTCTTAA GAGATGTAAA ATTTTCATGA TGTTTTCTTT TTTGCTAAAA
361 CTAAAGAATT ATTCTTTTAC ATTTCAGTTT TTCTTGATCA TGAAAACGCC AACAAAATTC
421 TGAATCGGCC AAAGAGGTAT AATTCAGGTA AATTGGAAGA GTTTGTTCAA GGGAATCTAG
481 AGAGAGAATG TATGGAAGAA AAGTGTAGTT TTGAAGAAGC ACGAGAAGTT TTTGAAAACA
541 CTGAAAGAAC AACTGAATTT TGGAAGCAGT ATGTTGATGG AGATCAGTGT GAGTCCAATC
601 CATGTTTAAA TGGCGGCAGT TGCAAGGATG ACATTAATTC CTATGAATGT TGGTGTCCCT
661 TTGGATTTGA AGGAAAGAAC TGTGAATTAG ATGTAACATG TAACATTAAG AATGGCAGAT
721 GCGAGCAGTT TTGTAAAAAT AGTGCTGATA ACAAGGTGGT TTGCTCCTGT ACTGAGGGAT
781 ATCGACTTGC AGAAAACCAG AAGTCCTGTG AACCAGCAGT GCCATTTCCA TGTGGAAGAG
841 TTTCTGTTTC ACAAACTTCT AAGCTCACCC GTGCTGAGAC TGTTTTTCCT GATGTGGACT
901 ATGTAAATTC TACTGAAGCT GAAACCATTT TGGATAACAT CACTCAAAGC ACCCAATCAT
961 TTAATGACTT CACTCGGGTT GTTGGTGGAG AAGATGCCAA ACCAGGTCAA TTCCCTTGGC
1021 AGGTTGTTTT GAATGGTAAA GTTGATGCAT TCTGTGGAGG CTCTATCGTT AATGAAAAAT
1081 GGATTGTAAC TGCTGCCCAC TGTGTTGAAA CTGGTGTTAA AATTACAGTT GTCGCAGGTG
1141 AACATAATAT TGAGGAGACA GAACATACAG AGCAAAAGCG AAATGTGATT CGAATTATTC
1201 CTCACCACAA CTACAATGCA GCTATTAATA AGTACAACCA TGACATTGCC CTTCTGGAAC
1261 TGGACGAACC CTTAGTGCTA AACAGCTAGC TTACACCTAT TTGCATTGCT GACAAGGAAT
1321 ACACGAACAT CTTCCTCAAA TTTGGATCTG GCTATGTAAG TGGCTGGGGA AGAGTCTTCC
1381 ACAAAGGGAG ATCAGCTTTA GTTCTTCAGT ACCTTAGAGT TCCACTTGTT GACCGAGCCA
1441 CATGTCTTCG ATCTACAAAG TTCACCATCT ATAACAACAT GTTCTGTGCT GGCTTCCATG
1501 AAGGAGGTAG AGATTCATGT CAAGGAGATA GTGGGGGACC CCATGTTACT GAAGTGGAAG
1561 GGACCAGTTT CTTAACTGGA ATTATTAGCT GGGGTGAAGA GTGTGCAATG AAAGGCAAAT
1621 ATGGAATATA TACCAAGGTG TCCCGGTATG TCAACTGGAT TAAGGAAAAA ACAAAGCTCA
1681 CTGACAAAAC TCACACATGC CCACCGTGCC CAGCTCCGGA ACTCCTGGGC GGACCGTCAG
1741 TCTTCCTCTT CCCCCCAAAA CCCAAGGACA CCCTCATGAT CTCCCGGACC CCTGAGGTCA
1801 CATGCGTGGT GGTGGACGTG AGCCACGAAG ACCCTGAGGT CAAGTTCAAC TGGTACGTGG
1861 ACGGCGTGGA GGTGCATAAT GCCAAGACAA AGCCGCGGGA GGAGCAGTAC AACAGCACGT
1921 ACCGTGTGGT CAGCGTCCTC ACCGTCCTGC ACCAGGACTG GCTGAATGGC AAGGAGTACA
1981 AGTGCAAGGT CTCCAACAAA GCCCTCCCAG CCCCCATCGA GAAAACCATC TCCAAAGCCA
2041 AAGGGCAGCC CCGAGAACCA CAGGTGTACA CCCTGCCCCC ATCCCGGGAT GAGCTGACCA
2101 AGAACCAGGT CAGCCTGACC TGCCTGGTCA AAGGCTTCTA TCCCAGCGAC ATCGCCGTGG
2161 AGTGGGAGAG CAATGGGCAG CCGGAGAACA ACTACAAGAC CACGCCTCCC GTGTTGGACT
2221 CCGACGGCTC CTTCTTCCTC TACAGCAAGC TCACCGTGGA CAAGAGCAGG TGGCAGCAGG
2281 GGAACGTCTT CTCATGCTCC GTGATGCATG AGGCTCTGCA CAACCACTAC ACGCAGAAGA

-continued

DRAFT SEQUENCE LISTING

2341 GCCTCTCCCT GTCTCCGGGT AAAGGTGGCG GCGGATCAGG TGGGGGTGGA TCAGGCGGTG
2401 GAGGTTCCGG TGGCGGGGGA TCAGACAAAA CTCACACATG CCCACCGTGC CCAGCACCTG
2461 AACTCCTGGG AGGACCGTCA GTCTTCCTCT TCCCCCCAAA ACCCAAGGAC ACCCTCATGA
2521 TCTCCCGGAC CCCTGAGGTC ACATGCGTGG TGGTGGACGT GAGCCACGAA GACCCTGAGG
2581 TCAAGTTCAA CTGGTACGTG GACGGCGTGG AGGTGCATAA TGCCAAGACA AAGCCGCGGG
2641 AGGAGCAGTA CAACAGCACG TACCGTGTGG TCAGCGTCCT CACCGTCCTG CACCAGGACT
2701 GGCTGAATGG CAAGGAGTAC AAGTGCAAGG TCTCCAACAA AGCCCTCCCA GCCCCCATCG
2761 AGAAAACCAT CTCCAAAGCC AAAGGGCAGC CCCGAGAACC ACAGGTGTAC ACCCTGCCCC
2821 CATCCCGCGA TGAGCTGACC AAGAACCAGG TCAGCCTGAC CTGCCTGGTC AAAGGCTTCT
2881 ATCCCAGCGA CATCGCCGTG GAGTGGGAGA GCAATGGGCA GCCGGAGAAC AACTACAAGA
2941 CCACGCCTCC CGTGTTGGAC TCCGACGGCT CCTTCTTCCT CTACAGCAAG CTCACCGTCG
3001 ACAAGAGCAG GTGGCAGCAG GGGAACGTCT TCTCATGCTC CGTGATGCAT GAGGCTCTGC
3061 ACAACCACTA CACGCAGAAG AGCCTCTCCC TGTCTCCGGG TAAAGGTGGC GGTGGCTCCG
3121 GCGGAGGTGG GTCCGGTGGC GGCGGATCAG GTGGGGGTGG ATCAGGCGGT GGAGGTTCCG
3181 GTGGCGGGGG ATCAGCGCAG GTGCAGCTGC AGGAGTCTGG GGGAGGCTTG GTACAGCCTG
3241 GGGGGTCCCT GAGACTCTCC TGTGCAGCCT CTGGATTCAT GTTTAGCAGG TATGCCATGA
3301 GCTGGGTCCG CCAGGCTCCA GGGAAGGGGC CAGAGTGGGT CTCAGGTATT AGTGGTAGTG
3361 GTGGTAGTAC ATACTACGCA GACTCCGTGA AGGGCCGGTT CACCGTCTCC AGAGACAATT
3421 CCAAGAACAC GCTGTATCTG CAAATGAACA GCCTGAGAGC CGAGGACACG GCTGTATATT
3481 ACTGCGCCCG GGGCGCCACC TACACCAGCC GGAGCGACGT GCCCGACCAG ACCAGCTTCG
3541 ACTACTGGGG CCAGGGAACC CTGGTCACCG TCTCCTCAGG GAGTGCATCC GCCCCAAAGC
3601 TTGAAGAAGG TGAATTTTCA GAAGCACGCG TATCTGAACT GACTCAGGAC CCTGCTGTGT
3661 CTGTGGCCTT GGGACAGACA GTCAGGATCA CATGCCAAGG AGACAGCCTC AGAAACTTTT
3721 ATGCAAGCTG GTACCAGCAG AAGCCAGGAC AGGCCCCTAC TCTTGTCATC TATGGTTTAA
3781 GTAAAAGGCC CTCAGGGATC CCAGACCGAT TCTCTGCCTC CAGCTCAGGA AACACAGCTT
3841 CCTTGACCAT CACTGGGGCT CAGGCGGAAG ATGAGGCTGA CTATTACTGC CTGCTGTACT
3901 ACGGCGGCGG CCAGCAGGGC GTGTTCGGCG GCGGCACCAA GCTGACCGTC CTACGTCAGC
3961 CCAAGGCTGC CCCCTCGGTC ACTCTGTTCC CGCCCTCTTC TGCGGCCTGA

FIX-088 amino acid sequence. Signal sequence is shown in dotted underline, propeptide is double underlined, linker connecting both Fc regions is underlined and linker connecting the Fc region to SCE5 is in bold 1 MQRVNMIMAE SPGLITICLL GYLLSAECTV FLDHENANKI LNRPKRYNSG KLEEFVQGNL
61 ERECMEEKCS FEEAREVFEN TERTTEFWKQ YVDGDQCESN PCLNGGSCKD DINSYECWCP
121 FGFEGKNCEL DVTCNIKNGR CEQFCKNSAD NKVVCSCTEG YRLAENQKSC EPAVPFPCGR
181 VSVSQTSKLT RAETVFPDVD YVNSTEAETI LDNITQSTQS FNDFTRVVGG EDAKPGQFPW
241 QVVLNGKVDA FCGGSIVNEK WIVTAAHCVE TGVKITVVAG EHNIEETEHT EQKRNVIRII
301 PHHNYNAAIN KYNHDIALLE LDEPLVLNSY VTPICIADKE YTNIFLKFGS GYVSGWGRVF
361 HKGRSALVLQ YLRVPLVDRA TCLRSTKFTI YNNMFCAGFH EGGRDSCQGD SGGPHVTEVE
421 GTSFLTGIIS WGEECAMKGK YGIYTKVSRY VNWIKEKTKL TDKTHTCPPC PAPELLGGPS
481 VFLFPPKPKD TLMISRTPEV TCVVVDVSHE DPEVKFNWYV DGVEVHNAKT KPREEQYNST
541 YRVVSVLTVL HQDWLNGKEY KCKVSNKALP APIEKTISKA KGQPREPQVY TLPPSRDELT
601 KNQVSLTCLV KGFYPSDIAV EWESNGQPEN NYKTTPPVLD SDGSFFLYSK LTVDKSRWQQ
661 GNVFSCSVMH EALHNHYTQK SLSLSPGKGG GGSGGGGSGG GGSGGGGSDK THTCPPCPAP
721 ELLGGPSVFL FPPKPKDTLM ISRTPEVTCV VVDVSHEDPE VKFNWYVDGV EVHNAKTKPR
781 EEQYNSTYRV VSVLTVLHQD WLNGKEYKCK VSNKALPAPI EKTISKAKGQ PREPQVYTLP
841 PSRDELTKNQ VSLTCLVKGF YPSDIAVEWE SNGQPENNYK TTPPVLDSDG SFFLYSKLTV
901 DKSRWQQGNV FSCSVMHEAL HNHYTQKSLS LSPGKGGGGS GGGGSGGGGS GGGGSGGGGS
961 GGGGSAQVQL QESGGGLVQP GGSLRLSCAA SGFMFSRYAM SWVRQAPGKG PEWVSGISGS
1021 GGSTYYADSV KGRFTVSRDN SKNTLYLQMN SLRAEDTAVY YCARGATYTS RSDVPDQTSF
1081 DYWGQGTLVT VSSGSASAPK LEEGEFSEAR VSELTQDPAV SVALGQTVRI TCQGDSLRNF
1141 YASWYQQKPG QAPTLVIYGL SKRPSGIPDR FSASSSGNTA SLTITGAQAE DEADYYCLLY
1201 YGGGQQGVFG GGTKLTVLRQ PKAAPSVTLF PPSSAA*

DNA sequence for FIX-089

1 ATGCAGCGCG TGAACATGAT CATGGCAGAA TCACCAGGCC TCATCACCAT CTGCCTTTTA
61 GGATATCTAC TCAGTGCTGA ATGTACAGGT TTGTTTCCTT TTTTAAAATA CATTGAGTAT
121 GCTTGCCTTT TAGATATAGA AATATCTGAT GCTGTCTTCT TCACTAAATT TTGATTACAT
181 GATTTGACAG CAATATTGAA GAGTCTAACA GCCAGCACGC AGGTTGGTTA GTACTGTGGG
241 AACATCACAG ATTTTGGCTC CATGCCCTAA AGAGAAATTG GCTTTCAGAT TATTTGGATT
301 AAAAACAAAG ACTTTCTTAA GAGATGTAAA ATTTTCATGA TGTTTTCTTT TTTGCTAAAA
361 CTAAAGAATT ATTCTTTTAC ATTTCAGTTT TTCTTGATCA TGAAAACGCC AACAAAATTC
421 TGAATCGGCC AAAGAGGTAT AATTCAGGTA AATTGGAAGA GTTTGTTCAA GGGAATCTAG
481 AGAGAGAATG TATGGAAGAA AAGTGTAGTT TTGAAGAAGC ACGAGAAGTT TTTGAAAACA
541 CTGAAAGAAC AACTGAATTT TGGAAGCAGT ATGTTGATGG AGATCAGTGT GAGTCCAATC
601 CATGTTTAAA TGGCGGCAGT TGCAAGGATG ACATTAATTC CTATGAATGT TGGTGTCCCT
661 TTGGATTTGA AGGAAAGAAC TGTGAATTAG ATGTAACATG TAACATTAAG AATGGCAGAT
721 GCGAGCAGTT TTGTAAAAAT AGTGCTGATA ACAAGGTGGT TTGCTCCTGT ACTGAGGGAT
781 ATCGACTTGC AGAAAACCAG AAGTCCTGTG AACCAGCAGT GCCATTTCCA TGTGGAAGAG
841 TTTCTGTTTC ACAAACTTCT AAGCTCACCC GTGCTGAGAC TGTTTTTCCT GATGTGGACT
901 ATGTAAATTC TACTGAAGCT GAAACCATTT TGGATAACAT CACTCAAAGC ACCCAATCAT
961 TTAATGACTT CACTCGGGTT GTTGGTGGAG AAGATGCCAA ACCAGGTCAA TTCCCTTGGC
1021 AGGTTGTTTT GAATGGTAAA GTTGATGCAT TCTGTGGAGG CTCTATCGTT AATGAAAAAT
1081 GGATTGTAAC TGCTGCCCAC TGTGTTGAAA CTGGTGTTAA AATTACAGTT GTCGCAGGTG
1141 AACATAATAT TGAGGAGACA GAACATACAG AGCAAAAGCG AAATGTGATT CGAATTATTC
1201 CTCACCACAA CTACAATGCA GCTATTAATA AGTACAACCA TGACATTGCC CTTCTGGAAC
1261 TGGACGAACC CTTAGTGCTA AACAGCTACG TTACACCTAT TTGCATTGCT GACAAGGAAT
1321 ACACGAACAT CTTCCTCAAA TTTGGATCTG GCTATGTAAG TGGCTGGGGA AGAGTCTTCC

-continued

DRAFT SEQUENCE LISTING

```
1381 ACAAAGGGAG ATCAGCTTTA GTTCTTCAGT ACCTTAGAGT TCCACTTGTT GACCGAGCCA
1441 CATGTCTTCG ATCTACAAAG TTCACCATCT ATAACAACAT GTTCTGTGCT GGCTTCCATG
1501 AAGGAGGTAG AGATTCATGT CAAGGAGATA GTGGGGGACC CCATGTTACT GAAGTGGAAG
1561 GGACCAGTTT CTTAACTGGA ATTATTAGCT GGGGTGAAGA GTGTGCAATG AAAGGCAAAT
1621 ATGGAATATA TACCAAGGTG TCCCGGTATG TCAACTGGAT TAAGGAAAAA ACAAAGCTCA
1681 CTGACAAAAC TCACACATGC CCACCGTGCC CAGCTCCGGA ACTCCTGGGA GGACCGTCAG
1741 TCTTCCTCTT CCCCCCAAAA CCCAAGGACA CCCTCATGAT CTCCCGGACC CCTGAGGTCA
1801 CATGCGTGGT GGTGGACGTG AGCCACGAAG ACCCTGAGGT CAAGTTCAAC TGGTACGTGG
1861 ACGGCGTGGA GGTGCATAAT GCCAAGACAA AGCCGCGGGA GGAGCAGTAC AACAGCACGT
1921 ACCGTGTGGT CAGCGTCCTC ACCGTCCTGC ACCAGGACTG GCTGAATGGC AAGGAGTACA
1981 AGTGCAAGGT CTCCAACAAA GCCCTCCCAG CCCCCATCGA GAAAACCATC TCCAAAGCCA
2041 AAGGGCAGCC CCGAGAACCA CAGGTGTACA CCCTGCCCCC ATCCCGGGAT GAGCTGACCA
2101 AGAACCAGGT CAGCCTGACC TGCCTGGTCA AAGGCTTCTA TCCCAGCGAC ATCGCCGTGG
2161 AGTGGGAGAG CAATGGGCAG CCGGAGAACA ACTACAAGAC CACGCCTCCC GTGTTGGACT
2221 CCGACGGCTC CTTCTTCCTC TACAGCAAGC TCACCGTCGA CAAGAGCAGG TGGCAGCAGG
2281 GGAACGTCTT CTCATGCTCC GTGATGCATG AGGCTCTGCA CAACCACTAC ACGCAGAAGA
2341 GCCTCTCCCT GTCTCCGGGT AAAGGCGGTG GCGGTTCAGG TGGAGGAGGG TCAGGCGGTG
2401 GTGGATCCGG CGGGGGCGGA TCCGGTGGCG GAGGGTCAGG CGGTGGCGGA TCAGCCTGCA
2461 CCGAGCGGAT GGCCCTGCAC AACCTGTGCG GTGGCGGTGG CTCCGGCGGA GGTGGGTCCG
2521 GTGGCGGCGG ATCAGGTGGG GGTGGATCAG GCGGTGGAGG TTCCGGTGGC GGGGGATCCG
2561 ACAAAACTCA CACATGCCCA CCGTGCCCAG CACCGGAACT CCTGGGCGGA CCGTCAGTCT
2641 TCCTCTTCCC CCCAAAACCC AAGGACACCC TCATGATCTC CCGGACCCCT GAGGTCACAT
2701 GCGTGGTGGT GGACGTGAGC CACGAAGACC CTGAGGTCAA GTTCAACTGG TACGTGGACG
2761 GCGTGGAGGT GCATAATGCC AAGACAAAGC CGCGGGAGGA GCAGTACAAC AGCACGTACC
2821 GTGTGGTCAG CGTCCTCACC GTCCTGCACC AGGACTGGCT GAATGGCAAG GAGTACAAGT
2881 GCAAGGTCTC CAACAAAGCC CTCCCAGCCC CCATCGAGAA AACCATCTCC AAAGCCAAAG
2941 GGCAGCCCCG AGAACCACAG GTGTACACCC TGCCCCCATC CCGGGATGAG CTGACCAAGA
3001 ACCAGGTCAG CCTGACCTGC CTGGTCAAAG GCTTCTATCC CAGCGACATC GCCGTGGAGT
3061 GGGAGAGCAA TGGGCAGCCG GAGAACAACT ACAAGACCAC GCCTCCCGTG TTGGACTCCG
3121 ACGGCTCCTT CTTCCTCTAC AGCAAGCTCA CCGTGGACAA GAGCAGGTGG CAGCAGGGGA
3181 ACGTCTTCTC ATGCTCCGTG ATGCATGAGG CTCTGCACAA CCACTACACG CAGAAGAGCC
3241 TCTCCCTGTC TCCGGGTAAA TGA
```

FIX-089 amino acid sequence. Signal sequence is shown in dotted underline, propeptide is double underlined, linker regions connecting OS1 to Fc regions are underlined, and OS1 peptide is italicized

```
  1 MQRVNMIMAE SPGLITICLL GYLLSAECTV FLDHENANKI LNRPKRYNSG KLEEFVQGNL
 61 ERECMEEKCS FEEAREVFEN TERTTEFWKQ YVDGDQCESN PCLNGGSCKD DINSYECWCP
121 FGFEGKNCEL DVTCNIKNGR CEQFCKNSAD NKVVCSCTEG YRLAENQKSC EPAVPFPCGR
181 VSVSQTSKLT RAETVFPDVD YVNSTEAETI LDNITQSTQS FNDFTRVVGG EDAKPGQFPW
241 QVVLNGKVDA FCGGSIVNEK WIVTAAHCVE TGVKITVVAG EHNIEETEHT EQKRNVIRII
301 PHHNYNAAIN KYNHDIALLE LDEPLVLNSY VTPICIADKE YTNIFLKFGS GYVSGWGRVF
361 HKGRSALVLQ YLRVPLVDRA TCLRSTKFTI YNNMFCAGFH EGGRDSCQGD SGGPHVTEVE
421 GTSFLTGIIS WGEECAMKGK YGIYTKVSRY VNWIKEKTKL TDKTHTCPPC PAPELLGGPS
481 VFLFPPKPKD TLMISRTPEV TCVVVDVSHE DPEVKFNWYV DGVEVHNAKT KPREEQYNST
541 YRVVSVLTVL HQDWLNGKEY KCKVSNKALP APIEKTISKA KGQPREPQVY TLPPSRDELT
601 KNQVSLTCLV KGFYPSDIAV EWESNGQPEN NYKTTPPVLD SDGSFFLYSK LTVDKSRWQQ
661 GNVFSCSVMH EALHNHYTQK SLSLSPGKGG GGSGGGGSGG GGSGGGGSGG GGSGGGGSAC
721 TERMALHNLC GGGGSGGGGS GGGGSGGGGS GGGGSGGGGS DKTHTCPPCP APELLGGPSV
781 FLFPPKPKDT LMISRTPEVT CVVVDVSHED PEVKFNWYVD GVEVHNAKTK PREEQYNSTY
841 RVVSVLTVLH QDWLNGKEYK CKVSNKALPA PEIKTISKAK GQPREPQVYT LPPSRDELTK
901 NQVSLTCLVK GFYPSDIAVE WESNGQPENN YKTTPPVLDS DGSFFLYSKL TVDKSRWQQG
961 NVFSCSVMHE ALHNHYTQKS LSLSPGK*
```

DNA sequence for FIX-090

```
   1 ATGCAGCGCG TGAACATGAT CATGGCAGAA TCACCAGGCC TCATCACCAT CTGCCTTTTA
  61 GGATATCTAC TCAGTGCTGA ATGTACAGGT TTGTTTCCTT TTTTAAAATA CATTGAGTAT
 121 GCTTGCCTTT TAGATATAGA AATATCTGAT GCTGTCTTCT TCACTAAATT TTGATTACAT
 181 GATTTGACAG CAATATTGAA GAGTCTAACA GCCAGCACGC AGGTTGGTAA GTACTGTGGG
 241 AACATCACAG ATTTTGGCTC CATGCCCTAA AGAGAAATTG GCTTTCAGAT TATTTGGATT
 301 AAAAACAAAG ACTTTCTTAA GAGATGTAAA ATTTTCATGA TGTTTTCTTT TTTGCTAAAA
 361 CTAAAGAATT ATTCTTTTAC ATTTCAGTTT TTCTTGATCA TGAAAACGCC AACAAAATTC
 421 TGAATCGGCC AAAGAGGTAT AATTCAGGTA AATTGGAAGA GTTTGTTCAA GGGAATCTAG
 481 AGAGAGAATG TATGGAAGAA AAGTGTAGTT TTGAAGAAGC ACGAGAAGTT TTTGAAAACA
 541 CTGAAAGAAC AACTGAATTT TGGAAGCAGT ATGTTGATGG AGATCAGTGT GAGTCCAATC
 601 CATGTTTAAA TGGCGGCAGT TGCAAGGATG ACATTAATTC CTATGAATGT TGGTGTCCCT
 661 TTGGATTTGA AGGAAAGAAC TGTGAATTAG ATGTAACATG TAACATTAAG AATGGCAGAT
 721 GCGAGCAGTT TTGTAAAAAT AGTGCTGATA ACAAGGTGGT TTGCTCCTGT ACTGAGGGAT
 781 ATCGACTTGC AGAAAACCAG AAGTCCTGTG AACCAGCAGT GCCATTTCCA TGTGGAAGAG
 841 TTTCTGTTTC ACAAACTTCT AAGCTCACCC GTGCTGAGAC TGTTTTTCCT GATGTGGACT
 901 ATGTAAATTC TACTGAAGCT GAAACCATTT TGGATAACAT CACTCAAAGC ACCCAATCAT
 961 TTAATGACTT CACTCGGGTT GTTGGTGGAG AAGATGCCAA ACCAGGTCAA TTCCCTTGGC
1021 AGGTTGTTTT GAATGGTAAA GTTGATGCAT TCTGTGGAGG CTCTATCGTT AATGAAAAAT
1081 GGATTGTAAC TGCTGCCCAC TGTGTTGAAA CTGGTGTTAA AATTACAGTT GTCGCAGGTG
1141 AACATAATAT TGAGGAGACA GAACATACAG AGCAAAAGCG AAATGTGATT CGAATTATTC
1201 CTCACCACAA CTACAATGCA GCTATTAATA AGTACAACCA TGACATTGCC CTTCTGGAAC
1261 TGGACGAACC CTTAGTGCTA AACAGCTACG TTACACCTAT TTGCATTGCT GACAAGGAAT
1321 ACACGAACAT CTTCCTCAAA TTTGGATCTG GCTATGTAAG TGGCTGGGGA AGAGTCTTCC
```

-continued

DRAFT SEQUENCE LISTING

```
1381 ACAAAGGGAG ATCAGCTTTA GTTCTTCAGT ACCTTAGAGT TCCACTTGTT GACCGAGCCA
1441 CATGTCTTCG ATCTACAAAG TTCACCATCT ATAACAACAT GTTCTGTGCT GGCTTCCATG
1501 AAGGAGGTAG AGATTCATGT CAAGGAGATA GTGGGGGACC CCATGTTACT GAAGTGGAAG
1561 GGACCAGTTT CTTAACTGGA ATTATTAGCT GGGGTGAAGA GTGTGCAATG AAAGGCAAAT
1621 ATGGAATATA TACCAAGGTG TCCCGGTATG TCAACTGGAT TAAGGAAAAA ACAAAGCTCA
1681 CTGGTGGCGG TGGCTCCGGC GGAGGTGGGT CCGGTGGCGG CGGATCAGGT GGGGGTGGAT
1741 CAGGCGGTGG AGGTTCCGGT GGCGGGGGAT CAGCGCAGGT GCAGCTGCAG GAGTCTGGGG
1801 GAGGCTTGGT ACAGCCTGGG GGGTCCCTGA GACTCTCCTG TGCAGCCTCT GGATTCATGT
1861 TTAGCAGGTA TGCCATGAGC TGGGTCCGCC AGGCTCCAGG GAAGGGGCCA GAGTGGGTCT
1921 CAGGTATTAG TGGTAGTGGT GGTAGTACAT ACTACGCAGA CTCCGTGAAG GGCCGGTTCA
1981 CCGTCTCCAG AGACAATTCC AAGAACACGC TGTATCTGCA AATGAACAGC CTGAGAGCCG
2041 AGGACACGGC TGTATATTAC TGCGCCCGGG GCGCCACCTA CACCAGCCGG AGCGACGTGC
2101 CCGACCAGAC CAGCTTCGAC TACTGGGGCC AGGGAACCCT GGTCACCGTC TCCTCAGGGA
2161 GTGCATCCGC CCCAAAGCTT GAAGAAGGTG AATTTTCAGA AGCACGCGTA TCTGAACTGA
2221 CTCAGGACCC TGCTGTGTCT GTGGCCTTGG GACAGACAGT CAGGATCACA TGCCAAGGAG
2281 ACAGCCTCAG AAACTTTTAT GCAAGCTGGT ACCAGCAGAA GCCAGGACAG GCCCCTACTC
2341 TTGTCATCTA TGGTTTAAGT AAAAGGCCCT CAGGGATCCC AGACCGATTC TCTGCCTCCA
2401 GCTCAGGAAA CACAGCTTCC TTGACCATCA CTGGGGCTCA GGCGGAAGAT GAGGCTGACT
2461 ATTACTGCCT GCTGTACTAC GGCGGCGGCC AGCAGGGCGT GTTCGGCGGC GGCACCAAGC
2521 TGACCGTCCT ACGTCAGCCC AAGGCTGCCC CCTCGGTCAC TCTGTTCCCG CCCTCTTCTG
2581 CGGCCTGA
```

FIX-90 amino acid sequence. Signal sequence is shown in dotted underline, propeptide is double underlined, and linker regions connecting FIX to SCE5 is underlined

```
  1 MQRVNMIMAE SPGLITICLL GYLLSAECTV FLDHENANKI LNRPKRYNSG KLEEFVQGNL
 61 ERECMEEKCS FEEAREVFEN TERTTEFWKQ YVDGDQCESN PCLNGGSCKD DINSYECWCP
121 FGFEGKNCEL DVTCNIKNGR CEQFCKNSAD NKVVCSCTEG YRLAENQKSC EPAVPFPCGR
181 VSVSQTSKLT RAETVFPDVD YVNSTEAETI LDNITQSTQS FNDFTRVVGG EDAKPGQFPW
241 QVVLNGKVDA FCGGSIVNEK WIVTAAHCVE TGVKITVVAG EHNIEETEHT EQKRNVIRII
301 PHHNYNAAIN KYNHDIALLE LDEPLVLNSY VTPICIADKE YTNIFLKFGS GYVSGWGRVF
361 HKGRSALVLQ YLRVPLVDRA TCLRSTKFTI YNNMFCAGFH EGGRDSCQGD SGGPHVTEVE
421 GTSFLTGIIS WGEECAMKGK YGIYTKVSRY VNWIKEKTKL TGGGGSGGGG SGGGGSGGGG
481 SGGGGSGGGG SAQVQLQESG GGLVQPGGSL RLSCAASGFM FSRYAMSWVR QAPGKGPEWV
541 SGISGSGGST YYADSVKGRF TVSRDNSKNT LYLQMNSLRA EDTAVYYCAR GATYTSRSDV
601 PDQTSFDYWG QGTLVTVSSG SASAPKLEEG EFSEARVSEL TQDPAVSVAL GQTVRITCQG
661 DSLRNFYASW YQQKPGQAPT LVIYGLSKRP SGIPDRFSAS SSGNTASLTI TGAQAEDEAD
721 YYCLLYYGGG QQGVFGGGTK LTVLRQPKAA PSVTLFPPSS AA*
```

DNA sequence for FVII-088

```
   1 ATGGTCTCCC AGGCCCTCAG GCTCCTCTGC CTTCTGCTTG GGCTTCAGGG CTGCCTGGCT
  61 GCAGTCTTCG TAACCCAGGA GGAAGCCCAC GGCGTCCTGC ACCGGCGCCG GCGCGCCAAC
 121 GCGTTCCTGG AGGAGCTGCG GCCGGGCTCC CTGGAGAGGG AGTGCAAGGA GGAGCAGTGC
 181 TCCTTCGAGG AGGCCCGGGA GATCTTCAAG GACGCGGAGA GGACGAAGCT GTTCTGGATT
 241 TCTTACAGTG ATGGGGACCA GTGTGCCTCA AGTCCATGCC AGAATGGGGG CTCCTGCAAG
 301 GACCAGCTCC AGTCCTATAT CTGCTTCTGC CTCCCTGCCT TCGAGGGCCG GAACTGTGAG
 361 ACGCACAAGG ATGACCAGCT GATCTGTGTG AACGAGAACG GCGGCTGTGA GCAGTACTGC
 421 AGTGACCACA CGGGCACCAA GCGCTCCTGT CGGTGCCACG AGGGGTACTC TCTGCTGGCA
 481 GACGGGGTGT CCTGCACACC CACAGTTGAA TATCCATGTG GAAAAATACC TATTCTAGAA
 541 AAAAGAAATG CCAGCAAACC CCAAGGCCGA ATTGTGGGGG GCAAGGTGTG CCCCAAAGGG
 601 GAGTGTCCAT GGCAGGTCCT GTTGTTGGTG AATGGAGCTC AGTTGTGTGG GGGGACCCTG
 661 ATCAACACCA TCTGGGTGGT CTCCGCGGCC CACTGTTTCG ACAAAATCAA GAACTGGAGG
 721 AACCTGATCG CGGTGCTGGG CGAGCACGAC CTCAGCGAGC ACGACGGGGA TGAGCAGAGC
 781 CGGCGGGTGG CGCAGGTCAT CATCCCCAGC ACGTACGTCC CGGGCACCAC CAACCACGAC
 841 ATCGCGCTGC TCCGCCTGCA CCAGCCCGTG GTCCTCACTG ACCATGTGGT GCCCCTCTGC
 901 CTGCCCGAAC GGACGTTCTC TGAGAGGACG CTGGCCTTCG TGCGCTTCTC ATTGGTCAGC
 961 GGCTGGGGCC AGCTGCTGGA CCGTGGCGCC ACGGCCCTGG AGCTCATGGT CCTCAACGTG
1021 CCCCGGCTGA TGACCCAGGA CTGCCTGCAG CAGTCACGGA AGGTGGGAGA CTCCCCAAAT
1081 ATCACGGAGT ACATGTTCTG TGCCGGCTAC TCGGATGGCA GCAAGGACTC CTGCAAGGGG
1141 GACAGTGGAG GCCCACATGC CACCCACTAC CGGGGCACGT GGTACCTGAC GGGCATCGTC
1201 AGCTGGGGCC AGGGCTGCGC AACCGTGGGC CACTTTGGGG TGTACACCAG GGTCTCCCAG
1261 TACATCGAGT GGCTGCAAAA GCTCATGCGC TCAGAGCCAC GCCCAGGAGT CCTCCTGCGA
1321 GCCCCATTTC CCGGTGGCGG TGGCTCCGGC GGAGGTGGGT CCGGTGGCGG CGGATCAGGT
1381 GGGGGTGGAT CAGGCGGTGG AGGTTCCGGT GGCGGGGGAT CCGACAAAAC TCACACATGC
1441 CCACCGTGCC CAGCTCCGGA ACTCCTGGGA GGACCGTCAG TCTTCCTCTT CCCCCCAAAA
1501 CCCAAGGACA CCCTCATGAT CTCCCGGACC CCTGAGGTCA CATGCGTGGT GGTGGACGTG
1561 AGCCACGAAG ACCCTGAGGT CAAGTTCAAC TGGTACGTGG ACGGCGTGGA GGTGCATAAT
1621 GCCAAGACAA AGCCGCGGGA GGAGCAGTAC AACAGCACGT ACCGTGTGGT CAGCGTCCTC
1681 ACCGTCCTGC ACCAGGACTG GCTGAATGGC AAGGAGTACA AGTGCAAGGT CTCCAACAAA
1741 GCCCTCCCAG CCCCCATCGA GAAAACCATC TCCAAAGCCA AAGGGCAGCC CCGAGAACCA
1801 CAGGTGTACA CCCTGCCCCC ATCCCGGGAT GAGCTGACCA AGAACCAGGT CAGCCTGACC
1861 TGCCTGGTCA AAGGCTTCTA TCCCAGCGAC ATCGCCGTGG AGTGGGAGAG CAATGGGCAG
1921 CCGGAGAACA ACTACAAGAC CACGCCTCCC GTGTTGGACT CCGACGGCTC CTTCTTCCTC
1981 TACAGCAAGC TCACCGTCGA CAAGAGCAGG TGGCAGCAGG GGAACGTCTT CTCATGCTCC
2041 GTGATGCATG AGGCTCTGCA CAACCACTAC ACGCAGAAGA GCCTCTCCCT GTCTCCGGGT
2101 AAACGGCGCC GCCGGAGCGG TGGCGGCGGA TCAGGTGGGG GTGGATCAGG CGGTGGAGGT
2161 TCCGGTGGCG GGGGATCCGG CGGTGGAGGT TCCGGTGGGG GTGGATCAAG GAAGAGGAGG
2221 AAGAGGGACA TCGTGATGAC CCAGGCCGCC CCCAGCGTGC CCGTGACCCC CGGCGAGAGC
```

-continued

DRAFT SEQUENCE LISTING

2281 GTGAGCATCA GCTGCCGGAG CAGCCGGAGC CTGCTGCACA GCAACGGCAA CACCTACCTG
2341 TGCTGGTTCC TGCAGCGGCC CGGCCAGAGC CCCCAGCTGC TGATCTACCG GATGAGCAAC
2401 CTGGCCAGCG GCGTGCCCGA CCGGTTCAGC GGCAGCGGCA GCGGCACCGC CTTCACCCTG
2461 CGGATCAGCC GGGTGGAGGC CGAGGACGTG GGCGTGTACT ACTGCATGCA GCACCTGGAG
2521 TACCCCTTCA CCTTCGGCAG CGGCACCAAG CTGGAGATCA AGCGGGGCGG CGGCGGCAGC
2581 GGCGGCGGCG GCAGCGGCGG CGGCGGCAGC CAGGTGCAGC TGCAGCAGAG CGGCGCCGAG
2641 CTGGTGCGGC CCGGCACCAG CGTGAAGATC AGCTGCAAGG CCAGCGGCTA CACCTTCACC
2701 AACTACTGGC TGGGCTGGGT GAAGCAGCGG CCCGGCCACG GCCTGGAGTG GATCGGCGAC
2761 ATCTACCCCG GCGGCGGCTA CAACAAGTAC AACGAGAACT TCAAGGGCAA GGCCACCCTG
2821 ACCGCCGACA CCAGCAGCAG CACCGCCTAC ATGCAGCTGA GCAGCCTGAC CAGCGAGGAC
2881 AGCGCCGTGT ACTTCTGCGC CCGGGAGTAC GGCAACTACG ACTACGCCAT GGACAGCTGG
2941 GGCCAGGGCA CCAGCGTGAC CGTGAGCAGC GGTGGCGGTG GCTCCGGCGG AGGTGGGTCC
3001 GGTGGCGGCG GATCAGGTGG GGGTGGATCA GGCGGTGGAG GTTCCGGTGG CGGGGGATCA
3061 GACAAAACTC ACACATGCCC ACCGTGCCCA GCACCGGAAC TCCTGGGCGG ACCGTCAGTC
3121 TTCCTCTTCC CCCCAAAACC CAAGGACACC CTCATGATCT CCCGGACCCC TGAGGTCACA
3181 TGCGTGGTGG TGGACGTGAG CCACGAAGAC CCTGAGGTCA AGTTCAACTG GTACGTGGAC
3241 GGCGTGGAGG TGCATAATGC CAAGACAAAG CCGCGGGAGG AGCAGTACAA CAGCACGTAC
3301 CGTGTGGTCA GCGTCCTCAC CGTCCTGCAC CAGGACTGGC TGAATGGCAA GGAGTACAAG
3361 TGCAAGGTCT CCAACAAAGC CCTCCCAGCC CCCATCGAGA AAACCATCTC CAAAGCCAAA
3421 GGGCAGCCCC GAGAACCACA GGTGTACACC CTGCCCCCAT CCCGGGATGA GCTGACCAAG
3481 AACCAGGTCA GCCTGACCTG CCTGGTCAAA GGCTTCTATC CCAGCGACAT CGCCGTGGAG
3541 TGGGAGAGCA ATGGGCAGCC GGAGAACAAC TACAAGACCA CGCCTCCCGT GTTGGACTCC
3601 GACGGCTCCT TCTTCCTCTA CAGCAAGCTC ACCGTGGACA AGAGCAGGTG GCAGCAGGGG
3661 AACGTCTTCT CATGCTCCGT GATGCATGAG GCTCTGCACA ACCACTACAC GCAGAAGAGC
3721 CTCTCCCTGT CTCCGGGTAA ATGA

FVII-088 amino acid sequence. Signal sequence is shown in dotted underline, propeptide is double underlined, linker region connecting FVII or AP3 to Fc region is underlined, the AP3 scFv italicized, and linker with proprotein convertase processing sites is shown in bold 1 MVSQALRLLC LLLGLQGCLA AVGVTQEEAH GVLHRRRRAN AFLEELRPGS GERECKEEQC
61 SFEEAREIFK DAERTKLFWI SYSDGDQCAS SPCQNGGSCK DQLQSYICFC LPAFEGRNCE
121 THKDDQLICV NENGGCEQYC SDHTGTKRSC RCHEGYSLLA DGVSCTPTVE YPCGKIPILE
181 KRNASKPQGR IVGGKVCPKG ECPWQVLLLV NGAQLCGGTL INTIWVVSAA HCFDKIKNWR
241 NLIAVLGEHD LSEHDGDEQS RRVAQVIIPS TYVPGTTNHD IALLRLHQPV VLTDHVVPLC
301 LPERTFSERT LAFVRFSLVS GWGQLLDRGA TALELMVLNV PRLMTQDCLQ QSRKVGDSPN
361 ITEYMFCAGY SDGSKDSCKG DSGGPHATHY RGTWYLTGIV SWGQGCATVG HFGVYTRVSQ
421 YIEWLQKLMR SEPRPGVLLR APFPGGGGSG GGGSGGGGSG GGGSGGGGSG GGGSDKTHTC
481 PPCPAPELLG GPSVFLFPPK PKDTLMISRT REVTCVVVDV SHEDPEVKFN WYVDGVEVHN
541 AKTKPREEQY NSTYRVVSVL TVLHQDWLNG KEYKCKVSNK ALPAPIEKTI SKAKGQPREP
601 QVYTLPPSRD ELTKNQVSLT CLVKGFYPSD IAVEWESNGQ PENNYKTTPP VLDSDGSFFL
661 YSKLTVDKSR WQQGNVFSCS VMHEALHNHY TQKSLSLSPG KRRRRSGGGG SGGGGSGGGG
721 SGGGGSGGGG SGGGGSRKRR KR*DIVMTQAA PSVPVTPGES VSISCRSSRS LLHSNGNTYL*
781 *CWFLQRPGQS PQLLIYRMSN LASGVPDRFS GSGSGTAFTL RISRVEAEDV GVYYCMQHLE*
841 YPFTFGSGTK LEIKRGGGGS GGGGSGGGGS QVQLQQSGAE LVRPGTSVKI SCKASGYTFT
901 *NYWLGWVKQR PGHGLEWIGD IYPGGGYNKY NENFKGKATL TADTSSSTAY MQLSSLTSED*
961 *SAVYFCAREY GNYDYAMDSW GQGTSVTVSS* GGGGSGGGGS GGGGSGGGGS GGGGSGGGGS
1021 DKTHTCPPCP APELLGGPSV FLFPPKPKDT LMISRTPEVT CVVVDVSHED PEVKFNWYVD
1081 GVEVHNAKTK PREEQYNSTY RVVSVLTVLH QDWLNGKEYK CKVSNKALPA PIEKTISKAK
1141 GQPREPQVYT LPPSRDELTK NQVSLTCLVK GFYPSDIAVE WESNGQPENN YKTTPPVLDS
1201 DGSFFLYSKL TVDKSRWQQG NVFSCSVMHE ALHNHYTQKS LSLSPGK*

DNA sequence for FVIII-041

1 ATGCAAATAG AGCTCTCCAC CTGCTTCTTT CTGTGCCTTT TGCGATTCTG CTTTAGTGCC
61 ACCAGAAGAT ACTACCTGGG TGCAGTGGAA CTGTCATGGG ACTATATGCA AAGTGATCTC
121 GGTGAGCTGC CTGTGGACGC AAGATTTCCT CCTAGAGTGC CAAAATCTTT TCCATTCAAC
181 ACCTCAGTCG TGTACAAAAA GACTCTGTTT GTAGAATTCA CGGATCACCT TTTCAACATC
241 GCTAAGCCAA GGCCACCCTG GATGGGTCTG CTAGGTCCTA CCATCCAGGC TGAGGTTTAT
301 GATACAGTGG TCATTACACT TAAGAACATG GCTTCCCATC CTGTCAGTCT TCATGCTGTT
361 GGTGTATCCT ACTGGAAAGC TTCTGAGGGA GCTGAATATG ATGATCAGAC CAGTCAAAGG
421 GAGAAAGAAG ATGATAAAGT CTTCCCTGGT GGAAGCCATA CATATGTCTG GCAGGTCCTG
481 AAAGAGAATG GTCCAATGGC CTCTGACCCA CTGTGCCTTA CCTACTCATA TCTTTCTCAT
541 GTGGACCTGG TAAAAGACTT GAATTCAGGC CTCATTGGAG CCCTACTAGT ATGTAGAGAA
601 GGGAGTCTGG CCAAGGAAAA GACACAGACC TTGCACAAAT TTATACTACT TTTTGCTGTA
661 TTTGATGAAG GGAAAAGTTG GCACTCAGAA ACAAAGAACT CCTTGATGCA GGATAGGGAT
721 GCTGCATCTG CTCGGGCCTG GCCTAAAATG CACACAGTCA ATGGTTATGT AAACAGGTCT
781 CTGCCAGGTC TGATTGGATG CCACAGGAAA TCAGTCTATT GGCATGTGAT TGGAATGGGC
841 ACCACTCCTG AAGTGCACTC AATATTCCTC GAAGGTCACA CATTTCTTGT GAGGAACCAT
901 CGCCAGGCGT CCTTGGAAAT CTCGCCAATA ACTTTCCTTA CTGCTCAAAC ACTCTTGATG
961 GACCTTGGAC AGTTTCTACT GTTTTGTCAT ATCTCTTCCC ACCAACATGA TGGCATGGAA
1021 GCTTATGTCA AAGTAGACAG CTGTCCAGAG GAACCCCAAC TACGAATGAA AAATAATGAA
1081 GAAGCGGAAG ACTATGATGA TGATCTTACT GATTCTGAAA TGGATGTGGT CAGGTTTGAT
1141 GATGACAACT CTCCTTCCTT TATCCAAATT CGCTCAGTTG CCAAGAAGCA TCCTAAAACT
1201 TGGGTACATT ACATTGCTGC TGAAGAGGAG GACTGGGACT ATGCTCCCTT AGTCCTCGCC
1261 CCCGATGACA GAAGTTATAA AAGTCAATAT TTGAACAATG GCCCTCAGCG GATTGGTAGG
1321 AAGTACAAAA AAGTCCGATT TATGGCATAC ACAGATGAAA CCTTTAAGAC TCGTGAAGCT
1381 ATTCAGCATG AATCAGGAAT CTTGGGACCT TTACTTTATG GGAAGTTGGA AGACACACTG
1441 TTGATTATAT TTAAGAATCA AGCAAGCAGA CCATATAACA TCTACCCTCA CGGAATCACT

-continued

DRAFT SEQUENCE LISTING

1501 GATGTCCGTC CTTTGTATTC AAGGAGATTA CCAAAAGGTG TAAAACATTT GAAGGATTTT
1561 CCAATTCTGC CAGGAGAAAT ATTCAAATAT AAATGGACAG TGACTGTAGA AGATGGGCCA
1621 ACTAAATCAG ATCCTCGGTG CCTGACCCGC TATTACTCTA GTTTCGTTAA TATGGAGAGA
1681 GATCTAGCTT CAGGACTCAT TGGCCCTCTC CTCATCTGCT ACAAAGAATC TGTAGATCAA
1741 AGAGGAAACC AGATAATGTC AGACAAGAGG AATGTCATCC TGTTTTCTGT ATTTGATGAG
1801 AACCGAAGCT GGTACCTCAC AGAGAATATA CAACGCTTTC TCCCCAATCC AGCTGGAGTG
1861 CAGCTTGAGG ATCCAGAGTT CCAAGCCTCC AACATCATGC ACAGCATCAA TGGCTATGTT
1921 TTTGATAGTT TGCAGTTGTC AGTTTGTTTG CATGAGGTGG CATACTGGTA CATTCTAAGC
1981 ATTGGAGCAC AGACTGACTT CCTTTCTGTC TTCTTCTCTG GATATACCTT CAAACACAAA
2041 ATGGTCTATG AAGACACACT CACCCTATTC CCATTCTCAG GAGAAACTGT CTTCATGTCG
2101 ATGGAAAACC CAGGTCTATG GATTCTGGGG TGCCACAACT CAGACTTTCG GAACAGAGGC
2161 ATGACCGCCT TACTGAAGGT TTCTAGTTGT GACAAGAACA CTGGTGATTA TTACGAGGAC
2221 AGTTATGAAG ATATTTCAGC ATACTTGCTG AGTAAAAACA ATGCCATTGA ACCAAGAAGC
2281 TTCTCTCAAA ACCCACCAGT CTTGAAACGC CATCAACGGG AAATAACTCG TACTACTCTT
2341 CAGTCAGATC AAGAGGAAAT TGACTATGAT GATACCATAT CAGTTGAAAT GAAGAAGGAA
2401 GATTTTGACA TTTATGATGA GGATGAAAAT CAGAGCCCCC GCAGCTTTCA AAAGAAAACA
2461 CGACACTATT TTATTGCTGC AGTGGAGAGG CTCTGGGATT ATGGGATGAG TAGCTCCCCA
2521 CATGTTCTAA GAAACAGGGC TCAGAGTGGC AGTGTCCCTC AGTTCAAGAA AGTTGTTTTC
2581 CAGGAATTTA CTGATGGCTC CTTTACTCAG CCCTTATACC GTGGAGAACT AAATGAACAT
2641 TTGGGACTCC TGGGGCCATA TATAAGAGCA GAAGTTGAAG ATAATATCAT GGTAACTTTC
2701 AGAAATCAGG CCTCTCGTCC CTATTCCTTC TATTCTAGCC TTATTTCTTA TGAGGAAGAT
2761 CAGAGGCAAG GAGCAGAACC TAGAAAAAAC TTTGTCAAGC CTAATGAAAC CAAAACTTAC
2821 TTTTGGAAAG TGCAACATCA TATGGCACCC ACTAAAGATG AGTTTGACTG CAAAGCCTGG
2881 GCTTATTTCT CTGATGTTGA CCTGGAAAAA GATGTGCACT CAGGCCTGAT TGGACCCCTT
2941 CTGGTCTGCC ACACTAACAC ACTGAACCCT GCTCATGGGA GACAAGTGAC AGTACAGGAA
3001 TTTGCTCTGT TTTTCACCAT CTTTGATGAG ACCAAAAGCT GGTACTTCAC TGAAAATATG
3061 GAAAGAAACT GCAGGGCTCC CTGCAATATC CAGATGGAAG ATCCCACTTT TAAAGAGAAT
3121 TATCGCTTCC ATGCAATCAA TGGCTACATA ATGGATACAC TACCTGGCTT AGTAATGGCT
3181 CAGGATCAAA GGATTCGATG GTATCTGCTC AGCATGGGCA GCAATGAAAA CATCCATTCT
3241 ATTCATTTCA GTGGACATGT GTTCACTGTA CGAAAAAAAG AGGAGTATAA AATGGCACTG
3301 TACAATCTCT ATCCAGGTGT TTTTGAGACA GTGGAAATGT TACCATCCAA AGCTGGAATT
3361 TGGCGGGTGG AATGCCTTAT TGGCGAGCAT CTACATGCTG GGATGAGCAC ACTTTTTCTG
3421 GTGTACAGCA ATAAGTGTCA GACTCCCCTG GGAATGGCTT CTGGACACAT TAGAGATTTT
3481 CAGATTACAG CTTCAGGACA ATATGGACAG TGGGCCCCAA AGCTGGCCAG ACTTCATTAT
3541 TCCGGATCAA TCAATGCCTG GAGCACCAAG GAGCCCTTTT CTTGGATCAA GGTGGATCTG
3601 TTGGCACCAA TGATTATTCA CGGCATCAAG ACCCAGGGTG CCCGTCAGAA GTTCTCCAGC
3661 CTCTACATCT CTCAGTTTAT CATCATGTAT AGTCTTGATG GGAAGAAGTG GCAGACTTAT
3721 CGAGGAAATT CCACTGGAAC CTTAATGGTC TTCTTTGGCA ATGTGGATTC ATCTGGGATA
3781 AAACACAATA TTTTTAACCC TCCAATTATT GCTCGATACA TCCGTTTGCA CCCAACTCAT
3841 TATAGCATTC GCAGCACTCT TCGCATGGAG TTGATGGGCT GTGATTTAAA TAGTTGCAGC
3901 ATGCCATTGG GAATGGAGAG TAAAGCAATA TCAGATGCAC AGATTACTGC TTCATCCTAC
3961 TTTACCAATA TGTTTGCCAC CTGGTCTCCT TCAAAAGCTC GACTTCACCT CCAAGGGAGG
4021 AGTAATGCCT GGAGACCTCA GGTGAATAAT CCAAAAGAGT GGCTGCAAGT GGACTTCCAG
4081 AAGACAATGA AAGTCACAGG AGTAACTACT CAGGGAGTAA AATCTCTGCT TACCAGCATG
4141 TATGTGAAGG AGTTCCTCAT CTCCAGCAGT CAAGATGGCC ATCAGTGGAG TCTCTTTTTT
4201 CAGAATGGCA AAGTAAAGGT TTTTCAGGGA AATCAAGACT CCTTCACACC TGTGGTGAAC
4261 TCTCTAGACC CACCGTTACT GACTCGCTAC CTTCGAATTC ACCCCCAGAG TTGGGTGCAC
4321 CAGATTGCCC TGAGGATGGA GGTTCTGGGC TGCGAGGCAC AGGACCTCTA CGACAAAACT
4381 CACACATGCC CACCGTGCCC AGCTCCAGAA CTCCTGGGCG GACCGTCAGT CTTCCTCTTC
4441 CCCCCAAAAC CCAAGGACAC CCTCATGATC TCCCGGACCC CTGAGGTCAC ATGCGTGGTG
4501 GTGGACGTGA GCCACGAAGA CCCTGAGGTC AAGTTCAACT GGTACGTGGA CGGCGTGGAG
4561 GTGCATAATG CCAAGACAAA GCCGCGGGAG GAGCAGTACA ACAGCACGTA CCGTGTGGTC
4621 AGCGTCCTCA CCGTCCTGCA CCAGGACTGG CTGAATGGCA AGGAGTACAA GTGCAAGGTC
4681 TCCAACAAAG CCCTCCCAGC CCCCATCGAG AAAACCATCT CCAAAGCCAA AGGGCAGCCC
4741 CGAGAACCAC AGGTGTACAC CCTGCCCCCA TCCCGGGATG AGCTGACCAA GAACCAGGTC
4801 AGCCTGACCT GCCTGGTCAA AGGCTTCTAT CCCAGCGACA TCGCCGTGGA GTGGGAGAGC
4861 AATGGGCAGC CGGAGAACAA CTACAAGACC ACGCCTCCCG TGTTGGACTC CGACGGCTCC
4921 TTCTTCCTCT ACAGCAAGCT CACCGTGGAC AAGAGCAGGT GGCAGCAGGG GAACGTCTTC
4981 TCATGCTCCT TGATGCATGA GGCTCTGCAC AACCACTACA CGCAGAAGAG CCTCTCCCTG
5041 TCTCCGGGTA AAGGTGGCGG CGGATCAGGT GGGGGTGGAT CAGGCGGTGG AGGTTCCGGT
5101 GGCGGGGGAT CAGACAAAAC TCACACATGC CCACCGTGCC CAGCACCTGA ACTCCTGGGA
5161 GGACCGTCAG TCTTCCTCTT CCCCCCAAAA CCCAAGGACA CCCTCATGAT CTCCCGGACC
5221 CCTGAGGTCA CATGCGTGGT GGTGGACGTG AGCCACGAAG ACCCTGAGGT CAAGTTCAAC
5261 TGGTACGTGG ACGGCGTGGA GGTGCATAAT GCCAAGACAA AGCCGCGGGA GGAGCAGTAC
5341 AACAGCACGT ACCGTGTGGT CAGCGTCCTC ACCGTCCTGC ACCAGGACTG GCTGAATGGC
5401 AAGGAGTACA AGTGCAAGGT CTCCAACAAA GCCCTCCCAG CCCCCATCGA GAAAACCATC
5461 TCCAAAGCCA AAGGGCAGCC CCGAGAACCA CAGGTGTACA CCCTGCCCCC TCCCGCGAT
5521 GAGCTGACCA AGAACCAGGT CAGCCTGACC TGCCTGGTCA AAGGCTTCTA TCCCAGCGAC
5581 ATCGCCGTGG AGTGGGAGAG CAATGGGCAG CCGGAGAACA ACTACAAGAC CACGCCTCCC
5641 GTGTTGGACT CCGACGGCTC CTTCTTCCTC TACAGCAAGC TCACCGTGGA CAAGAGCAGG
5701 TGGCAGCAGG GGAACGTCTT CTCATGCTCC GTGATGCATG AGGCTCTGCA CAACCACTAC
5761 ACGCAGAAGA GCCTCTCCCT GTCTCCGGGT AAATGA

-continued

DRAFT SEQUENCE LISTING

FVIII-041 amino acid sequence. Signal sequence is shown in dotted underline, and linker region connecting the Fc regions is underlined

```
   1 MQIELSTCFF LCLLRFCFSA TRRYYLGAVE LSWDYMQSDL GELPVDARFP PRVPKSFPFN
  61 TSVVYKKTLF VEFTDHLFNI AKPRPPWMGL LGPTIQAEVY DTVVITLKNM ASHPVSLHAV
 121 GVSYWKASEG AEYDDQTSQR EKEDDKVFPG GSHTYVWQVL KENGPMASDP LCLTYSYLSH
 181 VDLVKDLNSG LIGALLVCRE GSLAKEKTQT LHKFILLFAV FDEGKSWHSE TKNSLMQDRD
 241 AASARAWPKM HTVNGYVNRS LPGLIGCHRK SVYWHVIGMG TTPEVHSIFL EGHTFLVRNH
 301 RQASLEISPI TFLTAQTLLM DLGQFLLFCH ISSHQHDGME AYVKVDSCPE EPQLRMKNNE
 361 EAEDYDDDLT DSEMDVVRFD DDNSPSFIQI RSVAKKHPKT WVHYIAAEEE DWDYAPLVLA
 421 PDDRSYKSQY LNNGPQRIGR KYKKVRFMAY TDETFKTREA IQHESGILGP LLYGEVGDTL
 481 LIIFKNQASR PYNIYPHGIT DVRPLYSRRL PKGVKHLKDF PILPGEIFKY KWTVTVEDGP
 541 TKSDPRCLTR YYSSFVNMER DLASGLIGPL LICYKESVDQ RGNQIMSDKR NVILFSVFDE
 601 NRSWYLTENI QRFLPNPAGV QLEDPEFQAS NIMHSINGYV FDSLQLSVCL HEVAYWYILS
 661 IGAQTDFLSV FFSGYTFKHK MVYEDTLTLF PFSGETVFMS MENPGLWILG CHNSDFRNRG
 721 MTALLKVSSC DKNTGDYYED SYEDISAYLL SKNNAIEPRS FSQNPPVLKR HQREITRTTL
 781 QSDQEEIDYD DTISVEMKKE DFDIYDEDEN QSPRSFQKKT RHYFIAAVER LWDYGMSSSP
 841 HVLRNRAQSG SVPQFKKVVF QEFTDGSFTQ PLYRGELNEH LGLLGPYIRA EVEDNIMVTF
 901 RNQASRPYSF YSSLISYEED QRQGAEPRKN FVKPNETKTY FWKVQHHMAP TKDEFDCKAW
 961 AYFSDVDLEK DVHSGLIGPL LVCHTNTLNP AHGRQVTVQE FALFFTIFDE TKSWYFTENM
1021 ERNCRAPCNI QMEDPTFKEN YRFHAINGYI MDTLPGLVMA QDQRIRWYLL SMGSNENIHS
1081 IHFSGHVFTV RKKEEYKMAL YNLYPGVFET VEMLPSKAGI WRVECLIGEH LHAGMSTLFL
1141 VYSNKCQTPL GMASGHIRDF QITASGQYGQ WAPKLARLHY SGSINAWSTK EPFSWIKVDL
1201 LAPMIIHGIK TQGARQKFSS LYISQFIIMY SLDGKKWQTY RGNSTGTLMW FFGNVDSSGI
1261 KHNIFNPPII ARYIRLHPTH YSIRSTLRME LMGCDLNSCS MPLGMESKAI SDAQITASSY
1321 FTNMFATWSP SKARLHLQGR SNAWRPQVNN PKEWLQVDFQ KTMKVTGVTT QGVKSLLTSM
1381 YVKEFLISSS QDGHQWTLFF QNGKVKVFQG NQDSFTPVVN SLDPPLLTRY LRIHPQSWVH
1441 QIALRMEVLG CEAQDLYDKT HTCPPCPAPE LLGGPSVFLF PPKPKDTLMI SRTPEVTCVV
1501 VDVSHEDPEV KFNWYVDGVE VHNAKTKPRE EQYNSTYRVV SVLTVLHQDW LNGKEYKCKV
1561 SNKALPAPIE KTISKAKGQP REPQVYTLPP SRDELTKNQV SLTCLVKGFY PSDIAVEWES
1621 NGQPENNYKT TPPVLDSDGS FFLYSKLTVD KSRWQQGNVF SCSVMHEALH NHYTQKSLSL
1681 SPGKGGGGSG GGGSGGGGSG GGGSDKTHTC PPCPAPELLG GPSVFLFPPK PKDTLMISRT
1741 PEVTCVVVDV SHEDPEVKFN WYVDGVEVHN AKTKPREEQY NSTYRVVSVL TVLHQDWLNG
1801 KEYKCKVSNK ALPAPIEKTI SKAKGQPREP QVYTLPPSRD ELTKNQVSLT CLVKGFYPSD
1861 IAVEWESNGQ PENNYKTTPP VLDLDGSFFL YSKLTVDKSR WQQGNVFSCS VMHEALHNHY
1921 TQKSLSLSPG K*
```

DNA sequence for FVIII-108

```
   1 ATGCAAATAG AGCTCTCCAC CTGCTTCTTT CTGTGCCTTT TGCGATTCTG CTTTAGTGCC
  61 ACCAGAAGAT ACTACCTGGG TGCAGTGGAA CTGTCATGGG ACTATATGCA AAGTGATCTC
 121 GGTGAGCTGC CTGTGGACGC AAGATTTCCT CCTAGAGTGC CAAAATCTTT TCCATTCAAC
 181 ACCTCAGTCG TGTACAAAAA GACTCTGTTT GTAGAATTCA CGGATCACCT TTTCAACATC
 241 GCTAAGCCAA GGCCACCCTG GATGGGTCTG CTAGGTCCTA CCATCCAGGC TGAGGTTTAT
 301 GATACAGTGG TCATTACACT TAAGAACATG GCTTCCCATC CTGTCAGTCT TCATGCTGTT
 361 GGTGTATCCT ACTGGAAAGC TTCTGAGGGA GCTGAATATG ATGATCAGAC CAGTCAAAGG
 421 GAGAAAGAAG ATGATAAAGT CTTCCCTGGT GGAAGCCATA CATATGTCTG GCAGGTCCTG
 481 AAAGAGAATG GTCCAATGGC CTCTGACCCA CTGTGCCTTA CCTACTCATA TCTTTCTCAT
 541 GTGGACCTGG TAAAAGACTT GAATTCAGGC CTCATTGGAG CCCTACTAGT ATGTAGAGAA
 601 GGGAGTCTGG CCAAGGAAAA GACACAGACC TTGCACAAAT TTATACTACT TTTTGCTGTA
 661 TTTGATGAAG GGAAAAGTTG GCACTCAGAA ACAAAGAACT CCTTGATGCA GGATAGGGAT
 721 GCTGCATCTG CTCGGGCCTG GCCTAAAATG CACACAGTCA ATGGTTATGT AAACAGGTCT
 781 CTGCCAGGTC TGATTGGATG CCACAGGAAA TCAGTCTATT GGCATGTGAT TGGAATGGGC
 841 ACCACTCCTG AAGTGCACTC AATATTCCTC GAAGGTCACA CATTTCTTGT GAGGAACCAT
 901 CGCCAGGCGT CCTTGGAAAT CTCGCCAATA ACTTTCCTTA CTGCTCAAAC ACTCTTGATG
 961 GACCTTGGAC AGTTTCTACT GTTTTGTCAT ATCTCTTCCC ACCAACATGA TGGCATGGAA
1021 GCTTATGTCA AAGTAGACAG CTGTCCAGAG GAACCCCAAC TACGAATGAA AAATAATGAA
1081 GAAGCGGAAG ACTATGATGA TGATCTTACT GATTCTGAAA TGGATGTGGT CAGGTTTGAT
1141 GATGACAACT CTCCTTCCTT TATCCAAATT CGCTCAGTTG CCAAGAAGCA TCCTAAAACT
1201 TGGGTACATT ACATTGCTGC TGAAGAGGAG GACTGGGACT ATGCTCCCTT AGTCCTCGCC
1261 CCCGATGACA GAAGTTATAA AAGTCAATAT TTGAACAATG GCCCTCAGCG GATTGGTAGG
1321 AAGTACAAAA AAGTCCGATT TATGGCATAC ACAGATGAAA CCTTTAAGAC TCGTGAAGCT
1381 ATTCAGCATG AATCAGGAAT CTTGGGACCT TTACTTTATG GGGAAGTTGG AGACACACTG
1441 TTGATTATAT TTAAGAATCA AGCAAGCAGA CCATATAACA TCTACCCTCA CGGAATCACT
1501 GATGTCCGTC CTTTGTATTC AAGGAGATTA CCAAAAGGTG TAAAACATTT GAAGAATTTT
1561 CCAATTCTGC CAGGAGAAAT ATTCAAATAT AAATGGACAG TGACTGTAGA AGATGGGCCA
1621 ACTAAATCAG ATCCTCGGTG CCTGACCCGC TATTACTCTA GTTTCGTTAA TATGGAGAGA
1681 GATCTAGCTT CAGGACTCAT TGGCCCTCTC CTCATCTGCT ACAAAGAATC TGTAGATCAA
1741 AGAGGAAACC AGATAATGTC AGACAAGAGG AATGTCATCC TGTTTTCTGT ATTTGATGAG
1801 AACCGAAGCT GGTACCTCAC AGAGAATATA CAACGCTTTC TCCCCAATCC AGCTGGAGTG
1861 CAGCTTGAGG ATCCAGAGTT CCAAGCCTCC AACATCATGC ACAGCATCAA TGGCTATGTT
1921 TTTGATAGTT TGCAGTTGTC AGTTTGTTTG CATGAGGTGG CATACTGGTA CATTCTAAGC
1981 ATTGGAGCAC AGACTGACTT CCTTTCTGTC TTCTTCTCTG GATATACCTT CAAACACAAA
2041 ATGGTCTATG AAGACACACT CACCCTATTC CCATTCTCAG GAGAAACTGT CTTCATGTCG
2101 ATGGAAAACC CAGGTCTATG GATTCTGGGG TGCCACAACT CAGACTTTCG GAACAGAGGC
2161 ATGACCGCCT TACTGAAGGT TTCTAGTTGT GACAAGAACA CTGGTGATTA TTACGAGGAC
2221 AGTTATGAAG ATATTTCAGC ATACTTGCTG AGTAAAAACA ATGCCATTGA ACCAAGAAGC
2281 TTCTCTCAAA ACCCACCAGT CTTGAAACGC CATCAACGGG AAATAACTCG TACTACTCTT
2341 CAGTCAGATC AAGAGGAAAT TGACTATGAT GATACCATAT CAGTTGAAAT GAAGAAGGAA
2401 GATTTTGACA TTTATGATGA GGATGAAAAT CAGAGCCCCC GCAGCTTTCA AAAGAAAACA
2461 CGACACTATT TTATTGCTGC AGTGGAGAGG CTCTGGGATT ATGGGATGAG TAGCTCCCCA
2521 CATGTTCTAA GAAACAGGGC TCAGAGTGGC AGTGTCCCTC AGTTCAAGAA AGTTGTTTTC
```

-continued

DRAFT SEQUENCE LISTING

2581 CAGGAATTTA CTGATGGCTC CTTTACTCAG CCCTTATACC GTGGAGAACT AAATGAACAT
2641 TTGGGACTCC TGGGGCCATA TATAAGAGCA GAAGTTGAAG ATAATATCAT GGTAACTTTC
2701 AGAAATCAGG CCTCTCGTCC CTATTCCTTC TATTCTAGCC TTATTTCTTA TGAGGAAGAT
2761 CAGAGGCAAG GAGCAGAACC TAGAAAAAAC TTTGTCAAGC CTAATGAAAC CAAAACTTAC
2821 TTTTGGAAAG TGCAACATCA TATGGCACCC ACTAAAGATG AGTTTGACTG CAAAGCCTGG
2881 GCTTATTTCT CTGATGTTGA CCTGGAAAAA GATGTGCACT CAGGCCTGAT TGGACCCCTT
2941 CTGGTCTGCC ACACTAACAC ACTGAACCCT GCTCATGGGA GACAAGTGAC AGTACAGGAA
3001 TTTGCTCTGT TTTTCACCAT CTTTGATGAG ACCAAAAGCT GGTACTTCAC TGAAAATATG
3061 GAAAGAAACT GCAGGGCTCC CTGCAATATC CAGATGGAAG ATCCCACTTT TAAAGAGAAT
3121 TATCGCTTCC ATGCAATCAA TGGCTACATA ATGGATACAC TACCTGGCTT AGTAATGGCT
3181 CAGGATCAAA GGATTCGATG GTATCTGCTC AGCATGGGCA GCAATGAAAA CATCCATTCT
3241 ATTCATTTCA GTGGACATGT GTTCACTGTA CGAAAAAAAG AGGAGTATAA AATGGCACTG
3301 TACAATCTCT ATCCAGGTGT TTTTGAGACA GTGGAAATGT TACCATCCAA AGCTGGAATT
3361 TGGCGGGTGG AATGCCTTAT TGGCGAGCAT CTACATGCTG GGATGAGCAC ACTTTTTCTG
3421 GTGTACAGCA ATAAGTGTCA GACTCCCCTG GGAATGGCTT CTGGACACAT TAGAGATTTT
3481 CAGATTACAG CTTCAGGACA ATATGGACAG TGGGCCCCAA AGCTGGCCAG ACTTCATTAT
3541 TCCGGATCAA TCAATGCCTG GAGCACCAAG GAGCCCTTTT CTTGGATCAA GGTGGATCTG
3601 TTGGCACCAA TGATTATTCA CGGCATCAAG ACCCAGGGTG CCCGTCAGAA GTTCTCCAGC
3661 CTCTACATCT CTCAGTTTAT CATCATGTAT AGTCTTGATG GGAAGAAGTG GCAGACTTAT
3721 CGAGGAAATT CCACTGGAAC CTTAATGGTC TTCTTTGGCA ATGTGGATTC ATCTGGGATA
3781 AAACACAATA TTTTTAACCC TCCAATTATT GCTCGATACA TCCGTTTGCA CCCAACTCAT
3841 TATAGCATTC GCAGCACTCT TCGCATGGAG TTGATGGGCT GTGATTTAAA TAGTTGCAGC
3901 ATGCCATTGG GAATGGAGAG TAAAGCAATA TCAGATGCAC AGATTACTGC TTCATCCTAC
3961 TTTACCAATA TGTTTGCCAC CTGGTCTCCT TCAAAAGCTC GACTTCACCT CCAAGGGAGG
4021 AGTAATGCCT GGAGACCTCA GGTGAATAAT CCAAAAGAGT GGCTGCAAGT GGACTTCCAG
4081 AAGACAATGA AAGTCACAGG AGTAACTACT CAGGGAGTAA AATCTCTGCT TACCAGCATG
4141 TATGTGAAGG AGTTCCTCAT CTCCAGCAGT CAAGATGGCC ATCAGTGGAC TCTCTTTTTT
4201 CAGAATGGCA AAGTAAAGGT TTTTCAGGGA AATCAAGACT CCTTCACACC TGTGGTGAAC
4261 TCTCTAGACC CACCGTTACT GACTCGCTAC CTTCGAATTC ACCCCCAGAG TTGGGTGCAC
4321 CAGATTGCCC TGAGGATGGA GGTTCTGGGC TGCGAGGCAC AGGACCTCTA CGACAAAACT
4381 CACACATGCC CACCGTGCCC AGCACCTGAA CTCCTGGGAG GACCGTCAGT CTTCCTCTTC
4441 CCCCCAAAAC CCAAGGACAC CCTCATGATC TCCCGGACCC CTGAGGTCAC ATGCGTGGTG
4501 GTGGACGTGA GCCACGAAGA CCCTGAGGTC AAGTTCAACT GGTACGTGGA CGGCGTGGAG
4561 GTGCATAATG CCAAGACAAA GCCGCGGGAG GAGCAGTACA ACAGCACGTA CCGTGTGGTC
4621 AGCGTCCTCA CCGTCCTGCA CCAGGACTGG CTGAATGGCA AGGAGTACAA GTGCAAGGTC
4681 TCCAACAAAG CCCTCCCAGC CCCCATCGAG AAAACCATCT CCAAAGCCAA AGGGCAGCCC
4741 CGAGAACCAC AGGTGTACAC CCTGCCCCCA TCCCGCGATG AGCTGACCAA GAACCAGGTC
4801 AGCCTGACCT GCCTGGTCAA AGGCTTCTAT CCCAGCGACA TCGCCGTGGA GTGGGAGAGC
4861 AATGGGCAGC CGGAGAACAA CTACAAGACC ACGCCTCCCG TGTTGGACTC CGACGGCTCC
4921 TTCTTCCTCT ACAGCAAGCT CACCGTCGAC AAGAGCAGGT GGCAGCAGGG GAACGTCTTC
4981 TCATGCTCCG TGATGCATGA GGCTCTGCAC AACCACTACA CGCAGAAGAG CCTCTCCCTG
5041 TCTCCGGGTA AACGGCGCCG CCGGAGCGGT GGCGGCGGAT CAGGTGGGGG TGGATCAGGC
5101 GGTGGAGGTT CCGGTGGCGG GGGATCCGGC GGTGGAGGTT CCGGTGGGGG TGGATCAAGG
5161 AAGAGGAGGA AGAGGGCGCA GGTGCAGCTG CAGGAGTCTG GGGGAGGCTT GGTACAGCCT
5221 GGGGGGTCCC TGAGACTCTC CTGTGCAGCC TCTGGATTCA TGTTTAGCAG GTATGCCATG
5281 AGCTGGGTCC GCCAGGCTCC AGGGAAGGGG CCAGAGTGGG TCTCAGGTAT TAGTGGTAGT
5341 GGTGGTAGTA CATACTACGC AGACTCCGTG AAGGGCCGGT TCACCGTCTC CAGAGACAAT
5401 TCCAAGAACA CGCTGTATCT GCAAATGAAC AGCCTGAGAG CCGAGGACAC GGCTGTATAT
5461 TACTGCGCCC GGGGCGCCAC CTACACCAGC CGGAGCGACG TGCCCGACCA GACCAGCTTC
5521 GACTACTGGG GCCAGGGAAC CCTGGTCACC GTCTCCTCAG GGAGTGCATC CGCCCCAAAG
5581 CTTGAAGAAG GTGAATTTTC AGAAGCACGC GTATCTGAAC TGACTCAGGA CCCTGCTGTG
5641 TCTGTGGCCT TGGGACAGAC AGTCAGGATC ACATGCCAAG GAGACAGCCT CAGAAACTTT
5701 TATGCAAGCT GGTACCAGCA GAAGCCAGGA CAGGCCCCTA CTCTTGTCAT CTATGGTTTA
5761 AGTAAAAGGC CCTCAGGGAT CCCAGACCGA TTCTCTGCCT CCAGCTCAGG AAACACAGCT
5821 TCCTTGACCA TCACTGGGGC TCAGGCGGAA GATGAGGCTG ACTATTACTG CCTGCTGTAC
5861 TACGGCGGCG GCCAGCAGGG CGTGTTCGGC GGCGGCACCA AGCTGACCGT CCTACGTCAG
5941 CCCAAGGCTG CCCCCTCGGT CACTCTGTTC CCGCCCTCTT CTGCGGCCGG TGGCGGTGGC
6001 TCCGGCGGAG GTGGGTCCGG TGGCGGCGGA TCAGGTGGGG GTGGATCAGG CGGTGGAGGT
6061 TCCGGTGGCG GGGGATCAGA CAAAACTCAC ACATGCCCAC CGTGCCCAGC ACCGGAACTC
6121 CTGGGCGGAC CGTCAGTCTT CCTCTTCCCC CCAAAACCCA AGGACACCCT CATGATCTCC
6181 CGGACCCCTG AGGTCACATG CGTGGTGGTG GACGTGAGCC ACGAAGACCC TGAGGTCAAG
6241 TTCAACTGGT ACGTGGACGG CGTGGAGGTG CATAATGCCA AGACAAAGCC GCGGGAGGAG
6301 CAGTACAACA GCACGTACCG TGTGGTCAGC GTCCTCACCG TCCTGCACCA GGACTGGCTG
6361 AATGGCAAGG AGTACAAGTG CAAGGTCTCC AACAAAGCCC TCCCAGCCCC CATCGAGAAA
6421 ACCATCTCCA AAGCCAAAGG GCAGCCCCGA GAACCACAGG TGTACACCCT GCCCCCATCC
6481 CGGGATGAGC TGACCAAGAA CCAGGTCAGC CTGACCTGCC TGGTCAAAGG CTTCTATCCC
6541 AGCGACATCG CCGTGGAGTG GGAGAGCAAT GGGCAGCCGG AGAACAACTA CAAGACCACG
6601 CCTCCCGTGT TGGACTCCGA CGGCTCCTTC TTCCTCTACA GCAAGCTCAC CGTGGACAAG

DRAFT SEQUENCE LISTING

```
6661 AGCAGGTGGC AGCAGGGGAA CGTCTTCTCA TGCTCCGTGA TGCATGAGGC TCTGCACAAC
6721 CACTACACGC AGAAGAGCCT CTCCCTGTCT CCGGGTAAAT GA
```

FVIII-108 amino acid sequence. Signal sequence is shown in dotted underline, linker region connecting SCE5 to Fc region is underlined, and linker with propotein convertase processing sites is shown in bold

```
   1 MQIELSTCFF LCLLRFCFSA TRRYYLGAVE LSWDYMQSDL GELPVDARFP PRVPKSFPFN
  61 TSVVYKKTLF VEFTDHLFNI AKPRPPWMGL LGPTIQAEVY DTVVITLKNM ASHPVSLHAV
 121 GVSYWKASEG AEYDDQTSQR EKEDDKVFPG GSHTYVWQVL KENGPMASDP LCLTYSYLSH
 181 VDLVKDLNSG LIGALLVCRE GSLAKEKTQT KHKFILLFAV FDEGKSWHSE TKNSLMQDRD
 241 AASARAWPKM HTVNGYVNRS LPGLIGCHRK SVYWHVIGMG TTPEVHSIFL EGHTFLVRNH
 301 RQASLEISPI TFLTAQTLLM DLGQFLLFCH ISSHQHDGME AYVKVDSCPE EPQLRMKNNE
 361 EAEDYDDDLT DSEMDVVRFD DDNSPSFIQI RSVAKKHPKT WVHYIAAEEE DWDYAPLVLA
 421 PDDRSYKSQY LNNGPQRIGR KYKKVRFMAY TDETFKTREA IQHESGILGP LLYGEVGDTL
 481 LIIFKNQASR PYNIYPHGIT DVRPLYSRRL PKGVKHLKDF PILPGEIFKY KWTVTVEDGP
 541 TKSDPRCLTR YYSSFVNMER DLASGLIGPL LICYKESVDQ RGNQIMSDKR NVILFSVFDE
 601 NRSWYLTENI QRFLPNPAGV QLEDPEFQAS NIMHSINGYV FDSLQLSVCL HEVAYWYILS
 661 IGAQTDFLSV FFSGYTFKHK MVYEDTLTLF PFSGETVFMS MENPGLWILG CHNSDFRNRG
 721 MTALLKVSSC DKNTGDYYED SYEDISAYLL SKNNAIEPRS FSQNPPVLKR HQREITRTTL
 781 QSDQEEIDYD DTISVEMKKE DFDIYDEDEN QSPRSFQKKT RHYFIAAVER LWDYGMSSSP
 841 HVLRNRAQSG SVPQFKKVVF QEFTDGSFTQ PLYRGELNEH LGLLGPYIRA EVEDNIMVTF
 901 RNQASRPYSF YSSLISYEED QRQGAEPRKN FVKPNETKTY FWKVQHHMAP TKDEFDCKAW
 961 AYFSDVDLEK DVHSGLIGPL LVCHTNTLNP AHGRQVTVQE FALFFTIFDE TKSWYFTENM
1021 ERNCRAPCNI QMEDPTFKEN YRFHAINGYI MDTLPGLVMA QDQRIRWYLL SMGSNENIHS
1081 IHFSGHVFTV RKKEEYKMAL YNLYPGVFET VEMLPSKAGI WRVECLIGEH LHAGMSTLFL
1141 VYSNKCQTPL GMASGHIRDF QITASGQYGQ WAPKLARLHY SGSINAWSTK EPFSWIKVDL
1201 LAPMIIHGIK TQGARQKFSS LYISQFIIMY SLDGKKWQTY RGNSTGTLMW FFGNVDSSGI
1261 KHNIFNPPII ARYIRLHPTH YSIRSTLRME LMGCDLNSCS MPLGMESKAI SDAQITASSY
1321 FTNMFATWSP SKARLHLQGR SNAWRPQVNN PKEWLQVDFQ KTMKVTGVTT QGVKSLLTSM
1381 YVKEFLISSS QDGHQWTLFF QNGKVKVFQG NQDSFTPVVN SLDPPLLTRY LRIHPQSWVH
1441 QIALRMEVLG CEAQDLYDKT HTCPPCPAPE LLGGPSVFLF PPKPKDTLMI SRTPEVTCVV
1501 VDVSHEDPEV KFNWYVDGVE VHNAKTKPRE EQYNSTYRVV SVLTVLHQDW LNGKEYKCKV
1561 SNKALPAPIE KTISKAKGQP REPQVYTLPP SRDELTKNQV SLTCLVKGFY PSDIAVEWES
1621 NGQPENNYKT TPPVLDSDGS FFLYSKLTVD KSRWQQGNVF SCSVMHEALH NHYTQKSLSL
1681 SPGKRRRRSG GGGSGGGGSG GGGSGGGGSG GGGSGGGGSR KRRKRAQVQL QESGGGLVQP
1741 GGSLRLSCAA SGFMFSRYAM SWVRQAPGKG PEWVSGISGS GGSTYYADSV KGRFTVSRDN
1801 SKNTLYLQMN SLRAEDTAVY YCARGATYTS RSDVPDQTSF DYWGQGTLVT VSSGSASAPK
1861 LEEGEFSEAR VSELTQDPAV SVALGQTVRI TCQGDSLRNF YASWYQQKPG QAPTLVIYGL
1921 SKRPSGIPDR FSASSSGNTA SLTITGAQAE DEADYYCLLY YGGGQQGVFG GGTKLTVLRQ
1984 PKAAPSVTLF PPSSAGGGG SGGGGSGGGG SGGGGSGGGG SGGGGSDKTH TCPPCPAPEL
2041 LGGPSVFLFP PKPKDTLMIS RTPEVTCVVV DVSHEDPEVK FNWYVDGVEV HANKTKPREE
2101 QYNSTYRVVS VLTVLHQDWL NGKEYKCKVS NKALPAPIEK TISKAKGQPR EPQVYTLPPS
2161 RDELTKNQVS LTCLVKGFYP SDIAVEWESN GQPENNYKTT PPVLDSDGSF FLYSKLTVDK
2221 SRWQQGNVFS CSVMHEALHN HYTQKSLSLS PGK*
```

DNA sequence for pSYN-FVIII-049

```
   1 ATGCAAATAG AGCTCTCCAC CTGCTTCTTT CTGTGCCTTT TGCGATTCTG CTTTAGTGCC
  61 ACCAGAAGAT ACTACCTGGG TGCAGTGGAA CTGTCATGGG ACTATATGCA AAGTGATCTC
 121 GGTGAGCTGC CTGTGGACGC AAGATTTCCT CCTAGAGTGC CAAAATCTTT TCCATTCAAC
 181 ACCTCAGTCG TGTACAAAAA GACTCTGTTT GTAGAATTCA CGGATCACCT TTTCAACATC
 241 GCTAAGCCAA GGCCACCCTG GATGGGTCTG CTAGGTCCTA CCATCCAGGC TGAGGTTTAT
 301 GATACAGTGG TCATTACACT TAAGAACATG GCTTCCCATC CTGTCAGTCT TCATGCTGTT
 361 GGTGTATCCT ACTGGAAAGC TTCTGAGGGA GCTGAATATG ATGATCAGAC CAGTCAAAGG
 421 GAGAAAGAAG ATGATAAAGT CTTCCCTGGT GGAAGCCATA CATATGTCTG GCAGGTCCTG
 481 AAAGAGAATG GTCCAATGGC CTCTGACCCA CTGTGCCTTA CCTACTCATA TCTTTCTCAT
 541 GTGGACCTGG TAAAAGACTT GAATTCAGGC CTCATTGGAG CCCTACTAGT ATGTAGAGAA
 601 GGGAGTCTGG CCAAGGAAAA GACACAGACC TTGCACAAAT TTATACTACT TTTTGCTGTA
 661 TTTGATGAAG GGAAAAGTTG GCACTCAGAA ACAAAGAACT CCTTGATGCA GGATAGGGAT
 721 GCTGCATCTG CTCGGGCCTG GCCTAAAATG CACACAGTCA ATGGTTATGT AAACAGGTCT
 781 CTGCCAGGTC TGATTGGATG CCACAGGAAA TCAGTCTATT GGCATGTGAT TGGAATGGGC
 841 ACCACTCCTG AAGTGCACTC AATATTCCTC GAAGGTCACA CATTTCTTGT GAGGAACCAT
 901 CGCCAGGCGT CCTTGGAAAT CTCGCCAATA ACTTTCCTTA CTGCTCAAAC ACTCTTGATG
 961 GACCTTGGAC AGTTTCTACT GTTTTGTCAT ATCTCTTCCC ACCAACATGA TGGCATGGAA
1021 GCTTATGTCA AAGTAGACAG CTGTCCAGAG GAACCCCAAC TACGAATGAA AAATAATGAA
1081 GAAGCGGAAG ACTATGATGA TGATCTTACT GATTCTGAAA TGGATGTGGT CAGGTTTGAT
1141 GATGACAACT CTCCTTCCTT TATCCAAATT CGCTCAGTTG CCAAGAAGCA TCCTAAAACT
1201 TGGGTACATT ACATTGCTGC TGAAGAGGAG GACTGGGACT ATGCTCCCTT AGTCCTCGCC
1261 CCCGATGACA GAAGTTATAA AAGTCAATAT TTGAACAATG GCCCTCAGCG GATTGGTAGG
1321 AAGTACAAAA AAGTCCGATT TATGGCATAC ACAGATGAAA CCTTTAAGAC TCGTGAAGCT
1381 ATTCAGCATG AATCAGGAAT CTTGGGACCT TTACTTTATG GGGAAGTTGG AGACACACTG
1441 TTGATTATAT TTAAGAATCA AGCAAGCAGA CCATATAACA TCTACCCTCA CGGAATCACT
1501 GATGTCCGTC CTTTGTATTC AAGGAGATTA CCAAAAGGTG TAAAACATTT GAAGGATTTT
1561 CCAATTCTGC CAGGAGAAAT ATTCAAATAT AAATGGACAG TGACTGTAGA AGATGGGCCA
1621 ACTAAATCAG ATCCTCGGTG CCTGACCCGC TATTACTCTA GTTTCGTTAA TATGGAGAGA
1681 GATCTAGCTT CAGGACTCAT TGGCCCTCTC CTCATCTGCT ACAAAGAATC TGTAGATCAA
1741 AGAGGAAACC AGATAATGTC AGACAAGAGG AATGTCATCC TGTTTTCTGT ATTTGATGAG
1801 AACCGAAGCT GGTACCTCAC AGAGAATATA CAACGCTTTC TCCCCAATCC AGCTGGAGTG
1861 CAGCTTGAGG ATCCAGAGTT CCAAGCCTCC AACATCATGC ACAGCATCAA TGGCTATGTT
1921 TTTGATAGTT TGCAGTTGTC AGTTTGTTTG CATGAGGTGG CATACTGGTA CATTCTAAGC
1981 ATTGGAGCAC AGACTGACTT CCTTTCTGTC TTCTTCTCTG GATATACCTT CAAACACAAA
```

-continued

DRAFT SEQUENCE LISTING

```
2041 ATGGTCTATG AAGACACACT CACCCTATTC CCATTCTCAG GAGAAACTGT CTTCATGTCG
2101 ATGGAAAACC CAGGTCTATG GATTCTGGGG TGCCACAACT CAGACTTTCG GAACAGAGGC
2161 ATGACCGCCT TACTGAAGGT TTCTAGTTGT GACAAGAACA CTGGTGATTA TTACGAGGAC
2221 AGTTATGAAG ATATTTCAGC ATACTTGCTG AGTAAAAACA ATGCCATTGA ACCAAGAAGC
2281 TTCTCTCAAA ACCCACCAGT CTTGAAACGC CATCAACGGG AAATAACTCG TACTACTCTT
2341 CAGTCAGATC AAGAGGAAAT TGACTATGAT GATACCATAT CAGTTGAAAT GAAGAAGGAA
2401 GATTTTGACA TTTATGATGA GGATGAAAAT CAGAGCCCCC GCAGCTTTCA AAAGAAAACA
2461 CGACACTATT TTATTGCTGC AGTGGAGAGG CTCTGGGATT ATGGGATGAG TAGCTCCCCA
2521 CATGTTCTAA GAAACAGGGC TCAGAGTGGC AGTGTCCCTC AGTTCAAGAA AGTTGTTTTC
2581 CAGGAATTTA CTGATGGCTC CTTTACTCAG CCCTTATACC GTGGAGAACT AAATGAACAT
2641 TTGGGACTCC TGGGGCCATA TATAAGAGCA GAAGTTGAAG ATAATATCAT GGTAACTTTC
2701 AGAAATCAGG CCTCTCGTCC CTATTCCTTC TATTCTAGCC TTATTTCTTA TGAGGAAGAT
2761 CAGAGGCAAG GAGCAGAACC TAGAAAAAAC TTTGTCAAGC CTAATGAAAC CAAAACTTAC
2821 TTTTGGAAAG TGCAACATCA TATGGCACCC ACTAAAGATG AGTTTGACTG CAAAGCCTGG
2881 GCTTATTTCT CTGATGTTGA CCTGGAAAAA GATGTGCACT CAGGCCTGAT TGGACCCCTT
2941 CTGGTCTGCC ACACTAACAC ACTGAACCCT GCTCATGGGA GACAAGTGAC AGTACAGGAA
3001 TTTGCTCTGT TTTTCACCAT CTTTGATGAG ACCAAAAGCT GGTACTTCAC TGAAAATATG
3061 GAAAGAAACT GCAGGGCTCC CTGCAATATC CAGATGGAAG ATCCCACTTT TAAAGAGAAT
3121 TATCGCTTCC ATGCAATCAA TGGCTACATA ATGGATACAC TACCTGGCTT AGTAATGGCT
3181 CAGGATCAAA GGATTCGATG GTATCTGCTC AGCATGGGCA GCAATGAAAA CATCCATTCT
3241 ATTCATTTCA GTGGACATGT GTTCACTGTA CGAAAAAAAG AGGAGTATAA AATGGCACTG
3301 TACAATCTCT ATCCAGGTGT TTTTGAGACA GTGGAAATGT TACCATCCAA AGCTGGAATT
3361 TGGCGGGTGG AATGCCTTAT TGGCGAGCAT CTACATGCTG GGATGAGCAC ACTTTTTCTG
3421 GTGTACAGCA ATAAGTGTCA GACTCCCCTG GGAATGGCTT CTGGACACAT TAGAGATTTT
3481 CAGATTACAG CTTCAGGACA ATATGGACAG TGGGCCCCAA AGCTGGCCAG ACTTCATTAT
3541 TCCGGATCAA TCAATGCCTG GAGCACCAAG GAGCCCTTTT CTTGGATCAA GGTGGATCTG
3601 TTGGCACCAA TGATTATTCA CGGCATCAAG ACCCAGGGTG CCCGTCAGAA GTTCTCCAGC
3661 CTCTACATCT CTCAGTTTAT CATCATGTAT AGTCTTGATG GGAAGAAGTG GCAGACTTAT
3721 CGAGGAAATT CCACTGGAAC CTTAATGGTC TTCTTTGGCA ATGTGGATTC ATCTGGGATA
3781 AAACACAATA TTTTTAACCC TCCAATTATT GCTCGATACA TCCGTTTGCA CCCAACTCAT
3841 TATAGCATTC GCAGCACTCT TCGCATGGAG TTGATGGGCT GTGATTTAAA TAGTTGCAGC
3901 ATGCCATTGG GAATGGAGAG TAAAGCAATA TCAGATGCAC AGATTACTGC TTCATCCTAC
3961 TTTACCAATA TGTTTGCCAC CTGGTCTCCT TCAAAAGCTC GACTTCACCT CCAAGGGAGG
4021 AGTAATGCCT GGAGACCTCA GGTGAATAAT CCAAAAGAGT GGCTGCAAGT GGACTTCCAG
4081 AAGACAATGA AAGTCACAGG AGTAACTACT CAGGGAGTAA AATCTCTGCT TACCAGCATG
4141 TATGTGAAGG AGTTCCTCAT CTCCAGCAGT CAAGATGGCC ATCAGTGGAC TCTCTTTTTT
4201 CAGAATGGCA AAGTAAAGGT TTTTCAGGGA AATCAAGACT CCTTCACACC TGTGGTGAAC
4261 TCTCTAGACC CACCGTTACT GACTCGCTAC CTTCGAATTC ACCCCCAGAG TTGGGTGCAC
4321 CAGATTGCCC TGAGGATGGA GGTTCTGGGC TGCGAGGCAC AGGACCTCTA CGACAAAACT
4381 CACACATGCC CACCGTGCCC AGCACCTGAA CTCCTGGGAG GACCGTCAGT CTTCCTCTTC
4441 CCCCCAAAAC CCAAGGACAC CCTCATGATC TCCCGGACCC CTGAGGTCAC ATGCGTGGTG
4501 GTGGACGTGA GCCACGAAGA CCCTGAGGTC AAGTTCAACT GGTACGTGGA CGGCGTGGAG
4561 GTGCATAATG CCAAGACAAA GCCGCGGGAG GAGCAGTACA ACAGCACGTA CCGTGTGGTC
4621 AGCGTCCTCA CCGTCCTGCA CCAGGACTGG CTGAATGGCA AGGAGTACAA GTGCAAGGTC
4681 TCCAACAAAG CCCTCCCAGC CCCCATCGAG AAAACCATCT CCAAAGCCAA AGGGCAGCCC
4741 CGAGAACCAC AGGTGTACAC CCTGCCCCCA TCCCGCGATG AGCTGACCAA GAACCAGGTC
4801 AGCCTGACCT GCCTGGTCAA AGGCTTCTAT CCCAGCGACA TCGCCGTGGA GTGGGAGAGC
4861 AATGGGCAGC CGGAGAACAA CTACAAGACC ACGCCTCCCG TGTTGGACTC CGACGGCTCC
4921 TTCTTCCTCT ACAGCAAGCT CACCGTCGAC AAGAGCAGGT GGCAGCAGGG GAACGTCTTC
4981 TCTCCGGGTA TGATGCATGA GGCTCTGCAC AACCACTACA CGCAGAAGAG CCTCTCCCTG
5041 TCTCCGGGTA AACGGCGCCG CCGGAGCGGT GGCGGCGGAT CAGGTGGGGG TGGATCAGGC
5101 GGTGGAGGTT CCGGTGGCGG GGGATCCGGC GGTGGAGGTT CCGGTGGGGG TGGATCAAGG
5161 AAGAGGAGGA AGAGGGACAA AACTCACACA TGCCCACCGT GCCCAGCTCC AGAACTCCTG
5221 GGCGGACCGT CAGTCTTCCT CTTCCCCCCA AAACCCAAGG ACACCCTCAT GATCTCCCGG
5281 ACCCCTGAGG TCACATGCGT GGTGGTGGAC GTGAGCCACG AAGACCCTGA GGTCAAGTTC
5341 AACTGGTACG TGGACGGCGT GGAGGTGCAT AATGCCAAGA CAAAGCCGCG GGAGGAGCAG
5401 TACAACAGCA CGTACCGTGT GGTCAGCGTC CTCACCGTCC TGCACCAGGA CTGGCTGAAT
5461 GGCAAGGAGT ACAAGTGCAA GGTCTCCAAC AAAGCCCTCC CAGCCCCCAT CGAGAAAACC
5521 ATCTCCAAAG CCAAAGGGCA GCCCCGAGAA CCACAGGTGT ACACCCTGCC CCCATCCCGG
5581 GATGAGCTGA CCAAGAACCA GGTCAGCCTG ACCTGCCTGG TCAAAGGCTT CTATCCCAGC
5641 GACATCGCCG TGGAGTGGGA GAGCAATGGG CAGCCGGAGA ACAACTACAA GACCACGCCT
5701 CCCGTGTTGG ACTCCGACGG CTCCTTCTTC CTCTACAGCA AGCTCACCGT GGACAAGAGC
```

-continued

DRAFT SEQUENCE LISTING

```
5761 AGGTGGCAGC AGGGGAACGT CTTCTCATGC TCCGTGATGC ATGAGGCTCT GCACAACCAC
5821 TACACGCAGA AGAGCCTCTC CCTGTCTCCG GGTAAATGA
```

FVIII-049 amino acid sequence. Signal sequence is shown in dotted underline, and linker with proprotein convertase processing sites is shown in bold

```
   1 MQIELSTCFF LCLLRFCFSA TRRYYLGAVE LSWDYMQSDL GELPVDARFP PRVPKSFPFN
  61 TSVVYKKTLF VEFTDHLFNI AKPRPPWMGL LGPTIQAEVY DTVVITLKNM ASHPVSLHAV
 121 GVSYWKASEG AEYDDQTSQR EKEDDKVFPG GSHTYVWQVL KENGPMASDP LCLTYSYLSH
 181 VDLVKDLNSG LIGALLVCRE GSLAKEKTQT LHKFILLFAV FDEGKSWHSE TKNSLMQDRD
 241 AASARAWPKM HTVNGYVNRS LPGLIGCHRK SVYWHVIGMG TTPEVHSIFL EGHTFLVRNH
 301 RQASLEISPI TFLTAQTLLM DLGQFLLFCH ISSHQHDGME AYVKVDSCPE EPQLRMKNNE
 361 EAEDYDDDLT DSEMDVVRFD DDNSPSFIQI RSVAKKHPKT WVHYIAAEEE DWDYAPLVLA
 421 PDDRSYKSQY LNNGPQRIGR KYKKVRFMAY TDETFKTREA IQHESGILGP LLYGEVGDTL
 481 LIIFKNQASR PYNIYPHGIT DVRPLYSRRL PKGVKHLKDF PILPGEIFKY KWTVTVEDGP
 541 TKSDPRCLTR YYSSFVNMER DLASGLIGPL LICYKESVDQ RGNQIMSDKR NVILFSVFDE
 601 NRSWYLTENI QRFLPNPAGV QLEDPEFQAS NIMHSINGYV FDSLQLSVCL HEVAYWYILS
 661 IGAQTDFLSV FFSGYTFKHK MVYEDTLTLF PFSGETVFMS MENPGLWILG CHNSDFRNRG
 721 MTALLKVSSC DKNTGDYYED SYEDISAYLL SKNNAIEPRS FSQNPPVLKR HQREITRTTL
 781 QSDQEEIDYD DTISVEMKKE DFDIYDEDEN QSPRSFQKKT RHYFIAAVER LWDYGMSSSP
 841 HVLRNRAQSG SVPQFKKVVF QEFTDGSFTQ PLYRGELNEH LGLLGPYIRA EVEDNIMVTF
 901 RNQASRPYSF YSSLISYEED QRQGAEPRKN FVKPNETKTY FWKVQHHMAP TKDEFDCKAW
 961 AYFSDVDLEK DVHSGLIGPL LVCHTNTLNP AHGRQVTVQE FALFFTIFDE TKSWYFTENM
1021 ERNCRAPCNI QMEDPTFKEN YRFHAINGYI MDTLPGLVMA QDQRIRWYLL SMGSNENIHS
1081 IHFSGHVFTV RKKEEYKMAL YNLYPGVFET VEMLPSKAGI WRVECLIGEH LHAGMSTLFL
1141 VYSNKCQTPL GMASGHIRDF QITASGQYGQ WAPKLARLHY SGSINAWSTK EPFSWIKVDL
1201 LAPMIIHGIK TQGARQKFSS LYISQFIIMY SLDGKKWQTY RGNSTGTLMV FFGNVDSSGI
1261 KHNIFNPPII ARYIRLHPTH YSIRSTLRME LMGCDLNSCS MPLGMESKAI SDAQITASSY
1321 FTNMFATWSP SKARLHLQGR SNAWRPQVNN PKEWLQVDFQ KTMKVTGVTT QGVKSLLTSM
1381 YVKEFLISSS QDGHQWTLFF QNGKVKVFQG NQDSFTPVVN SLDPPLLTRY LRIHPQSWVH
1441 QIALRMEVLG CEAQDLYDKT HTCPPCPAPE LLGGPSVFLF PPKPKDTLMI SRTPEVTCVV
1501 VDVSHEDPEV KFNWYVDGVE VHNAKTKPRE EQYNSTYRVV SVLTVLHQDW LNGKEYKCKV
1561 SNKALPAPIE KTISKAKGQP REPQVYTLPP SRDELTKNQV SLTCLVKGFY PSDIAVEWES
1621 NGQPENNYKT TPPVLDSDGS FFLYSKLTVD KSRWQQGNVF SCSVMHEALH NHYTQKSLSL
1681 SPGKRRRRSG GGGSGGGGSG GGGSGGGGSG GGGSGGGGSR KRRKRDKTHT CPPCPAPELL
1741 GGPSVFLFPP KPKDTLMISR TPEVTCVVVD VSHEDPEVKF NWYVDGVEVH NAKTKPREEQ
1801 YNSTYRVVSV LTVLHQDWLN GKEYKCKVSN KALPAPIEKT ISKAKGQPRE PQVYTLPPSR
1861 DELTKNQVSL TCLVKGFYPS DIAVEWESNG QPENNYKTTP PVLDSDGSFF LYSKLTVDKS
1921 RWQQGNVFSC SVMHEALHNH YTQKSLSLSP GK*
```

What is claimed is:

1. A chimeric clotting factor, comprising:

i) a clotting factor comprising a FVII polypeptide, ii) a targeting moiety which binds to platelets, and iii) a scaffold moiety comprising an FcRn binding moiety;

wherein the scaffold moiety is a dimeric Fc region comprising a first Fc moiety (F1) and a second Fc moiety (F2); wherein the clotting factor is covalently bonded to the N-terminus of F1 either directly or via a first spacer moiety; and wherein the targeting moiety is linked to F2 either directly or via a second spacer moiety.

2. The chimeric clotting factor of claim 1, wherein the clotting factor is fused to F1 via the first spacer moiety or the targeting moiety is fused to F2 via the second spacer moiety.

3. The chimeric clotting factor of claim 2, which comprises two polypeptides having:

(i) a first polypeptide comprising the clotting factor, the first spacer moiety, and F1, and a second polypeptide comprising the targeting moiety and F2;

(ii) a first polypeptide comprising the clotting factor, the first spacer moiety, and F1, and a second polypeptide comprising the targeting moiety, the second spacer moiety, and F2;

(iii) a first polypeptide comprising the clotting factor and F1, and a second polypeptide comprising the targeting moiety and F2; or (iv) a first polypeptide comprising the clotting factor and F1, and a second polypeptide comprising the targeting moiety, the second spacer moiety, and F2;

wherein the two polypeptides are linked by a covalent bond.

4. The chimeric clotting factor of claim 1, wherein the targeting moiety is fused to F2 via the second spacer moiety.

5. The chimeric clotting factor of claim 1, wherein the second spacer moiety comprises a cleavable linker, and wherein the targeting moiety is fused to F2 via the cleavable linker.

6. The chimeric clotting factor of claim 1, wherein the targeting moiety is selected from the group consisting of: an antibody molecule, an antigen binding fragment of an antibody molecule, an scFv molecule, a receptor binding portion of a receptor, and a peptide.

7. The chimeric clotting factor of claim 1 wherein the targeting moiety binds to resting platelets or activated platelets.

8. The chimeric clotting factor of claim 7, wherein the targeting moiety selectively binds to a target selected from the group consisting of: GPIba, GPVI, and the nonactive form of GPIIb/IIIa.

9. The chimeric clotting factor of claim 7, wherein the targeting moiety selectively binds to a target selected from the group consisting of: the active form of GPIIb/IIIa, P selectin, GMP-33, LAMP-1, LAMP-2, CD40L, and LOX-1.

10. The chimeric clotting factor of claim 7 wherein the targeting moiety is a peptide selected from the group consisting of PS4, OS1, and OS2.

11. The chimeric clotting factor of claim 7, wherein the targeting moiety comprises an antibody variable region from an antibody selected from the group consisting of SCE5, MB9, and AP3.

12. The chimeric clotting factor of claim 1, wherein the FVII polypeptide comprises a FVII light chain and a FVII heavy chain, wherein the FVII light chain is directly covalently bonded to the N-terminus of the FVII heavy chain, wherein the C-terminus of the FVII heavy chain is covalently bonded to the N-terminus of F1 by a linker, wherein the targeting moiety is covalently bonded to the N-terminus of F2 by a linker, and wherein the targeting moiety is an antibody variable region from an AP3 antibody.

13. The chimeric clotting factor of claim 12, wherein F1 and F2 are linked by a disulfide bond.

14. The chimeric clotting factor of claim 1, wherein the FVII polypeptide comprises a FVII light chain and a FVII heavy chain, wherein the FVII light chain is directly covalently bonded to the N-terminus of the FVII heavy chain, wherein the C-terminus of the FVII heavy chain is covalently bonded to the N-terminus of F1 by a linker, wherein the C-terminus of F1 is covalently bonded to the N-terminus of the targeting moiety by a cleavable single chain Fc (cscFc) linker, wherein the targeting moiety is covalently bonded to the N-terminus of F2 by a linker, and wherein the targeting moiety is a peptide selected from the group consisting of PS4, OS1, and OS2.

15. The chimeric clotting factor of claim 14, wherein F1 and F2 are linked by a disulfide bond.

16. The chimeric clotting factor of claim 1, wherein the FVII polypeptide comprises a FVII light chain and a FVII heavy chain, wherein the FVII light chain is directly covalently bonded to the N-terminus of the FVII heavy chain, wherein the C-terminus of the FVII heavy chain is covalently bonded to the N-terminus of F1 by a linker, wherein the C-terminus of F1 is covalently bonded to the N-terminus of F2 by a cleavable single chain Fc (cscFc) linker, wherein the targeting moiety is covalently bonded to the C-terminus of F2 by a linker, and wherein the targeting moiety is a peptide selected from the group consisting of PS4, OS1, and OS2.

17. The chimeric clotting factor of claim 16, wherein F1 and F2 are linked by a disulfide bond.

18. A composition comprising the chimeric clotting factor of claim 1 and a pharmaceutically acceptable carrier.

19. A method for improving hemostasis in a subject, comprising administering to a subject in need thereof an effective amount of the composition of claim 18.

20. A nucleic acid molecule encoding the chimeric clotting factor of claim 1.

21. An expression vector comprising the nucleic acid molecule of claim 20.

22. A host cell comprising the expression vector of claim 21.

23. A method for producing a chimeric clotting factor comprising culturing the host cell of claim 22 in culture medium and recovering the chimeric clotting factor from the medium.

* * * * *